United States Patent
Patron et al.

(10) Patent No.: US 11,758,933 B2
(45) Date of Patent: *Sep. 19, 2023

(54) HIGH INTENSITY SWEETENERS

(71) Applicant: Firmenich Incorporated, Plainsboro, NJ (US)

(72) Inventors: Andrew Patron, San Marcos, CA (US); Rama Manam, San Diego, CA (US); Justin Colquitt, San Diego, CA (US); Nicole Servant, San Diego, CA (US); Chris Edano Noriega, San Diego, CA (US); Jeffrey R. Hammaker, San Diego, CA (US); Nicole Gonsalves, San Diego, CA (US); Tanya Ditschun, San Diego, CA (US)

(73) Assignee: Firmenich Incorporated, Plainsboro, NJ (US)

( * ) Notice: Subject to any disclaimer, the term of this patent is extended or adjusted under 35 U.S.C. 154(b) by 35 days.

This patent is subject to a terminal disclaimer.

(21) Appl. No.: 17/211,144

(22) Filed: Mar. 24, 2021

(65) Prior Publication Data

US 2021/0227863 A1 Jul. 29, 2021

Related U.S. Application Data

(63) Continuation of application No. 15/336,579, filed on Oct. 27, 2016, now Pat. No. 11,357,246.

(60) Provisional application No. 62/248,206, filed on Oct. 29, 2015.

(51) Int. Cl.
| | |
|---|---|
| *A23L 27/20* | (2016.01) |
| *A23L 27/30* | (2016.01) |
| *A23L 2/60* | (2006.01) |
| *C07J 9/00* | (2006.01) |
| *A23L 27/00* | (2016.01) |
| *A23L 2/385* | (2006.01) |
| *A23P 10/20* | (2016.01) |
| *A23L 2/52* | (2006.01) |
| *C07J 17/00* | (2006.01) |

(52) U.S. Cl.
CPC ............ *A23L 27/204* (2016.08); *A23L 2/385* (2013.01); *A23L 2/52* (2013.01); *A23L 2/60* (2013.01); *A23L 27/00* (2016.08); *A23L 27/36* (2016.08); *A23P 10/20* (2016.08); *C07J 9/00* (2013.01); *C07J 17/005* (2013.01); *A23V 2002/00* (2013.01)

(58) Field of Classification Search
CPC ........ A23L 27/204; A23L 27/00; A23L 27/36; A23L 2/385; A23L 2/52; A23L 2/60; A23P 10/20; C07J 9/00; C07J 17/005; A23V 2002/00
USPC ...................... 426/548, 534, 538
See application file for complete search history.

(56) References Cited

U.S. PATENT DOCUMENTS

| | | |
|---|---|---|
| 6,468,576 B1 | 10/2002 | Sher et al. |
| 7,659,097 B2 | 2/2010 | Renninger et al. |
| 8,236,512 B1 | 8/2012 | Zhao et al. |
| 8,357,527 B2 | 1/2013 | Ubersax |
| 8,367,395 B2 | 2/2013 | Bailey et al. |
| 8,415,136 B1 | 4/2013 | Gardner et al. |
| 8,470,568 B2 | 6/2013 | Walker et al. |
| 8,481,286 B2 | 7/2013 | Julien et al. |
| 8,519,204 B2 | 8/2013 | Ohler et al. |
| 8,586,814 B2 | 11/2013 | Fisher et al. |
| 8,603,800 B2 | 12/2013 | Gardner et al. |
| 8,609,371 B2 | 12/2013 | Julien et al. |
| 8,753,842 B2 | 6/2014 | Julien et al. |
| 8,859,261 B2 | 10/2014 | Gardner et al. |
| 9,200,296 B2 | 12/2015 | Renninger et al. |
| 9,410,214 B2 | 8/2016 | Hawkins et al. |
| 9,540,662 B2 | 1/2017 | Walker et al. |
| 11,357,246 B2 * | 6/2022 | Patron ................... A23L 27/204 |
| 2005/0084506 A1 | 4/2005 | Tachdjian et al. |
| 2006/0228454 A1 | 10/2006 | Ackill et al. |
| 2006/0263411 A1 | 11/2006 | Tachdjian et al. |
| 2007/0116690 A1 | 5/2007 | Yang et al. |
| 2009/0111834 A1 | 4/2009 | Tachdjian et al. |
| 2009/0137014 A1 | 5/2009 | Tsuruta et al. |
| 2009/0220662 A1 | 9/2009 | Tachdjian et al. |
| 2010/0151519 A1 | 6/2010 | Julien et al. |
| 2010/0151555 A1 | 6/2010 | Julien et al. |
| 2011/0027413 A1 | 2/2011 | Jia |
| 2012/0201763 A1 | 8/2012 | Tachdjian |
| 2012/0226047 A1 | 9/2012 | Shigemura et al. |
| 2014/0170286 A1 | 6/2014 | Jia |

(Continued)

FOREIGN PATENT DOCUMENTS

| | | |
|---|---|---|
| CN | 105039274 | 11/2015 |
| EP | 2 783 009 B1 | 4/2016 |

(Continued)

OTHER PUBLICATIONS

US 8,486,659 B2, 07/2013, Julien et al. (withdrawn)

(Continued)

*Primary Examiner* — Leslie A Wong

(74) *Attorney, Agent, or Firm* — Knobbe, Martens, Olson & Bear, LLP

(57) ABSTRACT

Disclosed herein are compounds having structural Formula (I), or salts thereof. These compounds are useful as sweet tasting agents and/or sweetness enhancers. Also disclosed are compositions comprising the present compounds and methods of increasing the sweet taste of ingestible compositions. Furthermore, methods for preparing the compounds are also disclosed.

40 Claims, No Drawings

(56) References Cited

U.S. PATENT DOCUMENTS

| | | | |
|---|---|---|---|
| 2015/0064743 | A1 | 3/2015 | Liu et al. |
| 2015/0093339 | A1 | 4/2015 | Tachdjian et al. |
| 2015/0225754 | A1 | 8/2015 | Tange et al. |
| 2015/0320095 | A1 | 11/2015 | Jia |
| 2017/0029458 | A1 | 2/2017 | Siems et al. |
| 2017/0119032 | A1 | 5/2017 | Patron et al. |
| 2017/0145429 | A1 | 5/2017 | Walker et al. |
| 2017/0283844 | A1 | 10/2017 | Itkin et al. |
| 2018/0020709 | A1 | 1/2018 | Markosyan |
| 2019/0071705 | A1 | 3/2019 | Patron et al. |
| 2021/0324439 | A1 | 10/2021 | Patron et al. |

FOREIGN PATENT DOCUMENTS

| | | |
|---|---|---|
| WF | WO 16/130609 | 8/2016 |
| WO | WO 05/015158 | 2/2005 |
| WO | WO 05/041684 | 5/2005 |
| WO | WO 06/084186 | 8/2006 |
| WO | WO 06/138512 | 12/2006 |
| WO | WO 07/124152 | 11/2007 |
| WO | WO 08/154221 | 12/2008 |
| WO | WO 09/023975 | 2/2009 |
| WO | WO 09/100333 | 8/2009 |
| WO | WO 09/111447 | 9/2009 |
| WO | WO 10/014666 | 2/2010 |
| WO | WO 10/014813 | 2/2010 |
| WO | WO 11/112892 | 9/2011 |
| WO | WO 11/123693 | 10/2011 |
| WO | WO 12/021837 | 2/2012 |
| WO | WO 12/061698 | 5/2012 |
| WO | WO 12/103074 | 8/2012 |
| WO | WO 13/025560 | 2/2013 |
| WO | WO 13/076577 | 5/2013 |
| WO | WO 13/096420 | 6/2013 |
| WO | WO 14/025706 | 2/2014 |
| WO | WO 14/027118 | 2/2014 |
| WO | WO 14/086842 | 6/2014 |
| WO | WO 14/130513 | 8/2014 |
| WO | WO 14/140634 | 9/2014 |
| WO | WO 14/146089 | 9/2014 |
| WO | WO 14/130582 | 10/2014 |
| WO | WO 14/086842 A9 | 6/2015 |
| WO | WO 15/082012 | 6/2015 |
| WO | WO 15/168779 | 11/2015 |
| WO | WO 16/038617 | 3/2016 |
| WO | WO 16/050890 | 4/2016 |
| WO | WO 16/060276 | 4/2016 |
| WO | WO 16/073251 | 5/2016 |
| WO | WO 17/044659 | 3/2017 |
| WO | WO 17/172766 | 10/2017 |
| WO | WO 17/176873 | 10/2017 |
| WO | WO 18/016483 | 1/2018 |
| WO | WO 18/200663 | 11/2018 |
| WO | WO 18/229283 | 12/2018 |

OTHER PUBLICATIONS

Ager et al., 1998, Commercial, synthetic nonnutritive sweeteners, Angew. Chem. Int. Ed. 37:1802-1817.
Akihisa et al., 2007, Cucurbitane glycosides from the fruits of siraitia grosvenorii and their inhibitory effects on Epstein-Barr virus activation, J. Nat. Prod., 70:783-788.
Altschul et al., 1996, [27] Local Alignment Statistics, Methods in Enzymology, 266:460-480.
Altschul et al., 1997, Gapped BLAST and PSi-BLAST: a new generation of protein database search programs, Nucleic Acids Res., 25(17):3389-3402.
Andrade-Eiroa et al., Jun. 2016, Solid-phase extraction of organic compounds: A critical review (Part I), TrAC Trends in Analytical Chemistry, 80:641-654.
Cardenas et al., 2016, Engineering cofactor and transport mechanisms in Saccharomyces cerevisiae for enhanced acetyl-CoA and polyketide biosynthesis. Metab Eng, 36:80-89.

Chabrol, 2012, The hideous price of beauty An investigation into the market of deep-sea shark liver oil. Edited by: The Bloom Association.
Chang et al., 2007, Engineering Escherichia coli for production of functionalized terpenoids using plant P450s. Nat Chem Biol, 3:274-277.
Chaturvedula et al., 2011, Enzymatic and acid hydrolysis of steviol and cucurbitane glycosides, Int. J. Pharm. Biomed. Res., 2(2):135-139.
Chaturvedula et al., Jan. 2011, Comparative phytochemical studies of the commercial extracts of Siraitia grosvenorii, Journal of Pharmacy Research, 4(9):3166-3167.
Chen et al., 2018, Kumada arylation of secondary amides enabled by chromium catalysis for unsymmetric ketone synthesis under mild conditions, ACS Catalysis, 8:5864-5868.
Chen et al., Jan. 2005, Cucurbitacins and cucurbitane glycosies: structures and biologial activities, Natural Product Reports, 22(3), 14 pp.
Chiu et al., 2013, Biotransformation of mogrosides from siraitia grosvenorii swingle by Saccharomyces cerevisiae, J. Agric. Food Chem., 61:7127-7134.
Dai et al., 2015, Functional characterization of cucurbtadienol synthase and triperpene glycosyltransferase involved in biosynthesis of mogrosides from siraitia grosvenorii, Plant Cell Physiol., 56(6):1172-1182.
de Felipe et al., 2004, Targeting of Proteins Derived from Self-Processing Polyproteins Containing Multiple Signal Sequences, Traffic, 5:616-626.
de Felipe, 2004, Skipping the co-expression problem: the new 2A "Chysel" technology, Genetic Vaccines and Ther. 2:13.
Devos et al., 2000, Practical limits of function prediction, Proteins: Structure, Function, and Genetics, 41:98-107.
Donald et al., Sep. 1997, Effects of Overproduction of the Catalytic Domain of 3-Hydroxy-3-Methylglutaryl Coenzyme A Reductase on Squalene Synthesis in Saccharomyces cerevisiae, Appl Environ Microbiol., 63(9):3341-3344.
GenBank: AEM42982.1, cucurbitadienol synthase [Siraitia grosvenorii], Dec. 1, 2012, 2 pp.
Ghimire et al., 2009, Improved squalene production via modulation of the methylerythritol 4-phosphate pathway and heterologous expression of genes from Streptomyces peucetius ATCC 27952 in Escherichia coli. Appl Environ Microbiol, 75:7291-7293.
Ghimire et al., 2016, Advances in Biochemistry and Microbial Production of Squalene and Its Derivatives. J Microbiol Biotechnol, 26:441-451.
Gruchattka et al., Dec. 23, 2015, In Vivo Validation of In Silico Predicted Metabolic Engineering Strategies in Yeast: Disruption of α-Ketoglutarate Dehydrogenase and Expression of ATP-Citrate Lyase for Terpenoid Production. PLOS ONE, 10(12):e0144981.
Itkin et al., 2016 The biosynthetic pathway of the nonsugar, high-intensity sweetener mogroside V from siraitia grosvenorii, PNAS, 113(47):E7619-E7628 and supplemental material.
Jia et al., 2009, A minor, sweet cucurbitane glycoside from siraitia grosvenorii, Natural Product Communications, 4(6):769-772.
Joska et al., May 2014 A universal cloning method based on yeast homologous recombination that is simple, efficient, and versatile, J. Microbiol. Methods, 100: 46-51.
Kasai et al., 1988, Glycosides from Chinese medicinal plant, hemsleya panacis-scandens, and structure-taste relationship of cucurbitane glycosides, Chemical and Pharmaceutical Bulletin, 36(1):234-243.
Katabami et al., 2015, Production of squalene by squalene synthases and their truncated mutants in Escherichia coli. J Biosci Bioeng, 119:165-171.
Kinghorn et al., 1998, Noncariogenic intense natural sweeteners, Med. Res. Rev. 18(5):347-360.
Kirby et al. Engineering triterpene production in Saccharomyces cerevisiae-β-amyrin synthase from Artemisia annua, FEBS J. Apr. 2008; 275(8):1852-9.
Kisseiev, Jan. 2002, Polypeptide release factors in prokaryotes and eukaryotes: same function, different structure, Structure, 10:8-9.

(56) References Cited

OTHER PUBLICATIONS

Kozak et al., 2014, Engineering acetyl coenzyme A supply: functional expression of a bacterial pyruvate dehydrogenase complex in the cytosol of *Saccharomyces cerevisiae*. MBio, 5:e01696-01614.
Lemaigre and Rousseau, Transcriptional control of genes that regulate glycolysis and gluconeogenesis in adult liver, Biochem. J. 303:1-14 (1994).
LeVan et al., 2008, Section 16: Adsorbents and Ion Exchange, In Perry's Chemical Engineers' Handbook, 8th edition. Green ed., McGraw-Hill, New York, pp. 16-1-16-10.
Lewin, Genes V (Oxford University Press, Oxford), pp. 847-873.
Li et al., 2006, Cucurbitane glycosides from unripe fruits of Lo Han Kuo (siraitia grosvenori), Chem. Pharm. Bull, 54(10): 1425-1428.
Li et al., 2007, Cucurbitane glycosides from unripe fruits of siraitia grosvenori. Chem. Pharm. Bull. 55(7): 1082-1086.
Li et al., 2014, Chemistry and pharmacology of siraitia grosvenorii: a review, Chinese Journal of Natural Medicines, 12(2):89-102.
Li et al., 2017, Cucurbitane glycosides from the fruit of siraitia grosvenori and their effects on glucose uptake in human HepG2 cells in vitro, Food Chemistry, 228:567-573.
Loeken et al., 1993, Effects of mutation of the CREB binding site of the somatostatin promoter on cyclic AMP responsiveness in CV-1 cells, Gene Expr. 3:253-264.
Luo et al., 2016, Liquid chromatography with tandem mass spectrometry method for the simultaneous determination of multiple sweet mogrosides in the fruits of siraitia grosvenorii and its marketed sweeteners, J. Sep. Sci, 39:4124-4135.
Matsumoto et al., 1990, Minor cucurbitane-glycosides from fruits of siraitia grosvenori (cucurbitaceae). Chem. Pharm. Bull., 38(7):2030-2032.
McGehee et al., 1993, Differentiation-specific element: a cis-acting developmental switch required for the sustained transcriptional expression of the angiotensinogen gene during hormonal-induced differentiation of 3T3-L1 fibroblasts to adipocyteshee et al., Mol. Endocrinol. 7:551-560.
Mehrotra et al., 2014, Steviol glycosides and their use in food processing: a review, innovare Journal of Food Science, 2(1):7-13.
Narendranath et al., May 2005, Relationship between pH and Medium Dissolved Solids in Terms of Growth and Metabolism of Lactobacilli and *Saccharomyces cerevisiae* during Ethanol Production, Appl Environ Microbiol., 71(5): 2239-2243.
Newman et al., 2006, High-level production of amorpha-4,11-diene in a two-phase partitioning bioreactor of metabolically engineered *Escherichia coli*. Biotechnol Bioeng, 95:684-691.
Noguchi et al., May 2008, Sequential glucosylation of a furofuran lignan, (+)-sesaminol, by Sesamum indicum UGT71A9 and UGT94D1 glucosyltransferases, Plant J., 54(3):415-427.
O'Reilly et al., 1992, Identification of an Activating Transcription Factor( ATF) Binding Site in the Human Transforming Growth Factor-/32 Promoter, J. Biol. Chem. 267:19938-19943.
Pandey et ai., 2014, Enzymatic Biosynthesis of Novel Resveratrol Glucoside and Glycoside Derivatives, Applied and Environmental Microbiology, 80(23):7235-7243.
Peng et al., 2015, Controlling heterologous gene expression in yeast cell factories on different carbon substrates and across the diauxic shift: a comparison of yeast promoter activities, Microb Cell Fact, 14:91.
Ptotka-Wasylka J et al., New Polymeric Materials for Solid Phase Extraction, Crit Rev Anal Chem., published online on Apr. 11, 2017, pp. 373-383.
Prakash et al., 2014, Additional new minor cucurbitane clycosieds from Siraitia grosvenorii, Molecules, 19:3669-3680.
Prakash et al., Jul. 2008, development of rebiana, a natural, non-caloric sweetener, Food and Chemical Toxicology, 9 pp.
Qing et al., 2017, Systematic identification of flavonols, flavonol glycosides, triterpene and siraitic acid glycosides from siraitia grosvenorii using high-performance liquid chromatography/quadrupole-time-of-flight mass spectrometry combined with a screening strategy, Journal of Pharmaceutical and Biomedical Analysis, 138:240-248.
Rodriguez et al., 2016, ATP citrate lyase mediated cytosolic acety/-CoA biosynthesis increases mevalonate production in *Saccharomyces cerevisiae*, Microb Cell Fact, 15:48.
Sajid et al., May 2017, Porous membrane protected micro-solid-phase extraction: A review of features, advancements and applications, Anal Chim Acta., 965:36-53.
Salmon et al., Jul. 2016, A conserved amino acid residue critical for product and substrate specificity in plant triterpene synthases, Proc Natl Acad Sci U S A. 26; 113(30): E4407-E4414.
Sawai et al. Triterpenoid Biosynthesis and Engineering in Plants, Front Plant Sci. Jun. 30, 2011; 2:25.
Shen et al., 2014, Rapid identification and quantification of five major mogrosides in siraitia grosvenorii (Luo-Han-Guo) by high performance liquid chromatography-triple quadrupole linear trap tandem mass spectrometry combined with microwave-assisted extraction, Microchemical Journal, 116:142-150.
Shiba et al., 2007, Engineering of the pyruvate dehydrogenase bypass in *Saccharomyces cerevisiae* for high-level production of isoprenoids. Metab Eng, 9:160-168.
Shibuya et al., 2004, Cucurbitadienol synthase, the first committed enzyme for cucurbitacin biosyntheis, is a distinct enzyme from cycloartenol synthase for phytosterol biosynthesis, Tetrahedron 60:6995-7003.
Su et al. Jul. 2017, Molecular and biochemical characterization of squalene synthase from Siraitia grosvenorii, Biotechnol Lett. vol. 39, Issue 7, pp. 1009-1018.
Tai et al., 2013, Engineering the push and pull of lipid biosynthesis in oleaginous yeast Yarrowia lipolytica for biofuel production. Metab Eng, 15:1-9.
Takase et al. 2015, Control of the 1,2-rearrangement process by oxidosqualene cyclases during triterpene biosynthesis, Org Biomol Chem. 13(26):7331-6.
Takemoto et al., 1983, Studies on the constituents of fructus momordicae. III. Structure of mogrosides, Pharmaceutical Journal, 103(11):1167-1173.
Tang et al., 2011, An efficient approach to finding siraitia grosvenorii triterpene biosynthetic genes by RNA-seq and digital gene expression analysis, BMC Genomics, 12:343.
Thompson et al., 2014, Squalene production using *Saccharomyces cerevisiae*, i-ACES, 1(1), 7 pp.
Treisman et al., 1990, The SRE: a growth factor responsive transcriptional regulator. Seminars in Cancer Biol. 1:47-58.
U.S. FDA list of Everything Added to Food in the U.S. (EAFUS), available at http://www.accessdata.fda.gov/scripts/fcn/fcnNavigation.cfm?rpt=eafusListing, last accessed Nov. 16, 2015, 186 pp.
Wang et al., 2015, Hyperproduction of β-Glucanase Exg1 promotes the bioconversion of mogrosides in *Saccharomyces cerevisiae* mutants defective in mannoprotien deposition, Journal of Agricultural and Food Chemistry, 63:10271-10279.
Wang et al., 2019, Dekkera bruxeiiensis, a beer yeast that specifically bioconverts mogroside extracts into the intense natural sweetener siamensode I, Food Chemistry, 276:43-49.
Wang et al., Aug. 20, 2014, Cucurbitane glycosides derived from mogroside IIE: structure-taste relationships, antioxidant activity, and acute toxicity, Molecules, 19(8):12676-12689.
Westfall et al., 2012, Production of amorphadiene in yeast, and its conversion to dihydroartemisinic acid, precursor to the antimalariai agent artemisinin. Proc Natl Acad Sci U S A, 109:E111-118.
Whisstock et al., 2003, Prediction of protein function from protein sequence and structure, Quarterly Review of Biophysics, 36(3):307-340.
Wiet et al., 1993, Fat concentration affects sweetness and sensory profiles of sucrose, sucralose, and aspartame, J. Food Sci., 58(3):599-602.
Witkowski et al., 1999, Conversion of a β-ketoacyl synthyase to a malonyl decarboxylase by replacement of the active-site cysteine with glutamine, Biochemistry, 38:11643-11650.
Xu et al., 2015, Exploring in vitro, in vivo metabolism of mogroside V and distribution of its metabolites in rats by HPLC-ESI-IT-TOF-MS", Journal of Pharmaceutical and Biomedical Analysis, 115:418-430.
Yang et al., 2016, Metabolites of siamenoside I and their distributions in rats, Molecules, 21:1-20.

(56) References Cited

OTHER PUBLICATIONS

Yang et al., Sep. 2005, Grosmomoside I, a new cucurbitane triterpenoid glycoside from fruits of momordica grosvenori, Chinese Traditional and Herbal Drugs, 36(9):1285-1290.
Ye et al., 1994, Characterization of a Silencer Regulatory Element in the Human Interferon-y Promoter, J. Biol. Chem. 269:25728-25734.
Zhang et al., 2012, Identification of flavonol and triperpene glycosides in Lui-Han-Guo extract using ultra-high performance liquid chromatography/quadrupole time-of-flight mass spectrometry, Journal of Food Compsition and Analysis, 25:142-148.
Zhang et al., 2015, Functional pyruvate formate lyase pathway expressed with two different electron donors in *Saccharomyces cerevisiae* at aerobic growth. FEMS Yeast Res, 15:fov024.
Zhang et al., 2016, Oxidation of Cucurbitadienol Catalyzed by CYP87D18 in the Biosynthesis of Mogrosides from Siraitia grosvenorii. Plant Cell Physiol 57:1000-1007.
Zhou et al., 2012, Enhanced alpha-ketoglutarate production in Yarrowia lipolytica WSH-Z06 by alteration of the acetyl-CoA metabolism. J Biotechnol, 161:257-264.
Zhou et al., 2016, Comprehensive analysis of 61 characteristic constituents from siraitiae fructus using ultrahigh-pressure liquid chromatography with time-of-flight mass spectrometry, Journal of Pharmaceutical and Biomedical Analysis, 125:1-14.
Zhou et al., 2017, Biotransformation of total saponins in siraitia fructus by human intestinal microbiota of normal and type 2 diabetic patients: comprehensive metabolite identification and metabolic profile elucidation using LC-Q-TOF/MS, Journal of Agricultural and Food Chemistry, 65:1518-1524.
International Search Report and Written Opinion dated May 1, 2017 in PCT/US16/059187.
Chaturvedula et al., 2011, Cucurbitane glycosides form Siraitia grosvenorii, J. Carbohydr, Chem., 30(1):16-26.
Perez Gutierrez, 2007, Triperpenes, in Handbook of Compounds with Cytotoxic Activity Isolated from Pants, Nova Science Publishers Inc., p. 511.
Szarek et al., 1984, L-glucose. A convenient synthesis from D-glucose, Can. J. Chem., 62(4):671-674.
Broun et al., 1998, Catalytic plasticity of fatty acid modification enzymes underlying chemical diversity of plant lipids, Science, 282:1315-1317.
Dols et al., Apr. 1998, Characterization of the different dextransucrase activities excreted in glucose, fructose, or sucrose medium by Leuconostoc mesenteroides NRRL B-1299, Applied and Environmental Microbiology, 64(4):1298-1302.
Gotoh, Jan. 5, 1992, Substrate recognition sites in cytochrome P450 family 2 (CYPB) proteins inferred from comparative analyses of amino acid and coding nucleotide sequence, The Journal of Biological Chemistry, 267(1):83-90.
Seffernick et al., 2001, Melamine deaminase and atrazine chlorohydrolase: 98 percent identical but functionally difference. Journal of Bacteriology, 183(8):2405-2410.
Uitdehaag et ai., 2002, Catalytic mechanism and product specificity of cyclodextrin giycosytransferase, a prototypical transglycosylase from the α-amylase family, Enzyme and Microbial Technology, 30:195-304.
Wang et al., Jan. 5, 2018, Biotransformation of mogrosides, Sweeteners, pp. 153-165.
Xu et ai., 2021, Selective enzymatic α-1,6-monoglucosylation of mogroside IIIE for the bio-creation of α-siamenoside I, a potential high-intensity sweetener, Food Chemistry, 359:1-9.
Ahmad et al., Jun. 2000, Spectroscopic Data of Saponins, CRC-Press, pp. 963-965.
CAS Registry No. 1126032-65-2, Entered STN: Mar. 24, 2009.
CAS Registry No. 126105-11-1, Entered STN: Mar. 30, 1990.
CAS Registry No. 126105-12-2, Entered STN: Mar. 30, 1990.
CAS Registry No. 130567-83-8, Entered STN: Nov. 23, 1990.
CAS Registry No. 1421942-59-7, Entered STN: Feb. 27, 2013.
CAS Registry No. 1613527-65-3, Entered STN: Jul. 8, 2014.
CAS Registry No. 1707161-17-8, Entered STN: May 18, 2015.
CAS Registry No. 189307-15-1, Entered STN: May 30, 1997.
CAS Registry No. 2096516-68-4, Entered STN: May 22, 2017.
CAS Registry No. 88901-37-5, Entered STN: Nov. 16, 1984.
CAS Registry No. 88901-41-1, Entered STN: Nov. 16, 1984.
CAS Registry No. 88901-42-2, Entered STN: Nov. 16, 1984.
CAS Registry No. 88901-43-3, Entered STN: Nov. 16, 1984.
CAS Registry No. 88901-46-6, Entered STN: Nov. 16, 1984.
CAS Registry No. 88915-64-4, Entered STN: Nov. 16, 1984.
Chatzifragkou et al., 2021, Chapter 18: Analysis of carbohydrates and glycoconjugates in food by CE and HPLC, in Carbohydrate Analysis by Modern Liquid Phase Separation Techniques, El Rassi ed., Elsevier, pp. 815-842.
Gunjal et al., 2020, Chapter 5: Pectinase in degradation of lignocellulosic wastes, in Enzymes in Degradation of the Lignocellulosic Wastes, Springer, pp. 71-103.
Izawa et al., 2010, 4.16. Human-environment interaction—taste, in Comprehensive Natural Products II, Mander et al., eds., Elsevier, pp. 631-671.
Lim, 2012, Siraitia grosvenorii, in Edible Medicinal and Non-Medicinal Plants., vol. 2, Fruits, Springer, pp. 392-400.
McMurry, 2015, 25-3 D,L Sugars, in Organic Chemistry, Cengage Learning, p. 839.
Merino et al., 2007, Progress and challenges in enzyme development for biomass utilization, Adv Biochem Engin/Biotechnol, 108:105-120.
Plou et al., 2007, Application of glycosidases and transglycosidases in the synthesis of oligosaccharides, in Industrial Enzymes: Structure, Function and applications, Polaina et al., eds., Springer, pp. 141-157.
Schomburg et al., eds., 2006, Springer Handbook fo Enzymes, vol. 31, Sucrose synthase, 2.4.1.13, pp. 113-125.
Schomburg et al., eds., 2006, Springer Handbook of Enzymes, vol. 31, Class 2, Transferases IV, Dextransucrase, 2.4.1.5, pp. 49-59.
Shoda, Jul. 2001, Chapter 5.3.1: Enzymatic glycosylation, in Glycoscience; Chemistry and Chemical Biology I-III, Frasier-Reid et al., eds., Springer, pp. 1466-1496.
Stoddart, 1984, Chapters. Polysaccharide assembly in eukaryotes, in The Biosynthesis of Polysaccharides, Croom Helm, London & Sydney, pp. 179-261.
Veana et al., 2018, Chapter 10. Invertase: an enzyme with importance in confectionery food industry, in Enzymes in Food Technology, Kuddus ed., Springer, pp. 187-212.
Wagner et al., eds., 2015, Fructus Siraitiae/Momordicase-Luohanguo, in Chromatographic Fingerprint Analysis of Herbal Medicines., vol. 3, Springer International Publishing Switzerland, pp. 197-198.

* cited by examiner

HIGH INTENSITY SWEETENERS

INCORPORATION BY REFERENCE TO ANY PRIORITY APPLICATIONS

Any and all applications for which a foreign or domestic priority claim is identified in the Application Data Sheet as filed with the present application are hereby incorporated by reference under 37 CFR 1.57. For example, this application is a continuation of U.S. patent application Ser. No. 15/336, 579 having a filing date of Oct. 27, 2016, now U.S. Pat. No. 11,357,246 which claims the benefit of U.S. Provisional Application No. 62/248,206 filed on Oct. 29, 2015, the contents of each of which are hereby incorporated by reference in their entireties for all purposes.

BACKGROUND

Field

The present disclosure relates to the fields of chemistry and foods, beverages, and other ingestible compositions. More specifically, the present disclosure relates to sweet tasting compounds, sweet taste enhancers, and combinations thereof, for ingestible compositions such as foods and beverages, and other ingestible or orally administered medicinal products or compositions.

Background Description

The taste system provides sensory information about the chemical composition of the external world. Taste transduction is one of the most sophisticated forms of chemical-triggered sensation in animals. Signaling of taste is found throughout the animal kingdom, from simple metazoans to the most complex of vertebrates. Mammals are believed to have five basic taste modalities: sweet, bitter, sour, salty, and umami (the taste of monosodium glutamate, a.k.a. savory taste).

For centuries, various natural and unnatural compositions and/or compounds have been added to ingestible compositions, including foods and beverages, and/or orally administered medicinal compositions to improve their taste. Although it has long been known that there are only a few basic types of "tastes," the biological and biochemical basis of taste perception was poorly understood, and most taste improving or taste modifying agents have been discovered largely by simple trial and error processes.

With respect to the sweet taste, diabetes, and cardiovascular disease are health concerns on the rise globally, but are growing at alarming rates in the United States. Sugar and calories are key components that can be limited to render a positive nutritional effect on health. High-intensity sweeteners can provide the sweetness of sugar, with various taste qualities. Because they are many times sweeter than sugar, much less of the sweetener is required to replace the sugar.

High-intensity sweeteners have a wide range of chemically distinct structures and hence possess varying properties, such as, without limitation, odor, flavor, mouthfeel, and aftertaste. These properties, particularly flavor and aftertaste, are well known to vary over the time of tasting, such that each temporal profile is sweetener-specific.

There has been significant recent progress in identifying useful natural flavoring agents, such as for example sweeteners such as sucrose, fructose, glucose, erythritol, isomalt, lactitol, mannitol, sorbitol, xylitol, certain known natural terpenoids, flavonoids, or protein sweeteners. See, e.g, Kinghom, et al., "Noncariogenic Intense Natural Sweeteners," Med. Res. Rev. 18 (5) 347-360 (1998) (discussing discovered natural materials that are much more intensely sweet than common natural sweeteners such as sucrose, fructose, and the like.) Similarly, there has been recent progress in identifying and commercializing new artificial sweeteners, such as aspartame, saccharin, acesulfame-K, cyclamate, sucralose, and the like. See, e.g., Ager, et al., Angew. Chem. Int. Ed. 37, 1802-1817 (1998). The entire disclosure of the references identified above are hereby incorporated herein by reference in their entirety.

Sweeteners such as saccharin and 6-methyl-1,2,3-oxathiazin-4(3H)-one-2,2-dioxide potassium salt (acesulfame potassium) are commonly characterized as having bitter and/or metallic aftertastes. Products prepared with 2,4-dihydroxybenzoic acid are claimed to display reduced undesirable aftertastes associated with sweeteners, and do so at concentrations below those concentrations at which their own tastes are perceptible. Also, high intensity sweeteners such as sucralose and aspartame are reported to have sweetness delivery problems, i.e., delayed onset and lingering of sweetness. See S. G. Wiet, et al., J. Food Sci., 58(3):599-602, 666 (1993).

There is a need for new sweetening compounds, sweet taste enhancers, and compositions containing such compounds and enhancers, having improved taste and delivery characteristics. In addition there is a need for foods containing new sweetening compounds and/or sweet taste enhancers with such desirable characteristics.

SUMMARY

Some embodiments provide a compound having the structure of formula (I):

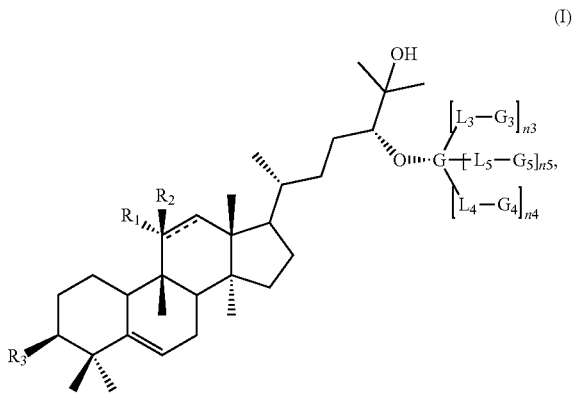

or a salt thereof.

In some embodiments, ═══ represents a carbon-carbon single bond or a carbon-carbon double bond.

In some embodiments, $R_1$ is absent or a hydroxy group and $R_2$ is hydrogen, or $R_1$ and $R_2$, together with the carbon atom to which they are attached, form an oxo group.

In some embodiments, $R_3$ is selected from —OH and

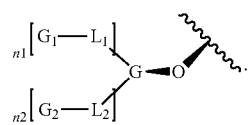

In some embodiments, each of $n^1$, $n^2$, $n^3$, $n^4$, and $n^5$ are independently an integer from 0 to 3.

In some embodiments, each G, $G_1$, $G_2$, $G_3$, $G_4$, and $G_5$ is independently a furanose or pyranose moiety.

In some embodiments, each $L_1$, $L_2$, $L_3$, $L_4$, and $L_5$ is independently a glycosidic bond.

When ===== a carbon-carbon double bond, $R_1$ is absent.

In some embodiments, the compound is in isolated form. In some embodiments, the compound is in purified form. In some embodiments, the compounds is in isolated and purified form.

Some embodiments provide a composition comprising one or more compounds having the structure of formula (I):

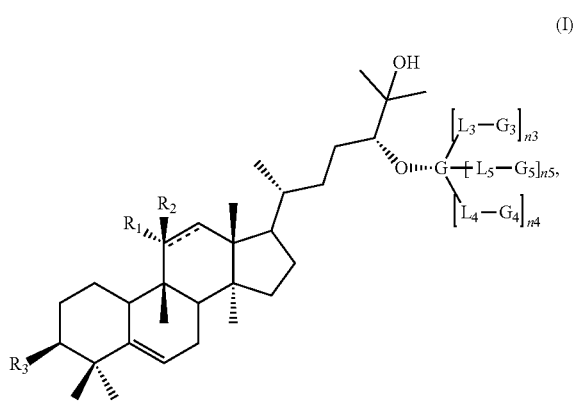

(I), or a salt thereof.

In some embodiments, the composition comprises greater than 50% by weight of the compound.

In some embodiments, the composition comprises less than 1% by weight of Mogroside III$_E$. In some embodiments, the composition comprises less than 0.5% by weight of Mogroside III$_E$. In some embodiments, the composition comprises less than 0.1% by weight of Mogroside III$_E$.

In some embodiments, the composition comprises less than 0.3% by weight of 11-oxo-Mogroside III$_E$. In some embodiments, the composition comprises less than 0.3% by weight of 11-oxo-Mogroside III$_E$. In some embodiments, the composition comprises less than 0.1% by weight of 11-oxo-Mogroside III$_E$. In some embodiments, the composition comprises less than 0.05% by weight of 11-oxo-Mogroside III$_E$. In some embodiments, the composition comprises less than 0.01% by weight of 11-oxo-Mogroside III$_E$.

In some embodiments, the composition comprises less than 1% by weight of all isomers of Mogroside I, Mogroside II, and Mogroside III. In some embodiments, the composition comprises less than 0.5% by weight of all isomers of Mogroside I, Mogroside II, and Mogroside III. In some embodiments, the composition comprises less than 0.1% by weight of all isomers of Mogroside I, Mogroside II, and Mogroside III. In some embodiments, the composition comprises less than 0.1% by weight of Mogroside III$_E$, 11-oxo-Mogroside III$_E$, Mogroside III$_{A2}$, Mogroside I$_E$, and Mogroside II$_E$.

In some embodiments, the composition comprises less than 1% by weight of 11-oxo-mogrol. In some embodiments, the composition comprises less than 0.5% by weight of 11-oxo-mogrol. In some embodiments, the composition comprises In some embodiments, the composition comprises less than 0.1% by weight of 11-oxo-mogrol.

In some embodiments, the composition comprises one or more additional compounds selected from the group consisting of mogrol, 11-oxo-mogrol,

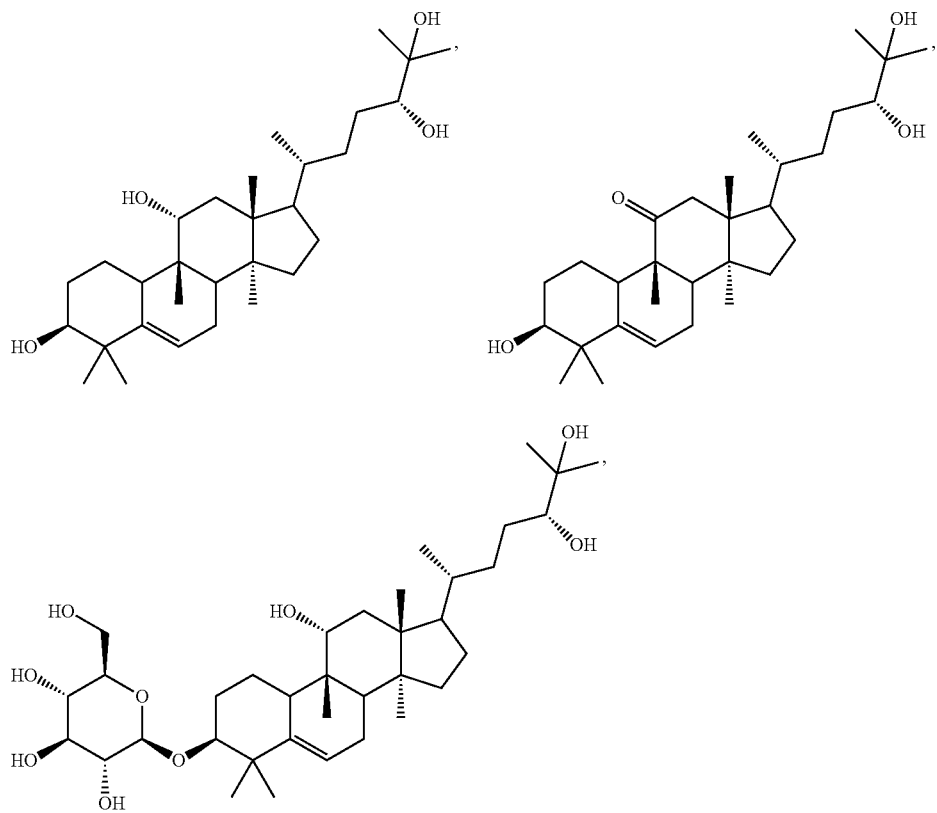

-continued
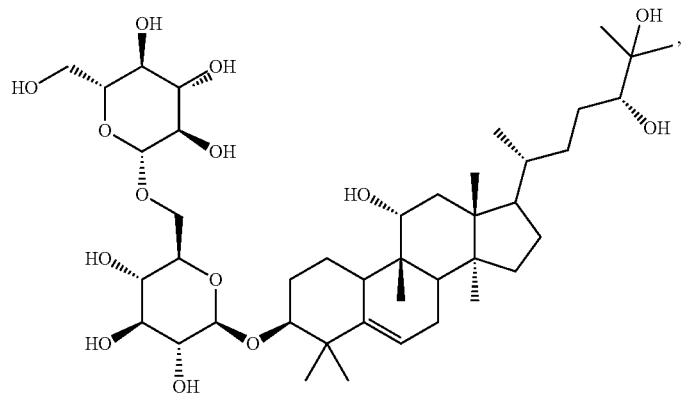
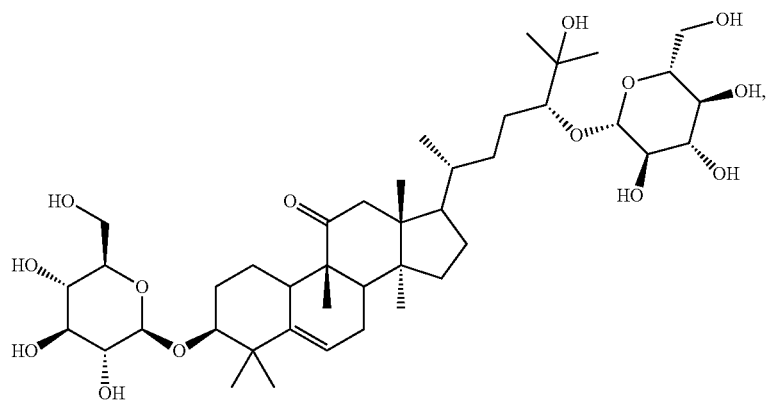
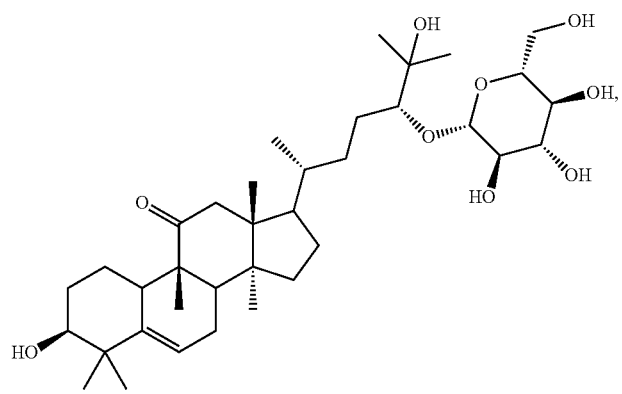
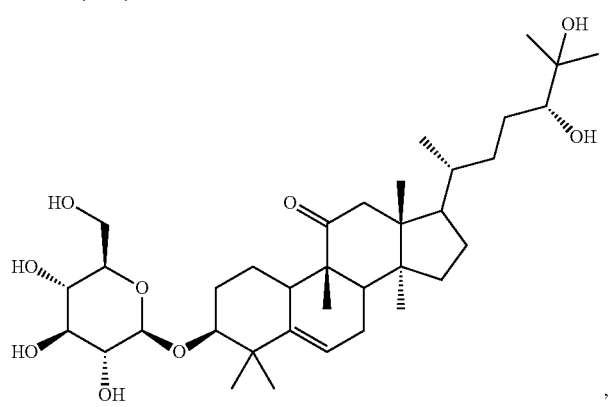

-continued
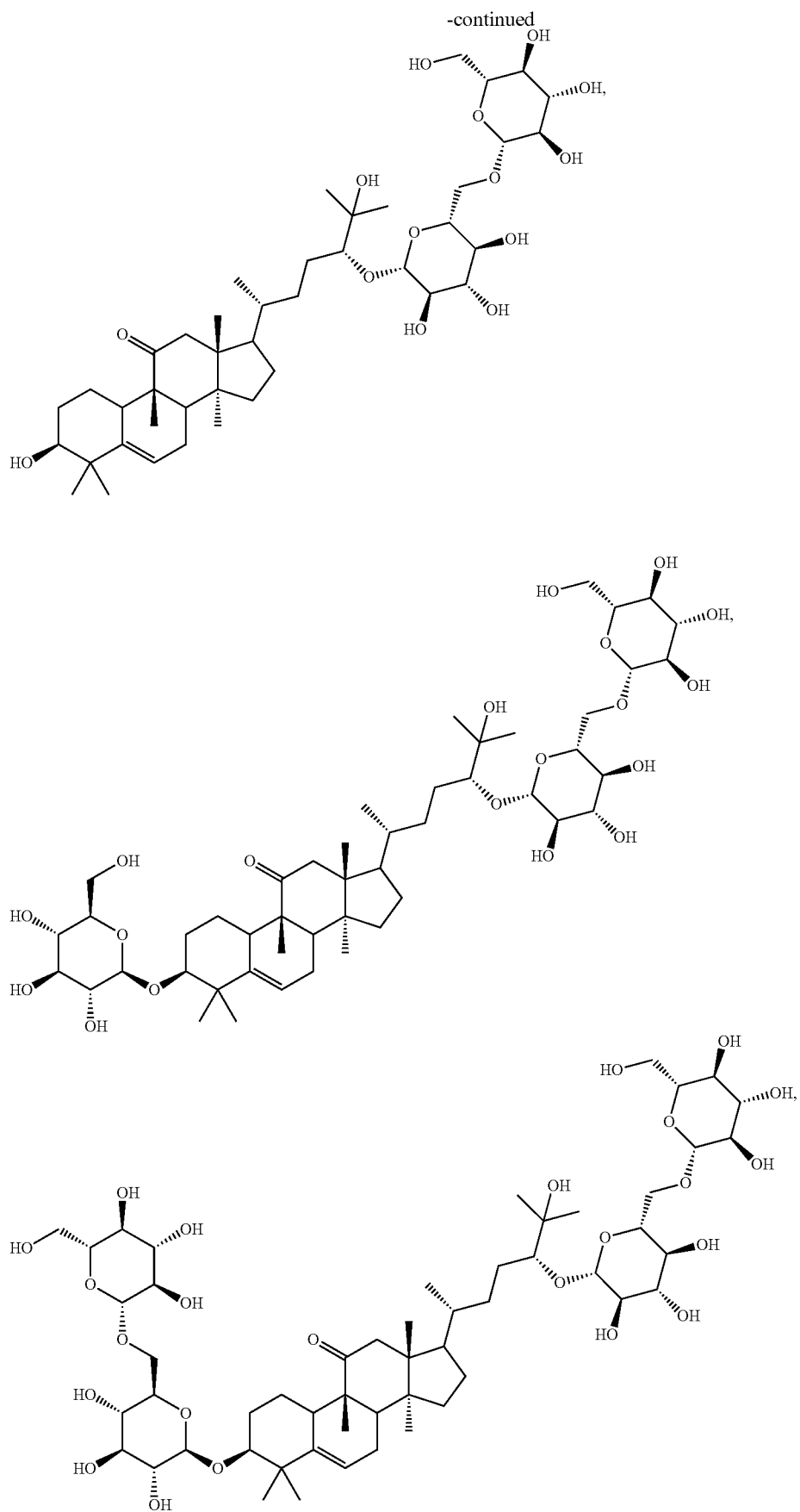

-continued
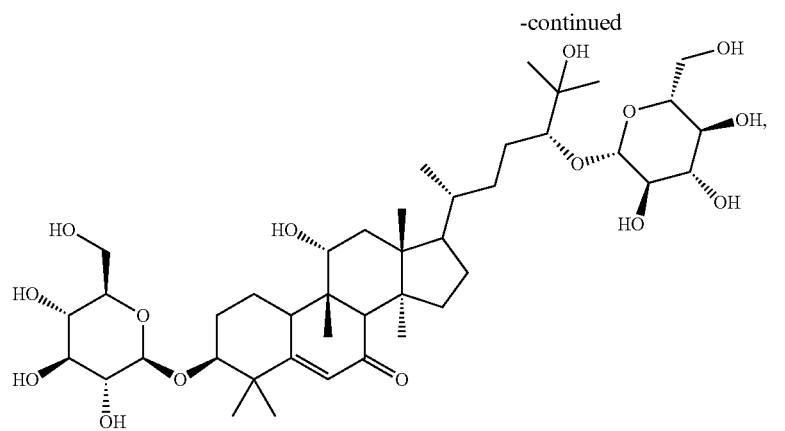
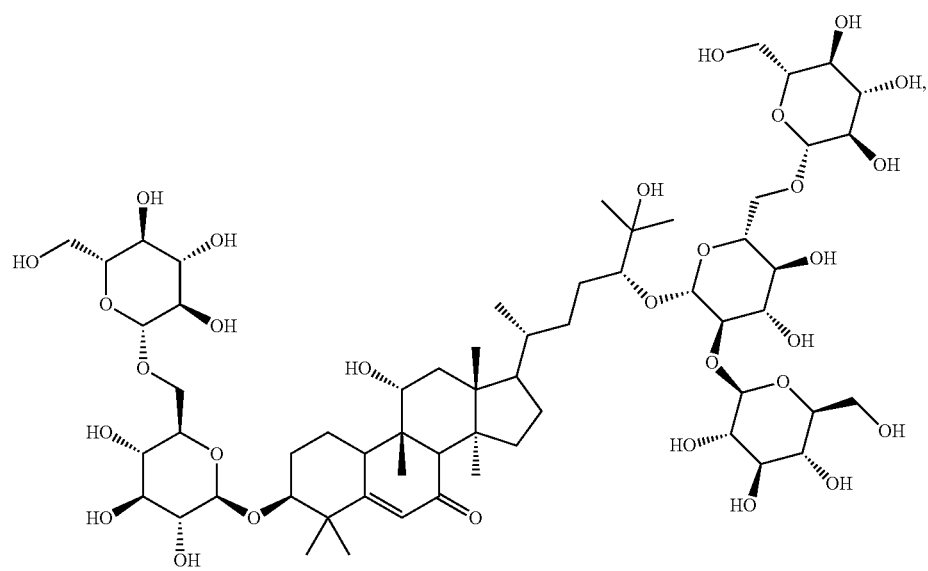
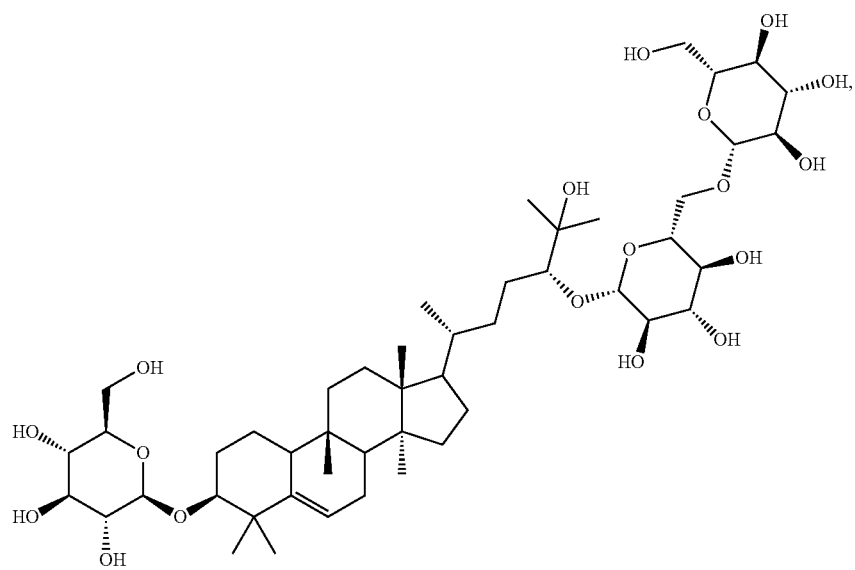

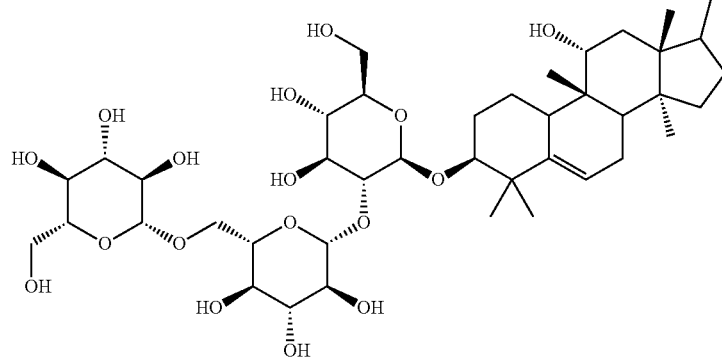
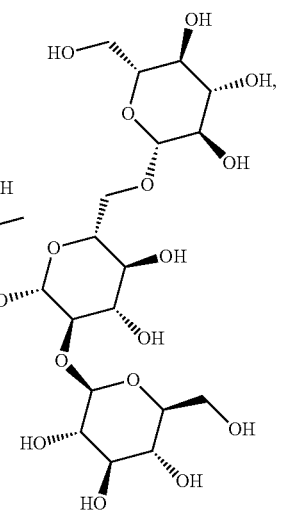
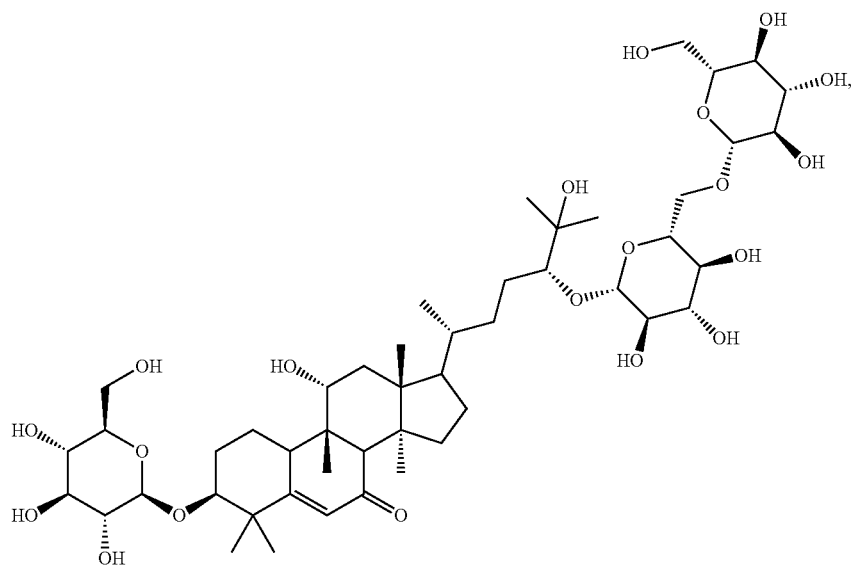

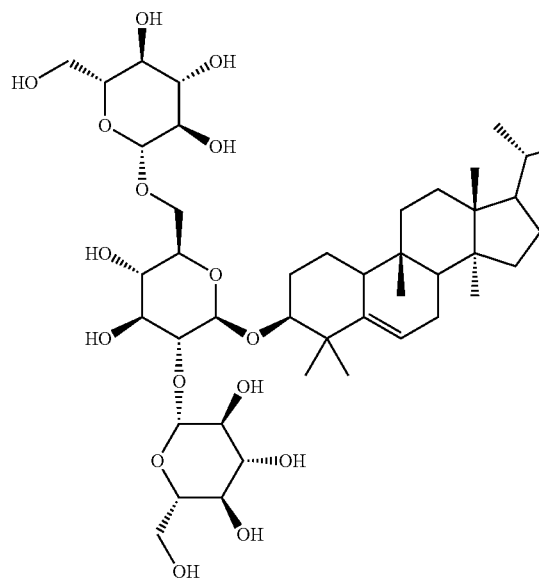
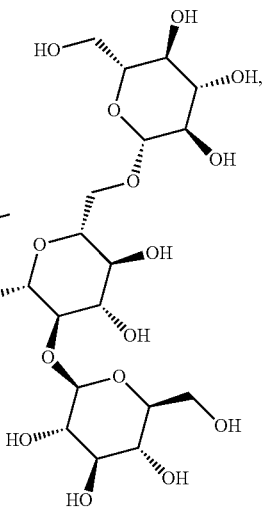
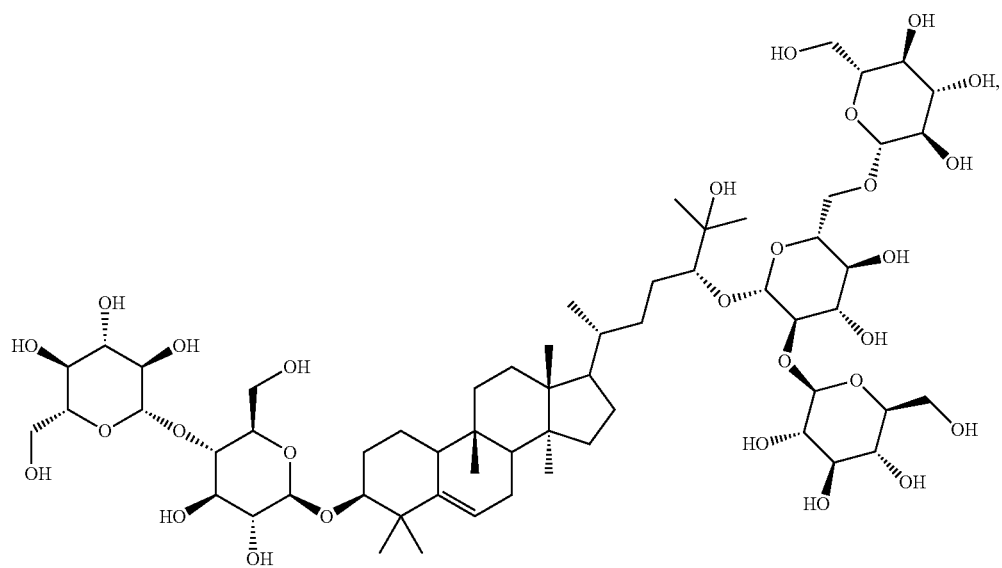

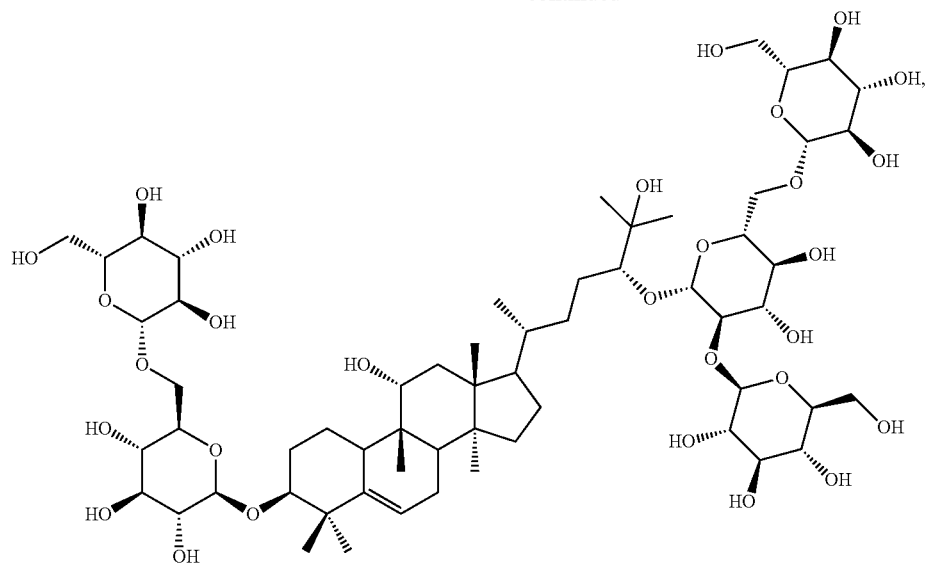
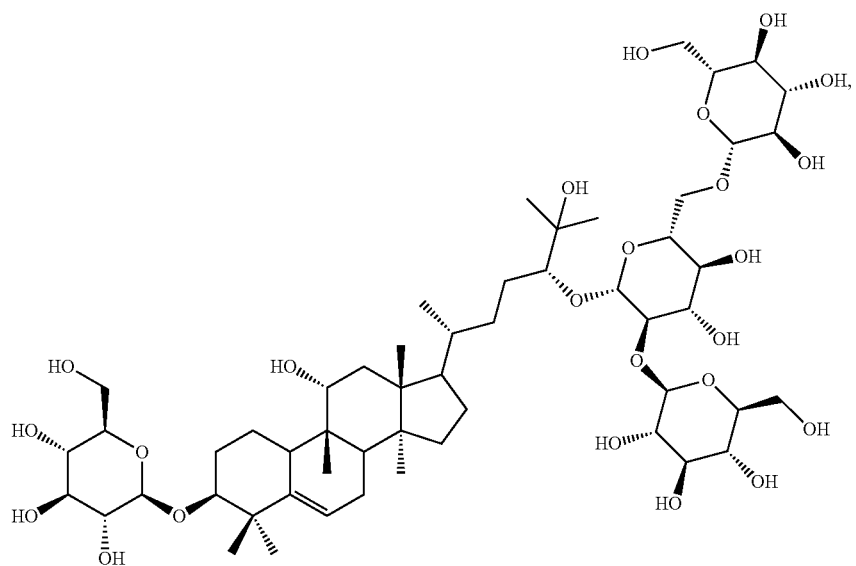
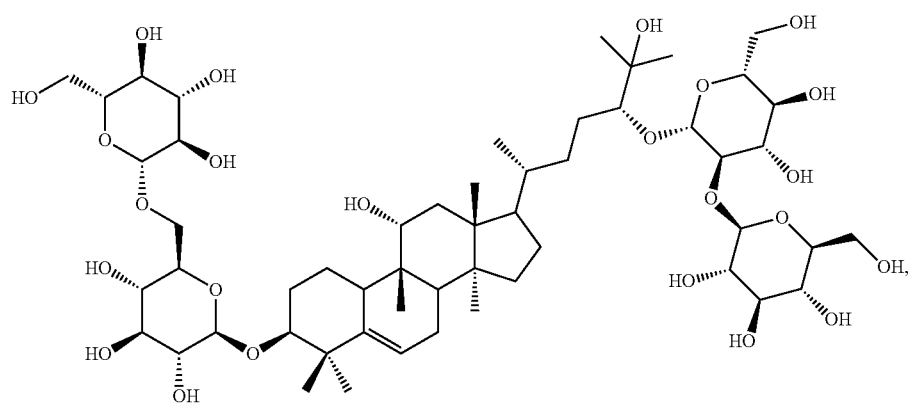

-continued
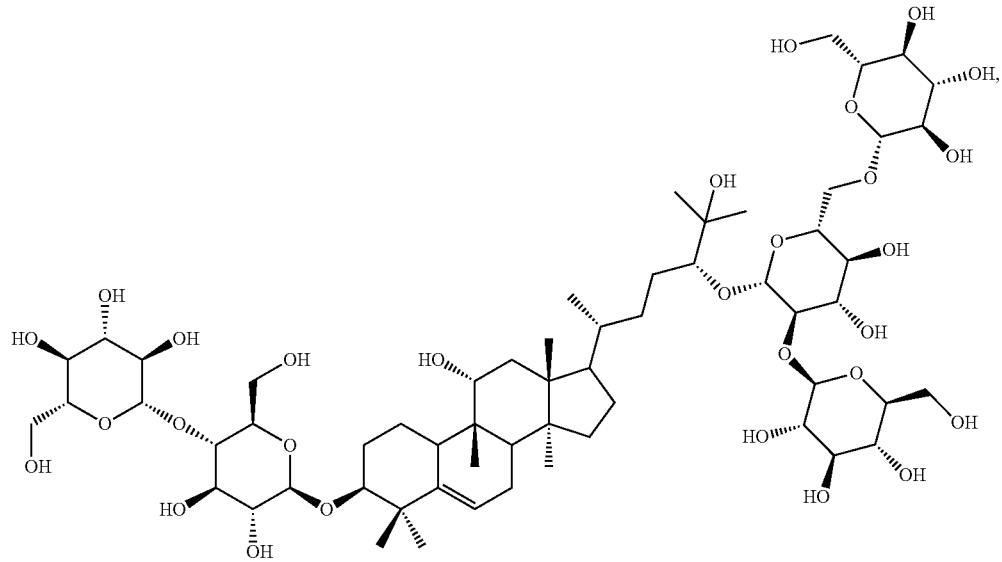
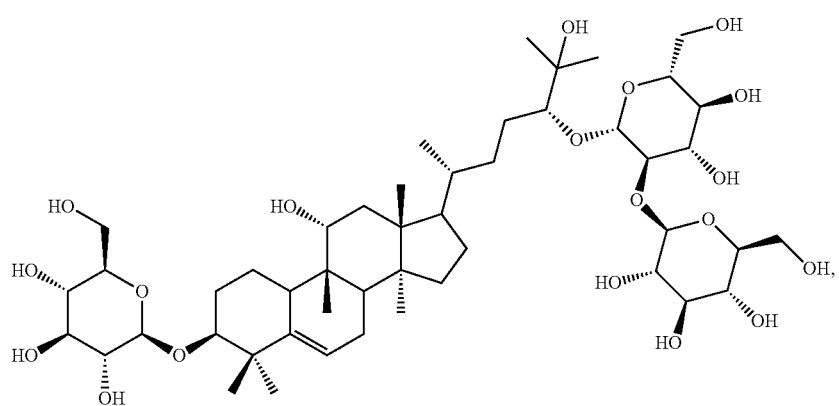
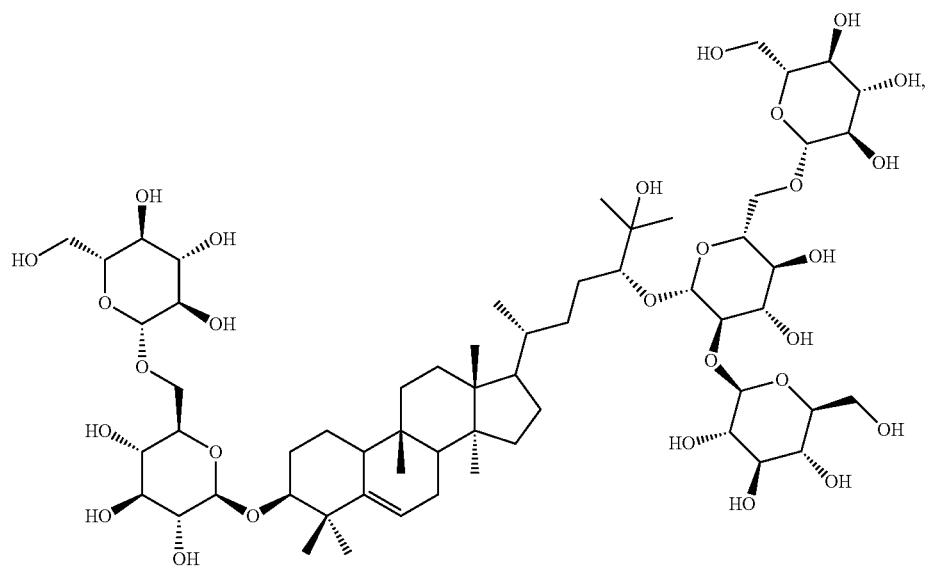

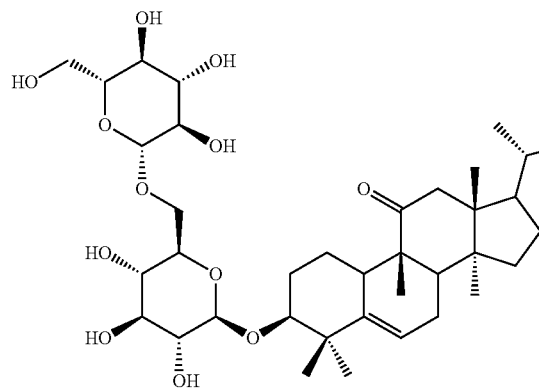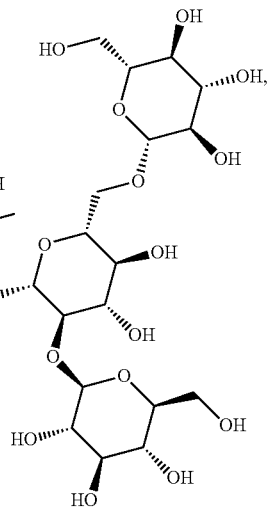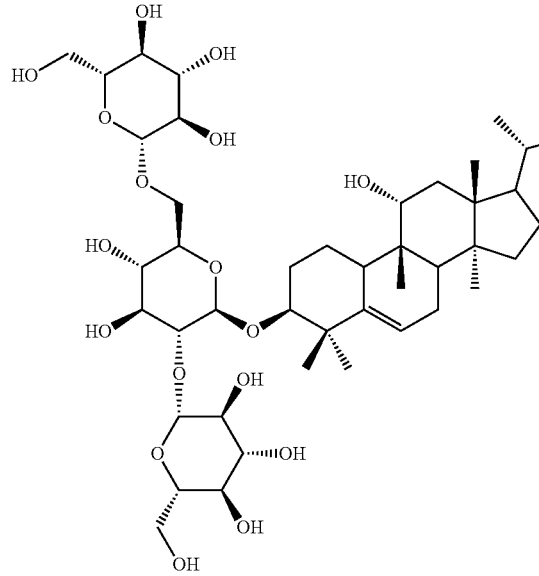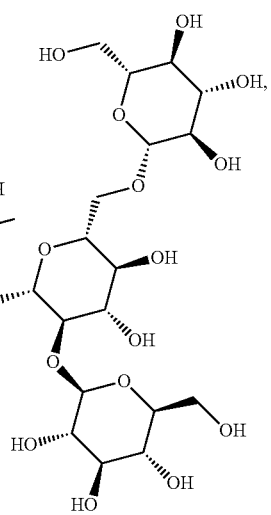

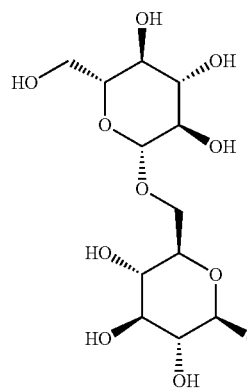
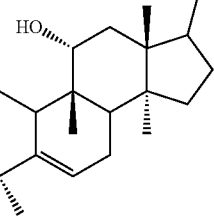
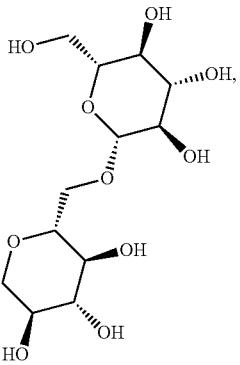
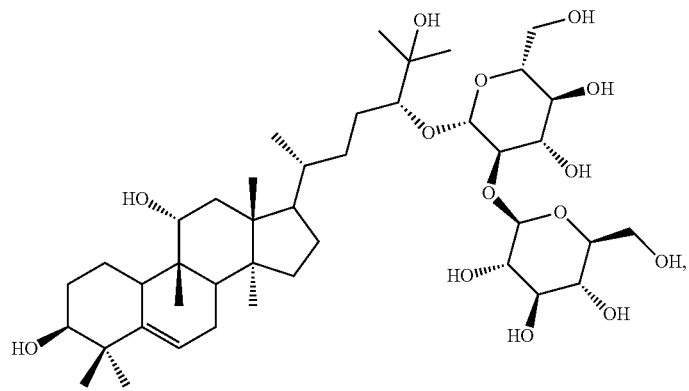
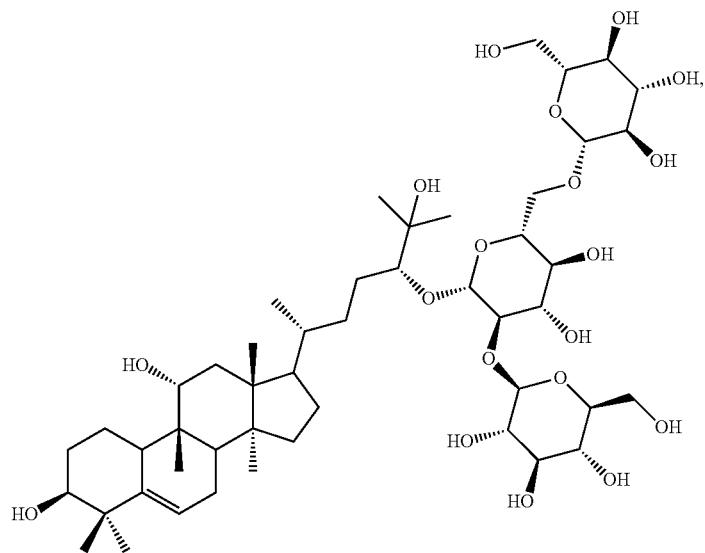

-continued
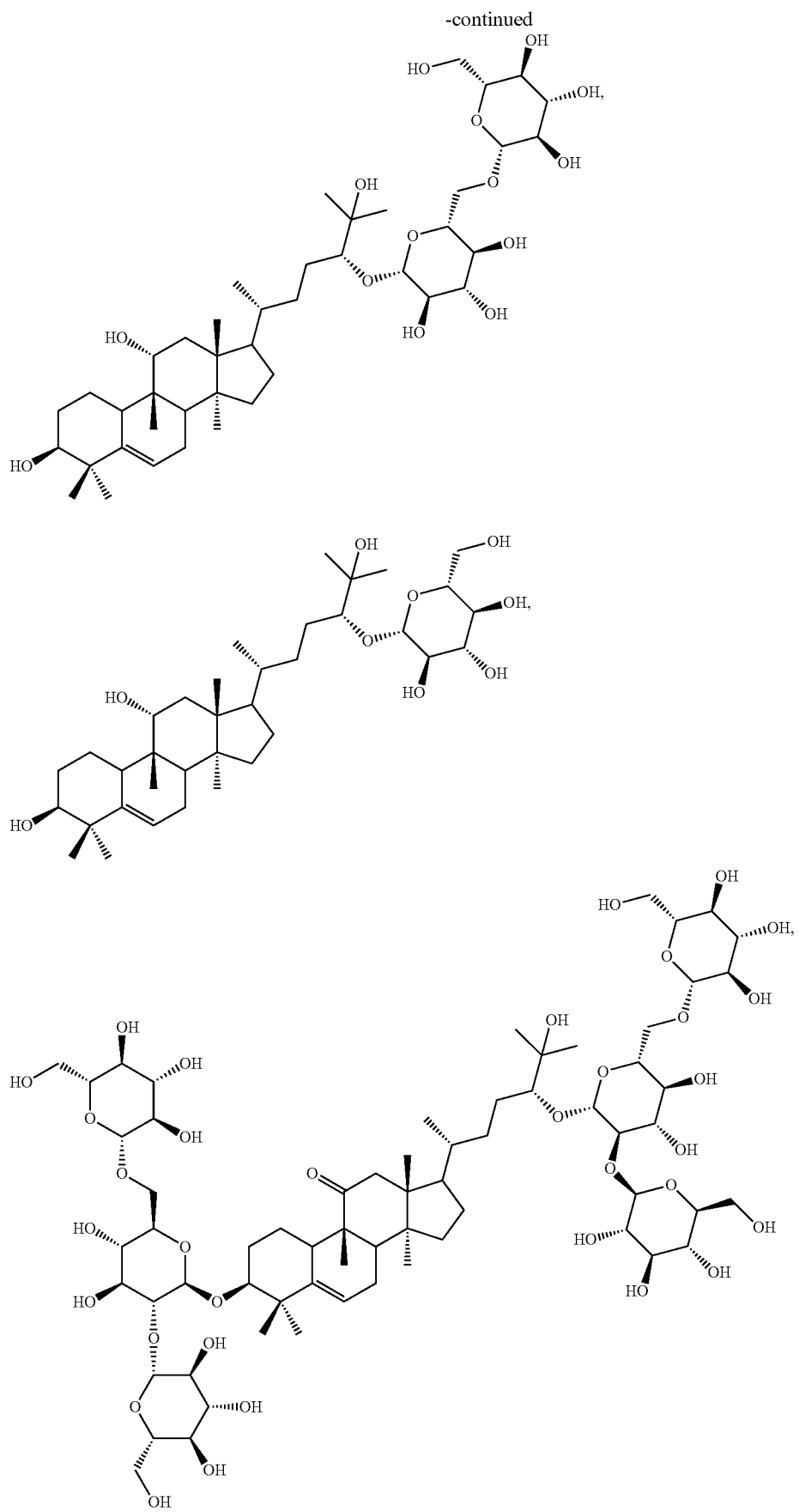

-continued
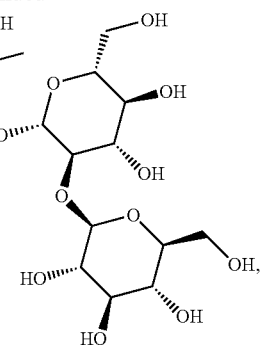
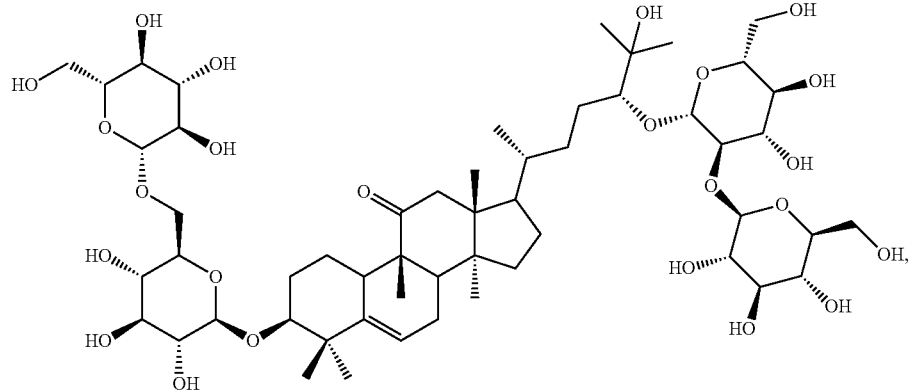
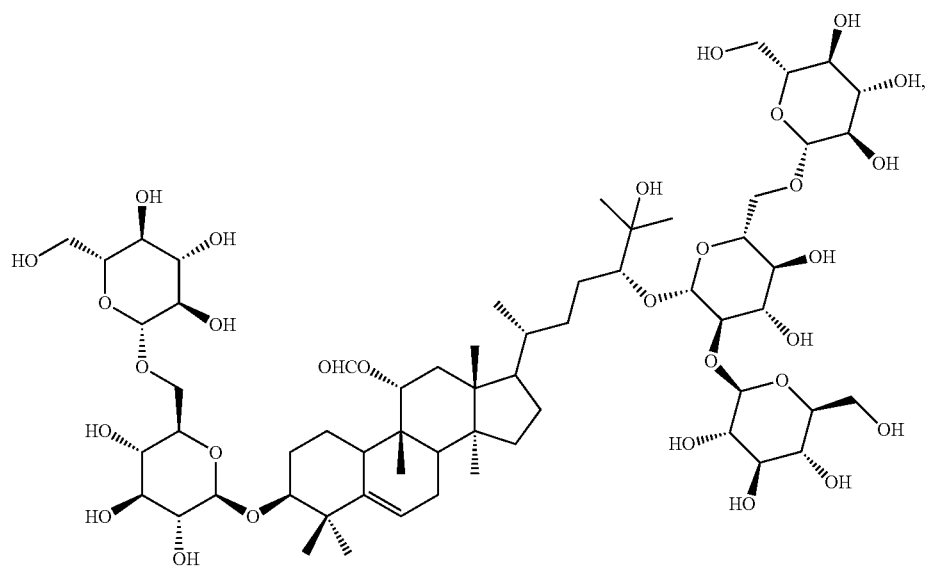

-continued

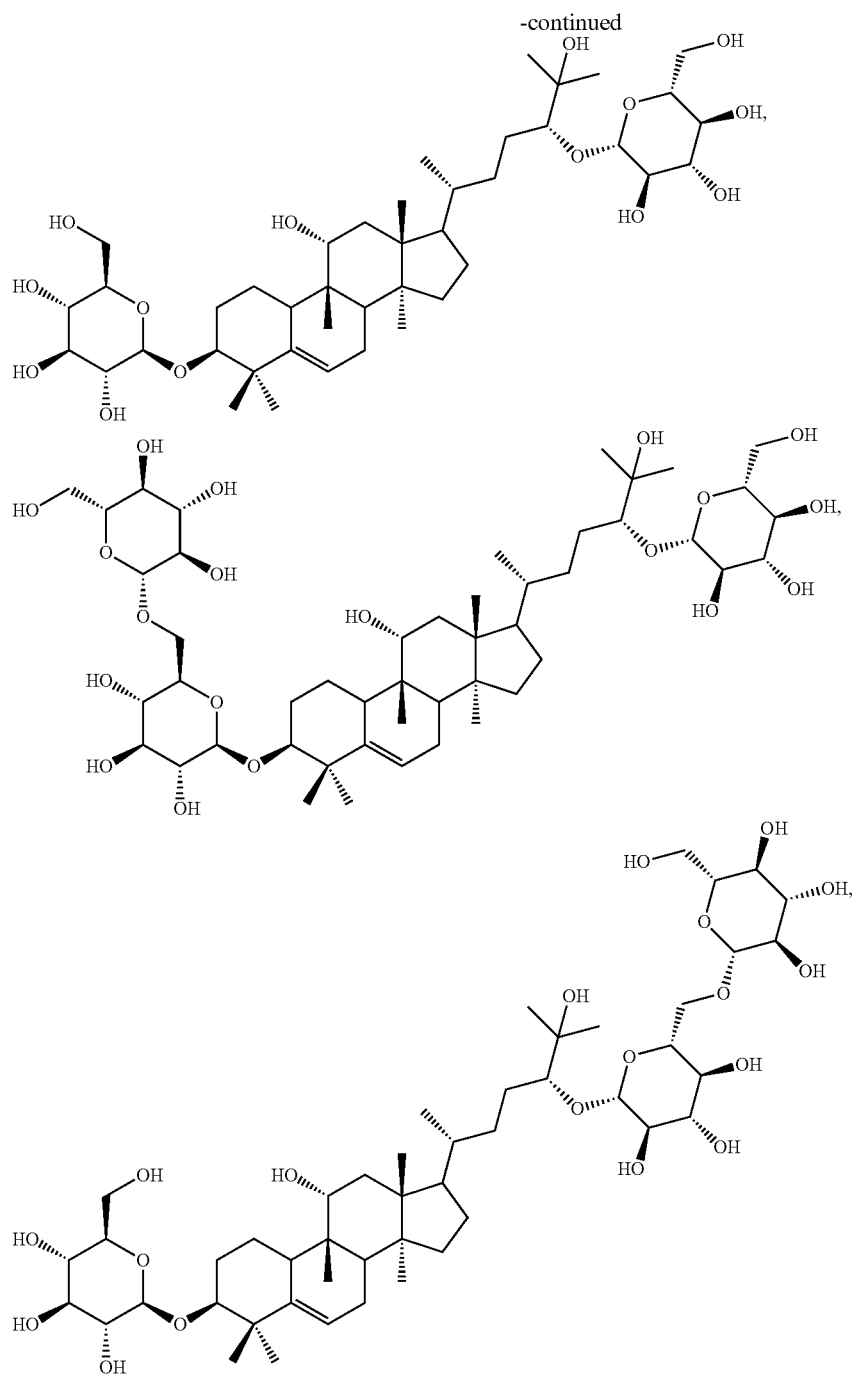

and salts and combinations thereof.

In some embodiments, the composition comprises greater than 70% by weight of one or more compounds of Formula (I). In some embodiments, the composition comprises greater than 80% by weight of one or more compounds of Formula (I). In some embodiments, the composition comprises greater than 90% by weight of one or more compounds of Formula (I).

In some embodiments, the composition is in solid form. In some embodiments, the compound is in crystalline form. In some embodiments, the compound is in amorphous form. In some embodiments, the compound is coating a solid carrier.

In some embodiments, the solid carrier are particles selected from the group consisting of lactose, modified food starch, gum Arabic, maltodextrin, modified corn starch, dextrose, xantham gum, carboxymethylcellulose, cellulose gel, cellulose gum, sodium caseinate, carrageenan, and combinations thereof.

In some embodiments, the composition is in particulate form.

In some embodiments, the composition has an average particle size between 50 μm and 300 μm. In some embodiments, the composition has an average particle size between 80 μm and 200 μm. In some embodiments, the composition has an average particle size between 80 μm and 150 μm.

Some embodiments provide a composition comprising solid particles of the composition a liquid carrier. In some embodiments, the solid particles are suspended in the liquid carrier. In some embodiments, the liquid carrier is selected from water, an alcohol, propylene glycol, triacetine, medium chain triglycerides, glycerin, and combinations thereof. In some embodiments, the liquid carrier is water. In some embodiments, the liquid carrier is an alcohol. In some embodiments, the alcohol is ethanol.

Some embodiments provide a composition comprising a solution of one or more compounds having the structure of formula (I):

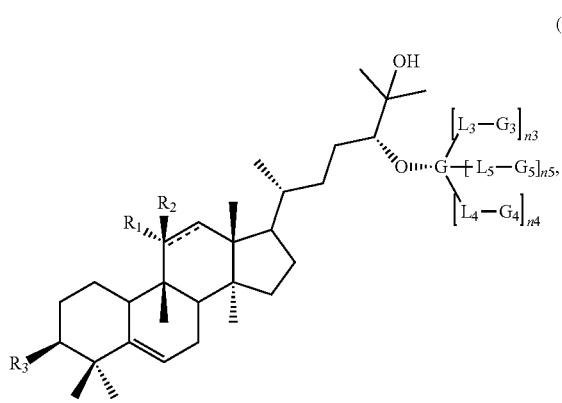

or a salt thereof.

In some embodiments, the concentration of the compound in the solution is greater than 300 ppm. In some embodiments, the concentration of the compound in the solution is greater than 500 ppm. In some embodiments, the concentration of the compound in the solution is greater than 800 ppm. In some embodiments, the concentration of the compound in the solution is greater than 0.1% by weight. In some embodiments, the concentration of the compound in the solution is greater than 0.5% by weight. In some embodiments, the concentration of the compound in the solution is greater than 1% by weight. In some embodiments, the concentration of the compound in the solution is greater than 5% by weight. In some embodiments, the concentration of the compound in the solution is greater than 10% by weight.

In some embodiments, the solution is aqueous. In some embodiments, the solution is an alcohol solution. In some embodiments, the alcohol is ethanol.

In some embodiments, the composition comprises a concentration of Mogroside $III_E$ that is less than 100 ppm. In some embodiments, the composition comprises a concentration of Mogroside $III_E$ that is less than 50 ppm. In some embodiments, the composition comprises a concentration of Mogroside $III_E$ that is less than 20 ppm.

In some embodiments, the composition comprises a concentration of Mogroside $III_E$ that is less than 5 ppm. In some embodiments, the composition comprises a concentration of 11-oxo-Mogroside $III_E$ of less than 30 ppm. In some embodiments, the composition comprises a concentration of 11-oxo-Mogroside $III_E$ of less than 10 ppm. In some embodiments, the composition comprises a concentration of 11-oxo-Mogroside $III_E$ of less than 1 ppm. In some embodiments, the composition comprises a concentration of 11-oxo-Mogroside $III_E$ of less than 0.1 ppm.

In some embodiments, the composition comprises a combined concentration of all isomers of Mogroside I, Mogroside II, and Mogroside III of less than 1% by weight. In some embodiments, the composition comprises a combined concentration of all isomers of Mogroside I, Mogroside II, and Mogroside III of less than 0.5% by weight. In some embodiments, the composition comprises a combined concentration of all isomers of Mogroside I, Mogroside II, and Mogroside III of less than 0.1% by weight.

In some embodiments, the composition comprises a combined concentration of all isomers of Mogroside I, Mogroside II, and Mogroside III of less than 500 ppm. In some embodiments, the composition comprises a combined concentration of all isomers of Mogroside I, Mogroside II, and Mogroside III of less than 100 ppm.

In some embodiments, the composition comprises a combined concentration of Mogroside $III_E$, 11-oxo-Mogroside $III_E$, Mogroside $III_{A2}$, Mogroside $I_E$, and Mogroside $II_E$ of less than 500 ppm. In some embodiments, the composition comprises a combined concentration of Mogroside $III_E$, 11-oxo-Mogroside $III_E$, Mogroside $III_{A2}$, Mogroside $I_E$, and Mogroside $II_E$ of less than 100 ppm.

In some embodiments, the composition comprises a concentration of 11-oxo-mogrol of less than 0.5% by weight. In some embodiments, the composition comprises a concentration of 11-oxo-mogrol of less than 0.1% by weight. In some embodiments, the composition comprises a concentration of 11-oxo-mogrol of less than 100 ppm.

In some embodiments, the composition comprises one or more additional compounds selected from the group consisting of Mogroside V, Siamenoside I, Mogroside $IV_E$, Iso-mogroside V, Mogroside $III_E$, 11-Deoxy-mogroside V, 11-Oxo-mogroside V, Mogroside VI, Mogroside $IV_A$, Mogroside $II_A$, Mogroside $II_{A1}$, Mogroside $II_{A2}$, Mogroside $I_A$, 11-oxo-Mogroside VI, 11-oxo-Mogroside $III_E$, 11-oxo-Mogroside $IV_E$, Mogroside $I_E$, Mogrol, 11-oxo-mogrol, Mogroside $II_E$, Mogroside $III_{A2}$, and Mogroside III.

In some embodiments, the composition comprises one or more additional compound selected from the group consisting of steviosides, rebaudiosides, glycyrrhizic acid, glycyrrhizin, GAMG (glycyrrhetinic acid monoglucuronide), thaumatin, monellin, brazzein, curculin, mabinlin, pentadin, monatin, abrusosides, albiziasaponins, Baiyunoside, bryoside, cussoracosides, cyclocarioside, mukurozioside, osladin, periandrin, phlomisoside, Polypodosides, pterocaryosides, rubusosides, telosmosides, selligueain A, hernandulcin, phlorizin, trilobatin, phylodulcin, dulcoside A, gaudichaudioside A, and combinations thereof.

In some embodiments, the composition has a pH of less than or equal to 7. In some embodiments, the composition has a pH of less than 7. In some embodiments, the composition has a pH greater than or equal to 7. In some embodiments, the composition has a pH of greater than 7. In some embodiments, the composition has a pH between 6 and 10. In some embodiments, the composition has a pH between 6 and 9. In some embodiments, the composition has a pH between 6 and 8. In some embodiments, the composition has a pH between 6 and 7. In some embodiments, the composition has a pH between 1 and 7. In some embodiments, the composition has a pH between 1 and 6. In some embodiments, the composition has a pH between 1 and 5. In some embodiments, the composition has a pH between 1 and 4. In some embodiments, the composition has a pH between 1 and 3. In some embodiments, the composition has a pH of about 2. In some embodiments, the composition has a pH of about 2.5. In some embodiments, the composition has a pH of about 1.5. In some embodiments, the composition has a pH of about 3. In some embodiments, the composition has a pH of about 3.5. In some embodiments, the composition has a pH of about 4. In some embodiments, the composition has a pH of about 4.5. In some embodiments, the composition has a pH of about 5.

Some embodiments provide a composition, comprising a bulking agent and one or more compounds having the structure of formula (I):

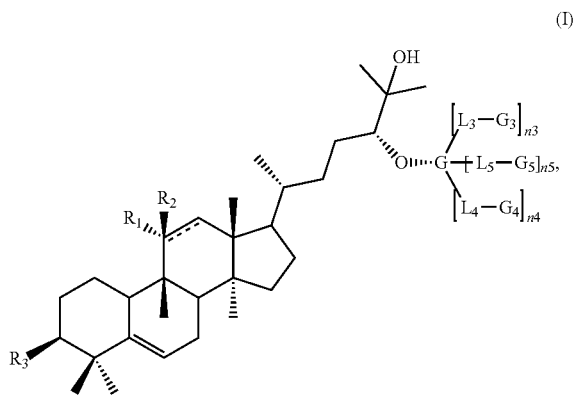

or a salt thereof.

In some embodiments, the composition comprises greater than 0.5% by weight of the compound. In some embodiments, the composition comprises greater than 1% by weight of the compound. In some embodiments, the composition comprises greater than 2% by weight of the compound. In some embodiments, the composition comprises greater than 3% by weight of the compound. In some embodiments, the composition comprises between 0.5% and 5% by weight of the compound. In some embodiments, the composition comprises between 1% and 5% by weight of the compound.

In some embodiments, the composition comprises between greater than 30% by weight of the bulking agent. In some embodiments, the composition comprises between greater than 40% by weight of the bulking agent. In some embodiments, the composition comprises between greater than 50% by weight of the bulking agent. In some embodiments, the composition comprises between greater than 70% by weight of the bulking agent. In some embodiments, the composition comprises between greater than 90% by weight of the bulking agent.

In some embodiments, the composition comprises between 30% and 99.5% by weight of the bulking agent. In some embodiments, the composition comprises between 30% and 95% by weight of the bulking agent. In some embodiments, the composition comprises between 50% and 99.5% by weight of the bulking agent.

In some embodiments, the bulking agent is selected from the group consisting of maltodextrin, dextro-maltodextrin blends, corn syrup solids, sucrose, fructose, glucose, invert sugar, sorbitol, xylose, ribulose, mannose, mannitol, galactitol, lactitol, isomalt, maltose, tagatose, lactose, inulin, glycerol, propylene glycol, polydextrose, fructooligosaccharides, cellulose, cellulose derivatives, erythritol, and combinations thereof.

In some embodiments, the bulking agent is maltodextrin. In some embodiments, the bulking agent is lactose. In some embodiments, the bulking agent is erythritol. In some embodiments, the bulking agent is mannitol.

In some embodiments, the bulking agent is in particulate form and the compound is present as a coating on the particles. In some embodiments, the composition is in particulate form.

In some embodiments, the average particle size is between 200 μm and 2 mm. In some embodiments, the average particle size is between 200 μm and 500 μm. In some embodiments, the average particle size is between 500 μm and 700 μm. In some embodiments, the average particle size is between 800 μm and 1.5 mm.

In some embodiments, the composition is a tabletop sweetener product, comprising a packet containing the composition. In some embodiments, the packet is a single serving packet. In some embodiments, the packet has a width between 0.2 inches and 2 inches. In some embodiments, the packet has a width between 0.5 inches and 1 inch. In some embodiments, the packet has a length between 1 inch and 5 inches. In some embodiments, the packet has a length between 1.5 inches and 3 inches. In some embodiments, the product comprises between 0.5 g and 3 g of the composition. In some embodiments, the product comprises between 0.75 g and 1.5 g of the composition.

Some embodiments provide an ingestible composition, comprising an ingestibly acceptable ingredient and one or more compounds having the structure of formula (I):

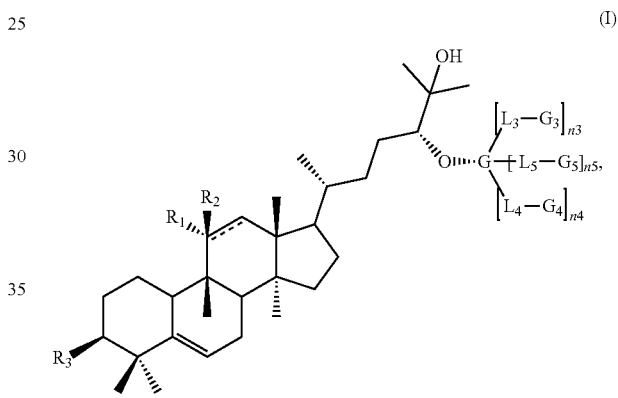

or a salt thereof.

In some embodiments, the concentration of the compound in the composition is greater than 100 ppm. In some embodiments, the concentration of the compound is greater than 300 ppm. In some embodiments, the concentration of the compound is greater than 500 ppm. In some embodiments, the concentration of the compound is greater than 800 ppm.

In some embodiments, the concentration of the compound is between 300 ppm and 2000 ppm. In some embodiments, the concentration of the compound is between 300 ppm and 1500 ppm. In some embodiments, the concentration of the compound is between 800 ppm and 1500 ppm.

In some embodiments, the ingestibly acceptable ingredient comprises vegetable juice, fruit juice, beer, or wine. In some embodiments, the ingestibly acceptable ingredient comprises an acid. In some embodiments, the acid is citric acid or phosphoric acid.

In some embodiments, the ingestibly acceptable ingredient comprises a bitterant.

In some embodiments, the ingestibly acceptable ingredient comprises a coloring agent.

In some embodiments, the ingestibly acceptable ingredient comprises a preservative.

In some embodiments, the ingestibly acceptable ingredient comprises a functional ingredient.

In some embodiments, the ingestibly acceptable ingredient comprises a buffer.

In some embodiments, the ingestibly acceptable ingredient comprises a natural flavor. In some embodiments, the ingestibly acceptable ingredient comprises an artificial flavor.

In some embodiments, the ingestibly acceptable ingredient comprises a food additive.

In some embodiments, the ingestibly acceptable ingredient comprises a sour flavorant.

In some embodiments, the ingestibly acceptable ingredient comprises one or more fats, oils, or emulsions.

In some embodiments, the ingestibly acceptable ingredient comprises a flour or a vegetable powder.

In some embodiments, the composition is a food or beverage product. In some embodiments, the food or beverage product is selected from colas, lemon-lime flavored sparkling beverages, orange flavored sparkling beverages, grape flavored sparkling beverages, strawberry flavored sparkling beverages, pineapple flavored sparkling beverages, ginger-ales, root beers, fruit juices, fruit-flavored juices, juice drinks, nectars, vegetable juices, vegetable-flavored juices, sports drinks, energy drinks, enhanced water drinks, enhanced water with vitamins, near water drinks, coconut waters, tea type drinks, coffees, cocoa drinks, beverages containing milk components, beverages containing cereal extracts and smoothies. In some embodiments, the food or beverage product is a soft drink.

In some embodiments, the composition has a pH of less than or equal to 7. In some embodiments, the composition has a pH of less than 7. In some embodiments, the composition has a pH greater than or equal to 7. In some embodiments, the composition has a pH of greater than 7. In some embodiments, the composition has a pH between 6 and 10. In some embodiments, the composition has a pH between 6 and 9. In some embodiments, the composition has a pH between 6 and 8. In some embodiments, the composition has a pH between 6 and 7. In some embodiments, the composition has a pH between 1 and 7. In some embodiments, the composition has a pH between 1 and 6. In some embodiments, the composition has a pH between 1 and 5. In some embodiments, the composition has a pH between 1 and 4. In some embodiments, the composition has a pH between 1 and 3. In some embodiments, the composition has a pH of about 2. In some embodiments, the composition has a pH of about 2.5. In some embodiments, the composition has a pH of about 1.5. In some embodiments, the composition has a pH of about 3. In some embodiments, the composition has a pH of about 3.5. In some embodiments, the composition has a pH of about 4. In some embodiments, the composition has a pH of about 4.5. In some embodiments, the composition has a pH of about 5.

Some embodiments provide a method of increasing the sweetness of an ingestible composition, comprising combining the ingestible composition with at least one compound of formula (I):

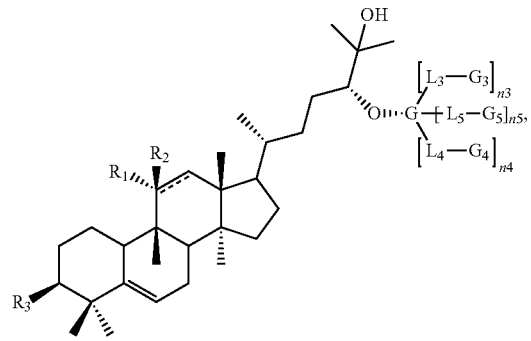

or a salt thereof.

Some embodiments provide a method of increasing the sweetness of a food or beverage product, comprising adding the composition to a food or beverage product, thereby increasing the sweetness of the food or beverage product.

Some embodiments provide a method of preparing a food or beverage product, comprising combining the composition with one or more ingestibly acceptable ingredients.

Some embodiments provide a method of preparing a food or beverage product, comprising combining a first plurality of ingestibly acceptable ingredients to form an intermediate mixture; and dispensing a dose of the composition into the intermediate mixture.

In some embodiments, the method further comprises, after dispensing the dose of the composition, adding one or more additional ingestibly acceptable ingredients.

In some embodiments, the method further comprises, mixing the ingestibly acceptable ingredients and the composition.

Some embodiments provide a flavoring concentrate, comprising a flavoring agent and a compound having the structure of formula (I):

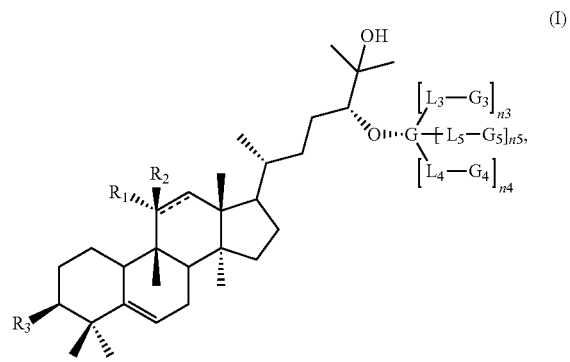

or a salt thereof.

In some embodiments, the flavoring agent is an artificial flavoring ingredient. In some embodiments, the flavoring agent is a natural flavoring ingredient.

In some embodiments, the compound is at a concentration greater than 0.1% by weight. In some embodiments, the compound is at a concentration greater than 0.5% by weight. In some embodiments, the compound is at a concentration greater than 1% by weight.

In some embodiments, the concentrate is a liquid. In some embodiments, the concentrate is a solution. In some embodiments, the concentrate is a solid.

In some embodiments, the compound is present in a concentration that is at least 2 times a concentration of the compound in a ready-to-use food or beverage product.

Some embodiments provide a method of preparing a food or beverage product, comprising combining the concentrate with a diluent. In some embodiments, the diluent is water. In some embodiments, the diluent is carbonated water. In some embodiments, the diluent is nitrogen infused water. In some embodiments, the diluent is aqueous ethyl alcohol.

In some embodiments, the food or beverage product is selected from colas, lemon-lime flavored sparkling beverages, orange flavored sparkling beverages, grape flavored sparkling beverages, strawberry flavored sparkling beverages, pineapple flavored sparkling beverages, ginger-ales, root beers, fruit juices, fruit-flavored juices, juice drinks, nectars, vegetable juices, vegetable-flavored juices, sports drinks, energy drinks, enhanced water drinks, enhanced water with vitamins, near water drinks, coconut waters, tea type drinks, coffees, cocoa drinks, beverages containing milk components, beverages containing cereal extracts and smoothies.

In some embodiments of the compounds, compositions, products, methods, or concentrates described above, formula (I) is not selected from:

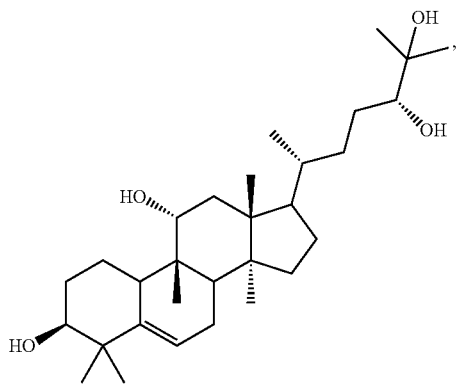

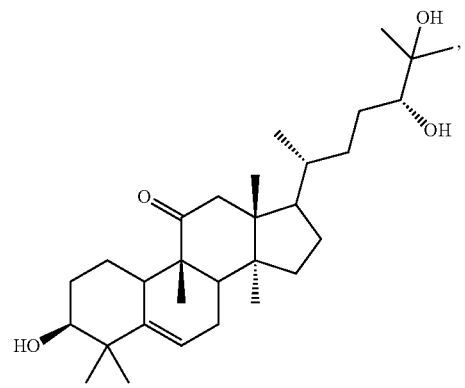

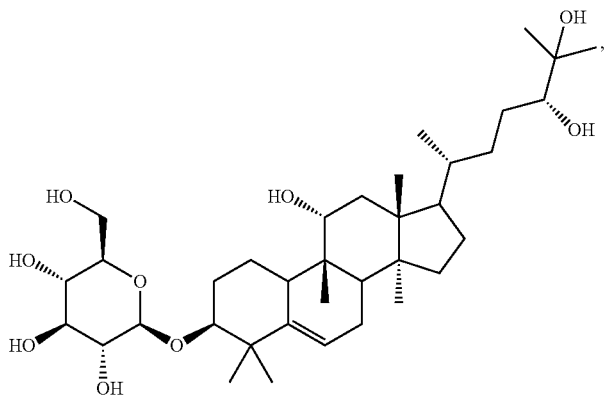

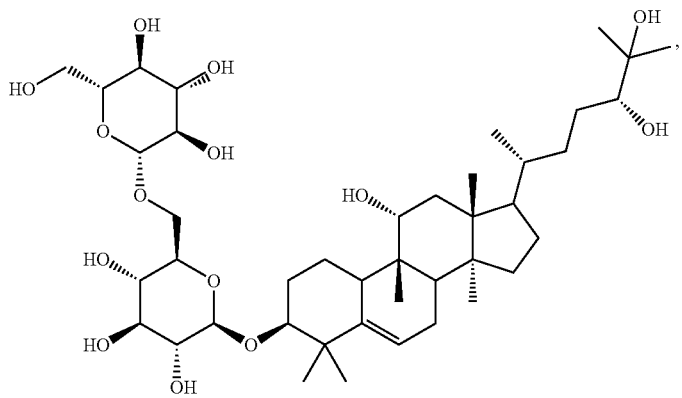

-continued
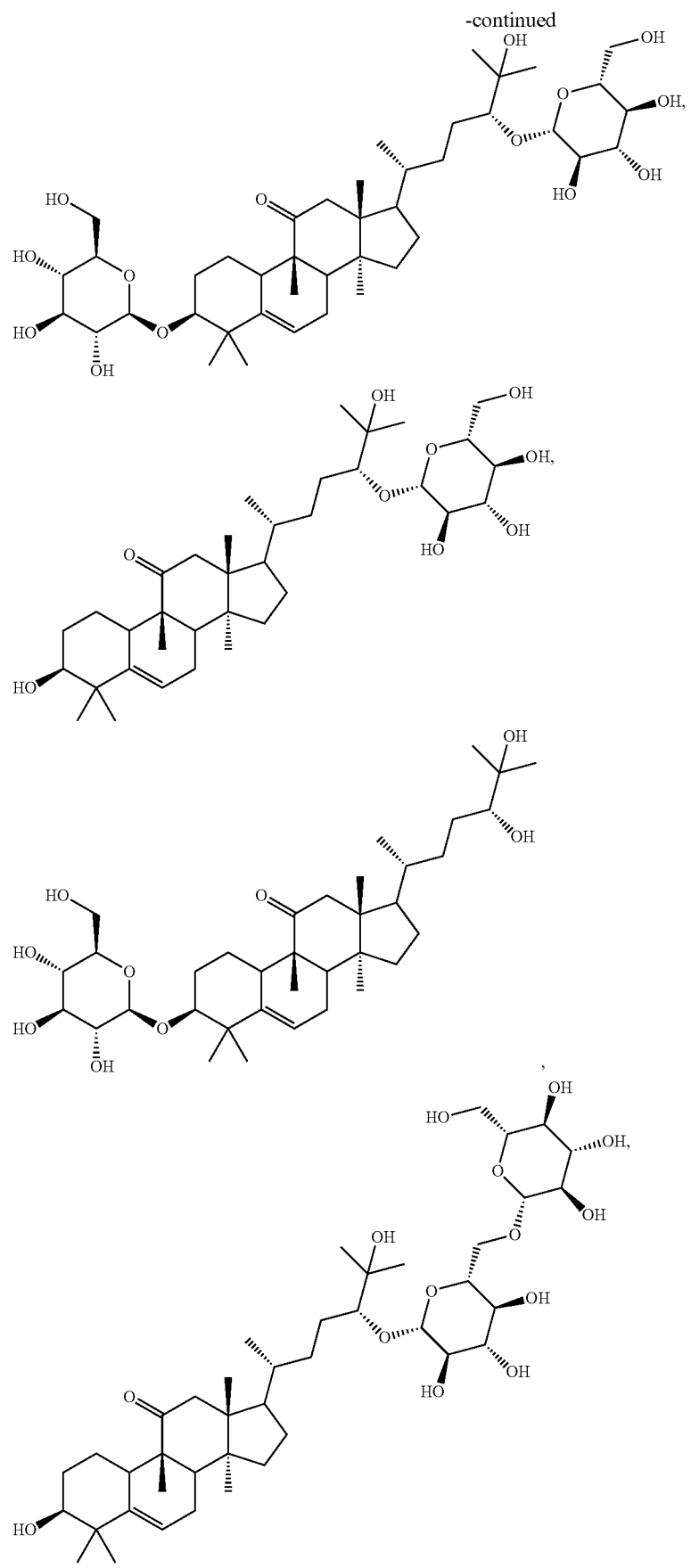

-continued
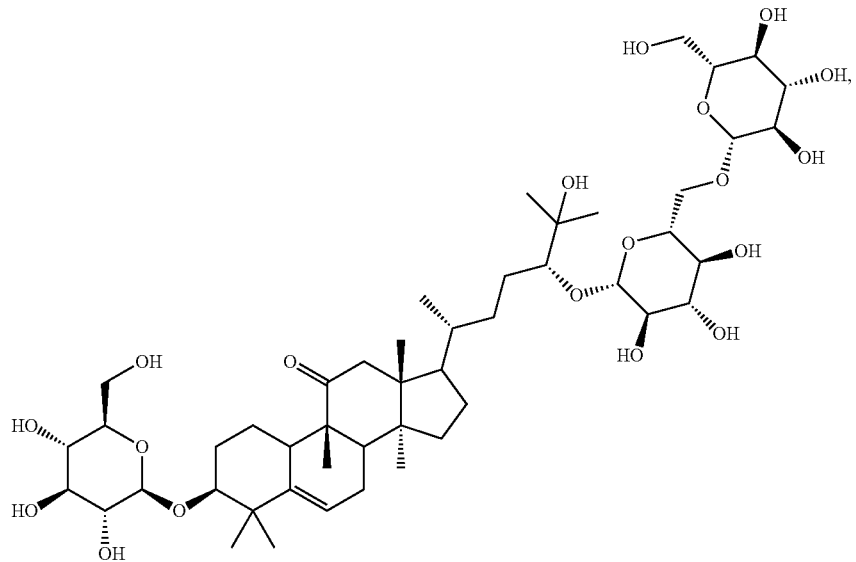
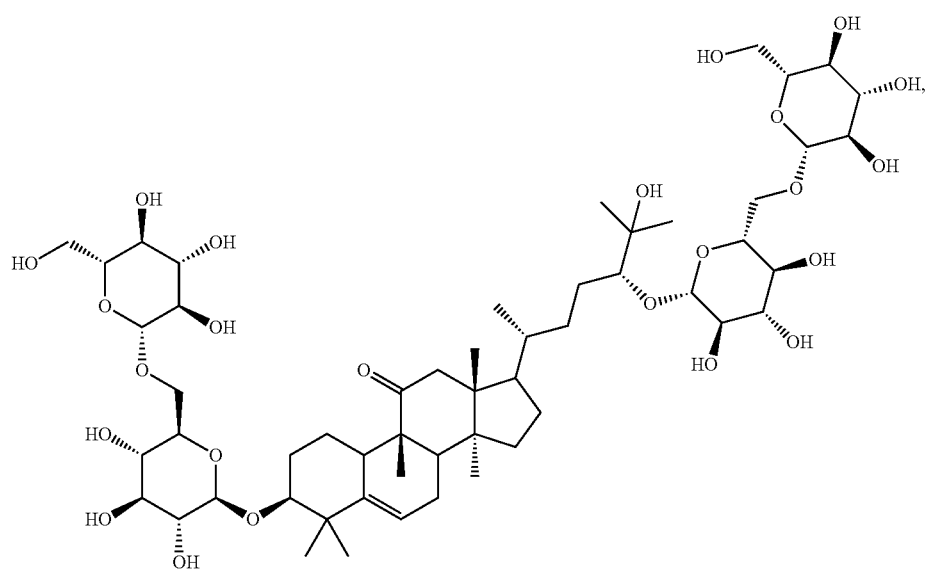
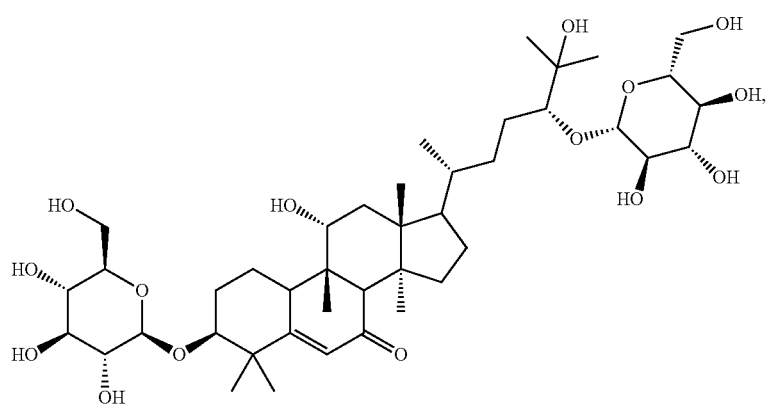

-continued
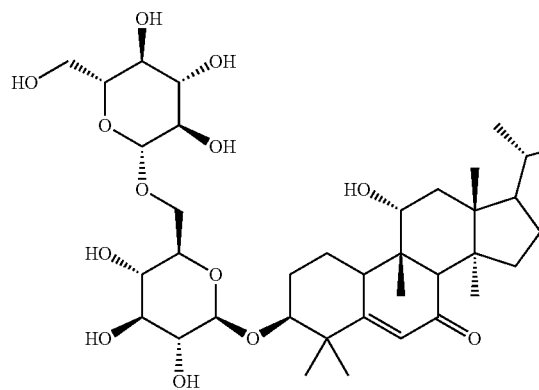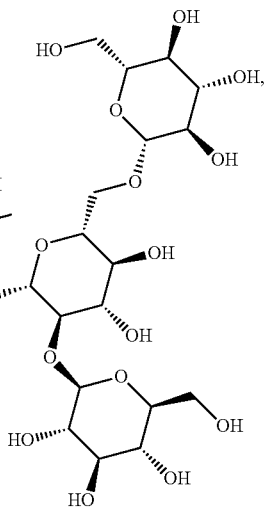
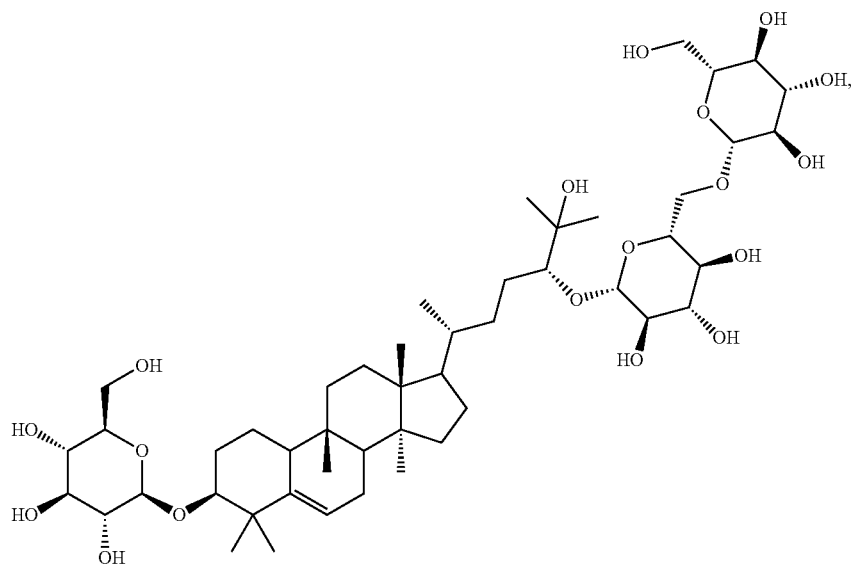

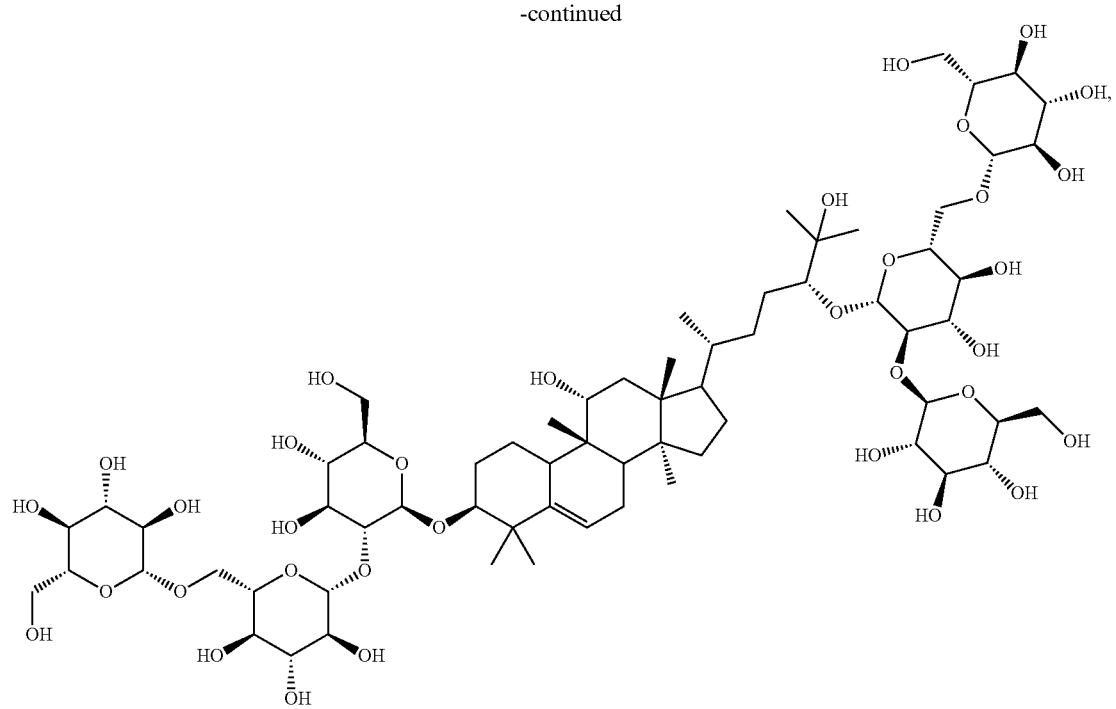
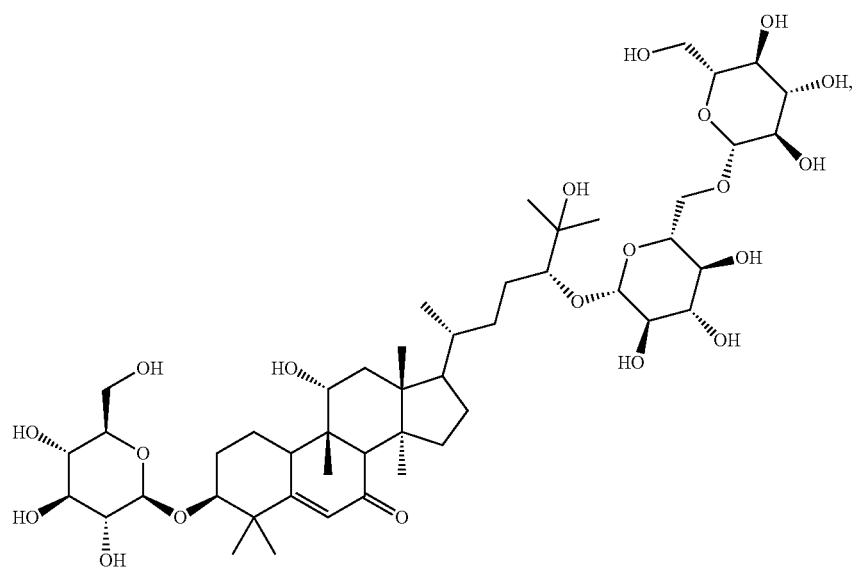

-continued
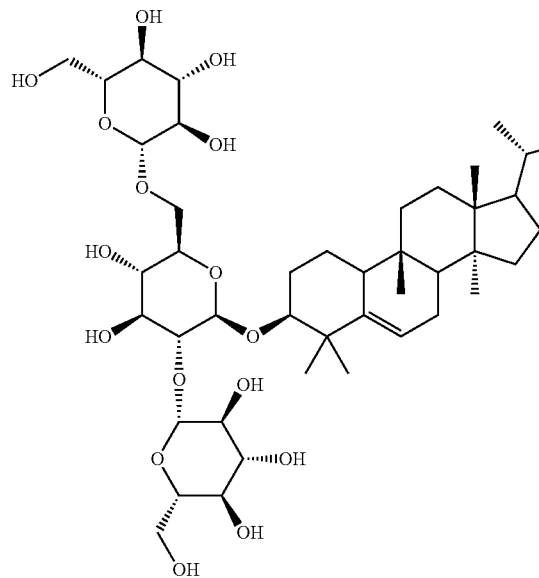
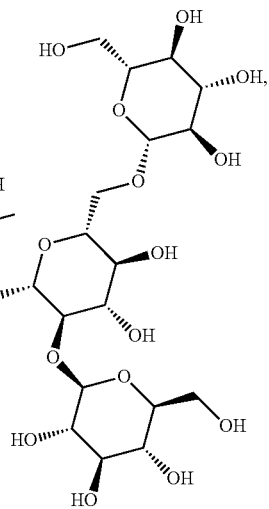
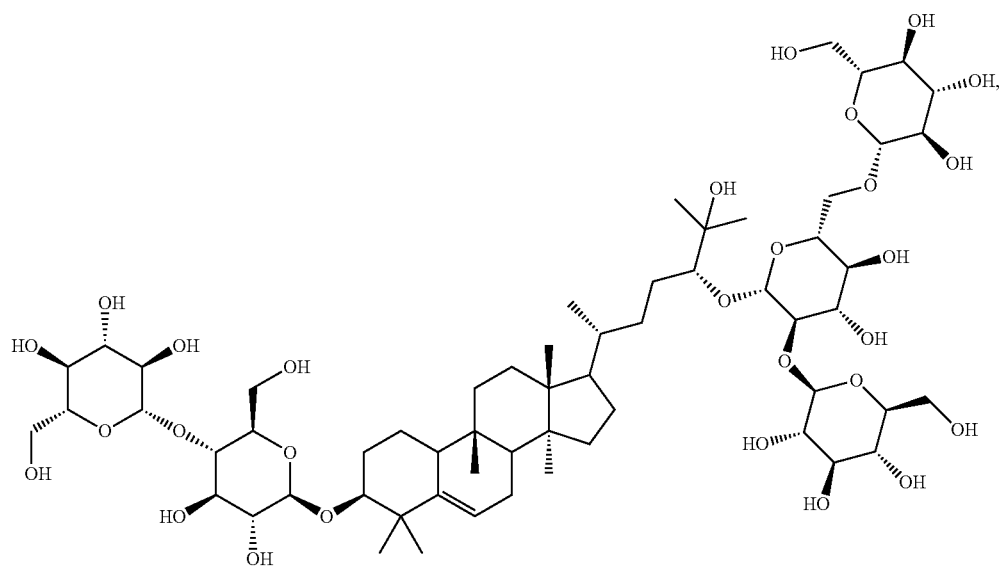

-continued
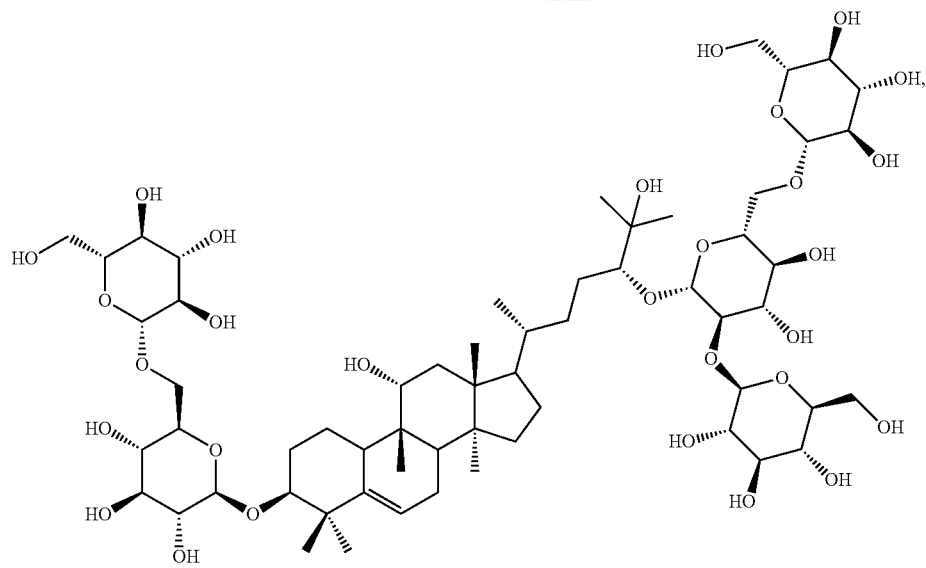
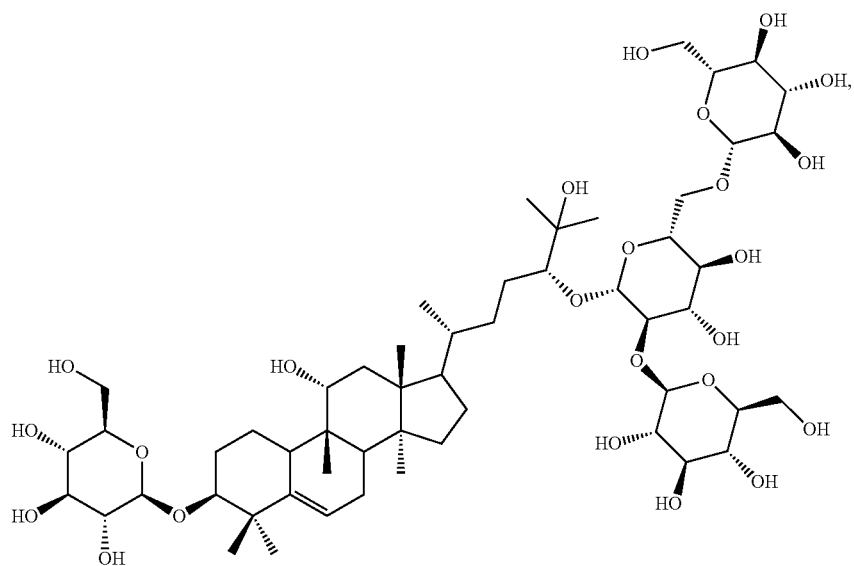
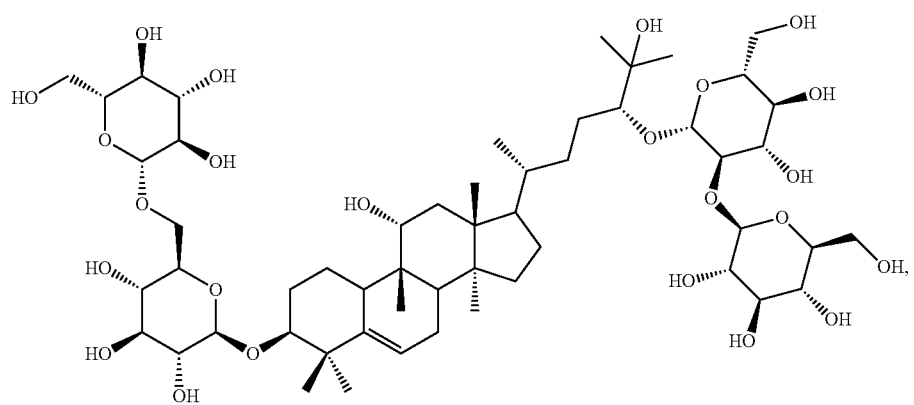

-continued
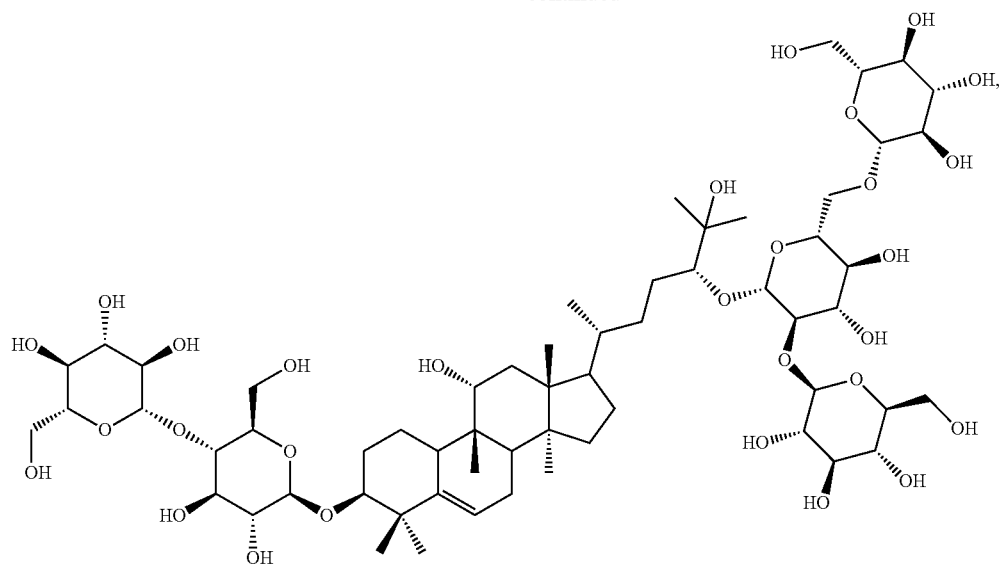
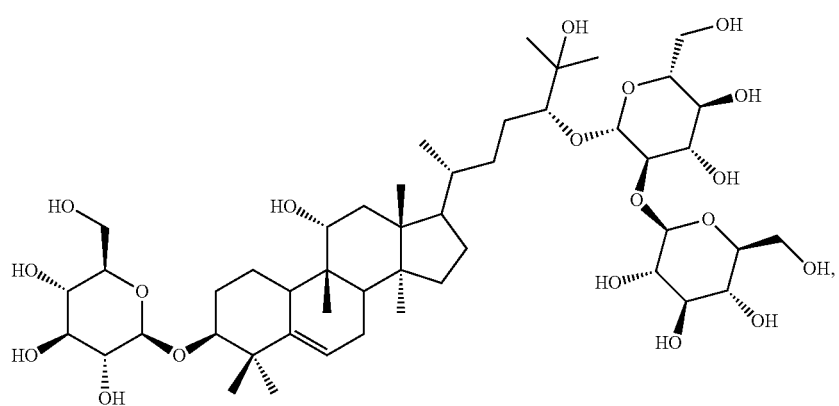
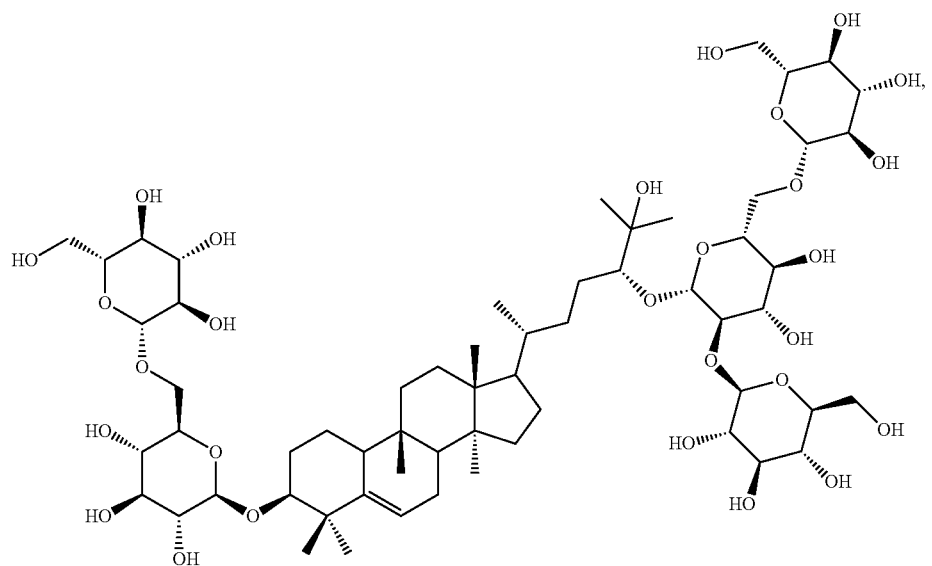

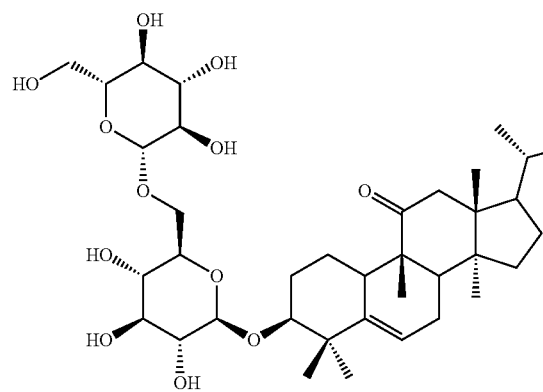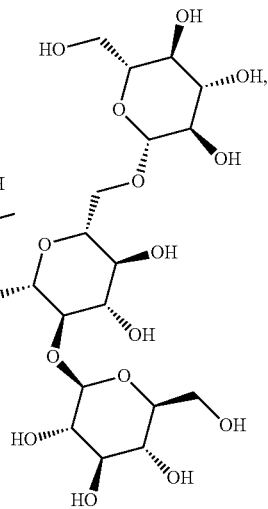
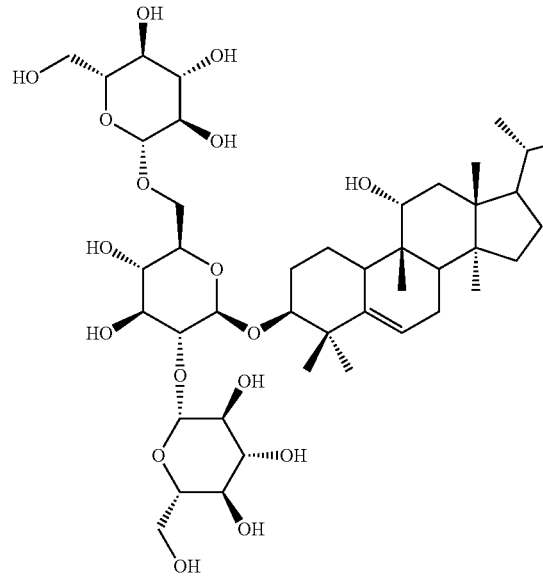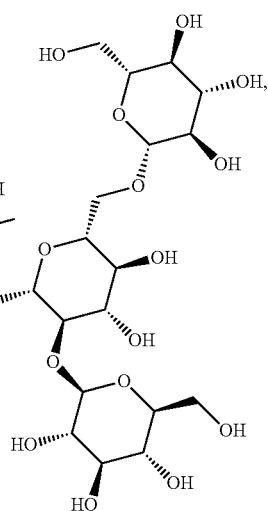

-continued
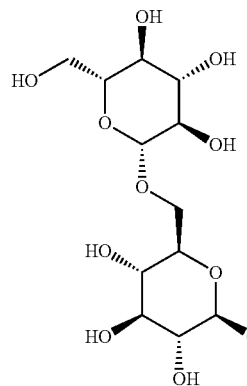
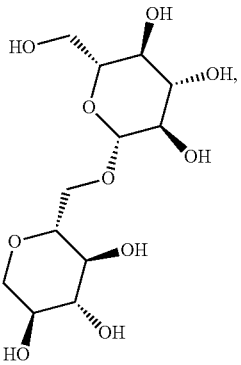
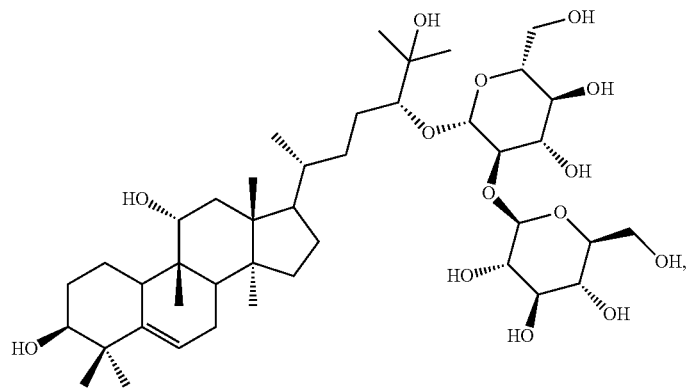
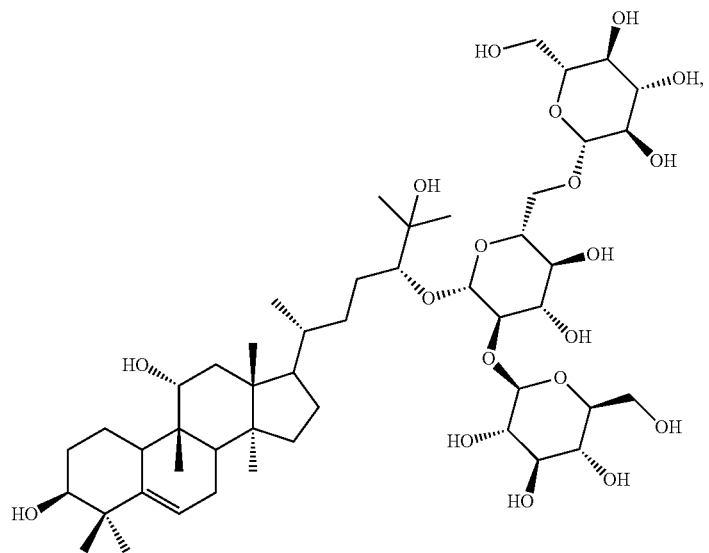

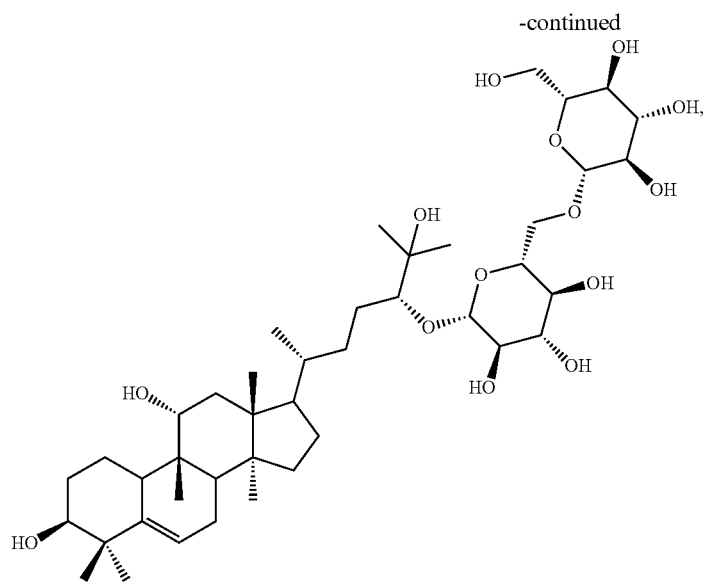
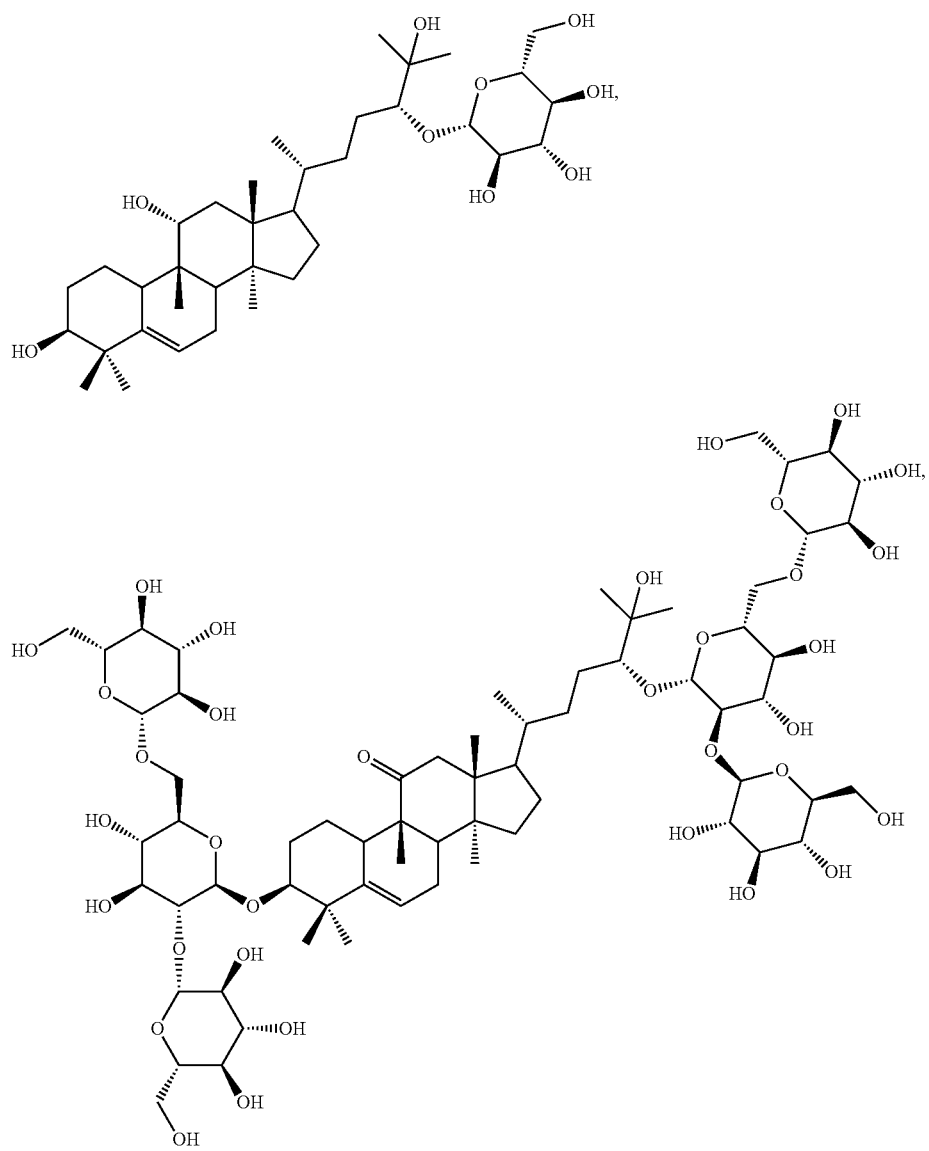

-continued
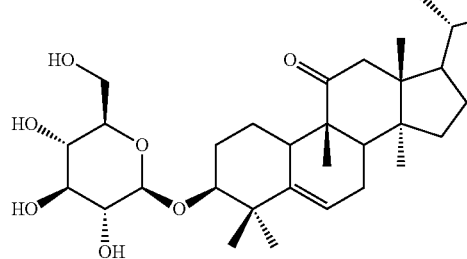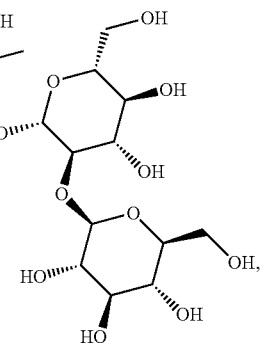
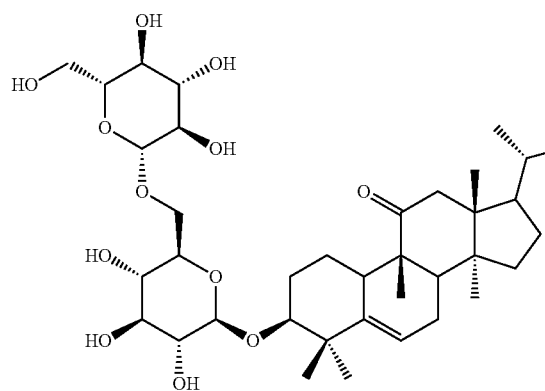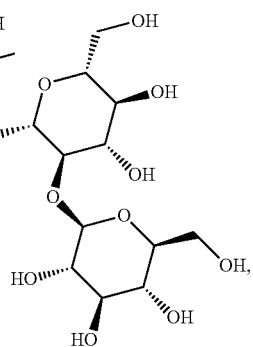
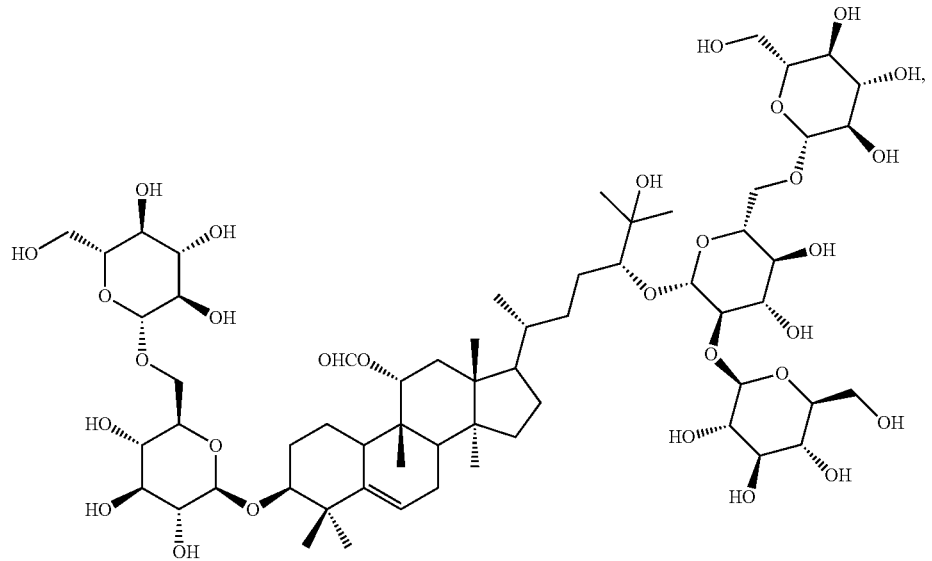

-continued
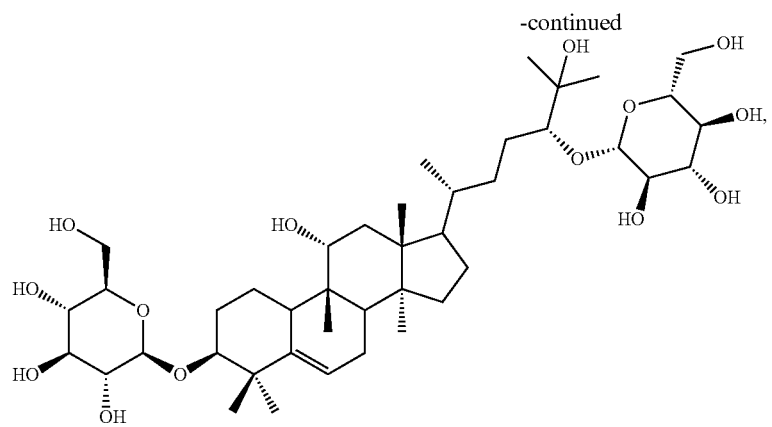
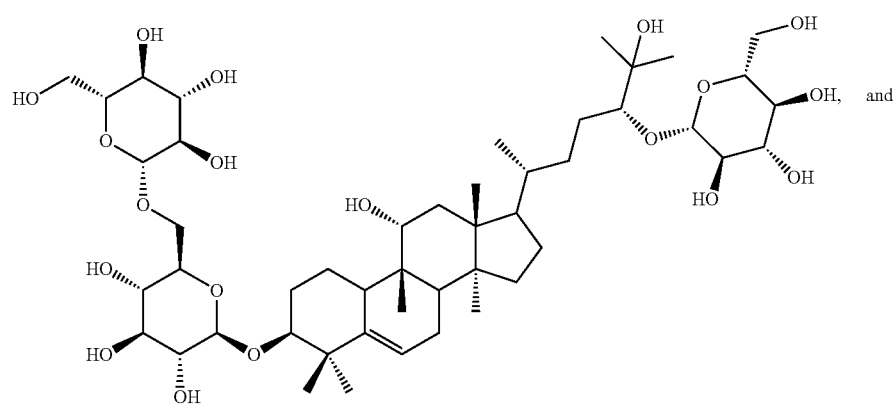
and
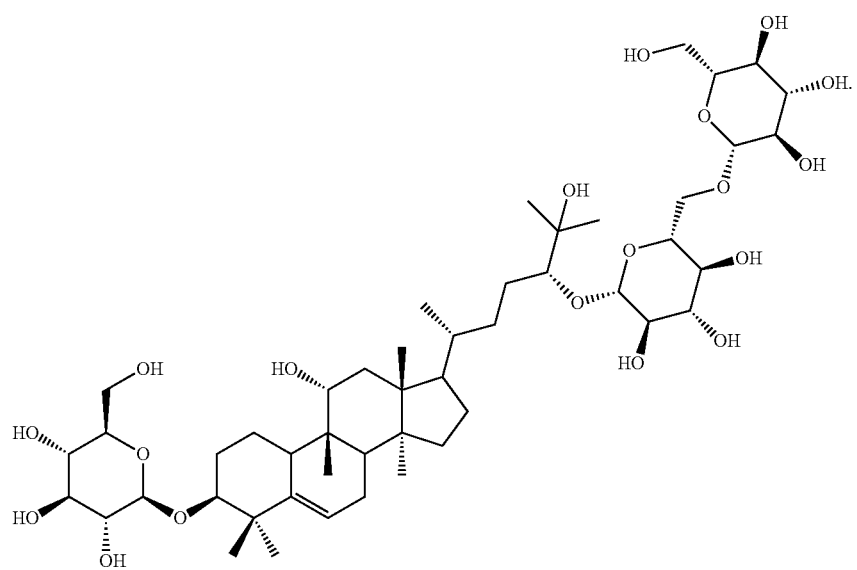

In some embodiments of the compounds, compositions, products, methods, or concentrates described above, formula (I) is not selected from:
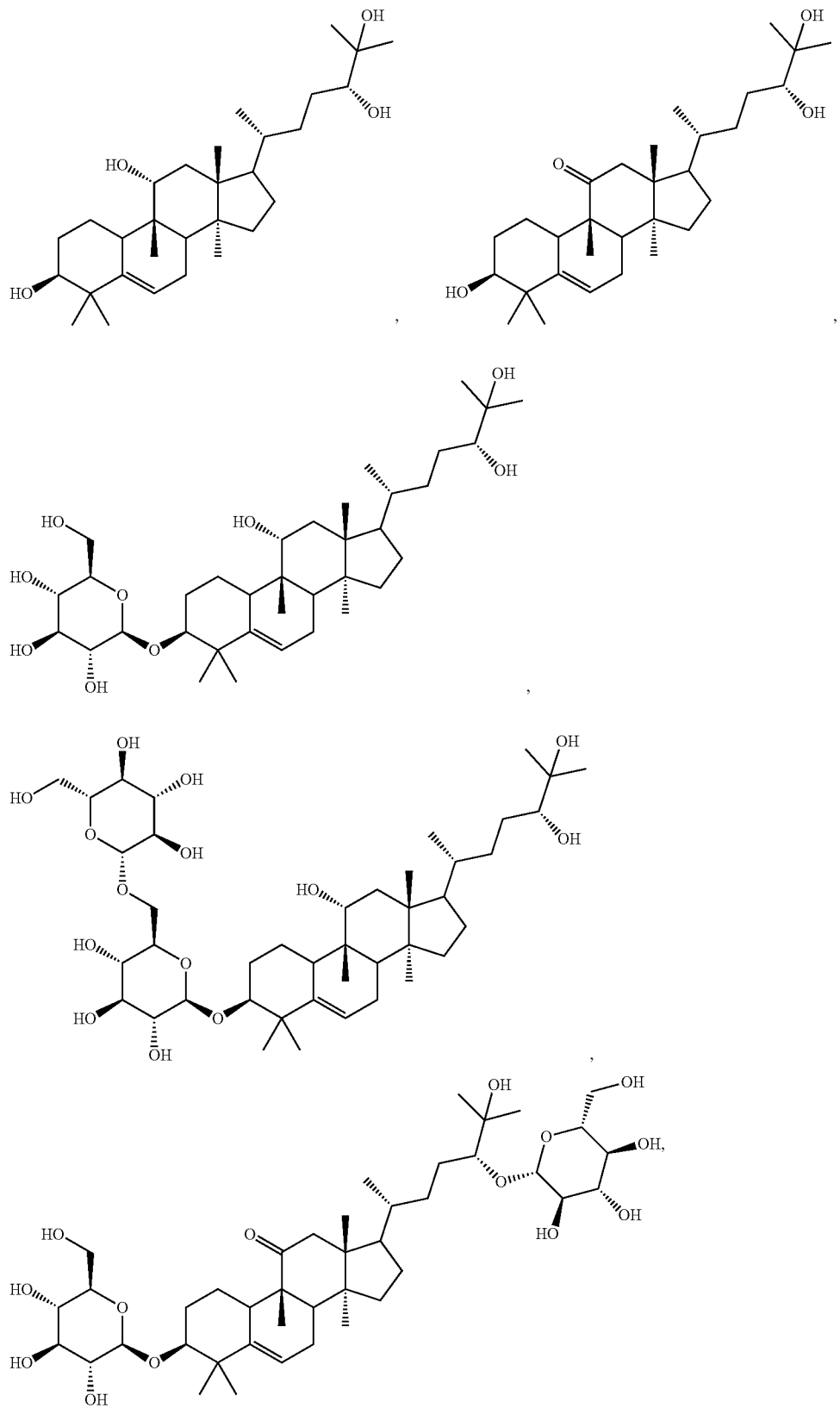

-continued
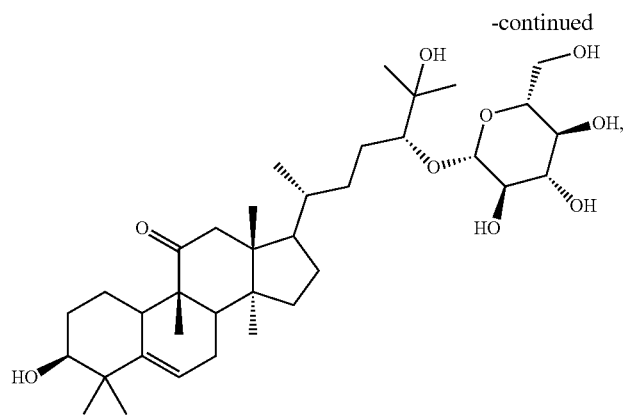
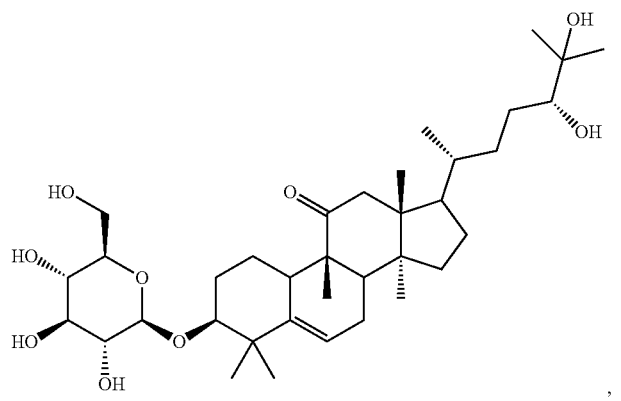
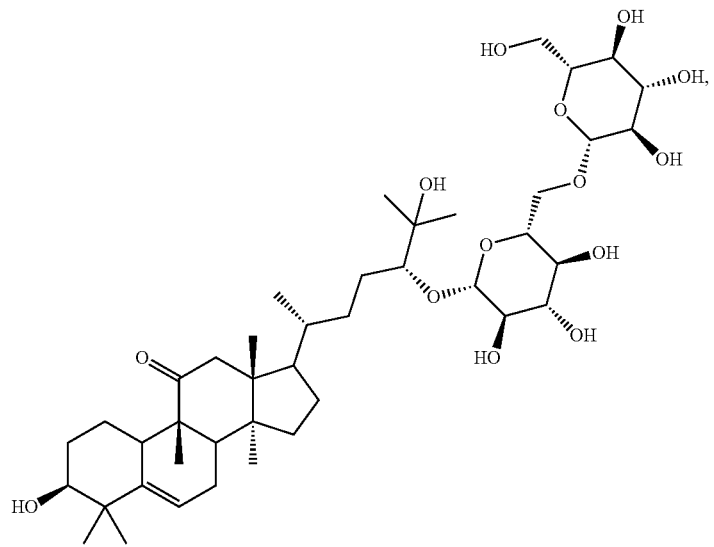

-continued
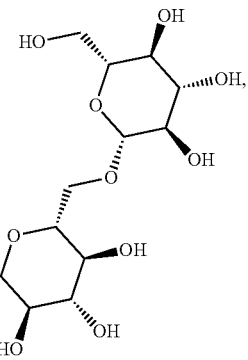
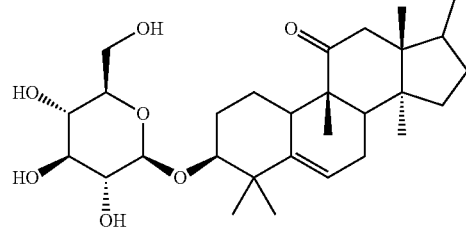
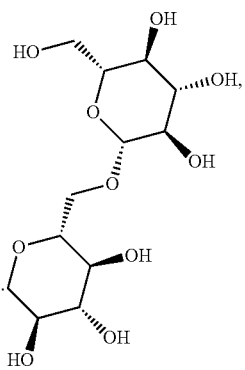
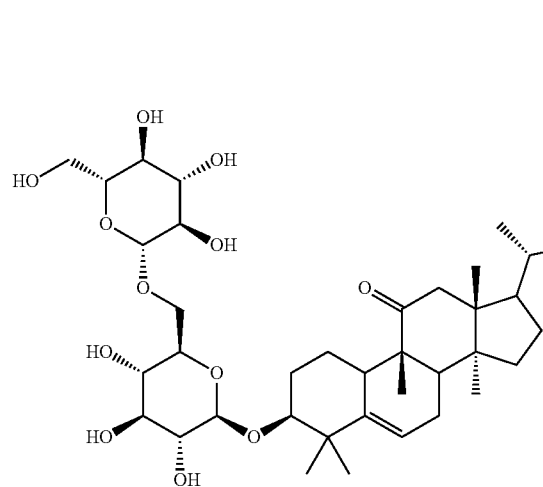
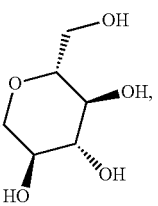
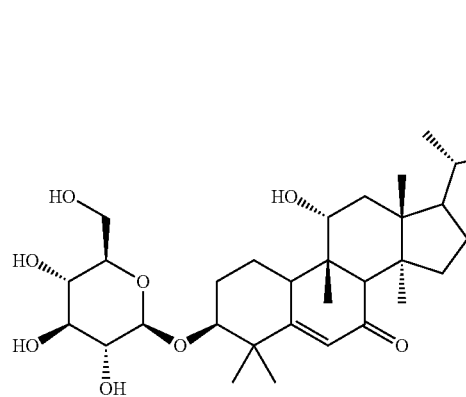

-continued
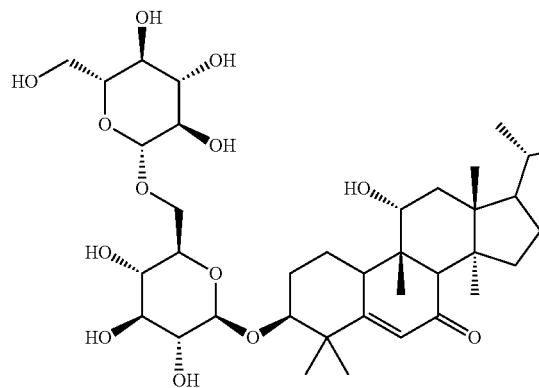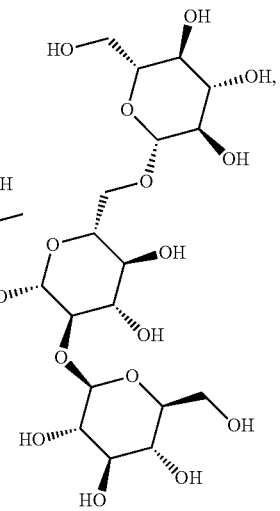
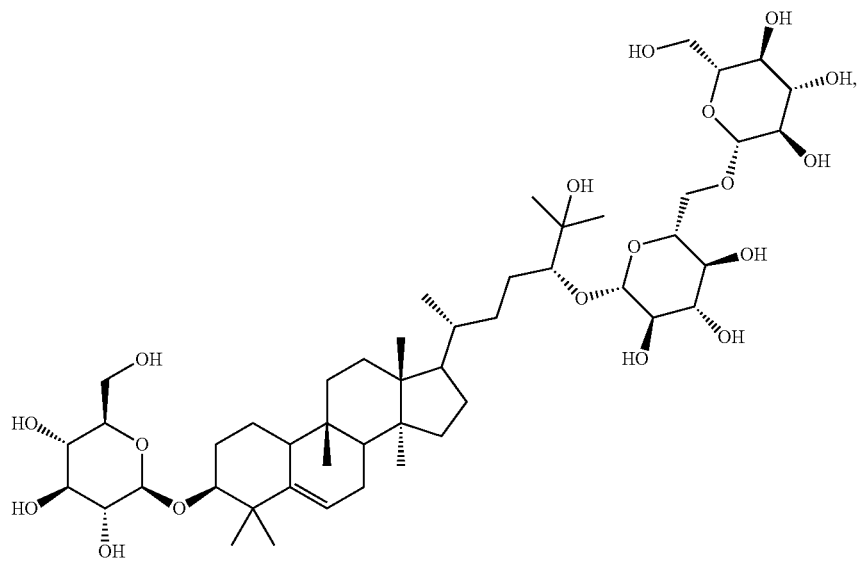

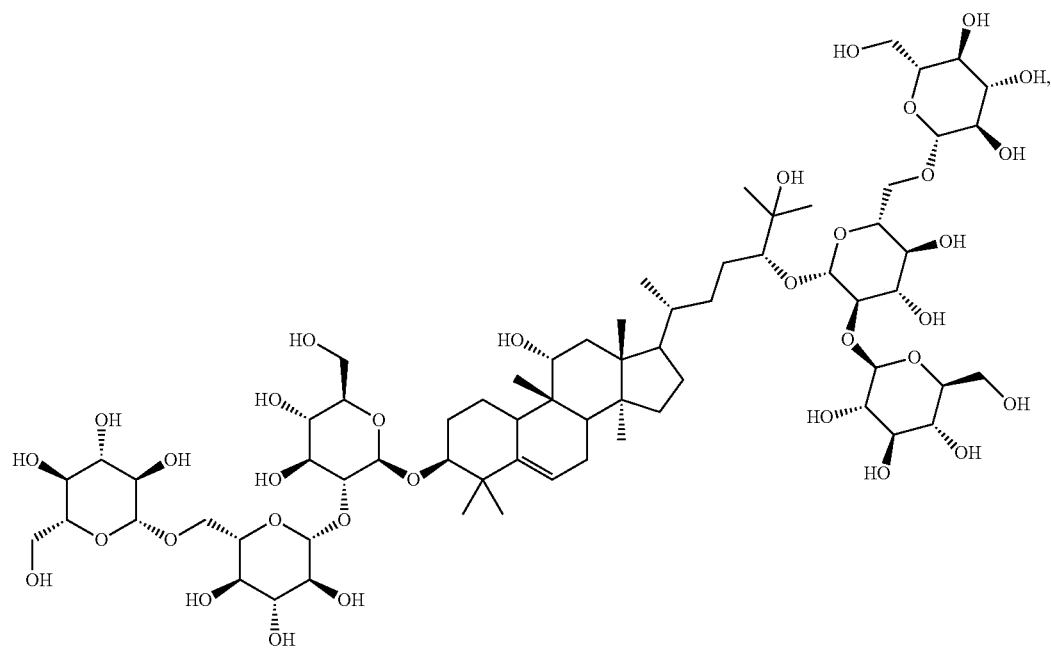
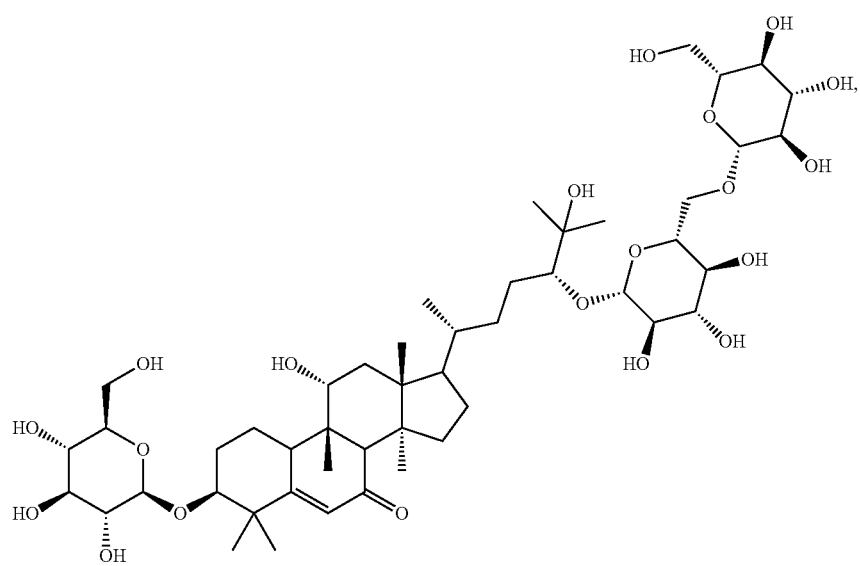

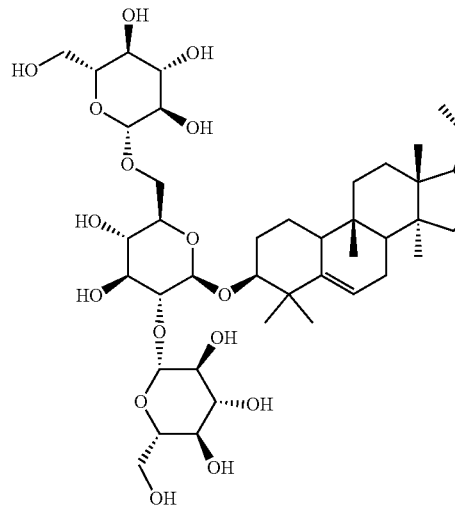
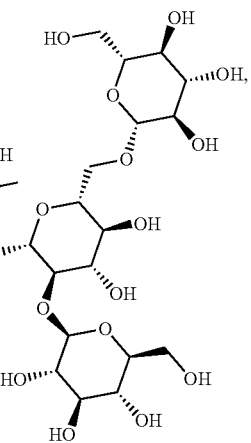
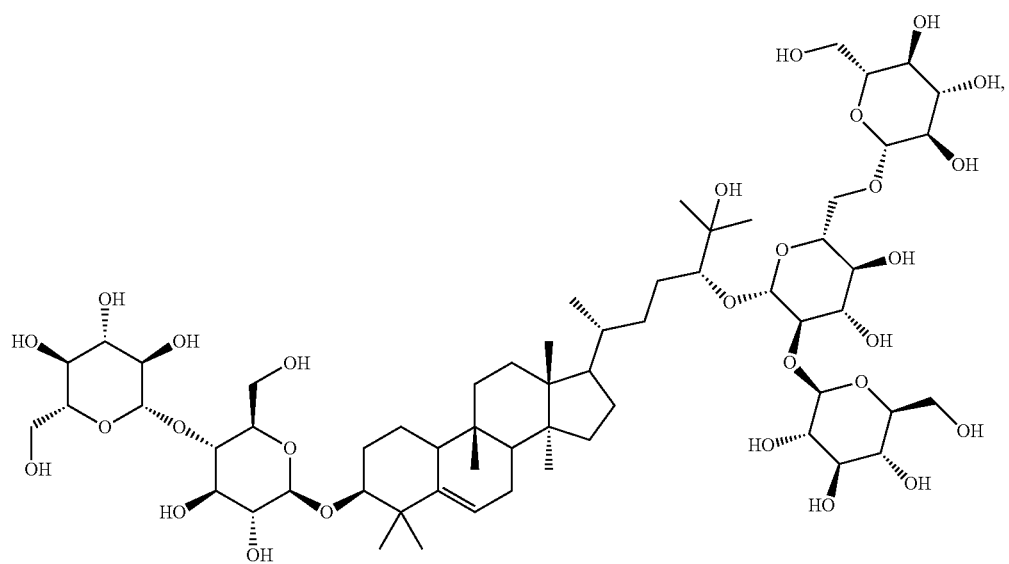

-continued
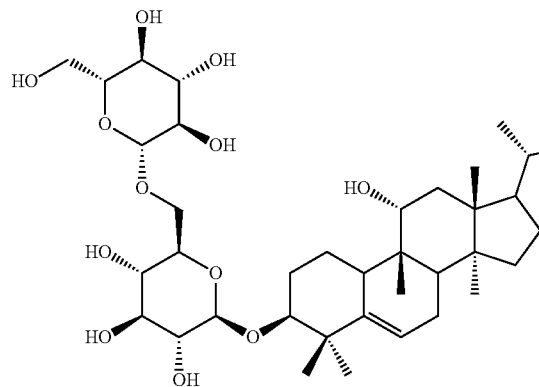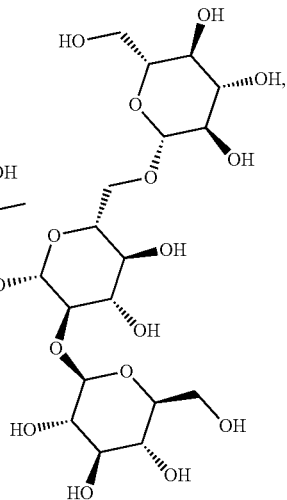
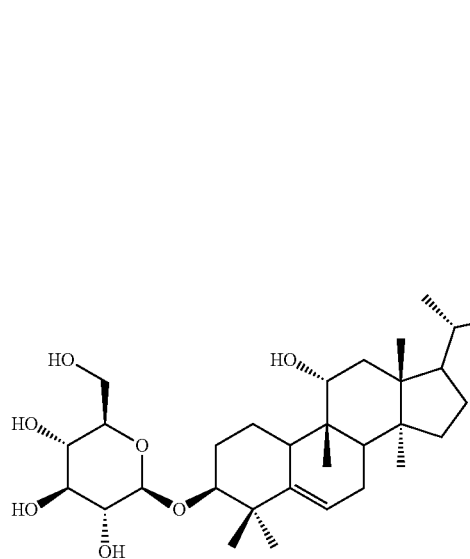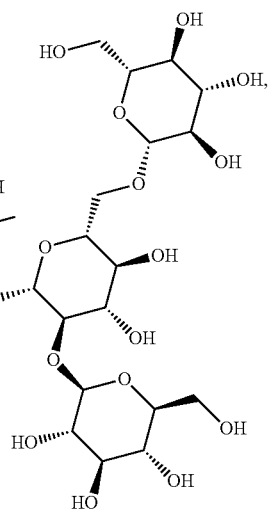
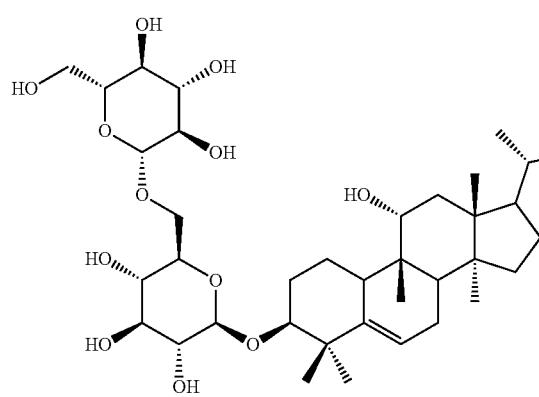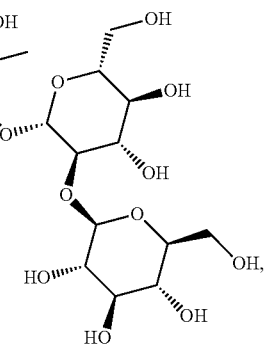

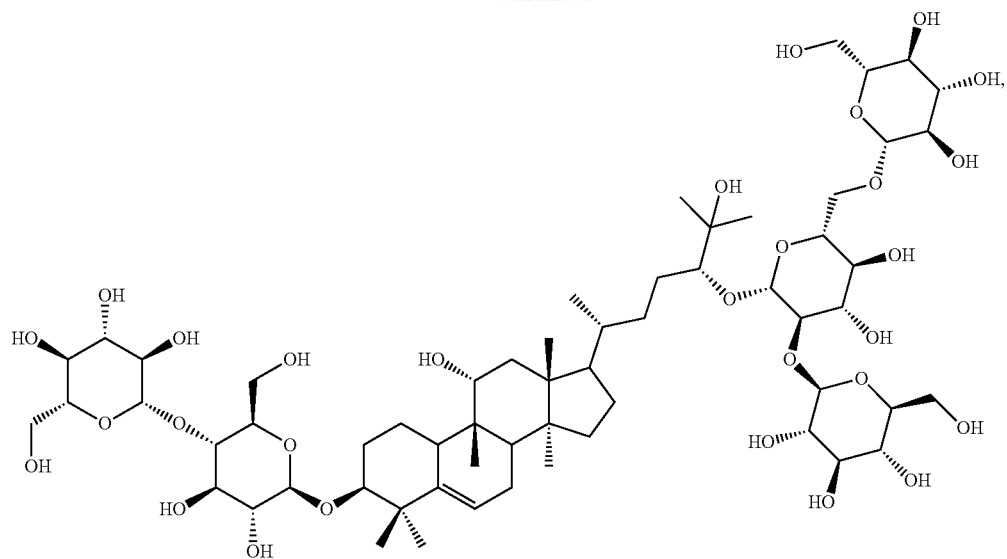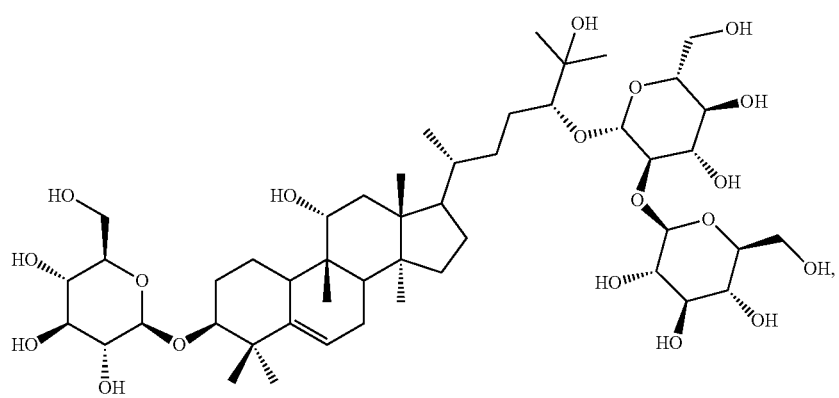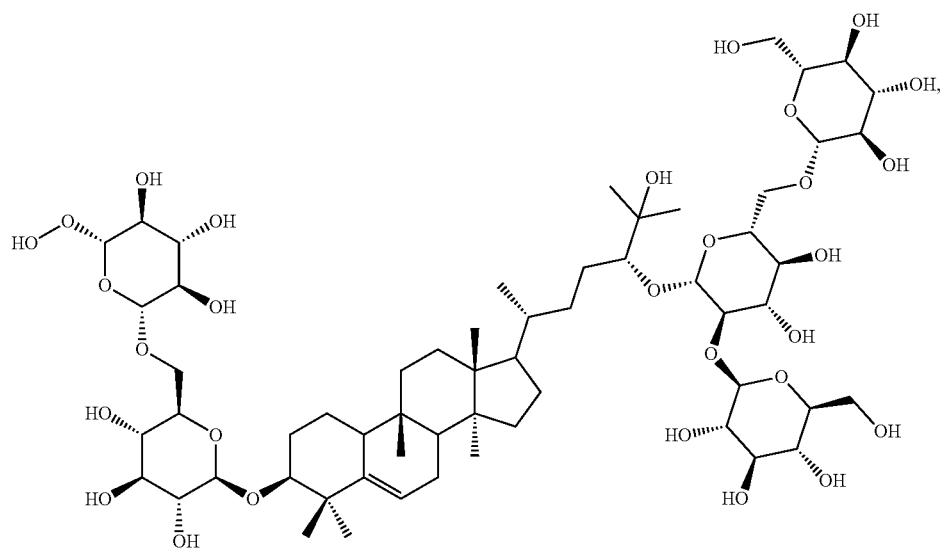

-continued
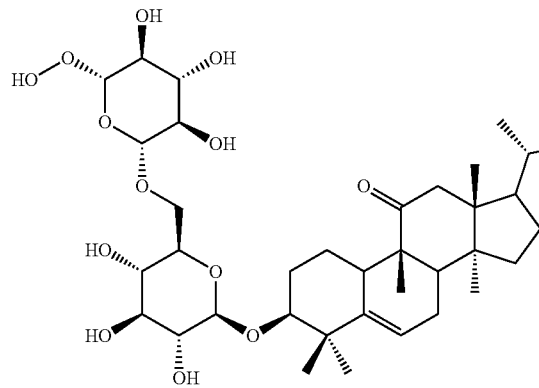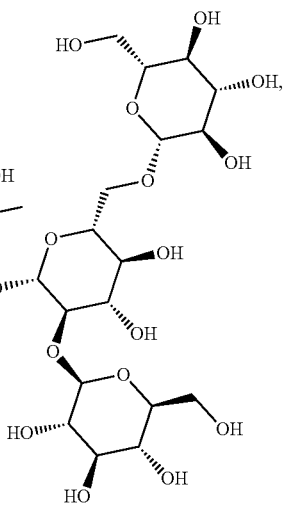
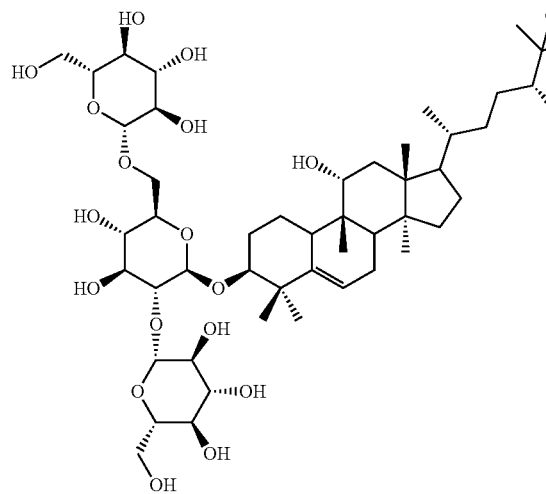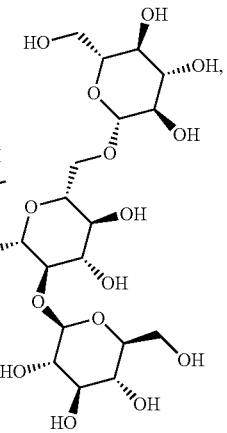
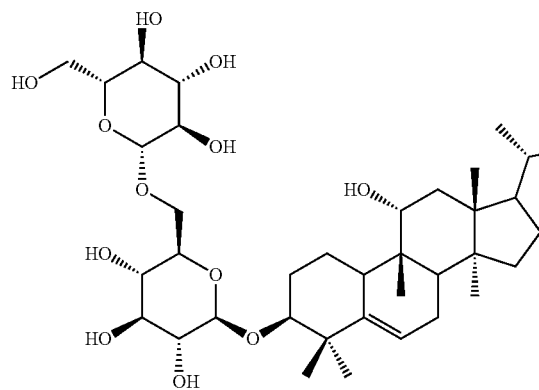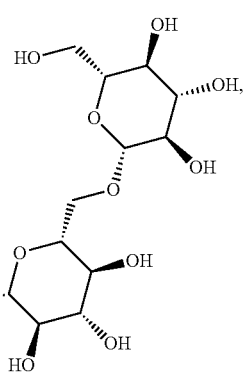

-continued
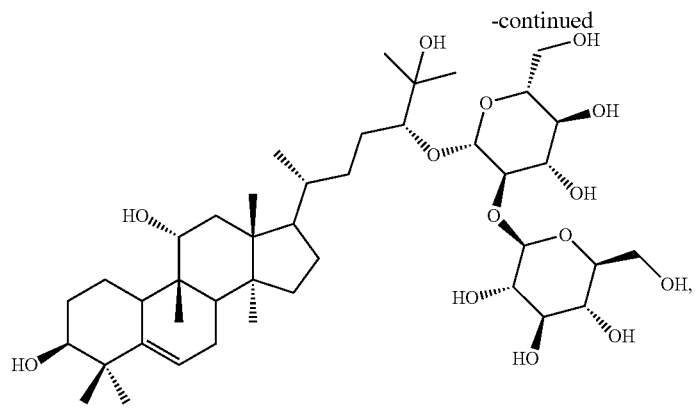
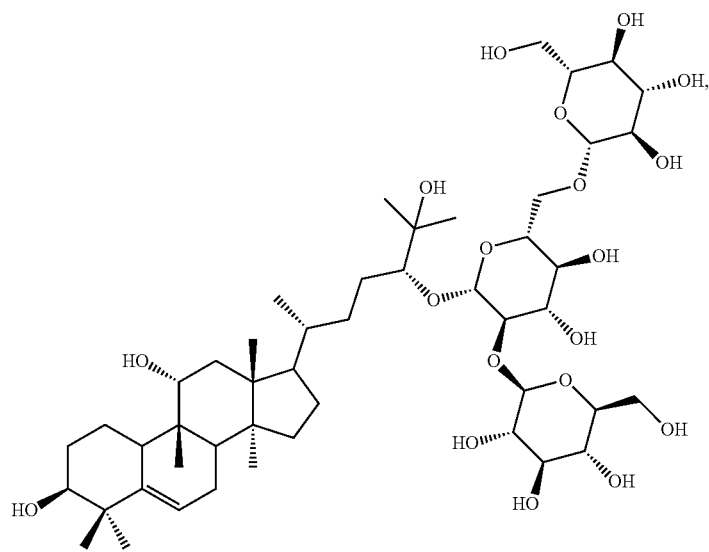
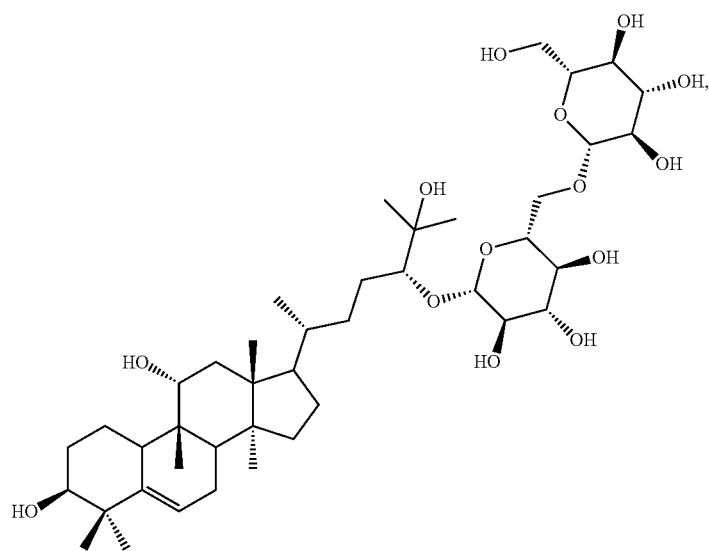

-continued
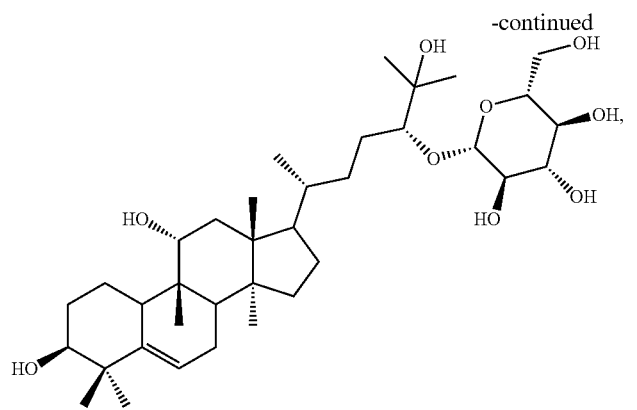
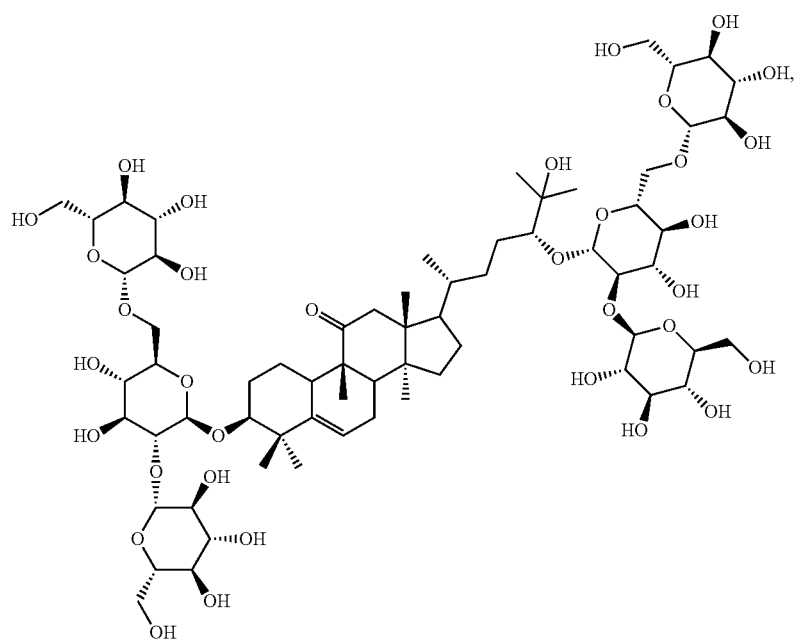
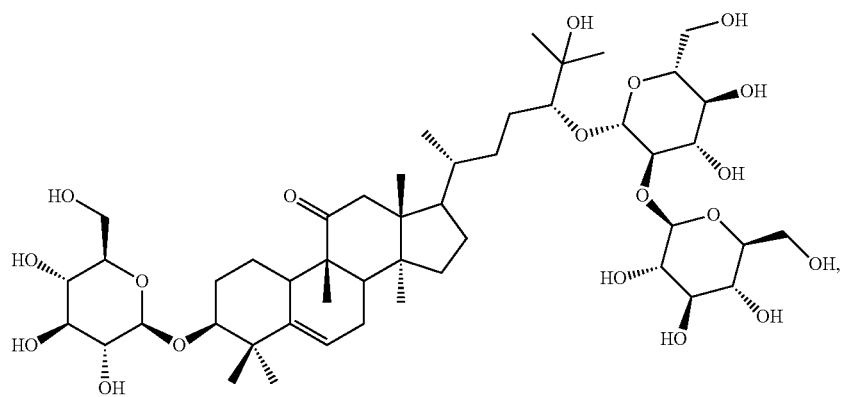

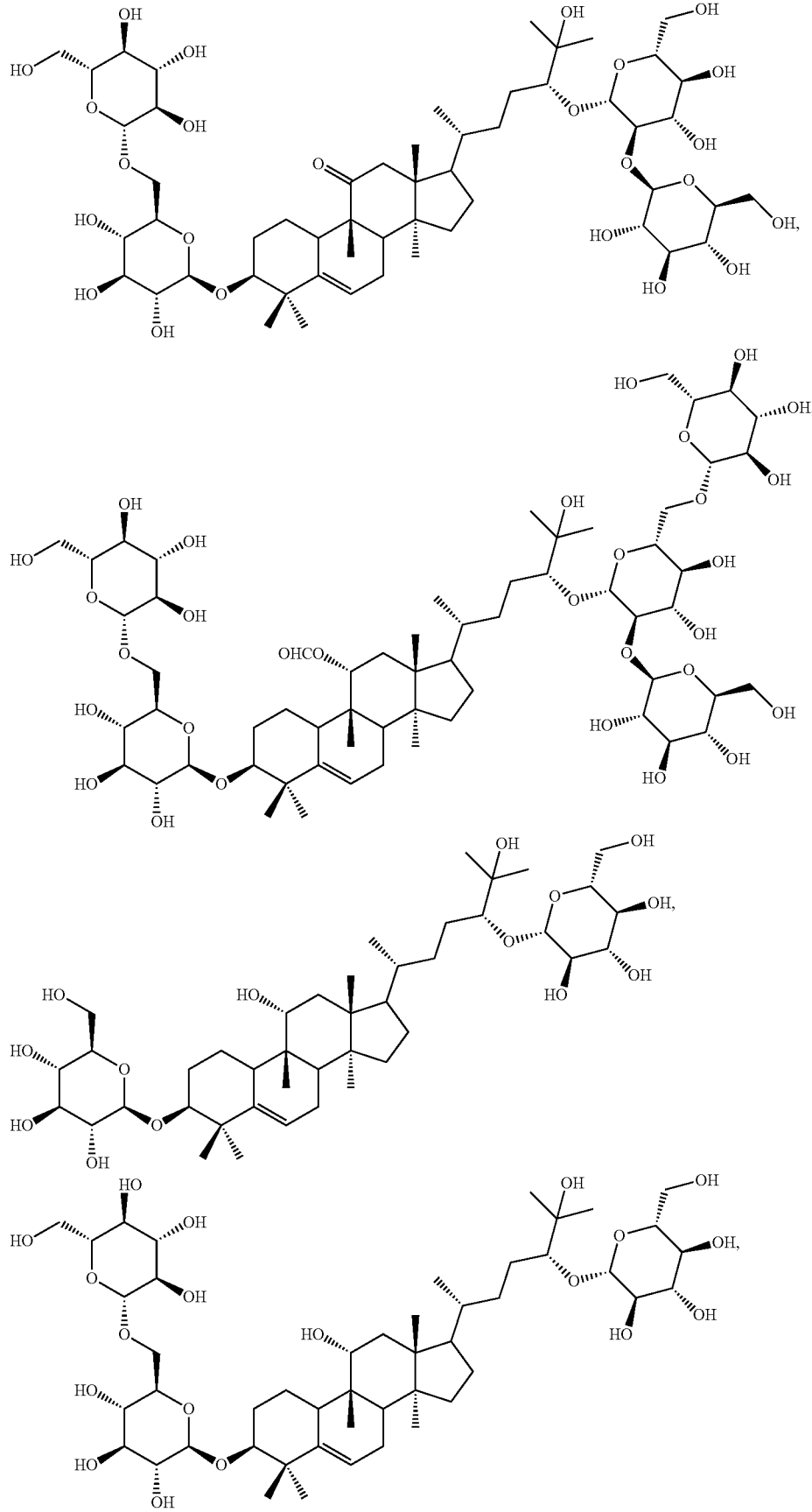

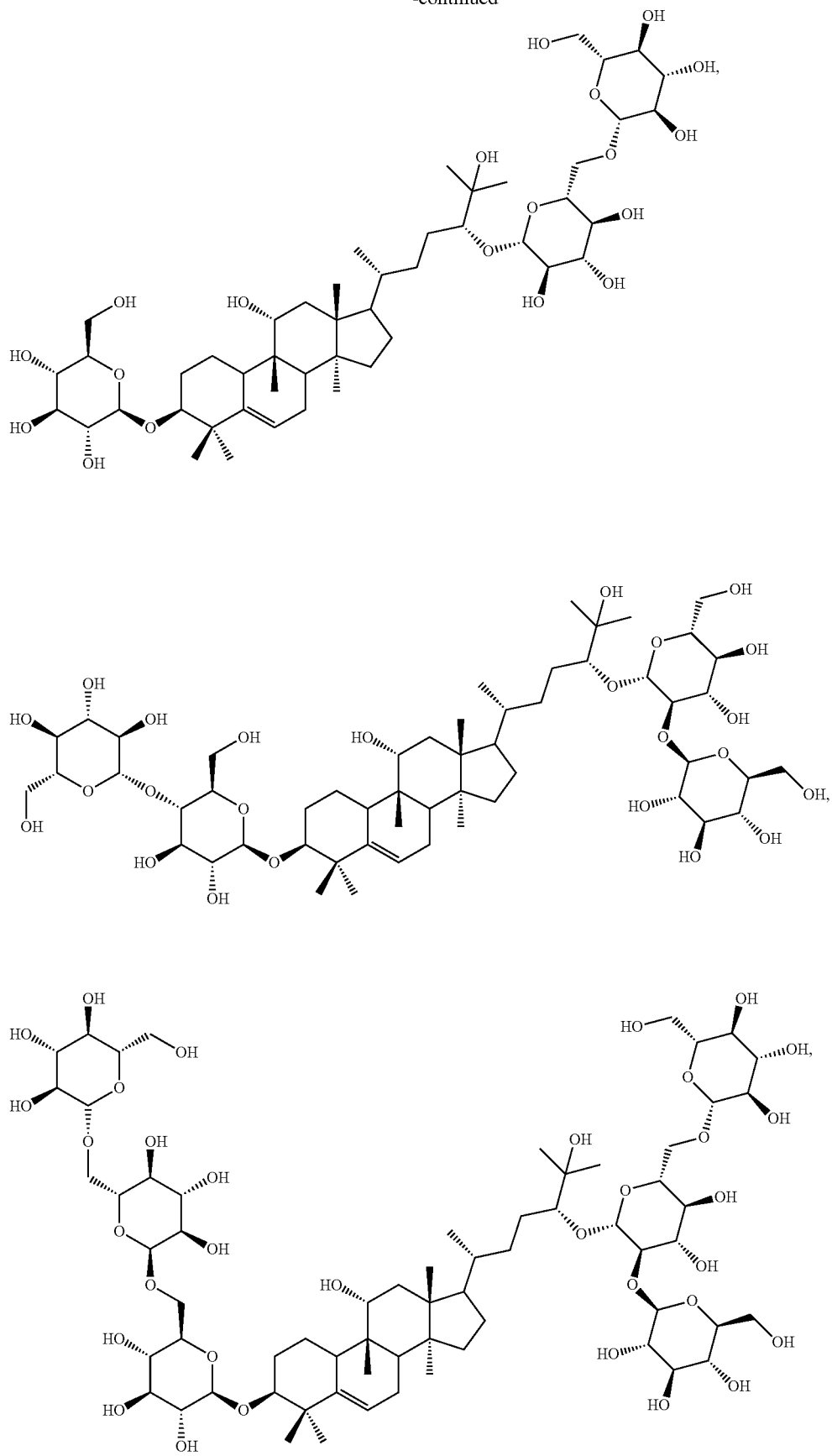

-continued
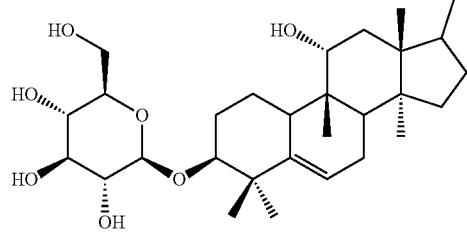
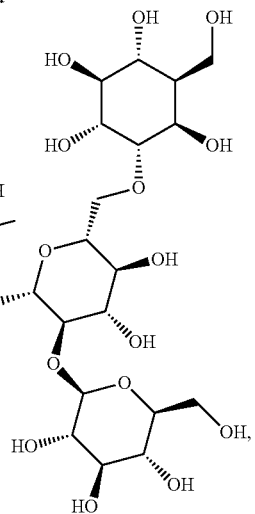
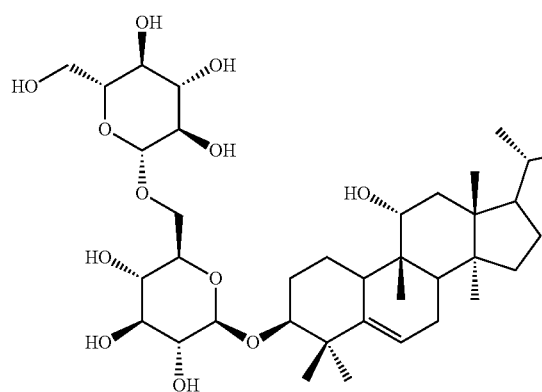
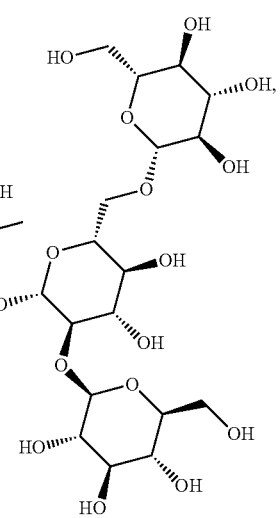
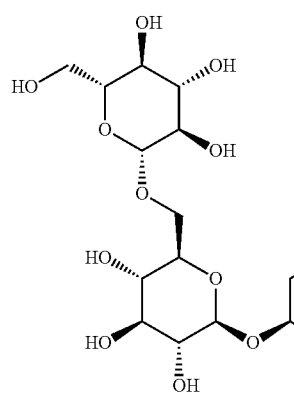
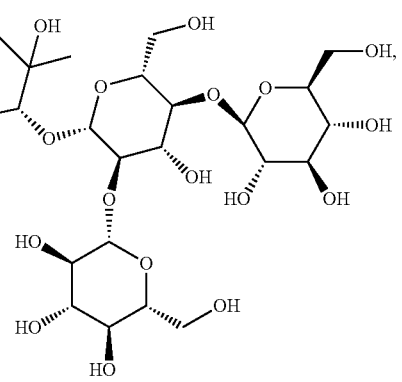

-continued
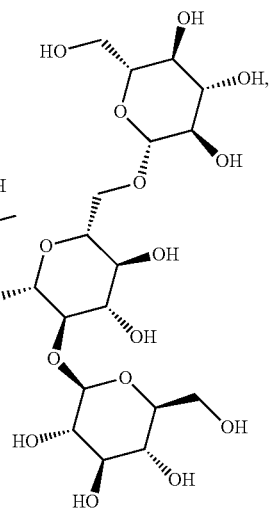
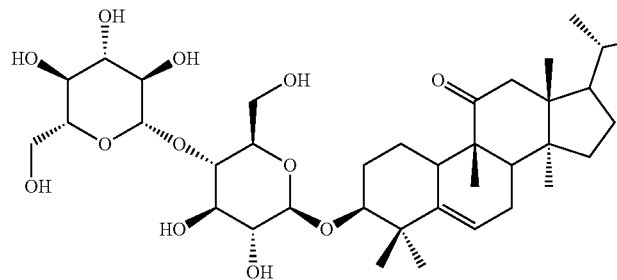
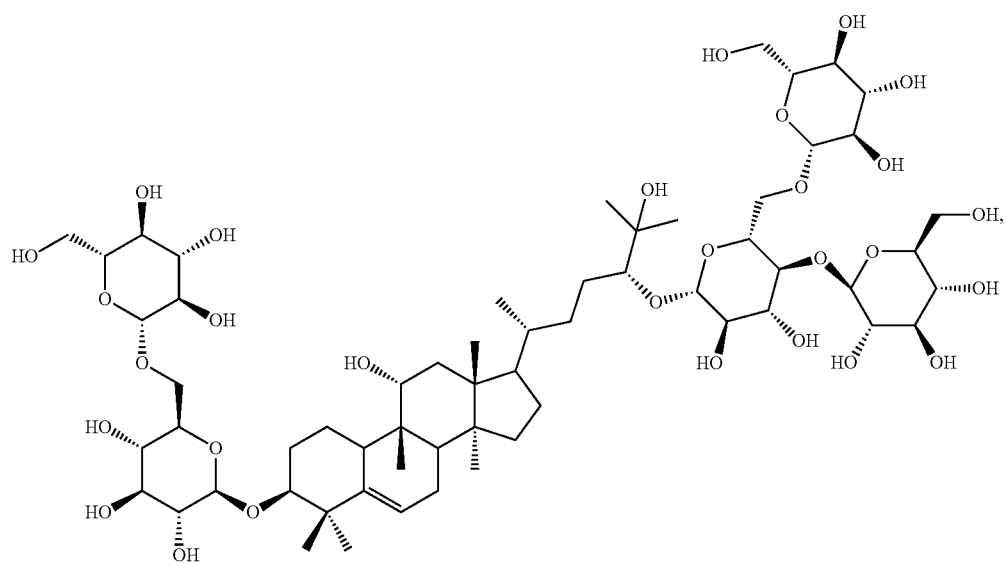

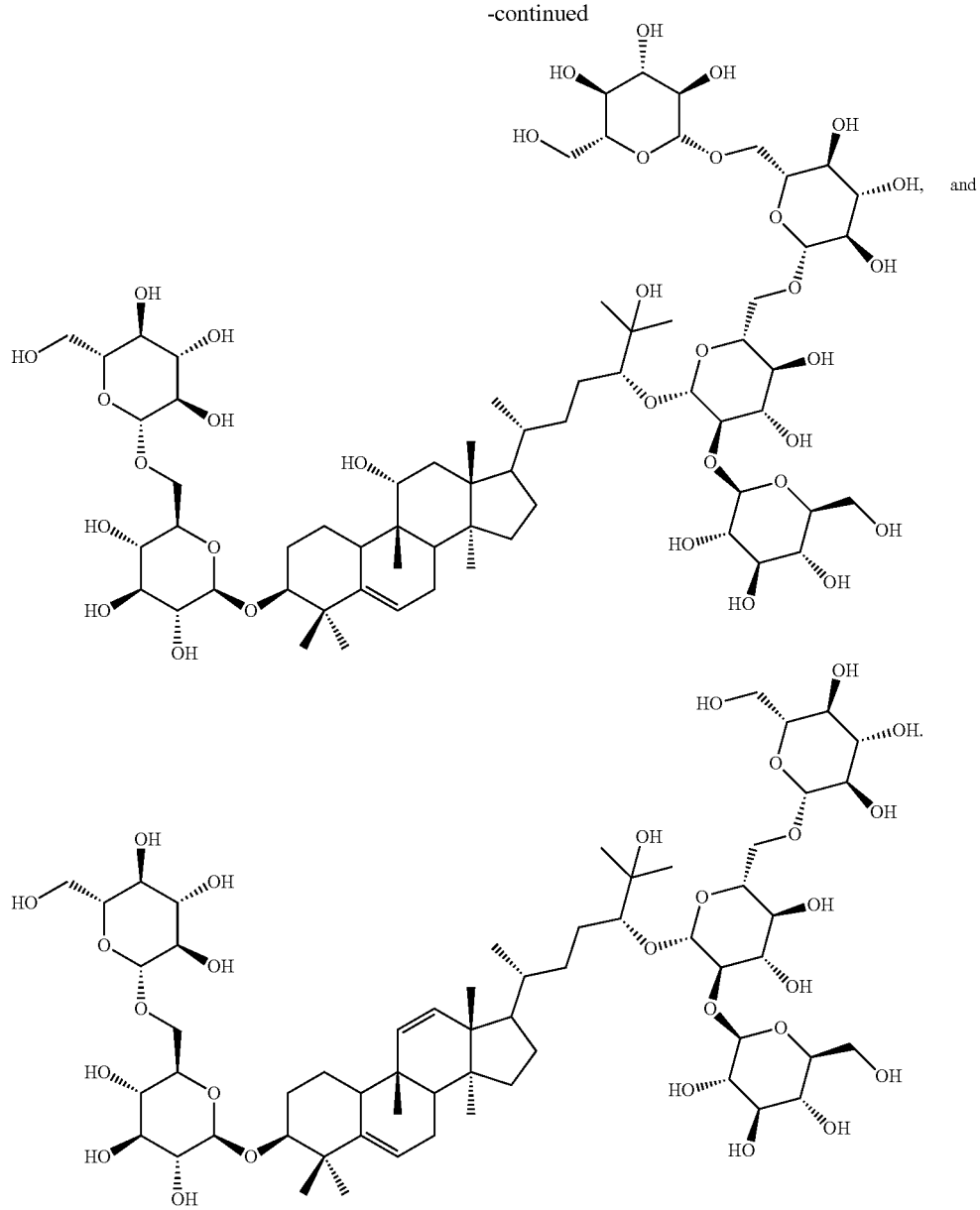
In some embodiments, the compound of Formula (I), composition, product, method, or concentrate comprises a compound having the structure of formula (Ia):
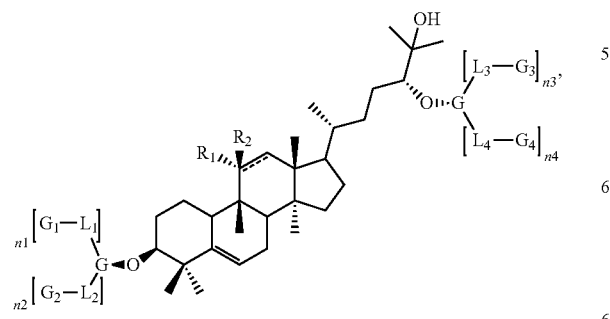
(Ia)
or a salt thereof.
In some embodiments, the compound of Formula (I), composition, product, method, or concentrate comprises a compound having the structure of formula (Ib):
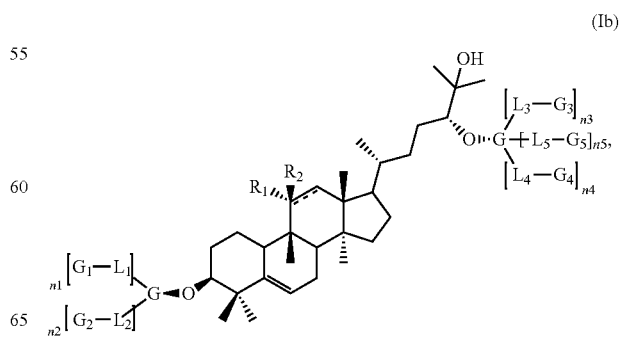
(Ib)
or a salt thereof.

In some embodiments, the compound of Formula (I), composition, product, method, or concentrate comprises a compound having the structure of formula (Ic):

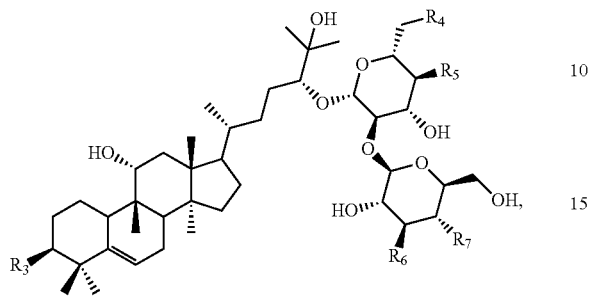

(Ic)

or a salt thereof.

In some embodiments, $R_4$ is selected from —OH and -$(L_3$-$G_3)_{n3}$.

In some embodiments, $R_5$ is selected from —OH and -$(L_5$-$G_5)_{n5}$.

In some embodiments, $R_6$ and $R_7$ are independently selected from —OH and -$L_6$-$G_6$, provided that $R_6$ and $R_7$ are not both -$L_6$-$G_6$.

In some embodiments, $G_6$ is a furanose or pyranose moiety.

In some embodiments, $L_6$ is a glycosidic bond.

In some embodiments, the compound of Formula (I), composition, product, method, or concentrate comprises a compound having the structure of formula (Id):

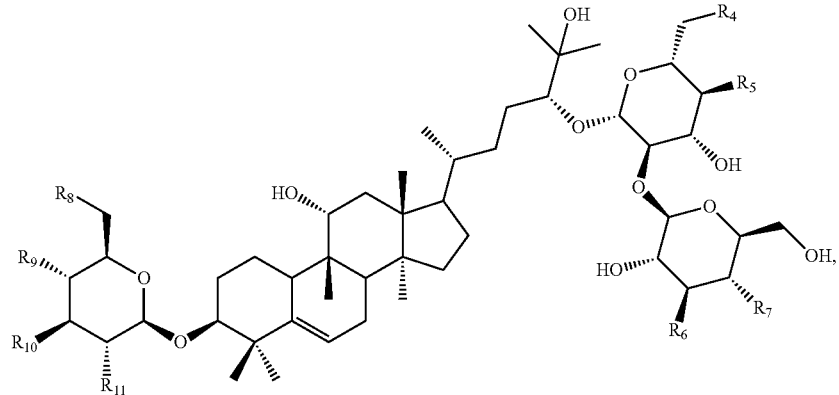

(Id)

or a salt thereof.

In some embodiments, $R_8$ and $R_9$ are independently selected from —OH and -$L_1$-$G_1$, provided that $R_8$ and $R_9$ are not both -$L_1$-$G_1$.

In some embodiments, $R_{10}$ and $R_{11}$ are independently selected from —OH and -$L_2$-$G_2$, provided that $R_{10}$ and $R_{11}$ are not both -$L_2$-$G_2$.

In some embodiments, the compound of Formula (I), composition, product, method, or concentrate comprises a compound having the structure of formula (Id):

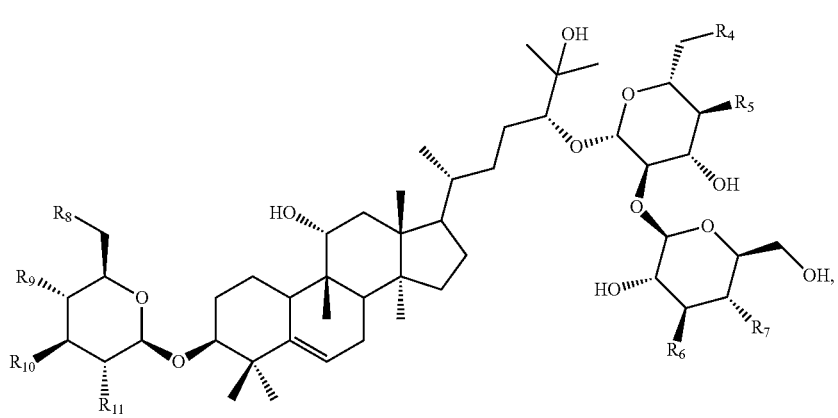

(Id)

or a salt thereof.

In some embodiments, $R_8$ and $R_{10}$ are independently selected from —OH and $-L_1-G_1$, provided that $R_8$ and $R_9$ are not both $-L_1-G_1$; and In some embodiments, $R_9$ and $R_{11}$ are independently selected from —OH and $-L_2-G_2$, provided that $R_{10}$ and $R_{11}$ are not both $-L_2-G_2$.

In some embodiments, the compound, composition, product, method, or concentrate, each of $R_8$, $R_9$, $R_{10}$, and $R_{11}$ are —OH. In some embodiments, the compound, composition, product, method, or concentrate, $R_8$ is $-L_1-G_1$ and each of $R_9$, $R_{10}$, and $R_{11}$ are —OH. In some embodiments, the compound, composition, product, method, or concentrate, $R_9$ is $L_1-G_1$ and each of $R_8$, $R_{10}$, and $R_{11}$ are —OH.

In some embodiments, the compound, composition, product, method, or concentrate, $R_4$ is —OH. In some embodiments, the compound, composition, product, method, or concentrate, $R_4$ is $-L_3-G_3$. In some embodiments, the compound, composition, product, method, or concentrate, $R_5$ is —OH. In some embodiments, the compound, composition, product, method, or concentrate, $R_5$ is $-L_5-G_5$. In some embodiments, the compound, composition, product, method, or concentrate, $R_6$ and $R_7$ are —OH. In some embodiments, the compound, composition, product, method, or concentrate, $R_6$ is $-L_6-G_6$ and $R_7$ is —OH. In some embodiments, the compound, composition, product, method, or concentrate, $R_6$ is —OH and $R_7$ is $-L_6-G_6$.

In some embodiments, the compound, composition, product, method, or concentrate, each G, $G_1$, $G_2$, $G_3$, $G_4$, and $G_5$ is independently selected from the group consisting of D-Glucopyranose, L-Glucopyranose, D-Fructopyranose, D-Mannopyranose, L-Mannopyranose, D-Galactopyranose, L-Galactopyranose, D-Tagatopyranose, L-Sorbopyranose, D-Xylopyranose, D-Ribopyranose, D-Arabopyranose, L-Arabopyranose, L-Xylulopyranose, D-Ribulopyranose, 6-deoxy-D-Glucopyranose, 6-deoxy-L-Glucopyranose, 6-deoxy-D-Galactopyranose, 6-deoxy-L-Galactopyranose, 6-deoxy-L-Mannopyranose, 2-deoxy-D-Ribopyranose, D-Hamamelopyranose, D-Glucofuranose, L-Glucofuranose, D-Fructofuranose, D-Mannofuranose, L-Mannofuranose, D-Galactofuranose, L-Galactofuranose, D-Tagatofuranose, L-Sorbofuranose, D-Xylofuranose, D-Ribofuranose, D-Arabofuranose, L-Arabofuranose, L-Xylulofuranose, D-Ribulofuranose, D-Threofuranose, D-Erythrofuranose, 6-deoxy-D-Glucofuranose, 6-deoxy-L-Glucofuranose, 6-deoxy-D-Galactofuranose, 6-deoxy-L-Galactofuranose, 6-deoxy-L-Mannofuranose, 2-deoxy-D-Ribofuranose, D-Apiofuranose, and D-Hamamelofuranose.

In some embodiments, the compound, composition, product, method, or concentrate, each $n^1$, $n^2$, $n^3$, $n^4$, and $n^5$ are independently an integer from 0 to 2. In some embodiments, the compound, composition, product, method, or concentrate, $n^4$ is 1, 2, or 3. In some embodiments, the compound, composition, product, method, or concentrate, $n^3$ is 0.

In some embodiments, the compound, composition, product, method, or concentrate, each $L_1$, $L_2$, $L_3$, $L_4$, and $L_5$ are β glycosidic bonds. In some embodiments, the compound, composition, product, method, or concentrate, each $L_1$, $L_2$, $L_3$, $L_4$, and $L_5$ are α glycosidic bonds. In some embodiments, the compound, composition, product, method, or concentrate, at least one of $L_1$, $L_2$, $L_3$, $L_4$, and $L_5$ is an α glycosidic bond.

In some embodiments of the compound, composition, product, method, or concentrate described above, the compound has the structure:

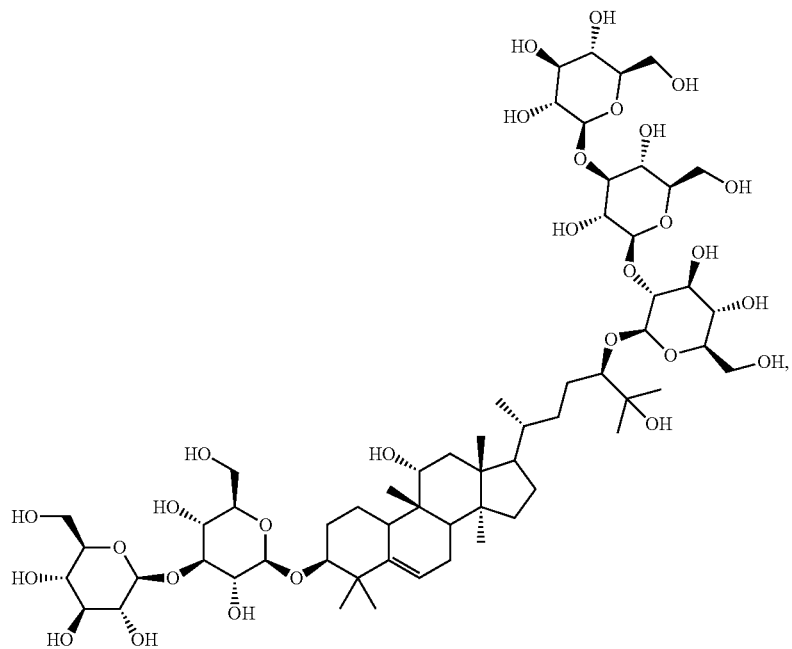 [SMILES: C[C@H](CC[C@@H](O[C@@H]1O[C@H](CO)[C@@H](O)[C@H](O)[C@H]1O[C@@H]1O[C@H](CO)[C@@H](O)[C@H](O[C@@H]2O[C@H](CO)[C@@H](O)[C@H](O)[C@H]2O)[C@H]1O)C(C)(C)O)C1CC[C@@]2(C)C3CC=C4C(CC[C@H](O[C@@H]5O[C@H](CO)[C@@H](O)[C@H](O[C@@H]6O[C@H](CO)[C@@H](O)[C@H](O)[C@H]6O)[C@H]5O)C4(C)C)[C@]3(C)[C@H](O)C[C@]12C]
or a salt thereof.
In some embodiments of the compound, composition, product, method, or concentrate described above, the compound has the structure:
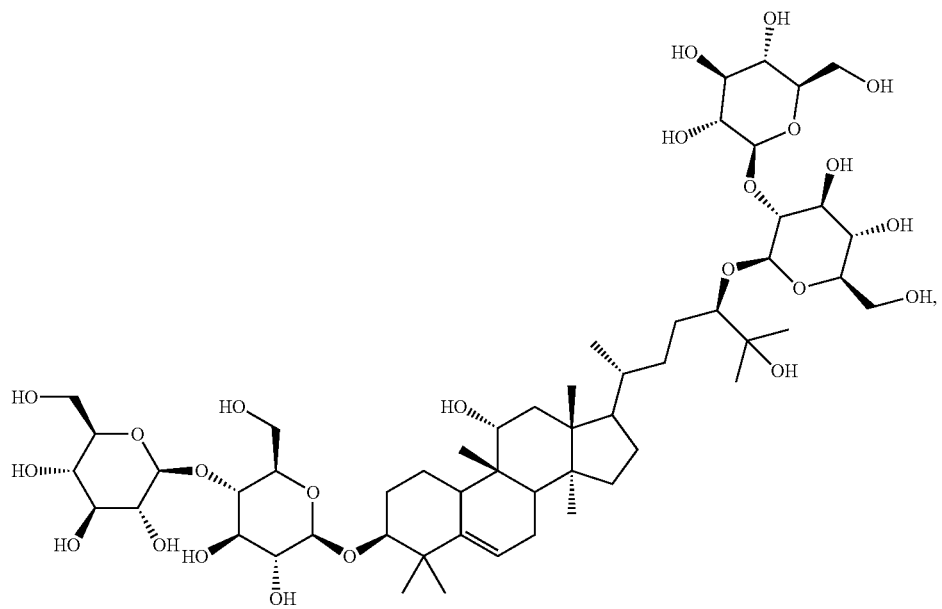 [SMILES: C[C@H](CC[C@@H](O[C@@H]1O[C@H](CO)[C@@H](O)[C@H](O)[C@H]1O[C@@H]1O[C@H](CO)[C@@H](O)[C@H](O)[C@H]1O)C(C)(C)O)C1CC[C@@]2(C)C3CC=C4C(CC[C@H](O[C@@H]5O[C@H](CO)[C@@H](O[C@@H]6O[C@H](CO)[C@@H](O)[C@H](O)[C@H]6O)[C@H](O)[C@H]5O)C4(C)C)[C@]3(C)[C@H](O)C[C@]12C]
or a salt thereof.
In some embodiments of the compound, Composition, product, method, or concentrate described above, the compound has a structure selected from:

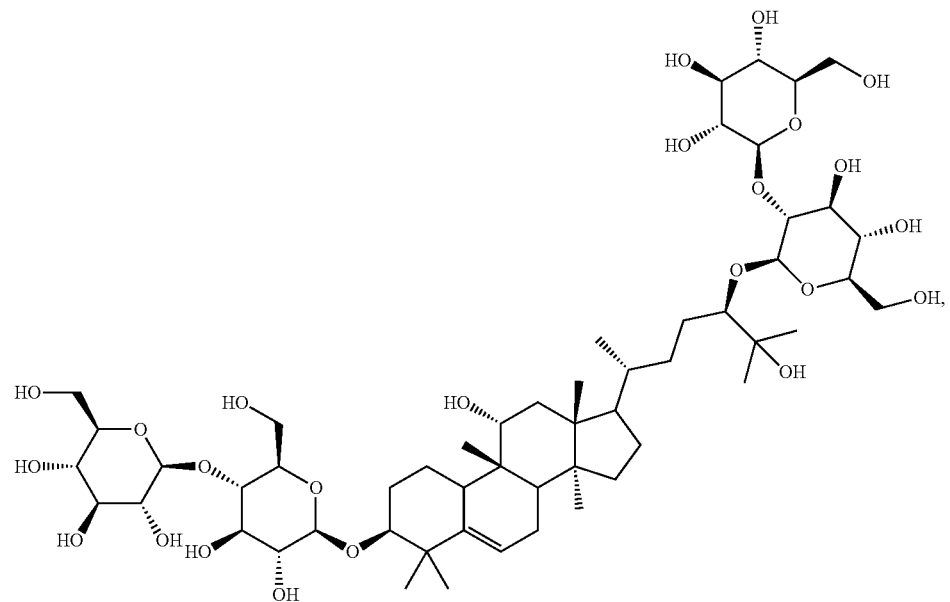
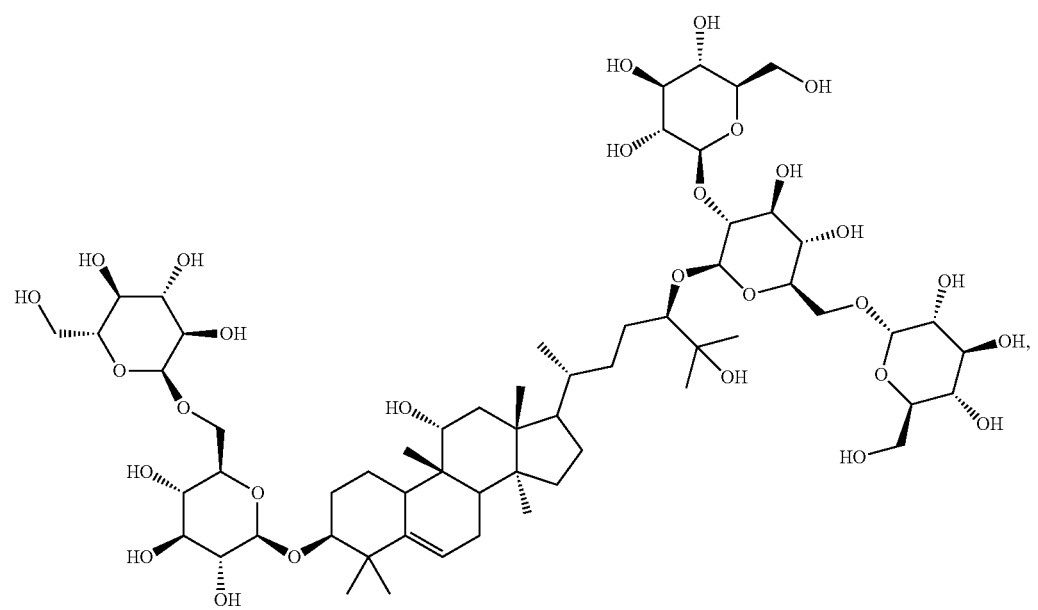

-continued
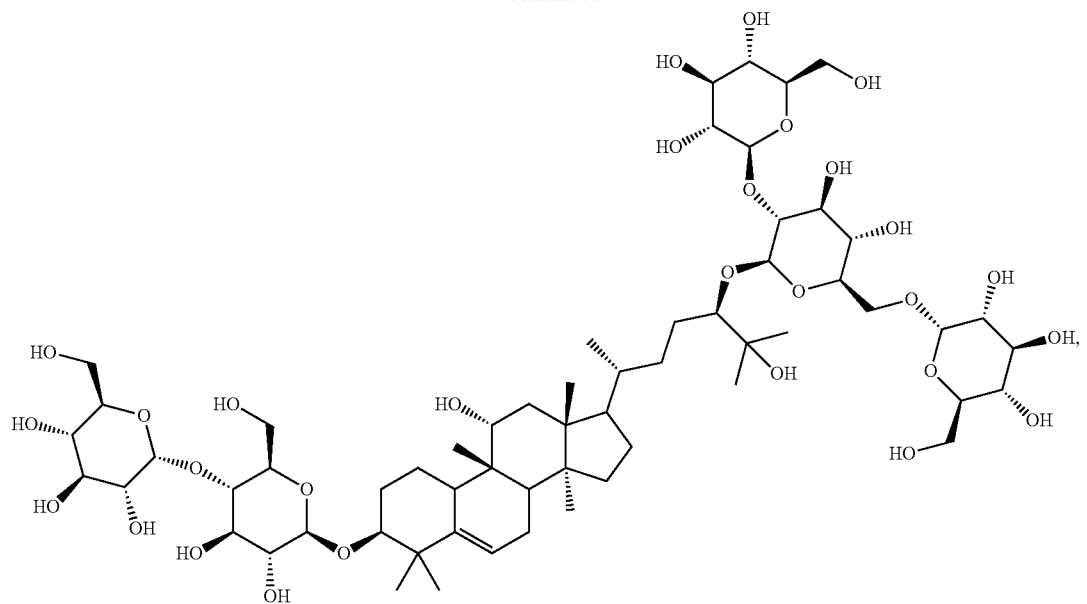
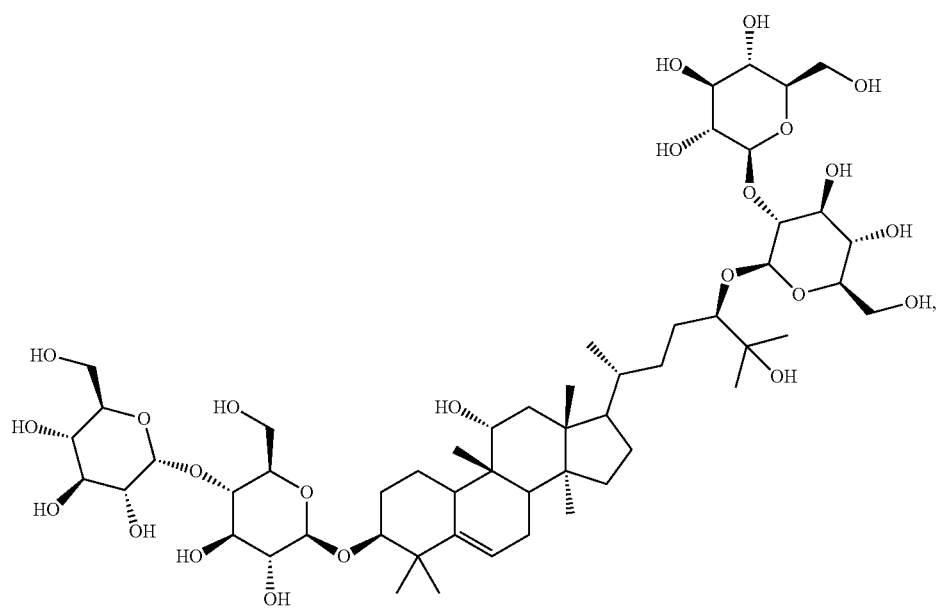

-continued
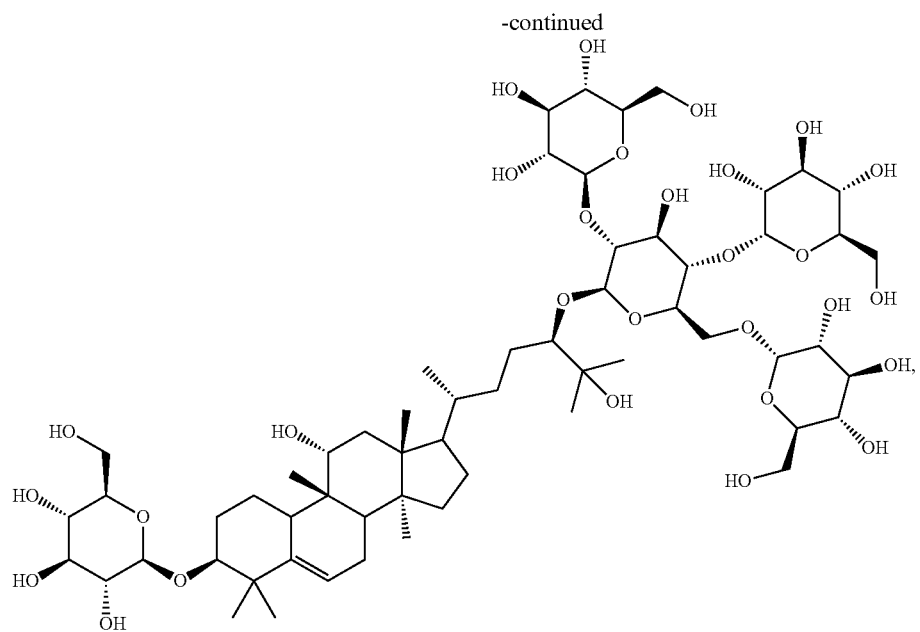
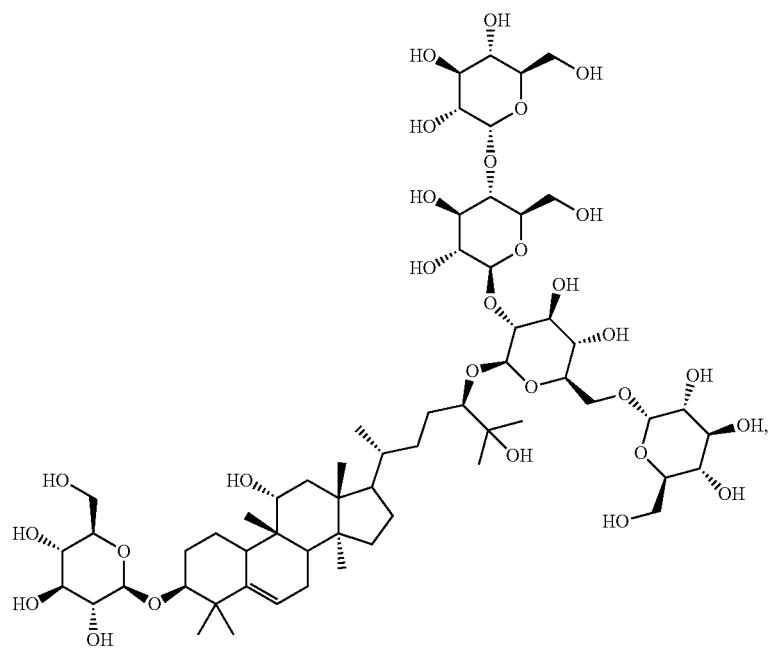

-continued
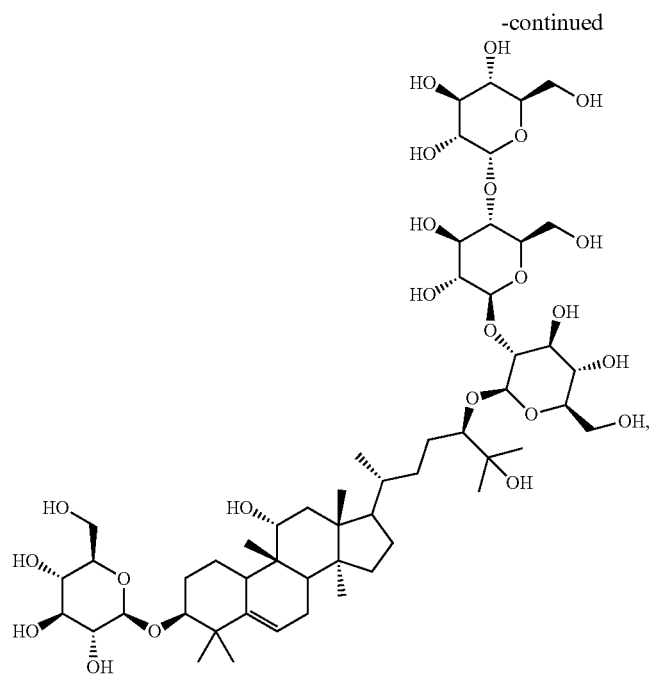
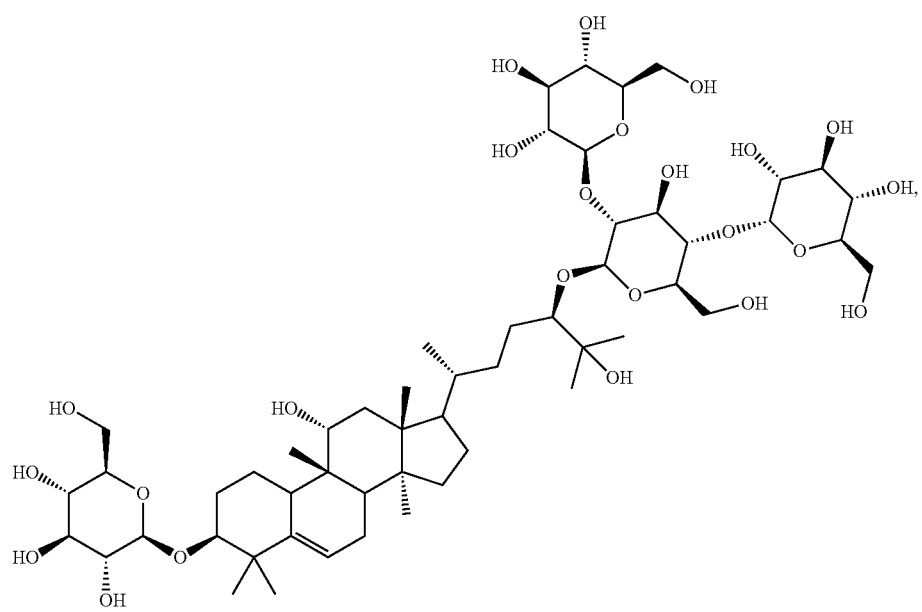

-continued
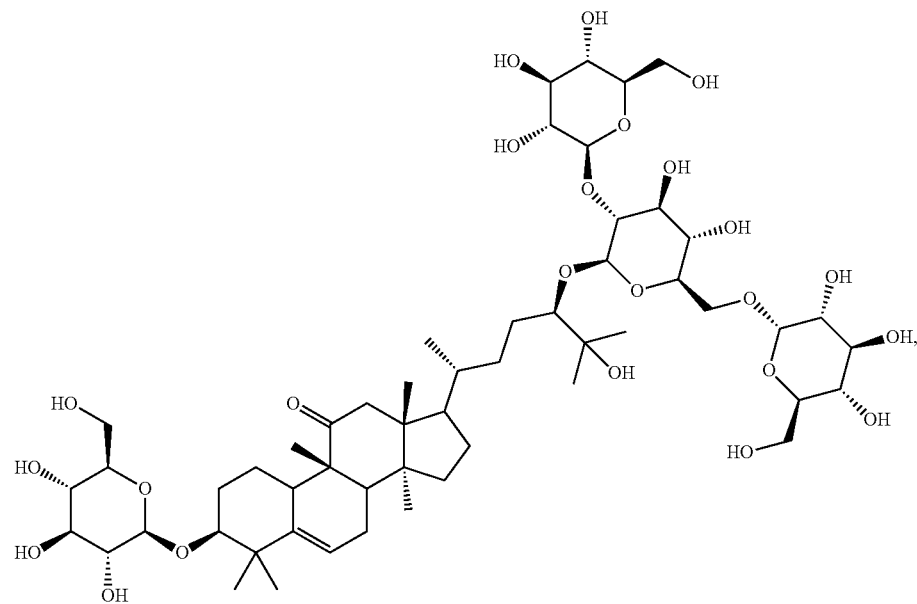
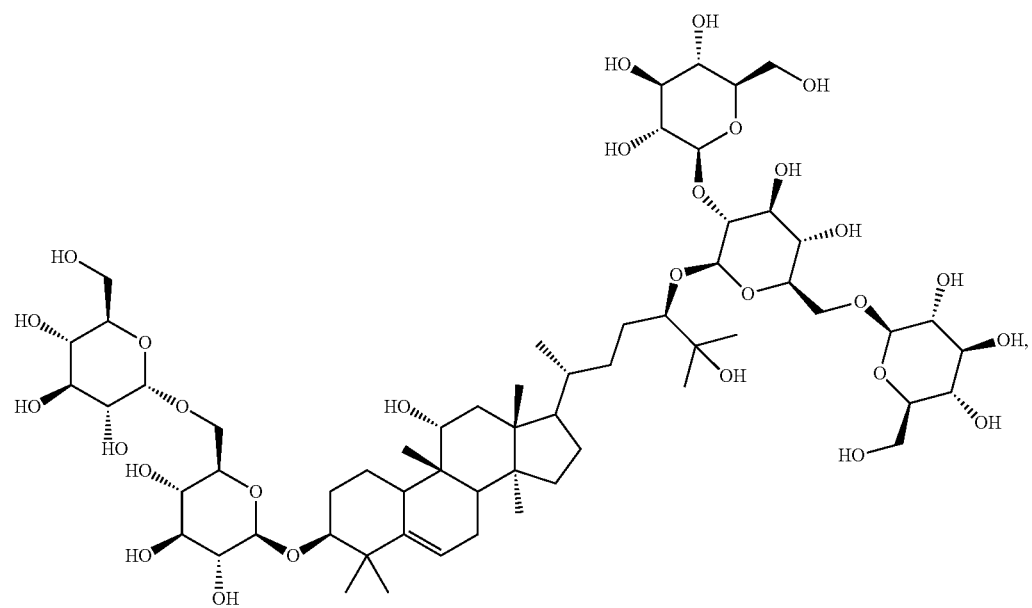

-continued
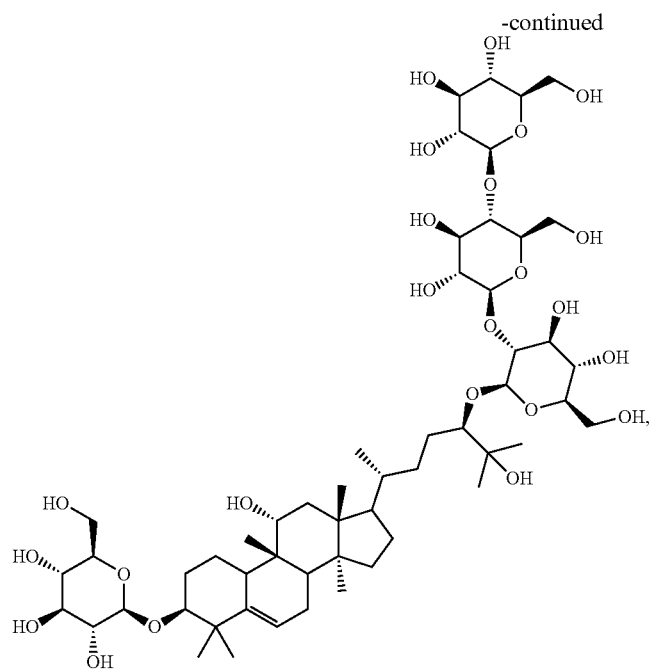
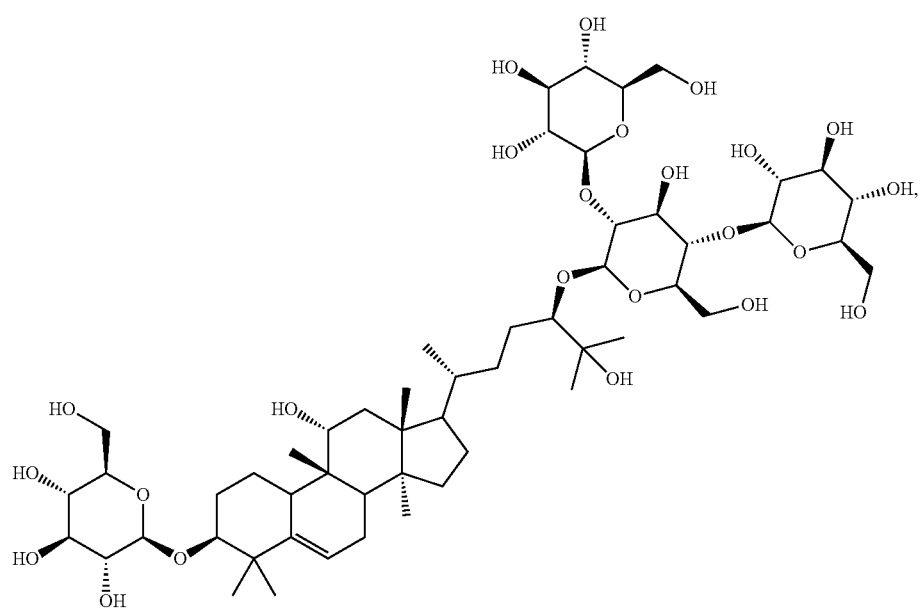

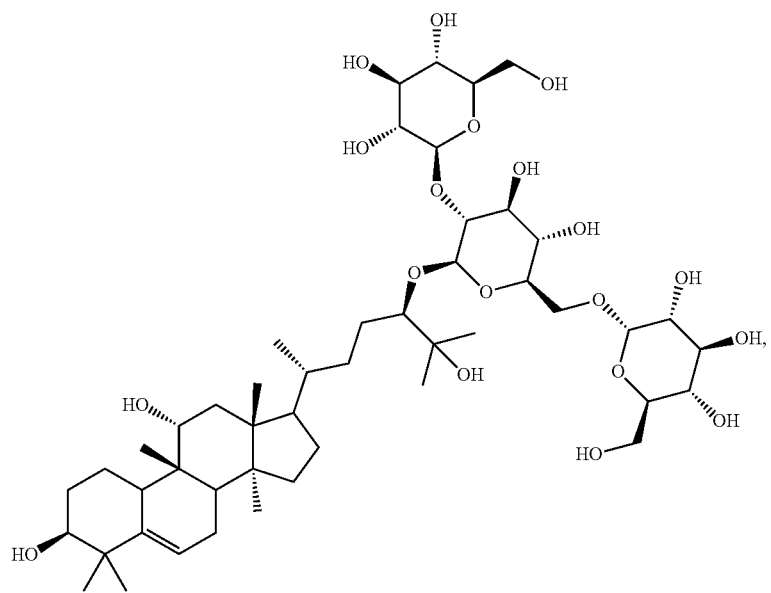
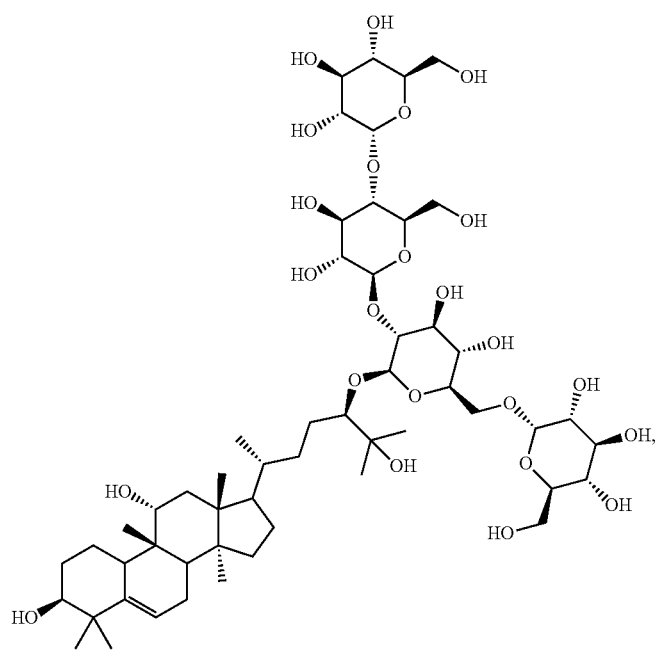

-continued
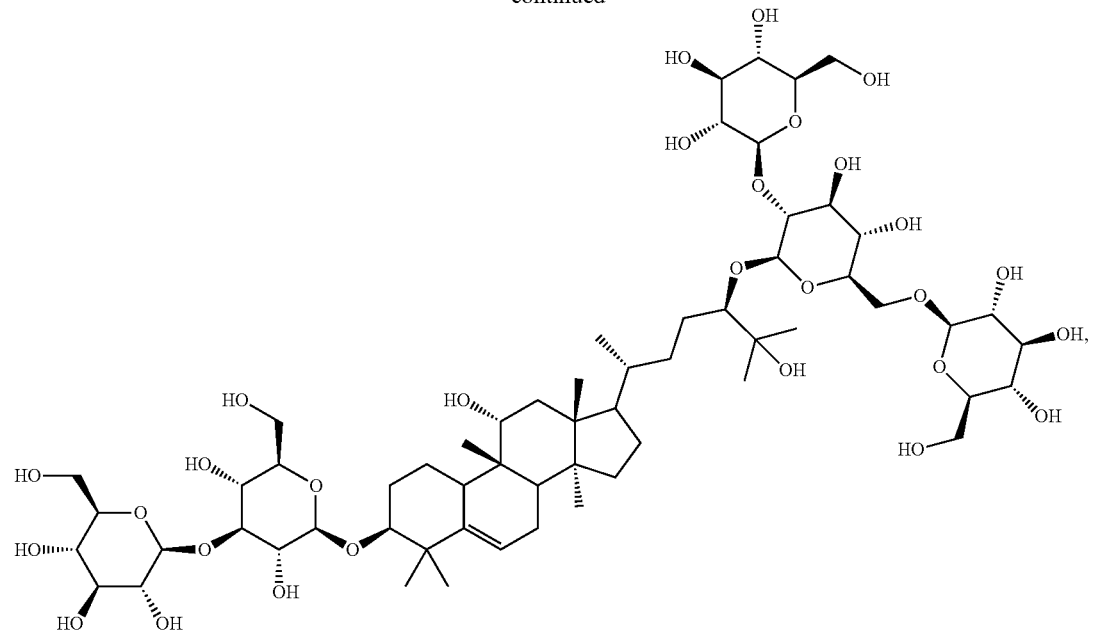
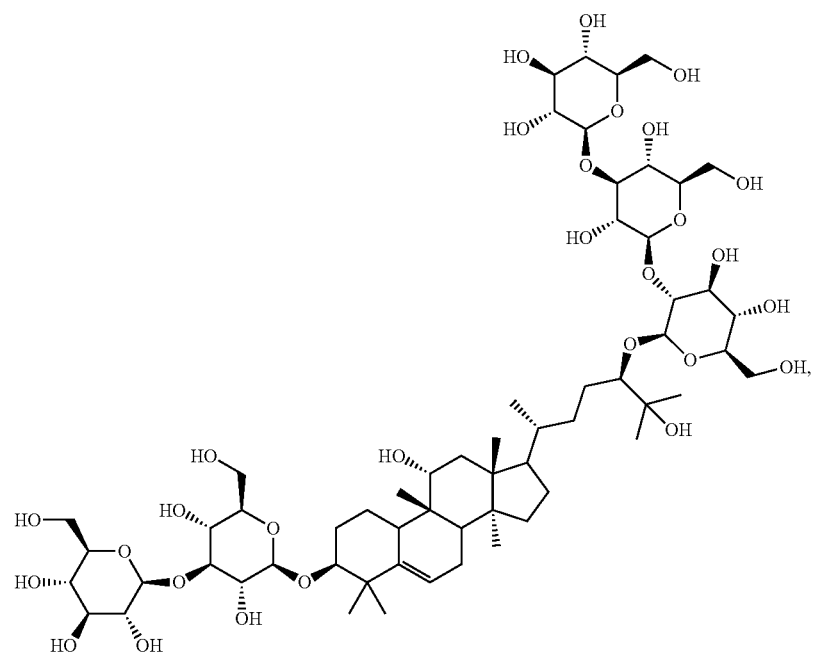

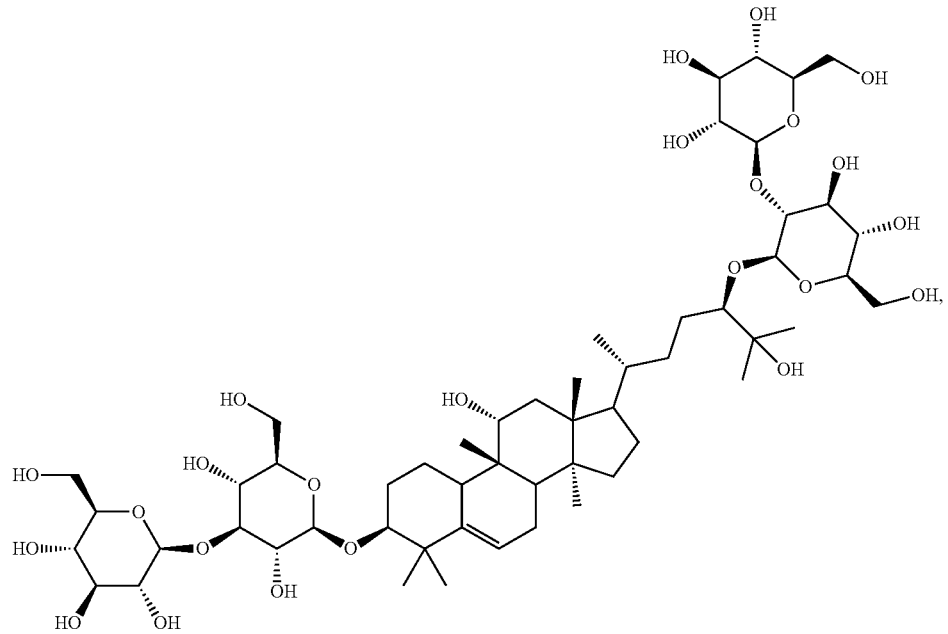
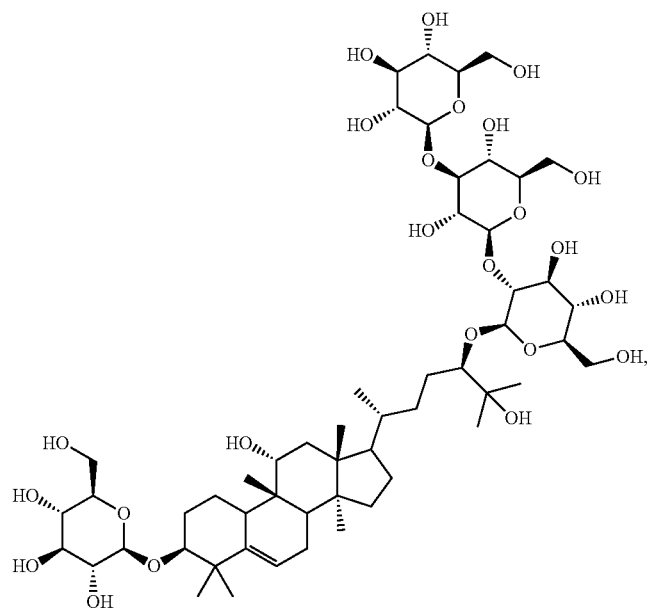

-continued
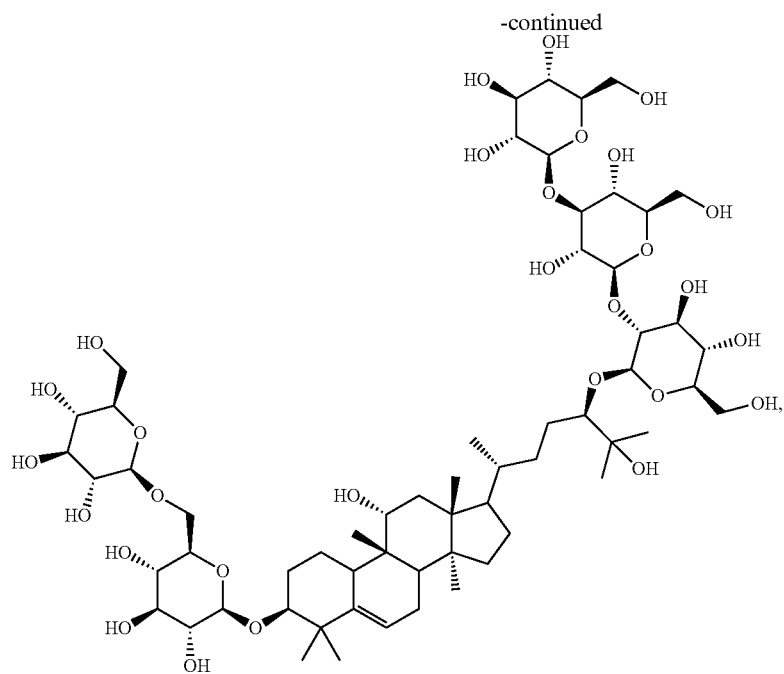
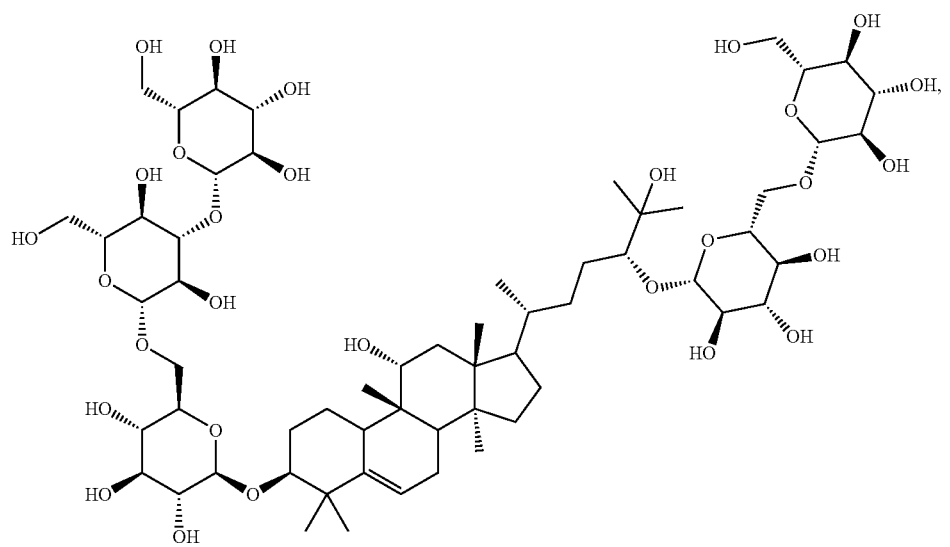

-continued
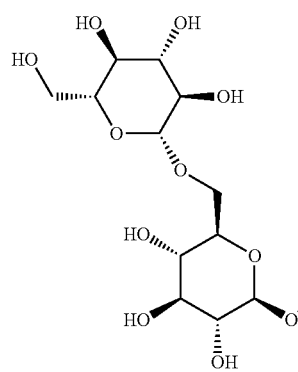
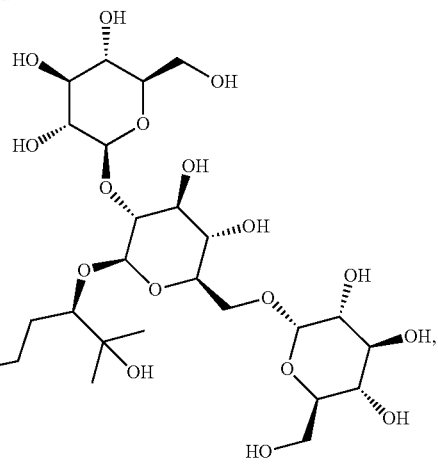
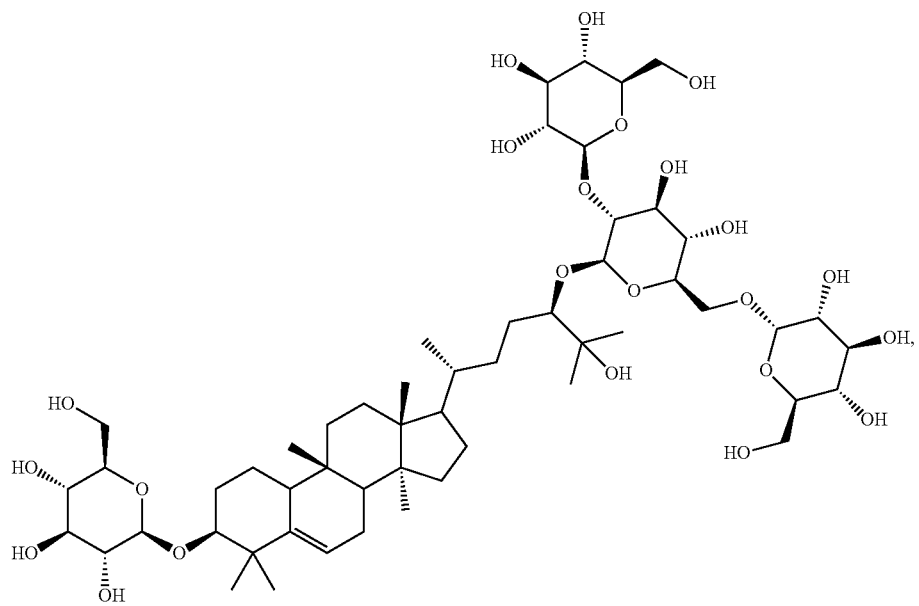

-continued
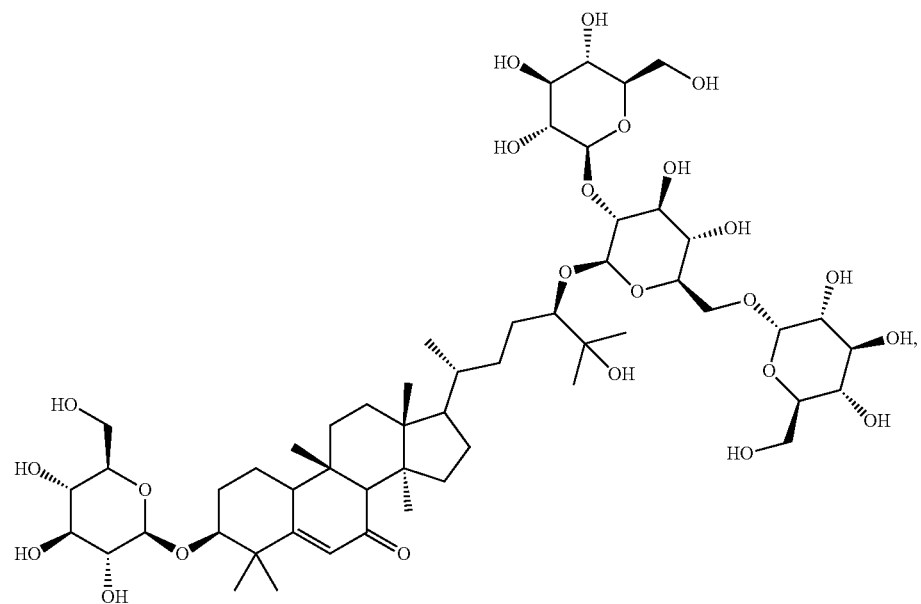
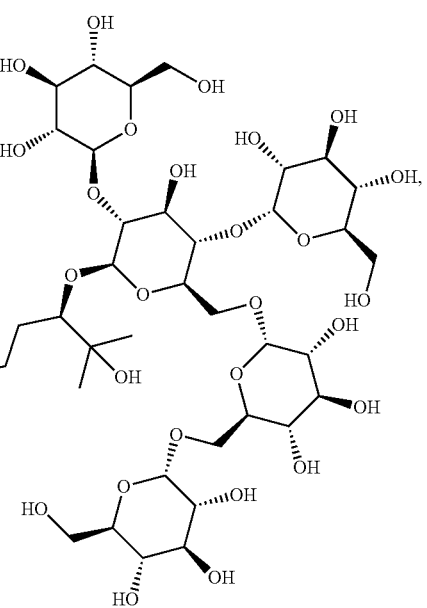

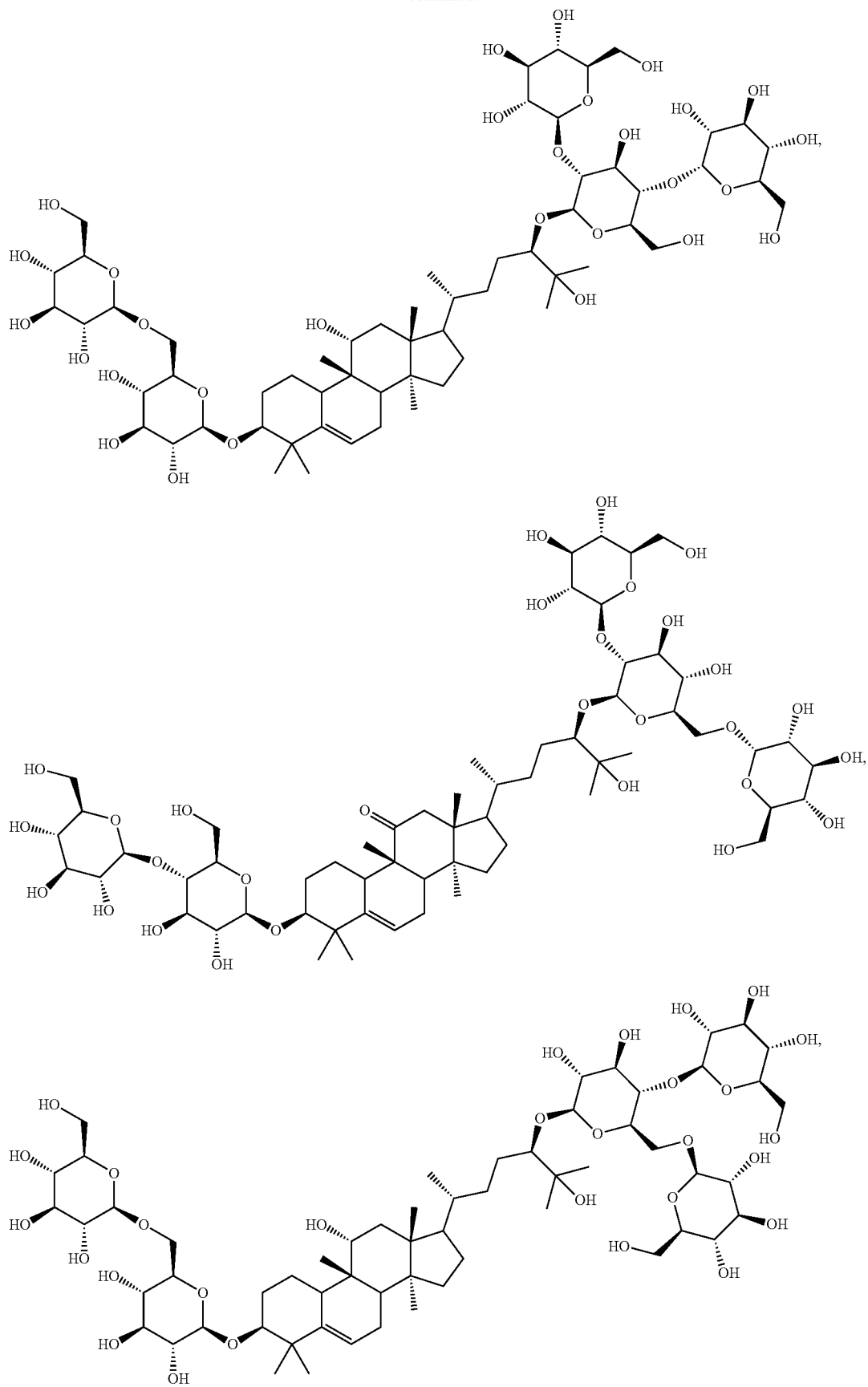

-continued
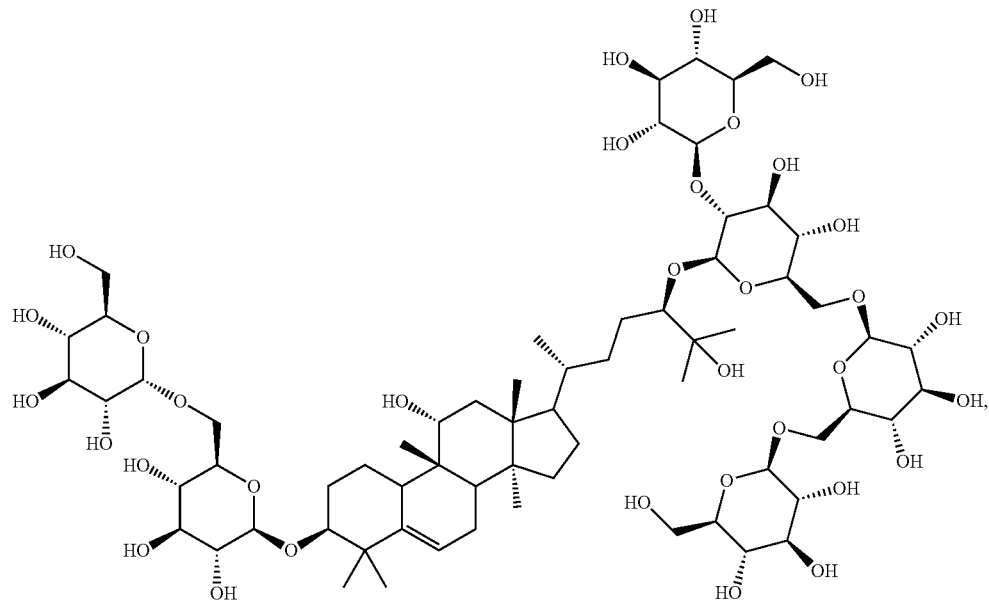
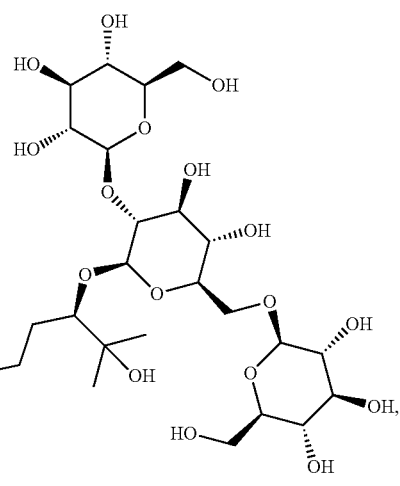

-continued
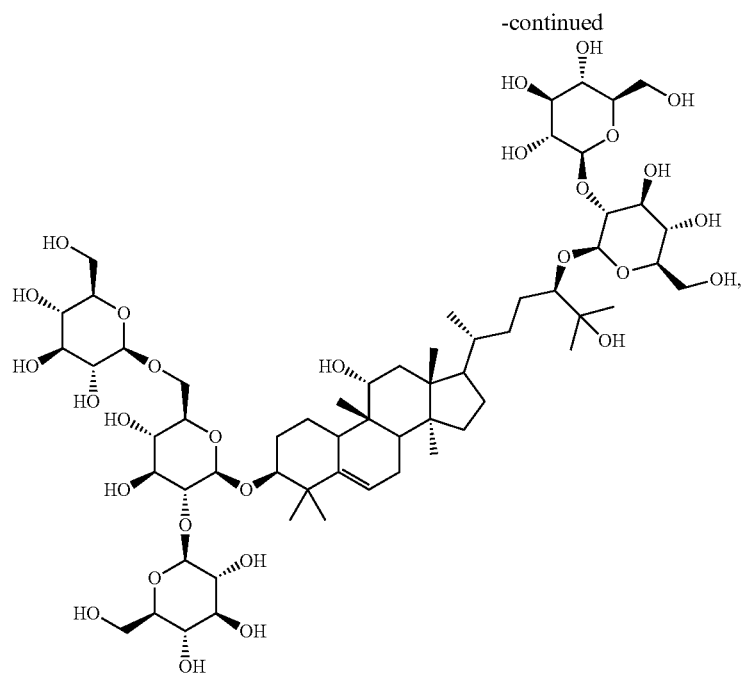
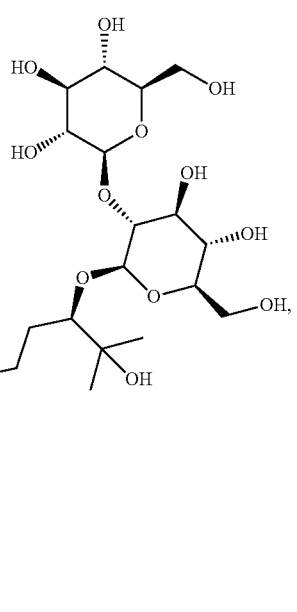

-continued
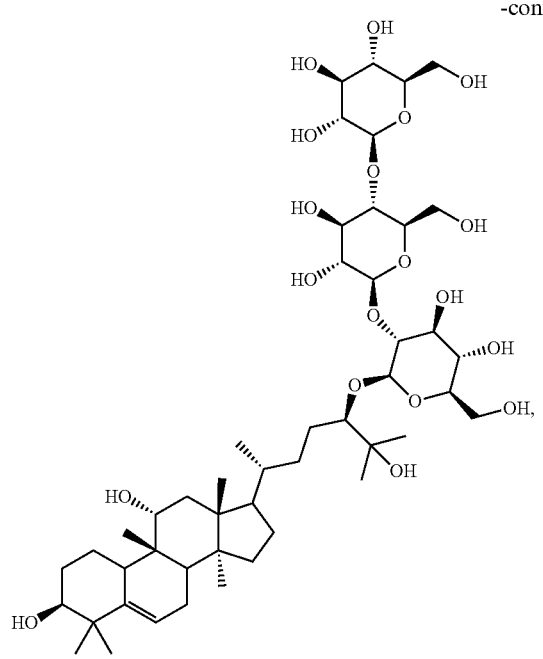
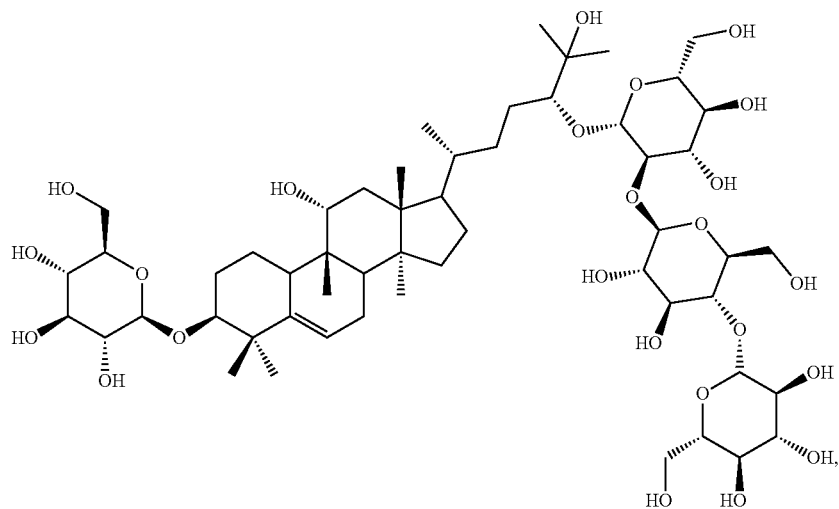
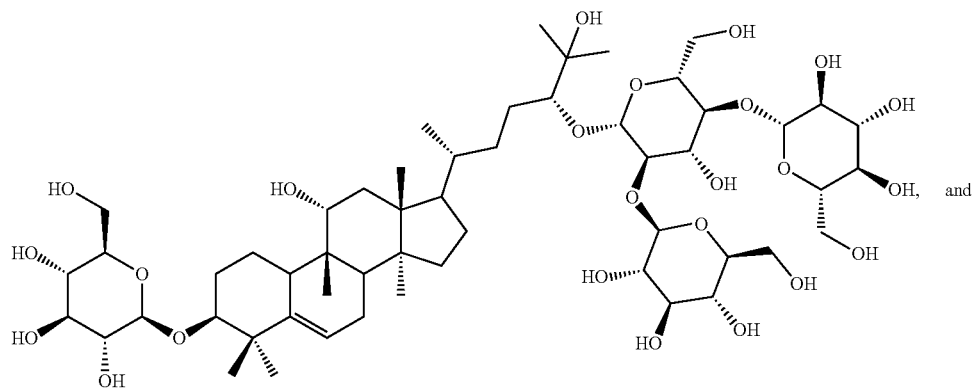
and

-continued
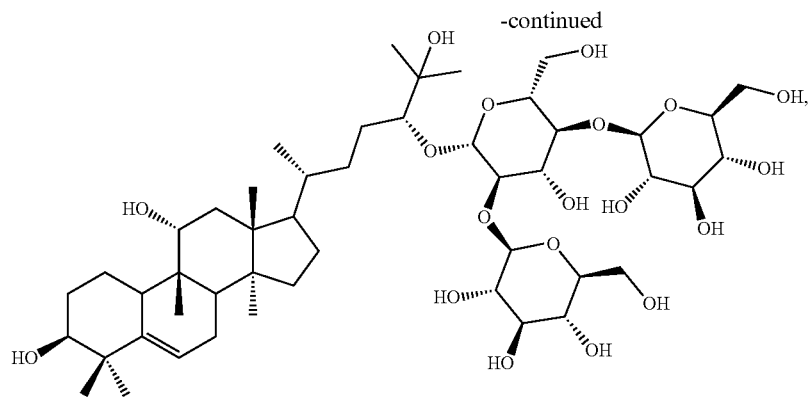
or a salt thereof.
Some embodiments provide a method of making a compound having the structure:
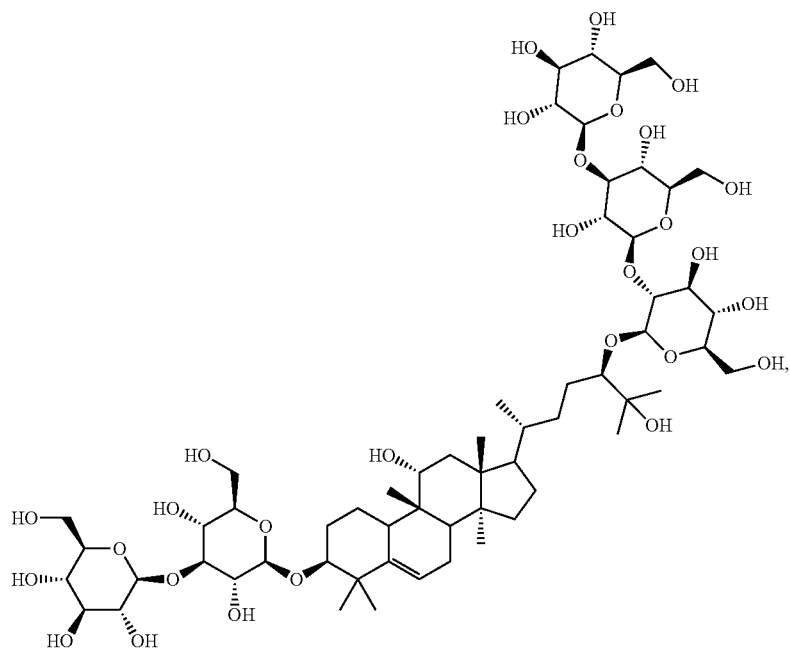 [SMILES: C[C@H](CC[C@@H](O[C@@H]1O[C@H](CO)[C@@H](O)[C@H](O)[C@H]1O[C@@H]1O[C@H](CO)[C@@H](O)[C@H](O[C@@H]2O[C@H](CO)[C@@H](O)[C@H](O)[C@H]2O)[C@H]1O)C(C)(C)O)C1CC[C@@]2(C)C3CC=C4C(CC[C@H](O[C@@H]5O[C@H](CO)[C@@H](O)[C@H](O[C@@H]6O[C@H](CO)[C@@H](O)[C@H](O)[C@H]6O)[C@H]5O)C4(C)C)[C@]3(C)[C@H](O)C[C@]12C]
the method comprising treating Mogroside III$_E$ with the glucose transferase enzyme UGT76G1.
Some embodiments provide a method of making a compound having the structure of Compound 1:

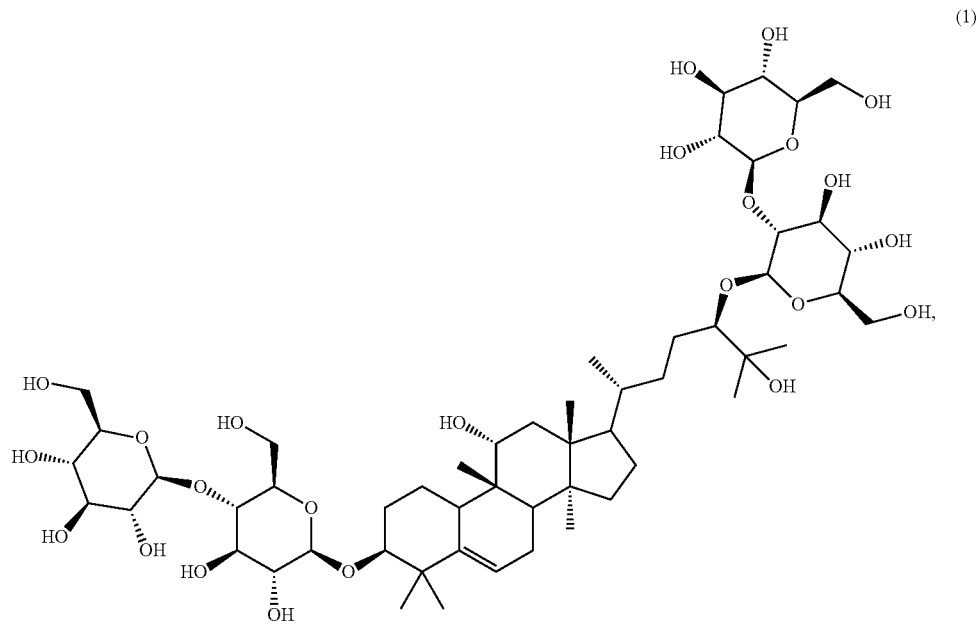 [SMILES: C[C@H](CC[C@@H](O[C@@H]1O[C@H](CO)[C@@H](O)[C@H](O)[C@H]1O[C@@H]1O[C@H](CO)[C@@H](O)[C@H](O)[C@H]1O)C(C)(C)O)C1CC[C@@]2(C)C3CC=C4C(CC[C@H](O[C@@H]5O[C@H](CO)[C@@H](O[C@@H]6O[C@H](CO)[C@@H](O)[C@H](O)[C@H]6O)[C@H](O)[C@H]5O)C4(C)C)[C@]3(C)[C@H](O)C[C@]12C]

(1)

the method comprising fractionating an extract of *Siraitia grosvenorii* on an HPLC column and collecting an eluted fraction comprising Compound 1.

DETAILED DESCRIPTION

Definitions

Unless defined otherwise, all technical and scientific terms used herein have the same meaning as is commonly understood by one of ordinary skill in the art to which this disclosure belongs. All patents, applications, published applications, and other publications are incorporated by reference in their entirety. In the event that there is a plurality of definitions for a term herein, those in this section prevail unless stated otherwise.

"Solvate" refers to the compound formed by the interaction of a solvent and a compound described herein or salt thereof. Suitable solvates are physiologically acceptable solvates including hydrates.

A "sweetener", "sweet flavoring agent", "sweet flavor entity", "sweet compound," or "sweet tasting compound," as used herein refers to a compound or physiologically acceptable salt thereof that elicits a detectable sweet flavor in a subject.

As used herein, the term "medicinal product" includes both solids and liquid compositions which are ingestible non-toxic materials which have medicinal value or comprise medicinally active agents such as cough syrups, cough drops, aspirin and chewable medicinal tablets.

An "oral care product" includes solids and liquids such as toothpaste or mouthwash.

As used herein, the term "anti-caking agent" refers to a compound placed in powdered or granulated materials to prevent the formation of aggregates (lumps). Suitable anti-caking agents include, but are not limited to cream of tartar, tricalcium phosphate, powdered cellulose (including microcrystalline cellulose), magnesium stearate, sodium bicarbonate, sodium ferrocyanide, potassium ferrocyanide, calcium ferrocyanide, sodium silicate, silicon dioxide, calcium silicate, magnesium trisilicate, talcum powder, sodium aluminosilicate, potassium aluminum silicate, calcium aluminosilicate, bentonite, aluminum silicate, stearic acid, polydimethylsiloxane.

As used herein, the term "chelating agent" refers to a compound that can form two or more bonds with a metal ion (e.g., a multidentate ligand). Suitable chelating agents include, but are not limited to ethylene diamine, ethylenediaminetetraacetic acid (EDTA), citric acid, and amino acids.

A "flavor modifying compound" or "flavor modifier" or "flavor modifying agent" herein refers to a compound or the ingestibly acceptable salt or solvate thereof that modulates, including enhancing or potentiating, and/or inducing, the tastes of a flavoring agent in an animal or a human. An example of a flavor modifying compound is a sweet flavor enhancer.

A "flavoring agent" herein refers to a compound or the ingestibly acceptable salt or solvate thereof that induces a flavor or taste in an animal or a human. The flavoring agent can be natural, semi-synthetic, or synthetic.

A "flavor enhancer" herein refers to a compound or ingestibly acceptable salt thereof that enhances and/or multiplies the tastes of a flavoring agent, or an ingestible composition comprising the flavoring agent.

An "enhancer" herein refers to a compound, or an ingestibly acceptable salt or solvate thereof that modulates (increases) a flavor (e.g., sweetness) or the activation of a particular receptor, preferably the chemosensory, e.g., T1R2/T1R3 receptor.

A "flavor" herein refers to the perception of taste in a subject, which include sweet, sour, salty, bitter and umami. The subject may be a human or an animal.

A "sweet flavor modifier" or "sweet flavor modifying agent" herein refers to a compound or ingestibly acceptable salt or solvate thereof that modulates, including enhancing or potentiating, inducing, or blocking, the sweet taste of a sweet flavoring agents in an animal or a human. The sweet flavor modifier includes both sweet flavor enhancer and sweet flavoring agent.

A "sweet flavor enhancer" or "sweet flavor enhancing agent" herein refers to an enhancer of a sweet flavor wherein the term enhancer is the same as defined above.

The "sugar-like" characteristics of the compounds of the present invention include any characteristic similar to that of sucrose and include, but are not limited to, maximal response, flavor profile, temporal profile, adaptation behavior, mouthfeel, concentration/response function, tastant/and flavor/sweet taste interactions, spatial pattern selectivity, and temperature effects. These characteristics are dimensions in which the taste of sucrose is different from the tastes of other compounds. Of these, the flavor profile and temporal profile are particularly important. In a single tasting of a sweet food or beverage, differences (1) in the attributes that constitute a sweetener's flavor profile and (2) in the rates of sweetness onset and dissipation, which constitute a sweetener's temporal profile, between those observed for sucrose and other compounds can be noted.

The flavor profile of a sweetener is a quantitative profile of the relative intensities of all of the taste attributes exhibited. Such profiles often are plotted as histograms or radar plots.

As used herein, "isolated" means that the indicated compound has been separated from its natural milieu, such that one or more other compounds or biological agents present with the compound in its natural state are no longer present.

As used herein, "purified" means that the indicated compound is present at a higher amount relative to other compounds typically found with the indicated compound (e.g., in its natural environment). In various embodiments, the relative amount of purified a purified compound is increased by greater than 1%, 5%, 10%, 20%, 30%, 40%, 50%, 80%, 90%, 100%, 120%, 150%, 200%, 300%, 400%, or 1000%. In some embodiments, a purified compound is present at a weight percent level greater than 1%, 5%, 10%, 20%, 30%, 40%, 50%, 60%, 70%, 80%, 90%, 95%, 98%, 99%, or 99.5% relative to other compounds combined with the compound.

As used herein, "pyranose" refers to carbohydrate groups having a chemical structure with a six-membered ring including five carbon atoms and one oxygen atom, optionally with additional atoms outside the ring. For example, the glucopyranose structures shown below. In some embodiments, a pyranose can be a pentose or a hexose. Non-limiting examples of pyranose include six-membered ring forms of ribose, arabinose, xylose, lyxose, allose, altrose, glucose, mannose, gulose, iodose, galactose, and talose. The pyranose may have either a D- or L-configuration. In the context of Formula (I), a pyranose moiety is present as a mono- or di-radical linked to other parts of the molecule (e.g., the mogrol scaffold or other pyranose or furanose moieties).

As used herein, "furanose" refers to carbohydrate groups having a chemical structure with a five-membered ring including four carbon atoms and one oxygen atom, optionally with additional atoms outside the ring. For example, the glucofuranose structures shown below. In some embodiments, a furanose can be a pentose or a hexose. Non-limiting examples of furanose include five-membered ring forms of ribose, arabinose, xylose, lyxose, allose, altrose, glucose, mannose, gulose, iodose, galactose, and talose. The furanose may have either a D- or L-configuration. In the context of Formula (I), a furanose moiety is present as a mono- or di-radical linked to other parts of the molecule (e.g., the mogrol scaffold or other pyranose or furanose moieties).

Pyranose and furanose moieties may be alpha (α) or beta (β), depending on the orientation of the anomeric hydroxyl group (indicated with an arrow in the structures of glucose, below).

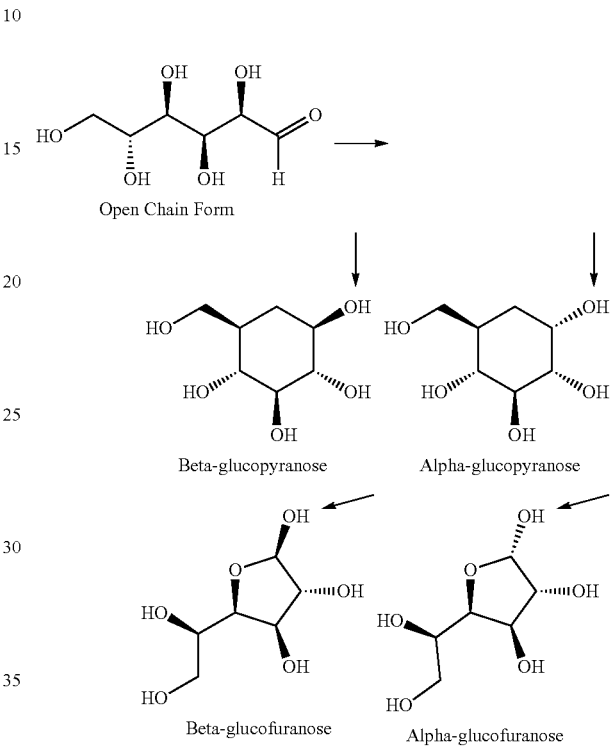

As used herein, a "glycosidic bond" refers to a covalent bond connecting two furanose and/or pyranose groups together. Generally, a glycosidic bond is the bond between the anomeric carbon of one furanose or pyranose moiety and an oxygen of another furanose or pyranose moiety. Glycosidic bonds are named using the numbering of the connected carbon atoms, and the alpha/beta orientation. α- and β-glycosidic bonds are distinguished based on the relative stereochemistry of the anomeric position and the stereocenter furthest from C1 in the ring. For example, sucrose is a disaccharide composed of one molecule of glucose and one molecule of fructose connected through an alpha 1-2 glycosidic bond, as shown below.

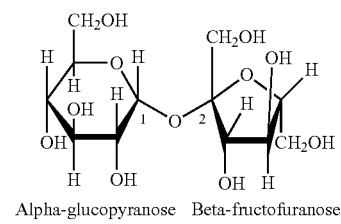

An example of a beta 1-4 glycosidic bond can be found in cellulose:

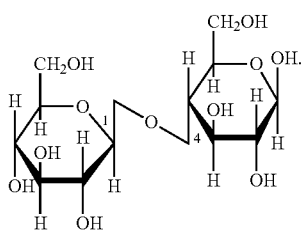

It must be noted that, as used in the specification and the appended claims, the singular forms "a," "an" and "the" include plural referents unless the context clearly dictates otherwise. Thus, for example, reference to "an aromatic compound" includes mixtures of aromatic compounds.

Often, ranges are expressed herein as from "about" one particular value, and/or to "about" another particular value. When such a range is expressed, another embodiment includes from the one particular value and/or to the other particular value. Similarly, when values are expressed as approximations, by use of the antecedent "about," it will be understood that the particular value forms another embodiment. It will be further understood that the endpoints of each of the ranges are significant both in relation to the other endpoint, and independently of the other endpoint.

Compounds

Some embodiments provide a compound having the structure of formula (I):

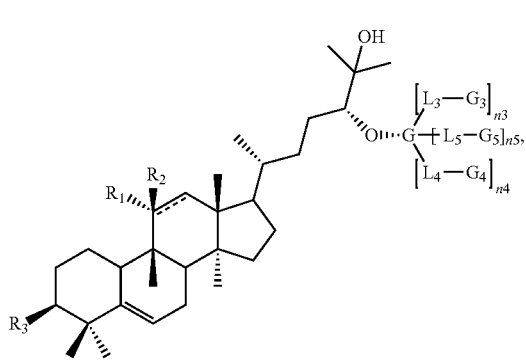

or a salt thereof.

In some embodiments, ═══ represents a carbon-carbon single bond or a carbon-carbon double bond.

In some embodiments, $R_1$ is absent or a hydroxy group and $R_2$ is hydrogen, or $R_1$ and $R_2$, together with the carbon atom to which they are attached, form an oxo group.

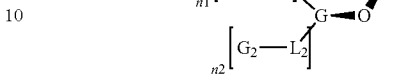

In some embodiments, $R_3$ is selected from —OH and

In some embodiments, each of $n^1$, $n^2$, $n^3$, $n^4$, and $n^5$ are independently an integer from 0 to 3.

In some embodiments, each G, $G_1$, $G_2$, $G_3$, $G_4$, and $G_5$ is independently a furanose or pyranose moiety.

In some embodiments, each $L_1$, $L_2$, $L_3$, $L_4$, and $L_5$ is independently a glycosidic bond.

When ═══ is a carbon-carbon double bond, $R_1$ is absent.

In some embodiments, the compound is in isolated and purified form.

In some embodiments, each of $L_1$, $L_2$, $L_3$, $L_4$, $L_5$ and $L_6$ is independently selected from an α-1,2; α-1,3; α-1,4; α-1,6; β-1,2; β-1,3; β-1,4; and β-1,6 glycosidic bond. In some embodiments, at least one of $L_1$, $L_2$, $L_3$, $L_4$, $L_5$ and $L_6$ is selected from an α-1,2; α-1,3; α-1,4; and α-1,6 glycosidic bond. In some embodiments, at least one of $L_1$, $L_2$, $L_3$, $L_4$, $L_5$ and $L_6$ is selected from an β-1,2; β-1,3; β-1,4; and β-1,6 glycosidic bond. In some embodiments, at least one of $L_1$, $L_2$, $L_3$, $L_4$, $L_5$ and $L_6$ is an α-1,2 glycosidic bond. In some embodiments, at least one of $L_1$, $L_2$, $L_3$, $L_4$, $L_5$ and $L_6$ is an α-1,3 glycosidic bond. In some embodiments, at least one of $L_1$, $L_2$, $L_3$, $L_4$, $L_5$ and $L_6$ is an α-1,4 glycosidic bond. In some embodiments, at least one of $L_1$, $L_2$, $L_3$, $L_4$, $L_5$ and $L_6$ is an α-1,6 glycosidic bond. In some embodiments, at least one of $L_1$, $L_2$, $L_3$, $L_4$, $L_5$ and $L_6$ is an β-1,2 glycosidic bond. In some embodiments, at least one of $L_1$, $L_2$, $L_3$, $L_4$, $L_5$ and $L_6$ is an β-1,3 glycosidic bond. In some embodiments, at least one of $L_1$, $L_2$, $L_3$, $L_4$, $L_5$ and $L_6$ is an β-1,4 glycosidic bond. In some embodiments, at least one of $L_1$, $L_2$, $L_3$, $L_4$, $L_5$ and $L_6$ is an β-1,6 glycosidic bond.

In some embodiments of the compounds, compositions, products, methods, or concentrates described above, formula (I) is not selected from:

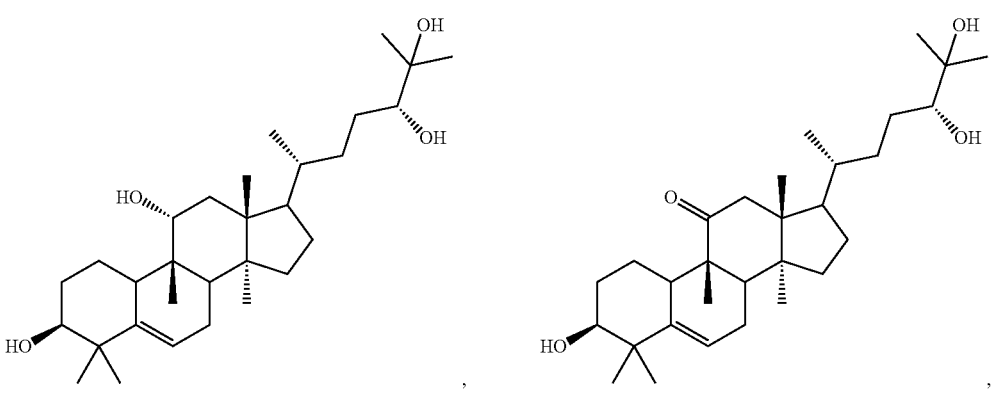

-continued
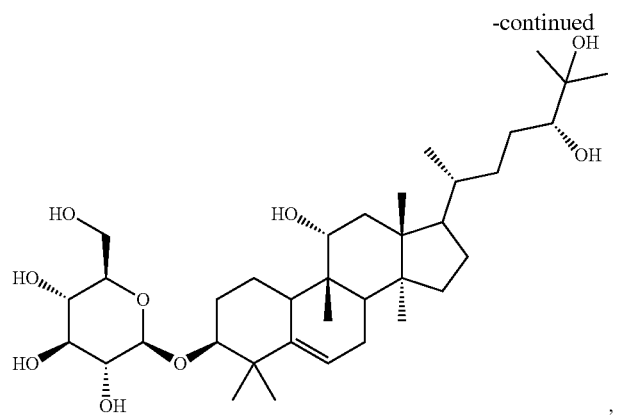
,
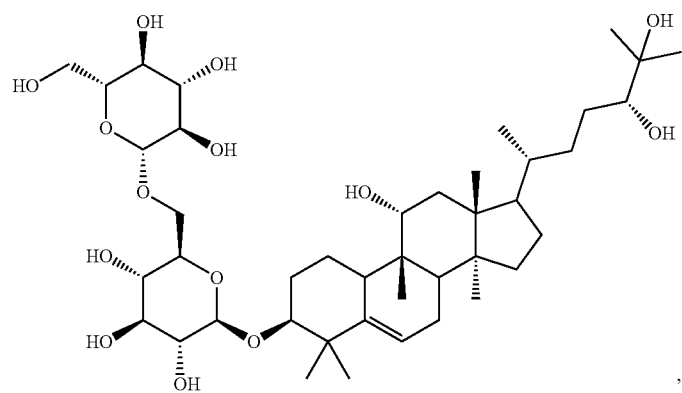
,
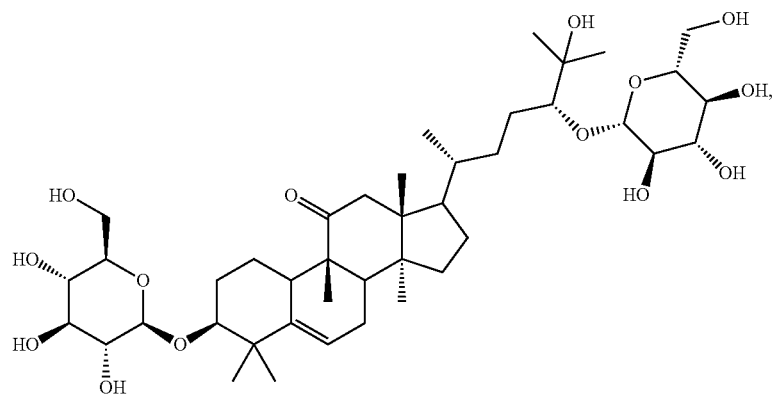
,
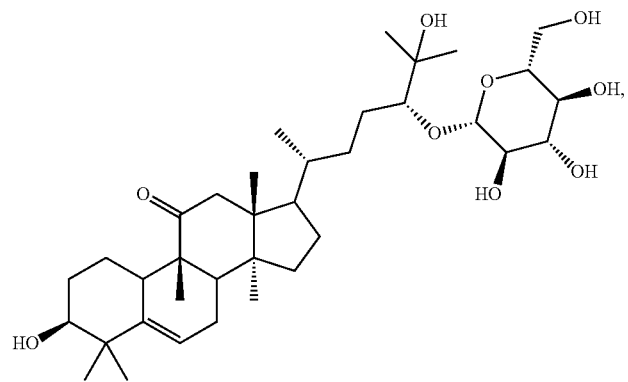

-continued
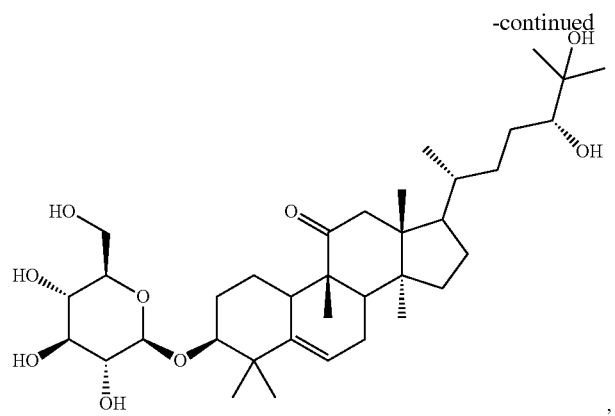
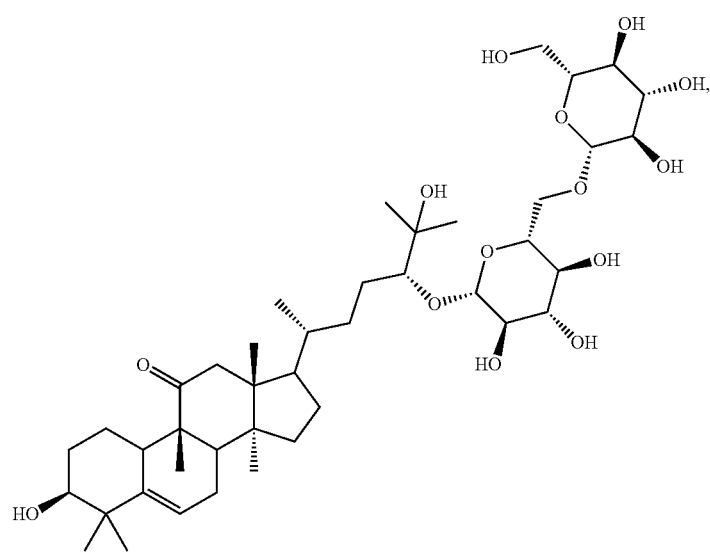
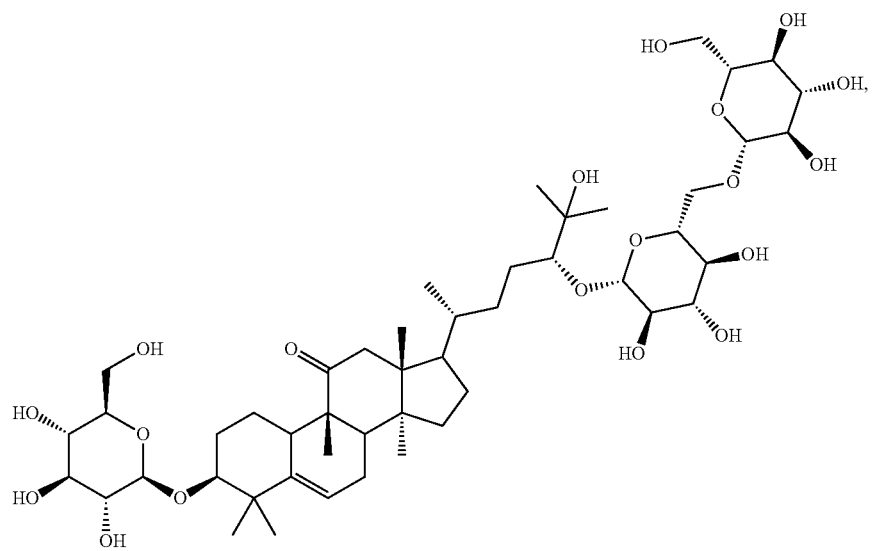

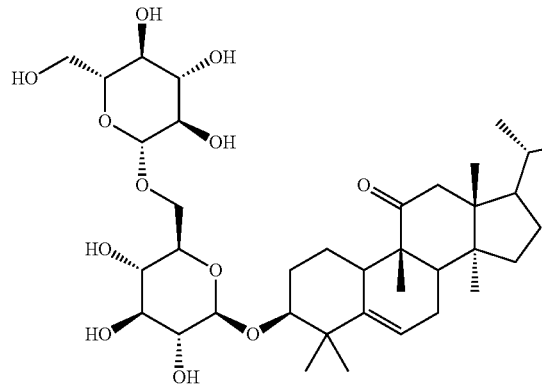
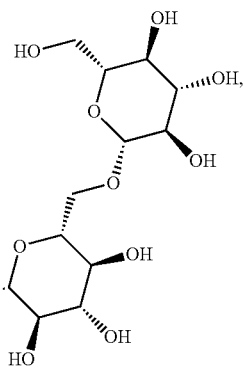
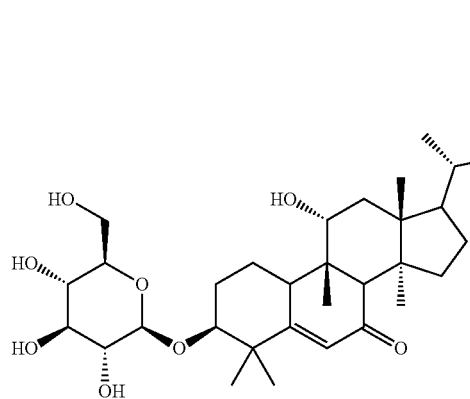
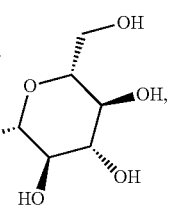
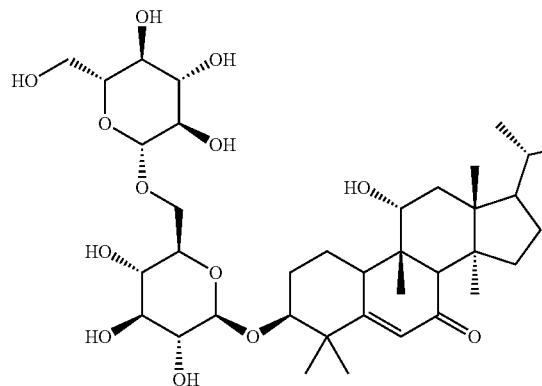
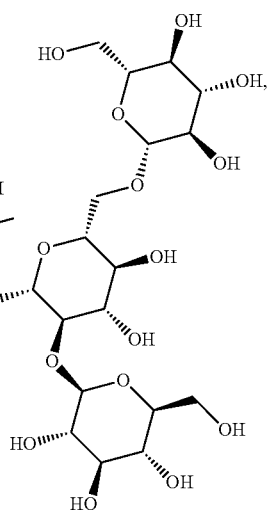

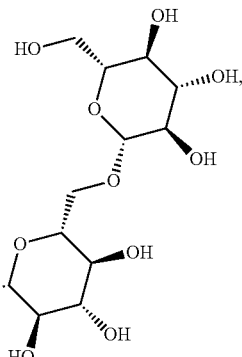
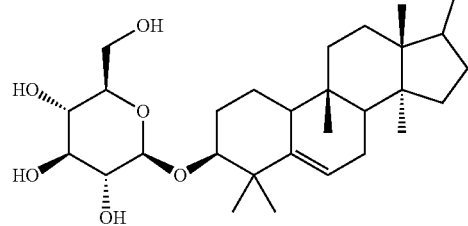
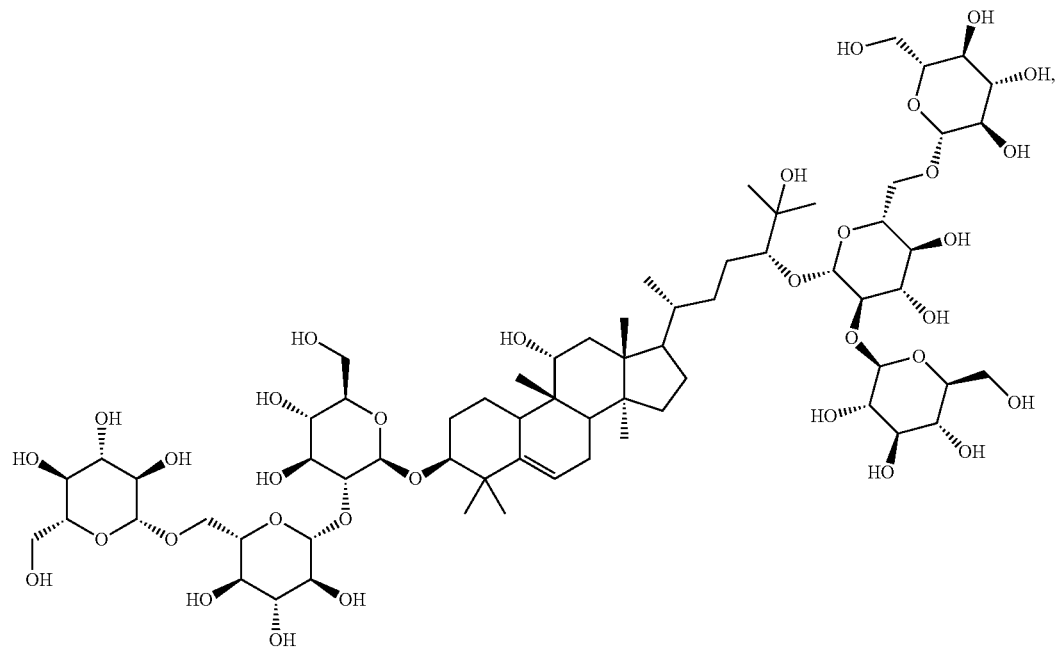

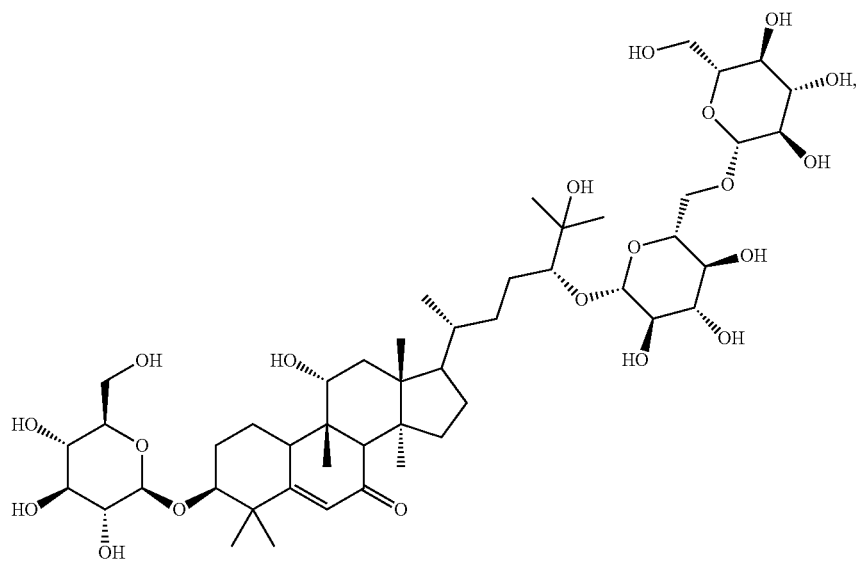
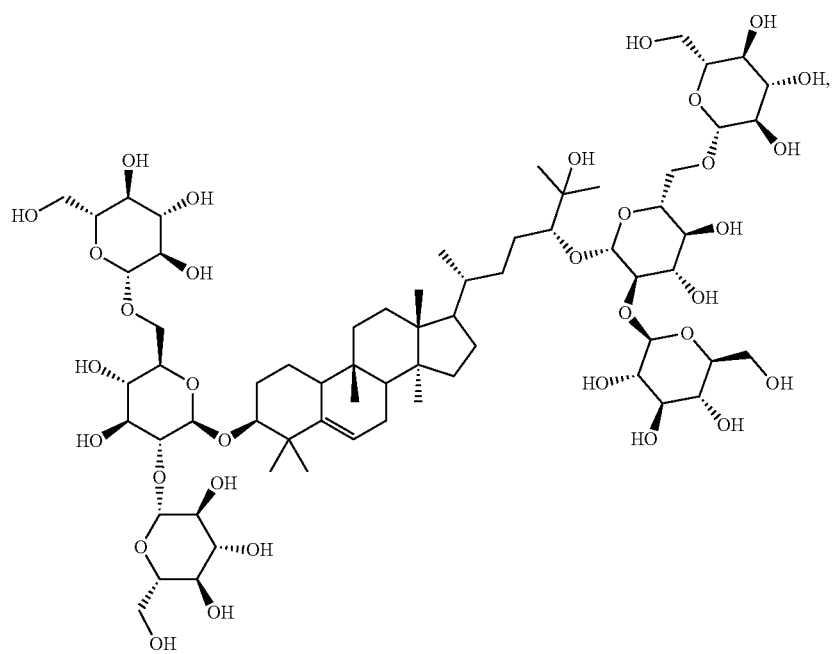

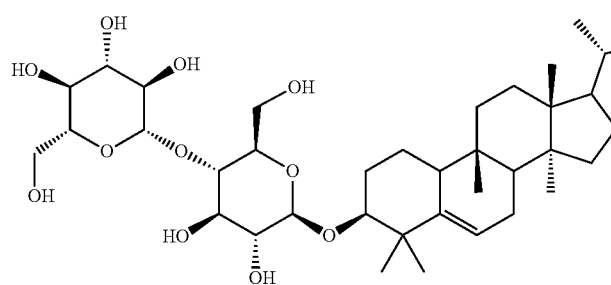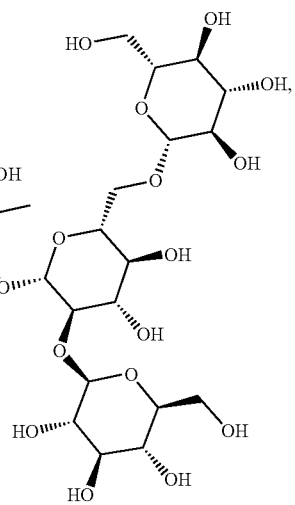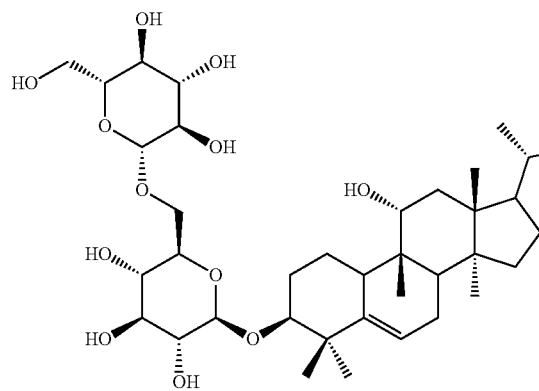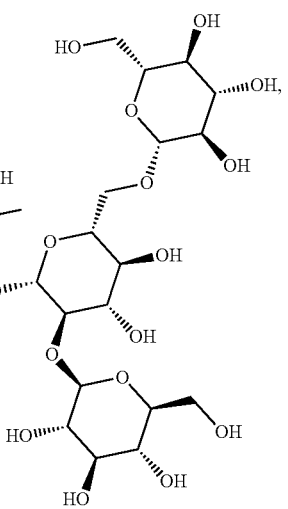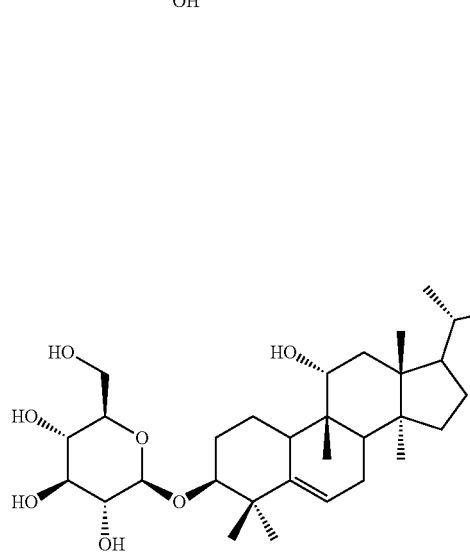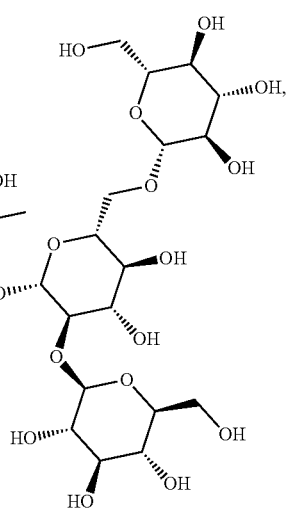

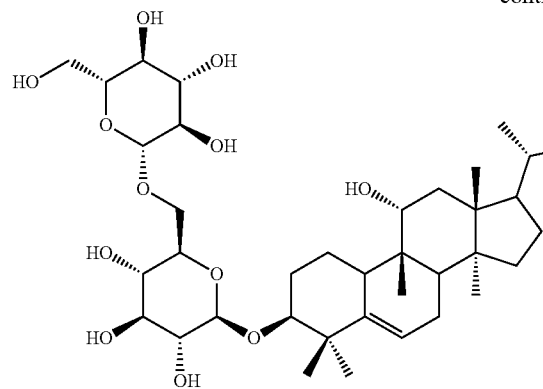
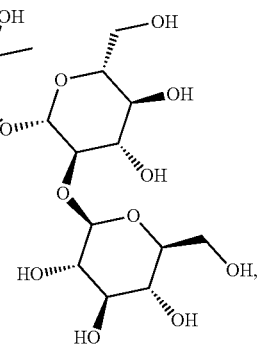
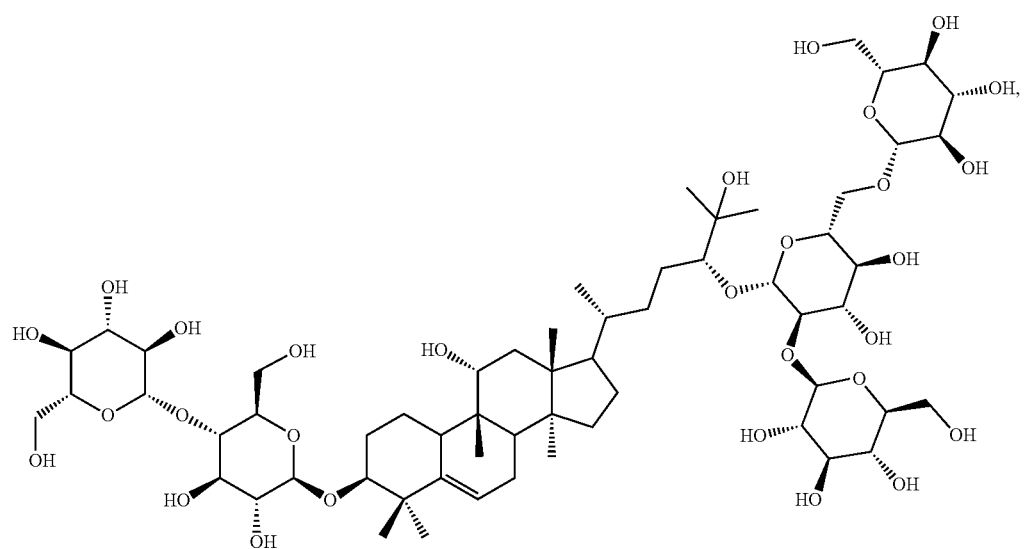
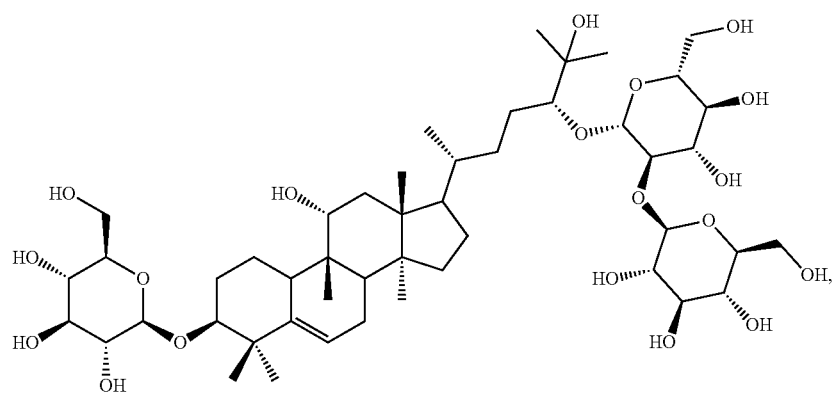

-continued
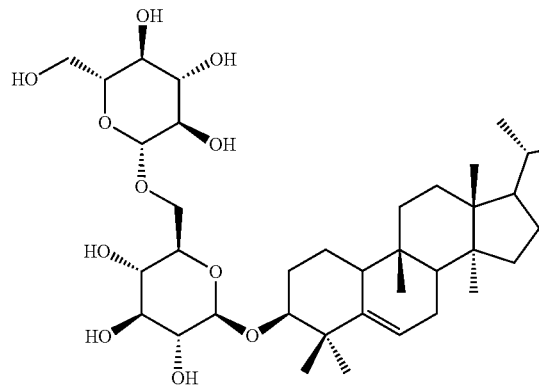
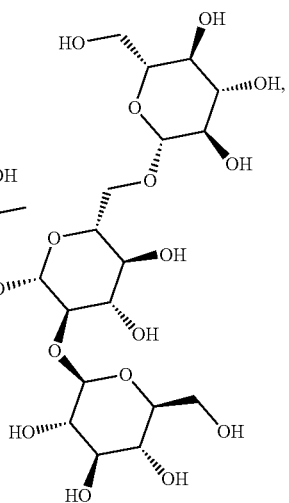
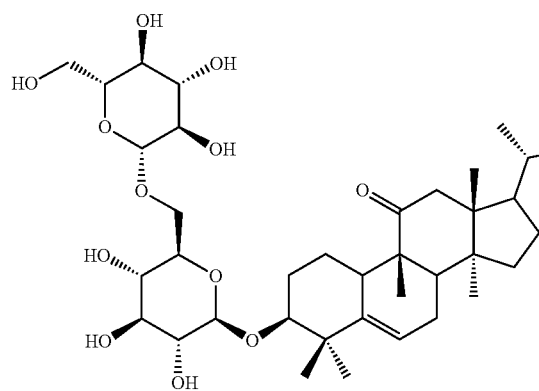
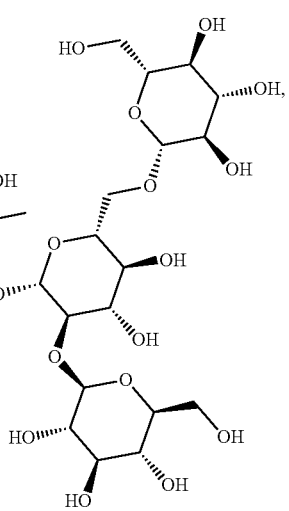
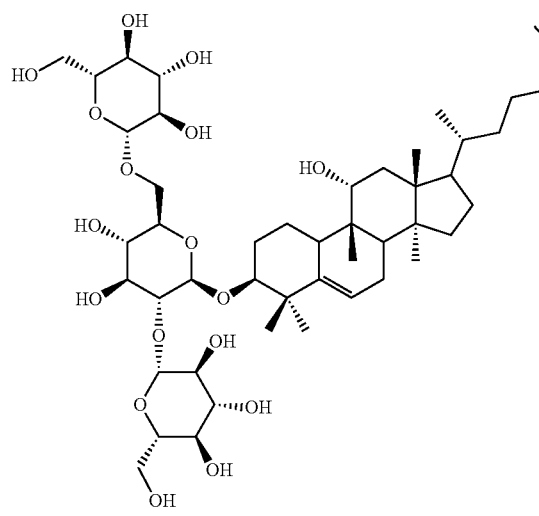
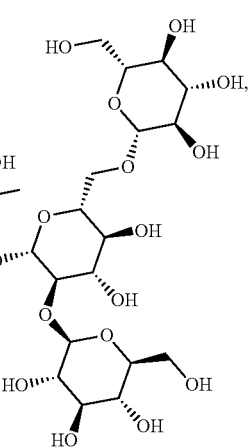

-continued
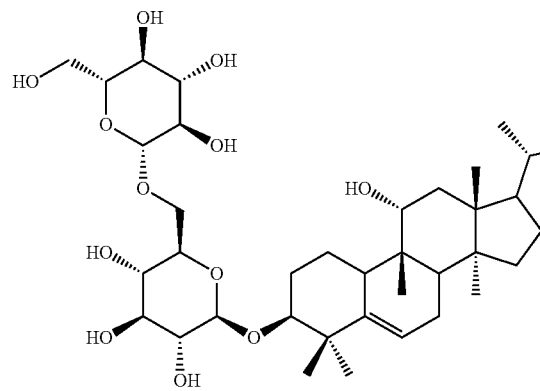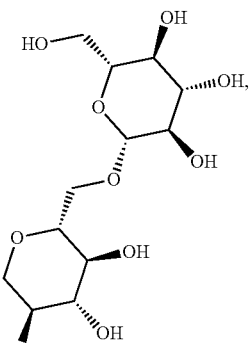
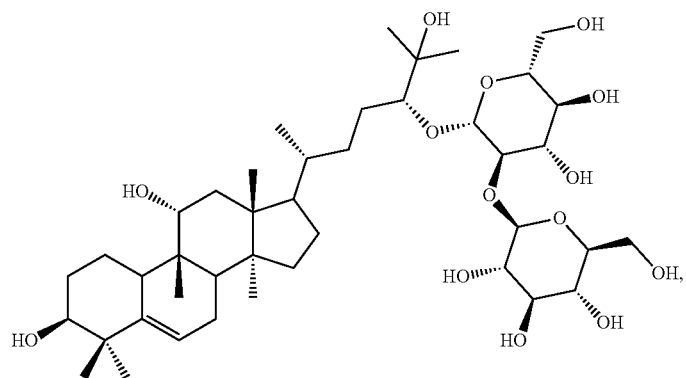
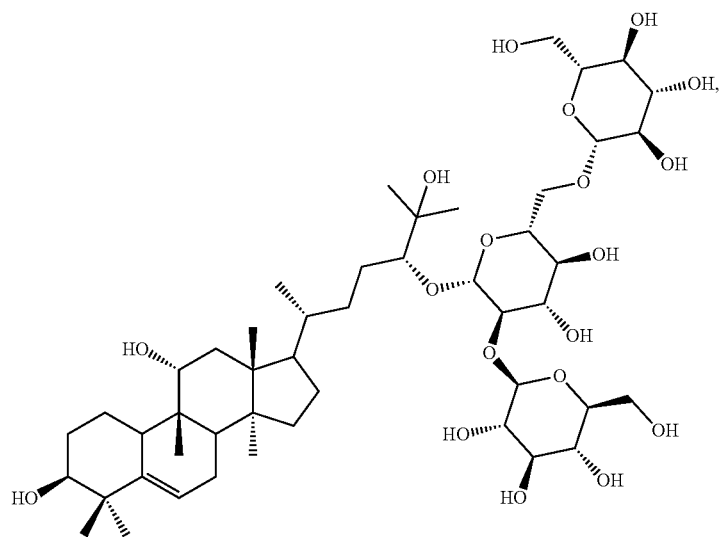

-continued
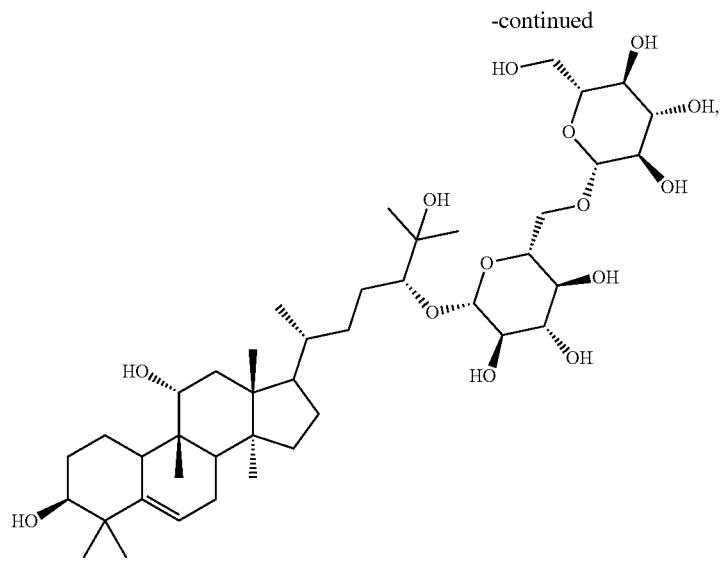
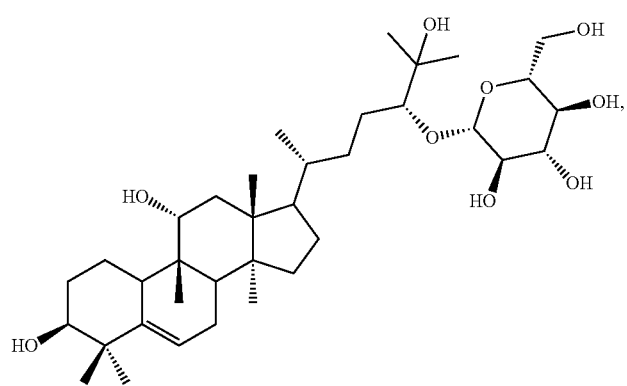
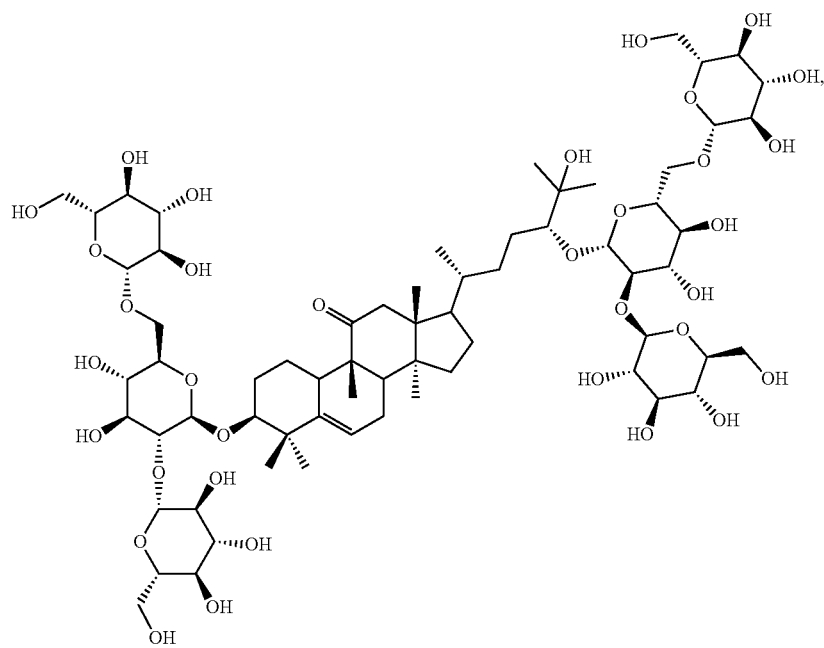

-continued
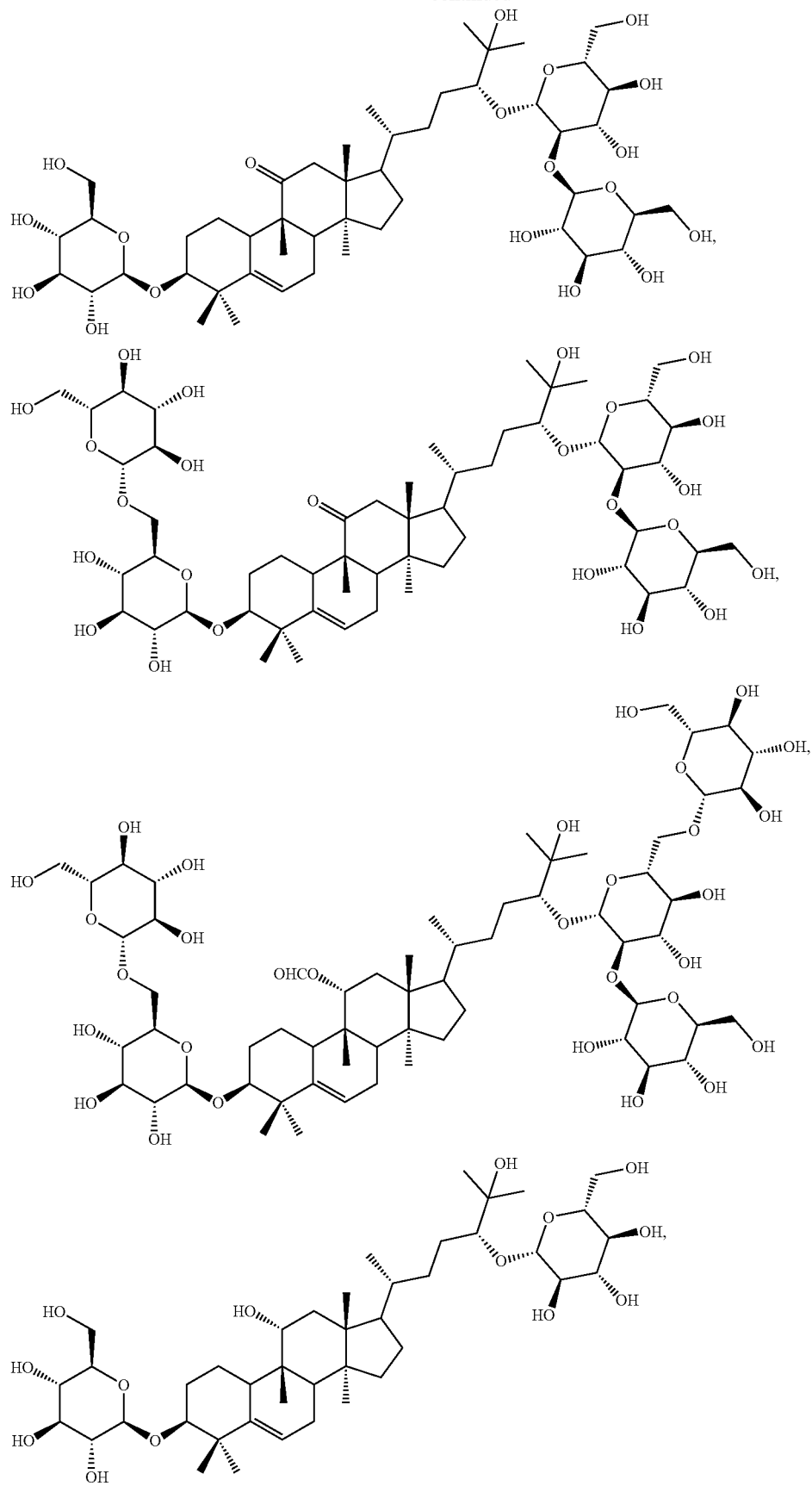

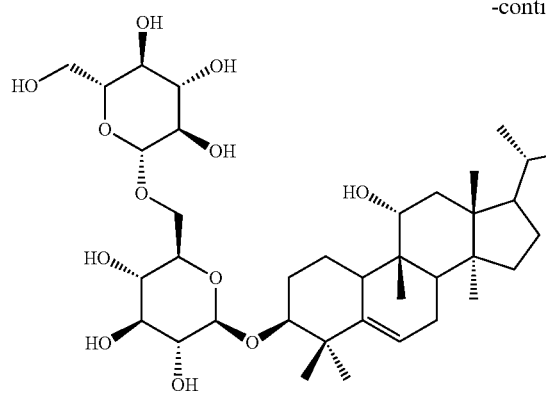
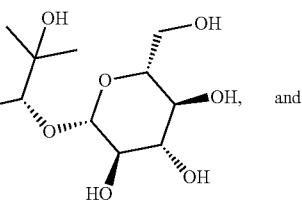
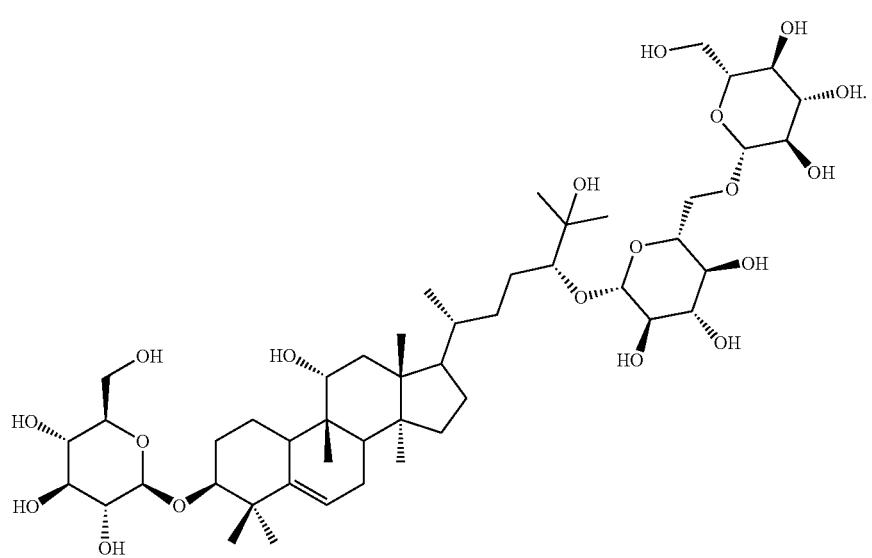
In some embodiments, formula (I) is not:
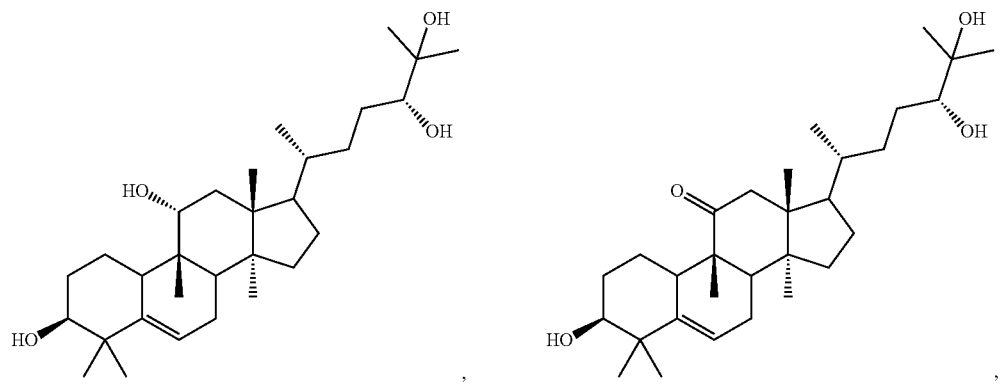

-continued
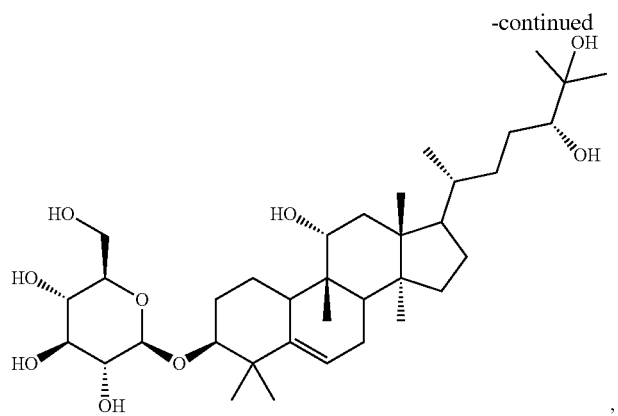
,
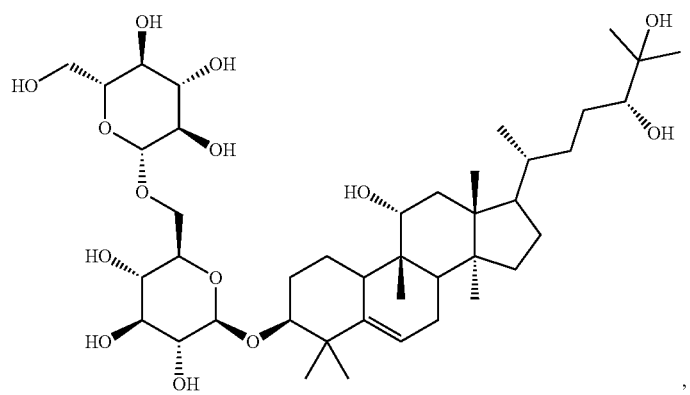
,
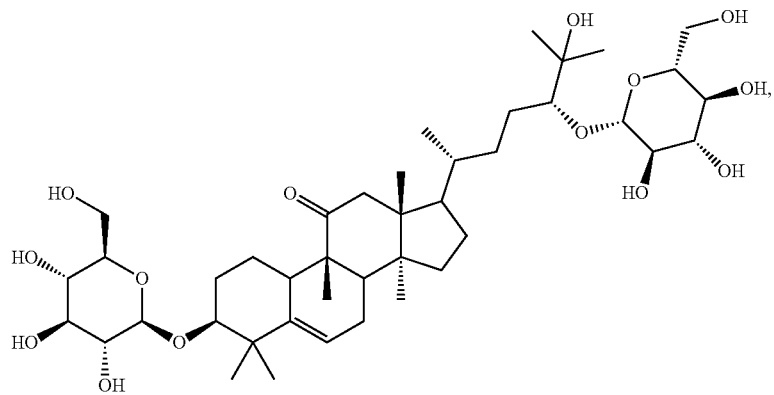
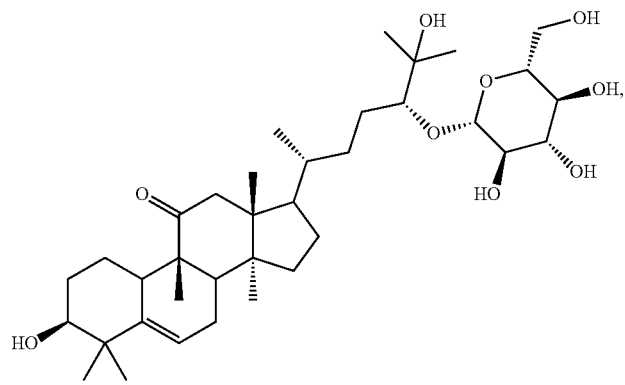

-continued
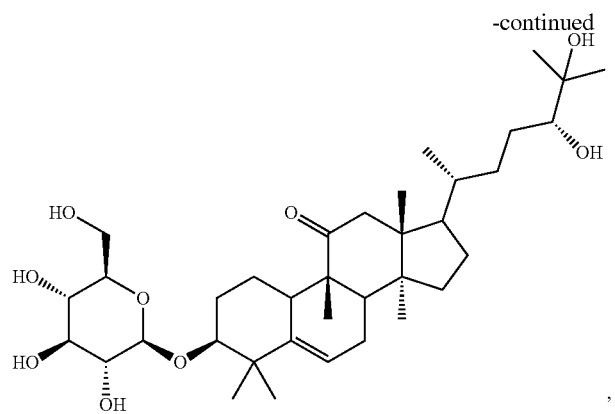
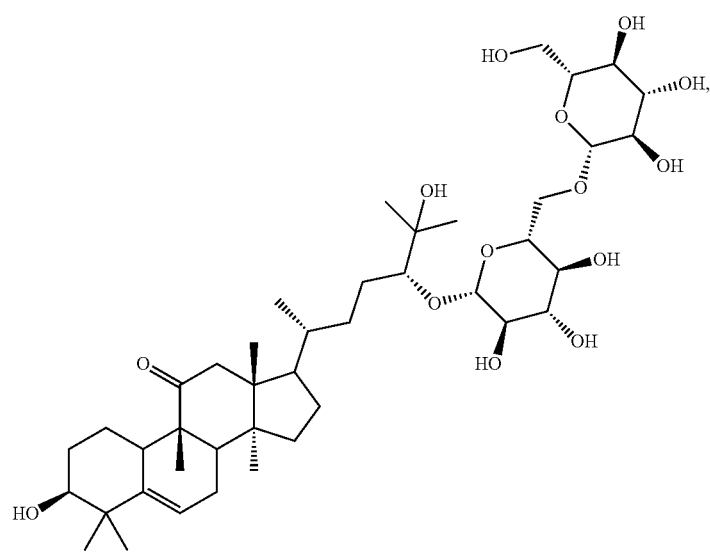
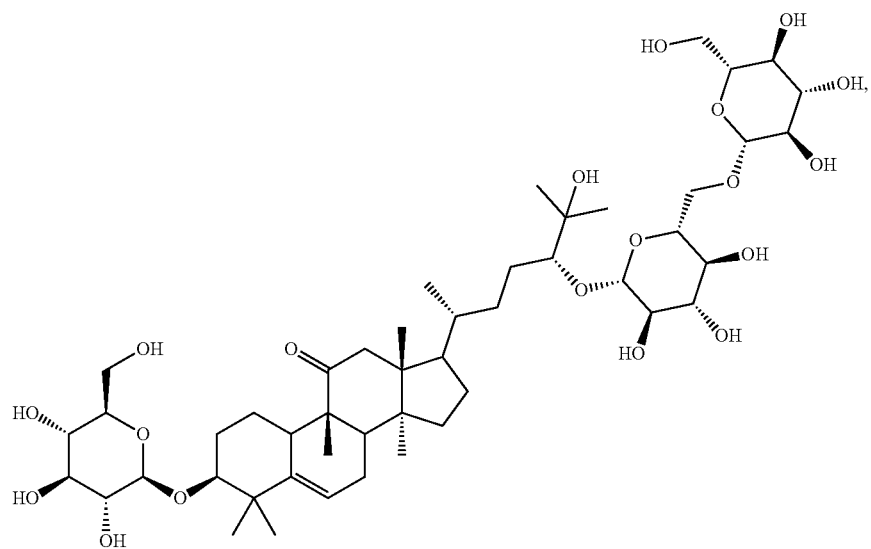

-continued
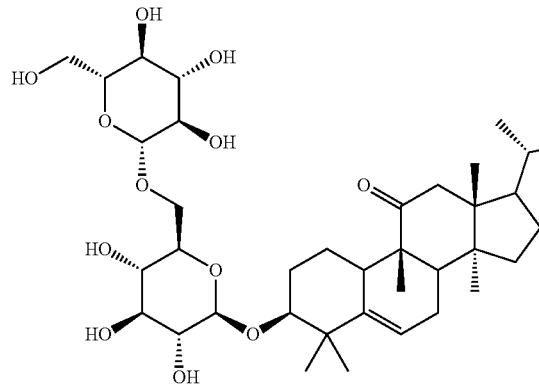
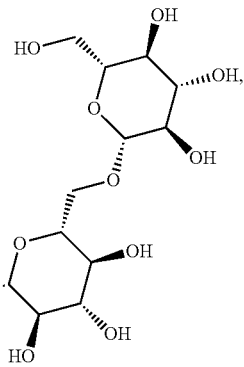
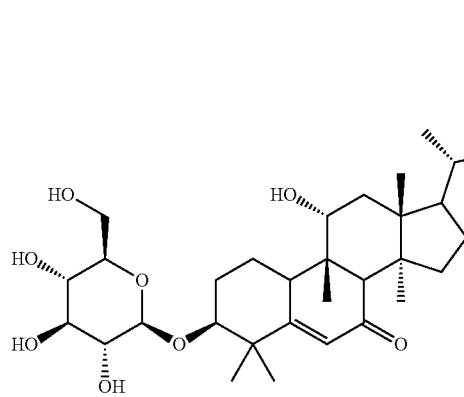
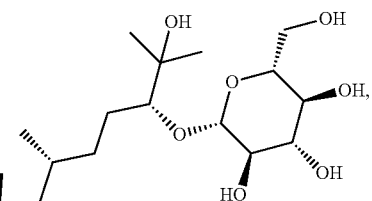
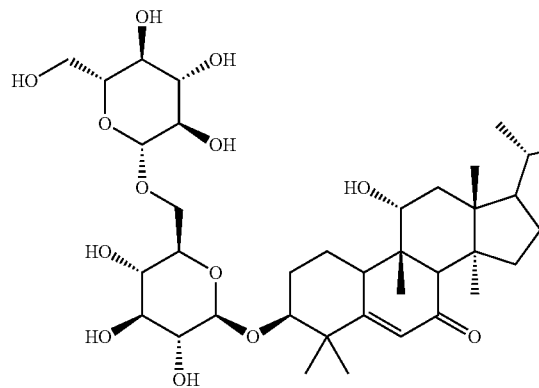
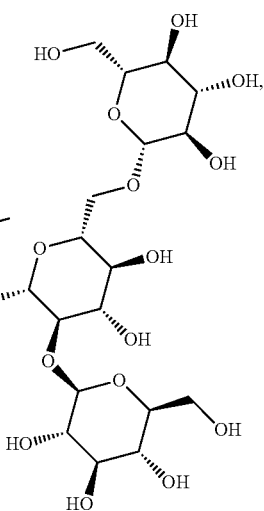

-continued
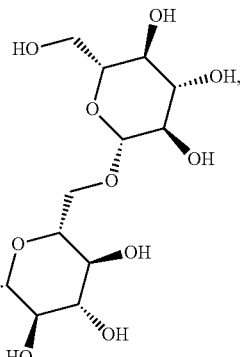
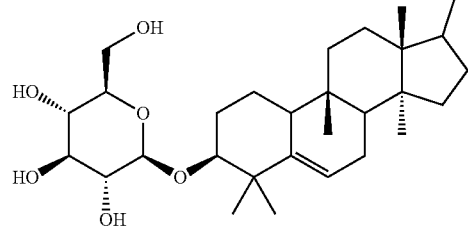
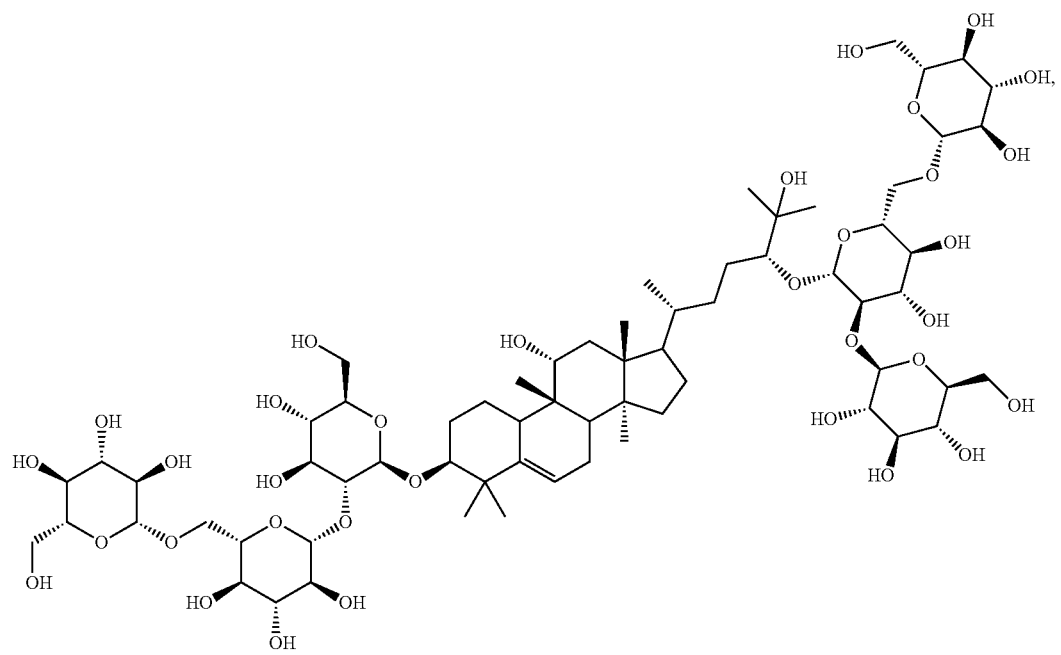

-continued
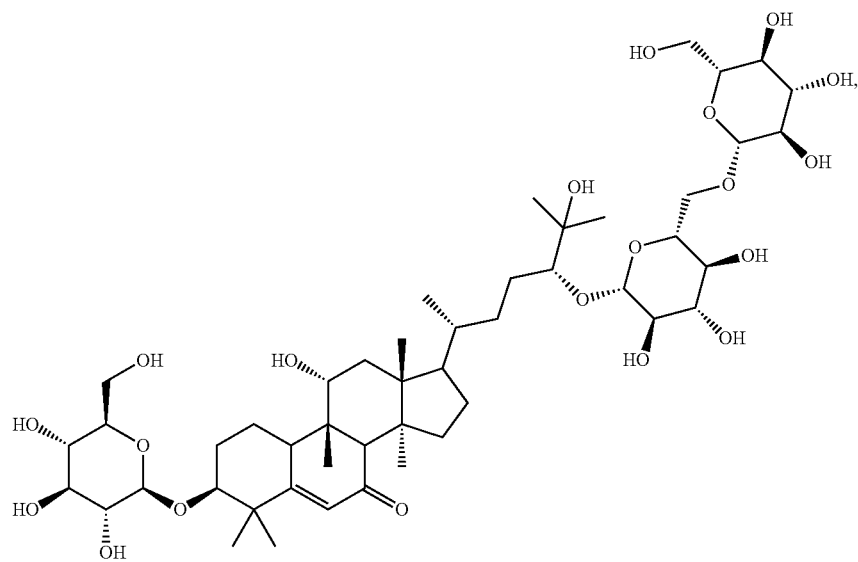
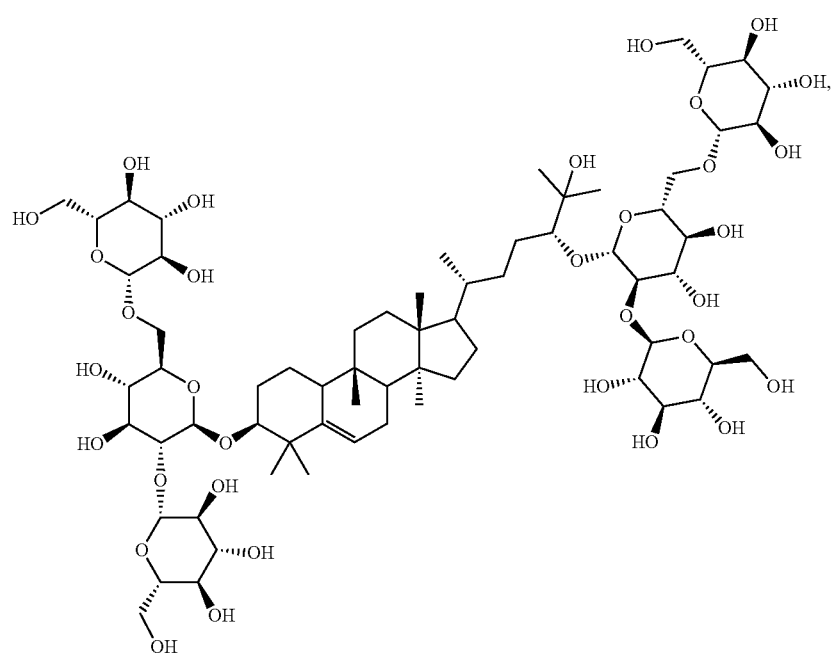

-continued
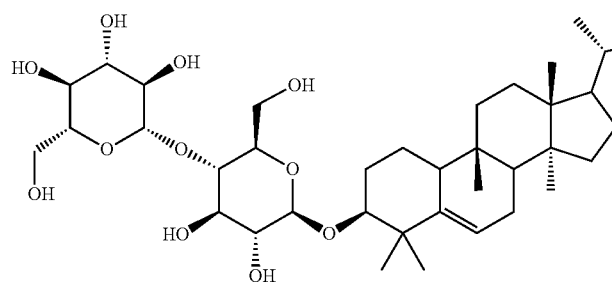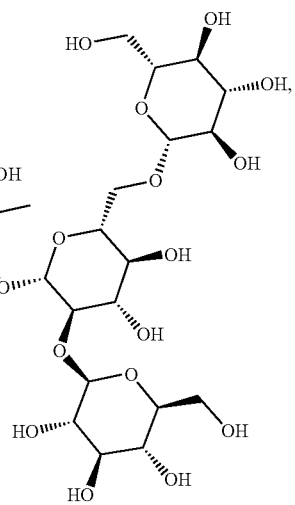
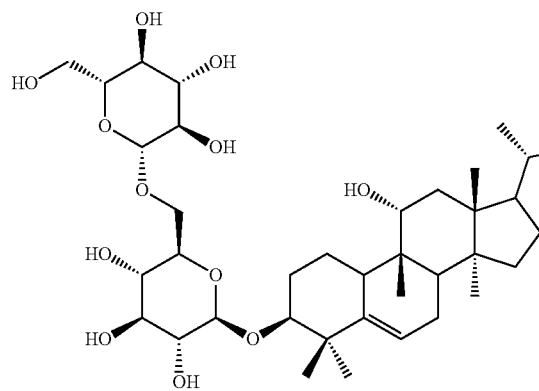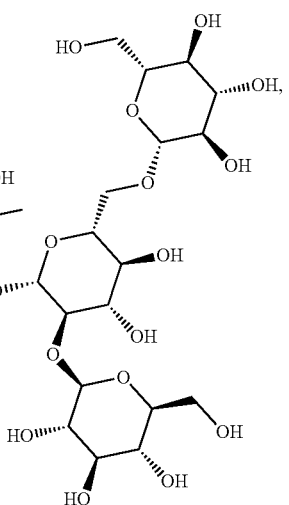
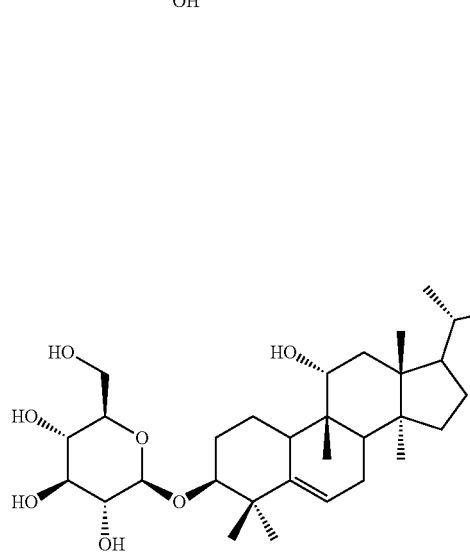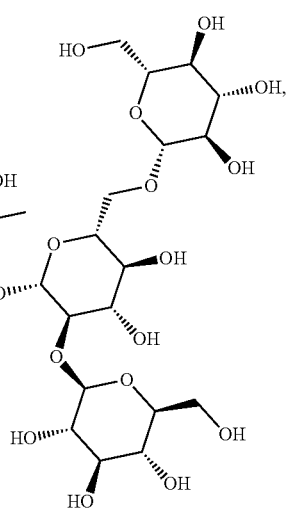

-continued
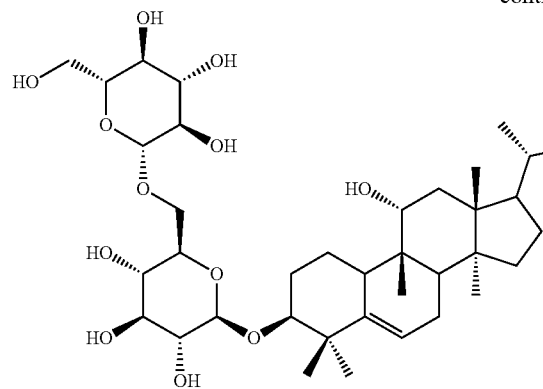
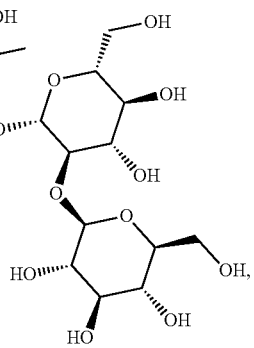
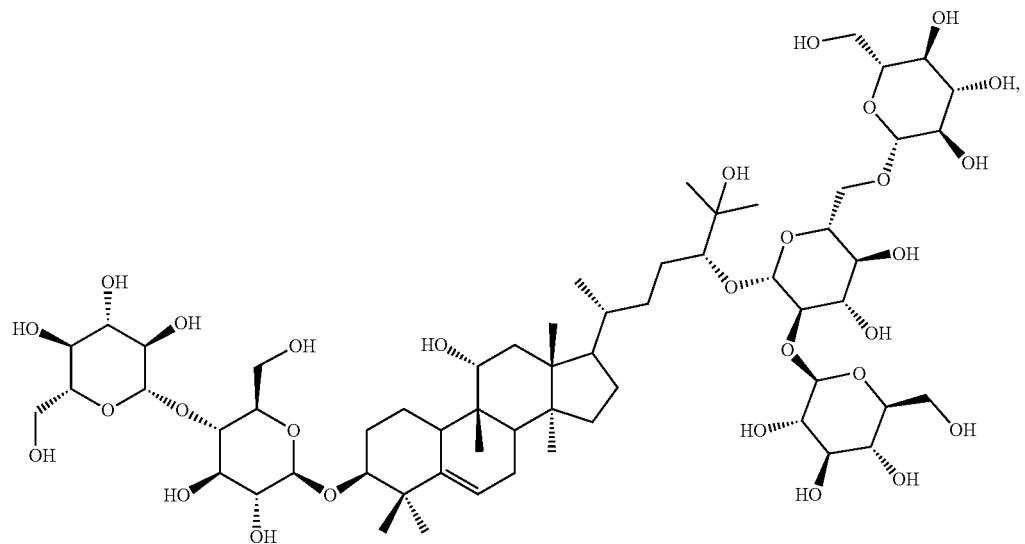
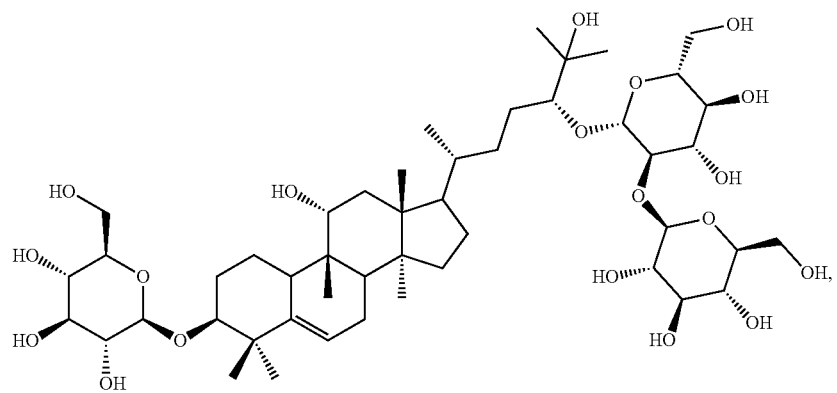

-continued
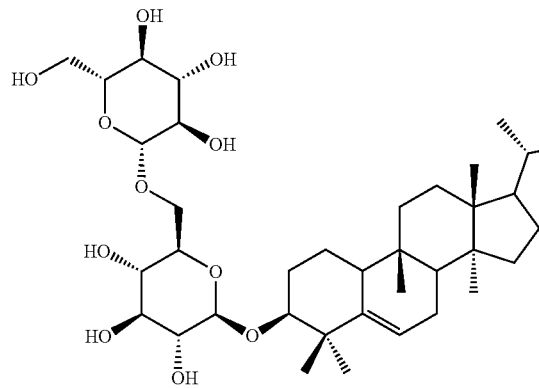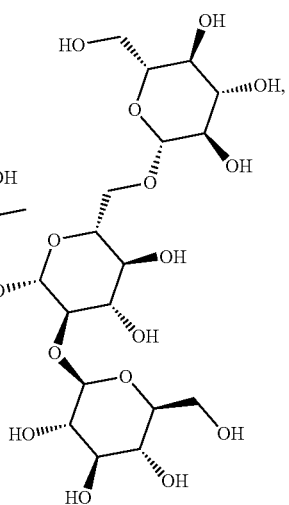
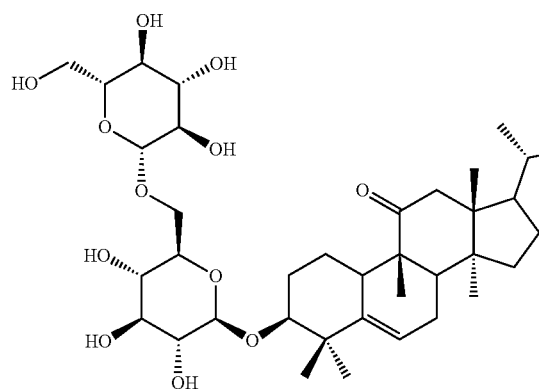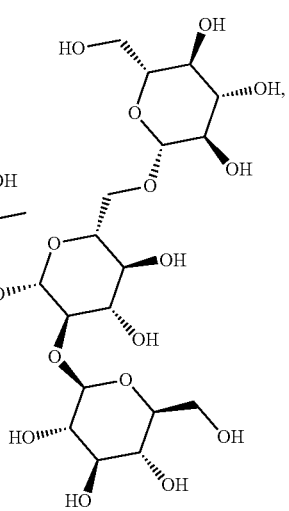
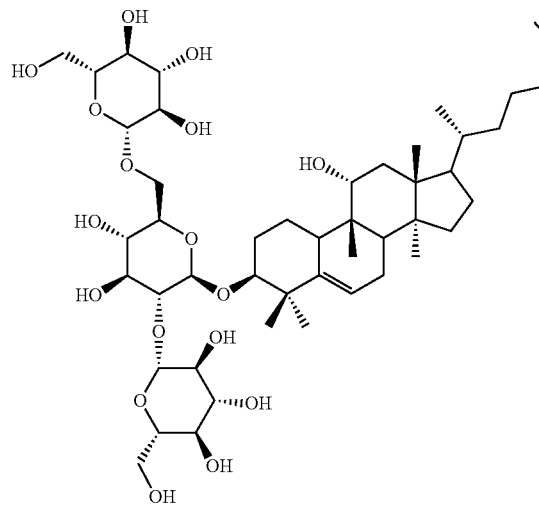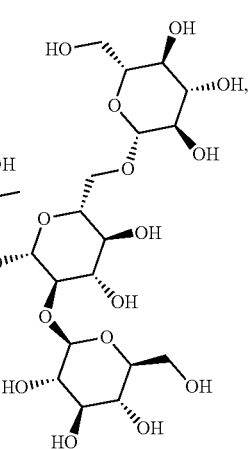

-continued
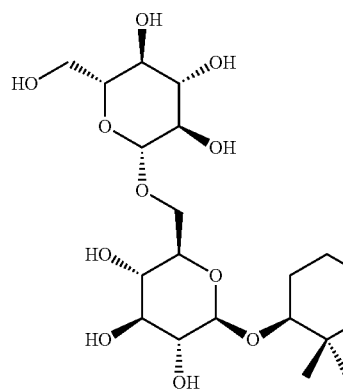
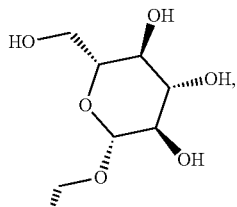
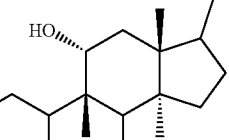
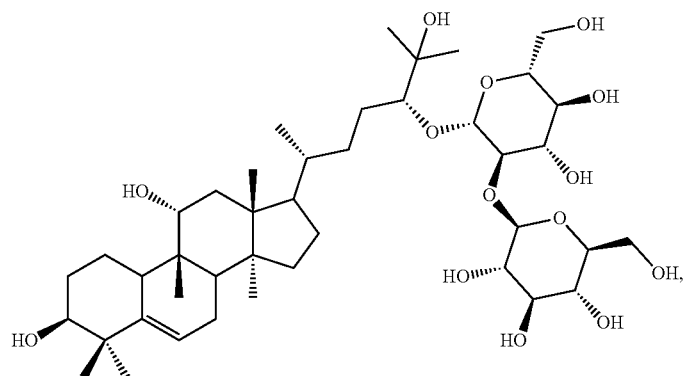
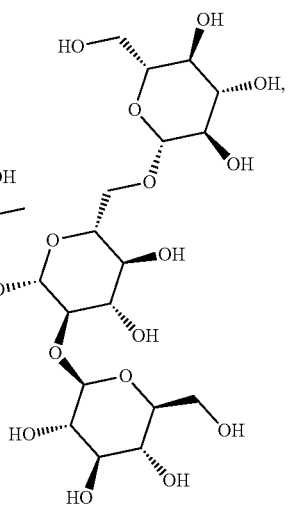

-continued
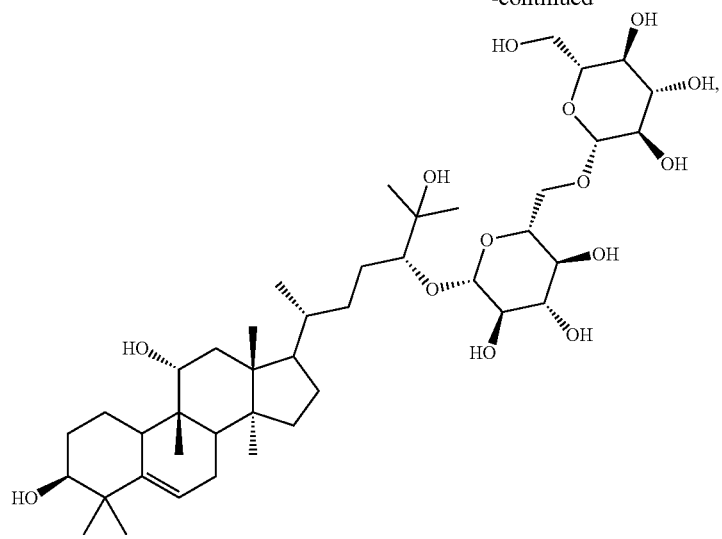
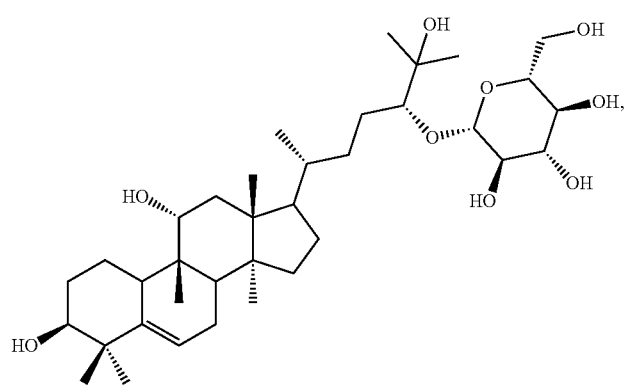
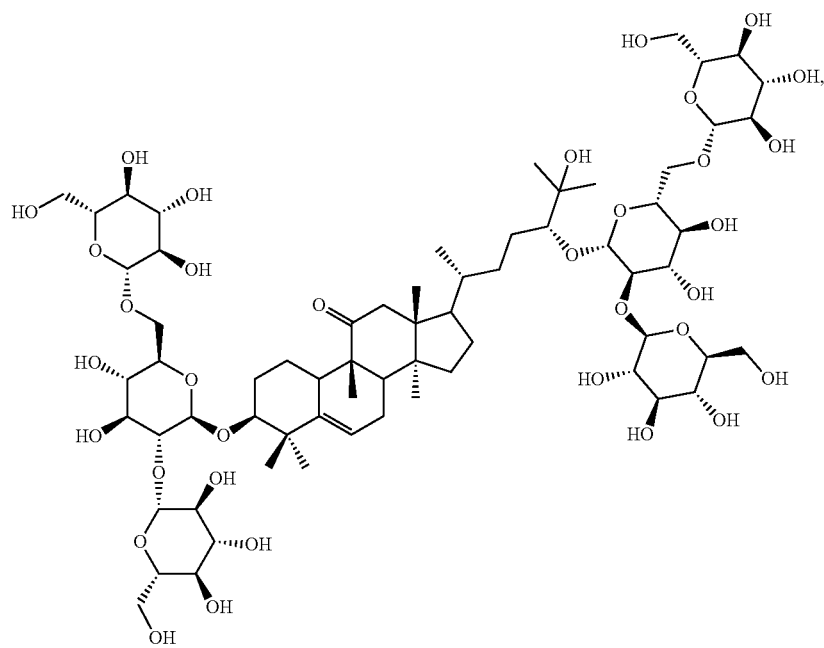

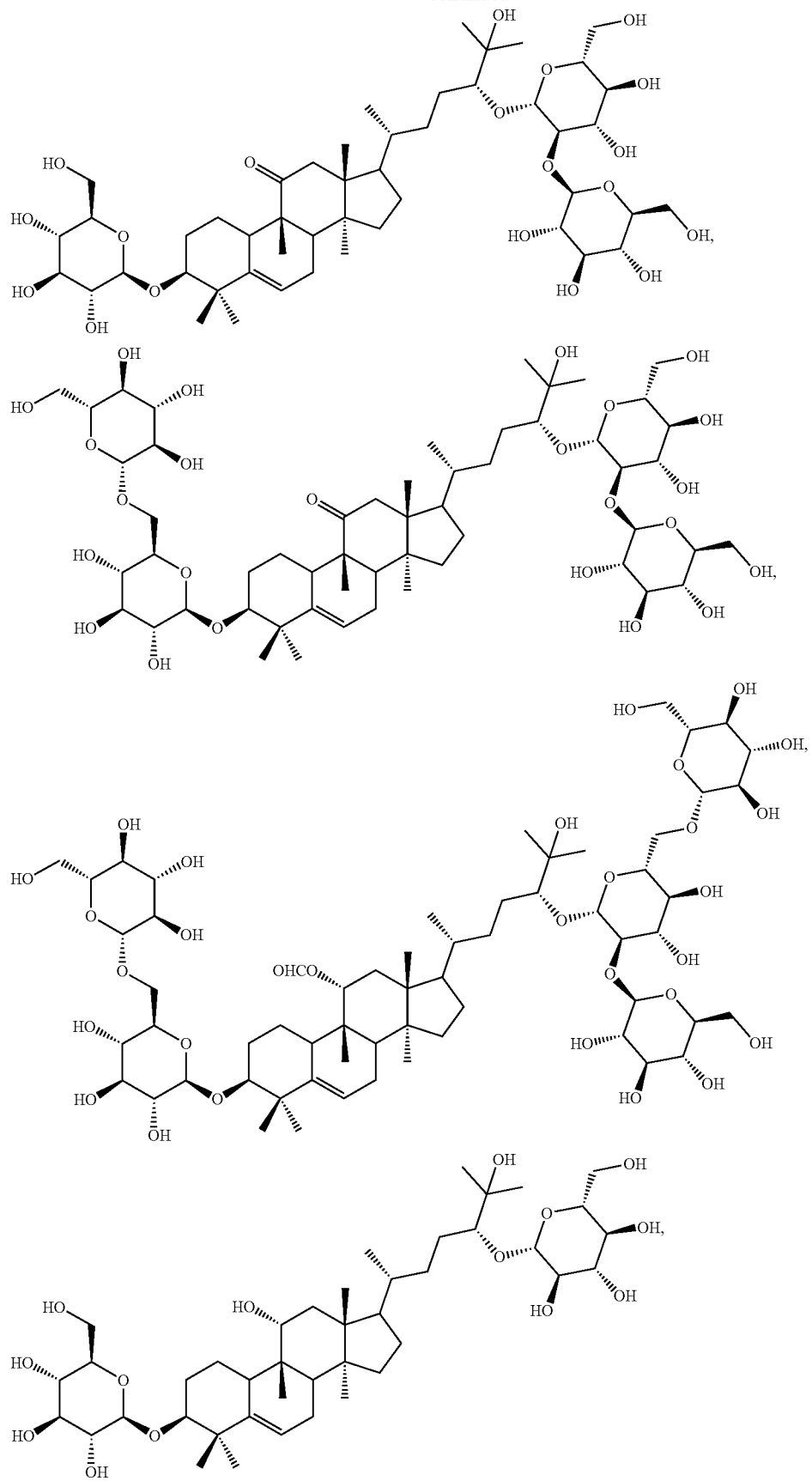

-continued
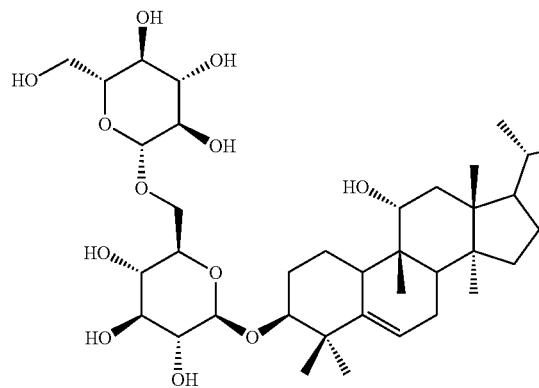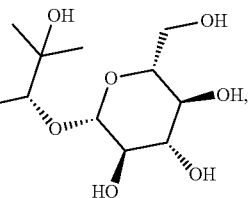
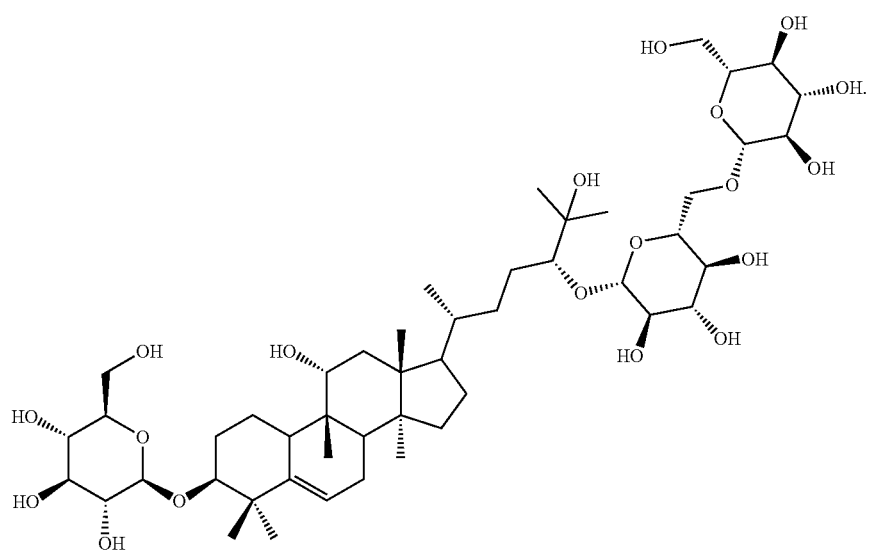
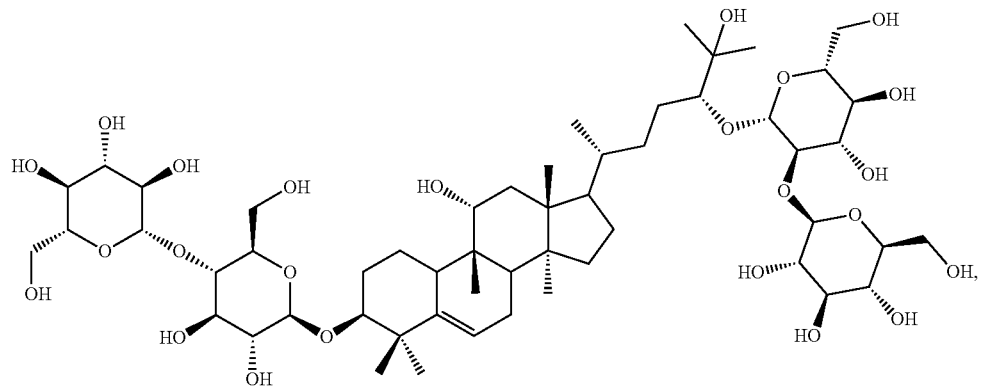

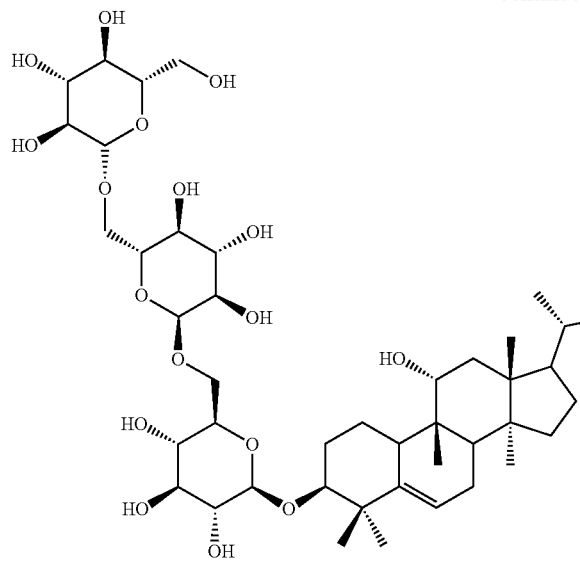
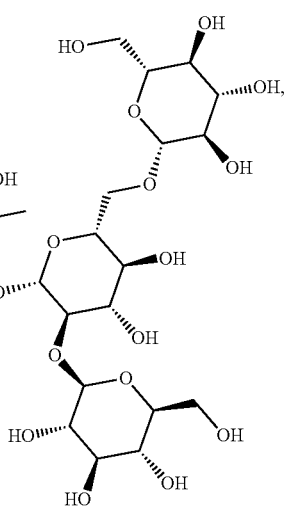
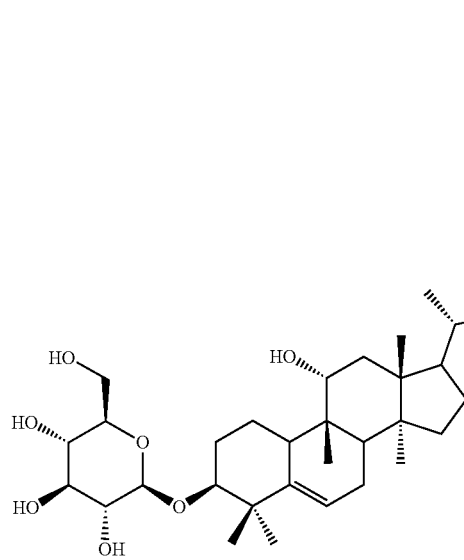
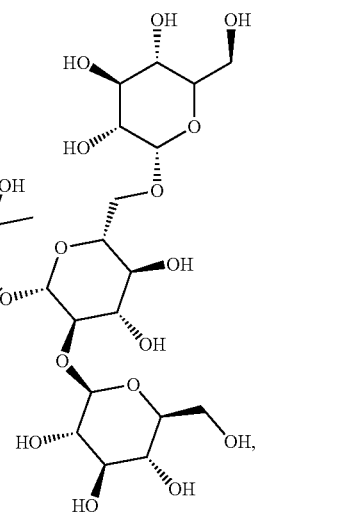
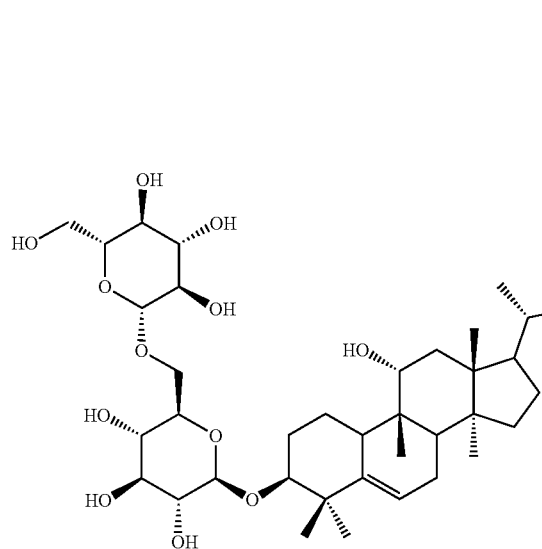
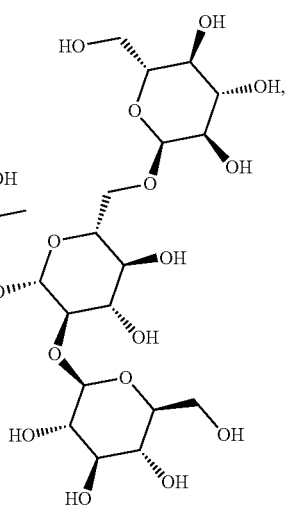

-continued
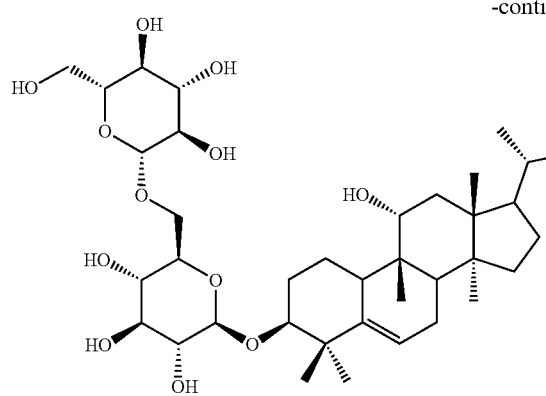
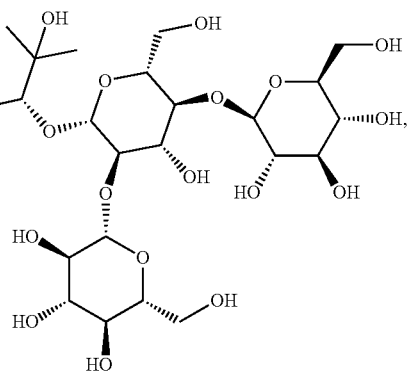
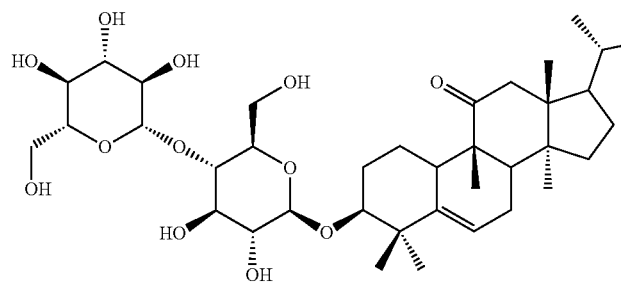
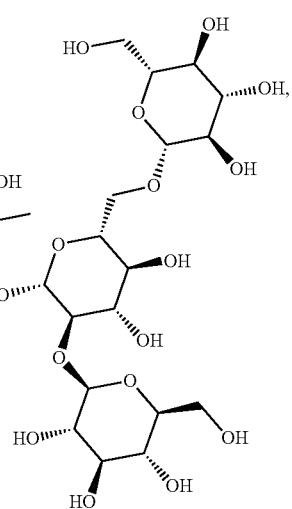
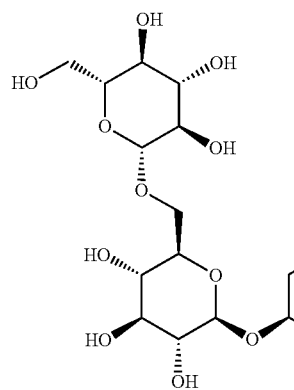
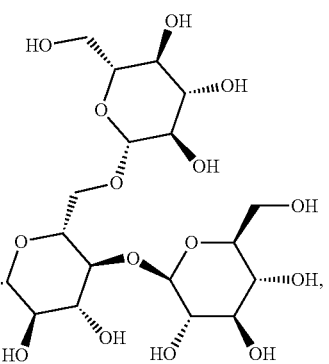

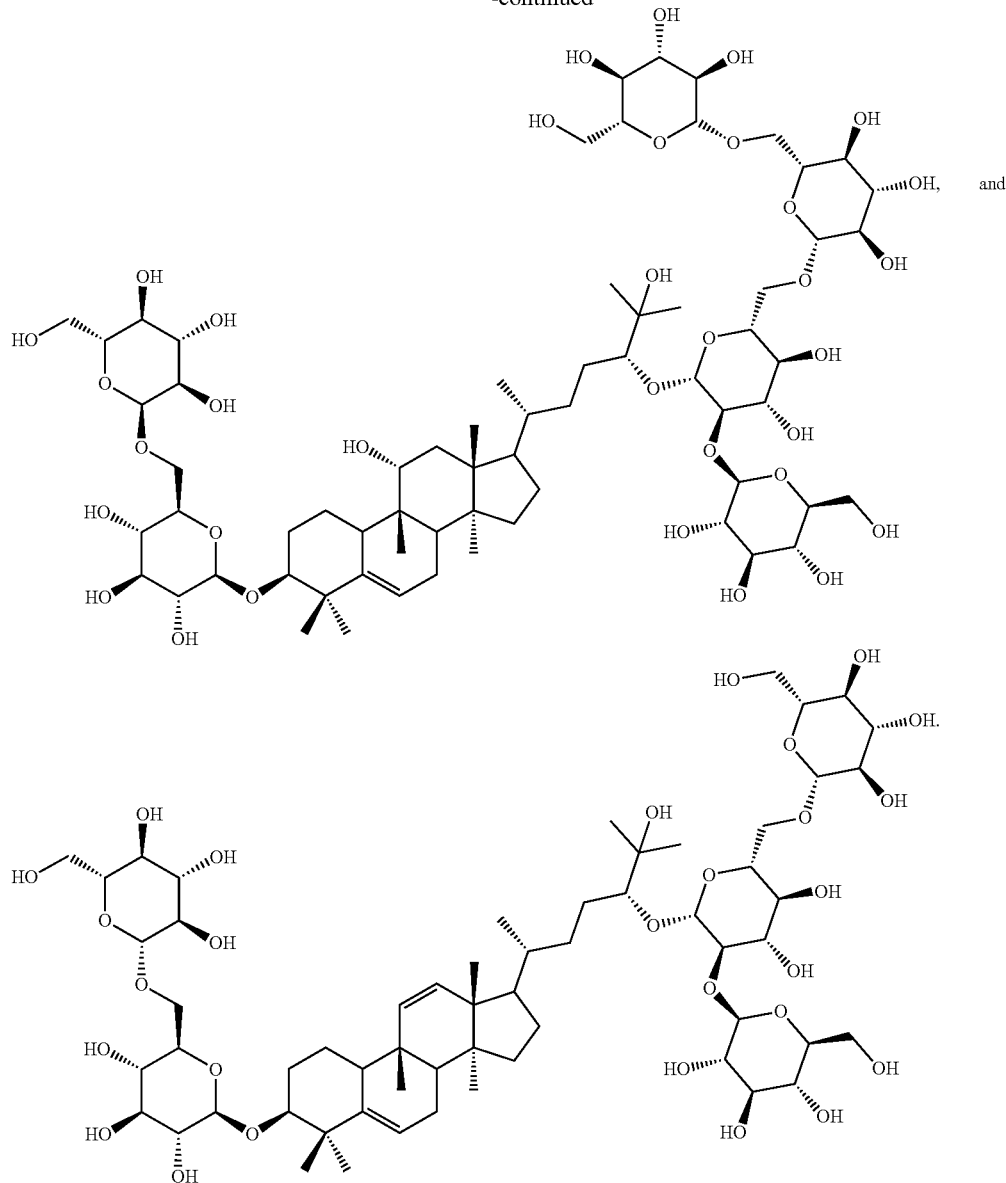

In some embodiments, the compounds of Formula (I) are selected from one of Compounds 1-35 (described below), or salts thereof. In some embodiments, the compounds of Formula (I), or salts thereof, are isolated and is in solid form. In some embodiments, the solid form is amorphous. In other embodiments, the solid form is crystalline. In some embodiments, the compound is in the form of a lyophile. In some embodiments the isolated compounds in form of a lyophile is one or more of Compounds 1-35, or salts thereof.

In some embodiments, the compound of Formula (I) is Compound 1. In some embodiments, the compound of Formula (I) is Compound 2. In some embodiments, the compound of Formula (I) is Compound 3. In some embodiments, the compound of Formula (I) is Compound 4. In some embodiments, the compound of Formula (I) is Compound 5. In some embodiments, the compound of Formula (I) is Compound 6. In some embodiments, the compound of Formula (I) is Compound 7. In some embodiments, the compound of Formula (I) is Compound 8. In some embodiments, the compound of Formula (I) is Compound 9. In some embodiments, the compound of Formula (I) is Compound 10.

In some embodiments, the compound of Formula (I) is Compound 11. In some embodiments, the compound of Formula (I) is Compound 12. In some embodiments, the compound of Formula (I) is Compound 13. In some embodiments, the compound of Formula (I) is Compound 14. In some embodiments, the compound of Formula (I) is Compound 15. In some embodiments, the compound of Formula (I) is Compound 16. In some embodiments, the compound of Formula (I) is Compound 17. In some embodiments, the compound of Formula (I) is Compound 18. In some embodiments, the compound of Formula (I) is Compound 19. In some embodiments, the compound of Formula (I) is Compound 20.

In some embodiments, the compound of Formula (I) is Compound 21. In some embodiments, the compound of Formula (I) is Compound 22. In some embodiments, the compound of Formula (I) is Compound 23. In some embodiments, the compound of Formula (I) is Compound 24. In some embodiments, the compound of Formula (I) is Compound 25. In some embodiments, the compound of Formula (I) is Compound 26. In some embodiments, the compound of Formula (I) is Compound 27. In some embodiments, the compound of Formula (I) is Compound 28. In some embodiments, the compound of Formula (I) is Compound 29. In some embodiments, the compound of Formula (I) is Compound 30.

In some embodiments, the compound of Formula (I) is Compound 31. In some embodiments, the compound of Formula (I) is Compound 32. In some embodiments, the compound of Formula (I) is Compound 33. In some embodiments, the compound of Formula (I) is Compound 34. In some embodiments, the compound of Formula (I) is Compound 35.

Where the compounds disclosed herein have at least one chiral center, they may exist as individual enantiomers and diastereomers or as mixtures of such isomers, including racemates. Separation of the individual isomers or selective synthesis of the individual isomers is accomplished by application of various methods which are well known to practitioners in the art. Unless otherwise indicated (e.g., where the stereochemistry of a chiral center is explicitly shown), all such isomers and mixtures thereof are included in the scope of the compounds disclosed herein. Furthermore, compounds disclosed herein may exist in one or more crystalline or amorphous forms. Unless otherwise indicated, all such forms are included in the scope of the compounds disclosed herein including any polymorphic forms. In addition, some of the compounds disclosed herein may form solvates with water (i.e., hydrates) or common organic solvents. Unless otherwise indicated, such solvates are included in the scope of the compounds disclosed herein.

The skilled artisan will recognize that some structures described herein may be resonance forms or tautomers of compounds that may be fairly represented by other chemical structures, even when kinetically; the artisan recognizes that such structures may only represent a very small portion of a sample of such compound(s). Such compounds are considered within the scope of the structures depicted, though such resonance forms or tautomers are not represented herein.

Isotopes may be present in the compounds described. Each chemical element as represented in a compound structure may include any isotope of said element. For example, in a compound structure a hydrogen atom may be explicitly disclosed or understood to be present in the compound. At any position of the compound that a hydrogen atom may be present, the hydrogen atom can be any isotope of hydrogen, including but not limited to hydrogen-1 (protium) and hydrogen-2 (deuterium). Thus, reference herein to a compound encompasses all potential isotopic forms unless the context clearly dictates otherwise. In some embodiments, compounds described herein are enrinched in one or more isotopes relative to the natural prevalence of such isotopes. In some embodiments, the compounds described herein are enriched in deuterium. For example, in some embodiments, greater than 0.0312% of hydrogen atoms in the compounds described herein are deuterium. In various embodiments, greater than 0.05%, 0.08%, or 0.1% of hydrogen atoms in the compounds described herein are deuterium.

In some embodiments, the compounds disclosed herein are capable of forming acid and/or base salts by virtue of the presence of amino and/or carboxyl groups or groups similar thereto. Physiologically acceptable acid addition salts can be formed with inorganic acids and organic acids. Inorganic acids from which salts can be derived include, for example, hydrochloric acid, hydrobromic acid, sulfuric acid, nitric acid, phosphoric acid, and the like. Organic acids from which salts can be derived include, for example, acetic acid, propionic acid, glycolic acid, pyruvic acid, oxalic acid, maleic acid, malonic acid, succinic acid, fumaric acid, tartaric acid, citric acid, benzoic acid, cinnamic acid, mandelic acid, methanesulfonic acid, ethanesulfonic acid, p-toluenesulfonic acid, salicylic acid, and the like. Physiologically acceptable salts can be formed using inorganic and organic bases. Inorganic bases from which salts can be derived include, for example, bases that contain sodium, potassium, lithium, ammonium, calcium, magnesium, iron, zinc, copper, manganese, aluminum, and the like; particularly preferred are the ammonium, potassium, sodium, calcium and magnesium salts. In some embodiments, treatment of the compounds disclosed herein with an inorganic base results in loss of a labile hydrogen from the compound to afford the salt form including an inorganic cation such as $Li^+$, $Na^+$, $K^+$, $Mg^{2+}$ and $Ca^{2+}$ and the like. Organic bases from which salts can be derived include, for example, primary, secondary, and tertiary amines, substituted amines including naturally occurring substituted amines, cyclic amines, basic ion exchange resins, and the like, specifically such as isopropylamine, trimethylamine, diethylamine, triethylamine, tripropylamine, and ethanolamine.

In some embodiments, the compounds of Formula (I) are substantially isolated. In some embodiments, the compound is in the form of a lyophile. In some embodiments, the compound is crystalline. In some embodiments, the compound is amorphous. In some embodiments, the compounds of Formula (I) are selected from one or more of Compounds 1-35.

Production Compositions

Some embodiments provide a composition comprising a relatively high content of one or more compounds described herein (e.g., a compound of Formula (I) such as Compound 1-35). For example, upon production of a compound described herein using a production method described herein, a composition may be formed that is enriched in the desired compound, but also contains other compounds. In various embodiments, the composition contains a weight percent greater than 50%, 55%, 60%, 65%, 70%, 75%, 80%, 85%, 90%, 95%, 98%, or 99% of the desired compound. In some embodiments, the composition comprises one or more additional compound according to Formula (I). In some embodiments, the composition comprises one or more of compounds selected from 195
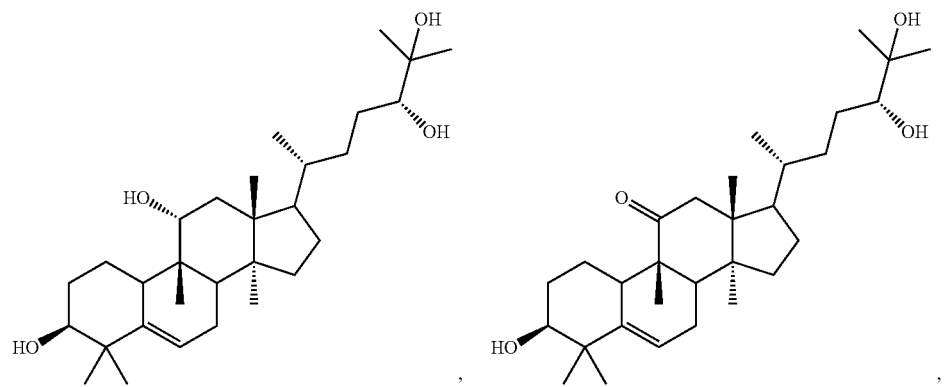
196
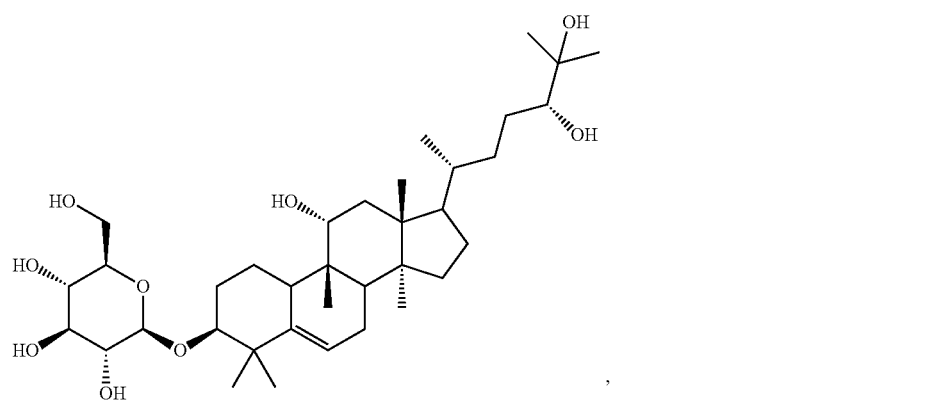
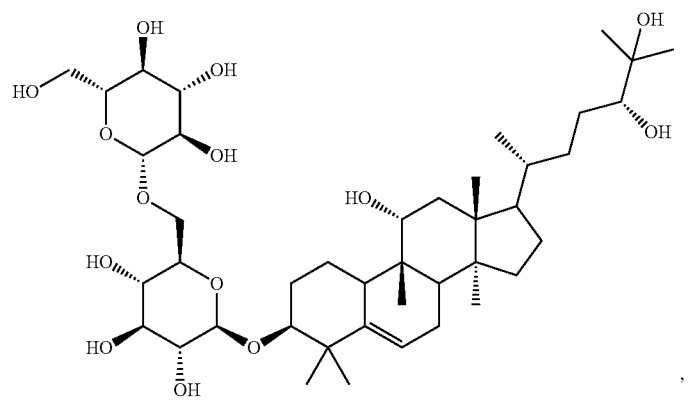
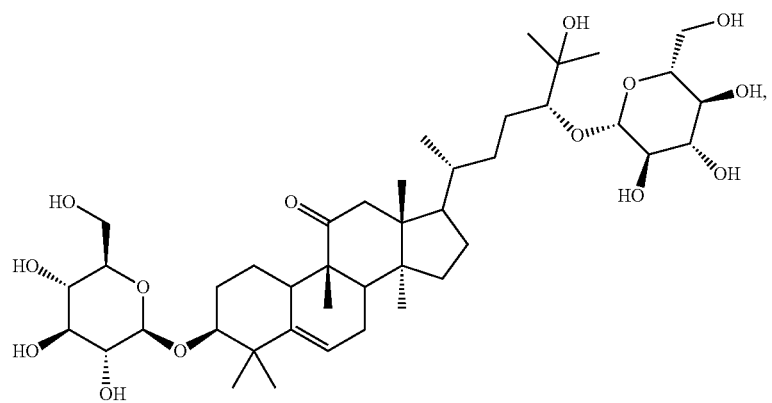

-continued
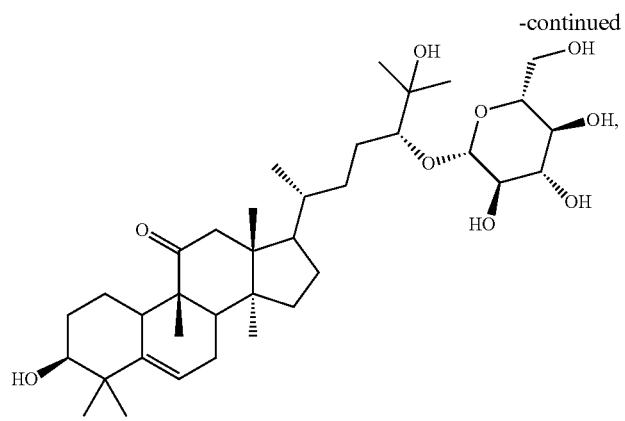
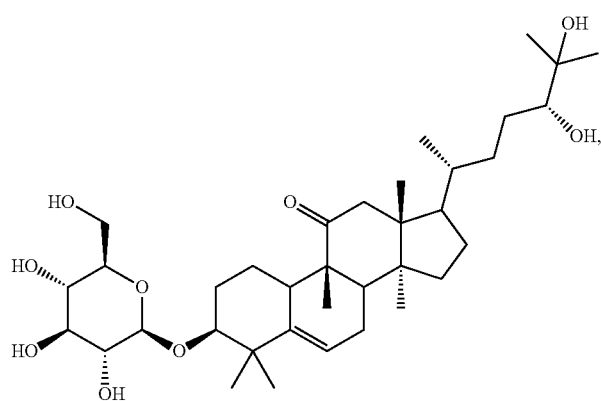
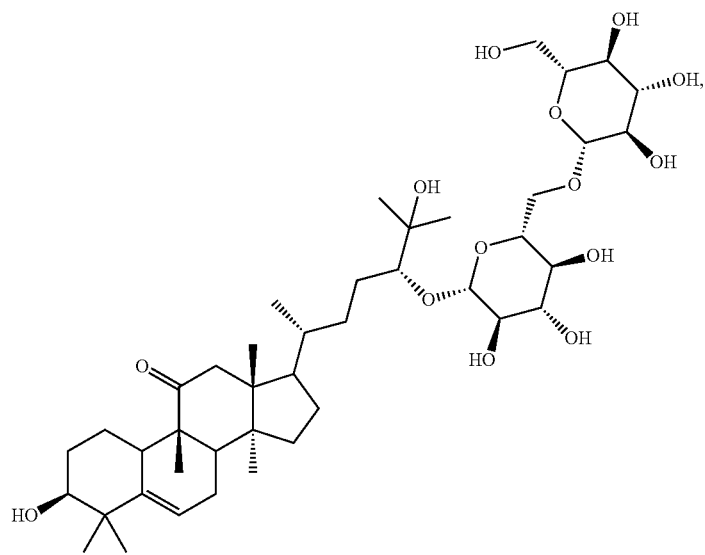

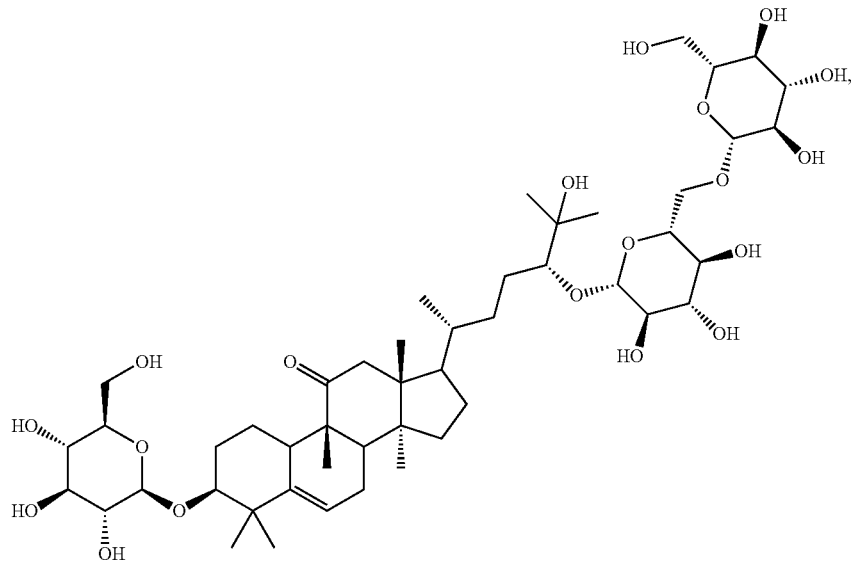
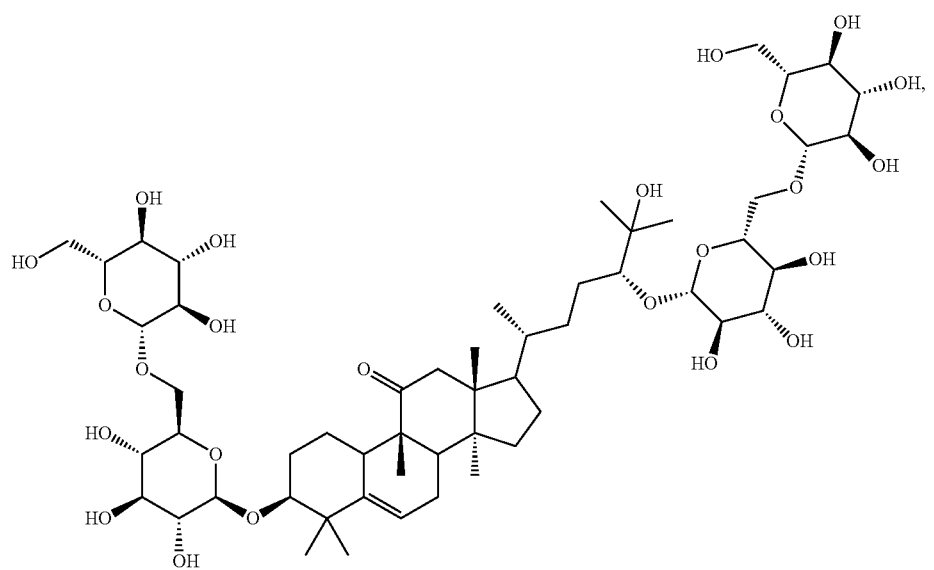
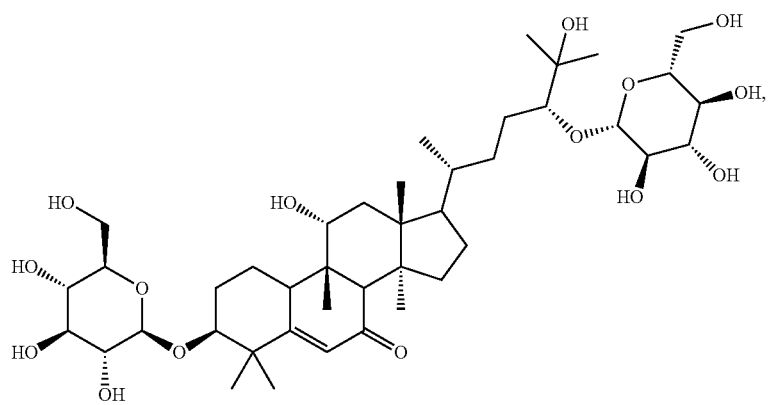

-continued
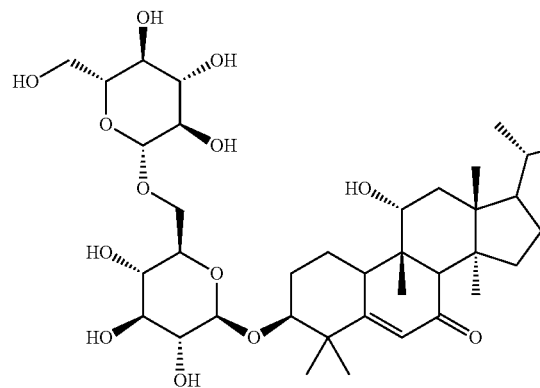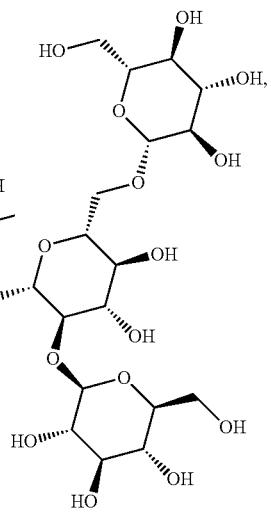
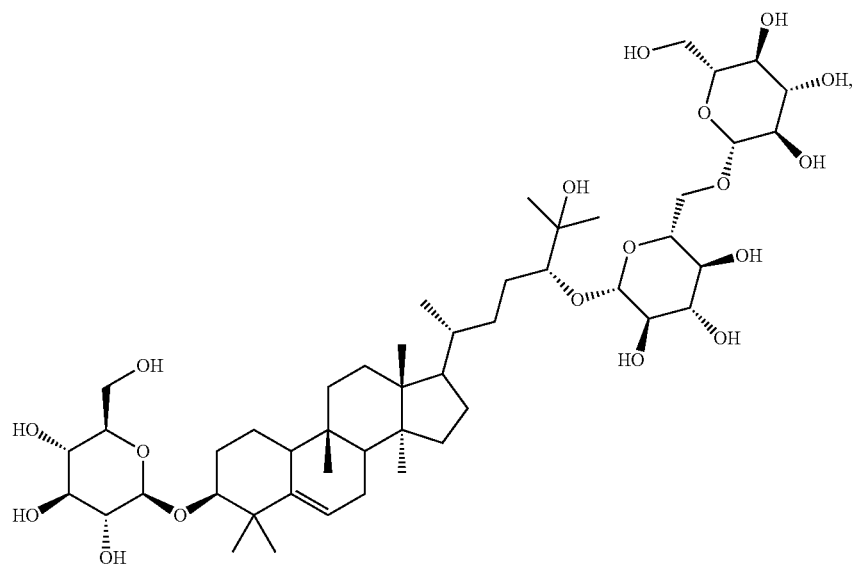

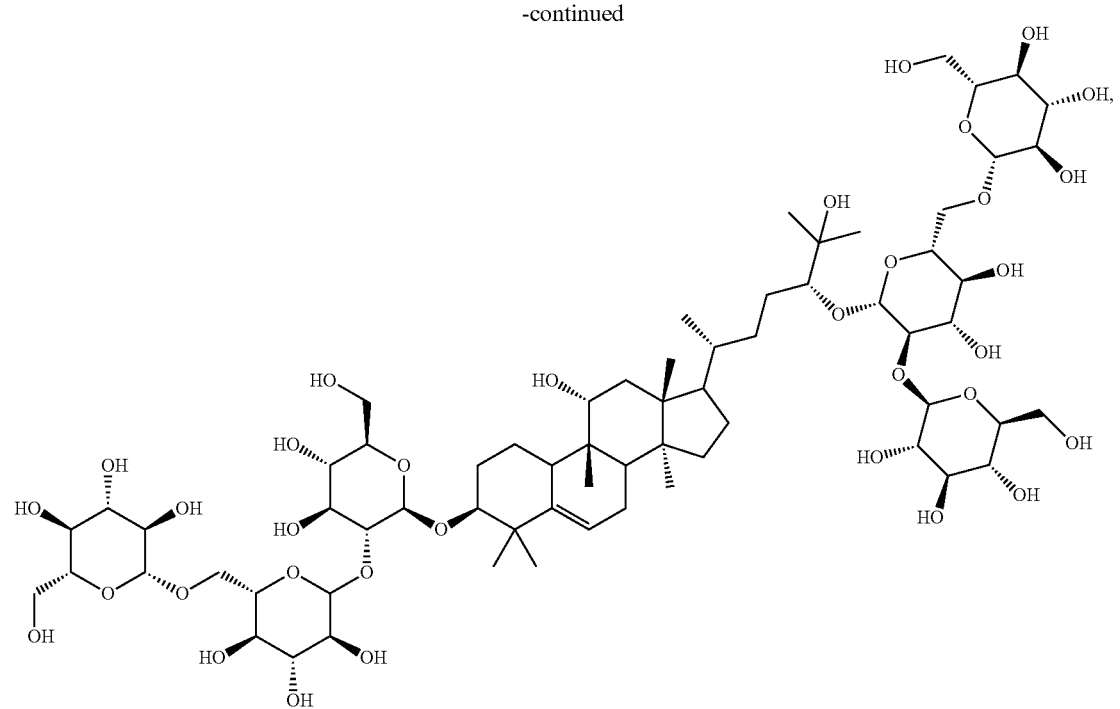
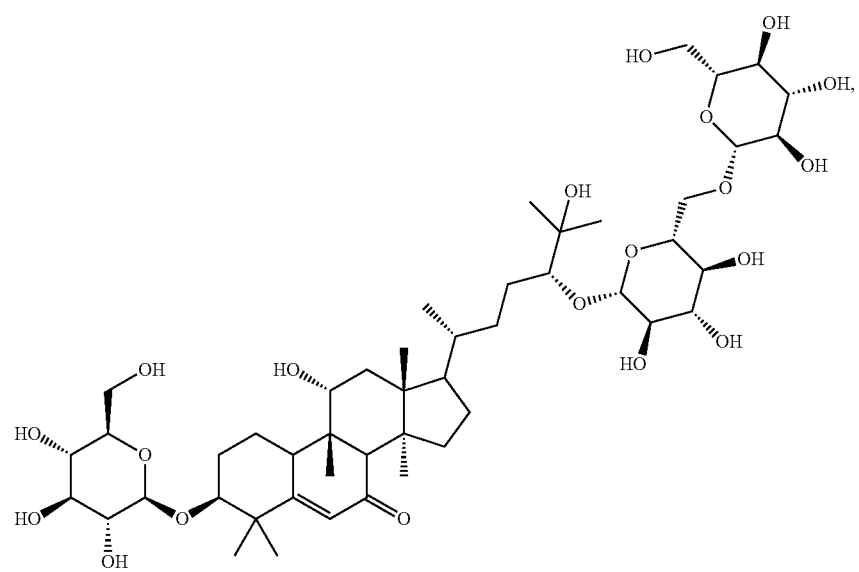

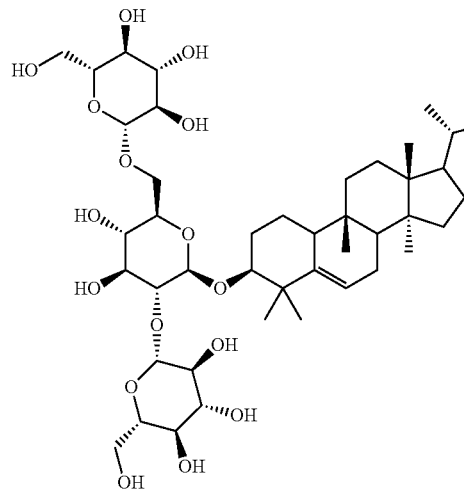
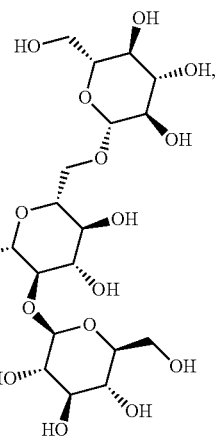
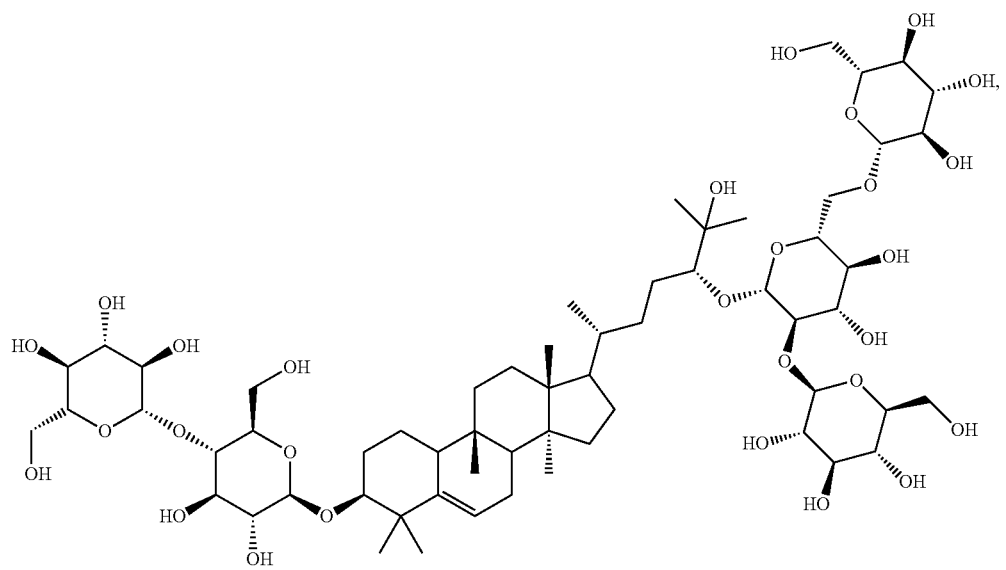

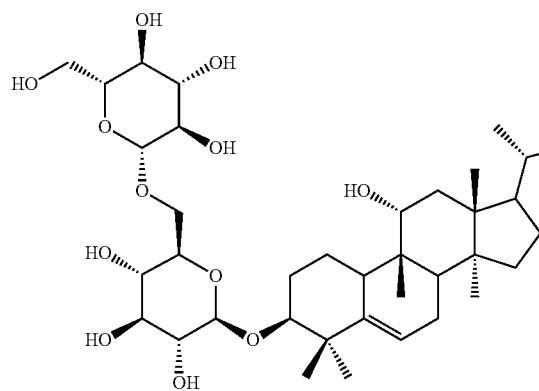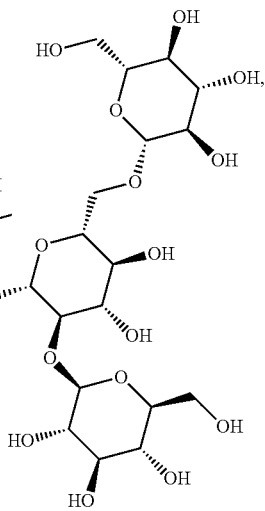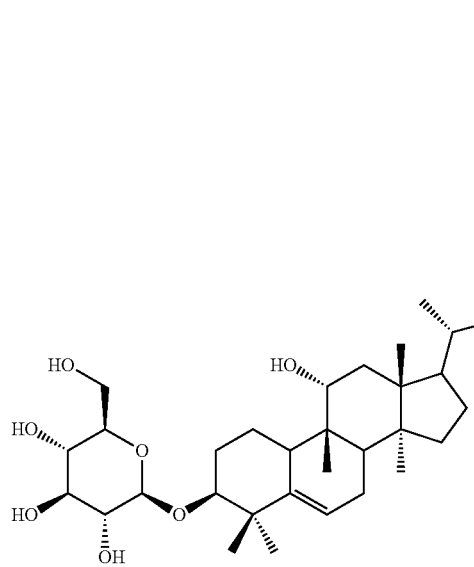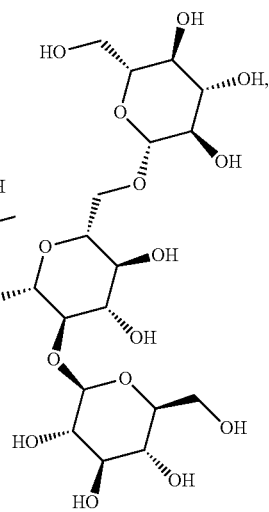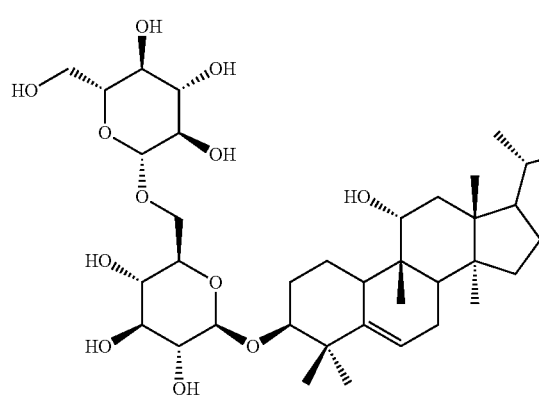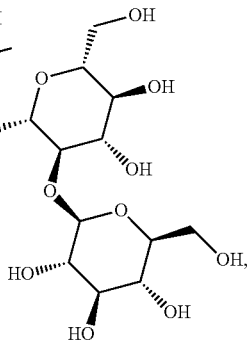

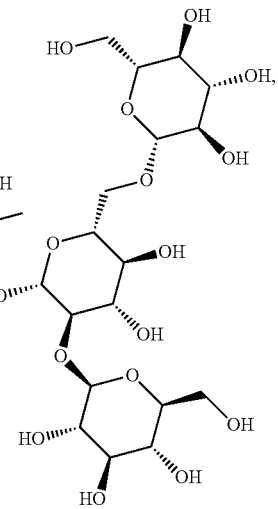
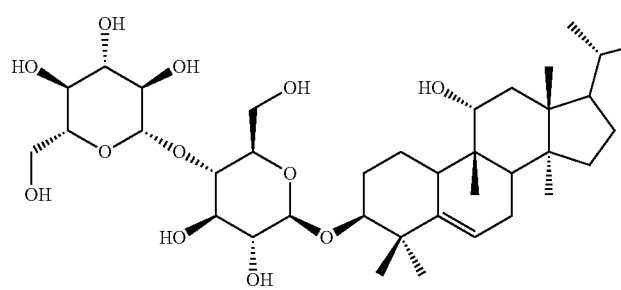
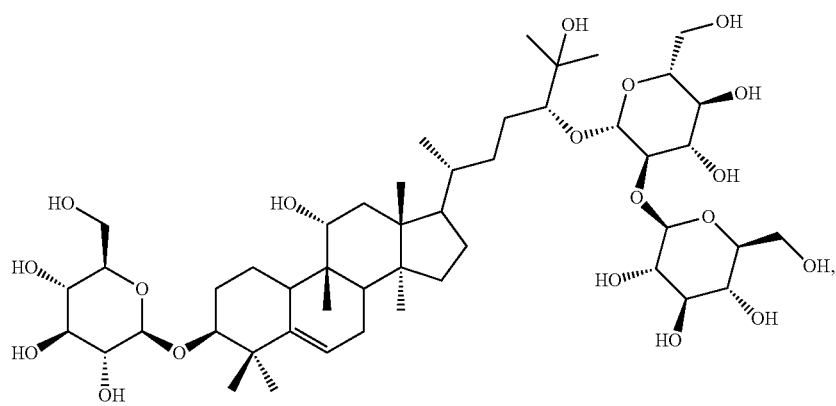
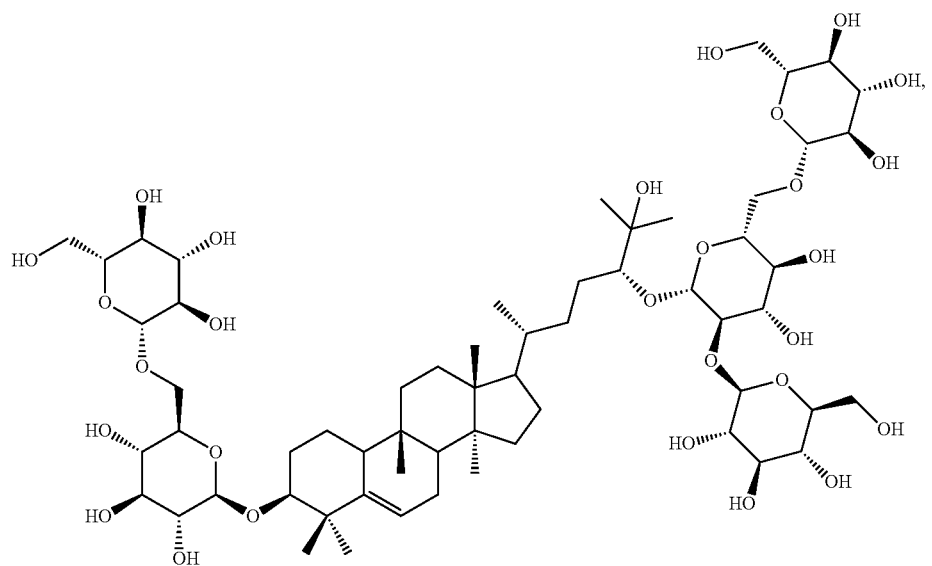

-continued
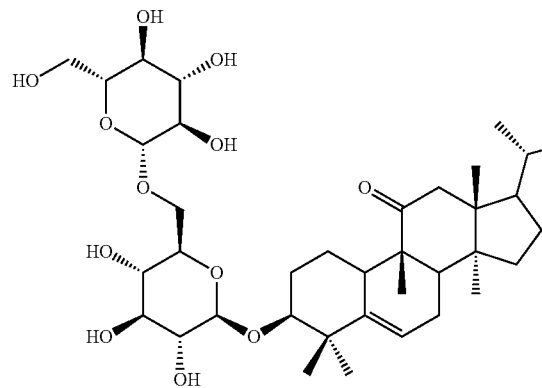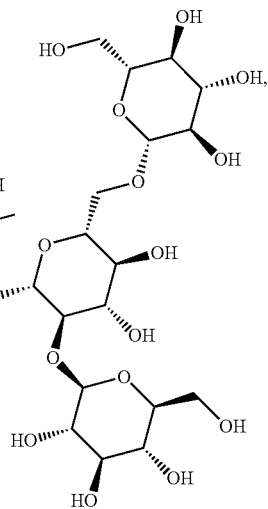
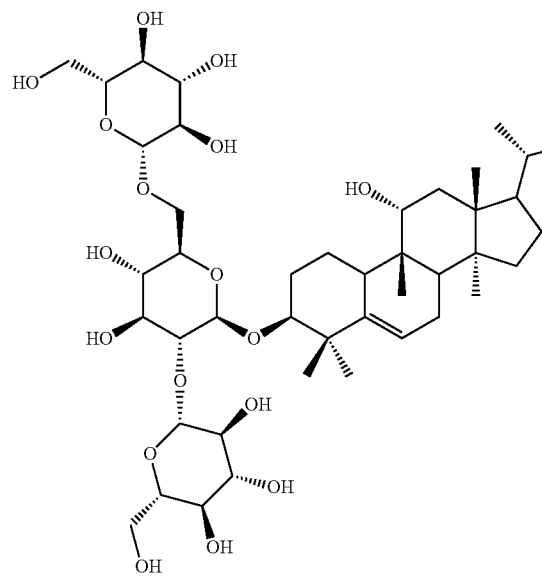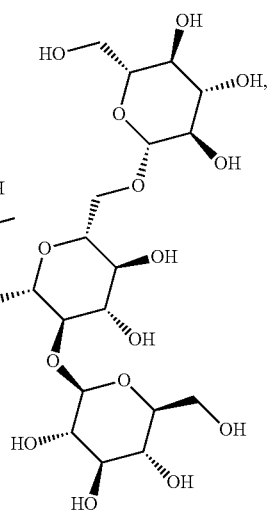

-continued
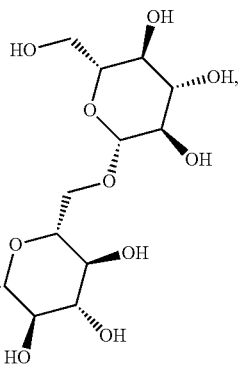
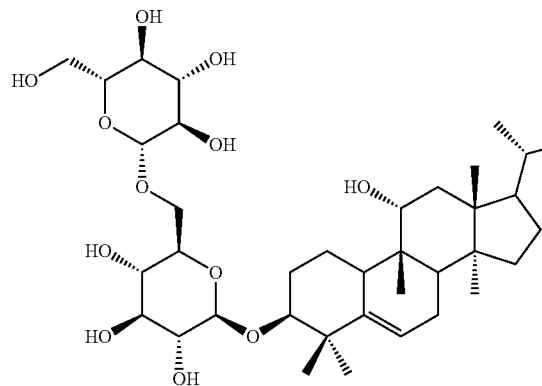
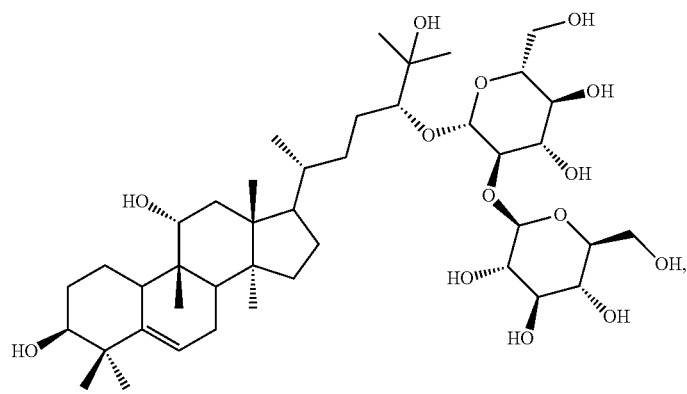
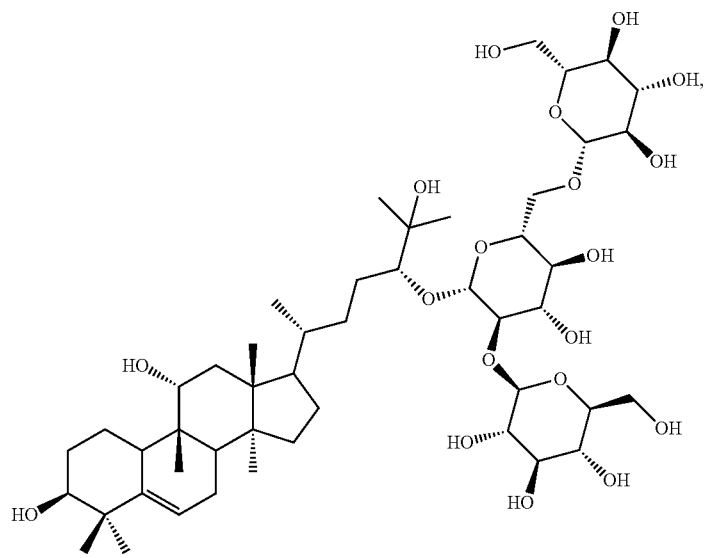

-continued
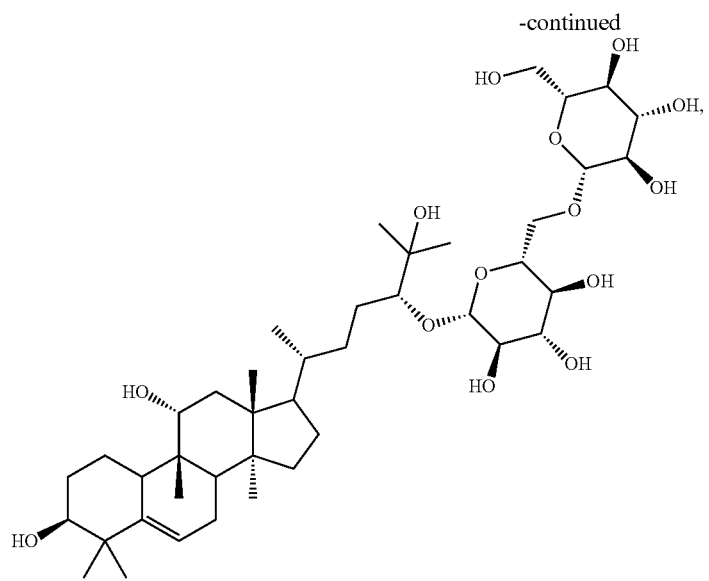
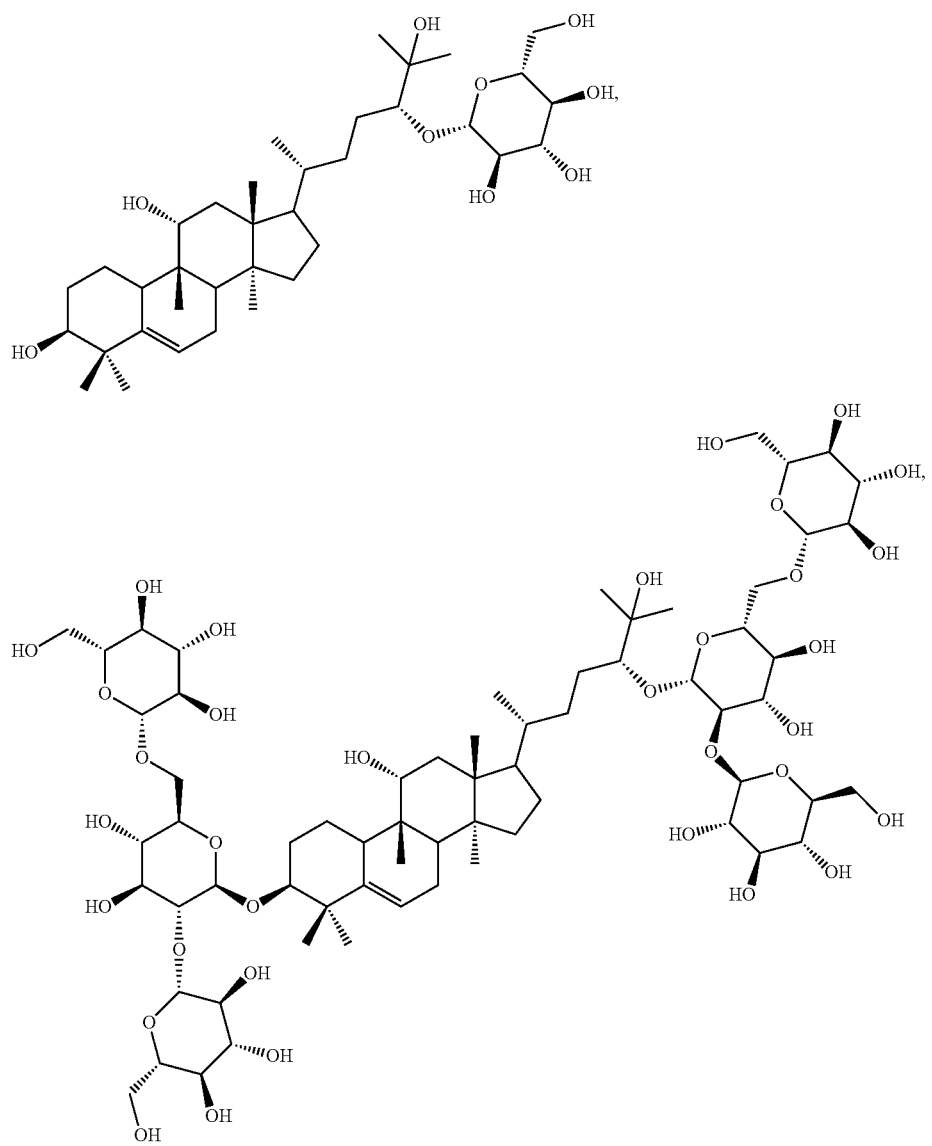

-continued
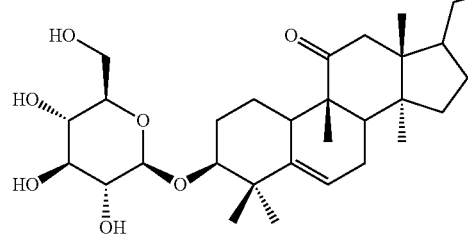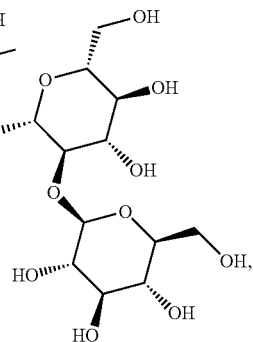
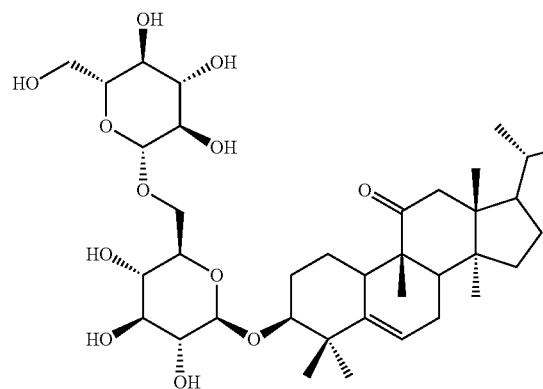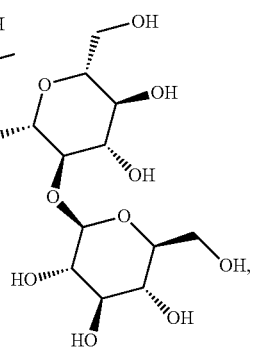
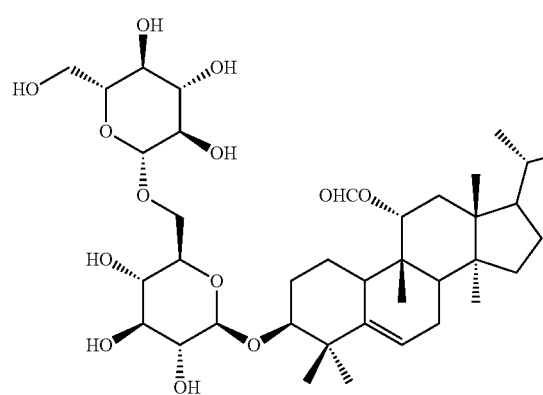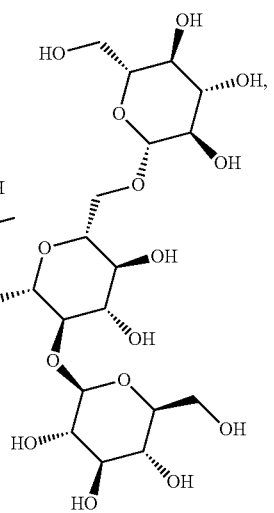

-continued
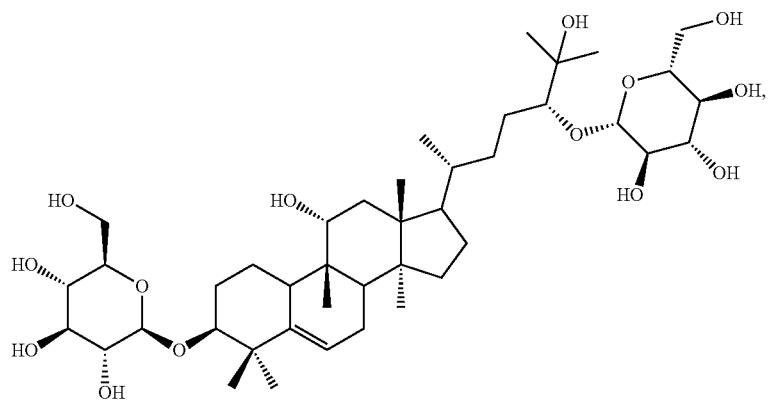
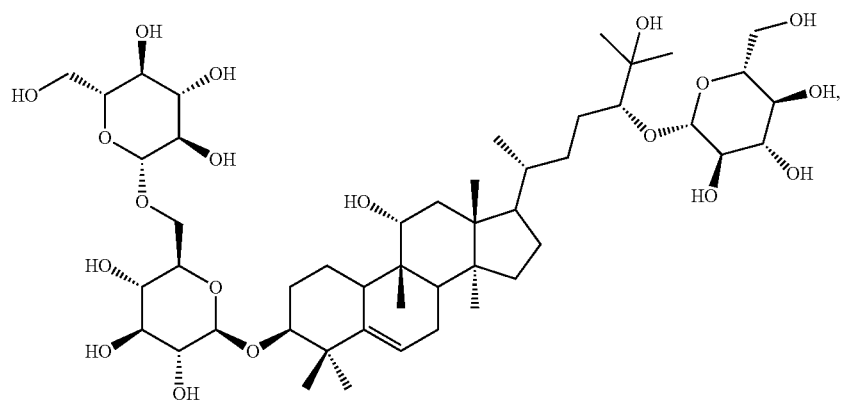
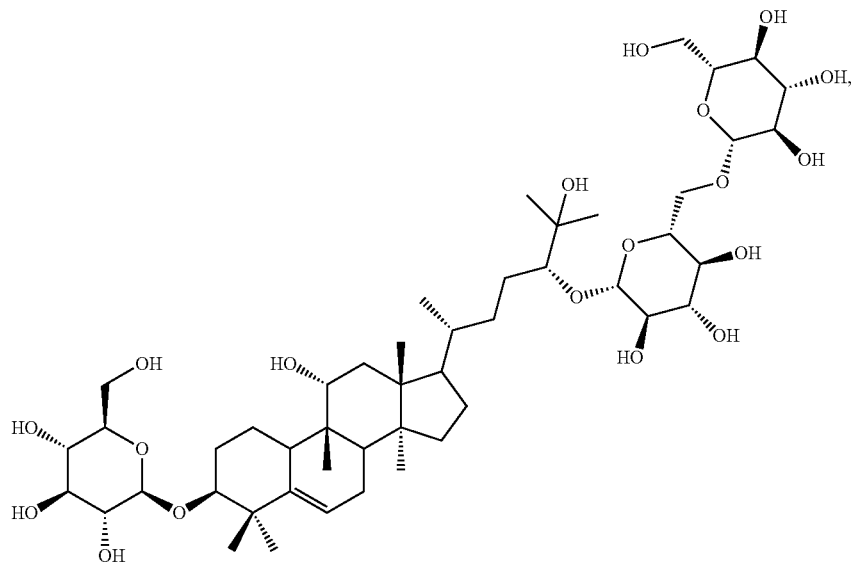

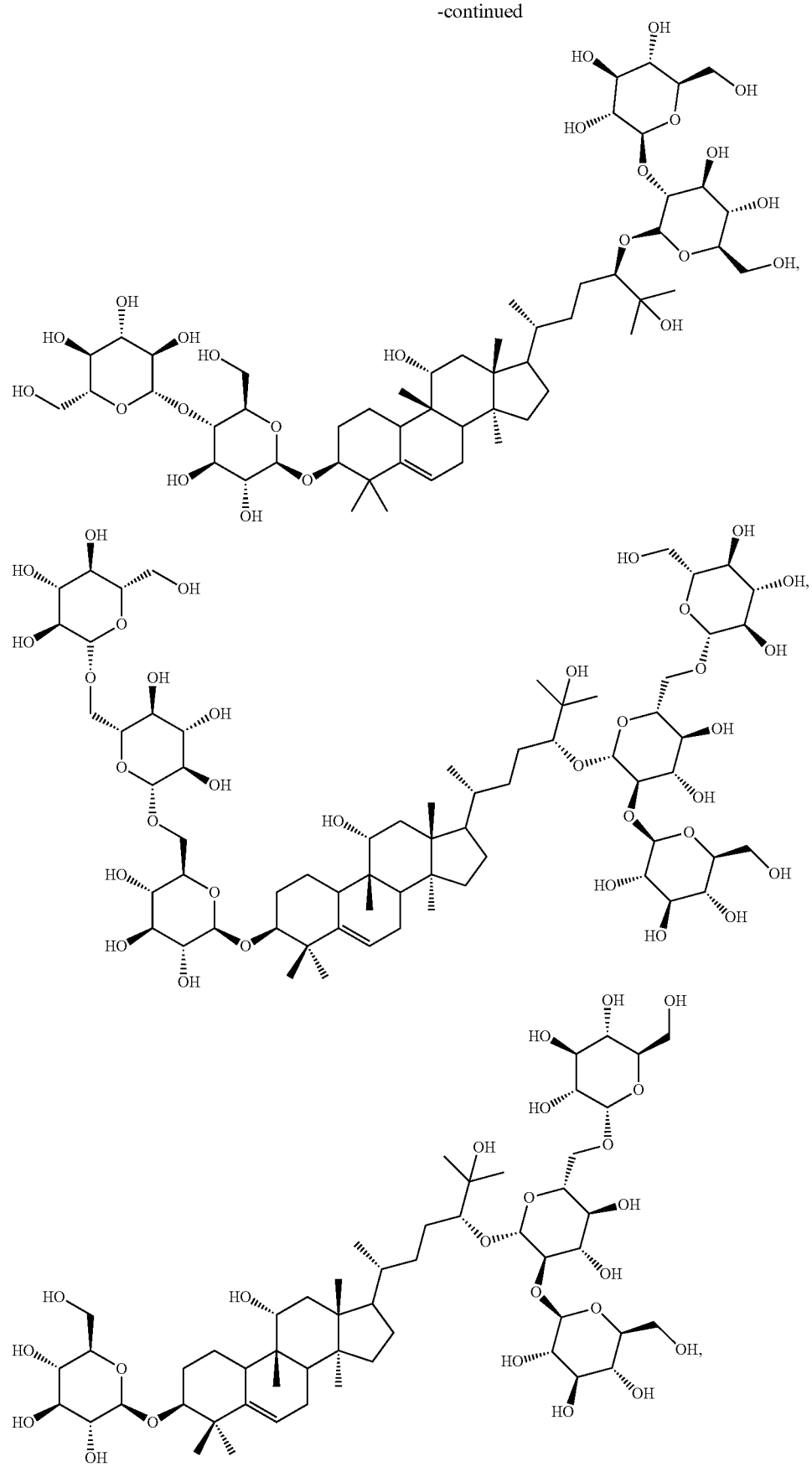

-continued
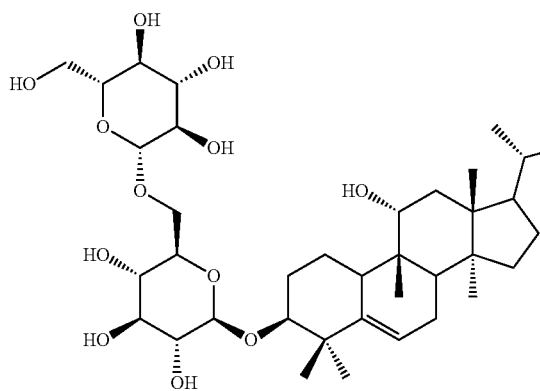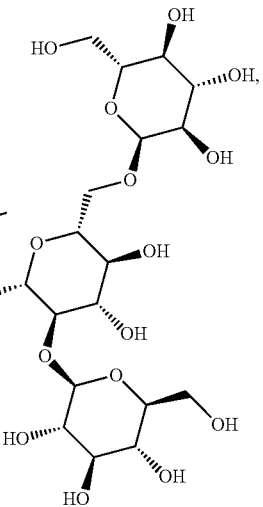
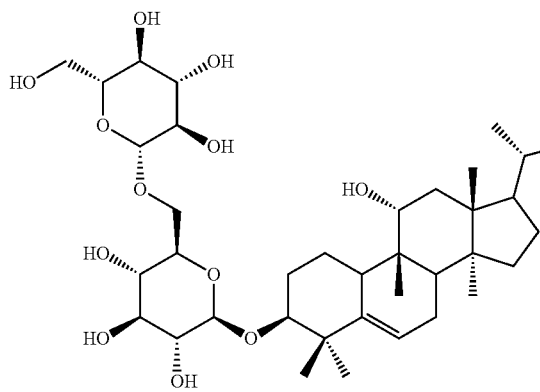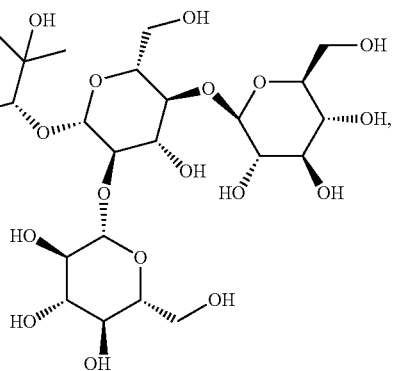
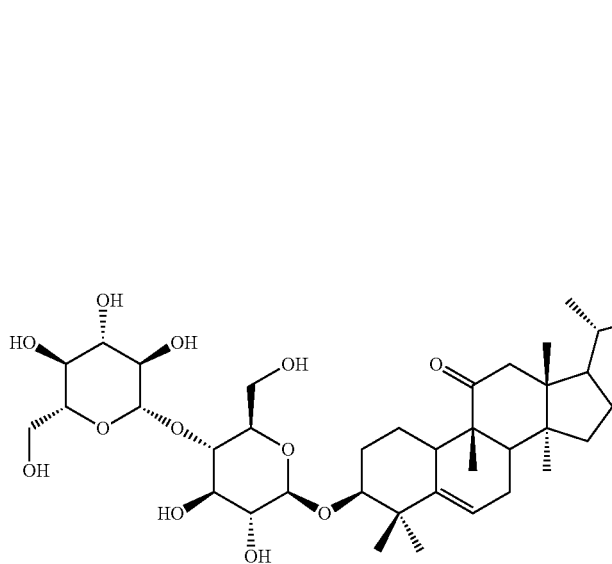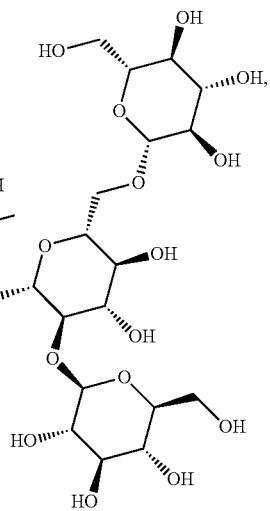

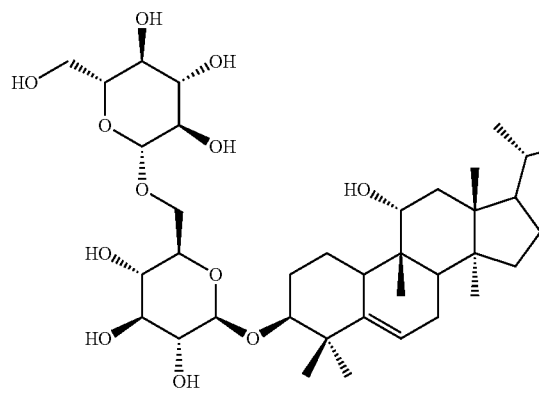
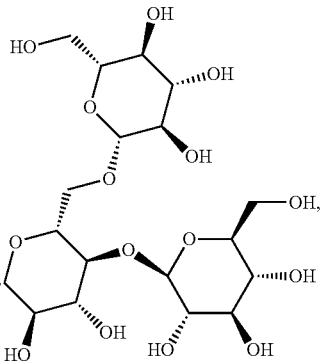
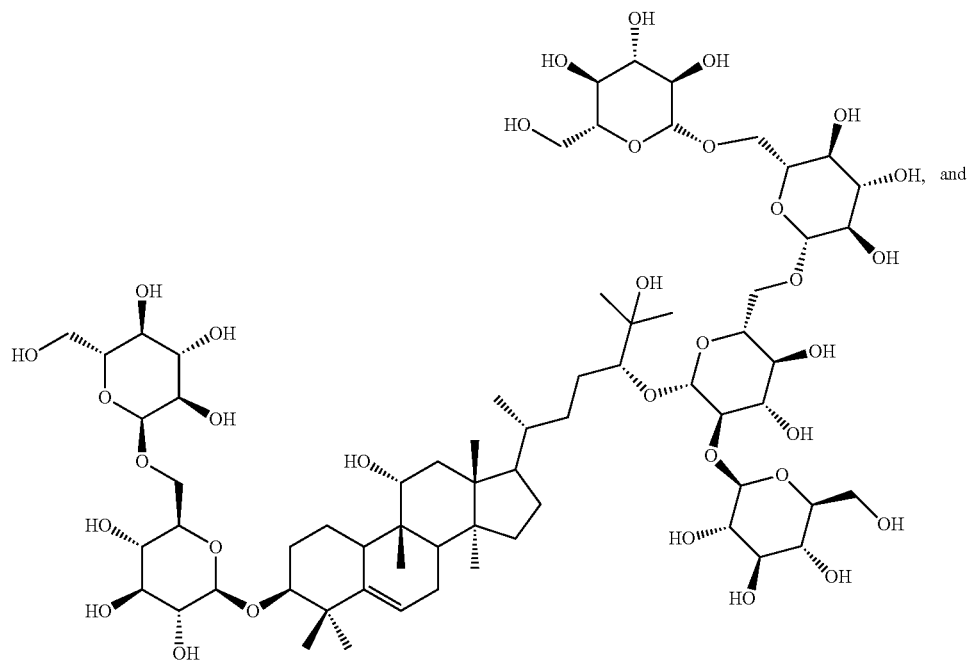

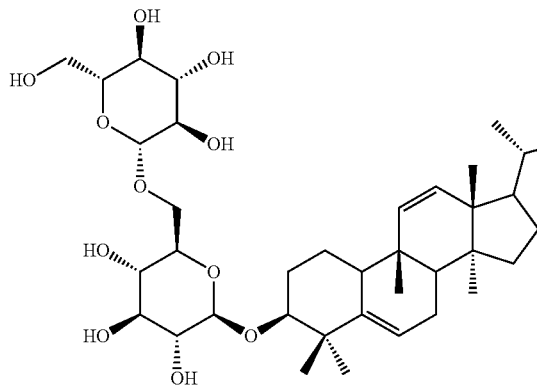
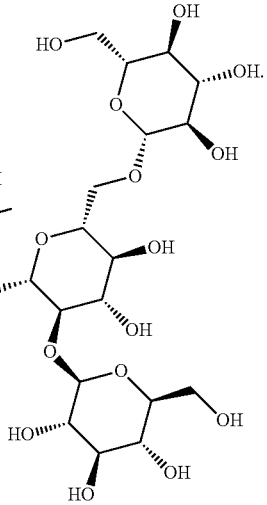

In various embodiments, the composition contains a weight percent of less than 50%, 40%, 30%, 20%, 10%, 5%, or 1% of Mogroside V. In various embodiments, the composition contains a weight percent of from 1% to 50%, from 5% to 40%, from 10% to 40%, from 10% to 30%, or from 10% to 20% of Mogroside V.

In some embodiments, the production composition contains none, or less than a certain amount, of undesirable compounds. In some embodiments, the composition does not contain one or more isomers of Mogroside I, Mogroside II, and Mogroside III. In various embodiments, the composition contains a weight percent of less than 5%, 3%, 2%, 1%, 0.5%, 0.3%, 0.1%, 800 ppm, 500 ppm, 200 ppm, or 100 ppm of all isomers of Mogroside I, Mogroside II, and Mogroside III. In some embodiments, the composition does not contain one or more of Mogroside IIIE, 11-oxo-Mogroside IIIE, Mogroside IIIA2, Mogroside IE, Mogroside IIE, and 11-oxo-mogrol. In various embodiments, the composition contains a weight percent of less than 5%, 3%, 2%, 1%, 0.5%, 0.3%, 0.1%, 800 ppm, 500 ppm, 200 ppm, or 100 ppm of one or more of Mogroside IIIE, 11-oxo-Mogroside IIIE, Mogroside IIIA2, Mogroside IE, Mogroside IIE, and 11-oxo-mogrol. In various embodiments, the composition contains a weight percent of less than 5%, 3%, 2%, 1%, 0.5%, 0.3%, 0.1%, 800 ppm, 500 ppm, 200 ppm, or 100 ppm of Mogroside IIIE. In various embodiments, the composition contains a weight percent of less than 5%, 3%, 2%, 1%, 0.5%, 0.3%, 0.1%, 800 ppm, 500 ppm, 200 ppm, or 100 ppm of 11-oxo-Mogroside IIIE. In various embodiments, the composition contains a weight percent of less than 5%, 3%, 2%, 1%, 0.5%, 0.3%, 0.1%, 800 ppm, 500 ppm, 200 ppm, or 100 ppm of 11-oxo-mogrol.

In some embodiments, the production composition is in solid form, which may by crystalline or amorphous. In some embodiments, the composition is in particulate form. The solid form of the composition may be produced using any suitable technique, including but not limited to re-crystallization, filtration, solvent evaporation, grinding, milling, spray drying, spray agglomeration, fluid bed agglomeration, wet or dry granulation, and combinations thereof. In some embodiments, a flowable particulate composition is provided to facilitate use in further food manufacturing processes. In some such embodiments, a particle size between 50 μm and 300 μm, between 80 μm and 200 μm, or between 80 μm and 150 μm is generated.

In some embodiments, the production composition is combined with a solid carrier. For example, the production composition may be mixed or coated with a solid carrier. In some embodiments, the solid carrier is a particulate. Any suitable coating technique may be used, including spray coating. Suitable solid carriers include but are not limited to lactose, cellulose, microcrystalline cellulose, modified food starch, gum Arabic, maltodextrin, modified corn starch, dextrose, xantham gum, carboxymethylcellulose, cellulose gel, cellulose gum, sodium caseinate, carrageenan, and combinations thereof.

In some embodiments, prior to further use, a particulate composition comprising a compound described herein is suspended in a liquid carrier. Suitable liquid carriers can include water, an alcohol, ethanol, propylene glycol, triacetine, medium chain triglycerides, glycerin, and combinations thereof.

Some embodiments provide a production composition that is in solution form. For example, in some embodiments a solution produced by one of the production processes described herein is used without further purification. In various embodiments, the concentration of the desired compound in the solution is greater than 300 ppm, 500 ppm, 800 ppm, 0.1%, 0.5%, 1%, 2%, 3%, 4%, 5%, 6%, 7%, 8%, 9%, 10%, 15%, or 20% by weight. In various embodiments, the concentration of all isomers of Mogroside I, Mogroside II, and Mogroside III is less than 5%, 3%, 2%, 1%, 0.5%, 0.3%, 0.1%, 800 ppm, 500 ppm, 200 ppm, or 100 ppm. In various embodiments, the concentration of one or more of Mogroside IIIE, 11-oxo-Mogroside IIIE, Mogroside IIIA2, Mogroside IE, Mogroside IIE, and 11-oxo-mogrol is less than 5%, 3%, 2%, 1%, 0.5%, 0.3%, 0.1%, 800 ppm, 500 ppm, 200 ppm, 100 ppm, 50 ppm, 30 ppm, 20 ppm, 10 ppm, 5 ppm, 1 ppm, or 0.1 ppm of one or more of Mogroside IIIE, 11-oxo-Mogroside IIIE, Mogroside IIIA2, Mogroside IE, Mogroside IIE, and 11-oxo-mogrol. In various embodiments, the concentration of Mogroside IIIE is less than 5%, 3%, 2%, 1%, 0.5%, 0.3%, 0.1%, 800 ppm, 500 ppm, 200 ppm, 100 ppm, 50 ppm, 30 ppm, 20 ppm, 10 ppm, 5 ppm, 1 ppm, or 0.1 ppm. In various embodiments, the concentration of 11-oxo-Mogroside IIIE is less than 5%, 3%, 2%, 1%, 0.5%, 0.3%, 0.1%, 800 ppm, 500 ppm, 200 ppm, 100 ppm, 50 ppm, 30 ppm, 20 ppm, 10 ppm, 5 ppm, 1 ppm, or 0.1 ppm. In various embodiments, the concentration of 11-oxo-mogrol is less than 5%, 3%, 2%, 1%, 0.5%, 0.3%, 0.1%, 800 ppm, 500 ppm, 200 ppm, 100 ppm, 50 ppm, 30 ppm, 20 ppm, 10 ppm, 5 ppm, 1 ppm, or 0.1 ppm.

In some embodiments, the production composition has a pH of less than or equal to 7. In some embodiments, the production composition has a pH of less than 7. In some embodiments, the production composition has a pH greater than or equal to 7. In some embodiments, the production composition has a pH of greater than 7. In some embodiments, the production composition has a pH between 6 and 10, between 6 and 9, between 6 and 8, between 6 and 7, between 1 and 7, between 1 and 6, between 1 and 5, between 1 and 4, between 1 and 3, or between 1 and 2. In some embodiments, the production composition has a pH of about 1, of about 1.5, of about 2, of about 2.5, of about 3, of about 3.5, of about 4, of about 4.5, of about 5, of about 5.5, of about 6, of about 6.5, or of about 7.

Ingestible Compositions

In general, compounds as disclosed and described herein, individually or in combination, can be provided in a composition, such as, e.g., an ingestible composition. In one embodiment, compounds as disclosed and described herein, individually or in combination, can provide a sweet flavor to an ingestible composition. In other embodiments, the compounds disclosed and described herein, individually or in combination, can act as a sweet flavor enhancer to enhance the sweetness of another sweetener. In other embodiments, the compounds disclosed herein impart a more sugar-like temporal profile and/or flavor profile to a sweetener composition by combining one or more of the compounds as disclosed and described herein with one or more other sweeteners in the sweetener composition. In another embodiment, compounds as disclosed and described herein, individually or in combination, can increase or enhance the sweet taste of a composition by contacting the composition thereof with the compounds as disclosed and described herein to form a modified composition. In another embodiment, compounds as disclosed and described herein, individually or in combination, can be in a composition that modulates the sweet receptors and/or their ligands expressed in the body other than in the taste buds.

Some embodiments provide an ingestible composition, comprising at least one compound of formula (I), or a salt thereof and an ingestibly acceptable ingredient. In some embodiments, the ingestible composition does not comprise mogroside V.

Some embodiments provide an ingestible composition, comprising at least one compound of any of compounds 1-35, and an ingestibly acceptable ingredient. In some embodiments, the composition comprises Compound 1, or a salt thereof, and an ingestibly acceptable ingredient. In some embodiments, the composition comprises Compound 2, or a salt thereof, and an ingestibly acceptable ingredient. In some embodiments, the composition comprises Compound 3, or a salt thereof, and an ingestibly acceptable ingredient. In some embodiments, the composition comprises Compound 4, or a salt thereof, and an ingestibly acceptable ingredient. In some embodiments, the composition comprises Compound 5, or a salt thereof, and an ingestibly acceptable ingredient. In some embodiments, the composition comprises Compound 6, or a salt thereof, and an ingestibly acceptable ingredient. In some embodiments, the composition comprises Compound 7, or a salt thereof, and an ingestibly acceptable ingredient. In some embodiments, the composition comprises Compound 8, or a salt thereof, and an ingestibly acceptable ingredient. In some embodiments, the composition comprises Compound 9, or a salt thereof, and an ingestibly acceptable ingredient. In some embodiments, the composition comprises Compound 10, or a salt thereof, and an ingestibly acceptable ingredient.

In some embodiments, the composition comprises Compound 11, or a salt thereof, and an ingestibly acceptable ingredient. In some embodiments, the composition comprises Compound 12, or a salt thereof, and an ingestibly acceptable ingredient. In some embodiments, the composition comprises Compound 13, or a salt thereof, and an ingestibly acceptable ingredient. In some embodiments, the composition comprises Compound 14, or a salt thereof, and an ingestibly acceptable ingredient. In some embodiments, the composition comprises Compound 15, or a salt thereof, and an ingestibly acceptable ingredient. In some embodiments, the composition comprises Compound 16, or a salt thereof, and an ingestibly acceptable ingredient. In some embodiments, the composition comprises Compound 17, or a salt thereof, and an ingestibly acceptable ingredient. In some embodiments, the composition comprises Compound 18, or a salt thereof, and an ingestibly acceptable ingredient. In some embodiments, the composition comprises Compound 19, or a salt thereof, and an ingestibly acceptable ingredient. In some embodiments, the composition comprises Compound 20, or a salt thereof, and an ingestibly acceptable ingredient.

In some embodiments, the composition comprises Compound 21, or a salt thereof, and an ingestibly acceptable ingredient. In some embodiments, the composition comprises Compound 22, or a salt thereof, and an ingestibly acceptable ingredient. In some embodiments, the composition comprises Compound 23, or a salt thereof, and an ingestibly acceptable ingredient. In some embodiments, the composition comprises Compound 24, or a salt thereof, and an ingestibly acceptable ingredient. In some embodiments, the composition comprises Compound 25, or a salt thereof, and an ingestibly acceptable ingredient. In some embodiments, the composition comprises Compound 26, or a salt thereof, and an ingestibly acceptable ingredient. In some embodiments, the composition comprises Compound 27, or a salt thereof, and an ingestibly acceptable ingredient. In some embodiments, the composition comprises Compound 28, or a salt thereof, and an ingestibly acceptable ingredient. In some embodiments, the composition comprises Compound 29, or a salt thereof, and an ingestibly acceptable ingredient. In some embodiments, the composition comprises Compound 30, or a salt thereof, and an ingestibly acceptable ingredient.

In some embodiments, the composition comprises Compound 31, or a salt thereof, and an ingestibly acceptable ingredient. In some embodiments, the composition comprises Compound 32, or a salt thereof, and an ingestibly acceptable ingredient. In some embodiments, the composition comprises Compound 33, or a salt thereof, and an ingestibly acceptable ingredient. In some embodiments, the composition comprises Compound 34, or a salt thereof, and an ingestibly acceptable ingredient. In some embodiments, the composition comprises Compound 35, or a salt thereof, and an ingestibly acceptable ingredient.

Some embodiments provide an ingestible composition, consisting of at least one compound of any of compounds 1-35, and an ingestibly acceptable ingredient. In some embodiments, the composition consists of Compound 1, or a salt thereof, and an ingestibly acceptable ingredient. In some embodiments, the composition consists of Compound 1, or a salt thereof, and an ingestibly acceptable ingredient. In some embodiments, the composition consists of Compound 2, or a salt thereof, and an ingestibly acceptable ingredient. In some embodiments, the composition consists of Compound 3, or a salt thereof, and an ingestibly acceptable ingredient. In some embodiments, the composition consists of Compound 4, or a salt thereof, and an ingestibly acceptable ingredient. In some embodiments, the composition consists of Compound 5, or a salt thereof, and an ingestibly acceptable ingredient. In some embodiments, the composition consists of Compound 6, or a salt thereof, and an ingestibly acceptable ingredient. In some embodiments, the composition consists of Compound 7, or a salt thereof, and an ingestibly acceptable ingredient. In some embodiments, the composition consists of Compound 8, or a salt thereof, and an ingestibly acceptable ingredient. In some embodiments, the composition consists of Compound 9, or a salt thereof, and an ingestibly acceptable ingredient. In some embodiments, the composition consists of Compound 10, or a salt thereof, and an ingestibly acceptable ingredient.

In some embodiments, the composition consists of Compound 11, or a salt thereof, and an ingestibly acceptable ingredient. In some embodiments, the composition consists of Compound 12, or a salt thereof, and an ingestibly acceptable ingredient. In some embodiments, the composition consists of Compound 13, or a salt thereof, and an ingestibly acceptable ingredient. In some embodiments, the composition consists of Compound 14, or a salt thereof, and an ingestibly acceptable ingredient. In some embodiments, the composition consists of Compound 15, or a salt thereof, and an ingestibly acceptable ingredient. In some embodiments, the composition consists of Compound 16, or a salt thereof, and an ingestibly acceptable ingredient. In some embodiments, the composition consists of Compound 17, or a salt thereof, and an ingestibly acceptable ingredient. In some embodiments, the composition consists of Compound 18, or a salt thereof, and an ingestibly acceptable ingredient. In some embodiments, the composition consists of Compound 19, or a salt thereof, and an ingestibly acceptable ingredient. In some embodiments, the composition consists of Compound 20, or a salt thereof, and an ingestibly acceptable ingredient.

In some embodiments, the composition consists of Compound 21, or a salt thereof, and an ingestibly acceptable ingredient. In some embodiments, the composition consists of Compound 22, or a salt thereof, and an ingestibly acceptable ingredient. In some embodiments, the composition consists of Compound 23, or a salt thereof, and an ingestibly acceptable ingredient. In some embodiments, the composition consists of Compound 24, or a salt thereof, and an ingestibly acceptable ingredient. In some embodiments, the composition consists of Compound 25, or a salt thereof, and an ingestibly acceptable ingredient. In some embodiments, the composition consists of Compound 26, or a salt thereof, and an ingestibly acceptable ingredient. In some embodiments, the composition consists of Compound 27, or a salt thereof, and an ingestibly acceptable ingredient. In some embodiments, the composition consists of Compound 28, or a salt thereof, and an ingestibly acceptable ingredient. In some embodiments, the composition consists of Compound 29, or a salt thereof, and an ingestibly acceptable ingredient. In some embodiments, the composition consists of Compound 30, or a salt thereof, and an ingestibly acceptable ingredient.

In some embodiments, the composition consists of Compound 31, or a salt thereof, and an ingestibly acceptable ingredient. In some embodiments, the composition consists of Compound 32, or a salt thereof, and an ingestibly acceptable ingredient. In some embodiments, the composition consists of Compound 33, or a salt thereof, and an ingestibly acceptable ingredient. In some embodiments, the composition consists of Compound 34, or a salt thereof, and an ingestibly acceptable ingredient. In some embodiments, the composition consists of Compound 35, or a salt thereof, and an ingestibly acceptable ingredient.

Some embodiments provide an ingestible composition, comprising at least two compounds of any of compounds 1-35. Some embodiments provide an ingestible composition, comprising at least three compounds of any of compounds 1-35. Some embodiments provide an ingestible composition, comprising at least four compounds of any of compounds 1-35. Some embodiments provide an ingestible composition, comprising at least five compounds of any of compounds 1-35. Some embodiments provide an ingestible composition, comprising at least six compounds of any of compounds 1-35. Some embodiments provide an ingestible composition, comprising at least seven compounds of any of compounds 1-35. Some embodiments provide an ingestible composition, comprising at least eight compounds of any of compounds 1-35. Some embodiments provide an ingestible composition, comprising at least nine compounds of any of compounds 1-35. Some embodiments provide an ingestible composition, comprising at least ten compounds of any of compounds 1-35.

In some embodiments, the ratio of, for example, two compounds, is between about 1:100 and 100:1. In some embodiments, the ratio of compounds is between about 1:50 and 50:1. In some embodiments, the ratio of compounds is between about 1:25 and 25:1. In some embodiments, the ratio of compounds is between about 1:10 and 10:1. In some embodiments, the ratio of compounds is between about 1:5 and 5:1. In some embodiments, the ratio of compounds is between about 1:2 and 2:1. In some embodiments, the ratio of compounds is about 1:1.

In some embodiments, the compound is present in an amount from about 0.01% to about 15% by weight. In some embodiments, the compound is present in an amount from about 0.05% to about 14% by weight. In some embodiments, the compound is present in an amount from about 0.1% to about 13% by weight. In some embodiments, the compound is present in an amount from about 0.2% to about 12% by weight. In some embodiments, the compound is present in an amount from about 0.3% to about 11% by weight.

In some embodiments, the compound is present in an amount from about 0.4% to about 1% by weight. In some embodiments, the compound is present in an amount from about 0.5% to about 9% by weight. In some embodiments, the compound is present in an amount from about 0.6% to about 8% by weight. In some embodiments, the compound is present in an amount from about 0.7% to about 7% by weight. In some embodiments, the compound is present in an amount from about 0.8% to about 6% by weight. In some embodiments, the compound is present in an amount from about 0.9% to about 5% by weight. In some embodiments, the compound is present in an amount from about 1% to about 4% by weight. In some embodiments, the compound is present in an amount from about 1% to about 3% by weight. In some embodiments, the compound is present in an amount from about 1% to about 2% by weight.

In some embodiments, the compound is present in the ingestible composition in an amount from about 0.01% to about 5% by weight. In some embodiments, the compound is present in the ingestible composition in an amount from about 0.02% to about 2% by weight. In some embodiments, the compound is present in the ingestible composition in an amount from about 0.05% to about 1.5% by weight. In some embodiments, the compound is present in the ingestible composition in an amount from about 0.1% to about 1% by weight.

In some embodiments, the compound is present in the ingestible composition in an amount greater than about 0.1%, 0.2%, 0.5%, 1%, 2%, 5%, or 10% by weight.

In some embodiments, the compound is present in an amount from about 0.1% to about 5% by weight. In some embodiments, the compound is present in an amount from about 0.1% to about 4% by weight. In some embodiments, the compound is present in an amount from about 0.1% to about 3% by weight. In some embodiments, the compound is present in an amount from about 0.1% to about 2% by weight. In some embodiments, the compound is present in an amount from about 0.1% to about 1% by weight. In some embodiments, the compound is present in an amount from about 0.1% to about 0.5% by weight. In some embodiments, the compound is present in an amount from about 0.5% to about 10% by weight. In some embodiments, the compound is present in an amount from about 2% to about 8% by weight.

In some embodiments, when used as a sweet flavor enhancer, the compound may be present at a concentration at or below its sweetness recognition threshold.

As used herein, an "ingestible composition" includes any composition that, either alone or together with another substance, is suitable to be taken by mouth whether intended for consumption or not. The ingestible composition includes both "food or beverage products" and "non-edible products". By "Food or beverage products", it is meant any edible product intended for consumption by humans or animals, including solids, semi-solids, or liquids (e.g., beverages) and includes functional food products (e.g., any fresh or processed food claimed to have a health-promoting and/or disease-preventing properties beyond the basic nutritional function of supplying nutrients). The term "non-food or beverage products" or "noncomestible composition" includes any product or composition that can be taken into the mouth by humans or animals for purposes other than consumption or as food or beverage. For example, the non-food or beverage product or noncomestible composition includes supplements, nutraceuticals, pharmaceutical and over the counter medications, oral care products such as dentifrices and mouthwashes, and chewing gum.

In some embodiments, an ingestible composition may be a beverage. In some embodiments, the beverage may be selected from the group consisting of enhanced sparkling beverages, colas, lemon-lime flavored sparkling beverages, orange flavored sparkling beverages, grape flavored sparkling beverages, strawberry flavored sparkling beverages, pineapple flavored sparkling beverages, ginger-ales, root beers, fruit juices, fruit-flavored juices, juice drinks, nectars, vegetable juices, vegetable-flavored juices, sports drinks, energy drinks, enhanced water drinks, enhanced water with vitamins, near water drinks, coconut waters, tea type drinks, coffees, cocoa drinks, beverages containing milk components, beverages containing cereal extracts and smoothies. In some embodiments, the beverage may be a soft drink.

An "ingestibly acceptable ingredient" is a substance that is suitable to be taken by mouth and can be combined with a compound described herein to form an ingestible composition. The ingestibly acceptable ingredient may be in any form depending on the intended use of a product, e.g., solid, semi-solid, liquid, paste, gel, lotion, cream, foamy material, suspension, solution, or any combinations thereof (such as a liquid containing solid contents). The ingestibly acceptable ingredient may be artificial or natural. Ingestibly acceptable ingredients includes many common food ingredients, such as water at neutral, acidic, or basic pH, fruit or vegetable juices, vinegar, marinades, beer, wine, natural water/fat emulsions such as milk or condensed milk, edible oils and shortenings, fatty acids and their alkyl esters, low molecular weight oligomers of propylene glycol, glyceryl esters of fatty acids, and dispersions or emulsions of such hydrophobic substances in aqueous media, salts such as sodium chloride, wheat flours, solvents such as ethanol, solid edible diluents such as vegetable powders or flours, or other liquid vehicles; dispersion or suspension aids; surface active agents; isotonic agents; thickening or emulsifying agents, preservatives; solid binders; lubricants and the like.

Additional ingestibly acceptable ingredients include acids, including, for example citric acid, phosphoric acid, ascorbic acid, sodium acid sulfate, lactic acid, or tartaric acid; bitter ingredients, including, for example caffeine, quinine, green tea, catechins, polyphenols, green robusta coffee extract, green coffee extract, whey protein isolate, or potassium chloride; coloring agents, including, for example caramel color, Red #40, Yellow #5, Yellow #6, Blue #1, Red #3, purple carrot, black carrot juice, purple sweet potato, vegetable juice, fruit juice, beta carotene, turmeric curcumin, or titanium dioxide; preservatives, including, for example sodium benzoate, potassium benzoate, potassium sorbate, sodium metabisulfate, sorbic acid, or benzoic acid; antioxidants including, for example ascorbic acid, calcium disodium EDTA, alpha tocopherols, mixed tocopherols, rosemary extract, grape seed extract, resveratrol, or sodium hexametaphosphate; vitamins or functional ingredients including, for example resveratrol, Co-Q10, omega 3 fatty acids, theanine, choline chloride (citocoline), fibersol, inulin (chicory root), taurine, panax ginseng extract, guanana extract, ginger extract, L-phenylalanine, L-carnitine, L-tartrate, D-glucoronolactone, inositol, bioflavonoids, Echinacea, ginko biloba, yerba mate, flax seed oil, *Garcinia cambogia* rind extract, white tea extract, ribose, milk thistle extract, grape seed extract, pyrodixine HCl (vitamin B6), cyanoobalamin (vitamin B12), niacinamide (vitamin B3), biotin, calcium lactate, calcium pantothenate (pantothenic acid), calcium phosphate, calcium carbonate, chromium chloride, chromium polynicotinate, cupric sulfate, folic acid, ferric pyrophosphate, iron, magnesium lactate, magnesium carbonate, magnesium sulfate, monopotassium phosphate, monosodium phosphate, phosphorus, potassium iodide, potassium phosphate, riboflavin, sodium sulfate, sodium gluconate, sodium polyphosphate, sodium bicarbonate, thiamine mononitrate, vitamin D3, vitamin A palmitate, zinc gluconate, zinc lactate, or zinc sulphate; clouding agents, including, for example ester gun, brominated vegetable oil (BVO), or sucrose acetate isobutyrate (SAIB); buffers, including, for example sodium citrate, potassium citrate, or salt; flavors, including, for example propylene glycol, ethyl alcohol, glycerine, gum Arabic (*Gum acacia*), maltodextrin, modified corn starch, dextrose, natural flavor, natural flavor with other natural flavors (natural flavor WONF), natural and artificial flavors, artificial flavor, silicon dioxide, magnesium carbonate, or tricalcium phosphate; and stabilizers, including, for example pectin, xanthan gum, carboxylmethylcellulose (CMC), polysorbate 60, polysorbate 80, medium chain triglycerides, cellulose gel, cellulose gum, sodium caseinate, modified food starch, gum Arabic (*Gum acacia*), or carrageenan.

In some embodiments, the ingestible composition further comprises a vehicle. In some embodiments, the vehicle is water. In some embodiments, the vehicle is carbonated water. In some embodiments, the vehicle is nitrogen infused water. In some embodiments, the vehicle is aqueous ethyl alcohol. In some embodiments, the vehicle is a ready-to-use beverage product.

In some embodiments, the composition comprises a sweetening compound and/or a sweet flavor enhancing compound as described herein, and one or more food additives. Representative food additives include but are not limited to, those declared to the U.S. Food and Drug Administration (See U.S. FDA list of Everything Added to Food in the U.S. (EAFUS), available at http://www.accessdata.fda.gov/scripts/fcn/fcnNavigation.cfm?rpt=eafusListing, last accessed Nov. 16, 2015). Such food additives include: Gum Acacia (*Acacia senegal* (L.) Willd.), Acai Berry Extract, Acesulfame Potassium, Acetal, Acetaldehyde, Acetaldehyde, Butyl Phenethyl Acetal, Acetaldehyde Di-Cis-3-Hexenyl Acetal, Acetaldehyde Diisoamyl Acetal, Acetaldehyde Di-Isobutylacetal, Acetaldehyde Ethyl Cis-3-Hexenyl Acetal, Acetaldehyde Ethyl Isobutyl Acetal, (+/−)-Acetaldehyde Ethyl Isopropyl Acetal, Acetaldehyde Hexyl Isoamyl Acetal, Acetaldehyde 1,3-Octanediol Acetal, Acetaldehyde Phenethyl Propyl Acetal, Acetamide, Acetanisole, Acetic Acid, Acetic Anhydride, Acetoin, Acetoin Propyleneglycol Ketal, Alpha-Acetolactate Decarboxylase Enzyme Preparation From *Bacillus subtilis* Recombinant, Acetolein, Acetone, Acetone Peroxides, Acetophenone, Acetostearin, 6-Acetoxydihydrotheaspirane, 4-Acetoxy-2,5-Dimethyl-3(2h)-Furanone, (+/−)-1-Acetoxy-1-Ethoxyethane, 4-(P-Acetoxyphenyl)-2-Butanone, 5-Acetyl-2,3-Dihydro-1,4-Thiazine, 2-Acetyl-3,5-Dimethylfuran, 3-Acetyl-2,5-Dimethylfuran, 4-Acetyl-2,5-Dimethyl-3(2h)-Furanone, 2-Acetyl-3, 5(Or 6)-Dimethylpyrazine, Mixture Of Isomers, 2-Acetyl-3-Ethylpyrazine, 4-Acetyl-2-Isopropenylpyridine, 2-Acetyl-4-Isopropenylpyridine, 2-Acetyl-4-Isopropylpyridine, 3-Acetylmercaptohexyl Acetate, N-Acetyl-L-Methionine, Acetyl Methyl Carbinyl Acetate, 2-Acetyl-5-Methylfuran, 2-Acetyl-3-Methylpyrazine, 4-Acetyl-2-Methylpyrimidine, 2-Acetyl-5-Methylthiophene, Acetylpyrazine, 2-Acetylpyridine, 3-Acetylpyridine, 2-Acetyl-1-Pyrroline, 4-Acetyl-6-Tert-Butyl-1,1-Dimethylindane, 2-Acetylthiazole, 2-Acetyl-2-Thiazoline, 3-(Acetylthio)-2-Methylfuran, Aconitic Acid, Acrolein, 3-(2-Furyl)Acrolein, Acrylamide-Acrylic Acid Resin, Acrylamide-Sodium Acrylate Resin, Acrylic Acid-2-Acrylamido-2-Methyl Propane Sulfonic Acid Copolymer, activated Carbon, Adipic Acid, Adipic Anhydride, Advantame, Agar (*Gelidium* Spp.), Alpha-Bisabolol, Dl-Alanine, L-Alanine, Beta-Alanine, L-Alanyl-L-Glutamine, Albumin, Alcohol, Denatured Formula 23a, Alcohol Sda-3a, Alfalfa, Extract (*Medicago sativa* L.), Alfalfa, Herb And Seed (*Medicago sativa* L.), Algae, Brown, Extract (*Macrocystis* And *Laminaria* Spp.), Algae, Red (*Porphyra* Spp. And *Gloiopeltis furcata* And *Rhodymenia palmata* (L.)), Algae, Red, Extract (*Porphyra* Spp. And *Gloiopeltis furcata* And *Rhodymenia palmata* (L.)), Alginate, Ammonium, Alginate, Calcium, Alginate, Potassium, Alginate, Sodium, Alginate, Sodium Calcium, Alginic Acid, Alkanet Root, Extract (*Alkanna tinctoria* Tausch), Alkanolamide Of Coconut Oil Fatty Acids And Diethanolamine, Alkylene Oxide Adducts Of Alkyl Alcohols/Phosphate Esters Of Same, (Mixture), N-Alkyl(C8-C18 From Coconut Oil) Amine Acetate, Alpha-Alkyl-Omega-Hydroxy-Poly(Oxyethylene), Allspice (*Pimenta officinalis* Lindl.), Allspice, Oil (*Pimenta officinalis* Lindl.), Allspice, Oleoresin (*Pimenta officinalis* Lindl.), Allyl Alpha-Ionone, Allyl Anthranilate, Allyl Butyrate, Allyl Cinnamate, Allyl Crotonate, Allyl Cyclohexaneacetate, Allyl Cyclohexanebutyrate, Allyl Cyclohexanehexanoate, Allyl Cyclohexanepropionate, Allyl Cyclohexanevalerate, S-Allyl-L-Cysteine, 4-Allyl-2,6-Dimethoxyphenol, Allyl Disulfide, Allyl 2-Ethylbutyrate, Allyl 2-Furoate, Allyl Heptanoate, Allyl Hexanoate, Allyl Hexenoate, Allyl Isothiocyanate, Allyl Isovalerate, Allyl Mercaptan, Allyl Methyl Disulfide, Allyl Methyl Trisulfide, Allyl Nonanoate, Allyl Octanoate, 4-Allylphenol, Allyl Phenoxyacetate, Allyl Phenylacetate, Allyl Propionate, Allyl Propyl Disulfide, Allyl Sorbate, Allyl Sulfide, Allyl Thiohexanoate, Allyl Thiopropionate, Allyl Tiglate, Allyl 10-Undecenoate, Allyl Valerate, Almond, Bitter, Oil (Ffpa) (*Prunus* Spp.), Aloe, Extract (*Aloe* Spp.), Alpha-Amylcinnamyl Isovalerate, Alpha-Ethyl Benzyl Butyrate, Alpha-Hydro-Omega-Hydroxy Poly(Oxyethylene) Poly(Oxypropylene) Poly(Oxyethylene) (15 Mole Minimum) Blocked Copolymer, Low Erucic Acid Rapeseed Oil Polymers, Alpha-Isobutylphenethyl Alcohol, Alpha-Methylbenzyl Butyrate, Alpha-Methylbenzyl Isobutyrate, Alpha-Tocopherol Acid Succinate, Althea Flowers (*Althea officinalis* L.), Althea Root (*Althea officinalis* L.), Alum (Double Sulfate Of Al And Nh4, K, Or Na), Aluminum Ammonium Sulfate, Aluminum Calcium Silicate, Aluminum Caprate, Aluminum Caprylate, Aluminum Hydroxide, Aluminum Laurate, Aluminum Myristate, Aluminum Nicotinate, Aluminum Oleate, Aluminum Palmitate, Aluminum Potassium Sulfate, Aluminum Salts Of Fatty Acids, Aluminum Sodium Sulfate, Aluminum Stearate, Aluminum Sulfate, Ambergris, Tincture, Ambrette, Absolute, Oil (*Hibiscus abelmoschus* L.), Ambrette Seed (*Hibiscus abelmoschus* L.), Ambrette Seed, Oil (*Hibiscus abelmoschus* L.), Ambrette, Tincture (*Hibiscus abelmoschus* L.), 1-Amino-2-Propanol, 2'-Aminoacetophenone, P-Aminobenzoic Acid, 4-Aminobutyric Acid, Dl-(3-Amino-3-Carboxypropyl)Dimethylsulfonium Chloride, 4-Amino-5,6-Dimethylthieno[2,3-D]Pyrimidin-2(1h)-One, 4-Amino-5,6-Dimethylthieno[2,3-D] Pyrimidin-2(1h)-One Hydrochloride, 3-[(4-Amino-2,2-Dioxido-1h-2,1,3-Benzothiadiazin-5-Yl)Oxy]-2,2-Dimethyl-N-Propylpropanamide, Aminoglycoside 3'-Phosphotransferase Ii, Aminopeptidase From *Lactococcus lactis*, Amino Tri(Methylene Phosphonic Acid), Sodium Salt, Ammonia (Also Includes Ammonium Chloride), Ammonium Acetate, Ammonium Bicarbonate, Ammonium Carbonate, Ammonium Caseinate, Ammonium Chloride, Ammonium Citrate, Dibasic, Ammonium Gluconate, Ammonium Hydroxide, Ammonium Isovalerate, Ammonium Pectinate, Ammonium Persulfate, Ammonium Phosphate, Dibasic, Ammonium Phosphate, Monobasic, Ammonium Sulfate, Ammonium Sulfide, Ammonium Sulfite, Amyl Alcohol, Alpha-Amylase Enzyme Preparation From *Bacillus stearothermophilus*, Amylase From *Aspergillus flavus*, Amylase From *Aspergillus niger*, Amylase From *Aspergillus oryzae*, Amylase From *Bacillus subtilis*, Amyl Butyrate, Alpha-Amylcinnamaldehyde, Alpha-Amylcinnamaldehyde Dimethyl Acetal, Alpha-Amylcinnamyl Acetate, Alpha-Amylcinnamyl Alcohol, Alpha-Amylcinnamyl Formate, Amyl Decanoate, Amyl Formate, Amyl 2-Furoate, Amyl Heptanoate, Amyl Hexanoate, Amyl Isothiocyanate, Amyl Methyl Disulfide, Amyl Octanoate, Amyloglucosidase From *Rhizopus niveus*, 2-Amyl-5 Or 6-Keto-1,4-Dioxane, Amyl Salicylate, Amyris (*Amyris balsamifera* L.), Amyris, Oil (*Amyris balsamifera* L.), (2,4)- And (3,5)- And (3,6)-Dimethyl-3-Cyclohexenylcarbaldehyde, Trans-Anethole, Angelica (*Angelica* Spp.), Beta-Angelicalactone, Angelica Root (*Angelica* Spp.), Angelica Root Extract (*Angelica archangelica* L.), Angelica Root Oil (*Angelica archangelica*

L.), Angelica Seed (*Angelica* Spp.), Angelica Seed Extract (*Angelica archangelica* L.), Angelica Seed Oil (*Angelica archangelica* L.), Angelica Stem Oil (*Angelica archangelica* L.), Angola Weed (*Roccella fuciformis* Ach.), Angostura (*Galipea offincinalis* Hancock), Angostura Extract (*Galipea officinalis* Hancock), Anisaldehyde Propyleneglycol Acetal, Anise (*Pimpinella anisum* L.), Anise Oil (*Pimpinella anisum* L.), Anise, Star (*Illicium verum* Hook, F.), Star Anise Oil (*Illicium verum* Hook, F.), Anisic Acid, Anisole, Anisyl Acetate, Anisyl Alcohol, Anisyl Butyrate, Anisyl Formate, Anisyl Phenylacetate, Anisyl Propionate, Annatto, Extract (*Bixa orellana* L.), Annatto, Seed (*Bixa orellana* L.), Anoxomer, Sulfonated Anthracite Coal, Beta-Apo-8'-Carotenal, Apple Essence, Apricot Kernel Oil (*Prunus armeniaca* L.), Arabinogalactan, L-Arabinose, L-Arginine, Arnica Flowers (*Arnica* Spp.), Arrowroot Starch, Artemisia (*Artemisia* Spp.), Artemisia Extract, Artemisia Oil, Artichoke Leaves (*Cynara scolymus* L.), Asafetida Fluid Extract (*Ferula assafoetida* L.), Asafetida Gum (*Ferula assafoetida* L.), Asafetida Oil (*Ferula assafoetida* L.), Ascorbic Acid, Ascorbyl Palmitate, Ascorbyl Stearate, L-Asparagine, Asparagus, Seed And Root, Extract, Aspartame, L-Aspartic Acid, *Aspergillus Niger* For Fermentation Production Of Citric Acid, Astaxanthin, Azodicarbonamide, Bacterial Catalase From *Micrococcus lysodeikticus*, Bakers Yeast Extract, Baker's Yeast Glycan, Baker's Yeast Protein, Balm (*Melissa officinalis* L.), Balm Leaves (*Melissa officinalis* L.), Balm Leaves Extract (*Melissa officinalis* L.), Balm Oil (*Melissa officinalis* L.), Balsam Fir Needles And Twigs (*Abies balsamea* (L.) Mill.), Balsam Fir Oil (*Abies balsamea* (L.) Mill.), Balsam Fir Oleoresin (*Abies balsamea* (L.) Mill.), Peru Balsam (*Myroxylon pereirae* Klotzsch), Peru Balsam, Oil (*Myroxylon pereirae* Klotzsch), Basil (*Ocimum basilicum* L.), Basil Bush (*Ocimum minimum* L.), Basil Extract (*Ocimum basilicum* L.), Basil Oil (*Ocimum basilicum* L.), Basil Oleoresin (*Ocimum basilicum* L.), Bay (*Laurus nobilis* L.), Sweet Bay Leaves Extract (*Laurus nobilis* L.), Sweet Bay Leaves Oil (*Laurus nobilis* L.), Bay Leaves, West Indian, Extract (*Pimenta acris* Kostel), Bay Leaves, West Indian, Oil (*Pimenta racemosa* (Mill.) J. W. Moore), Bay Leaves, West Indian, Oleoresin (*Pimenta acris* Kostel), Beechwood, Creosote (*Fagus* Spp.), Beeswax, Bleached Beeswax, Bentonite, Benzaldehyde, Benzaldehyde Dimethyl Acetal, Benzaldehyde Glyceryl Acetal, Benzaldehyde Propylene Glycol Acetal, Benzene, Benzenethiol, 2-Benzofurancarboxaldehyde, Benzoic Acid, Benzoin, Benzoin, Resin (*Styrax* Spp.), Benzophenone, Benzothiazole, N-Benzoylanthranilic Acid, Benzoyl Peroxide, Benzyl Acetate, Benzyl Acetoacetate, Benzyl Alcohol, Benzyl Benzoate, Benzyl Butyl Ether, Benzyl Butyrate, Benzyl Cinnamate, Benzyl 2,3-Dimethylcrotonate, Benzyl Disulfide, Benzyl Ethyl Ether, Benzyl Formate, 3-Benzyl-4-Heptanone, Benzyl Hexanoate, Benzyl Isobutyrate, Benzyl Isothiocyanate, Benzyl Isovalerate, Benzyl Levulinate, Benzyl Mercaptan, Benzyl Methoxyethyl Acetal, Benzyl Trans-2-Methyl-2-Butenoate, Benzyl Methyl Sulfide, Benzyl Nonanoate, Benzyl Phenylacetate, Benzyl Propionate, Benzyl Salicylate, Bergamot, Oil (*Citrus aurantium* L. Subsp. *bergamia* Wright Et Arn.), Betaine, Biotin, Biphenyl, Birch, Sweet, Oil (*Betula lenta* L.), Birch Tar, Oil (*Betula pendula* Roth And Related *Betula* Spp.), Bisabolene, Bis(2,5-Dimethyl-3-Furyl) Disulfide, Bis(2-Methyl-3-Furyl) Disulfide, Bis(1-Mercaptopropyl)Sulfide, Bis-(Methylthio)Methane, Bis(2-Methylphenyl) Disulfide, Bis(2-Methyl-3-Furyl) Tetrasulfide, Blackberry Bark, Extract (*Rubus*, Spp. Of Section Eubatus), Blackberry Fruit Extract, Bois De Rose, Oil (*Aniba rosaeodora* Ducke), Boldus Leaves (*Peumus boldus* Mol.), Bonito, Dried, Borax, Boric Acid, Borneol, L-Bornyl Acetate, Bornyl Acetate, Bornyl Butyrate, Bornyl Formate, Bornyl Isovalerate, Bornyl Valerate, Boronia, Absolute (*Boronia megastigma* Nees), Bouillon, Vegetable, Smoke, Beta-Bourbonene, Bromelain, Brominated Vegetable Oil, Bryonia Root (*Bryonia* Spp.), Buchu Leaves (*Barosma betulina* And *crenulata*), Buchu Leaves Extract, Buchu Leaves, Oil (*Barosma* Spp.), Buckbean Leaves (*Menyanthes trifoliata* L.), Buckbean Leaves, Extract (*Menyanthes trifoliata* L.), Butadiene-Styrene Rubber, 4-(Methylthio)Butanal, Butanal Dibenzyl Thioacetal, N-Butane, 1,3-Butanedithiol, 1,2-Butanedithiol, 2,3-Butanedithiol, 1-Butanethiol, 2-Butanol, 2-Butanone, Butan-3-One-2-Yl Butanoate, (E)-2-Butenoic Acid, 4-(2-Butenylidene)-3,5,5-Trimethylcyclohex-2-En-1-One, 3-Butenyl Isothiocyanate, 1-Buten-1-Yl Methyl Sulfide, Butter Acids, Butter Esters, Butter Fat (Enzyme-Modified, With Added Butyric Acid), Butter Starter Distillate, Butyl Acetate, Butyl Acetoacetate, Butyl Alcohol, Butylamine, Sec-Butylamine, Butyl Anthranilate, Butylated Hydroxyanisole, Butylated Hydroxytoluene, 2-Butyl-2-Butenal, Butyl Butyrate, Butyl Butyryllactate, Alpha-Butylcinnamaldehyde, Butyl Cinnamate, Butyl 2-Decenoate, 1,3-Butylene Glycol, Butyl Ethyl Disulfide, Butyl Ethyl Malonate, Butyl Formate, 2-Butylfuran, Butyl Heptanoate, Butyl Hexanoate, Butyl P-Hydroxybenzoate, Alpha-Butyl-Omega-Hydroxypoly (Oxyethylene) Poly(Oxypropylene), 3-Butylidenephthalide, Butyl Isobutyrate, 2-Butylisothiocyanate, Butyl Isothiocyanate, Butyl Isovalerate, Butyl Lactate, Butyl Laurate, Butyl Levulinate, N-Butyl 2-Methylbutyrate, Butyl Beta-(Methylthio)Acrylate, Butyl Beta-Naphthyl Ether, Butyl Oleate Sulfate, 2-Butyl-5 Or 6-Keto-1,4-Dioxane, Butyl Phenylacetate, 3-N-Butylphthalide, Butyl Propionate, Butyl Salicylate, Butyl Stearate, Butyl Sulfide, Butyl 10-Undecenoate, Butyl Valerate, Butyraldehyde, Butyramide, Butyric Acid, 2-Butyrylfuran, Cadinene, Caffeine, Cajeput, Oil (*Melaleuca leucadendron* L.), Calcium Acetate, Calcium Ascorbate, Calcium Benzoate, Calcium Bromate, Calcium Caprate, Calcium Caprylate, Calcium Carbonate, Calcium Caseinate, Calcium Chloride, Calcium Citrate, Calcium Diglutamate, Calcium Fumarate, Calcium Gluconate, Calcium Glycerophosphate, Calcium Hexametaphosphate, Calcium Hydroxide, Calcium Hypophosphite, Calcium Iodate, Calcium Lactate, Calcium Lactobionate, Calcium Laurate, Calcium Lignosulfonate, Calcium Myristate, Calcium Oleate, Calcium Oxide, Calcium Palmitate, Calcium Pantothenate, Calcium Pantothenate, Calcium Chloride Double Salt, Calcium Peroxide, Calcium Phosphate, Dibasic, Calcium Phosphate, Monobasic, Calcium Phosphate, Tribasic, Calcium Phytate, Calcium Propionate, Calcium Pyrophosphate, Calcium Salts Of Fatty Acids, Calcium Silicate, Calcium Sorbate, Calcium Stearate, Calcium Stearoyl-2-Lactylate, Calcium Sulfate, Calumba Root (*Jatrorrhiza palmata* (Lam.) Miers), Calumba Root, Extract (*Jatrorrhiza palmata* (Lam.) Miers), Camphene, Campholene Acetate, Alpha-Campholenic Alcohol, D-Camphor, Camphor, Japanese, White, Oil (*Cinnamomum camphora* (L.) Nees Et Eberm.), Camphor Oil, Formosan Ho-Sho, Leaves (*Cinnamomum camphora*), Cananga, Oil (*Cananga odorata* Hook. F. And Thoms.), Candelilla Wax (Wax From Stems And Branches Of *Euphorbia Cerifera*), Candida Guilliermondii, Candida Lipolytica, Canthaxanthin, Capers (*Capparis spinosa* L.), Caprolactam, Capsicum (*Capsicum* Spp.), Capsicum Extract (*Capsicum* Spp.), Capsicum, Oleoresin (*Capsicum* Spp.), Caramel, Caraway (*Carum carvi* L.), Caraway, Black (*Nigella sativa* L.), Caraway, Oil (*Carum carvi* L.), Carbohydrase And Cellulase From *Aspergillus niger*, Carbohydrase And Protease, Mixture, From *Bacillus subtilis*, Carbohydrase From *Aspergillus oryzae*, Carbohydrase From *Bacillus Amyloliquefaciens*, Carbohydrase From *Bacillus licheniformis*, Carbohydrase From *Bacillus Subtilis*, Carbohydrase From *Rhizopus oryzae*, Carbohydrase From *Saccharomyces* Spp., Carbohydrase/Proteinase Preparation, *Bacillus Licheniformis*, Carbon Dioxide, Carboxymethyl Cellulose, Carboxymethyl Cellulose, Sodium Salt, Carboxymethyl Hydroxyethyl Cellulose, Cardamom (*Elletaria cardamomum* (L.) Maton), Cardamom Oleoresin, Cardamom Seed, Oil (*Elletaria cardamomum* (L.) Maton), 3-Carene, Carmine (*Coccus cacti* L.), Carnauba Wax (*Copernicia cerifera* (Arruda) Mart.), L-Carnitine, Carob Bean, Extract (*Ceratonia siliqua* L.), Beta-Carotene, Carrageenan, Ammonium salt of Carrageenan, Ammonium salt of Carrageenan (With Polysorbate 80), Carrageenan And Salts Of Carrageenan, Calcium Salt of Carrageenan, Calcium Salt of Carrageenan (With Polysorbate 80), Potassium Salt of Carrageenan, Potassium Salt of Carrageenan (With Polysorbate 80), Carrageenan Salts With Polysorbate 80, Sodium Salt of Carrageenan, Sodium Salt of Carrageenan (With Polysorbate 80), Carrageenan With Polysorbate 80, Carrot (*Daucus carota* L.), Carrot, Dehydrated, Carrot, Extract, Carrot, Oil (*Daucus carota* L.), Carvacrol, Carvacryl Ethyl Ether, Carveol, 4-Carvomenthenol, Carvomenthol, Carvone, Cis-Carvone Oxide, Carvyl Acetate, Carvyl Palmitate, Carvyl Propionate, Beta-Caryophyllene, Beta-Caryophyllene Alcohol, Caryophyllene Alcohol, Beta-Caryophyllene Alcohol Acetate, Caryophyllene Alcohol Acetate, Beta-Caryophyllene Oxide, Cascara, Bitterless, Extract (*Rhamnus purshiana* Dc.), Cascarilla Bark, Extract (*Croton* Spp.), Cascarilla Bark, Oil (*Croton* Spp.), Casein, Cassia Buds (*Cinnamomum cassia* Blume), Cassie, Absolute (*Acacia farnesiana* (L.) Willd.), Castoreum, Extract (*Castor* Spp.), Castoreum, Liquid (*Castor* Spp.), Castor Oil (*Ricinus communis* L.), Catalase From *Aspergillus niger*, Catalase From Bovine Liver, Catalase From *Penicillium notatum*, Catechu, Black, Extract (*Acacia catechu* Willd.), Catechu, Black, Powder (*Acacia catechu* Willd.), Cedar Leaf Oil (*Thuja occidentalis* L.), Cedarwood Oil Alcohols, Cedarwood Oil Terpenes, (+)-Cedrol, Cedryl Acetate, Celery Seed (*Apium graveolens* L.), Celery Seed, Extract (*Apium graveolens* L.), Celery Seed, Extract Solid (*Apium graveolens* L.), Celery Seed, Oil (*Apium graveolens* L.), Celery Seed, Oleoresin, Cellulase From *Trichoderma longibrachiatum*, Cellulose Acetate, Cellulose, Diethylaminoethyl, Cellulose, Methyl, Cellulose, Methyl Ethyl, Cellulose, Microcrystalline, Cellulose Triacetate, Centaury (*Centaurium umbellatum* Gilib.), Cereal Solids, Hydrolyzed, Cetyl Alcohol, Chamomile Flower (*Matricaria chamomilla* L.), Chamomile Flower (*Anthemis nobilis* L.), Chamomile Flower, Hungarian, Oil (*Matricaria chamomilla* L.), Chamomile Flower, Oil (*Anthemis nobilis* L.), Chamomile Flower, Roman, Extract (*Anthemis nobilis* L.), Char Smoke Flavor, Cherry Bark, Wild, Extract (*Prunus serotina* Ehrh.), Cherry-Laurel Leaves (*Prunus laurocerasus* L.), Cherry Laurel, Oil (*Prunus laurocerasus* L.) (Ffpa), Cherry-Laurel Water (*Prunus laurocerasus* L.), Cherry Pits, Extract (*Prunus* Spp.), Chervil (*Anthriscus Cerefolium* (L.) Hoffm.), Chervil, Extract (*Anthriscus Cerefolium* L.), Chestnut Leaves (*Castanea dentata* (Marsh.) Borkh.), Chestnut Leaves, Extract (*Castanea dentata* (Marsh.) Borkh.), Chestnut Leaves, Extract Solid (*Castanea dentata* (Marsh.) Borkh.), Chicle (*Manilkara zapotilla* Gilly And M. Chicle Gilly), Chicle, Venezuelan (*Manilkara williamsii* Standley And Related Spp.), Chicory, Extract (*Cichorium intybus* L.), Chilte (*Cnidoscolus* (Also Known As *Jatropha*) Spp.), Chiquibul (*Manilkara zapotilla* Gilly), Chirata (*Swertia chirata* Buch.-Ham.), Chirata, Extract (*Swertia chirata* Buch.-Ham.), Chives (*Allium schoenoprasum* L.), Chlorine, Chlorine Dioxide, Chlorine Solution, Aqueous, Chloroform, Chloromethyl Methyl Ether, Chloropentafluoroethane, Chlorophyll, Cholic Acid, Choline Bitartrate, Choline Chloride, Choline Chloride (Also Includes Choline), Chrysanthemum Extract, Chymosin Preparation, *Aspergillus Niger* Var. *awamori*, Chymosin Preparation, *Escherichia Coli* K-12, Chymosin Preparation, *Kluyveromyces marxianus* Var. *lactis*, Cinchona Bark, Red (*Cinchona succirubra* Pav. Or Its Hybrids), Cinchona Bark, Red, Extract (*Cinchona succirubra* Pav. Or Its Hybrids), Cinchona Bark, Yellow (*Cinchona* Spp.), Cinchona Bark, Yellow, Extract (*Cinchona* Spp.), Cinchona, Extract (*Cinchona* Spp.), 1,4-Cineole, Cinnamaldehyde, Cinnamaldehyde Ethylene Glycol Acetal, Cinnamaldehyde Propyleneglycol Acetal, Cinnamic Acid, Cinnamon (*Cinnamomum* Spp.), Cinnamon Bark, Extract (*Cinnamomum* Spp.), Cinnamon Bark, Oil (*Cinnamomum* Spp.), Cinnamon Bark Oleoresin, Ceylon, Chinese, Or Saigon (*Cinnamomum* Spp.), Cinnamon Leaf, Oil (*Cinnamomum* Spp.), Cinnamon Leaf Oil, Rectified, Cinnamyl Acetate, Cinnamyl Alcohol, Cinnamyl Benzoate, Cinnamyl Butyrate, Cinnamyl Cinnamate, Cinnamyl Formate, Cinnamyl Isobutyrate, Cinnamyl Isovalerate, Cinnamyl Phenylacetate, Cinnamyl Propionate, Cis- And Trans-Ethyl 2,4-Dimethyl-1,3-Dioxolane-2-Acetate, Cis- And Trans-5-Ethyl-4-Methyl-2-(2-Butyl)-Thiazoline, Cis And Trans-5-Ethyl-4-Methyl-2-(2-Methylpropyl)-Thiazoline, Cis- And Trans-2-Isobutyl-4-Methyl-1,3-Dioxolane, Cis- And Trans-2-Isopropyl-4-Methyl-1,3-Dioxolane, Cis- And Trans-L-Mercapto-P-Menthan-3-One, (+−)-Cis- And Trans-2-Methyl-2-(4-Methyl-3-Pentenyl) Cyclopropanecarbaldehyde, (+/−)Cis- And Trans-2-Pentyl-4-Propyl-1,3-Oxathiane, Cis-4-Decenol, Cis-4-Heptenal, Cis-3-Hexenoic Acid, Cis-3-Hexen-1-Ol, Cis-3-Hexen-1-Yl Acetate, Cis-3-Hexenyl Acetoacetate, Cis-3-Hexenyl Butyrate, Cis-3-Hexenyl Cis-3-Hexenoate, Cis-3-Hexenyl Formate, Cis-3-Hexenyl Hexanoate, Cis-5-Isopropenyl-Cis-2-Methylcyclopentan-1-Carboxaldehyde, Cis-3-Nonen-1-Ol, Cis-9-Octadecenyl Acetate, Cis-5-Octenoic Acid, Cis-4-Octenol, Cis-2-Octenol, Citral, Citral Diethyl Acetal, Citral Dimethyl Acetal, Citral Glyceryl Acetal, Citral Propylene Glycol Acetal, Citric Acid, Citric And Fatty Acid Esters Of Glycerol, Citronellal, Citronella, Oil (*Cymbopogon nardus* Rendle), Dl-Citronellol, Citronelloxyacetaldehyde, Citronellyl Acetate, Citronellyl Anthranilate, Citronellyl Butyrate, Citronellyl Formate, Citronellyl Isobutyrate, Citronellyl Phenylacetate, Citronellyl Propionate, Citronellyl Trans-2-Methyl-2-Butenoate, Citronellyl Valerate, Citrus Peels, Extract (*Citrus* Spp.), Citrus Red No. 2, Civet, Absolute (*Viverra civetta* Schreber And *Viverra Zibetha* Schreber), Clary (*Salvia sclarea* L.), Clary Sage, Absolute, Clary, Oil (*Salvia sclarea* L.), Clary Sage, Concrete, Clay, Attapulgite, Clove Bud, Extract (*Eugenia* Spp.), Clove Bud, Oil (*Eugenia* Spp.), Clove Bud, Oleoresin (*Eugenia* Spp.), Clove Leaf, Oil (*Eugenia* Spp.), Clover (*Trifolium* Spp.), Clover, Extract (*Trifolium* Spp.), Clover Herb Distillate, Clover, Oil (*Trifolium* Spp.), Clover Tops, Red, Extract Solid (*Trifolium pratense* L.), Cloves (*Eugenia* Spp.), Clove Stem, Oil (*Eugenia* Spp.), Coca Leaf, Extract (Decocainized) (*Erythroxylon coca* Lam.), Cochineal Extract (*Coccus cacti* L.), Cocoa Butter Substitute From Coconut Oil, Palm Kernel Oil Or Both Oils, Cocoa Butter Substitute From Palm Oil, Cocoa Butter Substitute Primarily From High-Oleic Safflower Or Sunflower Oil, Cocoa Extract, Cocoa With Dioctyl Sodium Sulfosuccinate, Coconut Oil, Coconut Oil, Refined, Coffee Concentrate, Pure, Coffee Extract (*Coffea* Spp.), Coffee Extract, Solid, Cognac, Green, Oil, Cognac, White, Oil, Collagen, Combustion Product Gas, Copaiba (South American Spp. Of *Copaifera* L.), Copaiba, Oil (South American Spp. Of *Copaifera* L.), Copals, Manila, Copper Gluconate, Copper Sulfate, Coriander (*Coriandrum sativum* L.), Coriander Leaf Oil (*Coriandrum sativum* L.), Coriander, Oil (*Coriandrum sativum* L.), Cork, Oak (*Quercus* Spp.), Corn Endosperm Oil, Corn Gluten, Corn Mint Oil, Corn Silk, Corn Silk Extract (*Zea mays* L.), Corn Silk, Oil (*Zea mays* L.), Cornstarch, Cornstarch, Waxy, Corn Steep Liquor, Corn Syrup, Costmary (*Chrysanthemum balsamita* L.), Costus Root, Oil (*Saussurea lappa* Clarke), Cottonseed Flour, Defatted, Cottonseed Flour, Partially Defatted, Cooked, Cottonseed Flour, Partially Defatted, Cooked, Toasted, Cottonseed Kernels, Glandless, Raw, Cottonseed Kernels, Glandless, Roasted, Coumarone-Indene Resins, M-Cresol, P-Cresol, O-Cresol, Crown Gum, Cubeb (*Piper cubeba* L. F.), Cubeb, Oil (*Piper cubeba* L. F.), Cubebol, Cumin (*Cuminum cyminum* L.), Cuminaldehyde, Cumin, Oil (*Cuminum cyminum* L.), Cuprous Iodide, Curdlan, Currant Buds, Black, Absolute (*Ribes nigrum* L.), Currant Juice, Black, Currant Leaves, Black (*Ribes nigrum* L.), Beta-Cyclodextrin, Cycloheptadeca-9-En-1-One, Cyclohexane, Cyclohexaneacetic Acid, Cyclohexanecarboxylic Acid, Cyclohexaneethyl Acetate, Cyclohexanone, Cyclohexanone Diethyl Ketal, 2-Cyclohexenone, Cyclohexyl Acetate, Cyclohexylamine, Cyclohexyl Anthranilate, Cyclohexyl Butyrate, Cyclohexyl Cinnamate, Cyclohexyl Formate, Cyclohexyl Isovalerate, Cyclohexylmethyl Pyrazine, Cyclohexyl Propionate, Cycloionone, Cyclopentanethiol, Cyclopentanone, 2-Cyclopentylcyclopentanone, Cyclopropanecarboxylic Acid (2-Isopropyl-5-Methyl-Cyclohexyl)-Amide, N-Cyclopropyl-5-Methyl-2-Isopropylcyclohexanecarboxamide, N-Cyclopropyl-Trans-2-Cis-6-Nonadienamide, Cyclotene Butyrate, Cyclotene Propionate, P-Cymene, L-Cysteine, L-Cysteine Monohydrochloride, Dl-Cystine, L-Cystine, Daidai Peel Oil, Damar Gum (*Shorea dipterocarpaceae*), Alpha-Damascone, Delta-Damascone, Trans-Alpha-Damascone, Damiana Leaves (*Turnera diffusa* Willd.), Dandelion, Fluid Extract (*Taraxacum* Spp.), Dandelion Root, Extract Solid (*Taraxacum* Spp.), Davana Oil (*Artemesia pallens* Wall.), 2-Trans,4-Trans-Decadienal, (E,E)-2,4-Decadien-1-Ol, Delta-Decalactone, Gamma-Decalactone, *Decalepis Hamiltonii* Extract, Decanal, Decanal Dimethyl Acetal, Decanal Propyleneglycol Acetal, Decanoic Acid, 1-Decanol, 3-Decanol, 3-Decanone, 2-Decanone, 2-Trans-4-Trans-7-Cis-Decatrienal, 9-Decenal, 2-Decenal, 4-Decenal, 4-Decenoic Acid, (E)-2-Decenoic Acid, 9-Decenoic Acid, 6-Decenoic Acid, 5-Decenoic Acid, 1-Decen-3-Ol, 8-Decen-5-Olide, 9-Decen-5-Olide, 7-Decen-4-Olide, 9-Decen-2-One, 3-Decen-2-One, 6-[5(6)-Decenoyloxy]Decanoic Acid, 4-Decenyl Acetate, Cis-, Decyl Acetate, Decyl Butyrate, 2-Decylfuran, Decyl Propionate, Deertongue Solid Extract, Dehydrated Beets, Dehydroacetic Acid, Dehydrodihydroionol, Dehydrodihydroionone, Dehydromenthofurolactone, Dehydronootkatone, 8,9-Dehydrotheaspirone, Desoxycholic Acid, Dextrans (Avg M W Less Than 100,000), Dextrin, Dextrose, Diacetyl, Di-N-Alkyl (C8-C18 From Coconut Oil) Dimethyl Ammonium Chloride, Diallyl Polysulfides, Diallyl Trisulfide, Diamyl Ketone, Diastase From *Aspergillus oryzae*, Diatomaceous Earth, Dibenzyl Ether, 2,2-Dibromo-3-Nitrilopropionamide, 4,4-Dibutyl-Gamma-Butyrolactone, Dibutyl Sebacate, Dichlorodifluoromethane, Dicyclohexyl Disulfide, Diethanolamide Condensate From Soybean Oil Fatty Acids (C16-C18), Diethanolamide Condensate From Stripped Coconut Oil Fatty Acids (C10-C18), Diethylaminoethanol, Diethyl Disulfide, Diethylene Glycol Distearate, Diethylenetriamine, Diethylenetriamine Crosslinked With Epichlorohydrin, Diethyl Malate, Diethyl Malonate, 3,5-Diethyl-2-Methylpyrazine, 2,5-Diethyl-3-Methylpyrazine, 2,3-Diethyl-5-Methylpyrazine, 2,3-Diethylpyrazine, Diethyl Sebacate, Diethyl Succinate, Diethyl Sulfide, Diethyl Tartrate, 2,5-Diethyltetrahydrofuran, Diethyl Trisulfide, (+/−)-Cis- And Trans-3,5-Diethyl-1,2,4-Trithiolane, Difurfuryl Ether, 2,4-Difurfurylfuran, Di-2-Furylmethane, Digeranyl Ether, Dihydro-Alpha-Ionone, Dihydrocarveol, Cis-Dihydrocarvone, Dihydrocarvyl Acetate, Dihydrocoumarin, 6,7-Dihydro-2,3-Dimethyl-5h-Cyclopentapyrazine, 4,5-Dihydro-2,5-Dimethyl-4-Oxo-3-Furanyl Butyrate, (+/−)-Dihydrofarnesol, Dihydrogalangal Acetate, Dihydro-Beta-Ionol, Dihydro-Beta-Ionone, 3,6-Dihydro-4-Methyl-2(2-Methylpropen-1-Yl)-2h-Pyran, 5,7-Dihydro-2-Methylthieno(3,4-D)Pyrimidine, (+/−)-Dihydromintlactone, Dihydronootkatone, (+/−)-Cis- And Trans-1,2-Dihydroperillaldehyde, 4,5-Dihydro-3(2h)Thiophenone, Dihydro-2,4,6-Trimethyl-4h-1,3,5-Dithiazine, Dihydro-2,4,6-Tris(2-Methylpropyl)-4h-1,3,5-Dithiazine, Dihydroxyacetone (Dimer), Dihydroxyacetone (Monomer), Dihydroxyacetophenone, 2,4-Dihydroxybenzoic Acid, 3,4-Dihydroxybenzoic Acid, 2,5-Dihydroxy-1,4-Dithiane, 5,7-Dihydroxy-2-(3-Hydroxy-4-Methoxy-Phenyl)-Chroman-4-One, 3',7-Dihydroxy-4'-Methoxyflavan, Diisoamyl Disulfide, Diisoamyl Trisulfide, Diisobutyl Adipate, Diisobutyl Ketone, Diisopentyl Thiomalate, Diisopropyl Adipate, Diisopropyl Disulfide, Diisopropyl Trisulfide, Dilauryl Thiodipropionate, Dill (*Anethum graveolens* L.), Dill, Oil (*Anethum graveolens* L.), Dill Seed, Indian (*Anethum* Spp.), Dill Seed Oil (*Anethum sowa* Roxb.), Dimenthyl Glutarate, Dimercaptomethane, M-Dimethoxybenzene, P-Dimethoxybenzene, 1,2-Dimethoxybenzene, N1-(2,4-Dimethoxybenzyl)-N2-(2-(Pyridin-2-Yl)Ethyl)Oxalamide, 1,1-Dimethoxyethane, 1,1-Dimethoxy-Trans-2-Hexene, 2,6-Dimethoxyphenol, N-[2-(3,4-Dimethoxyphenyl)Ethyl]-3,4-Dimethoxycinnamic Acid Amide, 3,4-Dimethoxy-1-Vinylbenzene, 3,6-Dimethyl-2,3,3a,4,5,7a-Hexahydrobenzofuran, 2,4-Dimethylacetophenone, 1,4-Dimethyl-4-Acetyl-1-Cyclohexene, 2,4-Dimethyl-5-Acetylthiazole, Dimethyl Adipate, Dimethylamine, Dimethylamine-Epichlorohydrin Copolymer, 2,4-Dimethylanisole, 2,4-Dimethylbenzaldehyde, 2,3-Dimethylbenzofuran, P,Alpha-Dimethylbenzyl Alcohol, Dimethylbenzyl Carbinyl Crotonate, Dimethylbenzyl Carbinyl Hexanoate, Alpha,Alpha-Dimethylbenzyl Isobutyrate, 3,5-Dimethyl-1,2-Cyclopentadione, 3,4-Dimethyl-1,2-Cyclopentadione, (+/−)-Trans- And Cis-5-(2,2-Dimethylcyclopropyl)-3-Methyl-2-Pentenal, Dimethyl Dialkyl Ammonium Chloride, Dimethyl Dicarbonate, 2(3),5-Dimethyl-6,7-Dihydro-5h-Cyclopentapyrazine, 2,5-Dimethyl-2,5-Dihydroxy-1,4-Dithiane, 2,4-Dimethyl-1,3-Dioxolane, Dimethylethanolamine, 2,5-Dimethyl-4-Ethoxy-3(2h)-Furanone, 2,5-Dimethyl-4-Ethyloxazole, 4-(1,1-Dimethylethyl)Phenol, 4,5-Dimethyl-2-Ethyl-3-Thiazoline, 2,5-Dimethylfuran, 2,5-Dimethyl-3(2h)-Furanone, 2,5-Dimethyl-3-Furanthiol, 2,5-Dimethyl-3-Furanthiol Acetate, 2,6-Dimethyl-4-Heptanol, 2,6-Dimethyl-3-((2-Methyl-3-Furyl)Thio)-4-Heptanone, 2,6-Dimethyl-5-Heptenal, 2,6-Dimethyl-5-Heptenal Propyleneglycol Acetal, 2,6-Dimethyl-6-Hepten-1-Ol, 4,5-Dimethyl-3-Hydroxy-2,5-Dihydrofuran-2-One, 3,6-Dimethyl-2-Isobutylpyrazine, 3,5-Dimethyl-2-Isobutylpyrazine, 4,5-Dimethyl-2-Isobutylthiazole, 4,5-Dimethyl-2-Isobutyl-3-Thiazoline, 3-(1-((3,5-Dimethylisoxazol-4-Yl)Methyl)-1h-Pyrazol-4-Yl)-1-(3-Hydroxybenzyl)-5,5-Dimethylimidazolidine-2,4-Dione, 3-(1-((3,5-Dimethylisoxazol-4-Yl)Methyl)-1h-Pyrazol-4-Yl)-1-(3-Hydroxybenzyl) Imidazolidine-2,4-Dione, (+/−)-N,N-Dimethyl Menthyl Succinamide, 2,5-Dimethyl-3-Mercaptotetrahydrofuran, 2,5-Dimethyl-4-Methoxy-3(2h)-Furanone, 2,6-Dimethyl-10-Methylene-2,6,11-Dodecatrienal, 3,9-Dimethyl-6-(1-Methylethyl)-1,4-Dioxaspiro[4.5]Decan-2-One, 2,2-Dimethyl-5-(1-Methylpropen-1-Yl) Tetrahydrofuran, (+/−)-Trans- And Cis-4,8-Dimethyl-3,7-Nonadien-2-Ol, 4,8-Dimethyl-3,7-Nonadien-2-One, Cis-, 4,8-Dimethyl-3,7-Nonadien-2-One, 4,8-Dimethyl-3,7-Nonadien-2-One, Trans-, (+/−)-Trans- And Cis-4,8-Dimethyl-3,7-Nonadien-2-Yl Acetate, 2,4-Dimethyl-4-Nonanol, (E)-2-(3,7-Dimethyl-2,6-Octadienyl)Cyclopentanone, N-3,7-Dimethyl-2,6-Octadienylcyclopropylcarboxamide, 2-Trans-3,7-Dimethylocta-2,6-Dienyl 2-Ethylbutanoate, 2,6-Dimethyloctanal, 3,7-Dimethyloctanal, 3,7-Dimethyl-1-Octanol, (E)-3,7-Dimethyl-1,5,7-Octatrien-3-Ol, 3,7-Dimethyl-6-Octenoic Acid, 2,4-Dimethyl-3-Oxazoline, 2,4-Dimethyl-2-Pentenoic Acid, Alpha,Alpha-Dimethylphenethyl Acetate, Alpha,Alpha-Dimethylphenethyl Alcohol, N,N-Dimethylphenethylamine, Alpha,Alpha-Dimethylphenethyl Butyrate, Alpha,Alpha-Dimethylphenethyl Formate, Dimethylpolysiloxane, 2,5-Dimethylpyrazine, 2,6-Dimethylpyrazine, 2,3-Dimethylpyrazine, 2,6-Dimethylpyridine, 2,4-Dimethylpyridine, 2,5-Dimethylpyrrole, P,Alpha-Dimethylstyrene, Dimethyl Succinate, Dimethyl Sulfoxide, 2,5-Dimethylthiazole, 4,5-Dimethylthiazole, 2-(2-Butyl)-4,5-Dimethyl-3-Thiazoline, 2,5-Dimethyl-3-Thioisovalerylfuran, 3,4-Dimethylthiophene, 2,6-Dimethylthiophenol, Dimethyl Trisulfide, 3,5-Dimethyl-1,2,4-Trithiolane, 2,4-Dimethyl-5-Vinylthiazole, Dioctyl Adipate, Dioctyl Sodium Sulfosuccinate, Diphenyl Ether, 1,3-Diphenyl-2-Propanone, Dipotassium Phosphate, 1,1-Dipropoxyethane, Dipropyl Adipate, Dipropyl Trisulfide, Di-Sec-Butyl Disulfide, Disodium Citrate, Disodium Cyanodithioimidocarbonate, Disodium Ethylenebisdithiocarbamate, Disodium Guanylate, Disodium Inosinate, Disodium Succinate, Di-(Butan-3-One-1-Yl) Sulfide, 2,5-Dithiahexane, 1,4-Dithiane, 2,8-Dithianon-4-En-4-Carboxaldehyde, 2,2'-(Dithiodimethylene) Difuran, Dittany Of Crete (*Origanum dictamnus* L.), Dittany (Fraxinella) Roots (*Dictamnus albus* L.), Divanillin, D-Camphor, D-Limonen-10-Ol, D-Isoleucine, D-Isomenthone, D-Valine, Epsilon-Dodecalactone, Gamma-Dodecalactone, Delta-Dodecalactone, Dodecanal Dimethyl Acetal, (Z)-4-Dodecenal, 2-Dodecenal, 11-Dodecenoic Acid, 9-Dodecen-5-Olide, Dodecyl Butyrate, Dodecyl Gallate, Dodecyl Isobutyrate, Dodecyl Lactate, N-Dodecylmercaptan, Alpha-(P-Dodecylphenyl)-Omega-Hydroxypoly(Oxyethylene), Dodecyl Propionate, Dog Grass, Extract (*Agropyron repens* (L.) Beauv.), D-8-P-Menthene-1,2-Epoxide, Dragon's Blood, Extract (*Daemonorops* Spp. Or Other Botanical Sources), Dried Algae Meal, Edta, Calcium Disodium, Edta, Disodium, Edta, Disodium Iron, Edta, Tetrasodium, (2e,6e,8e)-N-(2-Methylpropyl)-2,6,8-Decatrienamide, Egg White Lysozyme, Elder Flowers (*Sambucus canadensis* L. Or *Sambucus Nigra* L.), Elder Flowers, Extract (*Sambucus canadensis* L. Or *Sambucus Nigra* L.), Elder Tree Leaves (*Sambucus nigra* L.), Elecampane Root, Extract (*Inula helenium* L.), Elecampane Root, Oil (*Inula helenium* L.), Elemi, Gum, Elemi, Oil (*Canarium* Spp.), Enzyme-Modified Fats, Enzymes, Bacterial, Enzymes, Proteolytic, Epichlorohydrin Crosslinked With Ammonia, (+/−)-2,8-Epithio-Cis-P-Menthane, 2,3-Epoxydecanal, 4,5-Epoxy-(E)-2-Decenal, 2,3-Epoxyheptanal, 2,3-Epoxyoctanal, Epoxyoxophorone, Epsilon-Decalactone, Erigeron, Oil (*Erigeron canadensis* L.), (?)-Eriodictyol, Erythorbic Acid, Esterase-Lipase From *Mucor miehei*, Estragole, 1,2-Ethanedithiol, Ethane-1,1-Dithiol, Ethanesulfonic Acid, 2-(1-(Difluoro-((Trifluoroethenyl)Oxy)Methyl)-1,2,2,2-Tetrafluoroethoxy)-1,1,2,2-Tetrafluoro-, Polymer With Tetrafluoroethane, Ethanethiol, P-Ethoxybenzaldehyde, N-[(Ethoxycarbonyl) Methyl)-P-Menthane-3-Carboxamide, 2-Ethoxy-3-Ethylpyrazine, 2-Ethoxy-3-Isopropylpyrazine, 1-Ethoxy-3-Methyl-2-Butene, O-(Ethoxymethyl)Phenol, Ethoxyquin, 2-Ethoxythiazole, (+−)-Ethyl 3-Hydroxy-2-Methylbutyrate, Ethyl Abietate, Ethyl (P-Tolyloxy)Acetate, Ethyl Acetate, Ethyl 2-(Methylthio)Acetate, Ethyl Acetoacetate, Ethyl Acetoacetate Ethyleneglycol Ketal, (+/−)-Ethyl 3-Acetoxy-2-Methylbutyrate, Ethyl 5-Acetoxyoctanoate, S-Ethyl 2-Acetylaminoethanethioate, Ethyl Alpha-Acetylcinnamate, Ethyl 2-Acetylhexanoate, Ethyl 2-Acetyloctanoate, Ethyl 2-Acetyl-3-Phenylpropionate, 1-Ethyl-2-Acetylpyrrole, Ethyl 4-(Acetylthio)Butyrate, Ethyl Aconitate (Mixed Esters), Ethyl Acrylate, Ethyl Alcohol, Ethylamine, Ethyl P-Anisate, Ethyl Anthranilate, 4-Ethylbenzaldehyde, Ethyl Benzoate, Ethyl Benzoylacetate, Ethyl Brassylate, 2-Ethylbutyl Acetate, 2-Ethylbutyraldehyde, Ethyl Butyrate, Ethyl 3-(Methylthio)Butyrate, 2-Ethylbutyric Acid, Ethyl Cellulose, Ethyl Cinnamate, Ethyl Crotonate, Ethyl Cyclohexanecarboxylate, Ethyl Cyclohexanepropionate, Ethyl Trans-2, Cis-4-Decadienoate, Ethyl Decanoate, Ethyl 2,4,7-Decatrienoate, Ethyl Trans-2-Decenoate, Ethyl Trans-4-Decenoate, Ethyl 4,5-Dihydro-2,5-Dimethyl-4-Oxo-3-Furancarboxylate, 2-Ethyl-2,5-Dihydro-4-Methylthiazole, 4-Ethyl-2,6-Dimethoxyphenol, 2(4)-Ethyl-4(2),6-Dimethyldihydro-1,3,5-Dithiazine (Mixture Of Isomers), 2-Ethyl-4,5-Dimethyloxazole, 3-Ethyl-2,6-Dimethylpyrazine, 5-Ethyl-2,3-Dimethylpyrazine, Ethyl 2,4-Dioxohexanoate, Ethylenediamine, Ethylenediaminetetraacetic Acid Disodium Salt, Ethylene Dichloride, Ethylene Glycol Distearate, Ethylene Glycol Monobutyl Ether, Ethylene Glycol Monoethyl Ether, Ethylene Glycol Monophenyl Ether, Ethylene Oxide, Ethylene Oxide Polymer, Ethylene Oxide Polymer, Alkyl Adduct, Ethylene Oxide Polymer, Alkyl Adduct, Phosphate Ester, Ethylene Oxide/Propylene Oxide Copolymer (Avg M W 9,760-13,200), Ethylene Oxide/Propylene Oxide Copolymer (Min Avg M W 1,900), Ethylene Oxide/Propylene Oxide Copolymer (Avg M W 14,000), Ethylene Oxide/Propylene Oxide Copolymer, Ethylene Oxide/Propylene Oxide Copolymer (Avg M W 3,500-4,125), Ethylene Oxide/Propylene Oxide Copolymer, Alkyl Adduct, Ethylene Oxide/Propylene Oxide Copolymer, Alkyl Adduct, Phosphate Ester, Ethyl Esters Of Fatty Acids (Edible), Ethyl N-Ethylanthranilate, Ethyl 2-Ethylbutyrate, Ethyl 2-Ethylhexanoate, Ethyl Alpha-Ethyl-Beta-Methyl-Beta-Phenylglycidate, Ethyl 2-Ethyl-3-Phenylpropanoate, Ethyl 3-(Ethylthio)Butyrate, Ethyl Formate, 2-Ethylfuran, Ethyl 2-Furanpropionate, Ethyl Furfuryl Ether, Ethyl 3-(Furfurylthio) Propionate, Ethyl 3-(2-Furyl)Acrylate, 4-Ethylguaiacol, Ethyl Heptanoate, 2-Ethyl-2-Heptenal, Ethyl 4-Heptenoate, Cis-,2-Ethylhexanethiol, Ethyl Hexanoate, 2-Ethyl-1-Hexanol, 2-Ethyl-2-Hexenal, Ethyl Cis-3-Hexenoate, Ethyl 5-Hexenoate, Ethyl 3-Hexenoate, Ethyl 2-Hexenoate, 2-Ethylhexyl Benzoate, 2-Ethylhexyl 3-Mercaptopropionate, 1-Ethylhexyl Tiglate, Ethyl 3-Hydroxybutyrate, 3-Ethyl-2-Hydroxy-2-Cyclopenten-1-One, Ethyl 5-Hydroxydecanoate, Ethyl 2-Hydroxyethyl Sulfide, Ethyl 3-Hydroxyhexanoate, (+/−)-Ethyl 2-Hydroxy-2-Methylbutyrate, 3-Ethyl-2-Hydroxy-4-Methylcyclopent-2-En-1-One, 5-Ethyl-2-Hydroxy-3-Methylcyclopent-2-En-1-One, 5-Ethyl-3-Hydroxy-4-Methyl-2(5h)-Furanone, 2-Ethyl-4-Hydroxy-5-Methyl-3(2h)-Furanone, (+/−)-Ethyl 2-Hydroxy-3-Methylvalerate, Ethyl 3-Hydroxyoctanoate, Ethyl 5-Hydroxyoctanoate, Ethyl 2-Hydroxy-3-Phenylpropionate, Ethyl Isobutyrate, N-Ethyl-2-Isopropyl-5-Methylcyclohexane Carboxamide, Ethyl Isothiocyanate, Ethyl Isovalerate, Ethyl Lactate, Ethyl Laurate, Ethyl Levulinate, Ethyl Levulinate Propyleneglycol Ketal, Ethyl Linalyl Ether, Ethyl Maltol, Ethyl Maltol Isobutyrate, Ethyl 3-Mercaptobutyrate, (+−)-Ethyl 3-Mercapto-2-Methylbutanoate, Ethyl 2-Mercapto-2-Methylpropionate, Ethyl 3-Mercaptopropionate, Ethyl 2-Mercaptopropionate, Ethyl N-Methylanthranilate, Ethyl 2-Methylbutyrate, Ethyl Methyl Disulfide, Ethyl 2-Methyl-3,4-Pentadienoate, Ethyl 4-Methylpentanoate, Ethyl 3-Methylpentanoate, Ethyl 2-Methylpentanoate, Ethyl 2-Methyl-3-Pentenoate, Ethyl 2-Methyl-4-Pentenoate, 3-Ethyl-2-Methylpyrazine, 2-Ethyl-6-Methylpyrazine, 2-Ethyl-5-Methylpyrazine, 5-Ethyl-2-Methylpyridine, 5-Ethyl-2-Methylthiazole, 2-Ethyl-4-Methylthiazole, Ethyl 4-(Methylthio) Butyrate, Ethyl 3-(Methylthio)-Cis-2-Propenoate, Ethyl 3-(Methylthio)-2-Propenoate, Ethyl 3-Methylthiopropionate, 2-Ethyl-3-Methylthiopyrazine, Ethyl 3-(Methylthio)-Trans-2-Propenoate, Ethyl 5-(Methylthio) Valerate, Ethyl Methyl-P-Tolylglycidate, 2-Ethyl-(3 Or 5 Or 6)-Mop(85%) And 2-Methyl-(3 Or 5 Or 6)-Mop (13%), Ethyl Myristate, Ethyl Nitrite, N-Ethyl Trans-2-Cis-6-Nonadienamide, Ethyl Nonanoate, Ethyl 2-Nonynoate, Ethyl Octadecanoate, Ethyl Cis-4,7-Octadienoate, (+/−)-4-Ethyloctanal, Ethyl Octanoate, 4-Ethyloctanoic Acid, Ethyl Cis-4-Octenoate, Ethyl 3-Octenoate, Ethyl Trans-2-Octenoate, Ethyl Oleate, 2-Ethyl-3,(5 Or 6)-Dimethylpyrazine, Ethyl 5-Oxodecanoate, Ethyl 3-Oxohexanoate, Ethyl Palmitate, Ethyl 4-Pentenoate, P-Ethylphenol, Ethyl Phenylacetate, Ethyl 4-Phenylbutyrate, Ethyl 3-Phenylglycidate, Ethyl 3-Phenylpropionate, Ethyl Propionate, Ethyl 2-(Methyldithio)Propionate, Ethyl Propyl Disulfide, Ethyl Propyl Trisulfide, 2-Ethylpyrazine, 3-Ethylpyridine, 1-Ethyl-2-Pyrrolecarboxaldehyde, Ethyl Pyruvate, Ethyl Salicylate, Ethyl Sorbate, Ethyl Thioacetate, (+/−)-3-(Ethylthio)Butanol, 2-Ethylthiophenol, Ethyl Tiglate, Ethyl Trans-2-Hexenoate, Ethyl Trans-2-Methyl-2-Pentenoate, 2-Ethyl-1,3,3-Trimethyl-2-Norbornanol, Ethyl Undecanoate, Ethyl 10-Undecenoate, Ethyl Valerate, Ethyl Vanillin, Ethyl Vanillin Beta-D-Glucopyranoside, Ethyl Vanillin Isobutyrate, Ethyl Vanillin Propylene Glycol Acetal, Eucalyptol, Eucalyptus, Oil (*Eucalyptus globulus* Labille), Eugenol, Eugenyl Acetate, Eugenyl Benzoate, Eugenyl Formate, Eugenyl Isovalerate, Eugenyl Methyl Ether, (2e,6z,8e)-N-(2-Methylpropyl)-2,6,8-Decatrienamide, Farnesal, Farnesene, Farnesol, Fatty Acids, Fatty Alcohols, Synthetic, Fd&C Blue No. 2, Fd&C Blue No. 1, Fd&C Blue No. 2, Aluminum Lake, Fd&C Blue No. 1, Aluminum Lake, Fd&C Blue No. 2, Calcium Lake, Fd&C Blue No. 1, Calcium Lake, Fd&C Green No. 3, Fd&C Green No. 3, Aluminum Lake, Fd&C Green No. 3, Calcium Lake, Fd&C Red No. 40, Fd&C Red No. 3, Fd&C Red No. 40, Aluminum Lake, Fd&C Red No. 3, Fd&C Red No. 40, Calcium Lake, Fd&C Red No. 3, Fd&C Yellow No. 6, Fd&C Yellow No. 5, Fd&C Yellow No. 5, Aluminum Lake, Fd&C Yellow No. 6, Aluminum Lake, Fd&C Yellow No. 5, Calcium Lake, Fd&C Yellow No. 6, Calcium Lake, D-Fenchone, Fenchyl Alcohol, Fennel, Common (*Foeniculum vulgare* Mill.), Fennel, Sweet (*Foeniculum vulgare* Mill. Var. Dulce (D.C.) Alef.), Fennel, Sweet, Oil (*Foeniculum vulgare* Mill. Var. Dulce (D.C.) Alef.), Fenugreek (*Trigonella foenum-graecum* L.), Fenugreek, Extract (*Trigonella foenum-graecum* L.), Fenugreek, Oleoresin (*Trigonella foenum-graecum* L.), Ferric Ammonium Citrate, Brown, Ferric Chloride, Ferric Citrate, Ferric Oxide, Ferric Peptonate, Ferric Phosphate, Ferric Pyrophosphate, Ferric Sodium Pyrophosphate, Ferric Sulfate, Ferrocyanide Salts, Ferrous Ascorbate, Ferrous Carbonate, Ferrous Citrate, Ferrous Fumarate, Ferrous Gluconate, Ferrous L-Lactate, Ferrous Lactate, Ferrous Peptonate, Ferrous Sulfate, Ficin, Fir (Pine) Needles And Twigs (*Abies sibirica* Ledeb.), Fir Needles And Twigs, Oil (*Abies* Spp.), Fish Oil (Hydrogenated), Fish Protein Concentrate, Whole, Fish Protein Isolate, Folic Acid, Formaldehyde, Formic Acid, 2-Formyl-6,6-Dimethylbicyclo(3.1.1)Hept-2-Ene, 4-Formyl-2-Methoxyphenyl 2-Hydroxypropanoate, Fruit Juice, Fullers Earth, Fumaric Acid, Fungal Hemicellulase, Fungal Pectinase, 2-Furanmethanethiol Formate, 4-((Furanmethyl) Thio)-2-Pentanone, Furcelleran, Ammonium Salt of Furcelleran, Furcelleran And Salts Of Furcelleran, Calcium Salt of Furcelleran, Potassium Salt of Furcelleran, Sodium Salt of Furcelleran, Furfural, Furfural Propyleneglycol Acetal, Furfuryl Acetate, Furfuryl Alcohol, Furfuryl Butyrate, Furfuryl Decanoate, Furfuryl Formate, 2-Furfurylidenebutyraldehyde, Furfuryl Isopropyl Sulfide, Furfuryl Mercaptan, Furfuryl 3-Methylbutanoate, Furfuryl Methyl Ether, Furfuryl 2-Methyl-3-Furyl Disulfide, Furfuryl Methyl Sulfide, Alpha-Furfuryl Octanoate, Alpha-Furfuryl Pentanoate, Furfuryl Propionate, Furfuryl Propyl Disulfide, N-Furfurylpyrrole, Furfuryl Thioacetate, 1-(2-Furfurylthio)Propanone, Furfuryl Thiopropionate, 3-(2-Furoylthio)-2,5-Dimethylfuran, 1-(2-Furyl)-1,3-Butanedione, 1-(2-Furyl)Butan-3-One, 4-(2-Furyl)-3-Buten-2-One, 2-Furyl Methyl Ketone, Fusel Oil, Refined, Alpha-Galactosidase From *Morteirella vinaceae* Raffinoseutilizer, Galanga, Greater (*Alpinia galanga* Willd), Galangal Root (*Alpinia* Spp.), Galangal Root, Extract (*Alpinia* Spp.), Galangal Root, Oil (*Alpinia* Spp.), Galbanum, Oil (*Ferula* Spp.), Galbanum, Resin (*Ferula* Spp.), Gambir (*Uncaria gambir* Roxb.), *Gardenia Gummifera* Distillate, Garlic, Garlic Extract, Garlic Oil (*Allium sativum* L.), Dehydrated Garlic, Garlic Powder, Gelatin, Gellan Gum, Genet Absolute (*Spartium junceum* L.), Genet Extract (*Spartium junceum* L.), Gentian Root Extract (*Gentiana lutea* L.), Gentian, Stemless (*Gentiana acaulis* L.), Geranic Acid, Geraniol, Geranium (*Pelargonium* Spp.), Geranium, East Indian, Extract (*Cymbopogon martini* Stapf.), Geranium, East Indian, Oil (*Cymbopogon martini* Stapf.), Geranium Extract (*Pelargonium* Spp.), Geranium, Oil (*Pelargonium* Spp.), Geranium, Rose, Oil (*Pelargonium graveolens* L'her.), Geranyl Acetate, Geranyl Acetoacetate, Geranyl Acetone, Geranyl Benzoate, Geranyl Butyrate, Geranyl Formate, Geranyl Hexanoate, Geranyl Isobutyrate, Geranyl Isovalerate, Geranyl 2-Methylbutyrate, Geranyl Phenylacetate, Geranyl Propionate, Geranyl Tiglate, Geranyl Valerate, Germander, Chamaedrys (*Teucrium chamaedrys* L.), Germander, Chamaedrys, Extract (*Teucrium chamaedrys* L.), Germander, Chamaedrys, Extract Solid (*Teucrium chamaedrys* L.), Germander, Golden (*Teucrium polium* L.), Ghatti, Gum (*Anogeissus latifolia* Wall.), Gibberellic Acid & Potassium Gibberellate, Ginger (*Zingiber officinale* Rosc.), Ginger, Extract (*Zingiber officinale* Rosc.), Ginger, Oil (*Zingiber officinale* Rosc.), Ginger, Oleoresin (*Zingiber officinale* Rosc.), D-Gluconic Acid, Glucono-Delta Lactone, N-Gluconyl Ethanolamine, N-Gluconyl Ethanolamine Phosphate, Glucose Isomerase From *Bacillus Coagulans*, Glucose Isomerase From Immobilized *Arthrobacter Globiformis*, Glucose Isomerase From *Streptomyces olivaceus*, Glucose Isomerase From *Streptomyces olivochromogenes*, Glucose Isomerase From *Streptomyces rubiginosus*, Glucose Oxidase Catalase Preparation, Glucose Oxidase From *Aspergillus niger*, Glucose Oxidase From *Penicillium Notatum*, Glucose Pentaacetate, Glucosidase From *Aspergillus flavus*, Glucosidase From *Aspergillus niger*, Glucosidase From *Aspergillus oryzae*, L-Glutamic Acid, Glutamic Acid Hydrochloride, L-Glutamine, Gamma-Glutamyl-Valyl-Glycine, Glutaraldehyde, Gluten, Gum, Glycerin, Glycerin, Synthetic, Glycerol Tributyrate, Glyceryl Behenate, Glyceryl 5-Hydroxydecanoate, Glyceryl 5-Hydroxydodecanoate, Glyceryl-Lacto Esters Of Fatty Acids, Glyceryl Lactooleate, Glyceryl Lactopalmitate, Glyceryl Monooleate, Glyceryl Monostearate, Glyceryl Palmitostearate, Glyceryl Tribenzoate, Glyceryl Tripropanoate, Glyceryl Tristearate, Glycine, Glycocholic Acid, Glycyrrhizin, Ammoniated (*Glycyrrhiza* Spp.), Grains Of Paradise (*Aframomum melegueta* (Rosc.) K. Schum.), Grape Color Extract, Grape Essence, Natural, Grapefruit Essence, Natural, Grapefruit, Extract, Grapefruit, Juice, Grapefruit, Oil (*Citrus paradisi* Macf.), Grapefruit Oil, Conc., Grapefruit, Oil, Terpeneless (*Citrus paradisi*), Grape Seed Extract, Grape Skin Extract, Ground Limestone, Guaiac Gum (*Guaiacum* Spp.), Guaiac Gum, Extract (*Guaiacum* Spp.), Guaiacol, Guaiacol Butyrate, Guaiacol Propionate, Guaiac Wood, Extract (*Guaiacum* Spp.), Guaiac Wood, Oil (*Guaiacum* Spp.), Guaiacyl Acetate, Guaiacyl Isobutyrate, Guaiacyl Phenylacetate, Guaiene, Guaiol Acetate, Guarana, Gum (*Paullinia cupana* Hbk), Guarana Seed, Extract, Guar, Gum (*Cyamopsis tetragonolobus* (L.)), Guava (*Psidium* Spp.), Guava Extract, Gum Arabic, Hydrogen Octenylbutane Dioate, Gutta Hang Kang (*Palaquium leiocarpum* Boerl. And *P. Oblongifolium* Burck.), Haematococcus Algae Meal, Haw Bark, Black, Extract (*Viburnum prunifolium* L.), *Heliopsis longipes* Extract, Helium, Hemlock (*Tsuga* Spp.), Hemlock Needles And Twigs, Oil (*Tsuga* Spp.), 2,4-Heptadienal, Trans-2-Trans-4-Heptadien-1-Ol, Gamma-Heptalactone, Heptanal, Heptanal Dimethyl Acetal, Heptanal Glyceryl Acetal (Mixed 1,2 And 1,3 Acetals), Heptanal Propyleneglycol Acetal, 2,3-Heptanedione, 2-Heptanethiol, Heptane-1-Thiol, Heptanoic Acid, 2-Heptanol, 3-Heptanol, 2-Heptanone, 3-Heptanone, 4-Heptanone, N-(Heptan-4-Yl)Benzo[D][1,3]Dioxole-5-Carboxamide, 2-Heptenal, 4-Heptenal Diethyl Acetal, (E)-2-Heptenoic Acid, (+/−)-1-Hepten-3-Ol, (Z)-4-Hepten-1-Ol, 3-Hepten-2-One, 2-Hepten-4-One, Hept-Trans-2-En-1-Yl Acetate, Hept-2-En-1-Yl Isovalerate, Trans-3-Heptenyl 2-Methylpropanoate, 3-Heptyl Acetate, Heptyl Acetate, Heptyl Alcohol, Heptyl Butyrate, 2-Heptyl Butyrate, Heptyl Cinnamate, Cis- And Trans-2-Heptylcyclopropanecarboxylic Acid, 3-Heptyldihydro-5-Methyl-2(3h)-Furanone, Heptyl Formate, 2-Heptylfuran, Heptyl Heptanoate, Heptyl Isobutyrate, Heptyl Octanoate, Heptylparaben, Hesperidin, Delta-Hexadecalactone, Omega-6-Hexadecenlactone, Hexadecyl Lactate, Trans, Trans-2,4-Hexadienal, 2,4-Hexadien-1-Ol, 2,4-Hexadienyl Acetate, 2,4-Hexadienyl Butyrate, 2,4-Hexadienyl Isobutyrate, 2,4-Hexadienyl Propionate, Delta-Hexalactone, Gamma-Hexalactone, Hexanal, Hexanal Butane-2,3-Diol Acetal, Hexanal Dihexyl Acetal, Hexanal Hexyl Isoamyl Acetal, Hexanal Octane-1,3-Diol Acetal, Hexane, 2,3-Hexanedione, 3,4-Hexanedione, 1,6-Hexanedithiol, 1-Hexanethiol, Hexanoic Acid, 3-Hexanol, 3-Hexanone, Cis-3-Hexenal, Trans-4-Hexenal, 3-Hexenal, Cis-4-Hexenal, Trans-3-Hexenal, 2-Hexenal, (+/−)-Trans- And Cis-2-Hexenal Glyceryl Acetal, (E)-2-Hexenal Diethyl Acetal, 4-Hexene-3-One, (Z)-3-Hexenyl (E)-2-Hexenoate, Trans-2-Hexenoic Acid, 3-Hexenoic Acid, 1-Hexen-3-Ol, 2-Hexen-1-Ol, 4-Hexen-1-Ol, 5-Hexenol, (Z)-2-Hexen-1-Ol, (Z)-3-Hexenyl Anthranilate, Cis-3-Hexenyl Benzoate, (E)-2-Hexenyl Butyrate, 3-Hexenyl Crotonate, Cis-, (E)-2-Hexenyl Formate, 2-Hexenyl Hexanoate, Trans-, (Z)-3-Hexenyl Isobutyrate, 5-Hexenyl Isothiocyanate, (E)-2-Hexenyl Isovalerate, 3-Hexenyl Isovalerate, Cis-3-Hexenyl Lactate, 3-Hexenyl 2-Methylbutyrate, 2-Hexenyl Octanoate, 3-Hexenyl Phenylacetate, (E)-2-Hexenyl Propionate, Cis-3 & Trans-2-Hexenyl Propionate, (Z)-3-Hexenyl Propionate, (Z)-3-Hexenyl Pyruvate, (Z)-3-Hexenyl Valerate, (E)-2-Hexenyl Valerate, Hexyl Acetate, 2-Hexyl-4-Acetoxytetrahydrofuran, Hexyl Alcohol, Hexylamine, Hexyl Benzoate, N-Hexyl 2-Butenoate, Hexyl Butyrate, Alpha-Hexylcinnamaldehyde, Hexyl Decanoate, 2-Hexyl-4,5-Dimethyl-1,3-Dioxolane, Hexyl Formate, Hexyl 2-Furoate, Hexyl Heptanoate, Hexyl Hexanoate, Hexyl Trans-2-Hexenoate, 2-Hexylidene Cyclopentanone, 2-Hexylidenehexanal, Hexyl Isobutyrate, Hexyl Isothiocyanate, Hexyl Isovalerate, 2-Hexyl-5 Or 6-Keto-1,4-Dioxane, Hexyl 3-Mercaptobutanoate, Hexyl 2-Methylbutyrate, Hexyl 2-Methyl-3(Or 4)-Pentenoate, Hexyl Nonanoate, Hexyl Octanoate, Hexyl Phenylacetate, Hexyl Propionate, 2-Hexylthiophene, Hickory Bark, Extract (*Carya* Spp.), Hickory Smoke Dist., High Fructose Corn Syrup, L-Histidine, (−)-Homoeriodictyol, Sodium Salt, Honeysuckle Extract, Hops, Extract (*Humulus lupulus* L.), Hops Extract, Modified, Hops, Extract Solid (*Humulus lupulus* L.), Hops, Oil (*Humulus lupulus* L.), Horehound Extract (*Marrubium vulgare* L.), Horehound (*Marrubium vulgare* L.), Horehound Solid, Extract, Horsemint Leaves, Extract (*Monarda* Spp.), Horseradish (*Armoracia lapathifolia* Gilib.), Horseradish Oil, Hyacinth, Absolute (*Hyacinthus orientalis* L.), Hyacinth Flowers (*Hyacinthus orientalis* L.), Hydratropic Aldehyde Propylene Glycol Acetal, Hydrazine, Hydrochloric Acid, Hydrogen Peroxide, Hydrogen Sulfide, Hydroquinone Monoethyl Ether, Hydroxyacetone, 4-Hydroxyacetophenone, 2-Hydroxyacetophenone, 4-Hydroxybenzaldehyde, 4-Hydroxybenzoic Acid, 3-Hydroxybenzoic Acid, 4-Hydroxybenzyl Alcohol, 4-Hydroxybutanoic Acid Lactone, 1-Hydroxy-2-Butanone, 4-Hydroxy-2-Butenoic Acid Gamma-Lactone, 6-Hydroxycarvone, Hydroxycitronellal, Hydroxycitronellal Diethyl Acetal, Hydroxycitronellal Dimethyl Acetal, Hydroxycitronellal Propyleneglycol Acetal, Hydroxycitronellol, 2-Hydroxy-2-Cyclohexen-1-One, 5-Hydroxy-2,4-Decadienoic Acid Delta-Lactone, 5-Hydroxy-2-Decenoic Acid Delta-Lactone, 5-Hydroxy-7-Decenoic Acid Delta-Lactone, 6-Hydroxydihydrotheaspirane, 4-Hydroxy-3,5-Dimethoxybenzaldehyde, 4-Hydroxy-2,5-Dimethyl-3(2h)-Furanone, 4-Hydroxy-2,3-Dimethyl-2,4-Nonadienoic Acid Gamma Lactone, 6-Hydroxy-3,7-Dimethyloctanoic Acid Lactone, (Z)-4-Hydroxy-6-Dodecenoic Acid Lactone, 5-Hydroxy-2-Dodecenoic Acid Lactone, 1-Hydroxyethylidene-1, 1-Diphosphonic Acid, 4-Hydroxy-4-(3-Hydroxy-1-Butenyl)-3,5,5-Trimethyl-2-Cyclohexen-1-One, Hydroxy(4-Hydroxy-3-Methoxyphenyl)Acetic Acid, 1-(2-Hydroxy-4-Isobutoxyphenyl)-3-(Pyridin-2-Yl)Propan-1-One, Hydroxylated Lecithin, 2-Hydroxy-4-Methoxybenzaldehyde, N-(4-Hydroxy-3-Methoxybenzyl)-8-Methyl-6-Nonenamide, 1-(4-Hydroxy-3-Methoxyphenyl)Decan-3-One, 1-(2-Hydroxy-4-Methoxyphenyl)-3-(Pyridin-2-Yl)Propan-1-One, 2-Hydroxy-5-Methylacetophenone, 2-Hydroxy-4-Methylbenzaldehyde, 2-(2-Hydroxy-4-Methyl-3-Cyclohexenyl)Propionic Acid Gamma-Lactone, 4-Hydroxy-4-Methyl-7-Cis-Decanoic Acid Gamma Lactone, 2-Hydroxymethyl-6,6-Dimethylbicyclo(3.1.1)Hept-2-Enyl Formate, 4-Hydroxymethyl-2,6-Di-Tertbutylphenol, 10-Hydroxymethylene-2-Pinene, 4-Hydroxy-5-Methyl-3(2h)-Furanone, 3-(Hydroxymethyl)-2-Heptanone, 5-Hydroxy-4-Methylhexanoic Acid Delta-Lactone, 3-Hydroxy-5-Methyl-2-Hexanone, 2-Hydroxy-5-Methyl-3-Hexanone, 4-Hydroxy-4-Methyl-5-Hexenoic Acid Gamma Lactone, (?)-3-Hydroxy-3-Methyl-2,4-Nonanedione, 4-Hydroxy-3-Methyloctanoic Acid Lactone, 1-Hydroxy-4-Methyl-2-Pentanone, 1-(3-Hydroxy-5-Methyl-2-Thienyl)Ethanone, HydroxynonanoicAcid, Delta-Lactone, 3-Hydroxy-2-Octanone, 5-Hydroxy-4-Octanone, 3-Hydroxy-2-Oxopropionicacid, 3-Hydroxy-2-Pentanone, 4-Hydroxy-3-Pentenoic Acid Lactone, 4-(P-Hydroxyphenyl)-2-Butanone, 3-Hydroxy-4-Phenylbutan-2-One, 2-(2-Hydroxyphenyl) Cyclopropanecarboxylic Acid Delta Lactone, 1-(2-Hydroxyphenyl)-3-(Pyridin-4-Yl)Propan-1-One, (+/−)-2-Hydroxypiperitone, L-Hydroxyproline, Hydroxypropyl Cellulose, Hydroxypropyl Methylcellulose, 2-Hydroxy-3,5,5-Trimethyl-2-Cyclohexenone, 5-Hydroxyundecanoic Acid Lactone, 5-Hydroxy-8-Undecenoic Acid Delta-Lactone, Hyssop, Extract (*Hyssopus officinalis* L.), Hyssop (*Hyssopus officinalis* L.), Hyssop, Oil (*Hyssopus officinalis* L.), Iceland Moss (*Cetraria islandica* Ach.), Immortelle, Absolute (*Helichrysum angustifolium* Dc), Immortelle, Extract (*Helichrysum angustifolium* Dc.), Imperatoria (*Peucedanum ostruthium* (L.) Koch (*Imperatoria ostruthium* L.)), Indole, Inositol, Insoluble Glucose Isomerase Enzyme Preparations, Invertase From *Saccharomyces cerevisiae*, Invert Sugar, Invert Sugar Syrup, Alpha-Ionene, Ion Exchange Membranes, Ion Exchange Resin, Beta-Ionol, Alpha-Ionol, Beta-Ionone, Gamma-Ionone, Alpha-Ionone, Beta-Ionone Epoxide, Beta-Ionyl Acetate, Iron Ammonium Citrate, Iron Caprylate, Iron-Choline Citrate Complex, Iron Citrate, Alpha-Irone, Iron, Elemental, Iron Linoleate, Iron Naphthenate, Iron Oxide, Iron Peptonate, Iron Polyvinylpyrrolidone, Iron Tallate, Isoambrettolide, Isoamyl Acetate, Isoamyl Acetoacetate, Isoamyl Alcohol, Isoamyl Benzoate, Isoamyl Butyrate, Isoamyl Cinnamate, Isoamyl Formate, Isoamyl 4-(2-Furan)Butyrate, Isoamyl 3-(2-Furan)Propionate, Isoamyl Hexanoate, Isoamyl Isobutyrate, Isoamyl Isothiocyanate, Isoamyl Isovalerate, Isoamyl Laurate, Isoamyl Levulinate, Isoamyl 2-Methylbutyrate, Isoamyl Nonanoate, Isoamyl Octanoate, Isoamyl Phenethyl Ether, Isoamyl Phenylacetate, Isoamyl Propionate, Isoamyl Pyruvate, Isoamyl Salicylate, Isoborneol, Isobornyl Acetate, Isobornyl Formate, Isobornyl Isobutyrate, Isobornyl Isovalerate, Isobornyl 2-Methylbutyrate, Isobornyl Propionate, Isobutane, Isobutyl Acetate, Isobutyl Acetoacetate, Isobutyl Alcohol, Isobutylamine, Isobutyl Angelate, Isobutyl Anthranilate, Isobutyl Benzoate, Isobutyl 2-Butenoate, Isobutyl Butyrate, Isobutyl Cinnamate, N-Isobutyldeca-Trans-2-Trans-4-Dienamide, 2(4)-Isobutyl-4(2),6-Dimethyldihydro-4h-1,3,5-Dithiazine, 2-Isobutyl-4,5-Dimethyloxazole, Isobutylene-Isoprene Copolymer, Isobutyl Formate, Isobutyl 2-Furanpropionate, Isobutyl Heptanoate, Isobutyl Hexanoate, Isobutyl Isobutyrate, Isobutyl Isothiocyanate, 2-Isobutyl-3-Methoxypyrazine, Isobutyl N-Methylanthranilate, 2-Isobutyl-3-Methylpyrazine, (+/−)-Isobutyl 3-Methylthiobutyrate, Isobutyl Phenylacetate, Isobutyl Propionate, Isobutyl Salicylate, 2-Isobutylthiazole, Isobutyl 10-Undecenoate, Isobutyraldehyde, Isobutyric Acid, Isocyclocitral, Isoeugenol, Isoeugenyl Acetate, Isoeugenyl Benzyl Ether, Isoeugenyl Ethyl Ether, Isoeugenyl Formate, Isoeugenyl Methyl Ether, Isoeugenyl Phenylacetate, Isojasmone, L-Isoleucine, Alpha-Isomethylionone, Beta-Isomethylionone, Alpha-Isomethylionyl Acetate, Isoparaffinic Petroleum Hydrocarbons, Synthetic, Isopentylamine, Isopentylideneisopentylamine, Isophorone, Isopropenyl Acetate, 5-Isopropenyl-2-Methyl-2-Vinyltetrahydrofuran, 3-Isopropenyl-6-Oxoheptanoic Acid, 3-Isopropenylpentanedioic Acid, Isopropenylpyrazine, Isopropyl Acetate, P-Isopropylacetophenone, Isopropyl Alcohol, Isopropylamine, Isopropyl Benzoate, P-Isopropylbenzyl Alcohol, Isopropyl Butyrate, Isopropyl Cinnamate, Isopropyl Citrate, Isopropyl-2-Cyclohexenone, 5-Isopropyl-2,6-Diethyl-2-Methyltetrahydro-2h-Pyran, 2(4)-Isopropyl-4(2),6-Dimethyldihydro-4h-1,3,5-Dithiazine, Isopropyl Formate, Isopropyl Hexanoate, Isopropylideneglyceryl 5-Hydroxydecanoate, Isopropyl Isobutyrate, Isopropyl Isothiocyanate, Isopropyl Isovalerate, S-Isopropyl 3-Methylbut-2-Enethioate, Isopropyl 2-Methylbutyrate, 2-Isopropyl-5-Methyl-2-Hexenal, (+/−)-[R-(E)]-5-Isopropyl-8-Methylnona-6,8-Dien-2-One, 2-Isopropyl-4-Methylthiazole, Isopropyl Myristate, Isopropyl Palmitate, 2-Isopropylphenol, P-Isopropylphenylacetaldehyde, Isopropyl Phenylacetate, 3-(P-Isopropylphenyl)Propionaldehyde, Isopropyl Propionate, 2-Isopropylpyrazine, Isopropyl Tiglate, 2-Isopropyl-N,2,3-Trimethylbutyramide, Isopulegol, Isopulegone, Isopulegyl Acetate, Isoquercitrin, Enzymatically Modified, Isoquinoline, Isovaleraldehyde Diethyl Acetal, Isovaleraldehyde Glyceryl Acetal, Isovaleric Acid, Iva (*Achillea moschata* Jacq.), Iva, Extract (*Achillea moschata* Jacq.), Jambu Oleoresin, Japan Wax, Jasmine, Absolute (*Jasminum* Spp.), Jasmine, Concrete (*Jasminum* Spp.), Jasmine, Oil (*Jasminum grandiflorum* L.), Jasmine, Spiritus (*Jasminum grandiflorum* L.), Jasmone, Cis-, Jelutong (*Dyera costulata* Hook, F. And D. Lowii Hook, F.), Juniper (Berries) (*Juniperus communis* L.), Juniper, Extract (*Juniperus communis* L.), Juniper Oil (*Juniperus communis* L.), Karaya, Gum (*Sterculia urens* Roxb.), Kelp, 2-Keto-4-Butanethiol, Alpha-Ketobutyric Acid, Kola Nut, Extract (*Cola acuminata* Schott Et Endl.), Labdanum, Absolute (*Cistus* Spp.), Labdanum, Oil (*Cistus* Spp.), Labdanum, Oleoresin (*Cistus* Spp.), Lactalbumin, Lactalbumin Phosphate, Lactase From *Saccharomyces fragilis*, Lactase From *Saccharomyces* (*Kluyveromyces*) *lactis*, Lactase Preparation, *Candida pseudotropicalis*, Lactic Acid, Lactose, Lactose, Hydrolyzed, N-Lactoyl Ethanolamine, N-Lactoyl Ethanolamine Phosphate, Lactylated Fatty Acid Esters Of Glycerol And Propylene Glycol, Lactylic Esters Of Fatty Acids, Lanolin, Lard, Lard Oil, Laurel Berries (*Laurus nobilis* L.), Lauric Acid, Lauric Aldehyde, Lauroyl Diethanolamide, Lauryl Acetate, Lauryl Alcohol, Lavandin Absolute, Lavandin, Concrete, Lavandin, Oil, Lavender, Absolute (*Lavandula officinalis* Chaix), Lavender, Concrete (*Lavandula officinalis* Chaix), Lavender (*Lavandula officinalis* Chaix), Lavender, Oil (*Lavandula officinalis* Chaix), Lavender, Spike (*Lavandula latifolia* Bill.), Lavender, Spike, Oil (*Lavandula* Spp.), Leche Caspi (*Couma macrocarpa* Barb. Rodr.), Leche De Vaca (*Brosimum utile* (H.B.K.) Pittier, And *Poulsenia* Spp.), Lecithin, Lecithin, Benzoyl Peroxide Modified, Lecithin, Enzyme-Modified, Lecithin, Hydrogen Peroxide Modified, Lecithin (Vegetable), Leek Oil, Lemon Essence, Lemon, Extract (*Citrus limon* (L.) Burm. F.), Lemon Grass, Oil (*Cymbopogon citratus* Dc. And *Cymbopogon Flexuosus-stapf*), Lemon, Juice, Lemon, Oil (*Citrus limon* (L.) Burm. F.), Lemon, Oil, Terpeneless (*Citrus limon* (L.) Burm. F.), Lemon Peel Extract, Lemon Peel Granules, Lemon Terpenes, Lemon-Verbena (*Lippia citriodora* Hbk.), Lemon Verbena, Oil (*Lippia citriodora*), Lepidine, L-Leucine, Levulinic Acid, Levulose, L-Fenchone, Licorice Extract (*Glycyrrhiza* Spp.), Licorice Extract Powder (*Glycyrrhiza* Spp.), Licorice (*Glycyrrhiza* Spp.), Lignin, Lignin Sodium Sulfonate, Lignosulfonic Acid, Lime, Essence, Lime, Juice, Lime Juice, Dehydrated, Lime Oil, Distilled, Lime Oil, Expressed, Lime, Oil, Terpeneless (*Citrus aurantifolia* (Christman) Swingle), L-Limonene, D-Limonene, Dl-Limonene, Linaloe Wood, Oil (*Bursera delpechiana* Poiss. And Other *Bursera* Spp.), Linalool, Linalool Oxide, Linalool Oxide Pyranoid, Linalyl Acetate, Linalyl Anthranilate, Linalyl Benzoate, Linalyl Butyrate, Linalyl Cinnamate, Linalyl Formate, Linalyl Hexanoate, Linalyl Isobutyrate, Linalyl Isovalerate, Linalyl Octanoate, Linalyl Phenylacetate, Linalyl Propionate, Linden Flowers, Extract (*Tilia* Spp.), Linden Flowers (*Tilia glabra* Vent.), Linden Leaves (*Tillia* Spp.), Linoleic Acid, Lipase, Lipase From Animal Tissue, Lipase From *Aspergillus Niger*, Lipase From *Aspergillus oryzae*, Lipase From *Rhizopus niveus*, Listeria-Specific Bacteriophage Preparation, *Litsea Cubeba* Berry Oil, L-Menthyl Butyrate, Locust (Carob) Bean Gum, Lovage, Extract (*Levisticum officinale* Koch), Lovage (*Levisticum officinale* Koch), Lovage, Oil (*Levisticum officinale* Koch), L-8-P-Menthene-1,2-Epoxide, Lungmoss (*Sticta pulmonacea* Ach.), Luo Han Fruit Concentrate, Lupulin (*Humulus lupulus* L.), L-Lysine, Mace (*Myristica fragrans* Houtt.), Mace, Oil (*Myristica fragrans* Houtt.), Mace, Oleoresin (*Myristica fragrans* Houtt.), Magnesium Caprate, Magnesium Caprylate, Magnesium Carbonate, Magnesium Chloride, Magnesium Fumarate, Magnesium Gluconate, Magnesium Glycerophosphate, Magnesium Hydroxide, Magnesium Laurate, Magnesium Myristate, Magnesium Oleate, Magnesium Oxide, Magnesium Palmitate, Magnesium Phosphate, Dibasic, Magnesium Phosphate, Tribasic, Magnesium Salts Of Fatty Acids, Magnesium Silicate, Magnesium Stearate, Magnesium Sulfate, Magnolol, Maidenhair Fern (*Adiantum capillus-Veneris* L.), L-Malic Acid, Malic Acid, Malt, Maltodextrin, Maltol, Maltol Propionate, Maltose, Malt Syrup (Malt Extract), Maltyl Isobutyrate, Mandarin, Oil (*Citrus reticulata* Blanco), Manganese Chloride, Manganese Citrate, Manganese Gluconate, Manganese Glycerophosphate, Manganese Hypophosphite, Manganese Sulfate, Manganous Oxide, Mannitol, Marigold, Pot (*Calendula officinalis* L.), Marjoram, Oleoresin (*Marjorana hortensis* Moench (*Origanum majorana* L.)), Marjoram, Pot (*Majorana onites* (L.) Benth. (*Origanum vulgare* L.)), Marjoram Seed (*Majorana hortensis* Moench (*Origanum majorana* L.)), Marjoram, Sweet (*Majorana hortensis* Moench (*Origanum majorana* L.)), Marjoram, Sweet, Oil (*Majorana hortensis* Moench (*Origanum majorana* L.)), Massaranduba Balata (*Manilkara huberi* (Ducke) Chevalier), Massaranduba Balata, Solvent-Free Resin Extract, Massaranduba Chocolate (*Manilkara solimoesensis* Gilly), Massoia Bark Oil, Mastic Gum, Mate, Absolute (*Ilex paraguariensis* St. Hil.), Mate, Leaves, Menadiol Sodium Diphosphate, Menhaden Oil, Menhaden Oil, Hydrogenated, Menhaden Oil, Partially Hydrogenated, D-2,8-P-Menthadien-1-Ol, Menthadienol, P-Mentha-1,8-Dien-7-Ol, Cis- And Trans-P-1(7),8-Menthadien-2-Yl Acetate, P-Menthan-2-One, P-Mentha-8-Thiol-3-One, P-Menth-1-Ene-9-Al, 8-P-Menthene-1,2-Diol, 1-P-Menthene-8-Thiol, P-Menth-1-En-3-Ol, P-Menth-3-En-1-Ol, 1-P-Menthen-9-Yl Acetate, Menthol, Menthone, Menthone 1,2-Glycerol Ketal, L-Menthone 1,2-Glycerol Ketal, Menthone-8-Thioacetate, 2-(L-Menthoxy)Ethanol, 3-(L-Menthoxy)-2-Methylpropane-1,2-Diol, 3-L-Menthoxypropane-1,2-Diol, Menthyl Acetate, L-Menthyl Acetoacetate, L-Menthyl Ethylene Glycol Carbonate, Menthyl Formate, L-Menthyl (R,S)-3-Hydroxybutyrate, Menthyl Isovalerate, L-Menthyl Lactate, 1-Menthyl Methyl Ether, 2-[2-(P-Menthyloxy)Ethoxy]Ethanol, Menthyl Propionate, Menthyl Propylene Glycol Carbonate, L-Menthyl 1,2-Propylene Glycol Carbonate, Menthyl Pyrrolidonecarboxylate, Menthyl Valerate, 2-Mercaptoanisole, 2-Mercapto-3-Butanol, 3-Mercapto-2-Butanone, (+/−)-3-Mercapto-1-Butyl Acetate, 2-Mercaptoethanol, 3-Mercaptoheptyl Acetate, 3-Mercaptohexanal, 3-Mercaptohexanol, 3-Mercaptohexyl Acetate, 3-Mercaptohexyl Butyrate, 3-Mercaptohexyl Hexanoate, 4-Mercapto-3-Methyl-2-Butanol, 3-Mercapto-2-Methyl-1-Butanol, 3-Mercapto-3-Methyl-1-Butanol, 3-Mercapto-3-Methyl-1-Butyl Acetate, 3-Mercapto-3-Methylbutyl Formate, 3-Mercapto-3-Methylbutyl Isovalerate, 4-Mercapto-4-Methyl-2-Hexanone, 3-Mercapto-2-Methylpentanal, 3-Mercapto-2-Methyl-1-Pentanol, (+/−)-4-Mercapto-4-Methyl-2-Pentanol, 2-Mercapto-2-Methyl-1-Pentanol, 4-Mercapto-4-Methyl-2-Pentanone, 2-Mercaptomethylpyrazine, 3-Mercapto-2-Pentanone, 4-Mercapto-2-Pentanone, 2,3 Or 10-Mercaptopinane, 1-Mercapto-2-Propanone, 2-Mercaptopropionic Acid, 3-Mercaptopropionic Acid, Mesquite Wood Extract, Methacrylic Acid-Divinylbenzene Copolymer, Methional Diethyl Acetal, L-Methionine, D-Methionine, Methionyl Butyrate, L-Methionylglycine, 2-Methoxyacetophenone, P-Methoxy-Alpha-Methylcinnamaldehyde, O-Methoxybenzaldehyde, P-Methoxybenzaldehyde, 4-Methoxybenzoic Acid, 3-Methoxybenzoic Acid, 2-Methoxybenzoic Acid, P-Methoxycinnamaldehyde, O-Methoxycinnamaldehyde, Trans- And Cis-1-Methoxy-1-Decene, (S1)-Methoxy-3-Heptanethiol, 2-Methoxy-(3 Or 5 Or 6)-Isopropylpyrazine, N1-(2-Methoxy-4-Methylbenzyl)-N2-(2-(5-Methylpyridin-2-Yl)Ethyl)Oxalamide, N1-(2-Methoxy-4-Methylbenzyl)-N2-(2-(Pyridin-2-Yl) Ethyl) Oxalamide, 4-Methoxy-2-Methyl-2-Butanethiol, 2-Methoxy-4-Methylphenol, (2 Or 5 Or 6)-Methoxy-3-Methylpyrazine (Mixture Of Isomers), 4-(P-Methoxyphenyl)-2-Butanone, 1-(P-Methoxyphenyl)-1-Penten-3-One, 2-Methoxy-6-(2-Propenyl)Phenol, 2-Methoxy-4-Propylphenol, 2-Methoxy-3-(1-Methylpropyl)Pyrazine, Methoxypyrazine, 2-Methoxypyridine, 6-Methoxyquinoline, 2-Methoxy-4-Vinylphenol, Methyl Methacrylate, Methyl Acetate, 4'-Methylacetophenone, 2-Methylacetophenone, Methyl 1-Acetoxycyclohexyl Ketone, (+/−)-Methyl 5-Acetoxyhexanoate, Methyl 3-Acetoxy-2-Methylbutyrate, Methyl 3-Acetoxyoctanoate, Methyl N-Acetylanthranilate, 1-Methyl-2-Acetylpyrrole, 2-Methyl-3-(2-Furyl)Acrolein, Methyl Acrylate, Methyl Acrylate-Divinylbenzene, Completely Hydrolyzed, Copolymer, Methyl Acrylate-Dvb-Acrylonitrile, Completely Hydrolyzed, Terpolymer, Methyl Acrylate-Dvb (3.5%), Copolymer, Aminolyzed With Dmapa, Methyl Acrylate-Dvb (2%), Copolymer, Aminolyzed With Dmapa, Methyl Acrylate-Dvb-(Deg-Divinyl Ether), Aminolyzed And Quarternized, Terpolymer, Methyl Acrylate-Dvb-(Deg-Divinyl Ether), Aminolyzed, Terpolymer, Methyl Alcohol, 2-Methylallyl Butyrate, Methyl-Alpha-Ionone, Methyl Anisate, P-Methylanisole, O-Methylanisole, Methyl Anthranilate, Methylated Silica, 4-Methylbenzaldehyde Propyleneglycol Acetal, Methyl Benzoate, 2-Methylbenzofuran, S-Methyl Benzothioate, 2-Methyl-4,5-Benzoxazole, Alpha-Methylbenzyl Acetate, Methylbenzyl Acetate (Mixed O-, M-, P-), Alpha-Methylbenzyl Alcohol, 4-Methylbenzyl Alcohol, Methyl Benzyl Disulfide, Alpha-Methylbenzyl Formate, Alpha-Methylbenzyl Propionate, 4-Methylbiphenyl, 3-Methylbutanethiol, 3-Methyl-2-Butanethiol, 2-Methyl-1-Butanethiol, 3-Methyl-2-Butanol, 2-Methyl-1-Butanol, 2-Methyl-2-Butenal, 3-Methyl-2-Butenal, (Z)-3-Hexenyl(E)-2-Methyl-2-Butenoate, Trans-2-Methyl-2-Butenoic Acid, 2-Methylbut-2-En-1-Ol, 3-Methyl-2-Buten-1-ol, 2-Methyl-3-Buten-2-Ol, 3-Methyl-3-Buten-2-One, 3-Methyl-3-Butenyl Acetate, 2-Methylbutyl Acetate, 2-Methylbutylamine, 2-Methylbutyl Isovalerate, 2-Methylbutyl 3-Methyl-2-Butenoate, 2-Methylbutyl 2-Methylbutyrate, 3-Methylbutyraldehyde, 2-Methylbutyraldehyde, Methyl Butyrate, 2-Methylbutyric Acid, Alpha-Methylcinnamaldehyde, P-Methylcinnamaldehyde, Methyl Cinnamate, 4-Methyl-Cis-2-Pentene, 6-Methylcoumarin, 3-Methylcrotonic Acid, 2-Methyl-1,3-Cyclohexadiene, 1-Methyl-2,3-Cyclohexadione, Methyl Cyclohexanecarboxylate, 4-Methylcyclohexanone, 3-Methylcyclohexanone, 2-Methylcyclohexanone, 3-Methyl-2-Cyclohexen-1-One, N-(2-Methylcyclohexyl)-2,3,4,5,6-Pentafluorobenzamide, 3-Methyl-1-Cyclopentadecanone, Methylcyclopentenolone, 1-Methyl-1-Cyclopenten-3-One, Methyl(E)-2-(Z)-4-Decadienoate, 3-Methyl-Gamma-Decalactone, Gamma-Methyldecalactone, Methyl 2-Decenoate, Methyl-Delta-Ionone, 5h-5-Methyl-6,7-Dihydrocyclopenta(B)Pyrazine, 2-Methyl-4,5-Dihydrofuran-3-Thiol, Methyl Dihydrojasmonate, 4-Methyl-2,6-Dimethoxyphenol, Methyl N,N-Dimethylanthranilate, Methyl 3,7-Dimethyl-6-Octenoate, Methyl Disulfide, 2-Methyl-1,3-Dithiolane, 1-(Methyldithio)-2-Propanone, Methylene Chloride, 4-(3,4-Methylenedioxyphenyl)-2-Butanone, 3-(3,4-Methylenedioxyphenyl)-2-Methylpropanal, Methyl Esters Of Fatty Acids (Edible), 2-Methyl-(3 Or 5 Or 6)-Ethoxypyrazine, Methyl Ethyl Sulfide, Methyl Ethyl Trisulfide, Methyl N-Formylanthranilate, 2-Methylfuran, 2-Methyl-3-(Methylthio)Furan, 2-Methyl-5-(Methylthio)Furan, 5-Methyl-3(2h)-Furanone, 2-Methyl-3-Furanthiol, Methyl Furfuracrylate, 5-Methylfurfural, 5-Methylfurfuryl Alcohol, Methyl Furfuryl Disulfide, 5-Methylfurfurylmercaptan, Methyl 3-(Furfurylthio)Propionate, Methyl 2-Furoate, 3-(5-Methyl-2-Furyl)-Butanal, 2-Methyl-3-Furyl 2-Methyl-3-Tetrahydrofuryl Disulfide, 2-Methyl-3-Furyl Methylthiomethyl Disulfide, 3-(5-Methyl-2-Furyl)Prop-2-Enal, 3-[(2-Methyl-3-Furyl)Thio]Butanal, (+/−)-3-[(2-Methyl-3-Furyl)Thio]-2-Butanone, 3-((2-Methyl-3-Furyl)Thio)-4-Heptanone, Methyl Glucoside-Coconut Oil Ester, 6-Methyl-3,5-Heptadien-2-One, 6-Methylheptanal, Methyl Heptanoate, 2-Methylheptanoic Acid, 2-Methyl-3-Heptanone, 6-Methyl-5-Hepten-2-Ol, 5-Methyl-2-Hepten-4-One, 6-Methyl-3-Hepten-2-One, Trans-, 6-Methyl-5-Hepten-2-One, 6-Methyl-5-Hepten-2-One Propyleneglycol Acetal, 6-Methyl-5-Hepten-2-Yl Acetate, 3-Methylhexanal, 5-Methyl-2,3-Hexanedione, S-Methyl Hexanethioate, Methyl Hexanoate, 2-Methylhexanoic Acid, 5-Methylhexanoic Acid, Methyl 3-Hexenoate, Methyl Cis-3-Hexenoate, Methyl 2-Hexenoate, 5-Methyl-5-Hexen-2-One, 5-Methyl-3-Hexen-2-One, 5-Methylhexyl Acetate, Methyl Hexyl Ether, 1-Methyl-1h-Pyrrole-2-Carboxaldehyde, Methyl P-Hydroxybenzoate, Methyl 3-Hydroxybutyrate, Methyl 3-Hydroxyhexanoate, Methyl 2-Hydroxy-4-Methylpentanoate, Alpha-Methyl-Beta-Hydroxypropyl Alpha-Methyl-Beta-Mercaptopropyl Sulfide, Methyl-Beta-Ionone, Methyl Isobutanethioate, Methyl Isobutyl Ketone, Methyl Isobutyrate, Methyl Isopentyl Disulfide, 2-Methyl-5-Isopropylpyrazine, Methyl Isothiocyanate, Methyl Isovalerate, Methyl Jasmonate, Methyl Laurate, Methyl Levulinate, Methyl Linoleate (48%) Methyl Linolenate (52%) Mixture, Methyl Mercaptan, Methyl 3-Mercaptobutanoate, Methyl O-Methoxybenzoate, 1-Methyl-3-Methoxy-4-Isopropylbenzene, 2-Methyl-5-Methoxythiazole, Methyl N-Methylanthranilate, S-Methyl 3-Methylbutanethioate, Methyl 3-Methyl-1-Butenyl Disulfide, 3-Methyl-2(3-Methylbut-2-En-1-Yl)Furan, Methyl 2-Methylbutyrate, Methyl 2-Methyl-3-Furyl Disulfide, S-Methyl 4-Methylpentanethioate, Methyl 2-Methylpentanoate, Methyl 2-Methylphenyl Disulfide, Methyl (Methylthio)Acetate, Methyl 3-(Methylthio)Butanoate, 2-Methyl-1-Methylthio-2-Butene, Methyl 4-(Methylthio)Butyrate, Methyl 2-Methylthiobutyrate, Methyl (Methylthio)Methyl Disulfide, 4-Methyl-2-(Methylthiomethyl)-2-Hexenal, 5-Methyl-2-(Methylthiomethyl)-2-Hexenal, 4-Methyl-2-(Methylthiomethyl)-2-Pentenal, Methyl 3-Methylthiopropionate, Methyl 4-Methylvalerate, Methyl Myristate, 1-Methylnaphthalene, Methyl Beta-Naphthyl Ketone, Methyl Nicotinate, 3-Methyl-2,4-Nonanedione, Methyl Nonanoate, 4-Methylnonanoic Acid, Methyl 2-Nonenoate, Methyl 3-Nonenoate, Methyl 2-Nonynoate, 2-Methyloctanal, (+/−)-6-Methyloctanal, Methyl Octanoate, 4-Methyloctanoic Acid, 2-Methyl-2-Octenal, Methyl 2-Octenoate, Methyl Cis-4-Octenoate, Methyl Trans-2-Octenoate, Methyl Cis-5-Octenoate, (E)-7-Methyl-3-Octen-2-One, Methyl Octyl Sulfide, Methyl 2-Octynoate, 2-Methyl-3 Or 5 Or 6-(Furfurylthio)Pyrazine (Mixture Of Isomers), 3-Methyl-2-Oxobutanoic Acid, Methyl 2-Oxo-3-Methylpentanoate, 3-Methyl-2-Oxopentanoic Acid, 4-Methyl-2-Oxopentanoic Acid, 2-Methylpentanal, 4-Methyl-2,3-Pentanedione, 4-Methylpentanoic Acid, 3-Methylpentanoic Acid, 3-Methyl-1-Pentanol, 4-(Methylthio)-4-Methyl-2-Pentanone, 2-Methyl-2-Pentenal, 4-Methyl-2-Pentenal, Methyl 4-Pentenoate, 2-Methyl-4-Pentenoic Acid, 4-Methylpent-2-Enoic Acid, 2-Methyl-3-Pentenoic Acid, 2-Methyl-2-Pentenoic Acid, 1-(4-Methoxyphenyl)-4-Methyl-1-Penten-3-One, 4-Methyl-3-Penten-2-One, 4-Methyl-4-Penten-2-One, 4-Methyl-2-Pentyl-1,3-Dioxolane, 4-Methylpentyl Isovalerate, Beta-Methylphenethyl Alcohol, Alpha-Methylphenethyl Butyrate, Methyl Phenethyl Ether, Methyl Phenylacetate, 2-Methyl-4-Phenyl-2-Butanol, 3-Methyl-4-Phenyl-3-Butene-2-One, 2-Methyl-4-Phenyl-2-Butyl Acetate, 2-Methyl-4-Phenyl-2-Butyl Isobutyrate, 2-Methyl-4-Phenylbutyraldehyde, 3-Methyl-2-Phenylbutyraldehyde, Methyl 4-Phenylbutyrate, Methyl Phenyl Disulfide, Methyl Beta-Phenylglycidate, 3-Methyl-3-Phenyl Glycidic Acid Ethyl Ester, 5-Methyl-2-Phenyl-2-Hexenal, 4-Methyl-1-Phenyl-2-Pentanone, 4-Methyl-2-Phenyl-2-Pentenal, Methyl 3-Phenylpropionate, Methyl Phenyl Sulfide, 2-Methylpiperidine, Methylpolysilicone, 2-Methyl-2-(Methyldithio)Propanal, S-Methyl Propanethioate, 2-Methyl-1-Propanethiol, Methyl Propenyl Disulfide, Methyl 1-Propenyl Sulfide, 2-Methyl-3-(P-Isopropylphenyl) Propionaldehyde, Methyl Propionate, 3-Methyl-5-Propyl-2-Cyclohexen-1-One, Methyl Propyl Disulfide, 2-Methylpropyl-3-Methylbutyrate, (?)-4-Methyl-2-Propyl-1,3-Oxathiane, 2-Methyl-4-Propyl-1,3-Oxathiane, 2-(2-Methylpropyl)Pyridine, 2-(1-Methylpropyl)Thiazole, Methyl Propyl Trisulfide, Methyl-(3 Or 5 Or 6)-(Methylthio)Pyrazine (Mixture Of Isomers), 2-Methylpyrazine, Methyl 2-Pyrrolyl Ketone, 6-Methylquinoline, 5-Methylquinoxaline, Methyl Salicylate, Methyl Sorbate, Methyl Sulfide, Methyl P-Tert-Butylphenylacetate, 2-Methyltetrahydrofuran-3-One, 2-Methyl-3-Tetrahydrofuranthiol, (?)-2-Methyltetrahydrofuran-3-Thiol Acetate, 7-Methyl-4,4a,5,6-Tetrahydro-2(3h)-Naphthalenone, 2-Methyltetrahydrothiophen-3-One, 4-Methylthiazole, 4-Methyl-5-Thiazoleethanol, 4-Methyl-5-Thiazoleethanol Acetate, 4-Methyl-3-Thiazoline, 2-(4-Methyl-5-Thiazolyl)Ethyl Butanoate, 2-(4-Methyl-5-Thiazolyl)Ethyl Decanoate, 2-(4-Methyl-5-Thiazolyl)Ethyl Formate, 2-(4-Methyl-5-Thiazolyl)Ethyl Hexanoate, 2-(4-Methyl-5-Thiazolyl)Ethyl Isobutyrate, 2-(4-Methyl-5-Thiazolyl)Ethyl Octanoate, 2-(4-Methyl-5-Thiazolyl)Ethyl Propionate, 2-Methylthioacetaldehyde, S-Methyl Thioacetate, 2-Methyl-3-Thioacetoxy-4,5-Dihydrofuran, Methylthio 2-(Acetyloxy)Propionate, 3-(Methylthio)Butanal, 4-(Methylthio)Butanol, 1-(Methylthio)-2-Butanone, 4-(Methylthio)-2-Butanone, 3-(Methylthio)-2-Butanone, 4-(Methylthio)Butyl Isothiocyanate, Methyl Thiobutyrate, 1-(3-(Methylthio)-Butyryl)-2,6,6-Trimethylcyclohexene, 2-(Methylthio)Ethanol, 2-(Methylthio)Ethyl Acetate, Methyl 2-Thiofuroate, (+/−)-3-(Methylthio)Heptanal, 3-(Methylthio)-1-Hexanol, 3-Methylthiohexenal, 3-(Methylthio)Hexyl Acetate, 6-(Methylthio)Hexyl Isothiocyanate, 2-((Methylthio)Methyl)-2-Butenal, Methylthiomethyl Butyrate, Methylthiomethyl Hexanoate, Methylthiomethylmercaptan, 2-(Methylthiomethyl)-3-Phenylpropenal, 3-(Methylthio)Methylthiophene, 1-(Methylthio)-3-Octanone, 4-(Methylthio)-2-Oxobutanoic Acid, 4-(Methylthio)-2-Pentanone, 5-(Methylthio)Pentyl Isothiocyanate, 5-Methyl-2-Thiophenecarboxaldehyde, O-(Methylthio)Phenol, 1-Methylthio-2-Propanone, Methylthio 2-(Propionyloxy)Propionate, 3-(Methylthio)Propyl Acetate, 3-(Methylthio)Propylamine, 3-(Methylthio)Propyl Hexanoate, 3-Methylthiopropyl Isothiocyanate, 3-(Methylthio)Propyl Mercaptoacetate, 2-Methyl-3-Tolylpropionaldehyde (Mixed O-, M-, P-), 12-Methyltridecanal, 3-Methyl-1,2,4-Trithiane, 2-Methylundecanal, Methyl 9-Undecenoate, Methyl 10-Undecenoate, Methyl 2-Undecynoate, Methyl Valerate, 2-Methylvaleric Acid, 2-Methyl-5-Vinylpyrazine, (+/−)-2-(5-Methyl-5-Vinyltetrahydrofuran-2-Yl)Propionaldehyde, 4-Methyl-5-Vinylthiazole, Michelia Alba, Extract, Microparticulated Protein Product, Milk, Skim Milk, Nonfat Milk, Reduced-Fat Milk, Milk Clotting Enzyme, *Aspergillus Oryzae* Recombinant, Milk Clotting Enzyme From *Bacillus cereus* (Frankland And Frankland), Milk Clotting Enzyme From Endothia Parasitica, Milk Clotting Enzyme From *Mucor miehei* Cooney Et Emerson, Milk Clotting Enzyme From *Mucor pusillus* L., Milk Powder, Whole, Enzyme-Modified, Mimosa, Absolute (*Acacia decurrens* Willd. Var. *dealbata*), Mimosa Concrete (*Acacia decurrens* Willd. Var. *dealbata*), Mineral Oil, White, Mintlactone, Mixture Of 3,6-Diethyl-1,2,4,5-Tetrathiane And 3,5-Diethyl-1,2,4-Trithiolane, Mixture Of Methyl Cyclohexadiene And Methylene Cyclohexene, Mixture Of Butyl Propyl Disulfide And Propyl And Butyl Disulfide, Molasses, Concentrate, Molasses, Extract (*Saccharum officinarum* L.), Molasses (*Saccharum officinarum* L.), Molecular Sieve Resins, Monoammonium Glutamate, Mono- And Diglycerides, Mono- And Diglycerides, Acetic Acid Esters And Sodium And Calcium Salts, Mono- And Diglycerides, Acetyltartaric Acid Esters And Sodium And Calcium Salts, Mono- And Diglycerides, Citric Acid Esters And Sodium And Calcium Salts, Mono- And Diglycerides, Diacetyltartaric Acid Esters, Mono- And Diglycerides, Ethoxylated, Mono- And Diglycerides, Lactic Acid Esters And Sodium And Calcium Salts, Mono- And Diglycerides, Monosodium Phosphate Derivatives, Mono- And Diglycerides, Sodium Sulfoacetate Derivatives, Mono-, Di-, And Triglycerides, Monoethanolamine, Monoglyceride Citrate, Monoglycerides, Acetylated, Monoisopropyl Citrate, Monomenthyl Glutarate, L-, Monomenthyl Succinate, Monopotassium Glutamate, Monosodium Glutamate, Montan Wax Fatty Acids, Oxidatively Refined, Polyhydric Alcohol Diesters, Morpholine, Morpholine, Fatty Acid Salts, Mountain Maple (*Acer spicatum* Lam.), Mountain Maple Bark (*Acer spicatum* Lam.), Mountain Maple, Extract Solid (*Acer spicatum* Lam.), Mullein Flowers (*Verbascum* Spp.), Mushroom Oil, Distilled, Musk Ambrette, Musk, Ketone, Musk Tonquin (*Moschus moschiferus* L.), Mustard, Brown (*Brassica* Spp.), Mustard, Brown, Extract (*Brassica* Spp.), Mustard Flour, Mustard Oil, Mustard, Oriental, Mustard, Yellow (*Brassica* Spp.), Mustard, Yellow, Extract (*Brassica* Spp.), Beta-Myrcene, Myrcenyl Methyl Ether, Myricitrin, Myristaldehyde, Myristic Acid, Myristyl Alcohol, Myrrh, Extract, Myrrh, Gum (*Commiphora* Spp.), Myrrh, Oil (*Commiphora* Spp.), Myrtenol, Myrtenyl Acetate, Myrtle Leaves (*Myrtus communis* L.), Myrtle, Oil (*Myrtus communis* L.), Naphtha, 2-Naphthalenthiol, Beta-Naphthyl Anthranilate, Beta-Naphthyl Ethyl Ether, Beta-Naphthyl Isobutyl Ether, Beta-Naphthyl Methyl Ether, Naringin Dihydrochalcone, Naringin, Extract (*Citrus paradisi* Macf.), Natamycin, Natural Gas, N-(1,1-Dimethyl-2-Hydroxyethyl)-2,2-Diethylbutanamide, Neohesperidin Dihydrochalcone, D-Neomenthol, Neotame, Nerol, Neroli, Bigarade Oil (*Citrus aurantium* L.), Nerolidol, Nerolidol Oxide, Neryl Acetate, Neryl Butyrate, Neryl Formate, Neryl Isobutyrate, Neryl Isovalerate, Neryl Propionate, N-Ethyl-2,2-Diisopropylbutanamide, N-(2-Hydroxyethyl)-2,3-Dimethyl-2-Isopropylbutanamide, Niacin, Niacinamide, Nickel, Nicotinamide-Ascorbic Acid Complex, Niger Gutta (*Ficus platyphylla* Del.), Nisin Preparation, Nispero, Nitrates, Sodium & Potassium, Nitrites, Sodium & Potassium, Nitrogen, Nitrogen Oxides, Nitrosyl Chloride, Nitrous Oxide, (+/−)-N-Lactoyltyramine, 2,4-Nonadienal, 2-Trans-6-Trans-Nonadienal, 2,6-Nonadienal Diethyl Acetal, 2,4-Nonadien-1-Ol, (E)-3-(Z)-6-Nonadien-1-Ol, (Z)(Z)-3,6-Nonadien-1-Ol, 2,6-Nonadien-1-Ol, (E,Z)-2,6-Nonadien-1-Ol Acetate, (E,Z)-3,6-Nonadien-1-Ol Acetate, Cis,Cis-3,6-Nonadienyl Acetate, Gamma-Nonalactone, Nonanal, Nonanal Dimethyl Acetal, Nonanal Propyleneglycol Acetal, 1,3-Nonanediol Acetate (Mixed Esters), 1,4-Nonanediol Diacetate, 1,9-Nonanedithiol, Nonanoic Acid, 2-Nonanol, 4-((2-Methyl-3-Furyl)Thio)-5-Nonanone, 2-Nonanone, 3-Nonanone, 2-Nonanone Propyleneglycol Acetal, 3-Nonanon-1-Ol, 3-Nonanon-1-Yl Acetate, Nonanoyl 4-Hydroxy-3-Methoxybenzylamide, Nona-2,4,6-Trienal, Cis-6-Nonenal, 2-Nonenal, 1-Nonene, (E)-2-Nonenoic Acid, 2-Nonenoic Acid Gamma-Lactone, Cis-6-Nonen-1-Ol, Trans-2-Nonen-1-Ol, Cis-2-Nonen-1-Ol, 3-Nonen-2-One, 8-Nonen-2-One, 5-Nonen-Trans-2-One, Cis-6-Nonenyl Acetate, Cis-3-Nonenyl Acetate, 3-Nonyl Acetate, Nonyl Acetate, Nonyl Alcohol, Nonyl Isovalerate, Nonyl Octanoate, Nootkatone, N—P-Benzeneacetonitrile-menthanecarboxamide, N-(2-(Pyridin-2-Yl)Ethyl)-3-P-Menthanecarboxamide, Nutmeg (*Myristica fragrans* Houtt.), Nutmeg, Oil (*Myristica fragrans* Houtt.), Nutmeg Oleoresin, Oak Chips, White, Extract (*Quercus alba* L.), Oak Moss, Absolute (*Evernia* Spp.), Oak Moss, Concrete (*Evernia prunasti* Spp.), Oak Wood, English (*Quercus robur* L.), Oat Gum, Ocimene, 9,12-Octadecadienoic Acid (48%) And 9,12,15-Octadecatrienoic Acid (52%), Delta-Octadecalactone, Gamma-Octadecalactone, 9-Octadecenal, Octadecylamine, 2-Trans-6-Trans-Octadienal, Trans,Trans-2,4-Octadienal, (E,E)-2,4-Octadien-1-Ol, 3,5-Octadien-2-One, Trans, Trans-, 1,5-Octadien-3-One, Octafluorocyclobutane, Octahydro-4,8a-Dimethyl-4a(2h)-Naphthol, Octahydrocoumarin, Delta-Octalactone, Gamma-Octalactone, Octanal, Octanal Dimethyl Acetal, Octanal Propyleneglycol Acetal, 4,5-Octanedione, 2,3-Octanedione, 1,8-Octanedithiol, Octanoic Acid, 3-Octanol, 2-Octanol, 1-Octanol, 2-Octanone, 3-Octanone, 3-(Hydroxymethyl)-2-Octanone, 6-Octenal, 2-Octenal, Cis-5-Octenal, 1-Octene, 3-Octenoic Acid, (E)-2-Octenoic Acid, (E)-2-Octen-1-Ol, Cis-3-Octen-1-Ol, 1-Octen-3-Ol, (E)-2-Octen-4-Ol, Cis-5-Octen-1-Ol, Trans-3-Octen-2-Ol, 3-Octen-2-One, 2-Octen-4-One, 1-Octen-3-One, 4-Octen-3-One, Z-5-Octenyl Acetate, 1-Octen-3-Yl Acetate, Trans-2-Octen-1-Yl Acetate, Trans-2-Octen-1-Yl Butanoate, 1-Octen-3-Yl Butyrate, (E)-2-(2-Octenyl)Cyclopentanone, Cis-3-Octenyl Propionate, (Z)-5-Octenyl Propionate, 1-Octenyl Succinic Anhydride, 3-Octyl Acetate, Octyl Acetate, Octyl Alcohol, Synthetic, Octyl Butyrate, 3-Octyl Butyrate, Octyl Formate, 3-Octyl Formate, Octyl 2-Furoate, Octyl Gallate, Octyl Heptanoate, Octyl Isobutyrate, Octyl Isovalerate, Octyl 2-Methylbutyrate, Octyl Octanoate, Octyl Phenylacetate, Octyl Propionate, (?)-6-Octyltetrahydro-2h-Pyran-2-One, O-Ethyl S-(2-Furylmethyl)Thiocarbonate, Oiticica Oil, Oleic Acid, Oleic Acid, From Tall Oil Fatty Acids, Olestra, Oleyl Alcohol, Olibanum, Absolute (*Boswellia* Spp.), Olibanum, Gum, Resin (*Boswellia* Spp.), Olibanum, Oil (*Boswellia* Spp.), Olibanum, Resinoid (*Boswellia* Spp.), Onion, Oil (*Allium cepa* L.), Opopanax, Gum, Opopanax, Non-Specific, Opopanax, Oil, Opopanax Tincture, Orange B, Orange Essence, Natural, Orange Essence Oil, Natural, Orange, Extract, Orange Flowers, Absolute (*Citrus aurantium* L.), Orange Flowers, Bitter (*Citrus aurantium* L), Orange, Juice, Orange Leaf, Absolute (*Citrus aurantium* L.), Orange, Oil, Distilled (*Citrus sinensis* (L.) Osbeck), Orange, Oil, Terpeneless (*Citrus sinensis* (L.) Osbeck), Orange Peel, Extract (*Citrus sinensis* (L.) Osbeck), Orange Peel, Bitter, Extract (*Citrus aurantium* L.), Orange Peel, Bitter, Oil (*Citrus aurantium* L.), Orange Peel, Sweet, Extract (*Citrus sinensis* (L.) Osbeck), Orange Peel, Sweet, Oil (*Citrus sinensis* (L.) Osbeck), Orange Peel, Sweet, Oil, Terpeneless (*Citrus sinensis* (L.) Osbeck), Oregano, European (*Origanum* Spp.), Oregano (*Lippia* Spp., Usually L. *Graveolens* Hbk), Oregano (Other Genera Including *Coleus, Lantana* And *Hyptis*), Origanum Oil (Extractive)(*Thymus capitatus* Hoff. Et Link), Orin Lactone, L-Ornithine Monochlorohydrate/Ornithine, Orris, Concrete, Liquid, Oil (*Iris florentina* L.), Orris Root, Extract (*Iris florentina* L.), Osmanthus Absolute, Ox Bile Extract, Oxirane (Chloromethyl)-, Polymer With Ammonia, Reaction Product With Chloromethane, 3-Oxobutanal, Dimethyl Acetal, 5-Oxodecanoic Acid, 3-Oxodecanoic Acid Glyceride, 5-Oxododecanoic Acid, 3-Oxododecanoic Acid Glyceride, 2-Oxo-3-Ethyl-4-Butanolide, 3-Oxohexadecanoic Acid Glyceride, 3-Oxohexanoic Acid Diglyceride, 5-Oxooctanoic Acid, 3-Oxooctanoic Acid Glyceride, 2-Oxopentanedioic Acid, 2-Oxo-3-Phenylpropionic Acid, 3-Oxotetradecanoic Acid Glyceride, 2-Oxothiolane, Oxystearin, Ozone, Palmitic Acid, Pancreatin, Pansy (*Viola tricolor* L.), D-Pantothenamide, D-Pantothenyl Alcohol, Papain (*Carica papaya* L.), Paprika (*Capsicum annuum* L.), Paprika Oleoresin (*Capsicum annuum* L.), Paraffin And Succinic Derivatives, Synthetic, Paraffin Wax, Paraldehyde, Cheese, Cheddar Cheese, Cheese Powder, Parmesan Cheese, Reggiano Cheese, Parsley, Oil (*Petroselinum* Spp.), Parsley, Oleoresin (*Petroselinum* Spp.), Parsley (*Petroselinum* Spp.), Passion Flower Extract, Passion Flower (*Passiflora incarnata* L.), Patchouly, Oil (*Pogostemon* Spp.), Peach Kernel, Extract (*Prunus persica* Sieb Et Zucc.), Peach Leaves, Extract (*Prunus persica* (L.) Batsch), Peach Leaves (*Prunus persica* (L.) Batsch), Peanut Oil, Peanut Stearine (*Arachis hypogaea* L.), Pecan Shell Flour, Pectin, Pectin, Amidated, Pectinase From *Aspergillus niger*, Pectinase From *Bacillus subtilis*, Pectin, Modified, Peg Fatty Acid Esters And Mono-, Di-, And Triglycerides Mixture, Pendare (*Couma macrocarpa* Barb. Rodr. & *Couma Utilis* (Mart.) Muell. Arg.), Penicillinase From *Bacillus subtilis*, Penicillium Roqueforti, Pennyroyal, Oil, American (*Hedeoma pulegiodes* (L.)), Pennyroyal, Oil, European (*Mentha pulegium* L.), Omega-Pentadecalactone, Pentadecanoic Acid, 2-Pentadecanone, 2,4-Pentadienal, 2,3-Pentanedione, 3-Pentanethiol, 2-Pentanethiol, 1-Pentanethiol, 2-Pentanol, 2-Pentanone, 2-Pentanoylfuran, 2-Pentenal, 4-Pentenal, 2-Pentenoic Acid, 4-Pentenoic Acid, 1-Penten-3-Ol, 2-Penten-1-Ol, 3-Penten-2-One, 1-Penten-3-One, 4-Pentenyl Acetate, Pent-2-Enyl Hexanoate, 4-Pentenyl Isothiocyanate, 2-Pentenyl-4-Propyl-1,3-Oxathiane (Mixture Of Isomers), 2-Pentyl Acetate, Pentylamine, 2-Pentyl-1-Buten-3-One, 2-Pentyl Butyrate, 2-Pentylfuran, Pentyl 2-Furyl Ketone, 5-Pentyl-3h-Furan-2-One, 2-Pentyl-3-Methyl-2-Cyclopenten-1-One, 2-Pentyl 2-Methylpentanoate, 2-Pentylpyridine, 2-Pentylthiazole, 2-Pentylthiophene, Pepper, Black, Oil (*Piper nigrum* L.), Pepper, Black, Oleoresin (*Piper nigrum* L.), Pepper, Black (*Piper nigrum* L.), Pepper, Cayenne, Peppermint Leaves (*Mentha piperita* L.), Peppermint, Oil (*Mentha piperita* L.), Peppermint Plant, Pepper, Red, Pepper, White, Oil (*Piper nigrum* L.), Pepper, White, Oleoresin (*Piper nigrum* L.), Pepper, White (*Piper nigrum* L.), Pepsin, Peptones, Peracetic Acid, Perillaldehyde, Perillaldehyde Propyleneglycol Acetal, Perilla Leaf Oil, Perillo, Perillyl Acetate, Periodic Acid, Petitgrain, Lemon, Oil (*Citrus limon* (L.) Burm. F.), Petitgrain, Mandarin, Oil (*Citrus reticulata* Blanco Var. Mandarin), Petitgrain, Oil (*Citrus aurantium* L.), Petrolatum, Petroleum Hydrocarbons, Odorless, Light, Petroleum Naphtha, Petroleum Wax, Petroleum Wax, Synthetic, Phaffia Yeast, Alpha-Phellandrene, Phenethyl Acetate, Phenethyl Alcohol, Phenethylamine, Phenethyl Anthranilate, Phenethyl Benzoate, Phenethyl Butyrate, Phenethyl Cinnamate, Phenethyl Decanoate, Phenethyl Formate, Phenethyl 2-Furoate, Phenethyl Hexanoate, Phenethyl Isobutyrate, Phenethyl Isothiocyanate, Phenethyl Isovalerate, Phenethyl 2-Methylbutyrate, Phenethyl Octanoate, Phenethyl Phenylacetate, Phenethyl Propionate, Phenethyl Salicylate, Phenethyl Senecioate, Phenethyl Tiglate, Phenol, Phenol-Formaldehyde, Cross-Linked, Tetraethylenepentamine Activated, Phenol-Formaldehyde, Cross-Linked, Triethylenetetramine Activated, Phenol-Formaldehyde, Cross-Linked, Triethylenetetramine & Tetraethylenepentamine Activated, Phenol-Formaldehyde, Sulfite-Modified, Cross-Linked, Phenoxyacetic Acid, 2-Phenoxyethyl Isobutyrate, 2-Phenoxyethyl Propionate, Phenylacetaldehyde, Phenylacetaldehyde 2,3-Butylene Glycol Acetal, Phenylacetaldehyde Diethyl Acetal, Phenylacetaldehyde Diisobutyl Acetal, Phenylacetaldehyde Dimethyl Acetal, Phenylacetaldehyde Glyceryl Acetal, Phenylacetaldehyde Propyleneglycol Acetal, Phenyl Acetate, Phenylacetic Acid, D-Phenylalanine, L-Phenylalanine, 4-Phenyl-2-Butanol, 2-Phenyl-2-Butenal, 4-Phenyl-3-Buten-2-Ol, 4-Phenyl-3-Buten-2-One, 4-Phenyl-2-Butyl Acetate, Phenyl Butyrate, 2-Phenyl-3-Carbethoxy Furan, Phenyl Disulfide, (+/−)-1-Phenylethylmercaptan, Phenylethyl Mercaptan, (+/−)-2-Phenyl-4-Methyl-2-Hexenal, 1-Phenyl-3-Methyl-3-Pentanol, 1-Phenyl-3 Or 5-Propylpyrazole, 5-Phenylpentanol, 2-Phenyl-4-Pentenal, 3-Phenyl-4-Pentenal, O-Phenylphenol, 1-Phenyl-1,2-Propanedione, 3-Phenyl-1-Propanol, 1-Phenyl-1-Propanol, 2-Phenyl-3-(2-Furyl)-Prop-2-Enal, 3-Phenylpropionaldehyde, 2-Phenylpropionaldehyde, 2-Phenylpropionaldehyde Dimethyl Acetal, 3-Phenylpropionic Acid, 3-Phenylpropyl Acetate, 2-Phenylpropyl Butyrate, 3-Phenylpropyl Cinnamate, 3-Phenylpropyl Formate, 3-Phenylpropyl Hexanoate, 2-Phenylpropyl Isobutyrate, 3-Phenylpropyl Isobutyrate, 3-Phenylpropyl Isovalerate, 3-Phenylpropyl Propionate, 2-(3-Phenylpropyl)Pyridine, 2-(3-Phenylpropyl)Tetrahydrofuran, Phenyl Salicylate, Phosphoric Acid, Phosphorus Oxychloride, Phthalide, Phytol, Phytyl Acetate, Pimenta Leaf, Oil (*Pimenta officinalis* Lindl.), 3-Pinanone, Pine Bark, White, Extract Solid (*Pinus strobus* L.), Pine Bark, White, Oil (*Pinus strobus* L.), Pine Bark, White (*Pinus strobus* L.), Alpha-Pinene, Beta-Pinene, Pine Needle, Dwarf, Oil (*Pinus mugo* Turra Var. *pumilio* (Haenke) Zenari), Pine, Scotch, Oil (*Pinus sylvestris* L.), Pine Tar, Oil (*Pinus* Spp.), Pine, White, Oil (*Pinus* Spp.), Pinocarveol, Pinocarvyl Isobutyrate, Piperazine, Piperazine Dihydrochloride, Piperidine, Piperine, Piperitenone, Piperitenone Oxide, L-Piperitone, D-Piperitone, *Piper longum* Distillate, Piperonal, Piperonal Propyleneglycol Acetal, Piperonyl Acetate, Piperonyl Isobutyrate, Pipsissewa Leaves, Extract (*Chimaphila umbellata* Nutt.), 1,3-P-Menthadien-7-Al, P-Menthane-3,8-Diol, P-Menthan-7-Ol, P-Menth-1-En-9-Ol, Polyacrylamide, Polyacrylamide Resin, Modified, Poly(Acrylic Acid-Co-Hypophosphite), Sodium Salt, Polyacrylic Acid, Sodium Salt, Poly(Alkyl(C16-22)Acrylate), Polydextrose, Poly(Divinylbenzene-Co-Ethylstyrene), Poly(Divinylbenzene-Co-Trimethyl(Vinylbenzyl)Ammonium Chloride), Polyethylene (M W 2,000-21,000), Polyethylene Glycol (M W 200-9,500), Polyethylene Glycol (400) Dioleate, Polyethylene, Oxidized, Polyethylenimine Reaction Product W/1,2-Dichloroethane, Polyglycerol Esters Of Fatty Acids, Polyglyceryl Phthalate Ester Of Coconut Oil Fatty Acids, Polyisobutylene (Min M W 37,000), Polylimonene, Polymaleic Acid, Polymaleic Acid, Sodium Salt, Poly(Maleic Anhydride), Sodium Salt, Polyoxyethylene (600) Dioleate, Polyoxyethylene Dioleate, Polyoxyethylene (600) Monoricinoleate, Polyoxyethylene 40 Monostearate, Polypropylene Glycol (M W 1,200-3,000), Polysorbate 20, Polysorbate 60, Polysorbate 65, Polysorbate 80, Polystyrene, Cross-Linked, Chloromethylated, Then Aminated With Trimethylamine, Dimethylamine, Diethylenetriamine, Or Triethanolamine, Polyvinyl Acetate, Polyvinyl Alcohol, Polyvinyl Polypyrrolidone, Polyvinylpyrrolidone, Pomegranate Bark, Extract (*Punica granatum* L.), Poplar Buds (*Populus* Spp.), Poppy Seed (*Papaver somniferum* L.), Potassium Acetate, Potassium Acid Pyrophosphate, Potassium Acid Tartrate, Potassium Benzoate, Potassium Bicarbonate, Potassium Bisulfite, Potassium Borate, Potassium Bromate, Potassium Bromide, Potassium Caprate, Potassium Caprylate, Potassium Carbonate, Potassium Caseinate, Potassium Chloride, Potassium Citrate, 2-(1'-Ethoxy)Ethoxypropanoate, Potassium Fumarate, Potassium Gibberellate, Potassium Gluconate, Potassium Glycerophosphate, Potassium Hydroxide, Potassium Hypophosphate, Potassium Hypophosphite, Potassium Iodate, Potassium Iodide, Potassium Lactate, Potassium Laurate, Potassium Metabisulfite, Potassium N-Methyldithiocarbamate, Potassium Myristate, Potassium Nitrate, Potassium Nitrite, Potassium Oleate, Potassium Palmitate, Potassium Pectinate, Potassium Permanganate, Potassium Persulfate, Potassium Phosphate, Monobasic, Potassium Phosphate, Tribasic, Potassium Polymetaphosphate, Potassium Pyrophosphate, Potassium Salts Of Fatty Acids, Potassium Sorbate, Potassium Stearate, Potassium Sulfate, Potassium Sulfite, Potassium Tripolyphosphate, Potato Starch, Prenyl Acetate, Prenyl Benzoate, Prenyl Caproate, Prenyl Formate, Prenyl Isobutyrate, Prenyl Thioacetate, Prenylthiol, Prickly Ash Bark Extract (*Xanthoxylum* Spp.), Prickly Ash Bark, Oil, L-Proline, 1,2-(Di(1'-Ethoxy)Ethoxy)Propane, Propane, 1,3-Propanedithiol, 1,2-Propanedithiol, 1,1-Propanedithiol, 2-Propanethiol, 3-(Methylthio)Propanol, (2-Furyl)-2-Propanone, 1-(P-Methoxyphenyl)-2-Propanone, Di-(1-Propenyl)-Sulfide (Mixture Of Isomers), 4-Propenyl-2,6-Dimethoxyphenol, Propenylguaethol, (Z)-4-Propenylphenol, 4-(2-Propenyl)Phenyl-Beta-D-Glucopyranoside, Propenyl Propyl Disulfide, Propionaldehyde, 3-(Methylthio)Propionaldehyde, Propionic Acid, 2-(4-Methyl-2-Hydroxyphenyl)Propionic Acid-Gamma-Lactone, 2-Propionylpyrrole, 2-Propionylpyrroline, 2-Propionylthiazole, 2-Propionyl-2-Thiazoline, Propiophenone, Propyl Acetate, Propyl Alcohol, Propylamine, P-Propylanisole, Propyl Benzoate, Propyl Butyrate, Propyl Cinnamate, Propyl 2,4-Decadienoate, 4-Propyl-2,6-Dimethoxyphenol, 2-Propyl-4,5-Dimethyloxazole, Propyl Disulfide, Propylene Chlorohydrin, Propylene Glycol, Propylene Glycol Alginate, Propyleneglycol Diacetate, Propylene Glycol Dibenzoate, Propyleneglycol Dibutyrate, Propyleneglycol Dihexanoate, Propyleneglycol Di-2-Methylbutyrate, Propyleneglycol Dioctanoate, Propyleneglycol Dipropionate, Propylene Glycol Mono- And Diesters Of Fats And Fatty Acids, Propyleneglycol Monobutyrate, Propyleneglycol Monohexanoate, Propyleneglycol Mono-2-Methylbutyrate, Propylene Glycol Stearate, Propylene Oxide, Propyl Formate, Propyl 2-Furanacrylate, Propyl 2-Furoate, Propyl Gallate, Propyl Heptanoate, Propyl Hexanoate, Propyl P-Hydroxybenzoate, 3-Propylidenephthalide, Propyl Isobutyrate, Propyl Isovalerate, Propyl Levulinate, Propyl Mercaptan, Propyl 2-Mercaptopropionate, Propyl 2-Methyl-3-Furyl Disulfide, Alpha-Propylphenethyl Alcohol, P-Propylphenol, O-Propylphenol, Propyl Phenylacetate, Propyl Propane Thiosulfonate, Propyl Propionate, 2-Propylpyrazine, 2-Propylpyridine, Propyl Pyruvate, Propyl Sorbate, Propyl 4-Tert-Butylphenylacetate, Propyl Thioacetate, Protease From *Aspergillus flavus*, Protease From *Aspergillus Niger*, Protease From *Aspergillus oryzae*, Protease From *Bacillus amyloliquefaciens*, Protease From *Bacillus licheniformis*, Protease From *Bacillus subtilis*, Protein, Animal, Hydrolyzed, Protein Hydrolysate, Protein, Milk, Hydrolyzed, Protein, Vegetable, Hydrolyzed, Pseudoionone, Psyllium Seed Husk, Pulegone, Pulp, Pyrazine, Pyrazine Ethanethiol, Pyrazinyl Methyl Sulfide, 3-(2-Methylpropyl)Pyridine, Pyridine, 2-Pyridinemethanethiol, Pyridoxine, Pyridoxine Hydrochloride, Pyroligneous Acid, Pyroligneous Acid, Extract, Pyrrole, Pyrrolidine, Pyrrolidino-[1,2e]-4h-2,4-Dimethyl-1,3,5-Dithiazine, 1-Pyrroline, Pyruvaldehyde, Pyruvic Acid, Quassia, Extract (*Picrasma excelsa* (Sw.) Planch Or *Quassia Amara* L.), Quaternary Ammonium Chloride Combination, Quebracho Bark Extract, Quillaia Extract (*Quillaja saponaria* Molina), Quillaia (*Quillaja saponaria* Molina), Quince Seed, Extract (*Cydonia* Spp.), Quinine Bisulfate, Quinine Hydrochloride, Quinine Sulfate, Quinoline, Rapeseed Oil, Hydrogenated, Rapeseed Oil, Hydrogenated, Superglycerinated, Rapeseed Oil, Low Erucic Acid, Rapeseed Oil, Low Erucic Acid, Partially Hydrogenated, Rebaudioside C, Rebaudioside A, Rennet, Resin, From Formaldehyde, Acetone, And Tetraethylenepentamine, Resorcinol, L-Rhamnose, Rhatany, Extract (*Krameria* Spp.), Rhodinol, Rhodinyl Acetate, Rhodinyl Butyrate, Rhodinyl Formate, Rhodinyl Isobutyrate, Rhodinyl Isovalerate, Rhodinyl Phenylacetate, Rhodinyl Propionate, Rhubarb, Garden Root (*Rheum rhaponticum* L.), Rhubarb Root (*Rheum* Spp.), Riboflavin, Riboflavin 5'-Phosphate, Riboflavin 5'-Phosphate, Sodium, D-Ribose, Rice Bran Wax, Rice, Milled, Rice Starch, (R)-(−)-1-Octen-3-Ol, Rose, Absolute (*Rosa* Spp.), Rose, Bud (*Rosa* Spp.), Rose Flowers (*Rosa* Spp.), Rose Hips, Extract (*Rosa* Spp.), Rose Leaves (*Rosa* Spp.), Roselle (*Hibiscus sabdariffa* L.), Rosemary, Extract (*Rosmarinus officinalis* L.), Rosemary, Oil (*Rosemarinus officinalis* L.), Rosemary, Oleoresin, Rosemary (*Rosemarinus officinalis* L.), Rose, Oil (*Rosa* Spp.), Rose Water, Stronger (*Rosa centifolia* L.), Rosidinha (*Micropholis* (Also Known As *Sideroxylon*) Spp.), Rosin, Adduct With Fumaric Acid, Pentaerythritol Ester, Rosin, Glycerol Ester, Rosin, Gum, Glycerol Ester, Rosin, Gum Or Wood, Partially Hydrogenated, Glycerol Ester, Rosin, Gum Or Wood, Partially Hydrogenated, Pentaerythritol Ester, Rosin, Gum Or Wood, Pentaerythritol Ester, Rosin, Limed, Rosin, Methyl Ester, Partially Hydrogenated, Rosin, Partially Dimerized, Calcium Salt, Rosin, Partially Dimerized, Glycerol Ester, Rosin, Partially Hydrogenated, Rosin (*Pinus* Spp.) And Rosin Derivatives, Rosin, Polymerized, Glycerol Ester, Rosin, Tall Oil, Glycerol Ester, Rosin, Wood, Rosin, Wood, Glycerol Ester, Rosin, Wood, Maleic Anhyd. Mod., Pentaerythritol Ester, Acid #176-186, Rosin, Wood, Maleic Anhyd. Mod., Pentaerythritol Ester, Acid #134-145, (1r,2s,5r)-N-(4-Methoxyphenyl)-5-Methyl-2-(1-Methylethyl)Cyclohexanecarboxamide, Rubber, Natural-Smoked Sheet And Latex Solids (*Hevea brasiliensis*), Rue, Oil (*Ruta graveolens* L.), Rue (*Ruta graveolens* L.), Rum, Rum Ether, Rutin, Saccharin, Saccharin, Ammonium Salt, Saccharin, Calcium Salt, Saccharin, Sodium Salt, Saffron (*Crocus sativus* L.), Saffron, Extract (*Crocus sativus* L.), Safrole-Free Extract Of Sassafras, Sage, Greek (*Salvia triloba* L.), Sage, Oil (*Salvia officinalis* L.), Sage, Oleoresin (*Salvia officinalis* L.), Sage (*Salvia officinalis* L.), Sage, Spanish, Oil (*Salvia lavandulaefolia* Vahl.), Salicylaldehyde, Salicylic Acid, Salts Of Fatty Acids, Sandalwood, Red (*Pterocarpus santalinus* L.F.), Sandalwood, White (*Santalum album* L.), Sandalwood, Yellow, Oil (*Santalum album* L.), Sandarac (*Tetraclinis articulata* (Vahl.) Mast.), Santalol, Beta, Santalol, Alpha, Santalol (Alpha And Beta), Santalyl Acetate, Santalyl Phenylacetate, Sarcodactylis Oil, Sarsaparilla, Extract (*Smilax* Spp.), Sassafras Bark, Extract (Safrole-Free) (*Sassafras albidum* (Nutt.) Nees), Sassafras Leaves (Safrole-Free) (*Sassafras albidum* (Nutt.) Nees), Sausage Casing (Hcl And Cellulose Fibers), Savory, Summer, Oil (*Satureja hortensis* L.), Savory, Summer, Oleoresin (*Satureja hortensis* L.), Savory, Summer (*Satureja hortensis* L.), Savory, Winter, Oil (*Satureja montana* L.), Savory, Winter, Oleoresin (*Satureja montana* L.), Savory, Winter (*Satureja montana* L.), *Schinus molle*, Oil (*Schinus molle* L.), (−)-Sclareol, Sclareolide, Scotch Spearmint Oil, *Mentha cardiaca* L., 2-Sec-Butylcyclohexanone, Sec-Butyl Ethyl Ether, Senna, Alexandria (*Cassia acutifolia* Delile), L-Serine, Serpentaria (*Aristolochia serpentaria* L.), Sesame (*Sesamum indicum* L.), Sheanut Oil, Shellac, Purified, Shellac Wax, Silica Aerogel, Silicon Dioxide, Silver Fir, Needles And Twigs, Oil (*Abies alba* Mill.), Silver-Silver Dragees, Simaruba Bark (*Simaruba amara* Aubl.), Skatole, Sloe Berries, Extract (*Prunus spinosa* L.), Sloe Berries, Extract Solid (*Prunus spinosa* L.), Sloe Berries (*Prunus spinosa* L.), Snakeroot, Canadian, Oil (*Asarum canadense* L.), Sodium Acetate, Sodium Acid Pyrophosphate, Sodium N-Alkylbenzenesulfonate, Sodium Aluminate, Sodium Aluminum Phosphate, Acidic Or Basic, Sodium Aluminum Silicate, Sodium Ascorbate, Sodium Benzoate, Sodium Bicarbonate, Sodium Bisulfite, Sodium Borate, Sodium Borohydride, Sodium Calcium Aluminosilicate, Hydrated, Sodium Caprate, Sodium Caprylate, Sodium Carbonate, Sodium Caseinate, Sodium Chloride, Sodium Chlorite, Sodium Copper Chlorophyllin, Sodium Decylbenzenesulfonate, Sodium Dehydroacetate, Sodium Diacetate, Sodium Dimethyldithiocarbamate, Sodium Dodecylbenzenesulfonate, Sodium Erythorbate, Sodium 2-Ethylhexyl Sulfate, Sodium Ferricitropyrophosphate, Sodium Ferritripolyphosphate, Sodium Fluoride, Sodium Formate, Sodium Fumarate, Sodium Glucoheptonate, Sodium Gluconate, Sodium Hexametaphosphate, Sodium Humate, Sodium Hydrosulfite, Sodium Hydroxide, Sodium Hypochlorite, Sodium Hypophosphite, Sodium Lactate, Sodium Laurate, Sodium Lauryl Sulfate, Sodium 3-Mercaptooxopropionate, Sodium Metabisulfite, Sodium Metaphosphate, Sodium Metasilicate, Sodium (4-Methoxybenzoyloxy)Acetate, Sodium 3-Methoxy-4-Hydroxycinnamate, Sodium 2-(4-Methoxyphenoxy)Propanoate, Sodium Methyl Sulfate, Sodium Mono- And Dimethyl Naphthalene Sulfonates, Sodium Myristate, Sodium Nitrate, Sodium Nitrite, Sodium Oleate, Sodium Palmitate, Sodium Pantothenate, Sodium Pectinate, Sodium Phosphate, Dibasic, Sodium Phosphate, Monobasic, Sodium Phosphate, Tribasic, Sodium Polymethacrylate, Sodium Potassium Tartrate, Sodium Propionate, Sodium Pyrophosphate, Sodium Salts Of Fatty Acids, Sodium Sesquicarbonate, Sodium Silicate, Sodium Sorbate, Sodium Stearate, Sodium Stearoyl-2-Lactylate, Sodium Stearyl Fumarate, Sodium Sulfate, Sodium Sulfide, Sodium Sulfite, Sodium Tartrate, Sodium Taurocholate, Sodium Thiosulfate, Sodium Tripolyphosphate, Sodium Zinc Metasilicate, Sorbic Acid, Sorbitan Monooleate, Sorbitan Monostearate, D-Sorbitol, Sorbose, Soya Bean Oil Fatty Acids, Hydroxylated, Soya Fatty Acid Amine, Ethoxylated, Soybean Oil, Epoxidized, Soybean Oil, Hydrogenated, Soy Protein Concentrate, Enzyme Activated, Soy Protein, Isolate, Spearmint, Extract (*Mentha spicata* L.), Spearmint (*Mentha spicata* L.), Spearmint, Oil (*Mentha spicata* L.), Sperm Oil, Sperm Oil, Hydrogenated, Spikenard Extract, Spiro(2,4-Dithia-1-Methyl-8-Oxabicyclo(3.3.0)Octane-3,3'-(1'-Oxa-2'-Methyl)Cyclopentane), spruce Needles And Twigs, Extract (*Picea* Spp.), Spruce Needles And Twigs, Oil (*Picea* Spp.), (2s,5r)-N-[4-(2-Amino-2-Oxoethyl)Phenyl]-5-Methyl-2-(Propan-2-Yl)Cyclohexanecarboxamide, Stannic Chloride, Stannous Chloride, Starch, Acid Modified, Starch, Alpha-Amylase Modified, Starch, Bleached, Starch, Food, Modified, Starch, Food, Modified: Acetylated Distarch Adipate, Starch, Food, Modified: Acetylated Distarch Glycerol, Starch, Food, Modified: Acetylated Distarch Oxypropanol, Starch, Food, Modified: Acetylated Distarch Phosphate, Starch, Food, Modified: Beta-Amylase Modified Starch, Starch, Food, Modified: Beta-Amylase Sodium Starch Octenylsuccinate, Starch, Food, Modified: Distarch Glycerol, Starch, Food, Modified: Distarch Oxypropanol, Starch, Food, Modified: Distarch Phosphate (From Phosphorus Oxychloride), Starch, Food, Modified: Distarch Phosphate (From Sodium Trimetaphosphate), Starch, Food, Modified: Glucoamylase Modified Starch, Starch, Food, Modified: Hydroxypropyl Distarch Glycerol, Starch, Food, Modified: Hydroxypropyl Distarch Phosphate, Starch, Food, Modified: Hydroxypropyl Starch, Starch, Food, Modified: Isoamylase Modified Starch, Starch, Food, Modified: Oxidized Hydroxypropyl Starch, Starch, Food, Modified: Oxidized Starches, Starch, Food, Modified: Phosphated Distarch Phosphate, Starch, Food, Modified: Pullulanase Modified Starch, Starch, Food, Modified: Starch Acetate, Starch, Food, Modified: Starch Aluminum Octenyl Succinate, Starch, Food, Modified: Starch Phosphate, Starch, Food, Modified: Starch Sodium Octenyl Succinate, Starch, Food, Modified: Starch Sodium Succinate, Starch, Food, Modified: Succinyl Distarch Glycerol, Starch, Pregelatinized, Starch, Unmodified, Stearic Acid, Stearyl Alcohol, Stearyl Alcohol, Plus Beeswax, Stearyl Citrate, Stearyl Monoglyceridyl Citrate, S-(Tetrahydro-2,5-Dimethyl-3-Furanyl) Ethanethioate, St. Johnswort Leaves, Flowers And Caulis (*Hypericum perforatuml.*), Storax Extract (*Liquidambar* Spp.), Storax (*Liquidambar* Spp.), Storax Oil, Styrene, Styrene-Divinylbenzene-Acrylonitrile, Sulfonated Terpolymer, Styrene-Divinylbenzene Copolymer, Chloromethylated, Aminated, Oxidized, Styrene-Divinylbenzene-Methyl Acrylate, Sulfonated Terpolymer, Styrene, Divinylbenzene, Sulfonated Copolymer, Styrene-Dvb-Acrylonitrile-Methyl Acrylate, Sulfonated Tetrapolymer, Succinic Acid, Succinic Anhydride, Succinylated Gelatin, Succinylated Monoglycerides, Succistearin, Sucralose, Sucrose, Sucrose Acetate Isobutyrate, Sucrose Fatty Acid Esters, Sucrose Liquid, Sucrose Monopalmitate, Sucrose Octaacetate, Sucrose Oligoesters, Sugar Beet Juice Extract, Sugar Beet Extract Flavor Base, Sulfamic Acid, Sulfites, Strong Alkali, Sulfiting Agents, Sulfopropyl Cellulose, Sulfur Dioxide, Sulfuric Acid, Sulfurous Acid, Sweet Blackberry Leaves Extract, Tagetes Meal & Extract, Tagetes, Oil (*Tagetes* Spp.), Talc, Tallow Alcohol, Hydrogenated, Tallow, Beef, Tallow Flakes, Tallow, Hydrogenated, Tallow, Hydrogenated, Oxidized Or Sulfated, Tamarind Extract (*Tamarindus indica* L.), Tamarinds, Tangerine, Essence, Tangerine, Extract (*Citrus reticulata* Blanco), Tangerine, Oil (*Citrus reticulata* Blanco), Tannic Acid, Tansy, Oil (*Tanacetum vulgara* L.), Tansy (*Tanacetum vulgara* L.), Tapioca Starch, Tarragon (*Artemisia dracunculus* L.), Tarragon Extract (*Artemisia dracunculus* L.), Tarragon Oil (*Artemisia dracunculus* L.), Tartaric Acid, L, Taurine, Taurocholic Acid, Tea Extract (*Thea sinensis* L.), Tea Tree Oil (*Melaleuca alternifolia*), Terpene Resin, Terpene Resins, Natural, Terpene Resins, Synthetic, Alpha-Terpinene, Gamma-Terpinene, Alpha-Terpineol, Beta-Terpineol, Terpinolene, Terpinyl Acetate, Alpha-Terpinyl Anthranilate, Terpinyl Butyrate, Terpinyl Cinnamate, Terpinyl Formate, Terpinyl Isobutyrate, Terpinyl Isovalerate, Terpinyl Propionate, Tert-Butylhydroquinone, 2-Tert-Pentylcyclohexyl Acetate, Delta-Tetradecalactone, (Z)-8-Tetradecenal, Tetradec-2-Enal, 9-Tetradecen-5-Olide, Tetraethylenepentamine Crosslinked With Epichlorohydrin, 1,1'-(Tetrahydro-6a-Hydroxy-2,3a,5-Trimethylfuro[2,3-D]-1,3-Dioxole-2,5-Diyl)Bis-Ethanone, 1,2,5,6-Tetrahydrocuminic Acid, 4,5,6,7-Tetrahydro-3,6-Dimethylbenzofuran, Tetrahydrofurfuryl Acetate, Tetrahydrofurfuryl Alcohol, Tetrahydrofurfuryl Butyrate, Tetrahydrofurfuryl Cinnamate, 2-Tetrahydrofurfuryl 2-Mercaptopropionate, Tetrahydrofurfuryl Propionate, Tetrahydrolinalool, Tetrahydro-4-Methyl-2-(2-Methylpropen-1-Yl)Pyran, Tetrahydro-Pseudo-Ionone, 5,6,7,8-Tetrahydroquinoxaline, 2,2,6,7-Tetramethylbicyclo[4.3.0]Nona-4,9(1)-Dien-8-Ol, 2,2,6,7-Tetramethylbicyclo[4.3.0]Nona-4,9(1)-Dien-8-One, Alpha-(P-(1,1,3,3-Tetramethylbutyl)Phenyl)-Omega-Hydroxypoly(Oxyethylene)(1 Mol), Alpha-{P-(1,1,3,3-Tetramethylbutyl)Phenyl}-Omega-Hydroxypoly(Oxyethylene), Alpha-(P-(1,1,3,3-Tetramethylbutyl)Phenyl)-Omega-Hydroxypoly(Oxyethylene)(Greater Than 1 Mol), Tetramethyl Ethylcyclohexenone (Mixture Of Isomers), (+/−)-2,6,10,10-Tetramethyl-1-Oxaspiro[4,5]Deca-2,6-Dien-8-One, 1,5,5,9-Tetramethyl-13-Oxatricyclo(8.3.0.0(4,9))Tridecane, 2,3,5,6-Tetramethylpyrazine, Thaumatin, Thaumatin B, Recombinant, Theaspirane, Theobromine, Thiamine, Thiamine Hydrochloride, Thiamine Mononitrate, Thiazole, 2-Thienyl Disulfide, 1-(2-Thienyl)Ethanethiol, 2-Thienyl Mercaptan, 2-Thienylmethanol, Thioacetic Acid, 2,2'-(Thiodimethylene)-Difuran, Thiodipropionic Acid, Thiogeraniol, Thistle, Blessed (*Cnicus benedictus* L.), Thistle, Blessed, Extract (*Cnicus benedictus* L.), Thistle, Blessed, Extract Solid (*Cnicus benedictus* L.), Thistle, Blessed, Oil (*Cnicus benedictus* L.), L-Threonine, 4-Thujanol, Thujyl Alcohol, Thyme, Extract, Thyme Oil (*Thymus vulgaris* L. And T. Zygis Var. *Gracilis boiss.*), Thyme Oleoresin, Thyme (*Thymus serpyllum* L.), Thyme (*Thymus vulgaris* L.), Thyme, Wild Or Creeping, Extract (*Thymus serpyllum* L.), Thymol, Titanium Dioxide, Alpha-Tocopherol Acetate, Tocopherols, Tolualdehyde Glyceryl Acetal (Mixed O-, M-, P-), Tolualdehydes (Mixed O-, M-, P-), Tolu Balsam Extract (*Myroxylon* Spp.), Tolu Balsam Gum (*Myroxylon* Spp.), O-Toluenethiol, P-Tolylacetaldehyde, O-Tolyl Acetate, P-Tolyl Acetate, 4-(P-Tolyl)-2-Butanone, O-Tolyl Isobutyrate, P-Tolyl Isobutyrate, P-Tolyl Laurate, P-Tolyl 3-Methylbutyrate, P-Tolyl Octanoate, P-Tolyl Phenylacetate, 2-(P-Tolyl)-Propionaldehyde, O-Tolyl Salicylate, Tomato Lycopene, Tragacanth, Gum (*Astragalus* Spp.), (+/−)-Trans- And Cis-2-Hexenal Propylene Glycol Acetal, 2-Trans-6-Cis-Dodecadienal, 2-Trans-6-Cis-Nonadienal, O-Trans-Coumaric Acid, Trans-2-Decenol, Trans-3-Heptenyl Acetate, Trans-3-Hexenol, Trans-3-Hexenyl Acetate, Trans-2-Hexen-1-Yl Acetate, Trans-2-Hexenyl 2-Methylbutyrate, Trans-4-Nonenal, Trans-3-Nonen-1-Ol, Trans-2-Nonen-4-One, Trans-2-Nonenyl Acetate, Trans-4-Octenoic Acid, 2-(Trans-2-Pentenyl)Cyclopentanone, Trans-4-Tert-Butylcyclohexanol, Trans,Trans-2,4-Dodecadienal, Trans-2-Trans-4-Nonadiene, Trans-2-Tridecenol, Trefoil, Sweet (*Melilotus coerulea*), Trehalose, Dihydrate, Triacetin (Glycerol Triacetate), Tributyl Acetylcitrate, Trichloroethylene, Tridecanal, Tridecanoic Acid, 2-Tridecanone, 2-Trans,4-Cis,7-Cis-Tridecatrienal, 2-Tridecenal, Tridodecyl Amine, Triethanolamine, Triethylamine, Triethyl Citrate, Triethylenetetramine Cross-Linked With Epichlorohydrin, Trifluoromethane Sulfonic Acid, 2,4,5-Trihydroxybutyrophenone, (Trihydroxy-Phenyl)-Propan-1-One, Trilobatin, Trimethylamine, Trimethylamine Oxide, 2,6,6-Trimethyl-1 And 2-Cyclohexen-1-Carboxaldehyde, P,Alpha,Alpha-Trimethylbenzyl Alcohol, 4-(2,6,6-Trimethylcyclohexa-1,3-Dienyl)But-2-En-4-One, 2,6,6-Trimethylcyclohexa-1,3-Dienyl Methanal, 3,3,5-Trimethylcyclohexanol, 2,2,6-Trimethylcyclohexanone, 2,6,6-Trimethyl-1-Cyclohexen-1-Acetaldehyde, 2,6,6-Trimethylcyclohex-2-Ene-1,4-Dione, 4-(2,6,6-Trimethylcyclohex-1-Enyl)But-2-En-4-One, 3,3,5-Trimethylcyclohexyl Acetate, 2,2,3-Trimethylcyclopent-3-En-1-Yl Acetaldehyde, 4-(2,2,3-Trimethylcyclopentyl)Butanoic Acid, 3,7,11-Trimethyldodeca-2,6,10-Trienyl Acetate, 3,5,5-Trimethylhexanal, 3,5,5-Trimethyl-1-Hexanol, 2,6,6-Trimethyl-2-Hydroxycyclohexanone, (2,6,6-Trimethyl-2-Hydroxycyclohexylidene)Acetic Acid Gamma-Lactone, 2,3,3-Trimethylindanone, Trans- And Cis-2,4,8-Trimethyl-3,7-Nona-Dien-2-Ol, (+/−)-2,4,8-Trimethyl-7-Nonen-2-Ol, 1,3,3-Trimethyl-2-Norbornanyl Acetate, 2,2,4-Trimethyl-1,3-Oxacyclopentane, Trimethyloxazole, 2,4,5-Trimethyl-Delta-3-Oxazoline, 2,6,10-Trimethyl-2,6,10-Pentadecatrien-14-One, 2,3,4-Trimethyl-3-Pentanol, 2,4,6-Trimethylphenol, 2,3,6-Trimethylphenol, 2,3,5-Trimethylpyrazine, 2,4,5-Trimethylthiazole, 2,2,6-Trimethyl-6-Vinyltetrahydropyran, Tripropylamine, 1,2,3-Tris((1'-Ethoxy)Ethoxy)-Propane, Trisodium Citrate, Trisodium Nitrilotriacetate, 2,4,6-Trithiaheptane, Trithioacetone, Trypsin From Animal Tissue, L-Tryptophan, Tuberose Lactone, Tuberose, Oil (*Polianthes tuberosa* L.), Tunu (*Castilla fallax* Cook), Turmeric (*Curcuma longa* L.), Turmeric Extract (*Curcuma longa* L.), Turmeric Oleoresin (*Curcuma longa* L.), Turpentine, Turpentine, Gum (*Pinus* Spp.), Turpentine, Rectified, Turpentine, Steam Distilled (*Pinus* Spp.), Tyramine, L-Tyrosine, L-Tyrosine Ethyl Ester Hydrochloride, Ultramarine Blue, 2,4-Undecadienal, 2,5-Undecadienal, 2,3-Undecadione, Gamma-Undecalactone, Undecanal, Undecanal Propyleneglycol Acetal, Undecanoic Acid, 2-Undecanol, 2-Undecanone, 1,3,5,7-Undecatetraene, 1,3,5-Undecatriene, 9-Undecenal, 10-Undecenal, 2-Undecenal, (E)-4-Undecenal, 10-Undecenoic Acid, 2-Undecen-1-Ol, Undecen-1-Ol, 2-Undecen-1-Ol, 10-Undecen-2-One, 10-Undecen-1-Yl Acetate, Undecyl Alcohol, N-Undecylbenzenesulfonic Acid, Urea, Urease Enzyme Preparation (*Lactobacillus fermentum*), Valencene, Valeraldehyde, Valeraldehyde Dibutyl Acetal, Valeraldehyde Propyleneglycol Acetal, Valerian Root, Extract (*Valeriana officinalis* L.), Valerian Root, Oil (*Valeriana officinalis* L.), Valeric Acid, Gamma-Valerolactone, L-Valine, Vanilla, Absolute (*Vanilla* Spp.), Vanilla, Extract (*Vanilla* Spp.), Vanilla, Oleoresin (*Vanilla* Spp.), Vanilla (*Vanilla* Spp.), Vanillic Acid, Vanillin, Vanillin Acetate, Vanillin 1,2-Butylene Glycol Acetal, Vanillin Isobutyrate, Vanillin 3-(L-Menthoxy)Propane-1,2-Diol Acetal, Vanillin Propylene Glycol Acetal, Vanillyl Alcohol, Vanillyl Butyl Ether, Vanillyl Ethyl Ether, Vanillylidene Acetone, Vegetable Gum, Other Than Those Cfr Listed, Vegetable Juice, Veratraldehyde, Verbenol, Verbenone, Veronica (*Veronica officinalis* L.), Vervain, European (*Verbena officinalis* L.), Vetiver, Oil (*Vetiveria zizanioides* Stapf), Vetiverol, Vetiver (*Vetiveria zizaniodes* Stapf), Vetiveryl Acetate, Vinyl Acetate, O-Vinylanisole, Vinyl Chloride-Vinylidene Chloride Copolymer, P-Vinylphenol, Violet Leaves Absolute (*Viola odorata* L.), Violet, Swiss (*Viola calcarata* L.), Vitamin D-2, Vitamin D-3, Vitamin B-12, Vitamin A, Vitamin A Acetate, Vitamin B Complex And Syrup, Vitamin D, Vitamin K, Vitamin A Palmitate, Walnut Hull, Extract (*Juglans* Spp.), Walnut Leaves, Extract (*Juglans Spp.), Wheat Gluten, Wheat Starch, Whey, Whey, Delactosed, Whey, Demineralized, Whey, Partially Dimineralized And Partially Delactosed, Whey Protein Concentrate, Whey Powder, Wintergreen, Extract (*Gaultheria procumbens* L.), Wintergreen, Oil (*Gaultheria procumbens* L.), Woodruff, Sweet (*Asperula odorata* L.), Wort, Xanthan Gum, Xanthophyll, 2,6-Xylenol, 2,5-Xylenol, 3,4-Xylenol, Xylitol, D-Xylose, Yarrow, Herb (*Achillea millefolium* L.), Yarrow, Oil (*Achillea millefolium* L.), Yeast Autolysate, Yeast, Dried Irradiated, Yeast Extract Autolyzed, Yeast-Malt Sprout Extract, Yeasts, Dried Yeasts, Yellow Prussiate Of Soda, Yerba Santa, Fluid Extract (*Eriodictyon californicum* (Hook And Arn) Torr), Ylang-Ylang, Oil (*Cananga odorata* Hook. F. And Thomas), Yucca, Joshua-Tree (*Yucca brevifolia* Engelm.), Yucca, Mohave, Extract (*Yucca* Spp.), Yuzunone, Zedoary Bark, Extract (*Curcuma zedoaria* (Berg.) Rosc.), Zedoary (*Curcuma zedoaria* (Berg.) Rosc.), Zein Powder, Zinc Acetate, Zinc Carbonate, Zinc Chloride, Zinc Dithionite, Zinc Gluconate, Zinc Methionine Sulfate, Zinc Oxide, Zinc Stearate, Zinc Sulfate, and Zingerone.

Food additives may also include, without limitation, vanillin, ethyl vanillin, 2-hydroxy-4-methoxybenzaldehyde, ethyl vanillin isobutyrate (=3 ethoxy-4-isobutyryloxybenzaldehyde), Furaneol® (2,5-dimethyl-4-hydroxy-3(2H)-furanone) and derivatives (e.g. homofuraneol, 2-ethyl-4-hydroxy-5-methyl-3(2H)-furanone), homofuronol (2-ethyl-5-methyl-4-hydroxy-3(2H)-furanone and 5-ethyl-2-methyl-4-hydroxy-3(2H)-furanone), maltol and its derivatives (e.g. ethyl maltol), coumarin and its derivatives, gamma-lactones (e.g. gamma-undecalactone, gamma-nonalactone), delta-lactones (e.g. 4-methyl delta-lactone, massoia lactone, deltadecalactone, tuberolactone), methyl sorbate, divanillin, 4-hydroxy-2(or 5)-ethyl-5(or 2)-methyl-3(2H)furanone, 2-hydroxy-3-methyl-2-cyclopentenone, 3-hydroxy-4,5-dimethyl-2(5H)-furanone, fruit esters and fruit lactones (e.g. acetic acid n-butyl ester, acetic acid isoamyl ester, propionic acid ethyl ester, butyric acid ethyl ester, butyric acid n-butyl ester, butyric acid isoamyl ester, 3-methyl-butyric acid ethyl ester, n-hexanoic acid ethyl ester, n-hexanoic acid allyl ester, n-hexanoic acid n-butyl ester, n-octanoic acid ethyl ester, ethyl-3-methyl-3-phenylglycidate, ethyl-2-trans-4-cis-deca-dienoate), 4-(p-hydroxyphenyl)-2-butanone, 1,1-dimethoxy-2,2,5-trimethyl-4-hexane, 2,6-dimethyl-5-hepten-1-a1, and phenylacetaldehyde and mixtures thereof; (a2) carbohydrates selected from the group consisting of saccharose, trehalose, lactose, maltose, melizitose, melibiose, raffinose, palatinose, lactulose, D-fructose, D-glucose, D-galactose, L-rhamnose, D-sorbose, D-mannose, D-tagatose, D-arabinose, L-arabinose, D-ribose, D-glyceraldehyde, maltodextrins and mixtures thereof and plant formulations containing one or a plurality of the cited carbohydrates, preferably in a proportion of at least 5 wt %, preferably at least 15 wt %, whereby the carbohydrates can also be present as a naturally occurring or synthetically produced mixture, in this arrangement particularly as honey, invert sugar syrup or highly enriched fructose syrup from maize starch, and the physiologically acceptable salts of these carbohydrates, particularly sodium, potassium, calcium or ammonium salts; (a3) sugar alcohols, preferably naturally occurring sugar alcohols selected from the group consisting of glycerine, erythritol, threitol, arabitol, ribitol, xylitol, sorbitol, mannitol, maltitol, isomalt, dulcitol, lactitol and mixtures thereof, and the physiologically acceptable salts of these sugar alcohols, particularly sodium, potassium, calcium or ammonium salts; (a4) naturally occurring sweeteners, preferably selected from the group consisting of (a4-1) miraculin, monellin, mabinlin, thaumatin, curculin, brazzein, pentaidin, D-phenylalanine, D-tryptophan, and extracts or fractions obtained from natural sources containing these amino acids and/or proteins and mixtures thereof, and the physiologically acceptable salts of these amino acids and/or proteins, particularly the sodium, potassium, calcium or ammonium salts; (a4-2)neohesperidin dihydrochalcone, naringin dihydrochalcone, stevioside, steviolbioside, rebaudiosides, particularly rebaudioside A, rebaudioside B, rebaudioside C, rebaudioside D, rebaudioside E, rebaudioside F, rebaudioside G, rebaudioside H, dulcosides and rubusoside, suavioside A, suavioside B, suavioside G, suavioside H, suavioside I, suavioside J, baiyunoside 1 baiyunoside 2, phlomisoside 1, phlomisoside 2, phlomisoside 3, and phlomisoside 4, abrusoside A, abrusoside B, abrusoside C, abrusoside D, cyclocaryoside A and cyclocaryoside I, osladin, polypodoside A, strogin 1, strogin2,strogin 4, selligueain A, dihydroquercetin-3-acetate, perillartine, telosmoside A.sub.15, periandrin I-V, pterocaryosides, cyclocaryosides, mukuroziosides, trans-anethole, trans-cinnamaldehyde, bryosides, bryonosides, bryonodulcosides, carnosiflosides, scandenosides, gypenosides, trilobatin, phloridzin, dihydroflavanols, hematoxylin, cyanine, chlorogenic acid, albiziasaponin, telosmosides, gaudichaudioside, mogrosides, mogroside V, hernandulcins, monatin, phyllodulcin, glycyrrhetinic acid, and derivatives thereof and mixtures thereof, particularly its glycosides such as glycyrrhizin, and the physiologically acceptable salts of these compounds, particularly the sodium, potassium, calcium or ammonium salts; (a4-3) extracts or enriched fractions of extracts, selected from the group consisting of Thaumatococcus extracts (katemfe bush), extracts of *Stevia* ssp. (particularly *Stevia rebaudiana*), swingle extracts (*Momordica* or *Siratia grosvenorii*, Luo-Han-Guo), extracts of *Glycerrhyzia* ssp. (particularly *Glycerrhyzia glabra*), extracts of *Rubus* ssp. (particularly *Rubus suavissimus*), citrus extracts, and extracts of *Lippia dulcis* and mixtures thereof, and mixtures of any of (a4-1) to (a4-3); (a5) synthetically sweet-tasting substances, preferably selected from the group consisting of magap, sodium cyclamate or other physiologically acceptable salts of cyclamic acid, acesulfame K or other physiologically acceptable salts, neohesperidin dihydrochalcone, naringin dihydrochalcone, saccharin, saccharin-sodium salt, aspartame, superaspartame, neotame, alitame, advantame, perillartine, sucralose, lugduname, carrelame, sucrononate, and sucrooctate.

In some embodiments, the composition comprises a sweetening compound and/or sweet taste enhancer as described herein, and one or more flavorants. Representative flavorants include but are not limited to, those compounds identified as such by the Flavor and Extract Manufacturers Association (FEMA; see the FEMA Flavor Ingredient Library, accessible at http://www.femaflavor.org/flavor, last accessed Nov. 16, 2015). Such flavorants include: Acacia Gum (*Acacia senegal* (L.) Willd.), Acetal, Acetaldehyde, Propyl Phenethyl Acetal, Acetanisole, Acetic Acid, (Tri-) Acetin, Acetoin, Acetophenone, Aconitic Acid, Adipic Acid, Agar (*Gelidium* Spp.), Alfalfa Extract (*Medicago sativa* L.), Algin (*Laminaria* Spp. And Other Kelps), Alginates, Sodium, Calcium, And Ammonium, Allspice (*Pimenta officinalis* Lindl.), Allspice Oil (*Pimenta officinalis* Lindl.), Allspice Oleoresin (*Pimenta officinalis* Lindl.), Allyl Anthranilate, Allyl Butyrate, Allyl Cinnamate, Allyl Cyclohexaneacetate, Allyl Cyclohexanebutyrate, Allyl Cyclohexanehexanoate, Allyl Cyclohexanepropionate, Allyl Cyclohexanevalerate, Allyl Disulfide, Allyl 2-Ethylbutyrate, Allyl 2-Furoate, Allyl Heptanoate, Allyl Hexanoate, Allyl Alpha-Ionone, Allyl Isothiocyanate, Allyl Mercaptan, Allyl Nonanoate, Allyl Octanoate, Allyl Phenoxyacetate, Allyl Phenylacetate, Allyl Propionate, Allyl Sorbate, Allyl Sulfide, Allyl Tiglate, Allyl 10-Undecenoate, Allyl Isovalerate, Almond Oil, Bitter (Ffpa) (*Prunus* Spp.), Aloe Extract (*Aloe* Spp.), Althea Root (*Althea officinalis* L.), Ambergris Tincture, Ambrette Absolute Oil (*Hibiscus abelmoschus* L.), Ambrette Seed Oil (*Hibiscus abelmoschus* L.), Ambrette Tincture (*Hibiscus abelmoschus* L.), Ammonium Sulfide, Ammonium Isovalerate, Isoamyl Acetate, Amyl Alcohol, Isoamyl Alcohol, Isoamyl Benzoate, Amyl Butyrate, Isoamyl Butyrate, Alpha-Amylcinnamaldehyde, Alpha-Amylcinnamaldehyde Dimethyl Acetal, Isoamyl Cinnamate, Alpha-Amylcinnamyl Acetate, Alpha-Amylcinnamyl Alcohol, Alpha-Amylcinnamyl Formate, Alpha-Amylcinnamyl Isovalerate, Amyl Formate, Isoamyl Formate, Isoamyl 4(2-Furan)Butyrate, Isoamyl 3(2-Furan)Propionate, Amyl 2-Furoate, Amyl Heptanoate, Amyl Hexanoate, Isoamyl Hexanoate, 2-Amyl-5 Or 6-Keto-1,4-Dioxane, Isoamyl Laurate, Isoamyl Nonanoate, Amyl Octanoate, Isoamyl Octanoate, Isoamyl Phenylacetate, Isoamyl Propionate, Isoamyl Pyruvate, Isoamyl Salicylate, Isoamyl Isovalerate, Trans-Anethole, Angelica Root Extract (*Angelica archangelica* L.), Angelica Root Oil (*Angelica archangelica* L.), Angelica Seed Extract (*Angelica Archangelica* L.), Angelica Seed Oil (*Angelica archangelica* L.), Angelica Stem Oil (*Angelica archangelica* L.), Angostura Extract (*Galipea offincinalis* Hancock), Anise (*Pimpinella anisum* L.), Anise Oil (*Pimpinella anisum* L.), Anise, Star (*Illicium verum* Hook, F.), Anise, Star, Oil (*Illicium verum* Hook, F.), Anisole, P-Anisyl Acetate, Anisyl Alcohol, Anisyl Butyrate, Anisyl Formate, Anisyl Propionate, Annatto Extract (*Bixa orellana* L.), Annatto Seed (*Bixa orellana* L.), Apricot Kernel Oil (*Prunus armeniaca* L.), Asafetida Fluid Extract (*Ferula assafoetida* L.), Asafetida Gum (*Ferula assafoetida* L.), Asafoetida Oil (*Ferula asafoetida* L.), Ascorbic Acid, Ash Bark, Prickly, Extract (*Xanthoxylum* Spp.), Balm (*Melissa officinalis* L.), Balm Leaves Extract (*Melissa officinalis* L.), Balm Oil (*Melissa officinalis* L.), Balsam Fir Oil (*Abies balsamea* (L.) Mill.), Balsam Fir Oleoresin (*Abies balsamea* (L.) Mill.), Balsam, Peru (*Myroxylon pereirae* Klotzsch), Balsam Oil, Peru (*Myroxylon pereirae* Klotzsch), Basil (*Ocimum basilicum* L.), Basil Oil (*Ocimum basilicum* L.), Basil Oleoresin (*Ocimum basilicum* L.), Bay Leaves, West Indian, Extract (*Pimenta acris* Kostel), Bay Leaves, West Indian, Oil (*Pimenta acris* Kostel), Bay Leaves, West Indian, Oleoresin (*Pimenta acris* Kostel), Bay, Sweet (*Laurus nobilis* L.), Bay Oil, Sweet (*Laurus nobilis* L.), Beeswax, White (*Apis mellifera* L.), Benzaldehyde, Benzaldehyde Dimethyl Acetal, Benzaldehyde Glyceryl Acetal, Benzaldehyde Propylene Glycol Acetal, Benzoic Acid, Benzoin, Benzoin Resinoid, Benzophenone, Benzyl Acetate, Benzyl Acetoacetate, Benzyl Alcohol, Benzyl Benzoate, Benzyl Butyl Ether, Benzyl Butyrate, Benzyl Isobutyrate, Benzyl Cinnamate, Benzyl 2,3-Dimethylcrotonate, Benzyl Ethyl Ether, Benzyl Formate, 3-Benzyl-4-Heptanone, Benzyl Mercaptan, Benzyl Methoxyethyl Acetal, Benzyl Phenylacetate, Benzyl Propionate, Benzyl Salicylate, Benzyl Isovalerate, Bergamot Oil, Birch, Sweet, Oil (*Betula lenta* L.), Blackberry Bark Extract (*Rubus*, Spp. Of Section Eubatus), Bois De Rose Oil, Borneol, Isoborneol, Bornyl Acetate, Isobornyl Acetate, Bornyl Formate, Isobornyl Formate, Isobornyl Propionate, Bornyl Valerate, Bornyl Isovalerate (Endo-), Isobornyl Isovalerate, Boronia Absolute (*Boronia megastigma* Nees), Buchu Leaves Oil (*Barosma* Spp.), 2-Butanone, Butter Acids, Butter Esters, Butter Starter Distillate, Butyl Acetate, Isobutyl Acetate, Butyl Acetoacetate, Isobutyl Acetoacetate, Butyl Alcohol, Isobutyl Alcohol, Isobutyl Angelate, Butyl Anthranilate, Isobutyl Anthranilate, Butylated Hydroxyanisole, Butylated Hydroxytoluene, Isobutyl Benzoate, Butyl Butyrate, Isobutyl Butyrate, Butyl Isobutyrate, Isobutyl Isobutyrate, Butyl Butyryllactate, Alpha-Butylcinnamaldehyde, Butyl Cinnamate, Isobutyl Cinnamate, Butyl 2-Decenoate, Butyl Ethyl Malonate, Butyl Formate, Isobutyl Formate, Isobutyl 3-(2-Furan)Propionate, Butyl Heptanoate, Isobutyl Heptanoate, Butyl Hexanoate, Isobutyl Hexanoate, Butyl P-Hydroxy Benzoate, 2-Butyl-5- Or 6-Keto-1,4-Dioxane, Butyl Lactate, Butyl Laurate, Butyl Levulinate, Alpha-Isobutylphenethyl Alcohol, Butyl Phenylacetate, Isobutyl Phenylacetate, Butyl Propionate, Isobutyl Propionate, Isobutyl Salicylate, Butyl Stearate, Butyl Sulfide, Butyl 10-Undecenoate, Butyl Valerate, Butyl Isovalerate, Butyraldehyde, Isobutyraldehyde, Butyric Acid, Isobutyric Acid, (Tri-)Butyrin, Caffeine, Cajeput Oil (*Melaleuca Leucadendron* L.), Calcium Acetate, Camphene, D-Camphor, Camphor, Japanese, White, Oil (*Cinnamomum camphora* (L.) Nees Et Eberm.), Cananga Oil, Capsicum Extract (*Capsicum* Spp.), Capsicum Oleoresin (*Capsicum* Spp.), Caramel Color, Caraway (*Carum carvi* L.), Caraway, Black (*Nigella sativa* L.), Caraway Oil, Carboxymethylcellulose, Cardamom (*Elettaria cardamomum* (L.) Maton), Cardamom Seed Oil (*Elettaria cardamomum* (L.) Maton), Carmine (*Coccus cacti* L.), Carob Bean Extract (*Ceratonia siliqua* L.), Carrot Oil, Carvacrol, Carvacryl Ethyl Ether, Carveol, 4-Carvomenthenol, Carvone, Carvyl Acetate, Carvyl Propionate, Beta-Caryophyllene, Cascara Bitterless Extract (*Rhamnus purshiana* Dc.), Cascarilla Bark Extract (*Croton* Spp.), Cascarilla Bark Oil (*Croton* Spp.), Cassia (*Cinnamomum cassia* Blume), Cassia Bark Extract (*Cinnamomum cassia* Blume), Cassia Bark Oil, Cassia Buds (*Cinnamomum cassia* Blume), Cassie Absolute (*Acacia farnesiana* (L.) Willd.), Castoreum Oil, Castoreum, Liquid (*Castor* Spp.), Castor Oil (*Ricinus communis* L.), Catechu Extract (*Acacia catechu* Willd.), Catechu Powder (*Acacia catechu* Willd.), Cayenne (*Capsicum annuum* L. Var. *longum* Sendt), Cedar Leaf Oil (*Thuja occidentalis* L.), Celery Seed (*Apium graveolens* L.), Celery Seed Extract (*Apium graveolens* L.), Celery Seed Extract Solid (*Apium graveolens* L.), Celery Seed Oil, Chamomile Flower, English, Oil (*Anthemis nobilis* L.), Chamomile Flower, Hungarian, Oil (*Matricaria chamomilla* L.), Chamomile Flower, Roman, Extract (*Anthemis nobilis* L.), Chamomile Flower, Roman, Oil (*Anthemis nobilis* L.), Cherry Bark, Wild, Extract (*Prunus serotina* Ehrh.), Cherry Laurel Oil (Ffpa) (*Prunus laurocerasus* L.), Cherry Pits Extract (*Prunus* Spp.), Chervil (*Anthriscus Cerefolium* (L.) Hoffm.), Chicory Extract (*Cichorium intybus* L.), Cinchona Bark Red (*Cinchona succirubra* Pav. Or Its Hybrids), Cinchona Bark Red Extract (*Cinchona succirubra* Pav. Or Its Hybrids), Cinchona Bark Yellow (*Cinchona* Spp.), Cinchona Bark Yellow Extract (*Cinchona* Spp.), Cinchona Extract (*Cinchona* Spp.), Cinnamaldehyde, Cinnamaldehyde Ethylene Glycol Acetal, Cinnamic Acid, Cinnamon (*Cinnamomum* Spp.), Cinnamon Bark Extract (*Cinnamomum* Spp.), Cinnamon Bark Oil, Cinnamon Leaf Oil, Cinnamyl Acetate, Cinnamyl Alcohol, Cinnamyl Butyrate, Cinnamyl Isobutyrate, Cinnamyl Cinnamate, Cinnamyl Formate, Cinnamyl Phenylacetate, Cinnamyl Propionate, Cinnamyl Isovalerate, Citral, Citral Diethyl Acetal, Citral Dimethyl Acetal, Citric Acid, Citronellal, Citronella Oil, D-Citronellol, Citronelloxyacetaldehyde, Citronellyl Acetate, Citronellyl Butyrate, Citronellyl Isobutyrate, Citronellyl Formate, Citronellyl Phenylacetate, Citronellyl Propionate, Citronellyl Valerate, Citrus Peels Extract (*Citrus* Spp.), Civet Absolute (*Viverra civetta* Schreber And *Viverra zibetha* Schreber), Clary (*Salvia sclarea* L.), Clary Oil (*Salvia sclarea* L.), Clove Bud Extract (*Eugenia* Spp.), Clove Bud Oil (*Eugenia* Spp.), Clove Bud Oleoresin (*Eugenia* Spp.), Clove Leaf Oil, Madagascar, Clover Tops Red Extract Solid (*Trifolium pratense* L.), Cloves (*Eugenia* Spp.), Clove Stem, Oil (*Eugenia* Spp.), Coca Leaf Extract (Decocainized) (*Erythroxylon coca* Lam.), Cognac Oil, Green, Cognac Oil, White, Coriander (*Coriandrum sativum* L.), Coriander Oil (*Coriandrum sativum* L.), Corn Silk (*Zea mays* L.), Costus Root Oil (*Saussurea lappa* Clarke), P-Cresol, Cubebs (*Piper cubeba* L. F.), Cubeb Oil (*Piper cubeba* L. F.), Cumin (*Cuminum cyminum* L.), Cuminaldehyde, Cumin Black (*Nigella Sativa* L.), Cumin Oil, Curacao Peel Extract (*Citrus aurantium* L.), Curacao Peel Oil (*Citrus aurantium* L.), Currant Buds Black Absolute (*Ribes nigrum* L.), Cyclohexaneacetic Acid, Cyclohexaneethyl Acetate, Cyclohexyl Acetate, Cyclohexyl Anthranilate, Cyclohexyl Butyrate, Cyclohexyl Cinnamate, Cyclohexyl Formate, Cyclohexyl Propionate, Cyclohexyl Isovalerate, P-Cymene, Dandelion Fluid Extract (*Taraxacum* Spp.), Dandelion Root Extract Solid (*Taraxacum* Spp.), Davana Oil (*Artemisia pallens* Wall.), Gamma-Decalactone, Delta-Decalactone, Decanal, Decanal Dimethyl Acetal, Decanoic Acid, 1-Decanol, 2-Decenal, Decyl Acetate, Decyl Butyrate, Decyl Propionate, Diacetyl, Dibenzyl Ether, 4,4-Dibutyl-Gamma-Butyrolactone, Dibutyl Sebacate, Diethyl Malate, Diethyl Malonate, Diethyl Sebacate, Diethyl Succinate, Diethyl Tartrate, Dihydrocarveol, Dihydrocarvyl Acetate, Dihydrocoumarin, Dill (*Anethum graveolens* L.), Dill Oil (*Anethum graveolens* L.), Dill Seed Indian (*Anethum* Spp.), M-Dimethoxybenzene, P-Dimethoxybenzene, 2,4-Dimethylacetophenone, Alpha,Alpha-Dimethylbenzyl Isobutyrate, 2,6-Dimethyl-5-Heptenal, 2,6-Dimethyloctanal, 3,7-Dimethyl-1-Octanol, Alpha,Alpha-Dimethylphenethyl Acetate, Alpha, Alpha-Dimethylphenethyl Alcohol, Alpha,Alpha-Dimethylphenethyl Butyrate, Alpha,Alpha-Dimethylphenethyl Formate, Dimethyl Succinate, 1,3-Diphenyl-2-Propanone, Disodium Phosphate, Dittany Of Crete (*Origanum dictamnus* L.), Gamma-Dodecalactone, Delta-Dodecalactone, 2-Dodecenal, Doggrass Extract (*Agropyron repens* (L.) Beauv.), Dragon's Blood Extract (*Daemonorops* Spp. Or Other Botanical Sources), Dulse (*Rhodymenia palmata* (L.) Grev.), Elder Flowers (*Sambucus canadensis* L. Or *Sambucus Nigra* L.), Elemi Gum (*Canarium* Spp.), Elemi Oil (*Canarium* Spp.), Erigeron Oil (*Erigeron candensis* L.), Erythrobic Acid, Estragole, Estragon Oil (*Artemisia dracunculus* L.), P-Ethoxybenzaldehyde, Ethyl Acetate, Ethyl Acetoacetate, Ethyl 2-Acetyl-3-Phenylpropionate, Ethyl Aconitate (Mixed Esters), Ethyl Acrylate, Ethyl Alcohol, Ethyl P-Anisate, Ethyl Anthranilate, Ethyl Benzoate, Ethyl Benzoylacetate, Alpha-Ethylbenzyl Butyrate, 2-Ethylbutyl Acetate, 2-Ethylbutyraldehyde, Ethyl Butyrate, Ethyl Isobutyrate, 2-Ethylbutyric Acid, Ethyl Cinnamate, Ethyl Cyclohexanepropionate, Ethyl Decanoate, Ethyl Formate, Ethyl 3(2-Furyl)Propanoate, 4-Ethylguaiacol, Ethyl Heptanoate, 2-Ethyl-2-Heptenal, Ethyl Hexanoate, Ethyl Lactate, Ethyl Laurate, Ethyl Levulinate, Ethyl 2-Methylbutyrate, Ethyl Methylphenylglycidate, Ethyl Myristate, Ethyl Nitrite, Ethyl Nonanoate, Ethyl 2-Nonynoate, Ethyl Octanoate, Ethyl Oleate, Ethyl Palmitate, Ethyl Phenylacetate, Ethyl 4-Phenylbutyrate, Ethyl 3-Phenylglycidate, Ethyl 3-Phenylpropionate, Ethyl Propionate, Ethyl Pyruvate, Ethyl Salicylate, Ethyl Sorbate, Ethyl Tiglate, Ethyl 10-Undecenoate, Ethyl Valerate, Ethyl Isovalerate, Ethyl Vanillin, Eucalyptol, Eucalyptus Oil (*Eucalyptus globulus* Labille), Eugenol, Isoeugenol, Eugenyl Acetate, Isoeugenyl Acetate, Eugenyl Benzoate, Isoeugenyl Ethyl Ether, Eugenyl Formate, Isoeugenyl Formate, Eugenyl Methyl Ether, Isoeugenyl Methyl Ether, Isoeugenyl Phenylacetate, Farnesol, D-Fenchone, Fenchyl Alcohol, Fennel, Common (*Foeniculum vulgare* Mill.), Fennel, Sweet (*Foeniculum vulgare* Mill. Var *Dulce* (D.C.), Fennel Oil, Sweet (*Foeniculum vulgare* Mill. Var. *dulce* Dc.), Fenugreek (*Trigonella foenum-graecum* L.), Fenugreek Extract (*Trigonella foenum-graecum* L.), Fenugreek Oleoresin (*Trigonella foenumgraecum* L.), Formic Acid, Fumaric Acid, Furfural, Furfuryl Acetate, Furfuryl Alcohol, 2-Furfurylidene Butyraldehyde, Furfuryl Mercaptan, 3-(2-Furyl)Acrolein, 4-(2-Furyl)-3-Buten-2-One, (2-Furyl)-2-Propanone, Fusel Oil, Refined, Galangal Root (*Alpinia* Spp.), Galangal Root Extract (*Alpinia* Spp.), Galangal Root Oil (*Alpinia* Spp.), Galbanum Oil (*Ferula* Spp.), Galbanum Resin (*Ferula* Spp.), Garlic Oil (*Allium sativum* L.), Genet Absolute (*Spartium junceum* L.), Genet Extract (*Spartium junceum* L.), Gentian Root Extract (*Gentiana lutea* L.), Geraniol, Elemi Gum (*Canarium* Spp.), Elemi Oil (*Canarium* Spp.), Erigeron Oil (*Erigeron candensis* L.), Erythrobic Acid, Estragole, Estragon Oil (*Artemisia dracunculus* L.), P-Ethoxybenzaldehyde, Ethyl Acetate, Ethyl Acetoacetate, Ethyl 2-Acetyl-3-Phenylpropionate, Ethyl Aconitate (Mixed Esters), Ethyl Acrylate, Ethyl Alcohol, Ethyl P-Anisate, Ethyl Anthranilate, Ethyl Benzoate, Ethyl Benzoylacetate, Alpha-Ethylbenzyl Butyrate, 2-Ethylbutyl Acetate, 2-Ethylbutyraldehyde, Ethyl Butyrate, Ethyl Isobutyrate, 2-Ethylbutyric Acid, Ethyl Cinnamate, Ethyl Cyclohexanepropionate, Ethyl Decanoate, Ethyl Formate, Ethyl 3(2-Furyl)Propanoate, 4-Ethylguaiacol, Ethyl Heptanoate, 2-Ethyl-2-Heptenal, Ethyl Hexanoate, Ethyl Lactate, Ethyl Laurate, Ethyl Levulinate, Ethyl 2-Methylbutyrate, Ethyl Methylphenylglycidate, Ethyl Myristate, Ethyl Nitrite, Ethyl Nonanoate, Ethyl 2-Nonynoate, Ethyl Octanoate, Ethyl Oleate, Ethyl Palmitate, Ethyl Phenylacetate, Ethyl 4-Phenylbutyrate, Ethyl 3-Phenylglycidate, Ethyl 3-Phenylpropionate, Ethyl Propionate, Ethyl Pyruvate, Ethyl Salicylate, Ethyl Sorbate, Ethyl Tiglate, Ethyl 10-Undecenoate, Ethyl Valerate, Ethyl Isovalerate, Ethyl Vanillin, Eucalyptol, Eucalyptus Oil (*Eucalyptus globulus* Labille), Eugenol, Isoeugenol, Eugenyl Acetate, Isoeugenyl Acetate, Eugenyl Benzoate, Isoeugenyl Ethyl Ether, Eugenyl Formate, Isoeugenyl Formate, Eugenyl Methyl Ether, Isoeugenyl Methyl Ether, Isoeugenyl Phenylacetate, Farnesol, D-Fenchone, Fenchyl Alcohol, Fennel, Common (*Foeniculum vulgare* Mill.), Fennel, Sweet (*Foeniculum vulgare* Mill. Var *Dulce* (D.C.), Fennel Oil, Sweet (*Foeniculum vulgare* Mill. Var. *dulce* Dc.), Fenugreek (*Trigonella foenum-graecum* L.), Fenugreek Extract (*Trigonella foenum-graecum* L.), Fenugreek Oleoresin (*Trigonella foenumgraecum* L.), Formic Acid, Fumaric Acid, Furfural, Furfuryl Acetate, Furfuryl Alcohol, 2-Furfurylidene Butyraldehyde, Furfuryl Mercaptan, 3-(2-Furyl)Acrolein, 4-(2-Furyl)-3-Buten-2-One, (2-Furyl)-2-Propanone, Fusel Oil, Refined, Galangal Root (*Alpinia* Spp.), Galangal Root Extract (*Alpinia* Spp.), Galangal Root Oil (*Alpinia* Spp.), Galbanum Oil (*Ferula* Spp.), Galbanum Resin (*Ferula* Spp.), Garlic Oil (*Allium sativum* L.), Genet Absolute (*Spartium junceum* L.), Genet Extract (*Spartium junceum* L.), Gentian Root Extract (*Gentiana lutea* L.), Geraniol, Labdanum Absolute (*Cistus* Spp.), Labdanum Oil (*Cistus* Spp.), Labdanum Oleoresin (*Cistus* Spp.), Lactic Acid, Laurel Berries (*Laurus nobilis* L.), Laurel Leaves Extract (*Laurus nobilis* L.), Lauric Acid, Lauric Aldehyde, Lauryl Acetate, Lauryl Alcohol, Lavandin Oil (*Lavandula hybrida*), Lavender (*Lavandula officinalis* Chaix), Lavender Absolute (*Lavandula officinalis* Chaix), Lavender Concrete (*Lavandula officinalis* Chaix), Lavender Oil (*Lavandula officinalis* Chaix), Lemon Extract (*Citrus limon* (L.) Burm.

F.), Lemongrass Oil, Lemon Oil, Lemon Oil Terpeneless (*Citrus limon* (L.) Burm. F.), Levulinic Acid, Licorice Extract (*Glycyrrhiza* Spp.), Licorice Extract Powder (*Glycyrrhiza glabra* L.), Licorice Root (*Glycyrrhiza glabra* L.), Lime Oil, Lime Oil, Terpeneless (*Citrus aurantifolia* (Christman) Swingle), D-Limonene, Linaloe Wood Oil (*Bursera delpechiana* Poiss. And Other *Bursera* Spp.), Linalool, Linalyl Acetate, Linalyl Anthranilate, Linalyl Benzoate, Linalyl Butyrate, Linalyl Isobutyrate, Linalyl Cinnamate, Linalyl Formate, Linalyl Hexanoate, Linalyl Octanoate, Linalyl Propionate, Linalyl Isovalerate, Linden Flowers (*Tilia glabra* Vent.), Locust Gum (*Ceratonia siliqua* L.), Lovage (*Levisticum officinale* Koch), Lovage Extract (*Levisticum officinale* Koch), Lovage Oil (*Levisticum officinale* Koch), Mace (*Myristica fragrans* Houtt.), Mace Oil (*Myristica fragrans* Houtt.), Mace Oleoresin (*Myristica fragrans* Houtt.), L-Malic Acid, Maltol, Mandarin Oil, Expressed, Marigold, Pot (*Calendula officinalis* L.), Marjoram Oleoresin (*Majorana hortensis* Moench-*Origanum Majorana* L.), Marjoram, Pot (*Origanum vulgare* L.), Marjoram Seed (*Majorana hortensis* Moench-*Origanum Majorana* L.), Marjoram, Sweet (*Majorana hortensis* Moench-*Origanum Majorana* L.), Marjoram Oil, Sweet (*Origanum majorana*), P-Mentha-1,8-Dien-7-Ol, Menthol Racemic, (+)-Neoisomenthol, Menthone, Menthyl Acetate, Menthyl Isovalerate, P-Methoxybenzaldehyde, 2-Methoxy-4-Methylphenol, 4-(P-Methoxyphenyl)-2-Butanone, 1-(P-Methoxyphenyl)-1-Penten-3-One, 1-(P-Methoxyphenyl)-2-Propanone, 2-Methoxy-4-Vinylphenol, Methyl Acetate, 4'-Methylacetophenone, 2-Methylallyl Butyrate, Methyl Anisate, O-Methylanisole, P-Methylanisole, Methyl Anthranilate, Methyl Benzoate, Alpha-Methylbenzyl Acetate, Alpha-Methylbenzyl Alcohol, Alpha-Methylbenzyl Butyrate, Alpha-Methylbenzyl Isobutyrate, Alpha-Methylbenzyl Formate, Alpha-Methylbenzyl Propionate, Methyl P-Tert-Butylphenylacetate, 2-Methylbutyraldehyde, 3-Methylbutyraldehyde, Methyl Butyrate, Methyl Isobutyrate, 2-Methylbutyric Acid, Methyl Cellulose, Alpha-Methylcinnamaldehyde, Methyl Cinnamate, 6-Methylcoumarin, Methylcyclopentenolone, 4-(3,4-Methylenedioxyphenyl)-2-Butanone, 5-Methylfurfural, Methyl 2-Furoate, 2-Methyl-3(2-Furyl)Acrolein, Methyl Heptanoate, 2-Methylheptanoic Acid, 6-Methyl-5-Hepten-2-One, Methyl Hexanoate, Methyl 2-Hexenoate, Methyl P-Hydroxybenzoate, Methyl-Alpha-Ionone, Methyl-Beta-Ionone, Methyl-Delta-Ionone, Alpha-Iso-Methylionone, Methyl Laurate, Methyl Mercaptan, Methyl O-Methoxybenzoate, Methyl N-Methylanthranilate, Methyl 2-Methylbutyrate, Methyl 3-Methylthiopropionate, Methyl 4-Methylvalerate, Methyl Myristate, Methyl Beta-Naphthyl Ketone, Methyl Nonanoate, Methyl 2-Nonenoate, Methyl 2-Nonynoate, 2-Methyloctanal, Methyl Octanoate, Methyl 2-Octynoate, 4-Methyl-2,3-Pentanedione, 4-Methyl-2-Pentanone, Beta-Methylphenethyl Alcohol, Methyl Phenylacetate, 3-Methyl-4-Phenyl-3-Butene-2-One, 2-Methyl-4-Phenyl-2-Butyl Acetate, 2-Methyl-4-Phenyl-2-Butyl Isobutyrate, 2-Methyl-4-Phenylbutyraldehyde, 3-Methyl-2-Phenylbutyraldehyde, Methyl 4-Phenylbutyrate, 4-Methyl-1-Phenyl-2-Pentanone, Methyl 3-Phenylpropionate, Methyl Propionate, 2-Methyl-3-(P-Isopropylphenyl)Propionaldehyde, 6-Methylquinoline, Methyl Salicylate, Methyl Sulfide, 3-(Methylthio)Propionaldehyde, 2-Methyl-3-Tolylpropionaldehyde, 2-Methylundecanal, Methyl 9-Undecenoate, Methyl 2-Undecynoate, Methyl Valerate, Methyl Isovalerate, 2-Methylvaleric Acid, Mimosa Absolute (*Acacia decurrens* Willd. Var. *dealbata*), Monosodium Glutamate, Mountain Maple Extract Solid (*Acer spicatum* Lam.), Musk Tonquin (*Moschus moschiferus* L.), Mustard, Brown (*Brassica* Spp.), Mustard, Yellow (*Brassica* Spp.), Myrcene, Myristaldehyde, Myristic Acid, Myrrh Gum (*Commiphora* Spp.), Myrrh Oil (*Commiphora* Spp.), Beta-Naphthyl Anthranilate, Beta-Naphthyl Ethyl Ether, Naringen Extract (*Citrus paradisi* Macf.), Nerol, Neroli Bigarde Oil (*Citrus aurantium* L.), Nerolidol, Neryl Acetate, Neryl Butyrate, Neryl Isobutyrate, Neryl Formate, Neryl Propionate, Neryl Isovalerate, Nitrous Oxide, 2,6-Nonadien-1-Ol, Gamma-Nonalactone, Nonanal, 1,3-Nonanediol Acetate (Mixed Esters), Nonanoic Acid, 2-Nonanone, Nonanoyl 4-Hydroxy-3-Methoxybenzylamide, Nonyl Acetate, Nonyl Alcohol, Nonyl Octanoate, Nonyl Isovalerate, Nutmeg (*Myristica fragrans* Houtt.), Nutmeg Oil, Oak Chips Extract (*Quercus alba* L.), Oakmoss Absolute (*Evernia* Spp.), Gamma-Octalactone, Octanal, Octanal Dimethyl Acetal, Octanoic Acid, 1-Octanol, 2-Octanol, 2-Octanone, 3-Octanone, 3-(Hydroxymethyl)-2-Heptanone, 1-Octen-3-Ol, Octyl Acetate, Octyl Butyrate, Octyl Isobutyrate, Octyl Formate, Octyl Heptanoate, Octyl Octanoate, Octyl Phenylacetate, Octyl Propionate, Octyl Isovalerate, Oleic Acid, Olibanum Oil (*Boswellia* Spp.), Onion Oil (*Allium cepa* L.), Onion Flakes, Onion Powder, onion Extract, Orange Blossoms Absolute, Orange Flowers (*Citrus aurantium* L.), Orange Leaf Absolute (*Citrus aurantium* L.), Orange Oil Distilled (*Citrus sinensis* (L.) Osbeck), Orange Oil Terpeneless (*Citrus sinensis* (L.) Osbeck), Orange Peel Oil, Bitter (*Citrus aurantium* L.), Orange Peel, Sweet, Extract (*Citrus sinensis* L. Osbeck), Orange Peel Oil, Sweet (*Citrus sinensis* (L.) Osbeck), Orange Peel, Sweet, Oil, Terpeneless (*Citrus sinensis* L. Osbeck), Oregano (*Lippia* Spp.), Origanum Oil (Extractive) (*Thymus capitatus* L. Hoffmanns & Link), Orris Concrete Liquid Oil (*Iris florentina* L.), Orris Root Extract (*Iris florentina* L.), Palmarosa Oil (*Cymbopogon martini* (Roxb.) Stapf), Palmitic Acid, Paprika (*Capsicum annuum* L.), Paprika Oleoresin (*Capsicum annuum* L.), Parsley (*Petroselinum crispum* (Miller) Nyman-*P. Sativum* Hoffm.), Parsley Oil, Parsley Oleoresin (*Petroselinum* Spp.), Parsnip (*Pastinaca sativa*), Parsnip, Dehydrated, Parsnip Extract, Patchouly Oil, Pennyroyal Oil (*Mentha pulegium* L.), Omega-Pentadecalactone, 2,3-Pentanedione, 2-Pentanone, 4-Pentenoic Acid, Pepper, Black (*Piper nigrum* L.), Pepper, Black, Oil (*Piper nigrum* L.), Pepper, Black, Oleoresin (*Piper nigrum* L.), Peppermint Leaves (*Mentha piperita* L.), Peppermint Oil, Pepper (*Capsicum frutescens* L. (*Capsicum annuum* L.)), Pepper, Red (*Capsicum frutescens* L. (*Capsicum annuum* L.)), Pepper, Green (*Capsicum frutescens* L. (*Capsicum annuum* L.)), Pepper, Orange (*Capsicum frutescens* L. (*Capsicum annuum* L.)), Pepper, Yellow (*Capsicum frutescens* L. (*Capsicum annuum* L.)), Pepper, White (*Piper nigrum* L.), Pepper, White, Oil (*Piper nigrum* L.), Pepper, White, Oleoresin (*Piper nigrum* L.), Petitgrain, Lemon, Oil (*Citrus limon* L. Burm. F), Petitgrain Mandarin Oil (*Citrus reticulata* Blanco Var. Mandarin), Petitgrain Paraguay Oil, Alpha-Phellandrene, Phenethyl Acetate, Phenethyl Alcohol, Phenylethyl Anthranilate, Phenethyl Benzoate, Phenethyl Butyrate, Phenethyl Isobutyrate, Phenethyl Cinnamate, Phenethyl Formate, Phenethyl 2-Furoate, Phenethyl Phenylacetate, Phenethyl Propionate, Phenethyl Salicylate, Phenethyl Senecioate, Phenethyl Tiglate, Phenethyl Isovalerate, Phenoxyacetic Acid, 2-Phenoxyethyl Isobutyrate, Phenylacetaldehyde, Phenylacetaldehyde 2,3-Butylene Glycol Acetal, Phenylacetaldehyde Dimethyl Acetal, Phenylacetaldehyde Glyceryl Acetal, Phenylacetic Acid, 4-Phenyl-2-Butanol, 4-Phenyl-3-Buten-2-ol, 4-Phenyl-3-Buten-2-One, 4-Phenyl-2-Butyl Acetate, 1-Phenyl-3-Methyl-3-Pentanol, 1-Phenyl-1-Propanol, 3-Phenyl-1-Propanol, 2-Phenylpropionaldehyde, 3-Phenylpropionaldehyde, 2-Phenylpropionaldehyde Dimethyl Acetal, 3-Phenylpropionic Acid, 3-Phenylpropyl Acetate, 2-Phenylpropyl Butyrate, 2-Phenylpropyl Isobutyrate, 3-Phenylpropyl Isobutyrate, 3-Phenylpropyl Cinnamate, 3-Phenylpropyl Formate, 3-Phenylpropyl Hexanoate, 3-Phenylpropyl Propionate, 2-(3-Phenylpropyl)Tetrahydrofuran, 3-Phenylpropyl Isovalerate, Phosphoric Acid, Pimenta Leaf Oil, Alpha-Pinene, Beta-Pinene, Pine Needle, Dwarf, Oil (*Pinus mugo* Turra Var. *pumilio* (Haenke) Zenari), Pine Needle Oil (*Abies* Spp.), Pine Scotch Oil (*Pinus sylvestris* L.), Pine Tar Oil (*Pinus palustris* Mill. And Other *Pinus* Spp.), Piperidine, Piperine, D-Piperitone, Piperonal, Piperonyl Acetate, Piperonyl Isobutyrate, Pipsissewa Leaves Extract (*Chimaphila umbellata* Nutt.), Polysorbate 20, Polysorbate 60, Polysorbate 80, Pomegranate Bark Extract (*Punica granatum* L.), Poppy Seed (*Papaver somniferum* L.), Potassium Acetate, Potassium Sorbate, Propenylguaethol, Propionaldehyde, Propionic Acid, Propyl Acetate, Isopropyl Acetate, P-Isopropylacetophenone, Propyl Alcohol, Isopropyl Alcohol, P-Propylanisole, Propyl Benzoate, Isopropyl Benzoate, P-Isopropylbenzyl Alcohol, Propyl Butyrate, Isopropyl Butyrate, Propyl Isobutyrate, Isopropyl Isobutyrate, Propyl Cinnamate, Isopropyl Cinnamate, Propylene Glycol, Propylene Glycol Alginate, Propylene Glycol Stearate, Propyl Formate, Isopropyl Formate, Propyl 2-Furanacrylate, Propyl 2-Furoate, Propyl Gallate, Propyl Heptanoate, Propyl Hexanoate, Isopropyl Hexanoate, Propyl P-Hydroxybenzoate, 3-Propylidenephthalide, Alpha-Propylphenethyl Alcohol, P-Isopropyl Phenylacetaldehyde, Propyl Phenylacetate, Isopropyl Phenylacetate, 3-(P-Isopropylphenyl)Propionaldehyde, Propyl Propionate, Isopropyl Propionate, Propyl Isovalerate, Isopropyl Isovalerate, Isopulegol, Pulegone, Isopulegone, Isopulegyl Acetate, Pyridine, Pyroligneous Acid, Pyroligneous Acid, Extract, Pyruvaldehyde, Pyruvic Acid, Quassia Extract (*Picrasma excelsa* (Sw.) Planch.-*Quassia Amara* L.), Quebracho Bark Extract, Quillaia (*Quillaja saponaria* Molina), Quince Seed Extract (*Cydonia* Spp.), Quinine Bisulfate, Quinine Hydrochloride, Quinine Sulfate, Isoquinoline, Rhatany Extract (*Krameria* Spp.), Rhodinol, Rhodinyl Acetate, Rhodinyl Butyrate, Rhodinyl Isobutyrate, Rhodinyl Formate, Rhodinyl Phenylacetate, Rhodinyl Propionate, Rhodinyl Isovalerate, Rose Oil (*Rosa* Spp.), Rose Oil (*Rosa damascena* Mill.), Rose Hips Extract (*Rosa* Spp.), Rosemary (*Rosemarinus officinalis* L.), Rosemary Oil (*Rosemarinus officinalis* L.), Rose Water, Stronger (*Rosa centifolia* L.), Rue (*Ruta graveolens* L.), Rue Oil (*Ruta graveolens* L.), Rum Ether, Saccharine, Sodium Salt, Saffron (*Crocus sativus* L.), Saffron Extract (*Crocus sativus* L.), Sage (*Salvia officinalis* L.), Sage Oil (*Salvia officinalis* L.), Sage Oleoresin (*Salvia officinalis* L.), Sage Oil, Spanish (*Salvia lavandulaefolia* Vahl.), Salicylaldehyde, Sandalwood Yellow Oil (*Santalum album* L.), Santalol (Alpha And Beta), Santalyl Acetate, Santalyl Phenylacetate, Sarsaparilla Extract (*Smilax* Spp.), Sassafras Bark Extract (Safrol-Free) (*Sassafras albidum* (Nutt.) Nees), Sassafras Leaves (Safrol-Free) (*Sassafras albidum* (Nutt.) Nees), Savory, Summer (*Satureja hortensis* L.), Savory Summer Oil (*Satureja hortensis* L.), Savory, Summer, Oleoresin (*Satureja hortensis* L.), Savory, Winter (*Satureja montana* L.), Savory Winter Oil (*Satureja montana* L.), Savory, Winter, Oleoresin (*Satureja montana* L.), *Schinus Molle* Oil (*Schinus molle* L.), Skatole, Sloe Berries (*Prunus spinosa* L.), Sloe Berries Extract (*Prunus spinosa* L.), Sloe Berries Extract Solid (*Prunus spinosa* L.), Snakeroot Oil, Canadian (*Asarum canadense* L.), Sodium Acetate, Sodium Benzoate, Sodium Citrate, Sodium Hexametaphosphate, Sorbitan Monostearate, D-Sorbitol, Sour Cream, Sour Cream Solids, Spearmint (*Mentha spicata* L.), Spearmint Extract (*Mentha spicata* L.), Spearmint Oil (*Mentha spicata* L.), Spike Lavender Oil (*Lavandula* Spp.), Spruce Oil (*Tsuga* And *Picea* Spp.), Stearic Acid, Storax (*Liquidambar* Spp.), Styrax Extract (*Liquidambar* Spp.), Sucrose Octaacetate, Sulfur Dioxide, Tagetes Oil (*Tagetes erecta* L.; *T. patula* L.; Or *T. Glandulifera Schrank*), Tangerine Oil (*Citrus reticulata* Blanco), Tannic Acid (*Quercus* Spp.), Tarragon (*Artemisia dracunculus* L.), Tartaric Acid (D-, L-, Dl-, Meso-), Alpha-Terpineol, Terpinolene, Terpinyl Acetate (Isomer Mixture), Beta-Terpinyl Anthranilate, Terpinyl Butyrate, Terpinyl Isobutyrate, Terpinyl Cinnamate, Terpinyl Formate, Terpinyl Propionate, Terpinyl Isovalerate, Tetrahydrofurfuryl Acetate, Tetrahydrofurfuryl Alcohol, Tetrahydrofurfuryl Butyrate, TetrahydrofurfurylPropionate, 3,4,5,6-Tetrahydropseudoionone, Tetrahydrolinalool, Tetramethyl Ethylcyclohexenone (Mixture Of Isomers), 2-Thienyl Mercaptan, Thyme (*Thymus vulgaris* L.), Thyme Oil (*Thymus vulgaris* L.), Thyme, White, Oil (*Thymus vulgaris* L.), Thymol, Tolualdehyde Glyceryl Acetal (Mixed O-, M-, P-), Tolualdehydes (Mixed O,M,P), Tolu, Balsam, Extract (*Myroxylon* Spp.), Tolu, Balsam, Gum (*Myroxylon* Spp.), P-Tolylacetaldehyde, O-Tolyl Acetate, P-Tolyl Acetate, 4-(P-Tolyl)-2-Butanone, P-Tolyl Isobutyrate, P-Tolyl Laurate, P-Tolyl Phenylacetate, P-Tolyl Phenylacetate, 2-(P-Tolyl)Propionaldehyde, Tragacanth Gum (*Astragalus* Spp.), Tributyl Acetylcitrate, Tricalcium Phosphate, 2-Tridecenal, Triethyl Citrate, Tuberose Oil (*Polianthes tuberosa* L.), Turmeric (*Curcuma longa* L.), Turmeric Extract (*Curcuma longa* L.), Turmeric Oleoresin (*Curcuma longa* L.), Turpentine Gum (*Pinus* Spp.), Turpentine, Steam Distilled (*Pinus* Spp.), 2,3-Undecadione, Gamma-Undecalactone, Undecanal, 2-Undecanone, 9-Undecenal, 10-Undecenal, 10-Undecen-1-Yl Acetate, Undecyl Alcohol, Valeraldehyde, Valerian Root Extract (*Valeriana officinalis* L.), Valerian Root Oil (*Valeriana officinalis* L.), Valeric Acid, Isovaleric Acid, Gamma-Valerolactone, Vanilla (*Vanilla* Spp.), Vanilla Extract (*Vanilla* Spp.), Vanilla Oleoresin (*Vanilla* Spp.), Vanillin, Vanillin Acetate, Veratraldehyde, Violet Leaves Absolute (*Viola odorata* L.), Walnut Hull Extract (*Juglans* Spp.), Wintergreen Extract (*Gaultheria procumbens* L.), Wintergreen Oil (*Gaultheria procumbens* L.), Wormwood (*Artemisia Absinthium* L.), Wormwood Extract (*Artemisia absinthium* L.), Wormwood Oil (*Artemisia absinthium* L.), Yarrow Herb (*Achillea millefolium* L.), Yerba Santa Fluid Extract (*Eriodictyon californicum* (Hook And Am) Torr, Ylang Ylang Oil (*Cananga odorata* Hook. F. And Thomas), Yucca Joshua Tree (*Yucca brevifolia* Engelm.), Yucca Mohave Extract (*Yucca* Spp.), Zedoary (*Curcuma zedoaria* (Berg.) Rosc.), Zedoary Bark Extract (*Curcuma zedoaria* (Berg.) Rosc.), Zingerone, Acetaldehyde Butyl Phenethyl Acetal, Acetylpyrazine, Allyl Methyl Disulfide, 2-Benzofurancarboxaldehyde, Biphenyl, Butylamine, Sec-Butyl Ethyl Ether, 2-Isobutyl-3-Methoxypyrazine, 2-Isobutyl-3-Methylpyrazine,2-Isobutylthiazole, 2-Trans,4-Trans-Decadienal, 2,3-Diethylpyrazine, 2,6-Dimethoxyphenol, 3,4-Dimethoxy-1-Vinylbenzene, P-Alpha-Dimethylbenzyl Alcohol, 2,6-Dimethyl-4-Heptanol, 2,6-Dimethyl-10-Methylene-2,6,11-Dodecatrienal, 3,7-Dimethyl-6-Octenoic Acid, 2,4-Dimethyl-2-Pentenoic Acid, P,Alpha-Dimethylstyrene, 2,4-Dimethyl-5-Vinylthiazole, 2,2'-(Dithiodimethylene)-Difuran, 1-Ethyl-2-Acetylpyrrole, Ethyl Trans-2,Cis-4-Decadienoate, 2-Ethyl-3,(5 Or 6)-Dimethylpyrazine, 3-Ethyl-2,6-Dimethylpyrazine, 2-Ethyl-1-Hexanol, 3-Ethyl-2-Hydroxy-2-Cyclopenten-1-One, 5-Ethyl-3-Hydroxy-4-Methyl-2(5h)-Furanone, 2-Ethyl-5-Methylpyrazine, 2-Ethyl-3-

Methylpyrazine, P-Ethylphenol, Ethyl (P-Tolyloxy)Acetate, 2-Furanmethanethiol Formate, Furfuryl Methyl Ether, Furfuryl Methyl Sulfide, Furfuryl Isopropyl Sulfide, Furfuryl Thioacetate, 2-Furyl Methyl Ketone, (2e,4e)-Heptadienal, Trans-2-Heptenal, Nootkatone, Delta-Hexalactone, 3,4-Hexanedione, Trans-2-Hexenoic Acid, 3-Hexenoic Acid, Cis-3-Hexen-1-Yl Acetate, Hexyl Isobutyrate, 1-Hydroxy-2-Butanone, 4-Hydroxy-2,5-Dimethyl-3(2h)-Furanone, Gamma-Ionone, P-Menthan-2-One, P-Mentha-8-Thiol-3-One, P-Menth-1-Ene-9-Al, P-Menth-1-En-3-Ol, 2-Mercaptopropionic Acid, O-Methoxycinnamaldehyde, P-Methoxy-Alpha-Methylcinnamaldehyde, 2,5 Or 6-Methoxy-3-Methylpyrazine (Mixture Of Isomers), 1-Methyl-2-Acetylpyrrole, Methylated Silica, 4-Methylbiphenyl, 3-Methylcrotonic Acid, 2-Methyl-3-Furanthiol, 2-Methyl-3-,5 Or 6-(Furfurylthio)Pyrazine (Mixture Of Isomers), 5-Methyl-2,3-Hexanedione, 2-Methylhexanoic Acid, 2-Methyl-5-Methoxythiazole, 1-Methylnaphthalene, 2-Methyl-2-Pentenal, 2-Methyl-2-Pentenoic Acid, 3-Methyl-2-(2-Pentenyl)-2-Cyclopenten-1-One, Alpha-Methylphenethyl Butyrate, Methyl Phenethyl Ether, 5-Methyl-2-Phenyl-2-Hexenal, 4-Methyl-2-Phenyl-2-Pentenal, Methyl Propyl Disulfide, Methyl 2-Pyrrolyl Ketone, 5-Methylquinoxaline, 4-Methyl-5-Thiazoleethanol, 4-Methyl-5-Thiazoleethanol Acetate, 2-Methylthioacetaldehyde, 1-(Methylthio)-2-Butanone, (Methylthio)Methylpyrazine (Mixture Of Isomers), 5-Methyl-2-Thiophenecarboxaldehyde, O-(Methylthio)-Phenol, 2-Methyl-5-Vinylpyrazine (Re-Gras), 2,4-Nonadienal, 2-Nonenal, Delta-Octalactone, 2-Octenal, Paraffin Wax, 2,4-Pentadienal, 2-Pentenal, Isopentylamine, Phenethylamine, Phenethyl Hexanoate, Phenethyl Octanoate, Phenol, 2-Phenyl-2-Butenal, Phenyl Disulfide, 1-Phenyl-1,2-Propanedione, Propenyl Propyl Disulfide, Propyl Disulfide, Isopropyl Tiglate, Pyrazine Ethanethiol, Pyrazinyl Methyl Sulfide, 2-Pyridinemethanethiol, 4,5,6,7-Tetrahydro-3,6-Dimethylbenzofuran, Tetrahydro-4-Methyl-2-(2-Methylpropen-1-Yl)Pyran, 2,3,5,6-Tetramethylpyrazine, 2,2'-(Thiodimethylene)-Difuran, 4-Thujanol, O-Toluenethiol, Trimethylamine, P-Alpha,Alpha-Trimethylbenzyl Alcohol, 1-(2,6,6-Trimethyl-1-Cyclohexen-1-Yl)-2-Buten-1-One, 2,3,5-Trimethylpyrazine, Undecanoic Acid, 2-Undecanol, 10-Undecenoic Acid, 2,6-Xylenol, 2-Acetyl-3-Ethylpyrazine, 2-Acetylpyridine, Beta-Alanine, Allyl Methyl Trisulfide, Arabinogalactan, L-Arabinose, Benzothiazole, Bis(2-Methyl-3-Furyl) Disulfide, Bis(2-Methyl-3-Furyl) Tetrasulfide, 2-Sec-Butylcyclohexanone, Cyclopentanethiol, L-Cysteine, 4-Decenal, Diallyl Trisulfide, 4,5-Dihydro-3(2h)Thiophenone, 2,4-Dimethyl-5-Acetylthiazole, 3,4-Dimethyl-1,2-Cyclopentadione, 3,5-Dimethyl-1,2-Cyclopentadione, Spiro(2,4-Dithia-1-Methyl-8-Oxabicyclo(3.3.0)Octane-3,3'-(1'-Oxa-2'-Methyl)-Cyclopentane), 2,3-Dimethylpyrazine, 2,5-Dimethylpyrazine, 2,6-Dimethylpyrazine, 4,5-Dimethylthiazole, Dimethyl Trisulfide, Dipropyl Trisulfide, Disodium Succinate, Ethyl 2,4-Dioxohexanoate, Ethyl 2-Mercaptopropionate, 2-Ethyl(Or Methyl)-(3,5 And 6)-Methoxypyrazine, 2-Ethylpyrazine, Ethyl Thioacetate, Furfuryl 3-Methylbutanoate, N-Furfurylpyrrole, L-Glutamic Acid, Glyceryl Tripropanoate, Glycine, 2-Heptanol, 4-Heptenal, 3-Hexanone, 4-Hydroxybutanoic Acid Lactone, 3-(Hydroxymethyl)-2-Octanone, 4-Hydroxy-3-Pentenoic Acid Lactone, 5-Hydroxyundecanoic Acid Lactone, D,L-Isoleucine, Isopropenylpyrazine, L-Leucine, 3-Mercapto-2-Butanone, 2-Mercaptomethylpyrazine, 3-Mercapto-2-Pentanone, D,L-Methionine, Methoxypyrazine, 2-Methyl-1-Butanethiol, 3-Methyl-2-Butanethiol, 1-Methyl-2,3-Cyclohexadione, 5h-5-Methyl-6,7-Dihydrocyclopenta(B) Pyrazine, 3-(5-Methyl-2-Furyl)-Butanal, Methyl Propyl Trisulfide, 2-Methylpyrazine, Methyl Thiobutyrate, Methyl 2-Thiofuroate, 3-Methylthiopropyl Isothiocyanate, 4-Methyl-5-Vinylthiazole, 2-Naphthalenthiol, 2-Nonanol, 2-Pentanol, 2-Pentylfuran, 3-Phenyl-4-Pentenal, L-Proline, Tetrahydrofurfuryl Cinnamate, 5,6,7,8-Tetrahydroquinoxaline, Thiamine Hydrochloride, 2-Thienyl Disulfide, 3,5,5-Trimethyl-1-Hexanol, 2,4,5-Trimethylthiazole, Acetone, 2-Acetyl-3,5(And 6)-Dimethylpyrazine, 2-Acetylthiazole, Allyl Thiopropionate, Benzyl Trans-2-Methyl-2-Butenoate, Bisabolene, Butan-3-One-2-Yl Butanoate, 3-Butylidenephthalide, 3-N-Butylphthalide, Di(Butan-3-One-1-Yl) Sulfide, 2,3-Diethyl-5-Methylpyrazine, Difurfuryl Ether, 5,7-Dihydro-2-Methylthieno(3,4-D)Pyrimidine, 3,7-Dimethyl-octa-2,6-Dienyl 2-Ethylbutanoate, 2-Ethoxythiazole, Ethyl 2-Ethyl-3-Phenylpropanoate, Ethyl 3-Hexenoate, Ethyl 3-Methylthiopropionate, Ethyl Cis-4-Octenoate, 2-Ethylthiophenol, Furfuryl Propionate, Furfuryl Thiopropionate, Heptanoic Acid, 4-Heptenal Diethyl Acetal, 3-Heptyldihydro-5-Methyl-2(3h)-Furanone, 3-Hexanol, 4-Hexene-3-One, Cis-3-Hexenyl Formate, N-Hexyl 2-Butenoate, 6-Hydroxy-3,7-Dimethyloctanoic Acid Lactone, Hydroxynonanoic Acid, Delta-Lactone, 2-Keto-4-Butanethiol, 2-Methoxy-3(5 And 6)-Isopropylpyrazine, 2-Methylbutyl 2-Methylbutyrate, 3-Methyl-2-Cyclohexen-1-One, Methyl 3,7-Dimethyl-6-Octenoate, Methyl Furfuryl Disulfide, 6-Methyl-3,5-Heptadien-2-One, Methyl 3-Hexenoate, 5-Methyl-5-Hexen-2-One, 2-Methyl-5-(Methylthio)Furan, Methyl Cis-4-Octenoate, 4-Methyl-3-Penten-2-One, 2-Methylpropyl 3-Methylbutyrate, 2-(2-Methylpropyl)Pyridine, 3-(2-Methylpropyl)Pyridine, 2-(1-Methylpropyl)Thiazole, 2-Methyltetrahydrofuran-3-One, 3-(Methylthio)Butanal, 4-(Methylthio)-2-Butanone, 4-(Methylthio)-4-Methyl-2-Pentanone, Nona-2-Trans-6-Cis-Dienal, 2,6-Nonadienal Diethyl Acetal, Trans-2-Nonen-1-Ol, 9,12-Octadecadienoic Acid (48%) And 9,12,15-Octadecatrienoic Acid (52%), 3-Oxobutanal Dimethyl Acetal, 1-Penten-3-One, 2-Pentylpyridine, Phenylacetaldehyde Diisobutyl Acetal, Propyl Thioacetate, Pyrrole, P-Tolyl 3-Methylbutyrate, 2-Tridecanone, 2,6,6-Trimethylcyclohexa-1,3-Dienyl Methanal, 1,3,3-Trimethyl-2-Norbornanyl Acetate, 3-Acetyl-2,5-Dimethylfuran, 2-Butyl-2-Butenal, N-Butyl 2-Methylbutyrate, 3-Ethylpyridine, 2-Formyl-6,6-Dimethylbicyclo(3.1.1) Hept-2-Ene, Alpha-Furfuryl Octanoate, Alpha-Furfuryl Pentanoate, Glyceryl Tribenzoate, 2-Hepten-4-One, 3-Hepten-2-One, 2-Heptylfuran, Cis-3-Hexenyl Butyrate, Cis-3-Hexenyl Hexanoate, Capsaicin, 2-Hydroxymethyl-6,6-Dimethylbicyclo(3.1.1)Hept-2-Enyl Formate, 2-Isopropyl-5-Methyl-2-Hexenal, 2-Methyl-2-Butenal, Methyl Dihydrojasmonate, 5-Methyl-3-Hexen-2-One, Methyl Jasmonate, Methyl Linoleate (48%) Methyl Linolenate (52%) Mixture, Methyl 4-(Methylthio)Butyrate, 2-Methylpentanal, 4-(Methylthio)Butanal, 3-(Methylthio)Propanol, 3-Octen-2-One, 3-Penten-2-One, Pentyl 2-Furyl Ketone, Propylene Glycol Dibenzoate, 1-(2,6,6-Trimethylcyclohexa-1,3-Dienyl)-2-Buten-1-One, 2,6,6-Trimethylcyclohex-2-Ene-1,4-Dione, 2,4-Undecadienal, 2-Undecenal, 3-Acetylpyridine, Cycloheptadeca-9-En-1-One, 1,1-Dimethoxyethane, 2,4-Dimethylbenzaldehyde, Ethyl 3-Hydroxybutyrate, Trans, Trans-2,4-Hexadienal, 4-Hexen-1-Ol, Isobutyl 2-Butenoate, 2-Methoxy-3-(1-Methylpropyl)Pyrazine, 3-Methyl-1-Cyclopentadecanone, 1-Methyl-1-Cyclopenten-3-One, 1-Methyl-3-Methoxy-4-Isopropylbenzene, 3-Methylpentanoic Acid, 3-(Methylthio)-1-Hexanol, Myrtenol, 3-Nonanone, 2,2,4-Trimethyl-1,3-Oxacyclopentane, 2,6,10-Trimethyl-2,6,10-Pentadecatrien-14-One, Valencene, D,L-Valine, Dl-(3-Amino-3-Carboxypropyl)Dimethylsulfonium Chloride, Dehydrodihydroionol, Dehydrodihydroionone, Dicyclohexyl Disulfide, 1,4-Dimethyl-4-Acetyl-1-Cyclohexene, 2,5-Dimethyl-2,5-Dihydroxy-1,4-Dithiane, 2,5-Dimethyl-3-Furanthiol, Dodecyl Isobutyrate, 3-Ethyl-2-Hydroxy-4-Methylcyclopent-2-En-1-One, 5-Ethyl-2-Hydroxy-3-Methylcyclopent-2-En-1-One, N-Ethyl-2-Isopropyl-5-Methylcyclohexane Carboxamide, Ethyl 2-Methyl-3-Pentenoate, Hexyl Phenylacetate, 2-Hydroxy-2-Cyclohexen-1-One, 2-Hydroxy-3,5,5-Trimethyl-2-Cyclohexenone, D,L-Isomenthone, 2-Isopropylphenol, Maltyl Isobutyrate, 4-Methylpentanoic Acid, 2-Methyl-3-Pentenoic Acid, Cis-6-Nonen-1-Ol, 2-Trans-6-Trans-Octadienal, Cis-3-Octen-1-Ol, 2-Phenyl-3-Carbethoxy Furan, Propiophenone, 1,5,5,9-Tetramethyl-13-Oxatricyclo(8.3.0.0 (4,9))Tridecane, Thiogeraniol, 2,2,6-Trimethylcyclohexanone, 2,6,6-Trimethyl-1-Cyclohexen-1-Acetaldehyde, Trithioacetone, Bis(2,5-Dimethyl-3-Furyl) Disulfide, 2,3-Butanedithiol, 1-Butanethiol, Candelilla Wax (Wax From Stems And Branches Of *Euphorbia Cerifera*), O-Cresol, S-(2,5-Dimethyl-3-Furyl)Thio-2-Furoate, 2,5-Dimethyl-3-Thioisovalerylfuran, 2,8-Dithianon-4-En-4-Carboxaldehyde, 1,2-Ethanedithiol, O-(Ethoxymethyl)Phenol, Ethyl Trans-2-Butenoate, Ethyl Maltol, Ethyl 2-Methylpentanoate, Ethyl 2-Methyl-4-Pentenoate, Ethyl Octadecanoate, 2-Ethyl-1,3,3-Trimethyl-2-Norbornanol, Ethyl Undecanoate, Trans-3-Heptenyl Acetate, Trans-3-Heptenyl 2-Methylpropanoate, 1,6-Hexanedithiol, Cis-4-Hexenal, 3-Hexenyl 2-Methylbutanoate, 3-Hexenyl 3-Methylbutanoate, Hexyl 2-Methylbutanoate, Hexyl Isovalerate, Linalyl Phenylacetate, 2-Mercapto-3-Butanol, 2,3 Or 10-Mercaptopinane, Methyl Benzyl Disulfide, 3-Methylbutyl 2-Methylbutanoate, 2-Methylbutyl 3-Methylbutanoate, 3-Methylbutyl 2-Methylpropanoate, Methyl 3-Hydroxyhexanoate, Alpha-Methyl-Beta-Hydroxypropyl Alpha-Methyl-Beta-Mercaptopropyl Sulfide, 4-Methyl-2-Pentenal, 2-Methyl-4-Pentenoic Acid, 2-Methyltetrahydrothiophen-3-One, 1,9-Nonanedithiol, 1,8-Octanedithiol, 1-Octen-3-One, Trans-2-Octen-1-Yl Acetate, Trans-2-Octen-1-Yl Butanoate, Octyl 2-Furoate, 2-Phenyl-4-Pentenal, 1,2-Propanedithiol, Propanethiol, 0-Propylphenol, Pyrrolidine, 3,5,5-Trimethylhexanal, 2,4,5-Trimethyl-Delta-3-Oxazoline, 2-Acetoxy-3-Butanone, 1,2-Butanedithiol, 1,3-Butanedithiol, M-Cresol, Cyclohexanecarboxylic Acid, 3-Decen-2-One, Diallyl Polysulfides, 1,2-Di((1'-Ethoxy)Ethoxy)Propane, 2,3-Dimethylbenzofuran, Dimethyl Disulfide, 2,6-Dimethyl-4-Heptanone, 2,6-Dimethyl-3-((2-Methyl-3-Furyl)Thio)-4-Heptanone, 3,7-Dimethyl-1,3,6-Octatriene, 2,6-Dimethylpyridine, 3,5-Dimethyl-1,2,4-Trithiolane, 6,10-Dimethyl-5,9-Undecadien-2-One, Ethylene Brassylate, Ethyl Cyclohexanecarboxylate, Ethyl 3-Hydroxyhexanoate, 5-Ethyl-2-Methylpyridine, 3-Heptanol, 2-Hydroxyacetophenone, 6-Hydroxydihydrotheaspirane, 3-Hydroxy-2-Pentanone, Isoamyl Acetoacetate, Isojasmone, Isophorone, 5-Isopropyl-2-Methylpyrazine, 2-Isopropyl-4-Methylthiazole, Isopropyl Myristate, P-Mentha-1,8-Dien-7-Al, P-Mentha-1,3-Diene, P-Mentha-1,4-Diene, P-Mentha-1,4(8)-Dien-3-One, P-Mentha-1,8-Dien-7-Yl Acetate, P-Menthan-2-Ol, P-Menth-3-En-1-Ol, P-Menth-8-En-1-Ol, P-Menth-8-En-2-One, 1-P-Menthen-9-Yl Acetate, P-Methoxycinnamaldehyde, Methyl Cyclohexanecarboxylate, 2-Methyl-3,5 Or 6-Ethoxypyrazine, 3-((2-Methyl-3-Furyl)Thio)-4-Heptanone, 4-((2-Methyl-3-Furyl)Thio)-5-Nonanone, 5-Methylhexanoic Acid, Methyl 2-Methyl-3-Furyl Disulfide, 4-Methylnonanoic Acid, 4-Methyloctanoic Acid, Methyl 1-Propenyl Disulfide, 3-Methyl-5-Propyl-2-Cyclohexen-1-One, 2-Methyl-4-Propyl-1,3-Oxathiane, 1,4-Nonanediol Diacetate, Cis-6-Nonenal, 3-Octanol, 1-Octen-3-Yl Acetate, 3-Octyl Acetate, 1-Penten-3-Ol, L-Phenylalanine, 2-Phenyl-3-(2-Furyl)Prop-2-Enal, 2(10)-Pinen-3-Ol, 1,3-Propanedithiol, Resorcinol, Delta-Tetradecalactone, Theobromine, (2,2,3-Trimethylcyclopent-3-En-1-Yl)Acetaldehyde, 1,2,3-Tris((1'-Ethoxy)Ethoxy)Propane, Verbenol, 2,5-Xylenol, 3,4-Xylenol, Benzyl Methyl Sulfide, 2-Methoxy-4-Propylphenol, 2-Methyl-Trans-2-Butenoic Acid, 4-(Methylthio)Butanol, 2-(Methylthio)Methyl-2-Butenal, 3-Octen-2-Ol, 2-Octen-4-One, Octyl 2-Methylbutyrate, 3-Decanol, D-Xylose, Propyl 2-Methyl-3-Furyl Disulfide, 1-Hexen-3-Ol, 2-Acetyl-5-Methylfuran, Epsilon-Dodecalactone, 2-Propionylthiazole, 1-Octen-3-Yl Butyrate, Epsilon-Decalactone, 2-Propionylpyrrole, Thiazole, Benzenethiol, Benzyl Disulfide, 5-Phenylpentanol, 2-(2-Butyl)-4,5-Dimethyl-3-Thiazoline, 4,5-Dimethyl-2-Ethyl-3-Thiazoline, 4,5-Dimethyl-2-Isobutyl-3-Thiazoline, Delta-1-(2,6,6-Trimethyl-3-Cyclohexen-1-Yl)-2-Buten-1-One, 2-Ethyl-4-Hydroxy-5-Methyl-3(2h)-Furanone, Alpha-Ionol, Beta-Ionol, Dihydro-Beta-Ionone, Dihydro-Beta-Ionol, Dihydro-Alpha-Ionone, 2-Methyl-4-Phenyl-2-Butanol, 4-Methyl-2-Pentyl-1,3-Dioxolan, Cyclohexylmethyl Pyrazine, Phenylethyl 2-Methylbutyrate, 3-Hexenyl Phenylacetate, 4,5-Dimethyl-3-Hydroxy-2,5-Dihydrofuran-2-One, 4-Hydroxy-5-Methyl-3(2h)-Furanone, 2-Methyl-3-Thioacetoxy-4,5-Dihydrofuran, 2-Trans-6-Cis-Dodecadienal, 2-Trans-4-Cis-7-Cis-Tridecatrienal, 2,6,6-Trimethyl-1&2-Cyclohexen-1-Carboxaldehyde, P-Methylcinnamaldehyde, Ethyl Trans-2-Decenoate, Ethyl Trans-4-Decenoate, Ethyl Trans-2-Octenoate, 2-Methylbutyl Acetate, Cis-5-Isopropenyl-Cis-2-Methylcyclopentan-1-Carboxaldehyde, 3-Methyl-2-Butenal, 3-Methyl-2-Buten-1-ol, Propyl 2,4-Decadienoate, P-Propylphenol, Butyl Salicylate, 6-Acetoxydihydrotheaspirane, 4-(P-Acetoxyphenyl)-2-Butanone, 4-Acetyl-6-T-Butyl-1,1-Dimethylindan, 4-Acetyl-2-Methylpyrimidine, 4-Allyl-2,6-Dimethoxyphenol, L-Aspartic Acid, Campholene Acetate, 1,4-Cineole, Alpha-1-(2,6,6-Trimethyl-2-Cyclohexen-1-Yl)-2-Buten-1-One, 9-Decenoic Acid, Nerol Oxide, Dihydroxyacetophenone, 2,6-Dimethyl-6-Hepten-1-Ol, 2,5-Dimethyl-4-Methoxy-3(2h)-Furanone, 2,2-Dimethyl-5-(1-Methylpropen-1-Yl)Tetrahydrofuran, 2,6-Dimethylthiophenol, Diphenyl Ether, Disodium 5-Guanylate, Disodium 5-Inosinate, Trans,Trans-2,4-Dodecadienal, 4-Ethyl-2,6-Dimethoxyphenol, 2-Ethyl-4,5-Dimethyloxazole, 2-Ethylfuran, Ethyl 3-(Furfurylthio)Propionate, Ethyl Trans-2-Hexenoate, 1-Ethylhexyl Tiglate, Ethyl 3-Mercaptopropionate, Ethyl 2-Methyl-3,4-Pentadienoate, Ethyl 3-Methylpentanoate, 2-Ethyl-4-Methylthiazole, Ethyl 4-(Methylthio)Butyrate, Ethyl Cis-4,7-Octadienoate, Ethyl 3-Oxohexanoate, L-Glutamine, Glyceryl 5-Hydroxydecanoate, Glyceryl 5-Hydroxydodecanoate, Guaiacyl Acetate, Cis-3-Hexenyl Benzoate, Cis-3-Hexenyl Cis-3-Hexenoate, Cis-3-Hexenyl Lactate, Hexyl Benzoate, Hexyl Trans-2-Hexenoate, Hexyl 2-Methyl-3&4-Pentenoate, L-Histidine, Hydroquinone Monoethyl Ether, 5-Hydroxy-2,4-Decadienoic Acid Delta-Lactone, 2-Hydroxy-4-Methylbenzaldehyde, Isoeugenyl Benzyl Ether, Isopropyl 2-Methylbutyrate, 1-P-Menthene-8-Thiol, Methyl 1-Acetoxycyclohexyl Ketone, Methylbenzyl Acetate (Mixed O,M,P), 3-Methyl-2-Butanol, 4-Methyl-2,6-Dimethoxyphenol, 2-Methyl-1,3-Dithiolane, Methyl 2-Hydroxy-4-Methylpentanoate, Methyl 2-Methylpentanoate, Methyl 2-Methylthiobutyrate, Methyl Nicotinate, Methyl 3-Nonenoate, 2-Methyl-2-Octenal, Methyl Trans-2-Octenoate, Methyl 2-Oxo-3-Methylpentanoate, Methyl Sorbate, 7-Methyl-4,4a,5,6-Tetrahydro-2(3h)-Naphthalenone, 4-Methylthiazole, 2-(Methylthiomethyl)-3-Phenylpropenal, 3-Methyl-1,2,4-Trithiane, Beta-Naphthyl Isobutyl Ether, Cis-2-Nonen-1-Ol, Trans,Trans-2,4-Octadienal, Cis-5-

Octen-1-Ol, 2-Oxobutyric Acid, 2-Pentadecanone, 2-Pentyl-1-Buten-3-One, D,L-Phenylalanine, 1-Phenyl-3 Or 5-Propylpyrazole, 4-Propenyl-2,6-Dimethoxyphenol, 4-Propyl-2,6-Dimethoxyphenol, L-Rhamnose, 1,2,5,6-Tetrahydrocuminic Acid, Thaumatin, P-Tolyl Octanoate, O-Tolyl Salicylate, 2,2,6-Trimethyl-6-Vinyltetrahydropyran, L-Tyrosine, Vanillyl Alcohol, Vanillylidene Acetone, P-Vinylphenol, Anisyl Phenylacetate, Alpha-Campholenic Alcohol, 5- And 6-Decenoic Acid, 2,5-Diethyltetrahydrofuran, 5-Hydroxy-2-Decenoic Acid Delta-Lactone, 5-Hydroxy-7-Decenoic Acid Delta-Lactone, Linalool Oxide, Massoia Bark Oil (*Cryptocarya massoio*), L-Menthyl Lactate, Cis-5-Octenal, Osmanthus Absolute (*Osmanthus fragrans* Lour.), 2-(3-Phenylpropyl)Pyridine, Potassium 2-(1'-Ethoxy)Ethoxypropanoate, O-Tolyl Isobutyrate, Vanillin Isobutyrate, Dehydromenthofurolactone, 4-Ethylbenzaldehyde, Ethyl Methyl-P-Tolylglycidate, 5-Hydroxy-8-Undecenoic Acid Delta-Lactone, 5-Isopropenyl-2-Methyl-2-Vinyltetrahydrofuran, 1-(4-Methoxyphenyl)-4-Methyl-1-Penten-3-One, 5-Methyl-2-Hepten-4-One, 3-Methyl-1-Pentanol, 3-Methyl-2-(N-Pentanyl)-2-Cyclopenten-1-One, Mintlactone, Myrtenyl Acetate, 2-Trans-6-Trans-Nonadienal, 3-Oxodecanoic Acid Glyceride, 3-Oxododecanoic Acid Glyceride, 3-Oxohexadecanoic Acid Glyceride, 3-Oxohexanoic Acid Glyceride, 3-Oxooctanoic Acid Glyceride, 3-Oxotetradecanoic Acid Glyceride, Sodium 2-(4-Methoxyphenoxy)Propanoate, Theaspirane, Acetaldehyde Ethyl Cis-3-Hexenyl Acetal, Dihydronootkatone, 1-Ethoxy-3-Methyl-2-Butene, (Z)-3 & (E)-2-Hexenyl Propionate, Hydrogen Sulfide, 1,4-Dodec-6-Enolactone, 2 Or 4-Isobutyl-(4 Or 2),6-Dimethyldihydro-4h-1,3,5-Dithiazine, 2 Or 4-Isopropyl-(4 Or 2),6-Dimethyldihydro-4h-1,3,5-Dithiazine, Jambu Oleoresin, 3-L-Menthoxypropane-1,2-Diol, 4-Methoxy-2-Methyl-2-Butanethiol, Gamma-Methyldecalactone, 2-Methyl-3-Tetrahydrofuranthiol, Methylthio 2-(Acetyloxy) Propionate, 3-(Methylthio)Hexyl Acetate, Methylthio-2-(Propionyloxy)Propionate, Octahydrocoumarin, 2-Pentanethiol, D-Ribose, Sclareolide, 1,3,5-Undecatriene, Vanillyl Butyl Ether, 4-Acetoxy-2,5-Dimethyl-3(2h)Furanone, 2,4-Dihydroxybenzoic Acid, 1,2-Dimethoxybenzene, 4-Ethyloctanoic Acid, Ethyl Vanillin Beta-D-Glucopyranoside, 5-Hydroxy-2-Dodecenoic Acid Lactone, 4-Hydroxy-3-Methyloctanoic Acid Lactone, 2-Isopropyl-N,2,3-Trimethylbutyramide, L-Menthol Ethylene Glycol Carbonate, L-Menthol 1- And 2-Propylene Glycol Carbonate, L-Menthone 1,2-Glycerol Ketal, D,L-Menthone 1,2-Glycerol Ketal, Cis- And Trans-Menthone-8-Thioacetate, Mono-Menthyl Succinate, Neohesperidin Dihydrochalcone, Sodium 3-Methoxy-4-Hydroxycinnamate, Taurine, Thaumatin B-Recombinant, Vanillyl Ethyl Ether, 3-Acetylmercaptohexyl Acetate, 2-Acetyl-2-Thiazoline, Di-Alanine, L-Arginine, 1-Buten-1-Yl Methyl Sulfide, Delta-3-Carene, Cycloionone, Daidai Peel Oil, 1-Decen-3-Ol, Diethyl Sulfide, 2,5-Dihydroxy-1,4-Dithiane, Diisopropyl Disulfide, 2,4-Dimethylanisole, 2-(3,7-Dimethyl-2,6-Octadienyl)Cyclopentanone, (E,R)-3,7-Dimethyl-1,5,7-Octatrien-3-Ol, 1,4-Dithiane, Ethyl 2,4,7-Decatrienoate, 2-Ethylhexanethiol, Ethyl 2-(Methyldithio)Propionate, Ethyl 2-(Methylthio)Acetate, Ethyl 3-(Methylthio)Butyrate, Ethyl Vanillin Isobutyrate, Ethyl Vanillin Propylene Glycol Acetal, Alpha-Farnesene, 4-[(2-Furanmethyl)Thio]-2-Pentanone, (Z)-4-Hepten-1-Ol, 1-Hexanethiol, 3-Hydroxy-2-Oxopropionic Acid, Beta-Ionyl Acetate, Alpha-Isomethylionyl Acetate, *Litsea cubeba* Oil, L-Lysine, Cis- And Trans-P-1(7),8-Menthadien-2-Yl Acetate, 3-(L-Menthoxy)-2-Methylpropane-1,2-Diol, 3-Mercaptohexanol, 3-Mercaptohexyl Acetate, 3-Mercaptohexyl Butyrate, 3-Mercaptohexyl Hexanoate, 3-Mercapto-3-Methyl-1-Butanol, 3-Mercapto-3-Methylbutyl Formate, 1-Mercapto-2-Propanone, S-Methyl Benzothioate, 3-Methylbutanethiol, Methyl (E)-2-(Z)-4-Decadienoate, Methyl Ethyl Sulfide, Methyl Ethyl Trisulfide, S-Methyl Hexanethioate, 2-(4-Methyl-2-Hydroxyphenyl)Propionic Acid-Gamma-Lactone, S-Methyl 3-Methylbutanethioate, Methyl 3-Methyl-1-Butenyl Disulfide, 2-Methyl-2-(Methyldithio)Propanal, S-Methyl 4-Methylpentanethioate, (E)-7-Methyl-3-Octen-2-One, 3-Methyl-2-Oxobutanoic Acid, 3-Methyl-2-Oxopentanoic Acid, 4-Methyl-2-Oxopentanoic Acid, Methyl Phenyl Disulfide, Methyl Phenyl Sulfide, 2-Methyl-1-Propanethiol, Methylsulfinylmethane, S-Methyl Thioacetate, 3-Methylthiohexanal, Bis-(Methylthio)Methane, Methylthiomethyl Butyrate, Methylthiomethyl Hexanoate, 4-(Methylthio)-2-Oxobutanoic Acid, 1-Methylthio-2-Propanone, 3-(Methylthio)Propyl Acetate, (E)-3-(Z)-6-Nonadien-1-Ol,(Z)(Z)-3,6-Nonadien-1-Ol, 8-Ocimenyl Acetate, (E)-2-Octen-1-Ol, (E)-2-Octen-4-Ol, (E)-2-(2-Octenyl)Cyclopentanone, (Z)-5-Octenyl Propionate, 2-Oxopentanedioic Acid, 2-Oxo-3-Phenylpropionic Acid, 2-Pentyl Butyrate, Phenylethyl Mercaptan, Prenyl Thioacetate, Prenylthiol, 2-Propanethiol, 1-Pyrroline, Sarcodactylis Oil, Sodium Diacetate, Sodium 3-Mercaptooxopropionate, Tea Tree Oil, 2,3,4-Trimethyl-3-Pentanol, Vanillin 3-(L-Menthoxy)Propane-1,2-Diol Acetal, Vanillin Propylene Glycol Acetal, 2-Aminoacetophenone, Bornyl Butyrate, (E)-2-Butenoic Acid, Cyclohexanone, Cyclopentanone, 2,4-Decadien-1-Ol, 9-Decenal, 2-Decenoic Acid, 4-Decenoic Acid, 2,5-Diethyl-3-Methylpyrazine, 3,5-Diethyl-2-Methylpyrazine, 6,7-Dihydro-2,3-Dimethyl-5h-Cyclopentapyrazine, P-Tert-Butylphenol, 2-Ethyl-6-Methylpyrazine, (E)-2-Heptenoic Acid, 2,4-Hexadienoic Acid, (E,E)-, 2,4-Hexadien-1-Ol, 3-Hexenal, (Z)-2-Hexen-1-Ol, Cis-3-Hexenyl Anthranilate, Trans-2-Hexenyl Butyrate, (E)-2-Hexenyl Formate, 3-Hexenyl 2-Hexenoate, Cis-3-Hexenyl Isobutyrate, Trans-2-Hexenyl Isovalerate, Cis-3-Hexenyl Tiglate, Trans-2-Hexenyl Propionate, Cis-3-Hexenyl Propionate, 3-Hexenyl 2-Oxopropionate, Trans-2-Hexenyl Pentanoate, Cis-3-Hexenyl Valerate, 5-(Cis-3-Hexenyl)Dihydro-5-Methyl-2(3h)Furanone, 4-Isopropyl-2-Cyclohexenone, 2-Isopropylpyrazine, 2-Methyl-3-(1-Oxopropoxy)-4h-Pyran-4-One, Mesquite Wood Extract, 2-Methoxybenzoic Acid, 3-Methoxybenzoic Acid, 4-Methoxybenzoic Acid, 2-Methylcyclohexanone, 3-Methylcyclohexanone, 4-Methylcyclohexanone, 2-Methyl-3-(Methylthio)Furan, Michelia Alba Oil, 2,4-Nonadien-1-Ol, (E,Z)-2,6-Nonadien-1-Ol Acetate, (E,Z)-3,6-Nonadien-1-Ol Acetate, (E)-2-Nonenoic Acid, 3-Nonen-2-One, (E,E)-2,4-Octadien-1-Ol, (E)-2-Octenoic Acid, Phenyl Acetate, 2-Phenylphenol, Phenyl Salicylate, Propylpyrazine, 3,5,5-Trimethylcyclohexanol, 2,3,6-Trimethylphenol, 2-Acetyl-3-Methylpyrazine, 1-Amino-2-Propanol, 3-Decanone, Cis-4-Decenyl Acetate, Diisopropyl Trisulfide, (E) & (Z)-4,8-Dimethyl-3,7-Nonadien-2-One, 2,5-Dimethyl-3-Oxo-(2h)-Fur-4-Yl Butyrate, Cis And Trans-2,5-Dimethyltetrahydrofuran-3-Thiol, Cis And Trans-2,5-Dimethyltetrahydro-3-Furyl Thioacetate, Ethanethioic Acid, S-(2-Methyl-3-Furanyl) Ester, Ethyl 4-(Acetylthio)Butyrate, Ethyl Cis-4-Heptenoate, Ethyl 5-Hexenoate, (+/−)-Ethyl 3-Mercaptobutyrate, Ethyl 5-(Methylthio)Valerate, Furfuryl Propyl Disulfide, (+/−)-Heptan-3-Yl Acetate, (+/−)-Heptan-2-Yl Butyrate, (Z)-3-Hexenyl (E)-2-Butenoate, (E)-2-Hexenyl Hexanoate, 4-Hydroxybenzaldehyde, 2-Hydroxybenzoic Acid, 4-Hydroxybenzoic Acid, 4-Hydroxybenzyl Alcohol, 4-Hydroxy-3-Methoxybenzoic Acid, 3(2)-Hydroxy-5-Methyl-2(3)-Hexanone, Isopentylidene Isopentylamine, Isoprenyl Acetate, D,L-Menthol(+/−)-Propylene Glycol Carbonate, Erythro And Threo-3-Mercapto-2-Methylbutan-1-Ol, 3-Mercapto-2-Methylpentanal, (+/−)-2-Mercapto-2-Methylpentan-1-Ol, 3-Mercapto-2-Methylpentan-1-Ol (Racemic), 4-Mercapto-4-Methyl-2-Pentanone, (+/−)-2-Methyl-1-Butanol, (+/−)-3-Methyl-Gamma-Decalactone, 2-Methylheptan-3-One, (E)-6-Methyl-3-Hepten-2-One, Methyl 2-Methyl-2-Propenoate, Methyl (Methylthio)Acetate, 2-(Methylthio)Ethanol, 12-Methyltridecanal, L-Monomenthyl Glutarate, (+/−)-Nonan-3-Yl Acetate, (E,E)-3,5-Octadien-2-One, (+/−)-Octan-3-Yl Formate, Paraldehyde, 4-Pentenyl Acetate, 2-Pentyl Acetate, Perilla Leaf Oil, Phenethyl Isothiocyanate, Pyrazine, Sodium 4-Methoxybenzoyloxyacetate, 2,4,6-Triisobutyl-5,6-Dihydro-4h-1,3,5-Dithiazine, 2,4,6-Trimethyldihydro-4h-1,3,5-Dithiazine, 3,7,11-Trimethyl-2,6,10-Dodecatrienal, (+/−)-(2,6,6-Trimethyl-2-Hydroxycyclohexylidene)Acetic Acid Gamma-Lactone, Trithiahexane-2,3,5,6-Undecanone, Vanillin Erythro And Threo-Butan-2,3-Diol Acetal, Acetaldehyde Diisoamyl Acetal, Amyl Methyl Disulfide, Benzyl Hexanoate, Butyl Ethyl Disulfide, Beta-Cyclodextrin, Diethyl Trisulfide, (+/−)-3,5-Diethyl-1,2,4-Trithiolane, (+/−)-Dihydrofarnesol, Dihydromintlactone, Dihydroxyacetone, 2,5-Dimethyl-3-Furanthiol Acetate, 2,5-Dimethylthiazole, (Z)-4-Dodecenal, 4,5-Epoxy-(E)-2-Decenal, Ethyl 3-Acetoxy-2-Methyl Butyrate, S-Ethyl 2-Acetylamino Ethanethioate, Ethyl Methyl Disulfide, Ethyl Propyl Disulfide, Ethyl Propyl Trisulfide, O-Ethyl S-(2-Furylmethyl)Thiocarbonate, Geranyl Tiglate, Grape Seed Extract, Trans-4-Hexenal, (E)-2-Hexenal Diethyl Acetal, 2-Hexyl-4,5-Dimethyl-1,3-Dioxolane, 4-Hydroxy-3,5,-Dimethoxy Benzaldehyde, 4-Hydroxy-2,3-Dimethyl-2,4-Nonadienoic Acid Gamma Lactone, 4-Hydroxy-4-Methyl-5-Hexenoic Acid Gamma Lactone, 3-Hydroxy-4-Phenylbutan-2-One, P-Menthane-3,8-Diol, L-Menthyl Methylether, Methyl 5-Acetoxyhexanoate, 3-[(2-Methyl-3-Furyl)Thio]-2-Butanone, 3-Methyl-2,4-Nonanedione, (+/−)-2-(5-Methyl-5-Vinyl-Tetrahydrofuran-2-Yl)Propionaldehyde, 9-Octadecenal, 2,3-Octanedione, (+/−)-1-Phenylethylmercaptan, 4-Propenylphenol, 2-Propionylpyrroline, 2-Propionyl-2-Thiazoline, 2-Propylpyridine, (Z)-8-Tetradecenal, Tuberose Lactone, 2-Undecen-1-Ol, (+/−)-1-Acetoxy-1-Ethoxyethane, 4-Acetyl-2,5-Dimethyl-3(2h)-Furanone, 2-Acetyl-3,5-Dimethylfuran, Allyl Crotonate, Allyl Propyl Disulfide, Allyl Valerate, 4-Allylphenol, Allyl Thiohexanoate, O-Anisaldehyde, N-Benzoylanthranilic Acid, Thujyl Alcohol, L-Bornyl Acetate, 2-Butylfuran, Butyl Isothiocyanate, 2-Butyrylfuran, Carvone-5,6-Oxide, Beta-Caryophyllene Oxide, Citronellyl Anthranilate, N-Cyclopropyl-Trans-2-Cis-6-Nonadienamide, Trans-Alpha-Damascone, 2,4,7-Decatrienal, 2-Decylfuran, Dehydronootkatone, Diacetyl Tartaric Acid Esters Of Mono- And Diglycerides, Diethyl Disulfide, Mixture Of 3,6-Diethyl-1,2,4,5-Tetrathiane And 3,5-Diethyl-1,2,4-Trithiolane, 2,4-Difurfurylfuran, Diisopentyl Thiomalate, Dimercaptomethane, 1,1-Dimethoxy-Trans-2-Hexene, 2,4-Dimethyl-1,3-Dioxolane, 3,5- And 3,6-Dimethyl-2-Isobutylpyrazine, 2,5-Dimethyl-3(2h)-Furanone, (+/−)-Trans- And Cis-4,8-Dimethyl-3,7-Nonadien-2-Ol, (+/−)-Trans- And Cis-4,8-Dimethyl-3,7-Nonadien-2-Yl Acetate, 2,5-Dimethyl-4-Ethoxy-3(2h)-Furanone, (+/−)-Trans- And Cis-5-(2,2-Dimethylcyclopropyl)-3-Methyl-2-Pentenal, 2,5-Dimethylfuran, Divanillin, (+/−)-2,8-Epithio-Cis-P-Menthane, Epoxyoxophorone, Tomato Lycopene, Tomato Powder, Dehydrated Tomato, Tomato Extract, Tomato Juice, Tomato, Ethane-1,1-Dithiol, Ethyl Cis-3-Hexenoate, N-Ethyl Trans-2-Cis-6-Nonadienamide, Ethyl Furfuryl Ether, Ethyl N-Ethylanthranilate, Ethyl N-Methylanthranilate, (+/−)-4-Ethyloctanal, Eugenyl Isovalerate, Furfuryl 2-Methyl-3-Furyl Disulfide, 1-(2-Furyl)Butan-3-One, Geranic Acid, Geranyl 2-Methylbutyrate, Geranyl Valerate, Glyceryl-Lacto Esters Of Fatty Acids, Hept-Trans-2-En-1-Yl Acetate, Hept-2-En-1-Yl Isovalerate, Trans-2-Trans-4-Heptadien-1-Ol, 2-Heptanethiol, (+/−)-1-Hepten-3-Ol, Cis- And Trans-2-Heptylcyclopropanecarboxylic Acid, 2,4-Hexadienyl Propionate, 2,4-Hexadienyl Acetate, 2,4-Hexadienyl Butyrate, 2,4-Hexadienyl Isobutyrate, 2-Hexenyl Octanoate, Hexyl 3-Mercaptobutanoate, 2-Hexylthiophene, 4-Hydroxy-2-Butenoic Acid Gamma-Lactone, 3-Hydroxy-2-Octanone, 2-(2-Hydroxy-4-Methyl-3-Cyclohexenyl)Propionic Acid Gamma-Lactone, 5-Hydroxy-4-Methylhexanoic Acid Delta-Lactone, 1-(3-Hydroxy-5-Methyl-2-Thienyl)Ethanone, (+/−)-2-Hydroxypiperitone, Beta-Ionone Epoxide, Isoambrettolide, Isobornyl Isobutyrate, Isobornyl 2-Methylbutyrate, N-Isobutyldeca-Trans-2-Trans-4-Dienamide, Isobutyl N-Methylanthranilate, (+/−)-Isobutyl 3-Methylthiobutyrate, Beta-Isomethylionone, Isopropenyl Acetate, Lactylated Fatty Acid Esters Of Glycerol And Propylene Glycol, 2-(L-Menthoxy)Ethanol, Menthyl Pyrrolidone Carboxylate, Menthyl Valerate, 4-Mercapto-2-Pentanone, (+/−)-4-Mercapto-4-Methyl-2-Pentanol, 2-Mercaptoanisole, Methionyl Butyrate, Trans- And Cis-1-Methoxy-1-Decene, (S1)-Methoxy-3-Heptanethiol, 2-Methoxyacetophenone, Methyl Cis-3-Hexenoate, Methyl Cis-5-Octenoate, Methyl 3-(Methylthio)Butanoate, Methyl 3-Mercaptobutanoate, Methyl Isopentyl Disulfide, Methyl N,N-Dimethylanthranilate, Methyl N-Acetylanthranilate, Methyl N-Formylanthranilate, S-Methyl Propanethioate, 2-Methyl-1-Methylthio-2-Butene, 3-Methyl-2(3-Methylbut-2-En-1-Yl)Furan, 3-(5-Methyl-2-Furyl)Prop-2-Enal, 5-Methyl-3(2h)-Furanone, 6-Methyl-5-Hepten-2-Yl Acetate, 2-Methylbut-2-En-1-Ol, 2-Methylfuran, 4-Methylpent-2-Enoic Acid, 3-(Methylthio)-2-Butanone, 4-(Methylthio)-2-Pentanone, (+/−)-3-(Methylthio)Heptanal, 3-(Methylthio)Methylthiophene, Methylthiomethylmercaptan, Mono- And Diglycerides Of Fatty Acids, Nona-2,4,6-Trienal, 2-Nonenoic Acid Gamma-Lactone, Cis-3-Octenyl Propionate, L-Ornithine Monochlorohydrate/Ornithine, Pent-2-Enyl Hexanoate, 2-Pentanoylfuran, 2-Pentenoic Acid, (+/−)-2-Phenyl-4-Methyl-2-Hexenal, Phthalide, Phytol, Phytyl Acetate, 3-Pinanone, Piperitenone Oxide, L-Piperitone, Polyglycerol Esters Of Fatty Acids, Prenyl Acetate, Prenyl Benzoate, Prenyl Caproate, Prenyl Formate, Prenyl Isobutyrate, Propyl 2-Mercaptopropionate, Propylene Glycol Mono- And Diesters Of Fatty Acids, Tetradec-2-Enal, Thioacetic Acid, Trans- And Cis-2,4,8-Trimethyl-3,7-Nonadien-2-Ol, (+/−)-2,4,8-Trimethyl-7-Nonen-2-Ol, 3,7,11-Trimethyldodeca-2,6,10-Trienyl Acetate, 2,4,6-Trithiaheptane, Tyramine, Verbenone, Vetiverol, Vetiveryl Acetate, Cornmint Oil, *Mentha arvensis* L., *Heliopsis longipes* Extract, Scotch Spearmint Oil, *Mentha cardiaca* L., Natural Hickory Smoke Flavor, Betaine, Adenosine Monophosphate; Monosodium, Or Disodium Adenylate, Isoquercitrin, Enzymatically Modified, Glycerol Ester Of Rosin, Gum Arabic, Hydrogen Octenylbutane Dioate, (−)-Homoeriodictyol, Sodium Salt, Sugar Beet Juice Extract, (+/−)-N,N-Dimethyl Menthyl Succinamide, N1-(2-Methoxy-4-Methylbenzyl)-N2-(2-(Pyridin-2-Yl)Ethyl)Oxalamide, N-(Heptan-4-Yl)Benzo[D][1,3]Dioxole-5-Carboxamide, N1-(2,4-Dimethoxybenzyl)-N2-(2-(Pyridin-2-Yl)Ethyl)Oxalamide, N1-(2-Methoxy-4-Methylbenzyl)-N2-(2-(5-Methylpyridin-2-Yl)Ethyl)Oxalamide, 1,6-Hexalactam, Ethylamine, Propylamine, Isopropylamine, Isobutylamine, Sec-Butylamine, 2-Methylbutylamine, Pentylamine, Hexylamine, 2-Methylpiperidine, Trimethylamine Oxide, Triethylamine, Tripropylamine, N,N-Dimethylphenethylamine, 2-Acetyl-1-Pyrroline, Piperazine, Butyramide, Methyl 10-Undecenoate, N-Gluconyl Ethanolamine, N-Gluconyl Ethanolamine Phosphate, N-Lactoyl Ethanolamine, N-Lactoyl Ethanolamine Phosphate, Ethanethiol, Heptane-1-Thiol, S-Isopropyl 3-Methylbut-2-Enethioate, 3-Methylhexanal, 4-Pentenal, Propyl Propane Thiosulfonate, Alpha-Ionene, *Gardenia gummifera* Distillate, *Piper longum* Distillate, N-3,7-Dimethyl-2,6-Octadienylcyclopropylcarboxamide, (+/−)-Ethyl 2-Hydroxy-2-Methylbutyrate, (+/−)-Ethyl 2-Hydroxy-3-Methylvalerate, 2-(2-Hydroxyphenyl) Cyclopropanecarboxylic Acid Delta Lactone, 2-Decanone, (+/−)-Trans- And Cis-2-Hexenal Propylene Glycol Acetal, (+/−)-Trans- And Cis-2-Hexenal Glyceryl Acetal, Trans-2-Hexenyl 2-Methylbutyrate, 2-(4-Methyl-5-Thiazolyl)Ethyl Formate, 2-(4-Methyl-5-Thiazolyl)Ethyl Propionate, 2-(4-Methyl-5-Thiazolyl)Ethyl Butanoate, 2-(4-Methyl-5-Thiazolyl)Ethyl Isobutyrate, 2-(4-Methyl-5-Thiazolyl)Ethyl Hexanoate, 2-(4-Methyl-5-Thiazolyl)Ethyl Octanoate, 2-(4-Methyl-5-Thiazolyl)Ethyl Decanoate, (+/−)-3-(Ethylthio) Butanol, *Decalepis Hamiltonii* Extract, 2-(Trans-2-Pentenyl)Cyclopentanone, 3,9-Dimethyl-6-(1-Methylethyl)-1,4-Dioxaspiro[4.5]Decan-2-One, Cis- And Trans-2-Isobutyl-4-Methyl-1,3-Dioxolane, Cis- And Trans-2-Isopropyl-4-Methyl-1,3-Dioxolane, 4-Aminobutyric Acid, 3-Mercaptoheptyl Acetate, Ethyl Trans-2-Methyl-2-Pentenoate, Methyl Hexyl Ether, Trans-2-Trans-4-Nonadiene, 1-Octene, Cis- And Trans-Ethyl 2,4-Dimethyl-1,3-Dioxolane-2-Acetate, Citronellyl Trans-2-Methyl-2-Butenoate, 5-Acetyl-2,3-Dihydro-1,4-Thiazine, Bis(1-Mercaptopropyl) Sulfide, 2,5-Dithiahexane, Pseudoionone, Cis- And Trans-L-Mercapto-P-Menthan-3-One, Trans-2-Nonen-4-One, Trans-4-Nonenal, 1,1'-(Tetrahydro-6a-Hydroxy-2,3a,5-Trimethylfuro[2,3-D]-1,3-Dioxole-2,5-Diyl)Bis-Ethanone, Trans-2-Decenol, Cis-2-Pentenol, 2-Methylbutyl 3-Methyl-2-Butenoate, Citric And Fatty Acid Esters Of Glycerol, L-Menthyl (R,S)-3-Hydroxybutyrate, N-[(Ethoxycarbonyl) Methyl)-P-Menthane-3-Carboxamide, N-[2-(3,4-Dimethoxyphenyl)Ethyl]-3,4-Dimethoxycinnamic Acid Amide, Mixture Of Methyl Cyclohexadiene And Methylene Cyclohexene, (+/−)-Cis- And Trans-1,2-Dihydroperillaldehyde, 5,7-Dihydroxy-2-(3-Hydroxy-4-Methoxyphenyl)Chroman-4-One, Phenethyl Decanoate, 3,6-Dimethyl-2,3,3a,4,5,7a-Hexahydrobenzofuran, 2-Methylacetophenone, 1-Ethyl-2-Pyrrolecarboxaldehyde, Cis- And Trans-5-Ethyl-2,5-Dihydro-4-Methyl-2-(1-Methylpropyl)-Thiazole, Cis And Trans-5-Ethyl-4-Methyl-2-(2-Methylpropyl)-Thiazoline, 2-Methyl-3-Furyl Methylthiomethyl Disulfide, Pyrrolidino-[1,2e]-4h-2,4-Dimethyl-1,3,5-Dithiazine, S-Allyl-L-Cysteine, 5-Pentyl-3h-Furan-2-One, 3-Mercapto-3-Methyl-1-Butyl Acetate, (+/−)-3-Mercapto-1-Butyl Acetate, 5-Nonen-Trans-2-One, L-Menthyl Acetoacetate, 4-Octen-3-One, 2,4, 6-Trimethylphenol, 4-Hydroxyacetophenone, (+/−)-[R-(E)]-5-Isopropyl-8-Methylnona-6,8-Dien-2-One, 1-Methyl-h-Pyrrole-2-Carboxaldehyde, 1-Pentanethiol, Pentadecanoic Acid, Tridecanal, Tridecanoic Acid, Hexyl Heptanoate, Dodecyl Propionate, Hexyl Nonanoate, Dodecyl Butyrate, Heptyl Heptanoate, Hexyl Decanoate, Ethyl 4-Methylpentanoate, Ethyl 2-Ethylbutyrate, Ethyl 2-Ethylhexanoate, 5-Methylhexyl Acetate, 4-Methylpentyl Isovalerate, 3,7-Dimethyloctanal, Cis-4-Decenol, Cis-5-Octenoic Acid, 5-Hexenol, 3-Isopropenylpentanedioic Acid, Methyl 4-Pentenoate, Cis-4-Octenol, 11-Dodecenoic Acid, Trans-3-Hexenol, Trans-4-Octenoic Acid, Isobutyl 10-Undecenoate, Cis-9-Octadecenyl Acetate, Ethyl 4-Pentenoate, Ethyl 3-Octenoate, 3-Octenoic Acid, Cis-9-Octadecenol, Decanal Propyleneglycol Acetal, Acetaldehyde Hexyl Isoamyl Acetal, Dodecanal Dimethyl Acetal, Nonanal Dimethyl Acetal, Heptanal Propyleneglycol Acetal, Hexanal Hexyl Isoamyl Acetal, Hexanal Dihexyl Acetal, Isovaleraldehyde Diethyl Acetal, Valeraldehyde Propyleneglycol Acetal, Nonanal Propyleneglycol Acetal, Undecanal Propyleneglycol Acetal, Valeraldehyde Dibutyl Acetal, Acetaldehyde 1,3-Octanediol Acetal, Hexanal Octane-1,3-Diol Acetal, Isovaleraldehyde Glyceryl Acetal, Acetaldehyde Di-Cis-3-Hexenyl Acetal, 2,6-Dimethyl-5-Heptenal Propyleneglycol Acetal, Octanal Propyleneglycol Acetal, Hexanal Butane-2, 3-Diol Acetal, Pecan Shell Flour, Di-(1-Propenyl)-Sulfide (Mixture Of Isomers), 2-Pentylthiophene, 5-Ethyl-2-Methylthiazole, 2,4-Dimethylpyridine, 3-(4-Hydroxyphenyl)-1-(2,4,6-Trihydroxyphenyl)Propan-1-One, (+/−)-Ethyl 3-Hydroxy-2-Methylbutyrate, (+/−)-Ethyl 3-Mercapto-2-Methylbutanoate, (+/−)-Cis- And Trans-2-Methyl-2-(4-Methyl-3-Pentenyl)Cyclopropanecarbaldehyde, Trimethyloxazole,2,5-Dimethyl-4-Ethyloxazole,2-Propyl-4, 5-Dimethyloxazole, 2-Isobutyl-4,5-Dimethyloxazole, 2-Methyl-4,5-Benzoxazole, 2-Nonanone Propyleneglycol Acetal, 6-Methyl-5-Hepten-2-One Propyleneglycol Acetal, 2-Pentyl 2-Methylpentanoate, 3-Octyl Butyrate, Dimethylbenzyl Carbinyl Crotonate, Dimethylbenzyl Carbinyl Hexanoate, 1,5-Octadien-3-One, 10-Undecen-2-One, 2,4-Dimethyl-4-Nonanol, 8-Nonen-2-One, 8-P-Menthene-1,2-Diol, Caryophyllene Alcohol, D-2,8-P-Menthadien-1-Ol, Cis-3-Nonen-1-Ol, Trans-3-Hexenyl Acetate, 4-(Methylthio)Butyl Isothiocyanate, 6-(Methylthio)Hexyl Isothiocyanate, 5-(Methylthio)Pentyl Isothiocyanate, Amyl Isothiocyanate, 3-Butenyl Isothiocyanate, 2-Butylisothiocyanate, Ethyl Isothiocyanate, 5-Hexenyl Isothiocyanate, Hexyl Isothiocyanate, Isoamyl Isothiocyanate, Isobutyl Isothiocyanate, Isopropyl Isothiocyanate, Methyl Isothiocyanate, 4-Pentenyl Isothiocyanate, Benzyl Isothiocyanate, 2,4-Dimethyl-3-Oxazoline, 3,4-Dihydroxybenzoic Acid, 3-Hydroxybenzoic Acid, (+/−)-Acetaldehyde Ethyl Isopropyl Acetal, (+/−)-6-Methyloctanal, 5-Ethyl-2,3-Dimethylpyrazine, 2-Hydroxy-4-Methoxybenzaldehyde, 3-(Methylthio) Propyl Hexanoate, Sodium Lauryl Sulfate, Beta-Angelicalactone, 7-Decen-4-Olide, 9-Decen-5-Olide, 8-Decen-5-Olide, 6-[5(6)-Decenoyloxy]Decanoic Acid, Ethyl 5-Acetoxyoctanoate, Ethyl 5-Hydroxydecanoate, 9-Dodecen-5-Olide, Gamma-Octadecalactone, Delta-Octadecalactone, 9-Tetradecen-5-Olide, Orin Lactone, Methyl 3-Hydroxybutyrate, Methyl 3-Acetoxy-2-Methylbutyrate, Ethyl 2-Acetylhexanoate, Ethyl 3-Hydroxyoctanoate, Methyl 3-Acetoxyoctanoate, 5-Oxooctanoic Acid, 5-Oxodecanoic Acid, Ethyl 5-Oxodecanoate, 5-Oxododecanoic Acid, Ethyl 2-Acetyloctanoate, 2-Oxo-3-Ethyl-4-Butanolide, 3-Isopropenyl-6-Oxoheptanoic Acid, Hydroxyacetone, 1-Hydroxy-4-Methyl-2-Pentanone, Propyleneglycol Diacetate, Propyleneglycol Dipropionate, Propyleneglycol Dibutyrate, Propyleneglycol Mono-2-Methylbutyrate, Propyleneglycol Di-2-Methylbutyrate, Propyleneglycol Monohexanoate, Propyleneglycol Dihexanoate, Propyleneglycol Dioctanoate, Dimethyl Adipate, Dipropyl Adipate, Diisopropyl Adipate, Diisobutyl Adipate, Dioctyl Adipate, Ethyl Acetoacetate Ethyleneglycol Ketal, Methyl Levulinate, Ethyl Levulinate Propyleneglycol Ketal, Propyl Levulinate, Isoamyl Levulinate, Dodecyl Lactate, Hexadecyl Lactate, Propyl Pyruvate, Hydroxycitronellal Propyleneglycol Acetal, Citral Glyceryl Acetal, Mushroom Oil, Distilled, Propyleneglycol Monobutyrate, Cis-3-Hexenyl Acetoacetate, 2-Methoxy-6-(2-Propenyl)Phenol, Myricitrin, (R)-(−)-1-Octen-3-Ol, Cis-3-Hexenoic Acid, Ammonia (Also Includes Ammonium Chloride), Naringin Dihydrochalcone, N—P-Benzeneacetonitrilementhanecarboxamide, Cubebol, 6-Methylheptanal, (+/−)-Cis- And Trans-2-Pentyl-4-Propyl- 1,3-Oxathiane, Choline Chloride (Also Includes Choline), 3-[(2-Methyl-3-Furyl)Thio]Butanal, (−)-Sclareol, (+)-Cedrol, D-Limonen-10-Ol, (2,4)- And (3,5)- And (3,6)-Dimethyl-3-Cyclohexenylcarbaldehyde, 1,3-P-Menthadien-7-Al, P-Menthan-7-Ol, P-Menth-1-En-9-Ol, Menthyl Formate, Menthyl Propionate, Cyclotene Propionate, 3,3,5-Trimethylcyclohexyl Acetate, Dl-Camphor, 2-Cyclopentylcyclopentanone, Carvyl Palmitate, Cyclohexanone Diethyl Ketal, 2-Cyclohexenone, 8,9-Dehydrotheaspirone, L-Fenchone, Ethylenediaminetetraacetic Acid Disodium Salt, 2,2,6,7-Tetramethylbicyclo[4.3.0]Nona-4,9(1)-Dien-8-Ol, 2,2,6,7-Tetramethylbicyclo[4.3.0]Nona-4,9(1)-Dien-8-One, 6-Hydroxycarvone, L-Menthyl Butyrate, Pinocarvyl Isobutyrate, 2-Pentenyl-4-Propyl-1,3-Oxathiane (Mixture Of Isomers), Acetaldehyde Di-Isobutylacetal, Acetaldehyde Ethyl Isobutyl Acetal, 4-(2,2,3-Trimethylcyclopentyl)Butanoic Acid, Perillaldehyde Propyleneglycol Acetal, 2,6,6-Trimethyl-2-Hydroxycyclohexanone, Acetoin Propyleneglycol Ketal, 4,5-Octanedione, Ethyl Maltol Isobutyrate, 2-Tetrahydrofurfuryl 2-Mercaptopropionate, Nerolidol Oxide, Furfural Propyleneglycol Acetal, Methyl 3-(Furfurylthio)Propionate, Furfuryl Decanoate, Di-2-Furylmethane, (E)-Ethyl 3-(2-Furyl)Acrylate, Furfuryl Formate, 2-Methylbenzofuran, 5-Methylfurfuryl Alcohol, 2-Methyl-3-Furyl 2-Methyl-3-Tetrahydrofuryl Disulfide, Ethyl 2,5-Dimethyl-3-Oxo-4(2h)-Furyl Carbonate, Acai Berry Extract, 4-(2-Propenyl)Phenyl-Beta-D-Glucopyranoside, N-(2-(Pyridin-2-Yl)Ethyl)-3-P-Menthanecarboxamide, (+/−)-N-Lactoyl Tyramine, Cis,Cis-3,6-Nonadienyl Acetate, Trans-2-Nonenyl Acetate, Cis-3-Nonenyl Acetate, Cis-6-Nonenyl Acetate, Dihydrogalangal Acetate, 2,3,3-Trimethylindanone, N-Ethyl-2,2-Diisopropylbutanamide, Cyclopropanecarboxylic Acid (2-Isopropyl-5-Methylcyclohexyl)Amide, Magnolol, 2-(Methylthio)Ethyl Acetate, 3-(Methylthio)Propyl Mercaptoacetate, Ethyl 2-Hydroxyethyl Sulfide, Ethyl 3-(Methylthio)-Cis-2-Propenoate, Ethyl 3-(Methylthio)-Trans-2-Propenoate, Ethyl 3-(Methylthio)-2-Propenoate, 4-Methyl-2-(Methylthiomethyl)-2-Hexenal, 5-Methyl-2-(Methylthiomethyl)-2-Hexenal, 4-Methyl-2-(Methylthiomethyl)-2-Pentenal, 1-(3-(Methylthio)-Butyryl)-2,6,6-Trimethylcyclohexene, 2-Oxothiolane, Butyl Beta-(Methylthio) Acrylate, Ethyl 3-(Ethylthio)Butyrate, Methyl Octyl Sulfide, Methyl 1-Propenyl Sulfide, Diisoamyl Disulfide, Bis(2-Methylphenyl) Disulfide, Mixture Of Butyl Propyl Disulfide And Propyl And Butyl Disulfide, Di-Sec-Butyl Disulfide, Methyl 2-Methylphenyl Disulfide, Diisoamyl Trisulfide, Dodecanethiol, 2-Hydroxyethanethiol, 4-Mercapto-4-Methyl-2-Hexanone, 3-Mercapto-3-Methylbutyl Isovalerate, 3-Mercaptohexanal, Methyl Isobutanethioate, 3-Mercaptopropionic Acid, 2-Ethylhexyl 3-Mercaptopropionate, Butanal Dibenzyl Thioacetal, Methional Diethyl Acetal, Ethyl Linalyl Ether, Myrcenyl Methyl Ether, Linalool Oxide Pyranoid, 2-Hydroxy-5-Methylacetophenone, 2-Phenylpropanal Propyleneglycol Acetal, Cinnamaldehyde Propyleneglycol Acetal, Ethyl Alpha-Acetylcinnamate, Ethyl 2-Hydroxy-3-Phenylpropionate, 3-(3,4-Methylenedioxyphenyl)-2-Methylpropanal, Trehalose, Dihydrate, Rebaudioside A, N-(2-Hydroxyethyl)-2,3-Dimethyl-2-Isopropylbutanamide, N-(1,1-Dimethyl-2-Hydroxyethyl)-2,2-Diethylbutanamide, Dimenthyl Glutarate, Trans-3-Nonen-1-Ol, 4-Formyl-2-Methoxyphenyl 2-Hydroxypropanoate, Guaiacol Butyrate, Guaiacol Isobutyrate, Guaiacol Propionate, Ethyl 5-Hydroxyoctanoate, Isopropylideneglyceryl 5-Hydroxydecanoate, 2-Ethyl-2-Hexenal, Ethyl 2-Hexenoate, Propyl Sorbate, Cis-2-Octenol, 2-Hexylidenehexanal, Trans-2-Tridecenol, 2-Phenoxyethyl Propionate, Propyl 4-Tert-Butylphenylacetate, 2-Phenoxyethanol, Phenyl Butyrate, Piperonal Propyleneglycol Acetal, Benzyl Levulinate, 4-Methylbenzyl Alcohol, Phenylacetaldehyde Diethyl Acetal, Benzyl Nonanoate, Anisaldehyde Propyleneglycol Acetal, 4-Methylbenzaldehyde Propyleneglycol Acetal, Phenylacetaldehyde Propyleneglycol Acetal, 2-Ethylhexyl Benzoate, 2-Ethyl-3-Methylthiopyrazine, 2-Ethoxy-3-Isopropylpyrazine, 2-Ethoxy-3-Ethylpyrazine, Butyl Beta-Naphthyl Ether, Isoamyl Phenethyl Ether, 2-Acetyl-4-Isopropenylpyridine, 4-Acetyl-2-Isopropenylpyridine, 2-Acetyl-4-Isopropylpyridine, 2-Methoxypyridine, 6-Methoxyquinoline, 2-Pentylthiazole, 2-Thienylmethanol, 2-Acetyl-5-Methylthiophene, 4-Methyl-3-Thiazoline, 3,4-Dimethylthiophene, 1-(2-Thienyl)Ethanethiol, 4,5-Dimethyl-2-Isobutylthiazole, Cyclotene Butyrate, 3-(Methylthio)Propylamine, 4-Methyl-Cis-2-Pentene, 1-Nonene, 1,3,5,7-Undecatetraene, Ethyl Alpha-Ethyl-Beta-Methyl-Beta-Phenylglycidate, Methyl Beta-Phenylglycidate, D-8-P-Menthene-1,2-Epoxide, L-8-P-Menthene-1,2-Epoxide, 2,3-Epoxyoctanal, 2,3-Epoxyheptanal, 2,3-Epoxydecanal, Hydroxy(4-Hydroxy-3-Methoxyphenyl)Acetic Acid, 4-Hydroxy-4-(3-Hydroxy-1-Butenyl)-3,5,5-Trimethyl-2-Cyclohexen-1-One, (+/−)-2,6,10,10-Tetramethyl-1-Oxaspiro[4,5]Deca-2,6-Dien-8-One, 4-(2-Butenylidene)-3,5,5-Trimethylcyclohex-2-En-1-One, Digeranyl Ether, 1-(4-Hydroxy-3-Methoxyphenyl)Decan-3-One, Alpha-Bisabolol, 2(4)-Ethyl-4(2),6-Dimethyldihydro-1,3,5-Dithiazine (Mixture Of Isomers), (2e,6e/Z,8e)-N-(2-Methylpropyl)-2,6,8-Decatrienamide, 4-Amino-5,6-Dimethylthieno[2,3-D]Pyrimidin-2(1h)One And 4-Amino-5,6-Dimethylthieno[2,3-D]Pyrimidin-2(1h)One Hydrochloride, 1,1-Propanedithiol, Z-5-Octenyl Acetate, (E)-4-Undecenal, Delta-Hexadecalactone, Trilobatin, L-Isoleucine, 1-(2-Furfurylthio)-Propanone, (+/−)-4-Methyl-2-Propyl-1,3-Oxathiane, N-(2-Methylcyclohexyl)-2,3,4,5,6-Pentafluorobenzamide, Arachidonic Acid Enriched Oil, 5-Isopropyl-2,6-Diethyl-2-Methyltetrahydro-2h-Pyran, (1r,2s,5r)-N-(4-Methoxyphenyl)-5-Methyl-2-(1-Methylethyl) Cyclohexanecarboxamide, Octahydro-4,8a-Dimethyl-4a(2h)-Naphthol, 2-Methyl-4,5-Dihydrofuran-3-Thiol, (2s,5r)-N-[4-(2-Amino-2-Oxoethyl)Phenyl]-5-Methyl-2-(Propan-2-Yl)Cyclohexanecarboxamide, (+/−)-6-Octyltetrahydro-2h-Pyran-2-One, (+/−)-2-Methyltetrahydrofuran-3-Thiol Acetate, (+/−)-3-Hydroxy-3-Methyl-2,4-Nonanedione, 1,1-Dipropoxyethane, Chrysanthemum Extract, Honeysuckle Extract, Yuzunone, L-Methionylglycine, N-Cyclopropyl-5-Methyl-2-Isopropylcyclohexanecarboxamide, 3-Pentanethiol, 2-Ethyl-2,5-Dihydro-4-Methylthiazole, 1-(Methyldithio)-2-Propanone, 5-Methylfurfurylmercaptan, 4-Mercapto-3-Methyl-2-Butanol, Ferrous L-Lactate, O-Trans-Coumaric Acid, 3-[(4-Amino-2,2-Dioxido-1h-2,1,3-Benzothiadiazin-5-Yl)Oxy]-2,2-Dimethyl-N-Propylpropanamide, 2(3),5-Dimethyl-6,7-Dihydro-5h-Cyclopentapyrazine, Cinnamyl Benzoate, Beta-Naphthyl Methyl Ether, Rosemary Oleoresin, 9-Decen-2-One, 1-(Methylthio)-3-Octanone, 3',7-Dihydroxy-4'-Methoxyflavan, Glutamyl-Valyl-Glycine, L-Threonine, Luo Han Fruit Concentrate, L-Alanyl-L-Glutamine, Sucrose Monopalmitate, Ethyl 2-Mercapto-2-Methylpropionate, 2-(3,4-Dihydroxyphenyl)-5,7-Dihydroxy-4-Chromanon, N—[N-[3-(3-Hydroxy-4-Methoxyphenyl)Propyl]-L-Alpha-Aspartyl]-L-Phenylalanine 1-Methylester, Monohydrate, Sweet Blackberry Leaves Extract, 2-[(2-(P-Menthyloxy)Ethoxy]Ethanol, Succinic Acid, Rebaudioside C, 1-(2-Hydroxyphenyl)-3-(Pyridin-4-Yl)Propan-1-One, 1-(2-Hydroxy-4-Isobutoxyphenyl)-3-(Pyridin-2-Yl)Propan-1-One, 1-(2-Hydroxy-4-Methoxyphenyl)-3-(Pyridin-2-Yl)Propan-1-One, Trans-4-Tert-Butylcyclohexanol, 3-(1-((3,5-Dimethylisoxazol-4-Yl)

Methyl)-1h-Pyrazol-4-Yl)-1-(3-Hydroxybenzyl)
Imidazolidine-2,4-Dione, 3-(1-((3,5-Dimethylisoxazol-4-Yl)Methyl)-1h-Pyrazol-4-Yl)-1-(3-Hydroxybenzyl)-5,5-Dimethylimidazolidine-2,4-Dione, Clover Herb Distillate, Glucosyl Steviol Glycosides, Dl-Isomenthol, 0-Ethyl S-1-Methoxyhexan-3-Yl Carbonothioate, Cassyrane, 1,5-Octadien-3-Ol, (+/−)-2-Mercaptoheptan-4-Ol, 3-(Methylthio)Decanal, (4z,7z)-Trideca-4,7-Dienal, *Persicaria Odorata* Oil, Amacha Leaves Extract, Glutamyl-2-Aminobutyric Acid, Glutamyl-Norvalyl-Glycine, Glutamyl-Norvaline, N1-(2,3-Dimethoxybenzyl)-N2-(2-(Pyridin-2-Yl)Ethyl)Oxalamide, 1-(2-Hydroxy-4-Methylcyclohexyl)Ethanone, Mexican Lime Oil, Expressed, Persian Lime Oil, Expressed, (+/−)-6-Methoxy-2,6-Dimethylheptanal, 3,5-Undecadien-2-One, (+/−)-2,5-Undecadien-1-Ol, Triethylthialdine, 4-Methylpentyl 4-Methylvalerate, Cis-3-Hexenyl Salicylate, (R)—N-(1-Methoxy-4-Methylpentan-2-Yl)-3,4-Dimethylbenzamide, N-Acetyl Glutamate, 1,3-Propanediol, Szechuan Pepper Extract, *Tasmannia lanceolata* Extract, *Mentha longifolia* Oil, Mangosteen Distillate, Ethyl 3-(2-Hydroxyphenyl)Propanoate, 1-Cyclopropanemethyl-4-Methoxybenzene, Prenyl Thioisobutyrate, Prenyl Thioisovalerate, (−)-Matairesinol, Stevioside, 1-(2,4-Dihydroxyphenyl)-3-(3-Hydroxy-4-Methoxyphenyl)Propan-1-One, Ethyl 5-Formyloxydecanoate, 3-[3-(2-Isopropyl-5-Methyl-Cyclohexyl)Ureido]Butyric Acid Ethyl Ester, 2-Isopropyl-4-Methyl-3-Thiazoline, 2,6,10-Trimethyl-9-Undecenal, 5-Mercapto-5-Methyl-3-Hexanone, Meyer Lemon Oil, Cold Pressed, Citrus X Meyeri, Steviol Glycoside Extract, *Stevia rebaudiana*, Rebaudioside A 60%, Steviol Glycoside Extract, *Stevia rebaudiana*, Rebaudioside A 80%, (E)-N-[2-(1,3-Benzodioxol-5-Yl)Ethyl]-3-(3,4-Dimethoxyphenyl)Prop-2-Enamide, 4-Amino-5-(3-(Isopropylamino)-2,2-Dimethyl-3-Oxopropoxy)-2-Methylquinoline-3-Carboxylic Acid, 3-Methyl-5-(2,2,3-Trimethylcyclopent-3-En-1-Yl)Pent-4-En-2-Ol, (1-Methyl-2-(1,2,2-Trimethylbicyclo[3.1.0]Hex-3-Ylmethyl)Cyclopropyl)Methanol, Erospicata Oil, *Mentha spicata*, Curly Mint Oil, *Mentha spicata* Var. *crispa*, (+/−)-2-Mercapto-5-Methylheptan-4-One, Caryophylla-3(4),8-Dien-5-Ol, L-Cysteine Methyl Ester Hydrochloride, 2(3)-Hexanethiol, Mixture Of 1-Vinyl-3-Cyclohexenecarbaldehyde And 4-Vinyl-1-Cyclohexenecarbaldehyde, (+/−)-4-Hydroxy-6-Methyl-2-Heptanone, 2-Octyl-2-Dodecenal, 2-Hexyl-2-Decenal, Trans-6-Octenal, (E)-3-Benzo[1,3]Dioxol-5-Yl-N,N-Diphenyl-2-Propenamide, 2,6-Dimethyl-5-Heptenol, (+/−)-Bicyclo[2.2.1]Hept-5-Ene-2-Carboxylic Acid, Ethyl Ester, 3-(Acetylthio)Hexanal, (+/−)-3-Mercapto-1-Pentanol, (3r,3s)-3-[[(4-Amino-2,2-Dioxido-1h-2,1,3-Benzothiadiazin-5-Yl)Oxy]Methyl]-N-Cyclopentyl-2-Oxo-3-Piperidinecarboxamide, (+/−)-1-Cyclohexylethanol, (+/−)-8-Methyldecanal, Steviol Glycoside Extract, *Stevia rebaudiana*, Rebaudioside C 30%, (+/−)-Naringenin, 2-(((3-(2,3-Dimethoxyphenyl)-1h-1,2,4-Triazol-5-Yl)Thio)Methyl)Pyridine, (2r)-3',5-Dihydroxy-4'-Methoxyflavanone, Glucosylated *Rubus suavissimus* Extract, 20-30% Glucosylated Rubusoside Glycosides, Olive Fruit Extract, (S)-1-(3-(((4-Amino-2,2-Dioxido-1h-Benzo[C][1,2,6]Thiadiazin-5-Yl)Oxy)Methyl)Piperidin-1-Yl)-3-Methylbutan-1-One, 8-Methylnonanal, Mixture Of Ricinoleic Acid, Linoleic Acid, And Oleic Acid, Steviol Glycoside Extract, *Stevia rebaudiana*, Rebaudioside A 22%, Steviol Glycoside Extract, *Stevia rebaudiana*, Rebaudioside C 22%, Pinocarvyl Acetate, N-Ethyl-5-Methyl-2-(1-Methylethenyl)Cyclohexanecarboxamide, 2-(4-Methylphenoxy)-N-(1h-Pyrazol-3-Yl)-N-(Thiophen-2-Ylmethyl)Acetamide, Ethyl-2-(4-Hydroxy-3-Methoxy-Phenyl)Acetate, Ginger Mint Oil (*Mentha×Gracilis*), Palmitoylated Green Tea Extract Catechins, 2-(5-Isopropyl-2-Methyltetrahydrothiophen-2-Yl)Ethanol, Glucosylated *Rubus suavissimus* Extract, 60% Glucosylated Rubusoside Glycosides, Sandalwood Austrocaledonicum Oil, and Sugar Cane Distillate.

In various embodiments, the ingestibly acceptable ingredient may include one or more of sweetness enhancers, sweetening agents, umami flavor enhancers, umami flavoring agents, sour flavoring agents, and cooling agents.

In some embodiments, the ingestible composition further comprises an additional sweetener such as a sweetener described in detail below. In some embodiments, the sweetener is present in an amount from about 0.1% to about 12% by weight. In some embodiments, the sweetener is present in an amount from about 0.2% to about 10% by weight. In some embodiments, the sweetener is present in an amount from about 0.3% to about 8% by weight. In some embodiments, the sweetener is present in an amount from about 0.4% to about 6% by weight. In some embodiments, the sweetener is present in an amount from about 0.5% to about 5% by weight. In some embodiments, the sweetener is present in an amount from about 1% to about 2% by weight. In some embodiments, the sweetener is present in an amount from about 0.1% to about 5% by weight. In some embodiments, the sweetener is present in an amount from about 0.1% to about 4% by weight. In some embodiments, the sweetener is present in an amount from about 0.1% to about 3% by weight. In some embodiments, the sweetener is present in an amount from about 0.1% to about 2% by weight. In some embodiments, the sweetener is present in an amount from about 0.1% to about 1% by weight. In some embodiments, the sweetener is present in an amount from about 0.1% to about 0.5% by weight. In some embodiments, the sweetener is present in an amount from about 0.5% to about 10% by weight. In some embodiments, the sweetener is present in an amount from about 2% to about 8% by weight.

In some embodiments, the compound of Formula (I) and the additional sweetener are present in a ratio of about 1:100,000 to 100,000:1, or any ratio in between. In some embodiments, the compound of Formula (I) and the sweetener are present in a ratio of about 1:90,000, about 1:80,000, about 1:70,000, about 1:60,000, about 1:50,000, about 1:40,000, about 1:30,000, about 1:20,000, about 1:10,000, 1:9,000, about 1:8,000, about 1:7,000, about 1:6,000, about 1:5,000, about 1:4,000, about 1:3,000, about 1:2,000, about 1:1,000, about 1:900, about 1:800, about 1:700, about 1:600, about 1:500, about 1:450, about 1:400, about 1:350, about 1:300, about 1:250, about 1:200, about 1:150, about 1:100, about 1:90, about 1:85, about 1:80, about 1:75, about 1:70, about 1:65, about 1:60, about 1:55, about 1:50, about 1:45, about 1:40, about 1:35, about 1:30, about 1:25, about 1:20, about 1:19, about 1:18, about 1:17, about 1:16, about 1:15, about 1:14, about 1:13, about 1:12, about 1:11, about 1:10, about 1:9, about 1:8, about 1:7, about 1:6, about 1:5, about 1:4, about 1:3, about 1:2, about 1:1, about 2:1, about 3:1, about 4:1, about 5:1, about 6:1, about 7:1, about 8:1, about 9:1, about 10:1, about 11:1, about 12:1, about 13:1, about 14:1, about 15:1, about 16:1, about 17:1, about 18:1, about 19:1, about 20:1, about 25:1, about 30:1, about 35:1, about 40:1, about 45:1, about 50:1, about 55:1, about 60:1, about 65:1, about 70:1, about 75:1, about 80:1, about 85:1, about 90:1, about 95:1, about 100:1, about 150:1, about 200:1, about 250:1, about 300:1, about 350:1, about 400:1, about 450:1, about 500:1, about 600:1, about 700:1, about 800:1, about 900:1, about 1,000:1, about 1,000:1, about 2,000:1, about 3,000:1, about 4,000:1, about 5,000:1, about 6,000:1, about 7,000:1, about 8000:1, about 9,000:1, about 10,000:1, about 20,000:1, about 30,000:1, about 40,000:1, about 50,000:1, about 60,000:1, about 70,000:1, about 80,000:1, about 90,000:1, about 100,000:1, or any ratio in between.

Additional sweeteners have a wide range of chemically distinct structures and hence possess varying properties, such as, without limitation, odor, flavor, mouthfeel, and aftertaste.

In some embodiments, the sweetener may comprise combinations of two or more sweeteners as disclosed herein. In some embodiments, the sweetener may comprise combinations of two, three, four or five sweeteners as disclosed herein. In some embodiments, the sweetener may be a sugar. In some embodiments, the sweetener may be a combination of one or more sugars and other natural and artificial sweeteners. In some embodiments, the sweetener is a sugar. In some embodiments, the sugar is cane sugar. In some embodiments, the sugar is beet sugar. In some embodiments, the sugar may be sucrose, fructose, glucose or combinations thereof. In some embodiments, the sugar may be sucrose. In some embodiments, the sugar may be a combination of fructose and glucose. In some embodiments, the sugar may be a combination of about 55% fructose and about 42% glucose. In some embodiments, the sugar may be a combination of about 42% fructose and about 53% glucose. In some embodiments, the sugar may be a combination of about 90% fructose and about 10% glucose. In some embodiments, the sweetener may be a rare sugar. In some embodiments, the rare sugar is selected from the group consisting of D-allose, D-psicose, L-ribose, D-tagatose, L-glucose, L-fucose, L-arbinose, D-turanose, D-leucrose and combinations thereof. In some embodiments, the rare sugar is D-psicose. In some embodiments, the rare sugar is D-tagatose. In some embodiments, the sweetener is an artificial sweetener. In some embodiments, the artificial sweetener may be sucralose.

In some embodiments, the additional sweetener may be common saccharide sweeteners, e.g., sucrose, fructose, glucose, and sweetener compositions comprising natural sugars, such as corn syrup (including high fructose corn syrup) or other syrups or sweetener concentrates derived from natural fruit and vegetable sources; rare natural sugars including D-allose, D-psicose, L-ribose, D-tagatose, L-glucose, L-fucose, L-arabinose, D-turanose, and D-leucrose; semi-synthetic "sugar alcohol" sweeteners such as erythritol, isomalt, lactitol, mannitol, sorbitol, xylitol, maltodextrin, and the like; and artificial sweeteners such as aspartame, saccharin, acesulfame-K, cyclamate, sucralose, and alitame. In some embodiments, the sweetener may be selected from the group consisting of cyclamic acid, mogroside, tagatose, maltose, galactose, mannose, sucrose, fructose, lactose, neotame and other aspartame derivatives, glucose, D-tryptophan, glycine, maltitol, lactitol, isomalt, hydrogenated glucose syrup (HGS), hydrogenated starch hydrolyzate (HSH), stevioside, rebaudioside A and other sweet Stevia-based glycosides, carrelame and other guanidine-based sweeteners.

Natural or artificial sweeteners for use in the formulation comprising an additional sweetener in combination with at least one compounds described herein include but are not limited to natural or synthetic carbohydrates or carbohydrate analogues, including monosaccharides, disaccharides, oligosaccharides, and polysaccharides, and including rare sugars, or sugars in either of the D- or L- conformations, and include, for example, sucrose, fructose, glucose, L-arabinose, L-fucose, L-glucose, L-ribose, D-arabino-hexulose, psicose, altrose, arabinose, turanose, abequose, allose, abrusoside A, aldotriose, threose, xylose, xylulose, xylo-oligosaccharide (such as xylotriose and xylobiose), lyxose, polydextrose, oligofructose, fucose, galacto-oligosaccharide, galactosamine, galactose, gentio-oligosaccharide (such as gentiobiose, gentiotriose, and gentiotetraose), dextrose, cellobiose, D-leucrose, D-psicose, D-ribose, D-tagatose, trehalose (mycose), neotrehalose, isotrehalose, raffinose, idose, tagatose, melibiose, mannan-oligosaccharide, rhamnose, ribose, ribulose, malto-oligosaccharide (such as maltotriose, maltotetraose, maltopentaose, maltohexaose, and maltoheptaose), maltose, sucrose acetate isobutyrate, dextrose, erythrose, erythrulose, deoxyribose, gulose, ketotriose, lactose, lactulose, kestose, nystose, mannose, sucralose, palatinose, polydextrose, sorbose, sugaridextrose (blended sugar), or talose, or combinations of any two or more of the aforementioned sweeteners.

The additional sweetener can also include, for example, sweetener compositions comprising one or more natural or synthetic carbohydrate, such as corn syrup, high fructose corn syrup, high maltose corn syrup, glucose syrup, sucralose syrup, hydrogenated glucose syrup (HGS), hydrogenated starch hydrolyzate (HSH), or other syrups or sweetener concentrates derived from natural fruit and vegetable sources, or semi-synthetic "sugar alcohol" sweeteners such as polyols. Non-limiting examples of polyols in some embodiments include erythritol, maltitol, mannitol, sorbitol, lactitol, xylitol, isomalt, propylene glycol, glycerol (glycerin), threitol, galactitol, palatinose, reduced isomalto-oligosaccharides, reduced xylo-oligosaccharides, reduced gentio-oligosaccharides, reduced maltose syrup, reduced glucose syrup, isomaltulose, maltodextrin, and the like, and sugar alcohols or any other carbohydrates or combinations thereof capable of being reduced which do not adversely affect taste.

The additional sweetener may be a natural or synthetic sweetener that includes, but is not limited to, agave inulin, agave nectar, agave syrup, amazake, brazzein, brown rice syrup, coconut crystals, coconut sugars, coconut syrup, date sugar, fructans (also referred to as inulin fiber, fructo-oligosaccharides, or oligo-fructose), green stevia powder, *Stevia rebaudiana*, rebaudioside A, rebaudioside B, rebaudioside C, rebaudioside D, rebaudioside E, rebaudioside F, rebaudioside I, rebaudioside H, rebaudioside L, rebaudioside K, rebaudioside J, rebaudioside N, rebaudioside O, rebaudioside M and other sweet stevia-based glycosides, stevioside, stevioside extracts, honey, Jerusalem artichoke syrup, licorice root, luo han guo (fruit, powder, or extracts), lucuma (fruit, powder, or extracts), maple sap (including, for example, sap extracted from *Acer saccharum, Acer nigrum, Acer rubrum, Acer saccharinum, Acer platanoides, Acer negundo, Acer macrophyllum, Acer grandidentatum, Acer glabrum, Acer mono*), maple syrup, maple sugar, walnut sap (including, for example, sap extracted from *Juglans cinerea, Juglans nigra, Juglans ailatifolia, Juglans regia*), birch sap (including, for example, sap extracted from *Betula papyrifera, Betula alleghaniensis, Betula lenta, Betula nigra, Betula populifolia, Betula pendula*), sycamore sap (such as, for example, sap extracted from *Platanus occidentalis*), ironwood sap (such as, for example, sap extracted from *Ostrya virginiana*), mascobado, molasses (such as, for example, blackstrap molasses), molasses sugar, monatin, monellin, cane sugar (also referred to as natural sugar, unrefined cane sugar, or sucrose), palm sugar, panocha, piloncillo, rapadura, raw sugar, rice syrup, sorghum, sorghum syrup, cassava syrup (also referred to as tapioca syrup), thaumatin, yacon root, malt syrup, barley malt syrup, barley malt powder, beet sugar, cane sugar, crystalline juice crystals, caramel, carbitol, carob syrup, castor sugar, hydrogenated starch hydrolates, hydrolyzed can juice, hydrolyzed starch, invert sugar, anethole, arabinogalactan, arrope, syrup, P-4000, acesulfame potassium (also referred to as acesulfame K or ace-K), alitame (also referred to as aclame), advantame, aspartame, baiyunoside, neotame, benzamide derivatives, bernadame, canderel, carrelame and other guanidine-based sweeteners, vegetable fiber, corn sugar, coupling sugars, curculin, cyclamates, cyclocarioside I, demerara, dextran, dextrin, diastatic malt, dulcin, sucrol, valzin, dulcoside A, dulcoside B, emulin, enoxolone, maltodextrin, saccharin, estragole, ethyl maltol, glucin, gluconic acid, glucono-lactone, glucosamine, glucoronic acid, glycerol, glycine, glycyphillin, glycyrrhizin, golden sugar, yellow sugar, golden syrup, granulated sugar, gynostemma, hernandulcin, isomerized liquid sugars, jallab, chicory root dietary fiber, kynurenine derivatives (including N'-formyl-kynurenine, N'-acetyl-kynurenine, 6-chloro-kynurenine), galactitol, litesse, ligicane, lycasin, lugduname, guanidine, falernum, mabinlin I, mabinlin II, maltol, maltisorb, maltodextrin, maltotriol, mannosamine, miraculin, mizuame, mogrosides (including, for example, mogroside IV, mogroside V, and neomogroside), mukuroinoside, nano sugar, naringin dihydrochalcone, neohesperidine dihydrochalcone, nib sugar, nigero-oligosaccharide, norbu, orgeat syrup, osladin, pekmez, pentadin, periandrin I, perillaldehyde, perillartine, petphyllum, phenylalanine, phlomisoside I, phlorodizin, phyllodulcin, polyglycitol syrups, polypodoside A, pterocaryoside A, pterocaryoside B, rebiana, refiners syrup, rub syrup, rubusoside, selligueain A, shugr, siamenoside I, *Siraitia grosvenorii*, soybean oligosaccharide, Splenda, SRI oxime V, steviol glycoside, steviolbioside, stevioside, strogins 1, 2, and 4, sucronic acid, sucrononate, sugar, suosan, phloridzin, superaspartame, tetrasaccharide, threitol, treacle, trilobtain, tryptophan and derivatives (6-trifluoromethyl-tryptophan, 6-chloro-D-tryptophan), vanilla sugar, volemitol, birch syrup, aspartame-acesulfame, assugrin, and combinations or blends of any two or more thereof.

In some embodiments, the additional sweeter is selected from steviolbioside, stevioside, *Stevia rebaudiana*, rebaudioside A, rebaudioside B, rebaudioside C, rebaudioside D, rebaudioside E, rebaudioside F, rebaudioside I, rebaudioside H, rebaudioside L, rebaudioside K, rebaudioside J, rebaudioside N, rebaudioside O, rebaudioside M, glycyrrhetinic acid, glycyrrhizin, GAMG (glycyrrhetinic acid monoglucuronide), thaumatin, monellin, brazzelin, and combinations or blends of any two or more thereof.

In still other embodiments, the additional sweetener can be a chemically or enzymatically modified natural high potency sweetener. Modified natural high potency sweeteners include glycosylated natural high potency sweetener such as glucosyl-, galactosyl-, or fructosyl-derivatives containing 1-50 glycosidic residues. Glycosylated natural high potency sweeteners may be prepared by enzymatic transglycosylation reaction catalyzed by various enzymes possessing transglycosylating activity. In some embodiments, the modified sweetener can be substituted or unsubstituted.

Additional sweeteners also include combinations of any two or more of any of the aforementioned sweeteners. In some embodiments, the sweetener may comprise combinations of two, three, four or five sweeteners as disclosed herein. In some embodiments, the sweetener may be a sugar. In some embodiments, the sweetener may be a combination of one or more sugars and other natural and artificial sweeteners.

One of skill in the art will recognize that any one or more of any one of the aforementioned additional sweeteners can be combined in various ratios, amounts, or concentrations to yield an additional sweetener alone or a combination of two or more additional sweeteners, which is then combined with a compound described herein.

One of skill in the art will recognize that the aforementioned additional sweeteners for use in a formulation comprising one or more additional sweeteners and one or more compound described herein are provided by way of example and are not intended to be limiting.

In some embodiments, the ingestible composition does not comprise an additional sweetener. In some embodiments, the ingestible composition does not comprise one or more additional sweeteners selected from the group consisting of sucrose, fructose, or glucose.

In some embodiments, the composition comprises a sweetening compound and/or a sweet flavor enhancing compound, and one or more inactive ingredients. Representative inactive ingredients include but are not limited to, those declared to the U.S. Food and Drug Administration. Such inactive ingredients include: Alpha-Terpineol; Alpha-Tocopherol; Alpha-Tocopherol Acetate; Alpha-Tocopherol Acetate, Dl-; Alpha-Tocopherol, Dl-; Beta-Carotene; Beta-Cyclodextrin Sulfobutyl Ether Sodium; Beta-Ionone; 1-(Phenylazo)-2-Naphthylamine; 1,2,6-Hexanetriol; 1,2-Dimyristoyl-Sn-Glycero-3-(Phospho-S-(1-Glycerol)); 1,2-Dimyristoyl-Sn-Glycero-3-Phosphocholine; 1,2-Dioleoyl-Sn-Glycero-3-Phosphocholine; 1,2-Dipalmitoyl-Sn-Glycero-3-(Phospho-Rac-(1-Glycerol)); 1,2-Distearoyl-Sn-Glycero-3-(Phospho-Rac-(1-Glycerol)); 1,2-Distearoyl-Sn-Glycero-3-Phosphocholine; 1-Aminocyclohexanecarboxylic Acid, C-11; 1-O-Tolyl-biguanide; 2212 Fine Black; 2-Ethyl-1,6-Hexanediol; Acacia; Acacia Syrup; Acesulfame; Acesulfame Potassium; Acetaminophen; Acetic Acid; Acetic Anhydride; Acetone; Acetone Sodium Bisulfite; Acetonitrile; Acetophenone; Acetylated Lanolin Alcohols; Acetylcysteine; Acetyltributyl Citrate; Acetyltryptophan, Dl-; Acid Blue 9 Ammonium; Acid Orange 20; Acrylates Copolymer; Acryl-Eze 93018509 White; Acryl-Eze 93053823 Orange; Acryl-Eze 93084719 Pink; Acryl-Eze 93084720 Pink; Acrylic Acid-Isooctyl Acrylate Copolymer; Acrylic Adhesive 788; Activated Charcoal; Adcote 72a103; Adhesive Tape; Adipic Acid; Advantia Prime 190100ba01 White; Aerotex Resin 3730; Agar; Air; Alanine; Albumin Aggregated; Albumin Colloidal; Albumin Human; Albumins; Alcloxa; Alcohol; Alfadex; Algeldrate; Alginic Acid; Alkyl Ammonium Sulfonic Acid Betaine; Alkyl Aryl Sodium Sulfonate; Allantoin; Almond Oil; *Althaea officinalis* Root; Aluminum Acetate; Aluminum Hydroxide; Aluminum Hydroxide-Sucrose, Hydrated; Aluminum Monostearate; Aluminum Oxide; Aluminum Polyester; Aluminum Silicate; Aluminum Silicate Pentahydrate; Aluminum Starch Octenylsuccinate; Aluminum Stearate; Aluminum Subacetate; Aluminum Sulfate Anhydrous; Aluminum Sulfate Tetradecahydrate; Alzamer-39; Alzamer-50; Amaranth; Amberlite; Amberlite Xe-58; Amberlite Xe-88; Amerchol C; Amerchol-Cab; Aminobenzoate Sodium; Aminomethylpropanol; Ammonia; Ammonio Methacrylate Copolymer; Ammonio Methacrylate Copolymer Type A; Ammonio Methacrylate Copolymer Type B; Ammonium Acetate; Ammonium Calcium Alginate; Ammonium Chloride; Ammonium Glycyrrhizate; Ammonium Lauryl Sulfate; Ammonium Nonoxynol-4 Sulfate; Ammonium Phosphate, Dibasic; Ammonium Salt Of C-12-C-15 Linear Primary Alcohol Ethoxylate; Ammonium Sulfate; Ammonyx; Amphoteric-9; Amyl Acetate; Anethole; Anhydrous Citric Acid; Anhydrous Dextrose; Anhydrous Dibasic Calcium Phosphate; Anhydrous Lactose; Anhydrous Trisodium Citrate; Anidrisorb 85/70; Anise; Anise Oil; Anoxid Sbn; Antifoam; Antifoam Dc; Antifoam M; Antipyrine; Apaflurane; Apricot Kernel Oil Peg-6 Esters; Aquacel 126; Aquacoat; Aquacoat Ecd; Aquacoat Ecd-30; Aquaphor; Aquarius Bkt14090 Yellow; Aquarius Bp17066 Blue; Arginine; Arlacel; Ascorbic Acid; Ascorbyl Palmitate; Aspartame; Aspartic Acid; Attapulgite; Balsam Peru; Barium Sulfate; Beeswax, Synthetic; Beheneth-10; Bentonite; Benzaldehyde; Benzalkonium Chloride; Benzenesulfonic Acid; Benzethonium Chloride; Benzododecinium Bromide; Benzoic Acid; Benzoin Resin; Benzyl Acetate; Benzyl Alcohol; Benzyl Benzoate; Benzyl Chloride; Benzyl Violet; Betadex; Betanaphthol; Betose; Bibapcitide; Bismuth Subcarbonate; Bismuth Subgallate; Black Currant; Black Ink; Boric Acid; Brocrinat; Brown Iron Oxide; Buffered Soda; Butane; Butyl Alcohol; Butyl Ester Of Methyl Vinyl Ether/Maleic Anhydride Copolymer (125000 Mw); Butyl Stearate; Butylated Hydroxyanisole; Butylated Hydroxytoluene; Butylene Glycol; Butylparaben; Butyric Acid; C12-15 Alkyl Lactate; C20-40 Pareth-24; Caffeine; Calcium; Calcium Acetate; Calcium Alginate And Ammonium Alginate; Calcium Ascorbate; Calcium Carbonate; Calcium Carrageenan Sulfate; Calcium Chloride; Calcium Citrate; Calcium Cyclamate; Calcium Gluceptate; Calcium Hydroxide; Calcium Lactate; Calcium Phosphate Dibasic Dihydrate-Sucrose Agglomerate; Calcium Phosphate, Dibasic Monohydrate; Calcium Phosphate, Calcium Polycarbophil; Calcium Pyrophosphate; Calcium Salicylate; Calcium Silicate; Calcium Stearate; Calcium Sulfate Anhydrous; Calcium Sulfate Dihydrate; Calcium Sulfate Hemihydrate; Calcium Sulfate, Calcobutrol; Caldiamide Sodium; Caloxetate Trisodium; Calteridol Calcium; Canada Balsam; Candelilla Wax; Candesartan Cilexetil; Canola Oil; Caprylic/Capric Mono/Diglycerides; Caprylic/Capric/Stearic Triglyceride; Caprylic/Capric/Succinic Triglyceride; Caprylocaproyl Macrogolglycerides; *Capsicum oleoresin*; Captan; Caramel; Carbomer 1382; Carbomer Copolymer Type B (Allyl Pentaerythritol Crosslinked); Carbomer Homopolymer Type A (Allyl Pentaerythritol Crosslinked); Carbomer Homopolymer Type B (Allyl Pentaerythritol Crosslinked); Carbomer Homopolymer Type B (Allyl Pentaerythritol Or Allyl Sucrose Crosslinked); Carbomer Homopolymer Type C (Allyl Pentaerythritol Crosslinked); Carbon Dioxide; Carbon Tetrachloride; Carboxy Vinyl Copolymer; Carboxymethyl Starch; Carboxymethylamylopectinsodium; Carboxymethylcellulose; CarboxymethylcelluloseCalcium; Carboxymethylcellulose Sodium; Carboxypolymethylene; Carmine; Carmine 50; Carnauba Wax; Carrageenan; Carrageenan Calcium; Carrageenan Sodium; Carvone, (-)-; Castor Oil; Cedar Leaf Oil; Cellaburate; Cellacefate; Cellulose Acetate; Cellulose Acetate Ca-320s; Cellulose Acetate Ca-398-10; Cellulose Microcrystalline/Carboxymethylcellulose Sodium; Cellulose, Microcrystalline; Cellulose, Oxidized; Cellulosic Polymers; Ceresin; Ceteareth-12; Ceteareth-15; Ceteareth-30; Cetearyl Alcohol/Ceteareth-20; Cetearyl Ethylhexanoate; Ceteth-10; Ceteth-2; Ceteth-20; Ceteth-23; Cetostearyl Alcohol; Cetrimonium Chloride; Cetyl Alcohol; Cetyl Esters Wax; Cetyl Palmitate; Cetylpyridinium Chloride; Chemoderm 6401b; Cherry; Cherry Juice; Chinese Cinnamon Oil; Chlorobutanol; Chlorobutanol Hemihydrate; Chlorocresol; Chloroform; Chloroxylenol; Cholesterol; Choleth; Choleth-24; *Chondrus crispus* Carrageenan; Chromacote T 2700gn; Chromacote T 2716y; Chroma-Kote T2956-Y Yellow; Ciclopirox Olamine; Cinnamaldehyde; Cinnamon; Cinnamon Oil; Citric Acid Monohydrate; *Citrus sinensis* Flower Oil; Clove Oil; Coateric Ypa-6-7430 White; Cocamide Ether Sulfate; Cocamine Oxide; Coco Betaine; Coco Diethanolamide; Coco Monoethanolamide; Cocoa; Cocoa Butter; Coco-Caprylate/Caprate; Coco-Glycerides; Coconut Oil; Coconut Oil-Lecithin; Coconut Oil/Palm Kernel Oil Glycerides, Hydrogenated; Coffee Bean; Cola Nut; Collagen; Color Hs 290008cr01 White; Color Icg-U-10251 Brown; Coloring Suspension; Compressible Sugar; Copovidone K25-31; Coriander Oil; Corn Glycerides; Corn Oil; Corn Oil Peg-6 Esters; Corn Syrup; Cottonseed Oil; Cream Base; Creatine; Creatinine; Cresol; Croscarmellose; Croscarmellose Sodium; Crospovidone (15 Mpa.S At 5%); Crystal Gum; Cupric Sulfate; Cupric Sulfate Anhydrous; Cutina; Cyclamic Acid; Cyclomethicone; Cyclomethicone 5; Cyclomethicone/Dimethicone Copolyol; Cysteine; Cysteine Hydrochloride; Cysteine Hydrochloride Anhydrous; Cysteine, Dl-; D&C Black No. 2; D&C Blue No. 1 Lake; D&C Blue No. 1—Aluminum Lake; D&C Blue No. 2 Lake; D&C Blue No. 4; D&C Blue No. 6; D&C Blue No. 9; D&C Brown No. 1; D&C Green No. 3 Lake; D&C Green No. 5; D&C Green No. 6; D&C Orange No. 4; D&C Red No. 21—Aluminum Lake; D&C Red No. 22; D&C Red No. 27; D&C Red No. 27 Lake; D&C Red No. 27—Aluminum Lake; D&C Red No. 28; D&C Red No. 28—Aluminum Lake; D&C Red No. 30; D&C Red No. 30 Lake; D&C Red No. 33; D&C Red No. 33 Lake; D&C Red No. 36; D&C Red No. 39; D&C Red No. 4 Lake; D&C Red No. 40 Lake; D&C Red No. 6; D&C Red No. 6 Barium Lake; D&C Red No. 6 Lake; D&C Red No. 7; D&C Red No. 7 Lake; D&C Violet No. 2 Lake; D&C Yellow No. 10; D&C Yellow No. 10 Lake; D&C Yellow No. 10-Aluminum Lake; D&C Yellow No. 10—Aluminum Lake; D&C Yellow No. 11; D&C Yellow No. 5—Aluminum Lake; D&C Yellow No. 6 Lake; Daubert 1-5 Pestr (Matte) 164z; Dc Antifoam Af Trituration 1% On Sucrose; Decyl Methyl Sulfoxide; Dehydag Wax Sx; Dehydroacetic Acid; Dehymuls E; Denatonium Benzoate; Deoxycholic Acid; Dexbrompheniramine Maleate; Dextran; Dextran 40; Dextrates; Dextrins Modified; Dextrose Monohydrate; Dextrose; Diacetylated Monoglycerides; Diastase, Malt; Diatomaceous Earth; Diatrizoic Acid; Diazolidinyl Urea; Dibasic Calcium Phosphate Dihydrate; Dibutyl Sebacate; Dichlorobenzyl Alcohol; Dichlorodifluoromethane; Dichlorofluoromethane; Dichlorotetrafluoroethane; Diethanolamine; Diethyl Phthalate; Diethyl Pyrocarbonate; Diethyl Sebacate; Diethylaminoethyl Stearamide Phosphate; Diethylene Glycol Monoethyl Ether; Diethylhexyl Phthalate **See Cder Guidance: Limiting The Use Of Certain Phthalates As Excipients In Cder-Regulated Products; Dihydroxy aluminum Aminoacetate; Dihydroxyaluminum Sodium Carbonate; Diisopropanolamine; Diisopropyl Adipate; Diisopropyl Dilinoleate; Diisopropylbenzothiazyl-2-Sulfenamide; Dimethicone; Dimethicone 100; Dimethicone 1000; Dimethicone 20; Dimethicone 350; Dimethicone Mdx4-4210; Dimethiconol/Trimethylsiloxysilicate Crosspolymer (40/60 W/W; 1000000 Pa·S); Dimethyl Isosorbide; Dimethyl Phthalate; Dimethyl Sulfoxide; Dimethylaminoethyl Methacrylate-Butyl Methacrylate-Methyl Methacrylate Copolymer; Dimethyldioctadecylammonium Bentonite; Dimethylsiloxane/Methylvinylsiloxane Copolymer; Dinoseb-Ammonium; Dipalmitoylphosphatidylglycerol, Dl-; Dipentenedimercaptan; Dipropylene Glycol; Disodium Citrate Sesquihydrate; Disodium Cocoamphodiacetate; Disodium Hydrogen Citrate; Disodium Laureth Sulfosuccinate; Disodium Lauryl Sulfosuccinate; Disodium Oleamido Monoethanolamine Sulfosuccinate; Disodium Sulfosalicylate; Disofenin; Distearoylphosphatidylcholine, Dl-; Divinylbenzene Styrene Copolymer; Dmdm Hydantoin; Docosanol; Docusate Sodium; Docusate Sodium/Sodium Benzoate; Dri Klear; Dri Klear 042; Dri Klear Lv 609527;

Dry Flo; Dry-Clear Lv; Duro-Tak 280-2516; Duro-Tak 387-2516; Duro-Tak 80-1196; Duro-Tak 87-2070; Duro-Tak 87-2194; Duro-Tak 87-2287; Duro-Tak 87-2296; Duro-Tak 87-2888; Duro-Tak 87-2979; Dusting Powder; Dye Beige P-1437; Dye Black Lb-1171; Dye Black Lb-442; Dye Black Lb-636; Dye Black Lb-9972; Dye Black Oxide; Dye Blue Lake Blend Lb-1245; Dye Blue Lake Blend Lb-1939; Dye Blue Lake Blend Lb-332; Dye Blue Lakolene; Dye Blue Lb-781; Dye Brown Lake; Dye Brown Lake Blend; Dye Brown Lake Blend Lb-1685; Dye Brown Lake Blend Lb-1792; Dye Brown Lb-292; Dye Brown Lb-464; Dye Burnt Umber; Dye Caramel 105; Dye Caramel Acid Proof 100; Dye Carmine 09349; Dye Casing 27-75; Dye Chroma-Teric Deb-5037-Ore; Dye Chroma-Teric T3000-We; Dye Chroma-Teric Yellow T3277-Ye; Dye Chroma-Tone; Dye Chroma-Tone Pddb-8906w; Dye Chroma-Tone-P Ddb-8746-Or; Dye Dc Red Lake; Dye Dc Red Lb No. 9570; Dye Dc Red Lb Wj-9570; Dye Diolack 00f32892 Yellow; Dye Emerald Green Lb; Dye Emerald Green Lb-9207; Dye Fdc Black Lb260; Dye Fdc Blue No. 10; Dye Fdc Blue No. 40 Ht Lake; Dye Fdc Brown R Lb-56069; Dye Fdc Green Lb-1174; Dye Fdc Green Lb-3323; Dye Fdc Green Lb-9583; Dye Fdc Lb483; Dye Fdc Orange Lb-452; Dye Fdc Purple Lb588; Dye Fdc Purple Lb-694; Dye Grape; Dye Gray No. 2982; Dye Green 70363; Dye Green Al Lb-265; Dye Green Aluminum Lb; Dye Green Lake Blend Lb-1236; Dye Green Lake Blend Lb-1441; Dye Green Lake Blend Lb-1644; Dye Green Lake Blend Lb-333; Dye Green Lb; Dye Green Lb-1594; Dye Green Lb-1616; Dye Green Lb-279; Dye Green Lb-482; Dye Green Lb-555; Dye Green Lb-603; Dye Green Lb-820; Dye Green Lb-883; Dye Green Pb-1543; Dye Green Pb-1763; Dye Green Pb-1766; Dye Green Pms-579; Dye Green Pr-1333; Dye Green Pr-1339; Dye Lavender; Dye Lavender Lake Blend Lb-1603; Dye Lavender Lb-1356; Dye Mint Green; Dye Ochre 3506; Dye Orange 54172; Dye Orange Lake Blend 3810; Dye Orange Lake Blend Lb-1439; Dye Orange Lake Blend Lb-1944; Dye Orange Lb-1387; Dye Orange Lb-715; Dye Orange Pb-1657; Dye Orange Pb-2148; Dye Peach Lb-1576; Dye Pink; Dye Purple Lake; Dye Purple Lb-1902; Dye Purple Lb-562; Dye Purple Lb-639; Dye Purple Lb-694; Dye Red Cotolene-P; Dye Red Lake Blend 6053-R; Dye Red Pb-1595; Dye Red R07058; Dye Salmon Lb-1668; Dye Spectraspray Blue 50726; Dye Swedish Orange No. 2191; Dye Tan Pb-1388; Dye Tetrarome Orange; Dye Turquoise Lb-1430; Dye Violet; Dye White Coateric Ypa-6-7089; Dye White Cotolene-P; Dye White Tc-1032; Dye Wild Cherry 7598; Dye Yellow 70362; Dye Yellow Lake Blend Lb-1769; Dye Yellow Lb 104; Dye Yellow Lb 9706; Dye Yellow Lb-111; Dye Yellow Lb-1577; Dye Yellow Lb-1637; Dye Yellow Lb-282; Dye Yellow No. 62; Dye Yellow Pb1345; Dye Yellow Pb-1381; Dye Yellow Wd-2014; Edetate Calcium Disodium; Edetate Disodium; Edetate Disodium Anhydrous; Edetate Sodium; Edetic Acid; Egg Phospholipids; Eiderdown Soap; Entsufon; Entsufon Sodium; Epilactose; Epitetracycline Hydrochloride; Erythorbic Acid; Erythritol; Essence Bouquet 9200; Essence Fritzbro Orange; Essence Lemon; Essence Orange; Ethanolamine Hydrochloride; Ether; Ethyl Acetate; Ethyl Acrylate And Methyl Methacrylate Copolymer (2:1; 750000 Mw); Ethyl Maltol; Ethyl Oleate; Ethyl Vanillate; Ethyl Vanillin; Ethylcellulose (10 Mpa.S); Ethylcellulose (20 Mpa·S); Ethylcellulose (4 Mpa·S); Ethylcellulose (45 Mpa·S); Ethylcellulose (50 Mpa·S); Ethylcellulose (7 Mpa·S); Ethylcelluloses; Ethylene; Ethylene Glycol; Ethylene Glycol Monoethyl Ether; Ethylenediamine; Ethylenediamine Dihydrochloride; Ethylene-Propylene Copolymer; Ethylene-Vinyl Acetate Copolymer (15% Vinyl Acetate); Ethylene-Vinyl Acetate Copolymer (28% Vinyl Acetate); Ethylene-Vinyl Acetate Copolymer (9% Vinylacetate); Ethylene-Vinyl Acetate Copolymers; Ethylhexyl Hydroxystearate; Ethylparaben; Eucalyptol; Eucalyptus Oil; Eugenol; Exametazime; Ext. D&C Yellow No. 7; Fat, Edible; Fat, Hard; Fatty Acid Esters; Fatty Acid Esters, Saturated; Fatty Acid Glycerides; Fatty Acid Pentaerythriol Ester; Fatty Acids; Fatty Alcohol Citrate; Fatty Alcohols; Fd&C Blue No. 1; Fd&C Blue No. 1 Lake; Fd&C Blue No. 1—Aluminum Lake; Fd&C Blue No. 2; Fd&C Blue No. 2—Aluminum Lake; Fd&C Green No. 3; Fd&C Red No. 3; Fd&C Red No. 30—Aluminum Lake; Fd&C Red No. 3—Aluminum Lake; Fd&C Red No. 4; Fd&C Red No. 40; Fd&C Red No. 40—Aluminum Lake; Fd&C Yellow No. 5; Fd&C Yellow No. 5—Aluminum Lake; Fd&C Yellow No. 6; Fd&C Yellow No. 6-Aluminum Lake; Fd&C Yellow No. 6—Aluminum Lake; Feculose; Ferric Chloride; Ferric Oxide Brown; Ferric Oxide Green; Ferric Oxide Orange; Ferric Oxide Pink; Ferric Oxide Red; Ferric Oxide Yellow; Ferrosoferric Oxide; Ferrous Fumarate; Ferrous Oxide; Ferula Assa-Foetida Resin; Film Coating Solution, Aqueous Im-163; Firmenich 51.226/T; Flavor 18317; Flavor 57000 Iu; Flavor 57820/A; Flavor 89-186; Flavor 89-259; Flavor Anise 29653; Flavor Aniseed 501007 Bp0551; Flavor Apple Watermelon Pfc 9887; Flavor Apricot 23067; Flavor Apricot 24829; Flavor Apricot Peach; Flavor Aromalok 182608; Flavor Aromalok 262453; Flavor Banana 11090; Flavor Banana 15223; Flavor Banana 501013 Ap0551; Flavor Banana 59256c; Flavor Banana 71507; Flavor Banana 74546; Flavor Banana 8763; Flavor Banana 9.19081; Flavor Banana Durarome 860.095 Td09.91; Flavor Banana Fmc 23406; Flavor Banana Fn-6713; Flavor Banana Sa84; Flavor Bba-47769; Flavor Berry Citrus Blend 8409; Flavor Berry Citrus Blend 9621; Flavor Berry Citrus Blend 9756; Flavor Berry Fruit Punch 135846; Flavor Bitter Mask 9885; Flavor Bitterness Modifier 15555; Flavor Bitterness Modifier 36734; Flavor Bitterness Modifier 367343; Flavor Black Cherry 501027 Ap0551; Flavor Black Cherry 825.083; Flavor Blood Orange 51.226t; Flavor Blood Orange Sa; Flavor Bubble Gum 15864; Flavor Bubble Gum 175303; Flavor Bubble Gum 3266p; Flavor Bubble Gum Mc-4938; Flavor Burnt Sugar 680537; Flavor Burnt Sugar 687817; Flavor Burnt Sugar 994535; Flavor Butter Vanilla; Flavor Buttermint 24020; Flavor Butterscotch 61oo5-U; Flavor Butterscotch F-1785; Flavor C&K Mixed Fruit A13688; Flavor Candied Sugar 510155u; Flavor Cheri Beri Pcd-5580; Flavor Cheri-Beri Pfc-8573; Flavor Cheri-Beri Pfc-8580; Flavor Cherry 104613; Flavor Cherry 107026; Flavor Cherry 11539; Flavor Cherry 11929; Flavor Cherry 1566; Flavor Cherry 181612; Flavor Cherry 213; Flavor Cherry 231494; Flavor Cherry 3321; Flavor Cherry 338614; Flavor Cherry 349; Flavor Cherry 461566; Flavor Cherry 500910u; Flavor Cherry 57.679/A; Flavor Cherry 590271a; Flavor Cherry 594 S.D.; Flavor Cherry 598384; Flavor Cherry 825.382; Flavor Cherry 825.476wc; Flavor Cherry 842; Flavor Cherry 8513; Flavor Cherry A-22872; Flavor Cherry Beri Pfc-8573; Flavor Cherry Berry F-1194; Flavor Cherry Blend 770; Flavor Cherry Burgundy 11650; Flavor Cherry Cream 14850; Flavor Cherry Dp300684; Flavor Cherry Durarome 860.097 Td10.91; Flavor Cherry E.P.Modified 151; Flavor Cherry Ep-3699; Flavor Cherry F-232; Flavor Cherry Fi-8568; Flavor Cherry Fmc 22872; Flavor Cherry Fmc 8513; Flavor Cherry Fona 825.662; Flavor Cherry H&R Pharma 004; Flavor Cherry Iff 13530912; Flavor Cherry L-1233; Flavor Cherry Maraschino S-3531; Flavor Cherry Mint 5073a; Flavor Cherry N-2755; Flavor Cherry Nv-1489;

Flavor Cherry Pfc-9768; Flavor Cherry Pistachio Pfc-8450; Flavor Cherry R-6556; Flavor Cherry Vanilla Compound A77487; Flavor Cherry Wixon 3566; Flavor Cherry W1-1093; Flavor Cherry W1-18022; Flavor Cherry W1-4658; Flavor Cherry-Anise Pfc-9758; Flavor Chloroform 103589; Flavor Chocolate P727; Flavor Cinnamon; Flavor Cinnamon Sd 516; Flavor Cinnamon Veko 3726; Flavor Citrus Fn-7176; Flavor Citrus/Fruit Freeze 1100609500; Flavor Coconut 41; Flavor Coconut F-3893; Flavor Coconut Toasted 1323pg; Flavor Cola Fmc 15740; Flavor Cool Vanilla Bp18114; Flavor Cool Vanilla Bp18257; Flavor Cotton Candy 30-92-0011; Flavor Cotton Candy F-9967; Flavor Cough Syrup 110257; Flavor Cough Syrup 134681; Flavor Cough Syrup 819; Flavor Cream Ep-17688; Flavor Cream Soda; Flavor Creamy Vanilla 16345; Flavor Creme 46971; Flavor Creme De Menthe 14677; Flavor Creme De Vanilla 28156; Flavor Curacao; Flavor Curacao 50.397a; Flavor Custard 52.940/A Fir; Flavor Df-119; Flavor Df-1530; Flavor E-472; Flavor Enhancer; Flavor F-5397a; Flavor F-9843; Flavor Felton 6-R-9; Flavor Fig 827118; Flavor Fona 815.019wc; Flavor Fritzsche 21028-D; Flavor Fritzsche 46215; Flavor Fritzsche 73959; Flavor Fritzsche 75021; Flavor Fruit 01-10428; Flavor Fruit 84.6422; Flavor Fruit Fn-6714; Flavor Fruit Gum 912; Flavor Fruit Mint 75588; Flavor Fruit N&A Ws-605398; Flavor Fruit Punch 14761fm; Flavor Fruit Punch No. 28140; Flavor Fruit Punch No. 716; Flavor Fruit Tak 20008; Flavor Golden Punch; Flavor Grape 054158; Flavor Grape 10273; Flavor Grape 13403873; Flavor Grape 486939; Flavor Grape 501040a; Flavor Grape 501417c; Flavor Grape 59.145/Apo5.51; Flavor Grape 59.266/Apo5.51; Flavor Grape 61.13252; Flavor Grape 6175; Flavor Grape F&F 231460; Flavor Grape Firmenich 587.444; Flavor Grape Firmenich 597.303/C; Flavor Grape Givaudan 433160; Flavor Grape Iff 13549478; Flavor Grape Manheimer 522463; Flavor Grape Micron Zd-3876; Flavor Grape Nector Pfc-8599; Flavor Grape Pfc 8439; Flavor Grape Pfc-9711; Flavor Grape Pfc-9924; Flavor Grape St6835/09; Flavor Guarana Fmc-15417; Flavor Haverstroo Zd 49284; Flavor Iff Fp 69 F; Flavor Kiwi S-718; Flavor Lemon 812; Flavor Lemon Fmc-10471; Flavor Lemon Givaudan 74940-74; Flavor Lemon Lime Sd 935; Flavor Lemon Mint 862.547; Flavor Lemon Mint Fritzsche 54369; Flavor Lemon N&A 397; Flavor Lemon Spray V3398-1n1; Flavor Magnasweet 110; Flavor Mandarin 15228-71; Flavor Maque Tree 377 (Bush); Flavor Mask Rbt-Nv-7759; Flavor Masker Fn-6819; Flavor Masker Fn-6820; Flavor Masking 35321; Flavor Masking Agent 141.18074; Flavor Masking Tak-031431; Flavor Mcp Lemon Duramone 4409a; Flavor Mcp Lime Duramone 6419; Flavor Menthol 875.017; Flavor Menthol Mint Pfc-9926; Flavor Menthol Tak-020184; Flavor Menthol Veralock; Flavor Mint 287; Flavor Mint 501359; Flavor Mint 51296 Tp0551; Flavor Mint Sn027513; Flavor Mixed Fruit Pfc-9970; Flavor Orange 002.120; Flavor Orange 13334; Flavor Orange 249792; Flavor Orange 501071 Ap0551; Flavor Orange 57.458/Ap05.51; Flavor Orange 607217; Flavor Orange 739k (Pb82); Flavor Orange 74016-71; Flavor Orange 9/79j839; Flavor Orange Banana W1-18093; Flavor Orange Blood Silician Fn-12235; Flavor Orange G-10431; Flavor Orange Givaudan 74388-74; Flavor Orange No. 7679; Flavor Orange P-5614; Flavor Orange Pfw-730016u; Flavor Orange Pineapple Fv-43; Flavor Orange Wonf 608352; Flavor Orbit Serene 20340; Flavor Peach 10457; Flavor Peach 13503584; Flavor Peach 23070; Flavor Peach 302789; Flavor Peach 57695; Flavor Peach Mint Fritzsche 106109; Flavor Peach Pineapple Fmc 14258; Flavor Peppermint 104; Flavor Peppermint 131989; Flavor Peppermint 501500; Flavor Peppermint 517; Flavor Peppermint 894.115; Flavor Peppermint 894.143; Flavor Peppermint Art F-10012; Flavor Peppermint Extract Fn-2356; Flavor Peppermint F94249; Flavor Peppermint K373; Flavor Peppermint Pfc 9927; Flavor Peppermint Seelock 34907; Flavor Peppermint Sn583865; Flavor Peppermint Stick Fmc 16170; Flavor Peppermint Tak-022173; Flavor Peppermint W1-6167; Flavor Peppermint, Natural Spraylene; Flavor Perlarom Strawberry; Flavor Pharmaceutical 182608; Flavor Pharmasweet 10772900; Flavor Pineapple 182661; Flavor Pineapple 501085; Flavor Pineapple N-2566; Flavor Pineapple N-2766; Flavor Pineapple-Coconut; Flavor Prosweet 694; Flavor Punch 610962u; Flavor Punch W1-7126; Flavor Raspberry 1840; Flavor Raspberry 21028d; Flavor Raspberry 262085; Flavor Raspberry 28106; Flavor Raspberry 50776; Flavor Raspberry 65934; Flavor Raspberry 8456; Flavor Raspberry 954; Flavor Raspberry 954k (Bk77); Flavor Raspberry 998; Flavor Raspberry A11693; Flavor Raspberry Arome Pfc-9908; Flavor Raspberry Cream Pfc-9950; Flavor Raspberry D9599; Flavor Raspberry Dy-04447; Flavor Raspberry F-1784; Flavor Raspberry F-1840; Flavor Raspberry F-6887-S; Flavor Raspberry Pfc-8407; Flavor Raspberry Polak 5000064; Flavor Refrachessment Fd-8027d; Flavor Rhodia Pharmaceutical No. Rf 451; Flavor Rob Nv-23027; Flavor Root Beer 180339; Flavor Strawberry 052311 Ap0551; Flavor Strawberry 11545; Flavor Strawberry 133.5655; Flavor Strawberry 14953; Flavor Strawberry 17.36.8509; Flavor Strawberry 17c56217; Flavor Strawberry 52.311ap; Flavor Strawberry 5210(Fd&D); Flavor Strawberry 52312/A; Flavor Strawberry 52312/Ap0551; Flavor Strawberry 55058; Flavor Strawberry 5951; Flavor Strawberry 9843; Flavor Strawberry Banana 24020; Flavor Strawberry Cream 11407-33; Flavor Strawberry Cream Ph1-131991; Flavor Strawberry Dy-04359; Flavor Strawberry F-5665; Flavor Strawberry F-5930-A; Flavor Strawberry Fn-13819; Flavor Strawberry Guarana 586.997/Apo5.51; Flavor Strawberry Microseal; Flavor Strawberry Pfc-9626; Flavor Strawberry Phs-132962; Flavor Strawberry Trusil Windsor 2373031; Flavor Strawberry Wd Fo-1022; Flavor Strawberry W1-16650; Flavor Sweet 24052; Flavor Sweet 604978; Flavor Sweet Tone 28837; Flavor Sweet-Am 918.005; Flavor Sweetness Enhancer 5401b; Flavor Tangerine Fritzsche 51465; Flavor Tetrarome; Flavor Tm 313298; Flavor Tpf 135; Flavor Tpf 143; Flavor Tropical Blend Fv-50; Flavor Tropical Fruit Punch 1591; Flavor Tropical Fruit Punch N&A 50432; Flavor Tutti Frutti 0002028; Flavor Tutti Frutti 24093fm; Flavor Tutti Frutti 501.103/A; Flavor Tutti Frutti 51.880/Ap05.51; Flavor Tutti Frutti P-5400; Flavor Tutti Frutti W1-18481; Flavor Vanilla 20.4573.5p Pha; Flavor Vanilla 323453; Flavor Vanilla 33869; Flavor Vanilla 501441 Ap2004; Flavor Vanilla C7984; Flavor Vanilla F-6257; Flavor Vanilla Orange; Flavor Vanilla P-1160; Flavor Vanilla Pfc-8541; Flavor Vanilla Pfc-9772; Flavor Veralock Bubble Gum; Flavor Wild Cherry 29653; Flavor Wild Cherry 695047u; Flavor Wild Cherry Givaudan F-1813; Flavor Wild Cherry K-321; Flavor Wild Cherry Nv-101-1489; Flavor Wild Cherry Pfc-14783; Flavor Wild Cherry W1-1093; Flavor Wintergreen Pfc-8421; Flavor Yellow Plum Lemon 39k 20; Florasynth; Flour; Fluorescein; Fluorochlorohydrocarbons; Formaldehyde; Fosveset; Fragrance 3949-5; Fragrance 520a; Fragrance 6.007; Fragrance 91-122; Fragrance 9128-Y; Fragrance 93498g; Fragrance Balsam Pine; Fragrance Balsam Pine No. 5124; Fragrance Bouquet 10328; Fragrance Chemoderm 6401-B; Fragrance Chemoderm 6411; Fragrance Cream; Fragrance Cream No. 73457; Fragrance Cs-28197; Fragrance Felton 066m; Fragrance Firmenich 47373; Fragrance Givaudan Ess 9090/1c; Fragrance H-6540; Fragrance Herbal 10396; Fragrance Nj-1085; Fragrance P O F1-147; Fragrance Pa 52805; Fragrance Pera Derm D; Fragrance Rbd-9819; Fragrance Shaw Mudge U-7776; Fragrance Tf 044078; Fragrance Ungerer Honeysuckle K 2771; Fragrance Ungerer N5195; Fructose; Fumaric Acid; Fumaryl Diketopiperazine; Gadolinium Oxide; Galactose; Gamma Cyclodextrin; Gelatin; Gelatin 200 Bloom; Gelatin Capsule, Hard; Gelatin Type A, Pork; Gelatin, Crosslinked; Gelfoam Sponge; Gellan Gum (Low Acyl); Gelucire 33/01; Gelva 737; Gentisic Acid; Gentisic Acid Ethanolamide; Gentisic Acid Ethanolamine; Ginger; Gluceptate Sodium; Gluceptate Sodium Dihydrate; Gluconolactone; Glucuronic Acid; Glutamic Acid Hydrochloride; Glutamic Acid, Dl-; Glutathione; Glycerin; Glycerin Polymer Solution I-137; Glycerin Polymer Solution Im-137; Glycerol Ester Of Hydrogenated Rosin; Glyceryl 1-Stearate; Glyceryl Behenate/Eicosadioate; Glyceryl Caprylate; Glyceryl Dibehenate; Glyceryl Distearate; Glyceryl Isostearate; Glyceryl Laurate; Glyceryl Monostearate; Glyceryl Oleate; Glyceryl Oleate/Propylene Glycol; Glyceryl Palmitate; Glyceryl Palmitostearate; Glyceryl Ricinoleate; Glyceryl Stearate-Laureth-23; Glyceryl Stearate Se; Glyceryl Stearate/Peg Stearate; Glyceryl Stearate/Peg-100 Stearate; Glyceryl Stearate/Peg-40 Stearate; Glyceryl Stearate-Stearamidoethyl Diethylamine; Glyceryl Trioleate; Glycine; Glycine Hydrochloride; Glycol Distearate; Glycol Stearate; Glycyrrhizin; Green Starch Blend; Guanidine Hydrochloride; Guar Gum; Guinea Green B; Gum Base, Chewing; Hair Conditioner (18n195-1m); Heptane; Hetastarch; Hexane; Hexylene Glycol; Hexylresorcinol; High Density Polyethylene; High Fructose Corn Syrup; Histidine; *Hornstedtia costata* Seed; Human Albumin Microspheres; Hyaluronate Sodium; Hydrocarbon; Hydrocarbon Gel, Plasticized; Hydrochloric Acid; Hydrocortisone; Hydrogel Polymer; Hydrogen Peroxide; Hydrogenated Castor Oil; Hydrogenated Coconut Oil; Hydrogenated Cottonseed Oil; Hydrogenated Palm Oil; Hydrogenated Palm/Palm Kernel Oil Peg-6 Esters; Hydrogenated Polybutene 635-690; Hydrogenated Soybean Lecithin; Hydrogenated Soybean Oil; Hydrogenated Starch Hydrolysate; Hydrogenated Tallow Acid; Hydrolyzed Soy Protein (Enzymatic; 2000 Mw); Hydroxyethyl Cellulose; Hydroxyethyl Cellulose (140 Mpa·S At 5%); Hydroxyethyl Cellulose (5000 Mpa·S At 1%); Hydroxyethylpiperazine Ethane Sulfonic Acid; Hydroxymethyl Cellulose; Hydroxyoctacosanyl Hydroxystearate; Hydroxyprogesterone Caproate; Hydroxypropyl.Beta.-Cyclodextrin; Hydroxypropyl.Gamma.-Cyclodextrin; Hydroxypropyl Cellulose (Type H); Hydroxypropyl Cellulose (Type L); Hydroxypropyl Cellulose, Low Substituted; Hypromellose 2208 (100 Mpa·S); Hypromellose 2208 (100000 Mpa·S); Hypromellose 2208 (15000 Mpa·S); Hypromellose 2208 (3 Mpa·S); Hypromellose 2208 (4000 Mpa·S); Hypromellose 2208 (60000 Mpa·S); Hypromellose 2906 (4000 Mpa·S); Hypromellose 2910 (15 Mpa·S); Hypromellose 2910 (15000 Mpa·S); Hypromellose 2910 (3 Mpa·S); Hypromellose 2910 (4000 Mpa·S); Hypromellose 2910 (5 Mpa·S); Hypromellose 2910 (50 Mpa·S); Hypromellose 2910 (6 Mpa·S); Hypromellose Acetate Succinate; Hypromellose Acetate Succinate 06081224 (3 Mm2/S); Hypromellose Phthalate; Hypromellose Phthalate (24% Phthalate, 55 Cst); Hypromellose Phthalate (31% Phthalate, 40 Cst); Hypromelloses; Hystrene; Icodextrin; Imidurea; Indigotindisulfonate Sodium; Ink Black 2271; Ink Black A-10464; Ink Black A-10527; Ink Black Fge-1386; Ink Black Gg-606; Ink Black S-1-8100-Hv; Ink Black Sw-9007; Ink Black Sw-9008; Ink Black Sw-9009; Ink Black Sw-9010; Ink Blue And Yellow Imprint Gg-823; Ink Blue Black A-10463; Ink Blue Black A-9371; Ink Blue 5-1-10551; Ink Blue S-1-4118; Ink Blue Tek Print Sb-6029; Ink Blue Tekprint Sb-6008; Ink Blue Videojet V496-D; Ink Dark Yellow And Yellow Imprint Gg-824; Ink Edible Black; Ink Edible Blue; Ink Edible Brown; Ink Edible Gray; Ink Edible Orange; Ink Edible Pink; Ink Edible Red; Ink Edible Red A-8032; Ink Edible White; Ink Fine Black 2202c; Ink Fine Black 2212; Ink Flexographic Pink; Ink Green A-10454; Ink Green A-10629; Ink Orange And Yellow Imprint Gg-822; Ink Pink Imprinting Sb-1003; Ink Purple Tekprint Sb-7007; Ink Red 5-1-9034; Ink Red A-8032; Ink Red And Aqua Imprinting Gg-827; Ink Red And Caramel Imprinting Gg-825; Ink Red Imprinting Gg-826; Ink S-1-7085; Ink Thinner; Ink White A-8154; Ink White S-1-7075; Ink White Sb-0007p; Ink White Sw-0012; Ink White Tek Print Sb-007p; Ink/Polyethylene Terephthalate/Aluminum/Polyethylene/Sodium Polymethacrylate/Ethylene Vinylacetate Copolymer; Invert Sugar; Invert Syrup, Medium; Iobenguane; Iodine; Iodoxamic Acid; Iofetamine Hydrochloride; Iron Oxide Beige; Isobutane; Isobutyl Alcohol; Isoceteth-20; Isoleucine; Isomalt; Isooctyl Acrylate; Isooctyl Acrylate/Acrylamide/Vinyl Acetate Copolymer, Kollidon Va 64 Polymer; Isopropyl Alcohol; Isopropyl Isostearate; Isopropyl Myristate; Isopropyl Myristate-Myristyl Alcohol; Isopropyl Palmitate; Isopropyl Stearate; Isostearic Acid; Isostearyl Alcohol; Jelene; Kaolin; Karaya Gum; Karion 83 (D-Sorbitol Content 19-25%); Kathon Cg; Kathon Cg Ii; Lactic Acid, Dl-; Lactic Acid, L-; Lactic Acid; Lactitol Monohydrate; Lactobionic Acid; Lactoferrin, Bovine; Lactose Monohydrate; Lactose Monohydrate-Cellulose, Microcrystalline; Lactose; Laneth; Lanolin; Lanolin Alcohol-Mineral Oil; Lanolin Alcohols; Lanolin Cholesterols; Lanolin Nonionic Derivatives; Lanolin, Ethoxylated; Lauralkonium Chloride; Lauramine Oxide; Laurdimonium Hydrolyzed Animal Collagen; Laureth Sulfate; Laureth-2; Laureth-23; Laureth-4; Lauric Diethanolamide; Lauric/Myristic Diethanololamide; Lauroyl Polyoxylglycerides; Lauroyl Sarcosine; Lauryl Lactate; Lauryl Sulfate; *Lavandula angustifolia* Flowering Top; Lecithin; Lecithin Unbleached; Lecithin, Soybean; Lemon Oil; Leucine; Levomenthol; Levulinic Acid; Lidofenin; Light Green Cf Yellowish; Light Mineral Oil; Ligroin; Lime (Calcium Oxide); Lime Oil; Limonene, (+/-)-; Linoleoyl Macrogolglycerides; Lipocol Sc-15; Liquefied Petroleum Gas; Locust Bean Gum; Lubritab; Ludipress; Lysine; Lysine Acetate; Lysine Monohydrate; Magnesium Acetate; Magnesium Aluminum Silicate; Magnesium Aluminum Silicate Type Iia; Magnesium Aspartate; Magnesium Carbonate; Magnesium Chloride; Magnesium Citrate; Magnesium Hydroxide; Magnesium Nitrate; Magnesium Oxide; Magnesium Phosphate, Tribasic, Pentahydrate; Magnesium Silicate; Magnesium Stearate; Magnesium Sulfate Anhydrous; Magnesium Sulfate; Magnesium Tartrate; Magnesium Trisilicate; Maleic Acid; Malic Acid; Malic Acid, L-; Maltitol; Maltodextrin; Maltol; Maltose; Maltose Anhydrous; Mandarin Oil; Mannitol; Mannose, D-; Maprofix; Mebrofenin; Medical Antifoam Emulsion C; Medical Antiform A-F Emulsion; Medium-Chain Triglycerides; Medronate Disodium; Medronic Acid; Meglumine; Melojel; Menthol; Metacresol; Metanil Yellow; Metaphosphoric Acid; Methacrylic Acid; Methacrylic Acid-Ethyl Acrylate Copolymer (1:1) Type A; Methacrylic Acid-Methyl Methacrylate Copolymer (1:1); Methacrylic Acid-Methyl Methacrylate Copolymer (1:2); Methacrylic Acid Copolymer; Methanesulfonic Acid; Methionine; Methoxy Peg-16; Methyl Acrylate-Methyl Methacrylate; Methyl Alcohol; Methyl Chloride; Methyl Ethyl Ketone; Methyl Gluceth-10;

Methyl Gluceth-20; Methyl Glucose Sesquistearate; Methyl Hydroxyethyl Cellulose; Methyl Laurate; Methyl Pyrrolidone; Methyl Salicylate; Methyl Stearate; Methylated Spirits; Methylboronic Acid; Methylcellulose (15 Mpa·S); Methylcellulose (1500 Mpa·S); Methylcellulose (400 Mpa·S); Methylcellulose (4000 Mpa·S); Methylcelluloses; Methylchloroisothiazolinone; Methylene Blue; Methylene Chloride; Methylisothiazolinone; Methylparaben; Methylparaben Sodium; Methylphenidate; Microcrystalline Wax; Milk Protein Concentrate; Mineral Oil; Miripirium Chloride; Misoprostol; Mistron Spray Talc; Modified Corn Starch (1-Octenyl Succinic Anhydride); Mono And Diglyceride; Monoethanolamine; Monoglyceride Citrate; Monoglycerides; Monosodium Citrate; Monosodium Glutamate; Monostearyl Citrate; Monothioglycerol; Montan Wax; Multisterol Extract; Muscatel Wine; Myristic Acid; Myristyl Alcohol; Myristyl Lactate; Myvacet Type 5-00; N-(Carbonyl-Methoxypolyethylene Glycol 2000)-1,2-Distearoyl-Sn-Glycero-3-Phosphoethanolamine; N-(Carbonyl-MethoxypolyethyleneGlycol2000)-Distearoyl-Glycerophosphoethanolamine, Sodium Salt; N,N-Dimethylacetamide; Naphtha; Naphthol Blue Black; Neohesperidin Dihydrochalone; Neotame; Neutral Oil; Niacinamide; Nioxime; Nipasept; Nipastat; Nitric Acid; Nitrogen; Nonoxynol Iodine; Nonoxynol-15; Nonoxynol-9; Non-Pareil Seeds; Non-Pareil Seeds Blue; Non-Pareil Seeds Orange; Non-Pareil Seeds White; Norethindrone; Norflurane; Nutmeg Oil; Oatmeal; Octadecene-1/Maleic Acid Copolymer; Octanoic Acid; Octisalate; Octoxynol-1; Octoxynol-40; Octoxynol-9; Octreotide; Octyldodecanol; Octylphenol Polymethylene; Oil Cream Soda; Oil Orange Ss; Oil, Hydrogenated; Oleic Acid; Oleth-10/Oleth-5; Oleth-2; Oleth-20; Oleyl Alcohol; Oleyl Oleate; Oleyl Polyethylene Glycol Glyceride; Olive Oil; Opacoat Na2123; Opacoat Na2203; Opacoat Na4108 Blue; Opacoat Na4711 Lavender; Opacoat Na7013 Clear; Opacode A-10450 Black; Opacode A-10509 Black; Opacode Ns-78-10013-N; Opacode Ns-78-17502 Gray; Opacode Ns-78-17821 Wb Black; Opacode Ns-78-8000 Black; Opacode Ns-78-8001; Opacode Nsp-78-17734 Black; Opacode S-1-13001 Orange; Opacode S-1-15034-Fd Red; Opacode S-1-15038 Red; Opacode S-1-16507; Opacode S-1-1666 Red; Opacode S-1-1666-M Red; Opacode S-1-1681 Red; Opacode S-1-17706 Black; Opacode S-1-17711 Black; Opacode S-1-17734 Black; Opacode S-1-17749 Black; Opacode 5-1-17762 Black; Opacode 5-1-17797 Black; Opacode 5-1-17822 Black; Opacode 5-1-17823 Black; Opacode 5-1-18025 White; Opacode 5-1-26514 Brown; Opacode S-1-27794 Black; Opacode 5-1-3110 Green; Opacode 5-1-3171 Green; Opacode 5-1-4124 Blue; Opacode 5-1-4157; Opacode 5-1-4159 Black; Opacode 5-1-4160 Blue; Opacode 5-1-4172 Blue; Opacode 5-1-4172m Blue; Opacode 5-1-4362; Opacode 5-1-7020; Opacode 5-1-7077; Opacode 5-1-7078; Opacode 5-1-7085 White; Opacode 5-1-7090 White; Opacode 5-1-800hv Black; Opacode 5-1-8025 Black; Opacode 5-1-8081 Black; Opacode 5-1-8090 Black; Opacode 5-1-8092 Black; Opacode 5-1-8093 Black; Opacode 5-1-8094 Black; Opacode 5-1-8095; Opacode 5-1-8100-Hv Black; Opacode 5-1-8105 Black; Opacode 5-1-8106 Black; Opacode 5-1-8109 Black; Opacode 5-1-8110 Black; Opacode 5-1-8114 Black; Opacode 5-1-8115 Black; Opacode 5-1-8152hv Black; Opacode 5-1-8814 Black; Opacode 5-1-8815 Black; Opacode 5-1-9009 Brown; Opacode 5-1-9032; Opacode 5-1-9037 Brown; Opacode 5-1-9048c; Opacode 5-1-9460hv Brown; Opacode 5-19-7014 White; Opacode 5-8-20931; Opacode Sb-4028 Green; Opacode Wb Ns-78-10521 Blue; Opacode Wb Ns-78-17715 Black; Opacode Wb Ns-78-18001 White; Opacode Wb Nsp-78-18022 White; Opadry 00a28646; Opadry 00b53815 Orange; Opadry 00b57513 Grey; Opadry 00f44042 Red; Opadry 02a82904 Yellow; Opadry 02b14941 Pink; Opadry 02b22429 Yellow; Opadry 02b32413 Yellow; Opadry 02b58839 White; Opadry 02b94016 Pink; Opadry 02f34337 Pink; Opadry 02f54181 Pink; Opadry 02g22555 Yellow; Opadry 02g24523 Pink; Opadry 02g26637 Brown; Opadry 02g28619 White; Opadry 02g59011 Clear; Opadry 02-H-22703 Yellow; Opadry 03a 58900 White; Opadry 03a14309 Pink; Opadry 03b11434 Green; Opadry 03b12878 Yellow; Opadry 03b12896 Yellow; Opadry 03b12914 Yellow; Opadry 03b14424 Pink; Opadry 03b14436 Pink; Opadry 03b14899 Pink; Opadry 03b16083 Maroon; Opadry 03b17426 Beige; Opadry 03b17495 Beige; Opadry 03b17618 Gray; Opadry 03b20024 Purple; Opadry 03b20556 Blue; Opadry 03b21517 Green; Opadry 03b22426 Yellow; Opadry 03b23523 Orange; Opadry 03b24562 Peach; Opadry 03b28796 White; Opadry 03b32034 Yellow; Opadry 03b34239 Pink; Opadry 03b34399 Pink; Opadry 03b50899 Blue; Opadry 03b510003 Green; Opadry 03b53850 Orange; Opadry 03b54138 Pink; Opadry 03b54180 Pink; Opadry 03b54504 Pink; Opadry 03b54573 Pink; Opadry 03b54588 Pink; Opadry 03b54955 Pink; Opadry 03b56518 Brown; Opadry 03b56982 Brown; Opadry 03b57310 Brown; Opadry 03b57520 Grey; Opadry 03b57631 Grey; Opadry 03b58902 White; Opadry 03b58930 White; Opadry 03b58965 White; Opadry 03b68903 White; Opadry 03b80829 Blue; Opadry 03b80969 Blue; Opadry 03b82316 Yellow; Opadry 03b82419 Yellow; Opadry 03b82836 Yellow; Opadry 03b82849 Yellow; Opadry 03b82943 Yellow; Opadry 03b84681 Pink; Opadry 03b84755 Pink; Opadry 03b86585 Brown; Opadry 03b86625 Brown; Opadry 03b86636 Brown; Opadry 03b86737 Brown; Opadry 03b86811 Brown; Opadry 03b86891 Brown; Opadry 03b86892 Brown; Opadry 03c34219 Pink; Opadry 03f12920 Yellow; Opadry 03f12967 Yellow; Opadry 03f13325 Orange; Opadry 03f14895 Pink; Opadry 03f42192 Yellow; Opadry 03f43159 Brown; Opadry 03f51681 Green; Opadry 03f540000 Pink; Opadry 03f54568 Pink; Opadry 03f565001 Brown; Opadry 03f57311 Brown; Opadry 03f58741 White; Opadry 03f58991 White; Opadry 03f59016 Clear; Opadry 03f82329 Yellow; Opadry 03f82604 Yellow; Opadry 03f82726 Yellow; Opadry 03f82788 Yellow; Opadry 03f84641 Pink; Opadry 03f84782 Pink; Opadry 03f84793 Pink; Opadry 03f86762 Brown; Opadry 03f86776 Brown; Opadry 03f86845 Brown; Opadry 03f86990 Brown; Opadry 03g24389 Pink; Opadry 03g82464 Yellow; Opadry 03g82490 Yellow; Opadry 03j18312 White; Opadry 03k14881 Pink; Opadry 03k29121 Clear; Opadry 03k50891 Blue; Opadry 03k51211 Green; Opadry 03k52543 Yellow; Opadry 03k54121 Pink; Opadry 03k80846 Blue; Opadry 04e28779 White; Opadry 04f50603 Blue; Opadry 04f50702 Blue; Opadry 04f51279 Green; Opadry 04f52565 Yellow; Opadry 04f53544 Orange; Opadry 04f58804 White; Opadry 05b10446 Purple; Opadry 05b10457 Purple; Opadry 05b11552 Green; Opadry 05b11781 Green; Opadry 05b12337 Yellow; Opadry 05b15325 Red; Opadry 05b17055 Tan; Opadry 06f32500 Yellow; Opadry 06f34520 Pink; Opadry 06f34521 Orange; Opadry 06f34522 Pink; Opadry 06f34523 Pink; Opadry 12b58900 White; Opadry 12f20984 Blue; Opadry 12f21129 Green; Opadry 12f22609 Yellow; Opadry 12j18255 White; Opadry 13b50159 Purple; Opadry 13b50780 Blue; Opadry 13b51260 Green; Opadry 13b52329 Yellow; Opadry 13b58802 White; Opadry 13b58894 White; Opadry 13b80922 Blue; Opadry 13b82555 Yellow; Opadry 13f51381 Green; Opadry 13f52194 Yellow; Opadry 13f52195 Yellow; Opadry 13f54198 Pink; Opadry 13f58866 White; Opadry 13h52750 Yellow; Opadry 13h52754 Yellow; Opadry 13h54756 Pink; Opadry 13h54757 Pink; Opadry 13k52177 Yellow; Opadry 13m530001 Orange; Opadry 13m565001 Brown; Opadry 13m86920 Brown; Opadry 15b110003 Green; Opadry 15b11947 Green; Opadry 15b13335 Orange; Opadry 15b20780 Blue; Opadry 15b21340 Green; Opadry 15b22275 Yellow; Opadry 15b24473 Pink; Opadry 15b24879 Pink; Opadry 15b28665 White; Opadry 15b50612 Blue; Opadry 15b52000 Yellow; Opadry 15b52070 Yellow; Opadry 15b53449 Orange; Opadry 15b58810 White; Opadry 15b86703 Brown; Opadry 15b91211 Green; Opadry 15b92484 Yellow; Opadry 15b96558 Brown; Opadry 16b38982 White; Opadry 16b5900 Yellow; Opadry 20014832 Pink; Opadry 20a28569 White; Opadry 20a52229 Yellow; Opadry 20a52560 Yellow; Opadry 20a52900 Yellow; Opadry 20a54211 Pink; Opadry 20a54239 Pink; Opadry 20a54614 Pink; Opadry 20a54616 Pink; Opadry 20a54900 Pink; Opadry 20a54901 Pink; Opadry 20a56500 Brown; Opadry 20a56694 Brown; Opadry 20a56788 Brown; Opadry 20a58806 White; Opadry 20a58916 White; Opadry 20a59015 Clear; Opadry 20a91487 Green; Opadry 20a99171 Blue; Opadry 20a99172 Blue; Opadry 20b11521 Green; Opadry 20b17583 Gray; Opadry 20b50135 Purple; Opadry 20b50184 Purple; Opadry 20b97160 Beige; Opadry 20c15347 Red; Opadry 20h52619 Yellow; Opadry 20h58983 White; Opadry 21k84964 Pink; Opadry 31f20963 Blue; Opadry 31f32870 Yellow; Opadry 32f540014 Pink; Opadry 32k14834 Pink; Opadry 32k23123 Orange; Opadry 33g12976 Yellow; Opadry 33g25171 Brick Red; Opadry 40114278 Pink; Opadry 80w 12319 Yellow; Opadry 80w22657 Amb Yellow; Opadry 80w-93032 Amb Orange; Opadry 85f14999 Pink; Opadry 85f19250 Clear; Opadry 85f21445 Green; Opadry 85f21446 Green; Opadry 85f21450 Green; Opadry 85g689183 White; Opadry 85g93096 Orange; Opadry Amb 80w52110 Yellow; Opadry Amb 80w62680 Yellow; Opadry Amb 80w62681 Yellow; Opadry Amb 80w64837 Pink; Opadry Amb 80w68912 White; Opadry Amb Oy-B-28920 White; Opadry I 03b22409 Yellow; Opadry I 03b23197 Orange; Opadry I 03b24658 Pink; Opadry Ii 03b10903 Blue; Opadry Ii 30f84515 Pink; Opadry Ii 31f22088 Yellow; Opadry Ii 31f23111 Orange; Opadry Ii 31f24128 Pink; Opadry Ii 31f24239 Pink; Opadry Ii 31f27625 Gray; Opadry Ii 31f32090 Yellow; Opadry Ii 31f58914 White; Opadry Ii 31k34575 Pink; Opadry Ii 31k34581 Pink; Opadry Ii 31k52633 Yellow; Opadry Ii 31k84972 Pink; Opadry Ii 32b10817 Blue; Opadry Ii 32f28553 White; Opadry Ii 32f505001 Blue; Opadry Ii 32f540002 Pink; Opadry Ii 32f540012 Pink; Opadry Ii 32f58900 White; Opadry Ii 32f84835 Pink; Opadry Ii 32k10054 Purple; Opadry Ii 32k12160 Yellow; Opadry Ii 32k12884 Yellow; Opadry Ii 32k12942 Yellow; Opadry Ii 32k12968 Yellow; Opadry Ii 32k13357 Orange; Opadry Ii 32k13699 Orange; Opadry Ii 32k14826 Pink; Opadry Ii 32k14827 Pink; Opadry Ii 32k14833 Pink; Opadry Ii 32k15649 Red; Opadry Ii 32k16706 Brown; Opadry Ii 32k17089 Tan; Opadry Ii 32k17573 Gray; Opadry Ii 33f28627 White; Opadry Ii 33g10148 Purple; Opadry Ii 33g10907 Blue; Opadry Ii 33g11635 Green; Opadry Ii 33g11938 Green; Opadry Ii 33g28435 White; Opadry Ii 33g28707 White; Opadry Ii 33g32605 Yellow; Opadry Ii 33g34594 Pink; Opadry Ii 33g92112 Yellow; Opadry Ii 39b18529 White; Opadry Ii 40 L14235 Pink; Opadry Ii 40 L17589 Gray; Opadry Ii 40014876 Pink; Opadry Ii 40b12994 Beige; Opadry Ii 40b97172 Yellow; Opadry Ii 40c10881 Blue; Opadry Ii 40c13396 Orange; Opadry Ii 40c18303 White; Opadry Ii 40110412 Purple; Opadry Ii 40110884 Blue; Opadry Ii 40111438 Green; Opadry Ii 40111588 Green; Opadry Ii 40112917 Yellow; Opadry Ii 40112979 Yellow; Opadry Ii 40113950 Orange; Opadry Ii 40114190 Pink; Opadry Ii 40114336 Pink; Opadry Ii 40114836 Pink; Opadry Ii 40117427 Beige; Opadry Ii 40117587 Gray; Opadry Ii 40192058 Yellow; Opadry Ii 40193159 Orange; Opadry Ii 40o93122 Orange; Opadry Ii 45f22481 Yellow; Opadry Ii 45f24512 Yellow; Opadry Ii 49b10882 Blue; Opadry Ii 49b13460 Orange; Opadry Ii 49b16716 Brown; Opadry Ii 57u92682 Yellow; Opadry Ii 57u97337 Tan; Opadry Ii 57u97508 Gray; Opadry Ii 85f10129 Purple; Opadry Ii 85f10245 Purple; Opadry Ii 85f10447 Purple; Opadry Ii 85f10919 Blue; Opadry Ii 85f11881 Green; Opadry Ii 85f12345 Yellow; Opadry Ii 85f12372 Yellow; Opadry Ii 85f12375 Yellow; Opadry Ii 85f13751 Orange; Opadry Ii 85f13980 Orange; Opadry Ii 85f140024 Pink; Opadry Ii 85f14452 Pink; Opadry Ii 85f16876 Brown; Opadry Ii 85f18378 White; Opadry Ii 85f18422 White; Opadry Ii 85f18442 White; Opadry Ii 85f22055 Yellow; Opadry Ii 85f22075 Yellow; Opadry Ii 85f22079 Yellow; Opadry Ii 85f23470 Pink; Opadry Ii 85f23499 Orange; Opadry Ii 85f23976 Orange; Opadry Ii 85f24033 Pink; Opadry Ii 85f24035 Pink; Opadry Ii 85f24307 Pink; Opadry Ii 85f28751 White; Opadry Ii 85f32121 Yellow; Opadry Ii 85f32157 Yellow; Opadry Ii 85f32547 Yellow; Opadry Ii 85f32782 Yellow; Opadry Ii 85f34610 Pink; Opadry Ii 85f62534 Yellow; Opadry Ii 85f64712 Pink; Opadry Ii 85f64732 Pink; Opadry Ii 85f66775 Brown; Opadry Ii 85f66815 Brown; Opadry Ii 85f90093 Purple; Opadry Ii 85f91135 Green; Opadry Ii 85f91136 Green; Opadry Ii 85f91137 Green; Opadry Ii 85f91238 Green; Opadry Ii 85f92008 Yellow; Opadry Ii 85f92204 Yellow; Opadry Ii 85f92621 Yellow; Opadry Ii 85f92716 Yellow; Opadry Ii 85f93042 Orange; Opadry Ii 85f93314 Orange; Opadry Ii 85f94172 Pink; Opadry Ii 85f94552 Pink; Opadry Ii 85f97458 Beige; Opadry Ii 85f97531 Gray; Opadry Ii 85f97533 Gray; Opadry Ii 85f99126 Blue; Opadry Ii 85g20583 Blue; Opadry Ii 85g56434 Maroon; Opadry Ii 85g56867 Brown; Opadry Ii 85g57680 Grey; Opadry Ii 85g62591 Yellow; Opadry Ii Oy-L-22903; Opadry Ii Oy-L-23028 Orange; Opadry Ii Oy-L-24802 Pink; Opadry Ii Oy-L-24803 Pink; Opadry Ii Oy-L-24808; Opadry Ii Oy-L-28900 White; Opadry Ii Oy-L-32920; Opadry Ii Pink 85g94027; Opadry Ii Pink 85g94065; Opadry Ii Red 85g94101; Opadry Ii Y-19-19054 Clear; Opadry Ii Y-19-7483 Clear; Opadry Ii Y-22-10274 Lavender; Opadry Ii Y-22-10508 Blue; Opadry Ii Y-22-10519 Blue; Opadry Ii Y-22-10538 Blue; Opadry Ii Y-22-10702 Blue; Opadry Ii Y-22-10764 Blue; Opadry Ii Y-22-11184 Green; Opadry Ii Y-22-11210 Green; Opadry Ii Y-22-11251 Green; Opadry Ii Y-22-12098 Yellow; Opadry Ii Y-22-12553 Yellow; Opadry Ii Y-22-12664 Yellow; Opadry Ii Y-22-12718 Yellow; Opadry Ii Y-22-12720 Pale Yellow; Opadry Ii Y-22-12780 Yellow; Opadry Ii Y-22-13034 Orange; Opadry Ii Y-22-13061 Orange; Opadry Ii Y-22-13083 Orange; Opadry Ii Y-22-13089 Orange; Opadry Ii Y-22-13167 Orange; Opadry Ii Y-22-13526 Orange; Opadry Ii Y-22-13577 Flesh; Opadry Ii Y-22-13603 Orange; Opadry Ii Y-22-13613 Orange; Opadry Ii Y-22-13663 Orange; Opadry Ii Y-22-14001 Pink; Opadry Ii Y-22-14701 Pink; Opadry Ii Y-22-15061; Opadry Ii Y-22-16562 Brown; Opadry Ii Y-22-16577 Brown; Opadry Ii Y-22-17025 Beige; Opadry Ii Y-22-17165 Beige; Opadry Ii Y-22-17221 Beige; Opadry Ii Y-22-17279 Beige; Opadry Ii Y-22-17515 Gray; Opadry Ii Y-22-18238 White; Opadry Ii Y-22-7719 White; Opadry Ii Y-30-10671a Blue;

Opadry Ii Y-30-10701 Blue; Opadry Ii Y-30-12705 Yellow; Opadry Ii Y-30-12736a Yellow; Opadry Ii Y-30-12737a Yellow; Opadry Ii Y-30-12842a Yellow; Opadry Ii Y-30-12863a Yellow; Opadry Ii Y-30-13091 Orange; Opadry Ii Y-30-13242a Orange; Opadry Ii Y-30-13616 Orange; Opadry Ii Y-30-13642a Orange; Opadry Ii Y-30-14700a Pink; Opadry Ii Y-30-14758 Pink; Opadry Ii Y-30-17295a Tan; Opadry Ii Y-30-17296a Beige; Opadry Ii Y-30-17340a Beige; Opadry Ii Y-30-17528 Gray; Opadry Ii Y-30-18037 White; Opadry Ii Ys-1-12524a; Opadry Ii Ys-1-19025a Clear; Opadry Ii Ys-1-7006 Clear; Opadry Ii Ys-22-13571 Orange; Opadry Ii Ys-22-17227a Beige; Opadry Ii Ys-22-18096 White; Opadry Ii Ys-30-12788a Yellow; Opadry Ii Ys-30-13641a Orange; Opadry Ii Ys-30-14743a Pink; Opadry i Ys-30-14777a Pink; Opadry Ii Ys-30-17265a Beige; Opadry Ii Ys-30-17271a Beige; Opadry Ii Ys-30-18105 White; Opadry 02b24864 Pink; Opadry Os-F-32867 Yellow; Opadry Oy-22959 Yellow; Opadry Oy-23050 Orange; Opadry Oy-27202 Tan; Opadry Oy-27301 Butterscotch; Opadry Oy-3736 Butterscotch; Opadry Oy-38924 White; Opadry Oy-52945 Yellow; Opadry Oy-54937 Pink; Opadry Oy-58900 White; Opadry Oy-7240 Clear; Opadry Oy-7300 White; Opadry Oy-8764h Orange; Opadry Oy-B-28920 White; Opadry Oy-B-32830; Opadry Oy-Gm-28900; Opadry Oy-L-27204 Tan; Opadry Oy-L-27205 Beige; Opadry Oy-L-28906; Opadry Oy-L-34836 Pink; Opadry Oy-Ls-20921 Blue; Opadry Oy-Ls-23016 Orange; Opadry Oy-Ls-23018 Orange; Opadry Oy-Ls-28908 White; Opadry Oy-Ls-28914 White; Opadry Oy-Ls-33111 Orange; Opadry Oy-Ls-37200 Buff; Opadry Oy-Ls-58900 White; Opadry Oy-S-1387 Pink; Opadry Oy-S-20007 Purple; Opadry Oy-S-20900 Blue; Opadry Oy-S-20901 Blue; Opadry Oy-S-21001 Green; Opadry Oy-S-21027 Green; Opadry Oy-S-22802 Yellow; Opadry Oy-S-22815 Yellow; Opadry Oy-S-22907 Yellow; Opadry Oy-S-23049 Orange; Opadry Oy-S-24900 Pink; Opadry Oy-S-24972 Pink; Opadry Oy-S-26529 Red; Opadry Oy-S-26530 Red; Opadry Oy-S-28833 White; Opadry Oy-S-28849 White; Opadry Oy-S-28876 White; Opadry Oy-S-28924 White; Opadry Oy-S-29019 Clear; Opadry Oy-S-30013 Purple; Opadry Oy-S-30913 Blue; Opadry Oy-S-30953 Blue; Opadry Oy-S-32921 Yellow; Opadry Oy-S-32986 Yellow; Opadry Oy-S-33016 Orange; Opadry Oy-S-34800 Pink; Opadry Oy-S-34817 Pink; Opadry Oy-S-34923 Pink; Opadry Oy-S-34995 Pink; Opadry Oy-S-38928; Opadry Oy-S-38944 White; Opadry Oy-S-52902 Yellow; Opadry Oy-S-53010 Orange; Opadry Oy-S-54902 Pink; Opadry Oy-S-54904 Pink; Opadry Oy-S-6937 Pink; Opadry Oy-S-7322 White; Opadry Oy-S-7399 White; Opadry Oy-S-9476 Brown; Opadry Oy-S-9603 White; Opadry Oy-Sr-34907; Opadry S-1-1666 Red; Opadry Y-1-1518 Pink; Opadry Y-1-17272a Beige; Opadry Y-1-17517 Gray; Opadry Y-1-2102 Yellow; Opadry Y-1-2132 Yellow; Opadry Y-1-2516 Orange; Opadry Y-1-2553 Orange; Opadry Y-1-2605 Beige; Opadry Y-1-3211 Green; Opadry Y-1-4205 Blue; Opadry Y-1-4234 Blue; Opadry Y-1-7000 White; Opadry Y-1-7000b White; Opadry Y-1-7000h White; Opadry Y-1-7006 Blue; Opadry Y-1-7503 Gray; Opadry Y-22-10501 Blue; Opadry Y-22-12721 Light Yellow; Opadry Y-22-12751 Yellow; Opadry Y-22-13558 Orange; Opadry Y-22-14525 Pink; Opadry Y-22-15008 Red; Opadry Y-22-15119 Red; Opadry Y-22-18238 White; Opadry Y-30-13168a Orange; Opadry Y-30-14565 Pink; Opadry Y-30-17267 Beige; Opadry Y-33g-27241 Beige; Opadry Y-5-10272a Lavender; Opadry Y-5-10300 Lavender; Opadry Y-5-10670 Blue; Opadry Y-5-12539 Yellow; Opadry Y-5-12544a Yellow; Opadry Y-5-12584 Yellow; Opadry Y-5-13512 Orange; Opadry Y-5-13513 Orange; Opadry Y-5-14530a Pink; Opadry Y-5-1727 Red; Opadry Y-5-2028 Yellow; Opadry Y-5-2042 Yellow; Opadry Y-5-2086 Yellow; Opadry Y-5-2312 Yellow; Opadry Y-5-2328 Orange; Opadry Y-5-2371 Orange; Opadry Y-5-2394 Orange; Opadry Y-5-2450 Orange; Opadry Y-5-2644 Beige; Opadry Y-5-2646 Beige; Opadry Y-5-3140 Green; Opadry Y-5-3171 Green; Opadry Y-5-3193 Green; Opadry Y-5-3296 Green; Opadry Y-5-4129 Blue; Opadry Y-5-4270 Blue; Opadry Y-5-4287 Blue; Opadry Y-5-4295 Blue; Opadry Y-5-6233 Light Orange; Opadry Y-5-6301 Yellow; Opadry Y-5-6308; Opadry Y-5-7058 White; Opadry Y-5-7068 White; Opadry Y-5-7072 White; Opadry Y-5-7524 Grey; Opadry Y-5-8050 Black; Opadry Y-5-9006 Brown; Opadry Y-5-9020 Brown; Opadry Yellow; Opadry Yps-7-2127; Opadry Ys-1-003 White; Opadry Ys-1-10010 Purple; Opadry Ys-1-10291 Lavender; Opadry Ys-1-10523a Blue; Opadry Ys-1-10525 Blue; Opadry Ys-1-10533a; Opadry Ys-1-10542a Blue; Opadry Ys-1-10547a Blue; Opadry Ys-1-10563 Blue; Opadry Ys-1-10613a Blue; Opadry Ys-1-10618; Opadry Ys-1-10629; Opadry Ys-1-10654a Blue; Opadry Ys-1-10682 Blue; Opadry Ys-1-10690a Blue; Opadry Ys-1-10699 Blue; Opadry Ys-1-10745 Blue; Opadry Ys-1-10748a Light Blue; Opadry Ys-1-10755 Blue; Opadry Ys-1-10783a Blue; Opadry Ys-1-11000 Pink; Opadry Ys-1-11051 Green; Opadry Ys-1-11060 Green; Opadry Ys-1-1107 Green; Opadry Ys-1-11075a Green; Opadry Ys-1-11113 Green; Opadry Ys-1-11171 Green; Opadry Ys-1-11234 Green; Opadry Ys-1-11305 Green; Opadry Ys-1-11369 Green; Opadry Ys-1-1246 Pink; Opadry Ys-1-1252 Pink; Opadry Ys-1-12524a Yellow; Opadry Ys-1-12525a Yellow; Opadry Ys-1-12526a Yellow; Opadry Ys-1-12529 Yellow; Opadry Ys-1-12541 Yellow; Opadry Ys-1-1256-A Yellow; Opadry Ys-1-12573 Yellow; Opadry Ys-1-12581 Yellow; Opadry Ys-1-1262 Pink; Opadry Ys-1-12625 Yellow; Opadry Ys-1-12702a Yellow; Opadry Ys-1-12726a Yellow; Opadry Ys-1-12732 Yellow; Opadry Ys-1-1277 Pink; Opadry Ys-1-12789 Yellow; Opadry Ys-1-12826 Yellow; Opadry Ys-1-1283 Pink; Opadry Ys-1-12844 Yellow; Opadry Ys-1-12847 Yellow; Opadry Ys-1-1298 Pink; Opadry Ys-1-13013 Peach; Opadry Ys-1-13065a Orange; Opadry Ys-1-13119 Orange; Opadry Ys-1-13121 Yellow; Opadry Ys-1-13148a Orange; Opadry Ys-1-13214 Orange; Opadry Ys-1-13269 Orange; Opadry Ys-1-13271 Orange; Opadry Ys-1-13555 Orange; Opadry Ys-1-13591a Orange; Opadry Ys-1-13664a Orange; Opadry Ys-1-13673a Orange; Opadry Ys-1-13675a Orange; Opadry Ys-1-14012 Pink; Opadry Ys-1-14129 Pink; Opadry Ys-1-14130 Pink; Opadry Ys-1-14142 Pink; Opadry Ys-1-1418 Pink; Opadry Ys-1-1441g; Opadry Ys-1-1448g Pink; Opadry Ys-1-14518a Pink; Opadry Ys-1-14519a Pink; Opadry Ys-1-14532 Pink; Opadry Ys-1-1454 Pink; Opadry Ys-1-14555a Pink; Opadry Ys-1-14559 Pink; Opadry Ys-1-1456g Pink; Opadry Ys-1-14587a Pink; Opadry Ys-1-14593a Pink; Opadry Ys-1-14595 Pink; Opadry Ys-1-14608a; Opadry Ys-1-14643a Pink; Opadry Ys-1-14725 Pink; Opadry Ys-1-14756a Pink; Opadry Ys-1-14779a Pink; Opadry Ys-1-15050 Red; Opadry Ys-1-1510 Pink; Opadry Ys-1-1528 Pink; Opadry Ys-1-1543 Pink; Opadry Ys-1-15585a Red; Opadry Ys-1-16002 Maroon; Opadry Ys-1-16518a Brown; Opadry Ys-1-17169a; Opadry Ys-1-17180a Beige; Opadry Ys-1-17181a Beige; Opadry Ys-1-17192a; Opadry Ys-1-17209 Beige; Opadry Ys-1-17220; Opadry Ys-1-17222a Tan; Opadry Ys-1-17235a Peach; Opadry Ys-1-1724 Red; Opadry Ys-1-17274a Beige; Opadry Ys-1-17277a Beige; Opadry Ys-1-17307a Butterscotch; Opadry Ys-1-17505a Gray; Opadry Ys-1-17506a Gray; Opadry Ys-1-1751g Red; Opadry Ys-1-1755 Gray; Opadry Ys-1-18005 White; Opadry Ys-1-18022

White; Opadry Ys-1-18027 White; Opadry Ys-1-18027a White; Opadry Ys-1-18028 White; Opadry Ys-1-18097a White; Opadry Ys-1-1811 Red; Opadry Ys-1-18111 White; Opadry Ys-1-18130a White; Opadry Ys-1-1814 Red; Opadry Ys-1-18177a White; Opadry Ys-1-18202a White; Opadry Ys-1-18229 White; Opadry Ys-1-1846 Red; Opadry Ys-1-1847 Red; Opadry Ys-1-1891 Red; Opadry Ys-1-19025-A Clear; Opadry Ys-1-2007 Yellow; Opadry Ys-1-2013 Yellow; Opadry Ys-1-2053 White; Opadry Ys-1-2053 Yellow; Opadry Ys-1-2063 Yellow; Opadry Ys-1-2074 Yellow; Opadry Ys-1-2083 Yellow; Opadry Ys-1-2115 Yellow; Opadry Ys-1-2122 Yellow; Opadry Ys-1-2134 Yellow; Opadry Ys-1-2135 Yellow; Opadry Ys-1-2136 Yellow; Opadry Ys-1-2141 Yellow; Opadry Ys-1-2152 Yellow; Opadry Ys-1-2167 Yellow; Opadry Ys-1-2181 Yellow; Opadry Ys-1-2184 Gold; Opadry Ys-1-2186 Yellow; Opadry Ys-1-2192 Yellow; Opadry Ys-1-2305 Orange; Opadry Ys-1-2308 Dark Orange; Opadry Ys-1-2344 Yellow; Opadry Ys-1-2383 Orange; Opadry Ys-1-2398 Orange; Opadry Ys-1-2449 Orange; Opadry Ys-1-2455 Red; Opadry Ys-1-2465; Opadry Ys-1-2487 Orange; Opadry Ys-1-2522 Orange; Opadry Ys-1-2526 Orange; Opadry Ys-1-2527 Orange; Opadry Ys-1-2534; Opadry Ys-1-2546 Orange; Opadry Ys-1-2548 Orange; Opadry Ys-1-2549 Orange; Opadry Ys-1-2558 Orange; Opadry Ys-1-2563 Orange; Opadry Ys-1-2564; Opadry Ys-1-2578 Orange; Opadry Ys-1-2596 Orange; Opadry Ys-1-2604 Beige; Opadry Ys-1-2612 Beige; Opadry Ys-1-2619; Opadry Ys-1-2621 Rust; Opadry Ys-1-2623 Brown; Opadry Ys-12630 Yellow; Opadry Ys-1-2635 Tan; Opadry Ys-1-2660 Salmon; Opadry Ys-1-2665 Beige; Opadry Ys-1-2669 Rust; Opadry Ys-1-2671 Beige; Opadry Ys-1-3105 Green; Opadry Ys-1-3130 Green; Opadry Ys-1-3134 Green; Opadry Ys-1-3146 Green; Opadry Ys-1-3147; Opadry Ys-1-3166 Green; Opadry Ys-1-3256 Green; Opadry Ys-1-3288 Green; Opadry Ys-1-4014 Blue; Opadry Ys-1-4018 Blue; Opadry Ys-1-4112 Blue; Opadry Ys-1-4137 Blue; Opadry Ys-1-4215; Opadry Ys-1-4216; Opadry Ys-1-4221 Blue; Opadry Ys-1-4228 Blue; Opadry Ys-1-4229 Blue; Opadry Ys-1-4234 Blue; Opadry Ys-1-4235 Blue; Opadry Ys-1-4236 Blue; Opadry Ys-1-4240 Blue; Opadry Ys-1-4241 Blue; Opadry Ys-1-4245 Blue; Opadry Ys-1-4249 Blue; Opadry Ys-1-4251 Blue; Opadry Ys-1-4254; Opadry Ys-1-4255; Opadry Ys-1-4256 Blue; Opadry Ys-1-4282 Blue; Opadry Ys-1-4298 Blue; Opadry Ys-14644 Pink; Opadry Ys-1-4700 Purple; Opadry Ys-1-4710; Opadry Ys-1-4739 Lavender; Opadry Ys-1-4812 Lavender; Opadry Ys-1-4845 Purple; Opadry Ys-1-6275 Orange; Opadry Ys-1-6300; Opadry Ys-1-6312 Yellow; Opadry Ys-1-6318 Yellow; Opadry Ys-1-6320 Yellow; Opadry Ys-1-6357 Yellow; Opadry Ys-1-6370g Yellow; Opadry Ys-1-6378g Yellow; Opadry Ys-1-6381 Yellow; Opadry Ys-1-6382g Yellow; Opadry Ys-1-7000e White; Opadry Ys-1-7002 White; Opadry Ys-1-7003 White; Opadry Ys-1-7003h White; Opadry Ys-1-7006 Clear; Opadry Ys-1-7022 Off-White; Opadry Ys-1-7027 White; Opadry Ys-1-7040 White; Opadry Ys-1-7052 White; Opadry Ys-1-7059 White; Opadry Ys-1-7060 White; Opadry Ys-1-7079 White; Opadry Ys-1-7086 White; Opadry Y-S-17191 Brown; Opadry Ys-1-7444g White; Opadry Ys-1-7449 White; Opadry Ys-1-7472 Clear; Opadry Ys-1-7507 Grey; Opadry Ys-1-7552 Grey; Opadry Ys-1-7700 White; Opadry Ys-1-7706 Clear; Opadry Ys-1-7706g White; Opadry Ys-1-7724 White; Opadry Ys-1-8325 Beige; Opadry Ys-1-8343g Beige; Opadry Ys-1-8345g Beige; Opadry Ys-1-8608 Orange; Opadry Ys-1-8619 Orange; Opadry Ys-1-89193 Clear; Opadry Ys-1-9011 Brown; Opadry Ys-1-9012 Brown; Opadry Ys-1r-1418 Pink; Opadry Ys-1r-7006 Clear; Opadry Ys-2-10657 Blue; Opadry Ys-2-19071a Clear; Opadry Ys-2-19114a Clear; Opadry Ys-22-16576 Brown; Opadry Ys-22-18119 White; Opadry Ys-2-7013 Clear; Opadry Ys-2-7063 White; Opadry Ys-3-7011 Clear; Opadry Ys-3-7031 Clear; Opadry Ys-3-7413 Clear; Opadry Ys-5-12575 Yellow; Opadry Ys-5-12576 Yellow; Opadry Ys-5-1260 Pink; Opadry Ys-5-1296 Pink; Opadry Ys-5-17266 Tan; Opadry Ys-5-18011 White; Opadry Ys-5-18068 White; Opadry Ys-5-18074 White; Opadry Ys-5-19010 Clear; Opadry Ys-5-2085 Yellow; Opadry Ys-5-2370 Orange; Opadry Ys-5-3116 Green; Opadry Ys-5-4277 Blue; Opadry Ys-5-4278 Blue; Opadry Ys-5-7017; Opadry Ys-5-7042 Clear; Opadry Ys-5-7068; Opadry Ys-5-7099 White; Opaglos 2 97w19206 Clear; Opaglos 6000 White; Opaglos Gs 2-0300; Opaglos Gs 2-0310; Opaglos Ii 97w90646 Blue; Opaglos S 0750; Opalux As 1406 Pink; Opalux As 1459 Pink; Opalux As 1589 Pink; Opalux As 2006 Yellow; Opalux As 2007 Yellow; Opalux As 2052 Yellow; Opalux As 2062 Yellow; Opalux As 2086 Chartreuse; Opalux As 2094; Opalux As 2167 Yellow; Opalux As 2236; Opalux As 2269 Yellow; Opalux As 2324 Orange; Opalux As 2336 Orange; Opalux As 2395 Peach; Opalux As 2413; Opalux As 2433 Orange; Opalux As 2490 Coral; Opalux As 2498 Orange; Opalux As 2553 Orange; Opalux As 2612; Opalux As 2613 Tan; Opalux As 2620-B Tan; Opalux As 2676 Salmon Jasper Red; Opalux As 2754; Opalux As 2768; Opalux As 2787 Butterscotch; Opalux As 3140 Green; Opalux As 3287; Opalux As 3288 Green; Opalux As 3308 Green; Opalux As 3348-C Green; Opalux As 3376; Opalux As 3378-A Green; Opalux As 3381; Opalux As 3389 Green; Opalux As 3391 Green; Opalux As 3942 Maroon; Opalux As 4025; Opalux As 4151 Blue; Opalux As 4188 Blue; Opalux As 4193 Blue; Opalux As 4258 Blue; Opalux As 4270 Blue; Opalux As 4800 Lavender; Opalux As 4854 Lavender; Opalux As 4855 Purple; Opalux As 4891; Opalux As 5005-A Red; Opalux As 5034 Red; Opalux As 5107; Opalux As 5162 Green; Opalux As 5178 Green; Opalux As 5203 Green; Opalux As 5212 Green; Opalux As 7000-B; Opalux As 7000-P White; Opalux As 7001; Opalux As 7535 Gray; Opalux As 8010-A Black; Opalux As 8050-L Black; Opalux As 9010 Brown; Opalux As 9050 Brown; Opalux As-1475 Pink; Opalux As-9030 Brown; Opalux Blue; Opalux Green; Opaque Blue 100; Opaque Blue 147; Opaque Blue 605; Opaque Brown 85 Bfj; Opaque Green 1664; Opaque Green 97; Opaque Green/Flesh; Opaque Maroon 6 Dar; Opaque Pink 0439; Opaque White 001; Opaque White 002; Opaque White 535; Opaque White 536; Opaque White 538; Opaque White 8; Opaspray 3-1700; Opaspray 3-1810; Opaspray 3-1820; Opaspray 3-1830; Opaspray Im-176; Opaspray K-1-1230 Pink; Opaspray K-1-1243; Opaspray K-1-1254; Opaspray K-1-1279; Opaspray K-1-1289 Pink; Opaspray K-1-14016 Pink; Opaspray K-1-1413 Pink; Opaspray K-1-1414 Pink; Opaspray K-1-1432; Opaspray K-1-1437; Opaspray K-1-1455 Pink; Opaspray K-1-1526 Pink; Opaspray K-1-1563 Pink; Opaspray K-1-1573 Lavender; Opaspray K-1-1574; Opaspray K-1-1584; Opaspray K-1-1719 Red; Opaspray K-1-2004 Yellow; Opaspray K-1-2013 Yellow; Opaspray K-1-2043 Yellow; Opaspray K-1-2182 Yellow; Opaspray K-1-2186 Yellow; Opaspray K-1-2216-A Yellow; Opaspray K-1-2227 Yellow; Opaspray K-1-2228 Yellow; Opaspray K-1-2239; Opaspray K-1-2240 Yellow; Opaspray K-1-2256 Yellow; Opaspray K-1-2275 Yellow; Opaspray K-1-2300 Peach; Opaspray K-1-2301 Peach; Opaspray K-1-2303 Orange; Opaspray K-1-2304 Orange; Opaspray K-1-2314 Orange; Opaspray K-1-2327 Orange; Opaspray K-1-2330 Orange; Opaspray K-1-2335 Orange; Opaspray K-1-2406

Orange; Opaspray K-1-2410 Orange; Opaspray K-1-2417 Orange; Opaspray K-1-2430; Opaspray K-1-2441 Orange; Opaspray K-1-2471 Orange; Opaspray K-1-2473; Opaspray K-1-2492; Opaspray K-1-2531; Opaspray K-1-2533 Orange; Opaspray K-1-2554; Opaspray K-1-2568 Orange; Opaspray K-1-2570 Orange; Opaspray K-1-2588 Orange; Opaspray K-1-2614 Beige; Opaspray K-1-2621 Brown; Opaspray K-1-2626 Orange; Opaspray K-1-2656 Beige; Opaspray K-1-2670 Tan; Opaspray K-1-2674 Beige; Opaspray K-1-2711; Opaspray K-1-2723 Butterscotch; Opaspray K-1-2837; Opaspray K-1-3000; Opaspray K-1-3142 Green; Opaspray K-1-3144 Green; Opaspray K-1-3147; Opaspray K-1-3148 Green; Opaspray K-1-3156; Opaspray K-1-3173 Green; Opaspray K-1-3178 Green; Opaspray K-1-3197 Green; Opaspray K-1-3202 Green; Opaspray K-1-3209 Green; Opaspray K-1-3220 Green; Opaspray K-1-3227; Opaspray K-1-3300-A Green; Opaspray K-1-3300-C Green; Opaspray K-1-3843; Opaspray K-1-4108 Blue; Opaspray K-1-4119; Opaspray K-1-4122 Blue; Opaspray K-1-4136 Blue; Opaspray K-1-4205 Blue; Opaspray K-1-4210-A; Opaspray K-1-4213 Blue; Opaspray K-1-4214; Opaspray K-1-4227; Opaspray K-1-4234 Blue; Opaspray K-1-4235 Blue; Opaspray K-1-4728; Opaspray K-1-4731 Purple; Opaspray K-1-4743 Lavender; Opaspray K-1-4786; Opaspray K-1-7000 White; Opaspray K-1-70008 White; Opaspray K-1-7000b; Opaspray K-1-7076; Opaspray K-1-9027 Brown; Opaspray K-1-9039-L Brown; Opaspray K-1-9060 Red; Opaspray K-1-9080 Brown; Opaspray K-1-9112 Brown; Opaspray L-2113; Opaspray L-3305 Green; Opaspray L-3306 Green; Opaspray L-7000 White; Opaspray M-1-2042; Opaspray M-1-3459 B Orange; Opaspray M-1-4395b Blue; Opaspray M-1-7111-B; Opaspray M-1-711b White; Opaspray M-1-7120 White; Opaspray M-1-8429 Yellow; Opaspray Wd-1270 Pink; Opatint Ad-22901 Yellow; Opatint Ad-25000 Red; Opatint Dd-14000 Pink; Opatint Dd-18000 White; Orange Juice; Orange Juice, Synthetic; Orange Oil; Orange Oil Terpeneless; Orange Peel; Orvus K Liquid; Oxidronate Disodium; Palm Kernel Oil; Palm Oil-Soybean Oil, Hydrogenated; Palmitamine Oxide; Palmitic Acid; Parabens; Paraffin; Parfum Creme 45/3; Parmacoat 606; Pd Base-1000; Peanut Oil; Pectin; Peg 6-32 Stearate/Glycol Stearate; Peg Vegetable Oil; Peg/Ppg-18/18 Dimethicone; Peg-100 Stearate; Peg-12 Glyceryl Laurate; Peg-120 Glyceryl Stearate; Peg-120 Methyl Glucose Dioleate; Peg-15 Cocamine; Peg-150 Distearate; Peg-2 Stearate; Peg-20 Methyl Glucose Sesquistearate; Peg-20 Sorbitan Isostearate; Peg-20 Stearate; Peg-22 Methyl Ether/Dodecyl Glycol Copolymer; Peg-25 Propylene Glycol Stearate; Peg-4 Dilaurate; Peg-4 Laurate; Peg-40 Castor Oil; Peg-40 Sorbitan Diisostearate; Peg-45/Dodecyl Glycol Copolymer; Peg-5 Oleate; Peg-50 Stearate; Peg-54 Hydrogenated Castor Oil; Peg-6 Isostearate; Peg-60 Hydrogenated Castor Oil; Peg-7 Methyl Ether; Peg-75 Lanolin; Peg-8 Caprylic/Capric Glycerides; Peg-8 Laurate; Peg-8 Stearate; Pegoxol 7 Stearate; Pentadecalactone; Pentaerythritol Cocoate; Pentasodium Pentetate; Pentetate Calcium Trisodium; Pentetic Acid; Peppermint Oil; Perflutren; Perfume 25677; Perfume B-8412; Perfume Bouquet; Perfume E-1991; Perfume Gd 5604; Perfume Tana 90/42 Scba; Perfume W-1952-1; Petrolatum; Petroleum Distillates; Pharmaburst B1; Pharmaburst B2; Pharmaburst C1; Phenol; Phenonip; Phenoxyethanol; Phenylalanine; Phenylethyl Alcohol; Phenylmercuric Acetate; Phenylmercuric Nitrate; Phosphate Ion; Phospholipid; Phosphoric Acid; Pigment Blend 86620 Brown; Pigment Blend Pb-2145 Red; Pigment Blend Pb-2289 Yellow; Pigment Blend Pb-2389 Off-White; Pigment Blend Pb-2417 Pink; Pigment Blend Pb-2418 Black; Pigment Blend Pb-24899 Ih; Pine Needle Oil (*Pinus sylvestris*); Pineapple; Piperazine; Piperazine Hexahydrate; Placebo; Plasacryl; Plastibase-50w; Plusweet; Polacrilin; Polacrilin Potassium; Polidronium Chloride; Polish Wax 7625 P 100; Polishing Solution Im-182; Poloxamer; Poloxamer 70; Poloxamer 124; Poloxamer 181; Poloxamer 182; Poloxamer 188; Poloxamer 237; Poloxamer 331; Poloxamer 338; Poloxamer 407; Poly(Bis (P-Carboxyphenoxy)Propane Anhydride):Sebacic Acid; Poly(Dimethylsiloxane/Methylvinylsiloxane/Methylhydrogensiloxane) Dimethylvinyl Or Dimethylhydroxy Or Trimethyl Endblocked; Poly(Dl-Lactic-Co-Glycolic Acid), (50:50; 12000 Mw); Poly(Dl-Lactic-Co-Glycolic Acid), (75:25; 20000 Mw); Poly(D-Lactic-Co-Glycolic Acid), Ethyl Ester Terminated, (50:50; 12000 Mw); Poly(Methyl Acrylate-Co-Methyl Methacrylate-Co-Methacrylic Acid 7:3:1; 280000 Mw); Polyacrylic Acid (250000 Mw); Polybutene (1400 Mw); Polycarbophil; Polydextrose; Polydextrose K; Polyester; Polyester Polyamine Copolymer; Polyester Rayon; Polyester/Ethylene-Vinyl Acetate; Polyethylene Glycol 1000; Polyethylene Glycol 1450; Polyethylene Glycol 1500; Polyethylene Glycol 200; Polyethylene Glycol 20000; Polyethylene Glycol 300; Polyethylene Glycol 3000; Polyethylene Glycol 3350; Polyethylene Glycol 3500; Polyethylene Glycol 400; Polyethylene Glycol 4000; Polyethylene Glycol 4500; Polyethylene Glycol 540; Polyethylene Glycol 600; Polyethylene Glycol 6000; Polyethylene Glycol 7000; Polyethylene Glycol 800; Polyethylene Glycol 8000; Polyethylene Glycol 900; Polyethylene Glycols; Polyethylene High Density Containing Ferric Oxide Black (<1%); Polyethylene Low Density Containing Barium Sulfate (20-24%); Polyethylene Oxide 1000000; Polyethylene Oxide 200000; Polyethylene Oxide 2000000; Polyethylene Oxide 600000; Polyethylene Oxide 7000000; Polyethylene Oxide 900000; Polyethylene T; Polyethylene Terephthalates; Polygalacturonic Acid; Polyglactin; Polyglyceryl-10 Oleate; Polyglyceryl-10 Tetralinoleate; Polyglyceryl-3 Oleate; Polyglyceryl-4 Oleate; Polyhydroxyethyl Methacrylate; Polyisobutylene; Polyisobutylene (1100000 Mw); Polyisobutylene (2300 Mw); Polyisobutylene (35000 Mw); Polyisobutylene (55000 Mw); Polyisobutylene (800000 Mw); Polyisobutylene Low Molecular Weight; Polyisobutylene Medium Molecular Weight; Polyisobutylene/Polybutene Adhesive; Polylactide; Polyols; Polyoxyethylene-Polyoxypropylene 1800; Polyoxyethylene Alcohols; Polyoxyethylene Fatty Acid Esters; Polyoxyethylene Propylene; Polyoxyl 20 Cetostearyl Ether; Polyoxyl 35 Castor Oil; Polyoxyl 40 Hydrogenated Castor Oil; Polyoxyl 40 Stearate; Polyoxyl 6 And Polyoxyl 32 Palmitostearate; Polyoxyl Distearate; Polyoxyl Glyceryl Stearate; Polyoxyl Lanolin; Polyoxyl Palmitate; Polyoxyl Stearate; Polyoxylethylene Isononylphenyl Ester; Polypropylene; Polypropylene Glycol; Polyquaternium-10; Polyquaternium-7 (70/30 Acrylamide/Dadmac; 1600000 Mw); Polysaccharides; Polysaccharides Soy; Polysiloxane; Polysorbate 20; Polysorbate 40; Polysorbate 60; Polysorbate 65; Polysorbate 80; Polysorbate 85; Polystyrene Sulfonic Acid; Polyurethane; Polyvinyl Acetate; Polyvinyl Acetate Phthalate; Polyvinyl Alcohol; Polyvinyl Alcohol Graft Polyethylene Glycol Copolymer (3:1; 45000 Mw); Polyvinyl Chloride; Polyvinyl Chloride-Polyvinyl Acetate Copolymer; Polyvinylacetal; Polyvinylpyridine; Polyvinylpyrrolidone Ethylcellulose; Ponceau 3r; Ponceau Xylidine; Poppy Seed Oil; Potassium; Potassium Acetate; Potassium Alum; Potassium Bicarbonate; Potassium Bisulfite; Potassium Bitartrate; Potassium Carbonate; Potassium Chloride; Potassium Citrate; Potassium Citrate Anhydrous; Potassium Hydroxide; Potassium Metabisulfite; Potassium Metaphosphate; Potassium Phosphate, Dibasic; Potassium Phosphate, Monobasic; Potassium Soap; Potassium Sorbate; Povidone Acrylate Copolymer; Povidone Hydrogel; Povidone K12; Povidone K17; Povidone K25; Povidone K26/28; Povidone K29/32; Povidone K30; Povidone K90; Povidone/Eicosene Copolymer; Povidones; Powdered Cellulose; Ppg-11 Stearyl Ether; Ppg-12/Smdi Copolymer; Ppg-15 Stearyl Ether; Ppg-20 Methyl Glucose Ether Distearate; Ppg-26 Oleate; Pramoxine Hydrochloride; Primajel; Primary Taste Modifier No. 29275; Product Wat; Proline; Promulgen D; Promulgen G; Propane; Propenyl Guaethol; Propyl Gallate; Propylene Carbonate; Propylene Glycol; Propylene Glycol-Lecithin; Propylene Glycol Alginate; Propylene Glycol Diacetate; Propylene Glycol Dicaprylate; Propylene Glycol Laurates; Propylene Glycol Monolaurate; Propylene Glycol Monopalmitostearate; Propylene Glycol Monostearate; Propylene Glycol Ricinoleate; Propylene Glycol/Diazolidinyl Urea/Methylparaben/Propylparben; Propylparaben; Propylparaben Sodium; Prosolv; Prosolv 50; Prosolv 90; Prosolv Hd 90; Prosolv Smcc 50; Prosolv Smcc 90; Prosweet; Prosweet 604; Prosweet K; Protamine Sulfate; Protein Hydrolysate; Pvm/Ma Copolymer; Quaternium-15; Quaternium-15 Cis-Form; Quaternium-52; Ra-2397; Ra-3011; Raspberry; Raspberry Juice; Rhodamine B; Riboflavin; Rosin; Saccharin; Saccharin Calcium; Saccharin Sodium; Saccharin Sodium Anhydrous; Safflower Oil; Scandium; Sd Alcohol 3a; Sd Alcohol 3a Anhydrous; Sd Alcohol 40; Sd Alcohol 40-2; Sd Alcohol 40b; Sepifilm Lp-761 Blanc; Sepineo P 600; Sepisperse Ap 3527; Serine; Sesame Oil; Shea Butter; Shellac; Shellac P.V.P. Solution No. 4; Silastic Brand Medical Grade Tubing; Silastic Medical Adhesive, Silicone Type A; Silicon; Silicon Dioxide; Silicone; Silicone Emulsion; Silicone/Polyester Film Strip; Simethicone; Simethicone C; Simethicone Emulsion; Sipon Ls 20np; Soap; Sodium 1,2-Ethanedisulfonate; Sodium 2-Naphthalenesulfonate; Sodium Acetate; Sodium Acetate Anhydrous; Sodium Alginate; Sodium Alkyl Sulfate; Sodium Aluminium Silicate; Sodium Ascorbate; Sodium Benzoate; Sodium Bicarbonate; Sodium Bisulfate; Sodium Bisulfate Acetone; Sodium Bisulfite; Sodium Bitartrate; Sodium Borate; Sodium Carbonate; Sodium Carbonate Decahydrate; Sodium Carbonate Monohydrate; Sodium Carboxymethyl.Beta.-Glucan (Ds 0.65-0.85); Sodium Caseinate; Sodium Cellulose; Sodium Cetostearyl Sulfate; Sodium Chlorate; Sodium Chloride; Sodium Chlorite; Sodium Cholesteryl Sulfate; Sodium Citrate; Sodium Citrate; Sodium Cocoyl Sarcosinate; Sodium Cyclamate; Sodium Desoxycholate; Sodium Dithionite; Sodium Dodecylbenzenesulfonate; Sodium Ethylparaben; Sodium Formaldehyde Sulfoxylate; Sodium Gluconate; Sodium Hydroxide; Sodium Hypochlorite; Sodium Iodide; Sodium Lactate; Sodium Lactate, L-; Sodium Laureth-2 Sulfate; Sodium Laureth-3 Sulfate; Sodium Laureth-5 Sulfate; Sodium Lauroyl Sarcosinate; Sodium Lauryl Sulfate; Sodium Lauryl Sulfoacetate; Sodium Metabisulfite; Sodium Nitrate; Sodium Oleate; Sodium Phosphate; Sodium Phosphate Dihydrate; Sodium Phosphate P-32; Sodium Phosphate, Dibasic; Sodium Phosphate, Dibasic Dihydrate; Sodium Phosphate, Dibasic Dodecahydrate; Sodium Phosphate, Dibasic, Anhydrous; Sodium Phosphate, Dibasic, Dodecahydrate; Sodium Phosphate, Dibasic, Heptahydrate; Sodium Phosphate, Monobasic, Anhydrous; Sodium Phosphate, Monobasic, Dihydrate; Sodium Phosphate, Monobasic, Monohydrate; Sodium Phosphate, Monobasic; Sodium Phosphate, Tribasic; Sodium Phosphate, Tribasic, Anhydrous; Sodium Phosphate, Tribasic, Monohydrate; Sodium Phosphite; Sodium Polyacrylate; Sodium Polyacrylate (2500000 Mw); Sodium Polymetaphosphate; Sodium Polystyrene Sulfonate; Sodium Propionate; Sodium Pyrophosphate; Sodium Pyrrolidone Carboxylate; Sodium Starch Glycolate Type A Corn; Sodium Starch Glycolate Type A Potato; Sodium Starch Glycolate Type B Potato; Sodium Stearate; Sodium Stearyl Fumarate; Sodium Succinate Hexahydrate; Sodium Sulfate; Sodium Sulfate Anhydrous; Sodium Sulfite; Sodium Sulfosuccinated Undecyclenic Monoalkylolamide; Sodium Tartrate; Sodium Thioglycolate; Sodium Thiomalate; Sodium Thiosulfate; Sodium Thiosulfate Anhydrous; Sodium Trimetaphosphate; Sodium Tripolyphosphate; Sodium Xylenesulfonate; Solvent Red 49; Somay 44; Sorbic Acid; Sorbitan; Sorbitan Isostearate; Sorbitan Monolaurate; Sorbitan Monooleate; Sorbitan Monopalmitate; Sorbitan Monostearate; Sorbitan Sesquioleate; Sorbitan Trioleate; Sorbitan Tristearate; Sorbitol; Sorbitol Special Polyol Solution; Sorbitol-Glycerin Blend; Soybean; Soybean Oil; Spearmint; Spearmint Oil; Spectrablend Csl-15764 (Blue); Spermaceti; Squalane; Stannous 2-Ethylhexanoate; Stannous Chloride; Stannous Chloride Anhydrous; Stannous Fluoride; Stannous Tartrate; Star Anise; Starch; Starch 7150; Starch 825; Starch 826; Starch, Corn; Starch, Modified; Starch, Potato; Starch, Pregelatinized; Starch, Rice; Starch, Tapioca; Starch, Wheat; Stearalkonium Chloride; Stearalkonium Hectorite/Propylene Carbonate; Stearamidoethyl Diethylamine; Stearates; Steareth-10; Steareth-100; Steareth-2; Steareth-20; Steareth-21; Steareth-40; Stearic Acid; Stearic Diethanolamide; Stear-O-Wet C; Stear-O-Wet M; Stearoxytrimethylsilane; Stearoyl Polyoxylglycerides; Steartrimonium Hydrolyzed Animal Collagen; Stearyl Alcohol; Strawberry; Styrene/Isoprene/Styrene Block Copolymer; Succimer; Succinic Acid; Sucralose; Sucrose; Sucrose Laurate; Sucrose Palmitate; Sucrose Polyesters; Sucrose Stearate; Sucrose Stearate/Sucrose Distearate; Sugar Liquid Type No. 0; Sugar/Starch Insert Granules; Sulfacetamide Sodium; Sulfur Dioxide; Sulfuric Acid; Sulfurous Acid; Surelease E-719010 Clear; Surelease E-7-7050; Surfactol Qs; Synchron Oral Carrier; Synchron Oral Carrier Base Kf; Synchron Oral Carrier Vehicle Type Em; Synthetic Iron Oxides; Tagatose; Talc; Talc 127; Talc Triturate; Tall Oil; Tallow Glycerides; Tartaric Acid; Tartaric Acid, Dl-; Tegacid; Tenox; Tenox-2; Terpene Resin; Tert-Butyl Alcohol; Tert-Butyl Hydroperoxide; Tert-Butylhydroquinone; Tetrachloroethylene; Tetrakis(2-Methoxyisobutylisocyanide)Copper(I) Tetrafluoroborate; Tetrapropyl Orthosilicate; Tetrofosmin; Thimerosal; Threonine; Thymol; Timing Solution Clear N-7; Tin; Titanium Dioxide; Tocopherol; Tocophersolan; Tolterodine Tartrate; Tolu Balsam; Tragacanth; Trehalose; Triacetin; Tribasic Calcium Phosphate; Tribehenin; Tricaprylin; Triceteareth-4 Phosphate; Trichloroethane; Trichloroethylene; Trichloromonofluoromethane; Trideceth-10; Triethanolamine Lauryl Sulfate; Triethyl Citrate; Trifluoroacetic Acid; Triglyceride, Synthetic; Trihydroxystearin; Trilaneth-4 Phosphate; Trilaureth-4 Phosphate; Trimethylsilyl Treated Dimethiconol/Trimethylsiloxysilicate Crosspolymer (35/65 W/W; 50000000 Pa·S); Trimethylsilyl Treated Dimethiconol/Trimethylsiloxysilicate Crosspolymer (40/60 W/W; 5000000 Pa·S); Trimethylsilyl Treated Dimethiconol/Trimethylsiloxysilicate Crosspolymer (45/55 W/W; 100000 Pa·S); Trimyristin; Trisodium Citrate Dihydrate; Trisodium Hedta; Tristearin; Triton 720; Trolamine; Tromantadine; Tromethamine; Tryptophan; Turpentine Oil; Tyloxapol; Ty-Med Filler, Blue; Tyrosine; Undecylenic Acid; Union 76 Amsco-Res 6038; Urea; Urethane; Ursodiol; Valine; Vanilla; Vanillin; Vegetable Oil; Vegetable Oil Glyceride, Hydrogenated; Vegetable Oil, Hydrogenated; Vegetable Shortening; Velvetine Black Powder; *Verbascum densiflorum* Leaf; Versetamide; Vinyl Acetate-Crotonic Acid Copolymer; Viscose/Cotton; Water; Wax; Wax Blend; Wax, Emulsifying; Wax, Vegetable; Wecobee Fs; Wheat; Wheat Gluten; White Wax; Xanthan Gum; Xylitol; Xylitol 300; Yellow Ob; Yellow Wax; Zein; Zinc; Zinc Acetate; Zinc Carbonate; Zinc Chloride; Zinc Oxide; Zinc Stearate; Zinc Sulfate Monohydrate; Zinc Sulfate (anhydrous).

In some embodiments, the composition comprises a sweetening compound and/or a sweet flavor enhancing compound, and one or more texture modifying agents, including, for example, emulsifying agents, gelling agents, thickening agents, and binders. In some embodiments, the one or more texture modifying agents are selected from gums, alginates, gelatins, starches, pectins, agars, carageenans, and salts thereof.

In some embodiments, the composition comprises a sweet compound or sweet flavor enhancing compound and one or more bitterants, bitter flavor compounds, or bitterness-enhancing compounds. Representative bitterants, bitter flavor compounds, and bitterness-enhancing compounds include but are not limited to: Acteoside, Adhumulone, Adlupulone, Aesculetin, Aesculin, L-Alanine, L-alanyl-L-alanyl-L-Alanine, L-alanyl-L-isoleucyl-Alanine L-, L-valyl-L-valyl-Amarogentin, Amaropanin Amaroswerin, Amygdalin, Angustifoline, Antiacetylhumulone, Antiisohumulone, Arginine, L-Arginyl Leucine, Arginyl Leucy Leucine, Arginyl Proline, Asaronaldehyde, Aspartyl Aspartic acid, Asparasaponin I, Atropine, Benzyl beta-D-arabinoside, Benzyl beta-L-arabinoside, Benzyl beta-D-fructoside, Benzyl beta-D-galactoside, Benzyl alpha-D-glucoside, Benzyl beta-D-glucoside, Benzyl alpha-D-mannoside, Bitter Peptides, Bitter Peptides from Soy Proteins, Butyl alpha-D-glucoside, Butyl beta-D-glucoside, Caffeine, Carnosifloside II, Carnosifloside III, Carnosifloside IV, Catechin, Epicatechin, Epicatechin gallate, Chaconine, alpha-Chaconine, beta2-Chloramphenicol, Cholic Acid, Cichoriin, Cohumulone, Colupulone, Cryptochlorogenic Acid, gamma-lactone, Cucurbitacin B, Cucurbitacin D, Cyclo Alanine-glycine, Cyclo Alanine-phenylanaline, Cyclo Alanine-valine, Cyclo (L-arginylglycyl-L-prolyl-L-prolyl-L-phenylalanyl-L-isoleucyl-L-valyl), Cyclo Asparagine-phenylalanine, Cyclo Glycine-phenylalanine, Cycloheximide Cyclo Lucine-Tryptophan, Cyclopent(b)azepin-8(1H)-one, 7-Methyl-2,3,6,7-Tetrahydro-Cyclopent(b)azepin-8(1H)-one, 2,3,6,7-tetrahydro-7-hydroxy-7-methyl-Cyclopent-2-en-1-one, 2,5-dihydroxy-5-methyl-3-(1-piperidinyl)-Cyclopent-2-en-1-one, 2,5-dihydroxy-5-methyl-3-(1-pyrrolidinyl) Cyclopent-2-en-1-one, 2,3-di-1-pyrrolidinyl-Cyclopent-2-en-1-one, 5-hydroxy-5-methyl-2,3-di-1-piperidinyl-Cyclopent-2-en-1-one, 5-hydroxy-5-methyl-2,3-di-1-pyrrolidinyl-Cyclopent-2-en-1-one, 5-methyl-2,3-di-1-pyrrolidinyl-Cyclopent-2-en-1-one, 5-methylene-2,3-di-1-pyrrolidinyl-Cyclopent-2-en-1-one, 3-methyl-2-(1-pyrrolidinyl)-Cyclo Phenylalanine-aspartic acid, Cyclo Proline-alanine, Cyclo Proline-asparagine, Cyclo Proline-glycine, Cyclo Proline-isolucine, Cyclo Proline-leucine, Cyclo Proline-methionine, Cyclo Proline-phenylalanine, Cyclo Proline-proline, Cyclo Proline-valine, Cyclo Valine-phenylalanine, Cynaratriol, Cynaropicrin, Cynaropicrin, Daidzein, Daidzin Denatonium benzoate, Denatonium saccharide, Dhurrin, Dihydroxybenzoic Acid, 2,3-Dihydroxybenzoic Acid, 2,4-Ethyl b-L-arabinoside, Ethyl alpha-D-Glucoside, Ethyl beta-D-Glucoside, Eustomoroside, Eustomoside, Gallic Acid, Epigallocatechin, Epigallocatechin gallate, Gaudichaudioside F, Gelidoside, Genistein, Genistin, Gentiopicroside, Gentistic Acid, Gentomoside, Geshoidin, 6'-O-beta-D-Glucosylgentiopicroside, ucozaluzanin C, Glutamyl Aspartic Acid, Glutamyl Glutamic Acid, Glycyl Leucine, Goitrin, Gramine, Grosshemin, Haematoxylin Tetramethyl Ether Helicin, Heptadeca-16-ene, 1-Acetoxy-2,4-Dihydroxy-Heptadeca-16-ene, 1,2,4-Trihydroxy-Histidine, L-Hulupone, Humulinone, Humulone, Hydroxybenzoic Acid, 4-Hymenoside A, Hymenoside B, Hymenoside C, Hymenoside D, Hymenoside E, Hymenoside F, Isohumulone, cis-Isohumulone, trans-Isoleucine, L-Isolupanine, Isosparteine, beta-Isosparteine, 10,17-Dioxo-beta-Isosparteine, 10-oxo-beta-Lactucin, L-Leucine, L-alanyl-L-alanyl-L-Leucine, N—[(R2R)-6-amino-2-[(4S)-2,5-dioxo-4-(phenylmethyl)-1-imidazolidinyl]-1-oxohexyl]-L-leucyl-L-methionyl-N-methyl-L-phenylalanyl-, (4-1)-lactam, L-Leucine, glycyl-L-alanyl-Leucine, L-L-Leucine, N—(N2-L-leucyl-L-glytaminyl)-L-Leucine, N—(N-L-leucyl-L-a-glutamyl)-L-Leucine, N—[N2-[N2-[N-(1-L-leucyl-L-prolyl)-L-phenylalanyl]-L-asparaginyl]-L-gluta-minyl]-L-Leucine, N[N2-[N—[N-(1-L-leucyl-L-prolyl)-L-phenylalanyl]-L-seryl]-L-glutaminyl]-L-Leucine, L-leucyl-L-valyl-Leucy Leucine, Leucyl Phenylalanine, Limonin, Limoninmonolactone, Linamarin, Lotaustralin, Lupine, Lupanine, 13-Hydroxy-Lupanine, 7-hydroxy-Lupinine, Epilupinine Lupoxes B, Lupoxes C, Lupulone, Luputrione, Mellein, 6-Methoxy-Methionine, L-Methyl alpha-L-arabinoside, Methyl beta-L-arabinoside, Methyl beta-D-Glucoside, Methyl alpha-D-Glucoside 2,3-Di-isoleucine, Methyl alpha-D-Glucoside 2,3-Di-leucine, Methyl alpha-D-Glucoside 2,3-Di-L-phenylalanine, Methyl alpha-D-Glucoside 2,3-Di-threonine, Methyl alpha-D-Glucoside 2,3-Di-tyrosine, Methyl a-D-mannoside, Methyl beta-L-xylopyranoside, Methyl alpha-D-xyloside, Naringin, Neochlorogenic Acid, gamma-Lactone, Neohesperidin, Nuezhenide, Oleonuezhenide, Oleuropein, Olivieroside A, Olivieroside B, Olivieroside C, Perrottetin H, Phenylalanine, L-Phenyl alpha-D-galactoside, Phenyl alpha-D-glucoside, Phenyl beta-D-glucoside, Phenylthiourea, Phlomisoside II, Piperidine-2-carboxylic acid, 4-[(2-carboxy-2-hydroxyethyl(thio)]-Piperidinecarboxylic acid-2, 4-[(2-carboxy-2-hydroxyethyl)thio]-Prehumulone, Prelupulone, Propyl beta-D-fructoside, Propyl alpha-D-glucoside, Propyl beta-D-glucoside, Protocatechuic Acid, Prunasin, Pulcherrimine, Quinidine, Quinine, Quinolizinium-7-olate, Ranitidine, Rebaudioside C, Salicin, Salidroside, Scabraside, Scandenoside R5, Sclareolide, Scopolin, Septemfidoside, Seryl Lysyl Glycyl Leucine, Sinapine, Solanine, alpha-Sparteine, Sparteine, 17-oxo-Stevisalioside A, Strychnine, Suavioside C1, Suavioside D2, Suavioside F, Sucrose Octaacetate, Sweroside, Swertiamarin, Swertiapunimarin, Taxiphyllin, TFI (Furostan, beta-D-galactopyranoside), Theaflavin, Theaflavin Gallate A, Theaflavin Gallate B, Tomatidine, Tomatine, alpha-Tricyclodehydroisohumulone, Trifloroside, Trihydroxybenzoic Acid, 2,4,6-Tryptophan, L-Uracil, 6-propyl-2-thio-L-Valine, L-arginylglycyl-L-prolyl-L-prolyl-L-phenylalanyl-L-isoleucyl-(BPIa)Valine, L-Yohimbine, extract of wild cucumber, Denatonium, denatonium benzoate, and denatonium saccharide.

In some embodiments, the composition comprises a sweet compound or sweet flavor enhancing compound and one or more acids or sour flavorants. Representative sour flavorants include but are not limited to: ascorbic acid, benzoic acid, gallic acid, glucuronic acid, adipic acid, glutaric acid, malonic acid, succinic acid, malic acid, acetic acid, lactic acid, citric acid, tartaric acid, fumaraic acid, phosphoric acid, pyrophosphoric acid, tannic acid, vinegar, lemon juice, lime juice, acidic fruit juices, and acidic fruit extracts.

In some embodiments, the composition comprises a sweet compound or sweet flavor enhancing compound and one or more salts or salt flavor enhancers. Representative salts or salt flavor enhancers include but are not limited to: mineral salts, sodium chloride, potassium chloride, magnesium chloride, ammonium chloride, sodium gluconate, sodium phosphates, glycine, L-alanine, L-valine, L-leucine, L-isoleucine, L-phenylalanine, L-tyrosine, L-glutamine, L-glutamic acid, L-asparagine, L-aspartic acid, L-serine, L-threonine, L-cysteine, L-methionine, L-proline, L-lysine, L-arginine, L-tryptophan, L-histidine, L-pyrolysine, L-pyroglutamine, L-4-trans-hydroxyproline, L-3-cis-hydroxyproline, L-homoserine, L-homocysteine, L-cystine, L-ornithine and L-citrulline, L-glutamine, L-glutamic acid, L-asparagine, L-aspartic acid, L-valine, L-arginine and L-lysine.

In some embodiments, the composition comprises a sweet compound or sweet flavor enhancing compound and one or more umami flavors or umami flavor enhancers. Representative umami flavor compounds or umami flavor enhancing compounds include but are not limited to the compounds identified in U.S. Patent Application Publications 2005/0084506A1, U.S. 2009/0111834A1, U.S. 2012/0201763A1, U.S. 2015/0093339A1, U.S. 2006/0263411A1, U.S. 2012/0226047A1, and 2009/0220662A1. Additional representative umami flavor compounds or umami flavor enhancing compounds include but are not limited to: hydrolyzed soy protein, hydrolyzed corn protein, hydrolyzed wheat protein, anchovy, anchovy paste, fish sauce, yeast extract, nutritional yeast, hydrolyzed yeast extract, mushrooms, mushroom powder, dehydrated mushrooms, mushroom extract, kombucha, hydrolyzed vegetable protein, oyster sauce, soy sauce, soy extract, tamari, miso powder, miso paste, parmesan cheese, parmesan cheese solids, kombu powder, kombu, dehydrated kombu, kombu paste, nori, nori powder, nori paste, seaweed, dehydrated seaweed, seaweed powder, seaweed extract, tomato, dehydrated tomato, tomato powder, tomato extract, vegetable powder, vegetable extract, whey powder, whey solids, whey, collagen, gelatin, textured vegetable protein, sodium caseinate, calcium caseinate, magnesium caseinate, potassium caseinate, glyoxylic acid, 3-methyl-2-oxo-butanoic acid, 3-methyl-2-oxo-pentanoic acid, 4-methyl-2-oxo-pentanoic acid, 3-hydroxy-2-oxo-propanoic acid, oxalacetic acid, 2-oxo-glutaric acid, 2-oxo-3-phenyl-propanoic acid, 3-(4-hydroxyphenyl)-2-oxo-propanoic acid, 2-oxo-1H-indole-3-propanoic acid, 2-oxo-1H-imidazole-4-propanoic acid, 4-methylthio-2-oxo-butanoic acid, 3-mercapto-2-oxo-propanoic acid, 3-hydroxy-2-oxo-butanoic acid, 6-amino-2-oxohexanoic and 5-guanidino-2-oxo-pentanoic acid, 2-amino-butanoic acid, .alpha.-alanine, glycine, norvaline, valine, aspartic acid, norleucine, leucine, isoleucine, serine, threonine, glutamic acid, phenylalanine, tyrosine, cysteine, methionine, lysine, tryptophane, histidine, arginine, asparagine, glutamine, cystine, citrulline, theanine, .gamma.-methylene-glutamic acid, isoeugenol, 2-propylphenol, p-vinylguaiacol, 2-acetylpyrazine, 2-ethyl-3,5-dimethylpyrazine, 2,3,5-trimethylpyrazine, 2,3-diethyl-5-methylpyrazine, 3-ethyl-2-methylpyrazine, dimethyl sulfide, dimethyl disulfide, dimethyl trisulfide, methylpropyl disulfide, 2-methylthiophenol, methional (3-methylthiopropanal), 2-octenal, 2,4-nonadienal, 2,4-decadienal, 2,4-undecadienal, 2-methoxybenzaldehyde, 2,4-dodecadienal, decenal, methyl 2-furanecarboxylate, 2-ethyl-4-hydroxy-3-methyl 5(2H)-furanone, 2,6-dimethylbenzenethiol 2-nonen-1-ol, 10-undecenoic acid, undecanoic acid, isodecanoic acid and isononanoic acid, 2-oxo-butanoic acid, oxalacetic acid, 3-methyl-2-oxo-butanoic acid, 3-methyl-2-oxo-pentanoic acid, 2-oxo-glutaric and 3-mercapto-2-oxo-propanoic acid, NaCl, KCl, MSG, guanosine monophosphate (GMP), inosin monophosphate (IMP), ribonucleotides such as disodium inosinate, disodium guanylate, N-(2-hydroxyethyl)-lactamide, N-lactoyl-GMP, N-lactoyl tyramine, gamma amino butyric acid, allyl cysteine, 1-(2-hydroxy-4-methoxylphenyl)-3-(pyridine-2-yl)propan-1-one, arginine, potassium chloride, ammonium chloride, succinic acid, N-(2-methoxy-4-methyl benzyl)-N'-(2-(pyridin-2-yl)ethyl) oxalamide, N-(heptan-4-yl)benzo(D)(1,3)dioxole-5-carboxamide, N-(2,4-dimethoxybenzyl)-N'-(2-(pyridin-2-yl)ethyl) oxalamide, N-(2-methoxy-4-methyl benzyl)-N'-2(2-(5-methyl pyridin-2-yl)ethyl) oxalamide, cyclopropyl-E,Z-2,6-nonadienamide, glutamic acid, glutamate, monosodium glutamate, monopotassium glutamate, monoammonium glutamate, calcium diglutamate, magnesium diglutamate, L-asparagine or a salt thereof, 5'-ribonucleotides or their salts, calcium 5'-ribonucleotides, disodium 5'-ribonucleotides, dipotassium 5'-ribonucleotides, inosinic acid, guanylic acid, adenosinic acid, inosinates, guanylates, and adenylates, guanosine 5'-monophosphate, inosine 5'-monophosphate, 5'-adenylate, disodium guanylate, disodium inosinate, disodium adenylate; dipotassium guanylate, dipotassium inosinate, dipotassium adenylate, calcium guanylate, calcium inosinate, calcium adenylate, maltol, ethyl maltol, glycine, L-leucine, autolyzed or hydrolyzed proteins (e.g. autolyzed yeast, hydrolyzed yeast, hydrolyzed vegetable proteins), Koji-Aji (Ajinomoto Food Ingredients), fermented wheat gluten, Glutathione, Glutamyl Glutamic Acid, (Z)-6-Dodecen-4-olide, Inosinic acid, Dodec-Z6-en-4-olide, Glutamic Acid, L-Aconitic Acid, N-(1-deoxy-fructos-1-yl) glutamate, hydrolyzed vegetable protein, Methyl alpha-D-Glucoside, 2,3-Di-lysine, Methyl alpha-D-Glucoside 2,3-Di-ornithine, L-Asparagine, L-a-glutamyl-L-a-glutamyl-L-Glutamic acid, L-a-aspartyl-L-a-glutamyl-Glutamyl valine, Wheat gluten hydrolyzate, Aspartic acid L-, L-a-aspartyl-L-a-aspartyl-L-a-aspartyl-Docosahexaenoic acid, and (4Z,7Z,10Z,13Z,16Z,19Z)-L-Theanine, allyl cysteine, propenyl cysteine, S-(.alpha.,.beta.-dicarboxyethyl) .gamma.-L-glutamyl-L-cysteinyl-glycine, S-(.alpha., .beta.-dicarboxyethyl) cysteine, 3-(carboxymethoxy)-alanine, S-carboxymethyl-glutathione (glutaramic acid), S-carboxymethyl-cysteinyl-glycine, (S-carboxymethyl)-lysyl-cysteine, S-dicarboxymethyl-glutathione, S-carboxymethyl-cysteine, S-(1,2-dicarboxyethyl)-glutathione, and S-(1,2-dicarboxyethyl)-cysteine, N-acetyl GMP, N-formyl GMP, N-propanoyl GMP, N-butanoyl GMP, N-pentanoyl GMP, N-hexanoyl GMP, N-heptanoyl GMP, N-octanoyl GMP, N-oxalyl GMP, N-succinyl GMP, N-glutaryl GMP, N-fumaryl GMP, N-maleyl GMP, N-adipyl GMP, N-citryl GMP, N-galloyl GMP, N-oxalacetyl-GMP, N-feruloyl GMP, N-pyruvyl GMP, N-benzoyl GMP, N-vanilloyl GMP, N-anthranoyl GMP, N-caffeoyl GMP, N-cinnamoyl GMP, N-acetyl AMP, N-formyl AMP, N-propanoyl AMP, N-butanoyl AMP, N-pentanoyl AMP, N-hexanoyl AMP, N-heptanoyl AMP, N-octanoyl AMP, N-oxalyl AMP, N-succinyl AMP, N-glutaryl AMP, N-fumaryl AMP, N-maleyl AMP, N-adipyl AMP, N-citryl AMP, N-galloyl AMP, N-oxalacetyl-AMP, N-feruloyl AMP, N-pyruvyl AMP, N-benzoyl AMP, N-vanilloyl AMP, N-anthranoyl AMP, N-caffeoyl AMP, N-cinnamoyl AMP, N-acetyl CMP, N-formyl CMP, N-propanoyl CMP, N-butanoyl CMP, N-pentanoyl CMP, N-hexanoyl CMP, N-heptanoyl CMP, N-octanoyl CMP, N-oxalyl CMP, N-succinyl CMP, N-glutaryl CMP, N-fumaryl CMP, N-maleyl CMP, N-adipyl CMP, N-citryl CMP, N-galloyl CMP, N-oxalacetyl-CMP, N-feruloyl CMP, N-pyruvyl CMP, N-benzoyl CMP, N-vanilloyl CMP, N-anthranoyl CMP, N-caffeoyl CMP, N-cinnamoyl CMP, N-acetyl GMP, N-formyl GMP, N-propanoyl GMP, N-butanoyl GMP, N-pentanoyl GMP, N-hexanoyl GMP, N-heptanoyl GMP, N-octanoyl GMP, N-oxalyl GMP, N-succinyl GMP, N-glutaryl GMP, N-fumaryl GMP, N-maleyl GMP, N-adipyl GMP, N-citryl GMP, N-galloyl GMP, N-oxalacetyl-GMP, N-feruloyl GMP, N-pyruvyl GMP, N-benzoyl GMP, N-vanilloyl GMP, N-anthranoyl GMP, N-caffeoyl GMP, N-cinnamoyl GMP, flavor modifiers created by maillard reactions, S-(.alpha.,.beta.-dicarboxyethyl) .gamma.-L-glutamyl-L-cysteinyl-glycine, S-(.alpha., .beta.-dicarboxyethyl) cysteine, 3-(carboxymethoxy)-alanine, S-carboxymethyl-glutathione (glutaramic acid), S-carboxymethyl-cysteinyl-glycine, (S-carboxymethyl)-lysyl-cysteine, S-dicarboxymethyl-glutathione, S-carboxymethyl-cysteine, S-(1,2-dicarboxyethyl)-glutathione, and S-(1,2-dicarboxyethyl)-cysteine, Gamma-L-glutamyl-L-cysteinyl-glycine or y-Glu-Cys-Gly, Rubemamine, rubemamide, rubescenamine, Rubescenamide, zanthosine, zanthosinamide, dioxamide, dioxamine, zanthomamine, and zanthomamide.

Umami flavor compounds or umami flavor enhancing compounds may also include peptides with the sequence Lys-Ile-His-Pro-Phe, Gly-Pro-Phe-Pro-Ile, or Lys-Lys-Tyr-Lys-Val-Pro-Gln, Glu-Glu-Leu, Glu(Glu-Leu), Leu-Glu-Glu, Glu-Asp-Phe, Glu-Glu-Ile, Asp-Glu-Leu and Glu-Leu-Glu. And their N-lactoyl derivatives, Lys-Gly-Asp-Glu-Glu-Ser-Leu-Ala, Ser-Leu-Ala-Lys-Gly-Asp-Glu-Glu, Ser-Leu-Ala-Asp-Glu-Glu-Lys-Gly, Lys-Gly-Ser-Leu-Ala,-Asp-Glu-Glu, Lys-Gly-Asp-Glu-Glu, Glu-Glu-Asp-Gly-Lys, or Asp-Glu-Glu (See Nakata et al., Biosci. Biotechnol. Biochem. (1995) 59(4):689-93).

In some embodiments, the composition comprises a sweet compound or sweet flavor enhancing compound and one or more plant or animal products. Representative plant or animal products include but are not limited to: zedoary bark extract (*Curcuma zedoaria* (berg.) rosc.), zedoary (*Curcuma zedoaria* (berg.) rosc.), alfalfa extract (*Medicago sativa* l.), alfalfa herb and seed (*Medicago sativa* l.), algae brown extract (*Macrocystis* and *Laminaria* spp.), algae red (*Porphyra* spp. and *Gloiopeltis furcata* and *Rhodymenia palmata* (l.)), algae red extract (*Porphyra* spp. and *Gloiopeltis furcata* and rhodymenia, alkanet root extract (*Alkanna tinctoria* tausch), allspice (*Pimenta officinalis* lindl.), allspice, oil (*Pimenta officinalis* lindl.), allspice, oleoresin (*Pimenta officinalis* lindl.), almond, bitter, oil (ffpa) (*Prunus* spp.), aloe, extract (*Aloe* spp.), ambrette, absolute, oil (*Hibiscus abelmoschus* l.), ambrette seed (*Hibiscus abelmoschus* l.), ambrette seed, oil (*Hibiscus abelmoschus* l.), ambrette, tincture (*Hibiscus abelmoschus* l.), amyris (*Amyris balsamifera* l.), amyris, oil (*Amyris balsamifera* l.), angelica root (*Angelica* spp.), angelica root, extract (*Angelica archangelica* l.), angelica root, oil (*Angelica archangelica* l.), angelica seed (*Angelica* spp.), angelica seed, extract (*Angelica archangelica* l.), angelica seed, oil (*Angelica archangelica* l.), angelica stem, oil (*Angelica archangelica* l.), angola weed (*Roccella fuciformis* ach.), angostura (*Galipea offincinalis* hancock), angostura, extract (*Galipea officinalis* hancock), anisaldehyde propyleneglycol acetal, anise (*Pimpinella anisum* l.), anise, oil (*Pimpinella anisum* l.), anise, star (*Illicium verum* hook, f.), anise, star, oil (*Illicium verum* hook, f.), annatto, extract (*Bixa orellana* l.), annatto, seed (*Bixa orellana* l.), apple essence, natural, apricot kernel, oil (*Prunus armeniaca* l.), arnica flowers (*Arnica* spp.), arrowroot starch, artemisia (*Artemisia* spp.), artemisia extract, artemisia oil, artichoke leaves (*Cynara scolymus* l.), asafetida, fluid extract (*Ferula assafoetida* l.), asafetida, gum (*Ferula assafoetida* l.), asafetida, oil (*Ferula assafoetida* l.), asparagus, seed and root, extract, bakers yeast extract, baker's yeast glycan, baker's yeast protein, balm (*Melissa officinalis* l.), balm leaves (*Melissa officinalis* l.), balm leaves, extract (*Melissa officinalis* l.), balm, oil (*Melissa officinalis* l.), fir, balsam, needles and twigs (*Abies balsamea* (l.) mill.), balsam fir, oil (*Abies balsamea* (l.) mill.), balsam fir, oleoresin (*Abies balsamea* (l.) mill.), balsam, peru (*Myroxylon pereirae* klotzsch), balsam, peru, oil (*Myroxylon pereirae* klotzsch), basil (*Ocimum basilicum* l.), basil bush (*Ocimum minimum* l.), basil, extract (*Ocimum basilicum* l.), basil, oil (*Ocimum basilicum* l.), basil, oleoresin (*Ocimum basilicum* l.), bay (*Laurus nobilis* l.), bay leaves, sweet, extract (*Laurus nobilis* l.), bay leaves, sweet, oil (*Laurus nobilis* l.), bay leaves, west indian, extract (*Pimenta acris* kostel), bay leaves, west indian, oil (*Pimenta racemosa* (mill.) j.w. moore), bay leaves, west indian, oleoresin (*Pimenta acris* kostel), beechwood, creosote (*Fagus* spp.), benzoin, resin (*Styrax* spp.), bergamot, oil (*Citrus aurantium* l. subsp. *bergamia* wright et arn.), birch, sweet, oil (*Betula lenta* l.), birch tar, oil (*Betula pendula* roth and related *betula* spp.), blackberry bark, extract (*Rubus*, spp. of section eubatus), blackberry fruit extract, bois de rose, oil (*Aniba rosaeodora* ducke), boldus leaves (*Peumus boldus* mol.), bonito, dried, boronia, absolute (*Boronia megastigma* nees), bouillon, vegetable, smoke, bryonia root (*Bryonia* spp.), buchu leaves (*Barosma betulina* and *crenulata*), buchu leaves extract, buchu leaves, oil (*Barosma* spp.), buckbean leaves (*Menyanthes trifoliata* l.), buckbean leaves, extract (*Menyanthes trifoliata* l.), cajeput, oil (*Melaleuca leucadendron* l.), calumba root (*Jatrorrhiza palmata* (lam.) miers), calumba root, extract (*jatrorrhiza palmata* (lam.) miers), d-camphor, camphor, japanese, white, oil (*Cinnamomum camphora* (l.) nees et eberm.), camphor oil, formosan ho-sho, leaves (*Cinnamomum camphora*), cananga, oil (*Cananga odorata* hook. f. and thoms.), candelilla wax (wax from stems and branches of *Euphorbia cerifera*), capers (*Capparis spinosa* l.), capsicum (*Capsicum* spp.), capsicum extract (*Capsicum* spp.), capsicum, oleoresin (*Capsicum* spp.), caramel, caraway (*Carum carvi* l.), caraway, black (*Nigella sativa* l.), caraway, oil (*Carum carvi* l.), cardamom (*Elletaria cardamomum* (l.) maton), cardamom oleoresin, cardamom seed, oil (*Elletaria cardamomum* (l.) maton), carob bean, extract (*Ceratonia siliqua* l.), cascara, bitterless, extract (*Rhamnus purshiana* dc.), cascarilla bark, extract (*Croton* spp.), cascarilla bark, oil (*Croton* spp.), casein, cassia buds (*Cinnamomum cassia* blume), cassie, absolute (*Acacia farnesiana* (l.) willd.), castoreum, extract (*Castor* spp.), castoreum, liquid (*Castor* spp.), castor oil (*Ricinus communis* l.), catechu, black, extract (*Acacia catechu* willd.), catechu, black, powder (*Acacia catechu* willd.), cedar leaf, oil (*Thuja occidentalis* l.), cedarwood oil alcohols, cedarwood oil terpenes, celery seed (*Apium graveolens* l.), celery seed, extract (*Apium graveolens* l.), celery seed, extract solid (*Apium graveolens* l.), celery seed, oil (*Apium graveolens* l.), celery seed, centaury (*Centaurium umbellatum* gilib.), cereal solids, hydrolyzed, chamomile flower (*Matricaria chamomilla* l.), chamomile flower (*Anthemis nobilis* l.), chamomile flower, hungarian, oil (*Matricaria chamomilla* l.), chamomile flower, oil (*Anthemis nobilis* l.), chamomile flower, roman, extract (*Anthemis nobilis* l.), char smoke flavor, cherry bark, wild, extract (*Prunus serotina* ehrh.), cherry-laurel leaves (*Prunus laurocerasus* l.), cherry laurel, oil (*Prunus laurocerasus* l.) (ffpa), cherry-laurel water (*Prunus laurocerasus* l.), cherry pits, extract (*Prunus* spp.), chervil (*Anthriscus cerefolium* (l.) hoffm.), chervil, extract (*Anthriscus cerefolium* l.), chestnut leaves (*Castanea dentata* (marsh.) borkh.), chestnut leaves, extract (*Castanea dentata* (marsh.) borkh.), chestnut leaves, extract solid (*Castanea dentata* (marsh.) borkh.), chicory, extract (*Cichorium intybus* l.), chilte (*Cnidoscolus* (also known as *Jatropha*)

spp.), chiquibul (*Manilkara zapotilla* gilly), chirata (*Swertia chirata* buch.-ham.), chirata, extract (*Swertia chirata* buch.-ham.), chives (*Allium schoenoprasum* l.), cinchona bark, red (*Cinchona succirubra* pav. or its hybrids), cinchona bark, red, extract (*Cinchona succirubra* pav. or its hybrids), cinchona bark, yellow (*Cinchona* spp.), cinchona bark, yellow, extract (*Cinchona* spp.), cinchona, extract (*Cinchona* spp.), cinnamon (*Cinnamomum* spp.), cinnamon bark, extract (*Cinnamomum* spp.), cinnamon bark, oil (*Cinnamomum* spp.), cinnamon bark oleoresin, ceylon, chinese, or saigon (*Cinnamomum* spp.), cinnamon leaf, oil (*Cinnamomum* spp.), cinnamon leaf oil, rectified, citronella, oil (*Cymbopogon nardus* rendle), citrus peels, extract (*Citrus* spp.), clary (*Salvia sclarea* l.), clary sage, absolute, clary, oil (*Salvia sclarea* l.), clary sage, clove bud, extract (*Eugenia* spp.), clove bud, oil (*Eugenia* spp.), clove bud, oleoresin (*Eugenia* spp.), clove leaf, oil (*Eugenia* spp.), clover (*Trifolium* spp.), clover, extract (*Trifolium* spp.), clover herb distillate, clover, oil (*Trifolium* spp.), clover tops, red, extract solid (*trifoliumpratense* l.), cloves (*Eugenia* spp.), clove stem, oil (*Eugenia* spp.), coca leaf, extract (decocainized) (*Erythroxylon coca* lam.), cocoa extract, cocoa with dioctyl sodium sulfosuccinate, refined, coffee concentrate, pure, coffee extract (*Coffea* spp.), coffee extract, solid, cognac, green, oil, cognac, white, oil, copaiba (South american spp. of *Copaifera* l.), copaiba, oil (south american spp. of *Copaifera* l.), coriander (*Coriandrum sativum* l.), coriander leaf oil (*Coriandrum sativum* l.), coriander, oil (*Coriandrum sativum* l.), cork, oak (*Quercus* spp.), corn silk extract (*Zea mays* l.), corn silk, oil (*Zea mays* l.), costmary (*Chrysanthemum balsamita* l.), costus root, oil (*Saussurea lappa* clarke), cottonseed flour, defatted, cottonseed flour, partially defatted, cooked, cottonseed flour, partially defatted, cooked, toasted, cottonseed kernels, glandless, raw, cottonseed kernels, glandless, roasted, cubeb (*Piper cubeba* l. f.), cubeb, oil (*Piper cubeba* l. f.), cubebol, cumin (*Cuminum cyminum* l.), cumin, oil (*Cuminum cyminum* l.), currant buds, black, absolute (*Ribes nigrum* l.), currant juice, black, currant leaves, black (*Ribes nigrum* l.), daidai peel oil, damiana leaves (*Turnera diffusa* willd.), dandelion, fluid extract (*Taraxacum* spp.), dandelion root, extract solid (*Taraxacum* spp.), davana oil (*Artemesia pallens* wall.), dehydrated beets, dill (*Anethum graveolens* l.), dill, oil (*Anethum graveolens* l.), dill seed, indian (*Anethum* spp.), dill seed oil (*Anethum sowa* roxb.), dittany of crete (*Origanum dictamnus* l.), dittany (*fraxinella*) roots (*Dictamnus albus* l.), dog grass, extract (*Agropyron repens* (l.) beauv.), dragon's blood, extract (*Daemonorops* spp. or other botanical sources), dried algae meal, elder flowers (*Sambucus canadensis* l. or *Sambucus nigra* l.), elder flowers, extract (*Sambucus canadensis* l. or *Sambucus nigra* l.), elder tree leaves (*Sambucus nigra* l.), elecampane root, extract (*Inula helenium* l.), elecampane root, oil (*Inula helenium* l.), elemi, gum, elemi, oil (*Canarium* spp.), erigeron, oil (*Erigeron canadensis* l.), eucalyptol, eucalyptus, oil (*Eucalyptus globulus* labille), eugenol, fennel, common (*Foeniculum vulgare* mill.), fennel, sweet (*Foeniculum vulgare* mill. var. *dulce* (d.c.) alef.), fennel, sweet, oil (*Foeniculum vulgare* mill. var. *dulce* (d.c.) alef.), fenugreek (*Trigonella foenum-graecum* l.), fenugreek, extract (*Trigonella foenum-graecum* l.), fenugreek, oleoresin (*Trigonella foenum-graecum* l.), fir (Pine) needles and twigs (*Abies sibirica* ledeb.), fir needles and twigs, oil (*Abies* spp.), fish oil (hydrogenated), fish protein concentrate, whole, fish protein isolate, fruit juice, galanga, greater (*Alpinia galanga* willd), galangal root (*Alpinia* spp.), galangal root, extract (*Alpinia* spp.), galangal root, oil (*Alpinia* spp.), galbanum, oil (*Ferula* spp.), galbanum, resin (*Ferula* spp.), gambir (*Uncaria gambir* roxb.), *Gardenia gummifera* distillate, garlic, garlic extract, garlic, oil (*Allium sativum* l.), gelatin, genet, absolute (*Spartium junceum* l.), genet, extract (*Spartium junceum* l.), gentian root, extract (*Gentiana lutea* l.), gentian, stemless (*Gentiana acaulis* l.), geranium (*Pelargonium* spp.), geranium, east indian, extract (*Cymbopogon martini* stapf.), geranium, east indian, oil (*Cymbopogon martini* stapf.), geranium extract (*Pelargonium* spp.), geranium, oil (*Pelargonium* spp.), geranium, rose, oil (*Pelargonium graveolens* l'her.), germander, chamaedrys (*Teucrium chamaedrys* l.), germander, chamaedrys, extract (*Teucrium chamaedrys* l.), germander, chamaedrys, extract solid (*Teucrium chamaedrys* l.), germander, golden (*Teucrium polium* l.), ghatti, gum (*Anogeissus latifolia* wall.), ginger (*Zingiber officinale* rosc.), ginger, extract (*Zingiber officinale* rosc.), ginger, oil (*Zingiber officinale* rosc.), ginger, oleoresin (*Zingiber officinale* rosc.), glycyrrhizin, ammoniated (*Glycyrrhiza* spp.), grains of paradise (*Aframomum melegueta* (Rosc.) k. schum.), grape color extract, grape essence, natural, grapefruit essence, natural, grapefruit, extract, grapefruit, juice, grapefruit, oil (*Citrus paradisi* macf.), grapefruit oil, conc., grapefruit, oil, terpeneless (*Citrus paradisi*), grape seed extract, grape skin extract, ground limestone, guaiac gum (*Guaiacum* spp.), guaiac gum, extract (*Guaiacum* spp.), guaiac wood, extract (*Guaiacum* spp.), guaiac wood, oil (*Guaiacum* spp.), guarana, gum (*Paullinia cupana* hbk), guarana seed, extract, guava (*Psidium* spp.), guava extract, gum arabic, gutta hang kang (*Palaquium leiocarpum* boerl. and *P. oblongifolium* burck.), haematococcus algae meal, haw bark, black, extract (*Viburnum prunifolium* l.), *Heliopsis longipes* extract, hemlock (*Tsuga* spp.), hemlock needles and twigs, oil (*Tsuga* spp.), hickory bark, extract (*Carya* spp.), hickory smoke dist., honeysuckle extract, hops, extract (*Humulus lupulus* l.), hops extract, modified, hops, extract solid (*Humulus lupulus* l.), hops, oil (*Humulus lupulus* l.), horehound extract (*Marrubium vulgare* l.), horehound (*Marrubium vulgare* l.), horehound solid, extract, horsemint leaves, extract (*Monarda* spp.), horseradish (*Armoracia lapathifolia* gilib.), horseradish oil, hyacinth, absolute (*Hyacinthus orientalis* l.), hyacinth flowers (*Hyacinthus orientalis* l.), hyssop, extract (*Hyssopus officinalis* l.), hyssop (*Hyssopus officinalis* l.), hyssop, oil (*Hyssopus officinalis* l.), iceland moss (*Cetraria islandica* ach.), immortelle, absolute (*Helichrysum angustifolium* dc), immortelle, extract (*Helichrysum angustifolium* dc.), imperatoria (*Peucedanum ostruthium* (l.) koch (*Imperatoria ostruthium* l.)), iva (*Achillea moschata* jacq.), iva, extract (*Achillea moschata* jacq.), jambu oleoresin, japan wax, jasmine, absolute (*Jasminum* spp.), jasmine, concrete (*Jasminum* spp.), jasmine, oil (*Jasminum grandiflorum* l.), jasmine, spiritus (*Jasminum grandiflorum* l.), jelutong (*Dyera costulata* hook, f. and d. lowii hook, f.), juniper (berries) (*Juniperus communis* l.), juniper, extract (*Juniperus communis* l.), juniper oil (*Juniperus communis* l.), karaya, gum (*Sterculia urens* roxb.), kelp, kola nut, extract (*Cola acuminata* schott et endl.), labdanum, absolute (*Cistus* spp.), labdanum, oil (*Cistus* spp.), labdanum, oleoresin (*Cistus* spp.), laurel berries (*Laurus nobilis* l.), lavandin absolute, lavandin, concrete, lavandin, oil, lavender, absolute (*Lavandula officinalis* chaix), lavender, concrete (*Lavandula officinalis* chaix), lavender (*Lavandula officinalis* chaix), lavender, oil (*Lavandula officinalis* chaix), lavender, spike (*Lavandula latifolia* bill.), lavender, spike, oil (*Lavandula* spp.), leche caspi (*Couma macrocarpa* barb. rodr.), leche de vaca (*Brosimum utile* (h.b.k.) pittier, and *Poulsenia* spp.), leek oil, lemon essence, lemon, extract (*Citrus limon* (l.) burm. f.), lemon grass, oil (*Cymbopogon citratus* dc. and

*Cymbopogon flexuosusstapf*), lemon, juice, lemon, oil (*Citrus limon* (l.) burm. f.), lemon, oil, terpeneless (*Citrus limon* (l.) burm. f.), lemon peel extract, lemon peel granules, lemon terpenes, lemon-*verbena* (*Lippia citriodora* hbk.), lemon verbena, oil (*Lippia citriodora*), licorice extract (*Glycyrrhiza* spp.), licorice extract powder (*Glycyrrhiza* spp.), licorice (*Glycyrrhiza* spp.), lime, essence, lime, juice, lime juice, dehydrated, lime oil, distilled, lime oil, expressed, lime, oil, terpeneless (*Citrus aurantifolia* (Christman) swingle), linaloe wood, oil (*Bursera delpechiana* poiss. and other *Bursera* spp.), linden flowers, extract (*Tilia* spp.), linden flowers (*Tilia glabra* vent.), linden leaves (*Tillia* spp.), *Litsea cubeba* berry oil, locust (*carob*) bean gum, lovage, extract (*Levisticum officinale* koch), lovage (*Levisticum officinale* koch), lovage, oil (*Levisticum officinale* koch), luo han fruit concentrate, lupulin (*Humulus lupulus* l.), mace (*Myristica fragrans* houtt.), mace, oil (*Myristica fragrans* houtt.), mace, oleoresin (*Myristica fragrans* houtt.), maidenhair fern (*Adiantum capillus-veneris* l.), malt syrup (*Malt* extract), mandarin, oil (*Citrus reticulata* blanco), marigold, pot (*Calendula officinalis* l.), marjoram, oleoresin (*Marjorana hortensis* moench (*Origanum majorana* l.)), marjoram, pot (*Majorana onites* (l.) benth. (*Origanum vulgare* l.)), marjoram seed (*Majorana hortensis* moench (*Origanum majorana* l.)), marjoram, sweet (*Majorana hortensis* moench (*Origanum majorana* l.)), marjoram, sweet, oil (*Majorana hortensis* moench (*Origanum majorana* l.)), massaranduba balata (*Manilkara huberi* (Ducke) chevalier), massaranduba balata, solvent-free resin extract, massaranduba chocolate (*Manilkara solimoesensis* gilly), massoia bark oil, mastic gum, mate, absolute (*Ilex paraguariensis* st. hil.), mate, leaves, menhaden oil, menhaden oil, hydrogenated, menhaden oil, partially hydrogenated, menthol, mesquite wood extract, milk powder, whole, enzyme-modified, mimosa, absolute (*Acacia decurrens* willd. var. *dealbata*), mimosa concrete (*Acacia decurrens* willd. var. *dealbata*), mineral oil, white, molasses, concentrate, molasses, extract (*Saccharum officinarum* l.), molasses (*Saccharum officinarum* l.), mountain maple (*Acer spicatum* lam.), mountain maple bark (*Acer spicatum* lam.), mountain maple, extract solid (*Acer spicatum* lam.), mullein flowers (*Verbascum* spp.), mushroom oil, distilled, musk ambrette, musk, ketone, musk tonquin (*Moschus moschiferus* l.), mustard, brown (*Brassica* spp.), mustard, brown, extract (*Brassica* spp.), mustard flour, mustard oil, mustard, oriental, mustard, yellow (*Brassica* spp.), mustard, yellow, extract (*Brassica* spp.), myrrh, extract, myrrh, gum (*Commiphora* spp.), myrrh, oil (*Commiphora* spp.), myrtle leaves (*Myrtus communis* l.), myrtle, oil (*Myrtus communis* l.), naringin, extract (*Citrus paradisi* macf.), nisin preparation, nutmeg (*Myristica fragrans* houtt.), nutmeg, oil (*Myristica fragrans* houtt.), white, extract (*Quercus alba* l.), oak moss, absolute (*Evernia* spp.), oak moss, concrete (*Evernia prunasti* spp.), oak wood, english (*Quercus robur* l.), oat gum, oiticica oil, oleic acid, oleic acid, from tall oil fatty acids, olestra, oleyl alcohol, olibanum, absolute (*Boswellia* spp.), olibanum, gum, resin (*Boswellia* spp.), olibanum, oil (*Boswellia* spp.), olibanum, resinoid (*Boswellia* spp.), onion, oil (*Allium cepa* l.), opopanax, gum, opopanax, non-specific, opopanax, oil, opopanax tincture, orange b, orange essence, natural, orange essence oil, natural, orange, extract, orange flowers, absolute (*Citrus aurantium* l.), orange flowers, bitter (*Citrus aurantium*l), orange, juice, orange leaf, absolute (*Citrus aurantium*l.), orange, oil, distilled (*Citrus sinensis* (l.) osbeck), orange, oil, terpeneless (*Citrus sinensis* (l.) osbeck), orange peel, orange peel, bitter, extract (*Citrus aurantium* l.), orange peel, bitter, oil (*Citrus aurantium* l.), orange peel, sweet, extract (*Citrus sinensis* (l.) osbeck), orange peel, sweet, oil (*Citrus sinensis* (l.) osbeck), orange peel, sweet, oil, terpeneless (*Citrus sinensis* (l.) osbeck), oregano, european (*Origanum* spp.), oregano (*Lippia* spp., usually l. *graveolens* hbk), oregano (other genera including *Coleus, Lantana* and *Hyptis*), origanum oil (Extractive)(*Thymus capitatus* hoff. et link), orin lactone, 1-ornithine monochlorohydrate/ornithine, orris, concrete, liquid, oil (*Iris florentina* l.), orris root, extract (*Iris florentina* l.), osmanthus absolute, ox bile extract, pansy (*Viola tricolor* l.), papain (*Carica papaya* l.), paprika (*Capsicum annuum* l.), paprika oleoresin (*Capsicum annuum* l.), parsley, oil (*Petroselinum* spp.), parsley, oleoresin (*Petroselinum* spp.), parsley (*Petroselinum* spp.), passion flower extract, passion flower (*Passiflora incarnata* l.), patchouly, oil (*Pogostemon* spp.), peach kernel, extract (*Prunus persica* sieb et zucc.), peach leaves, extract (*Prunus persica* (l.) batsch), peach leaves (*Prunus persica* (l.) batsch), peanut oil, peanut stearine (*Arachis hypogaea* l.), pecan shell flour, pennyroyal, oil, american (*Hedeoma pulegiodes* (l.)), pennyroyal, oil, european (*Mentha pulegium*l.), pepper, black, oil (*Piper nigrum*l.), pepper, black, oleoresin (*Piper nigrum* l.), pepper, black (*Piper nigrum* l.), pepper, cayenne, peppermint leaves (*Mentha piperita* l.), peppermint, oil (*Mentha piperita* l.), peppermint plant, pepper, red, pepper, white, oil (*Piper nigrum* l.), pepper, white, oleoresin (*Piper nigrum*l.), pepper, white (*Piper nigrum*l.), perilla leaf oil, petitgrain, lemon, oil (*Citrus limon* (l.) burm. f.), petitgrain, mandarin, oil (*Citrus reticulata* blanco var. mandarin), petitgrain, oil (*Citrus aurantium* l.), pimenta leaf, oil (*Pimenta officinalis* lindl.), 3-pinanone, pine bark, white, extract solid (*Pinus strobus* l.), pine bark, white, oil (*Pinus strobus* l.), pine bark, white (*Pinus strobus* l.), pine needle, dwarf, oil (*Pinus mugo* turra var. pumilio (Haenke) zenari), pine, scotch, oil (*Pinus sylvestris* l.), pine tar, oil (*Pinus* spp.), pine, white, oil (*Pinus* spp.), pomegranate bark, extract (*Punica granatum* l.), poplar buds (*Populus* spp.), poppy seed (*Papaver somniferum* l.), prickly ash bark extract (*Xanthoxylum* spp.), prickly ash bark, oil, protein, animal, hydrolyzed, protein hydrolysate, protein, milk, hydrolyzed, protein, vegetable, hydrolyzed, pulegone, extract (*Picrasma excelsa* (sw.) planch or *Quassia amara* l.), quebracho bark extract, quillaia extract (*Quillaja saponaria* molina), quillaia (*Quillaja saponaria* molina), quince seed, extract (*Cydonia* spp.), rhatany, extract (*Krameria* spp.), rhubarb, garden root (*Rheum rhaponticum* l.), rhubarb root (*Rheum* spp.), rose, absolute (*Rosa* spp.), rose, bud (*Rosa* spp.), rose flowers (*Rosa* spp.), rose hips, extract (*Rosa* spp.), rose leaves (*Rosa* spp.), roselle (*Hibiscus sabdariffa* l.), rosemary, extract (*Rosmarinus officinalis* l.), rosemary, oil (*Rosemarinus officinalis* l.), rosemary, oleoresin, rosemary (*Rosemarinus officinalis* l.), rose, oil (*Rosa* spp.), rose water, stronger (*Rosa centifolia* l.), rosidinha (*Micropholis* (also known as sideroxylon) spp.), rosin, glycerol ester, rosin, gum, glycerol ester, rosin, gum or wood, partially hydrogenated, glycerol ester, rosin, gum or wood, partially hydrogenated, pentaerythritol ester, rosin, gum or wood, pentaerythritol ester, rosin, limed, rosin, methyl ester, partially hydrogenated, rosin, partially dimerized, calcium salt, rosin, partially dimerized, glycerol ester, rosin, partially hydrogenated, rosin (*Pinus* spp.) and rosin derivatives, rosin, polymerized, glycerol ester, rosin, tall oil, glycerol ester, rosin, wood, rosin, wood, glycerol ester, rosin, wood, oil (*Ruta graveolens* l.), rue (*Ruta graveolens* l.), rum, saffron (*Crocus sativus* l.), saffron, extract (*Crocus sativus* l.), safrole-free extract of *sassafras*, safrole-prohibited, sage, greek (*Salvia triloba* l.), sage, oil (*Salvia officinalis* l.), sage, oleoresin (*Salvia officinalis* l.), sage (*Salvia officinalis* l.), sage, spanish, oil (*Salvia lavandulaefolia* vahl.), sandalwood, red (*Pterocarpus santalinus* l.f.), sandalwood, white (*Santalum album* l.), sandalwood, yellow, oil (*Santalum album* l.), sandarac (*Tetraclinis articulata* (Vahl.) mast.), sarcodactylis oil, sarsaparilla, extract (*Smilax* spp.), sassafras bark, extract (Safrole-free) (*Sassafras albidum* (nutt.) nees), *sassafras* leaves (*Safrole*-free) (*Sassafras albidum* (nutt.) nees), sausage casing (hcl and cellulose fibers), savory, summer, oil (*Satureja hortensis* l.), savory, summer, oleoresin (*Satureja hortensis* l.), savory, summer (*Satureja hortensis* l.), savory, winter, oil (*Satureja montana* l.), savory, winter, oleoresin (*Satureja montana* l.), savory, winter (*Satureja montana* l.), *Schinus molle*, oil (*Schinus molle* l.), scotch spearmint oil, senna, alexandria (*Cassia acutifolia* delile), serpentaria (*Aristolochia serpentaria* l.), sesame (*Sesamum indicum* l.), silver fir, needles and twigs, oil (*Abies alba* mill.), silver-silver dragees, simaruba bark (*Simaruba amara* aubl.), sloe berries, extract (*Prunus spinosa* l.), sloe berries, extract solid (*Prunus spinosa* l.), sloe berries (*Prunus spinosa* l.), snakeroot, canadian, oil (*Asarum canadense* l.), soya bean oil fatty acids, hydroxylated, soya fatty acid amine, ethoxylated, soybean oil, epoxidized, soybean oil, hydrogenated, soy protein concentrate, enzyme activated, soy protein, isolate, spearmint, extract (*Mentha spicata* l.), spearmint (*Mentha spicata* l.), spearmint, oil (*Mentha spicata* l.), spikenard extract, spruce needles and twigs, extract (*Picea* spp.), spruce needles and twigs, oil (*Picea* spp.), st. johnswort leaves, flowers and caulis (*hypericum* perforatuml.), storax extract (*Liquidambar* spp.), storax (*Liquidambar* spp.), storax oil, sugar beet juice extract, sugar beet extract flavor base, sweet blackberry leaves extract, tagetes meal & extract, tagetes, oil (*Tagetes* spp.), tallow alcohol, hydrogenated, tallow, beef, tallow flakes, tallow, hydrogenated, tallow, hydrogenated, oxidized or sulfated, tamarind extract (*Tamarindus indica* l.), tamarinds, tangerine, essence, tangerine, extract (*Citrus reticulata* blanco), tangerine, oil (*Citrus reticulata* blanco), tannic acid, tansy, oil (*Tanacetum vulgara* l.), tansy (*Tanacetum vulgara* l.), tarragon (*Artemisia dracunculus* l.), tarragon extract (*Artemisia dracunculus* l.), tarragon oil (*Artemisia dracunculus* l.), tea extract (*Thea sinensis* l.), tea tree oil (*Melaleuca alternifolia*), blessed (*Cnicus benedictus* l.), thistle, blessed, extract (*Cnicus benedictus* l.), thistle, blessed, extract solid (*Cnicus benedictus* l.), thistle, blessed, oil (*Cnicus benedictus* l.), thyme, extract, thyme oil (*Thymus vulgaris* l. and t. zygis var. *gracilis* boiss.), thyme oleoresin, thyme (*Thymus serpyllum* l.), thyme (*Thymus vulgaris* l.), thyme, wild or creeping, extract (*Thymus serpyllum* l.), thymol, balsam, extract (*Myroxylon* spp.), tolu, balsam, gum (*Myroxylon* spp.), tragacanth, gum (*Astragalus* spp.), trefoil, sweet (*Melilotus coerulea*), triacetin (Glycerol triacetate), oil (*Polianthes tuberosa* l.), tunu (*Castilla fallax* cook), turmeric (*Curcuma longa* l.), turmeric, extract (*Curcuma longa* l.), turmeric, oleoresin (*Curcuma longa* l.), valerian root, extract (*Valeriana officinalis* l.), valerian root, oil (*Valeriana officinalis* l.), vanilla, absolute (*Vanilla* spp.), vanilla, extract (*Vanilla* spp.), vanilla, oleoresin (*Vanilla* spp.), vanilla (*Vanilla* spp.), vegetable juice, veronica (*Veronica officinalis* l.), vervain, european (*Verbena officinalis* l.), vetiver, oil (*Vetiveria zizanioides* stapf), vetiverol, vetiver (*Vetiveria zizaniodes* stapf), violet leaves absolute (*Viola odorata* l.), violet, swiss (*Viola calcarata* l.), walnut hull, extract (*Juglans* spp.), walnut leaves, extract (*Juglans* spp.), wheat gluten, whey, whey, delactosed, whey, demineralized, whey, partially dimineralized and partially delactosed, whey protein concentrate, wintergreen, extract (*Gaultheria procumbens* l.), wintergreen, oil (*Gaultheria procumbens* l.), woodruff, sweet (*Asperula odorata* l.), wort, yarrow, herb (*Achillea millefolium* l.), yarrow, oil (*Achillea millefolium* l.), yeast autolysate, yeast, dried irradiated, yeast extract autolyzed, yeast-malt sprout extract, yeasts, yeasts, dried, yerba santa, fluid extract (*Eriodictyon californicum* (Hook and am) torr), ylang-ylang, oil (*Cananga odorata* hook. f. and thomas), yucca, joshua-tree (*Yucca brevifolia* engelm.), yucca, mohave, extract (*Yucca* spp.), and acai berry extract.

In some embodiments, the plant or animal product is a culinary herb or spice. Representative culinary herbs and spices include but are not limited to: carrot, dehydrated carrot, carrot extract, parsnip, dehydrated parsnip, parsnip extract, onion, dehydrated onion, onion powder, onion flakes, onion extract, garlic, dehydrated garlic, garlic flakes, garlic powder, garlic extract, buttermilk, buttermilk powder, buttermilk solids, whey, whey powder, whey solids, milk, reduced fat milk, milk powder, milk solids, cream, cheese, cheese powder, cheese solids, cheese cultures, annatto, turmeric, sodium caseinate, milk protein, enzymatic digest of milk protein, tomato, tomato paste, tomato powder, tomato sauce, tomato extract, dehydrated tomato, sour cream, sour cream solids, caramel color, soy flour, chives, dehydrated chives, chive powder, ajwain, carom seeds (*Trachyspermum ammi*), akudjura (*Solanum centrale*), alkanet (*Alkanna tinctoria*), for red color, alligator pepper, mbongo spice (*mbongochobi*), hepper pepper (*Aframomum danielli*, a. *citratum*, a. *exscapum*), allspice (*Pimenta dioica*), angelica (*Angelica archangelica*), anise (*Pimpinella anisum*), anise hyssop (*Agastache foeniculum*), aniseed myrtle (*Syzygium anisatum*), annatto (*Bixa orellana*), apple mint (*Mentha suaveolens, Mentha×Rotundifolia* and *Mentha×Villosa*), artemisia (*Artemisia* spp.), asafoetida (*Ferula assafoetida*), asarabacca (*Asarum europaeum*), avens (*Geum urbanum*), avocado leaf (*Persea americana*), barberry (*Berberis vulgaris* and other *berberis* spp.), basil, sweet (*Ocimum basilicum*), basil, holy (*Ocimum tenuiflorum*), basil, lemon (*Ocimum× Citriodorum*), basil, thai (o. *basilicum* var. *thyrsiflora*), bay leaf (*Laurus nobilis*), bay leaf, indian, tejpat, malabathrum, bee balm (*Monarda didyma*), boldo (*Peumus boldus*), borage (*Borago officinalis*), blue fenugreek, blue melilot (*Trigonella caerulea*), caper (*Capparis spinosa*), caraway (*Carum carvi*), cardamom (*Elettaria cardamomum*), cardamom, black (*Amomum subulatum, Amomum costatum*), cassia (*Cinnamomum aromaticum*), catnip (*Nepeta cataria*), cayenne pepper (*Capsicum annuum*), celery leaf (*Apiumi graveolens*), celery seed (*Apiumi graveolens*), chervil (*Anthriscus cerefolium*), chicory (*Cichorium intybus*), chili pepper (*Capsicum* spp.), cicely, sweet cicely (*Myrrhis odorata*), cilantro, coriander greens, coriander herb (*Coriandrum sativum*), cinnamon, indonesian (*Cinnamomum burmannii, cassia vera*), cinnamon, saigon or vietnamese (*Cinnamomum loureiroi*), cinnamon, true or ceylon (*Cinnamomum verum, c.* zeylanicum), cinnamon, white (*Canella winterana*), cinnamon myrtle (*Backhousia myrtifolia*), clary, clary sage (*Salvia sclarea*), clove (*Syzygium aromaticum*), coriander seed (*Coriandrum sativum*), coriander, vietnamese (*Persicaria odorata*), costmary (*Tanacetum balsamita*), cubeb pepper (*Piper cubeba*), cudweed (*Gnaphalium* spp.), culantro, culangot, long coriander (*Eryngium foetidum*), cumin (*Cuminum cyminum*), curry leaf (*Murraya koenigii*), curry plant (*Helichrysum italicum*), dill herb or weed (*Anethum graveolens*), dill seed (*Anethum graveolens*), elderflower (*Sambucus* spp.), epazote (*Dysphania ambrosioides*), fennel (*Foeniculum vulgare*), fenugreek (*trigonella foenum-graecum*), filé powder, gumbo filé (*Sassafras albidum*), fingerroot, krachai, temu kuntji (*Boesenbergia rotunda*), galangal, greater (*Alpinia galanga*), galangal, lesser (*Alpinia officinarum*), galingale (*Cyperus* spp.), garlic chives (*Allium tuberosum*), ginger (*Zingiber officinale*), ginger, torch, bunga siantan (*Etlingera elatior*), golpar, persian hogweed (*Heracleum persicum*), grains of paradise (*Aframomum melegueta*), grains of selim, kani pepper (*Xylopia aethiopica*), horseradish (*Armoracia rusticana*), houttuynia cordata (Vietnam), huacatay, mexican marigold, mint marigold (*Tagetes minuta*), hyssop (*Hyssopus officinalis*), indonesian bay leaf, daun salam (*Syzygium polyanthum*), jasmine flowers (*Jasminum* spp.), jiaogulan (*Gynostemma pentaphyllum*), jimbu (*Allium hypsistum*), juniper berry (*Juniperus communis*), kaffir lime leaves, makrud lime leaves (*Citrus hystrix*), kala zeera (or *Kala jira*), black cumin (*Bunium persicum*), kawakawa seeds (*Macropiper excelsum*), keluak, kluwak, kepayang (*Pangium edule*), kencur, galangal, kentjur (*Kaempferia galanga*), kinh gioi, vietnamese balm (*Elsholtzia ciliata*), kokam seed (*Garcinia indica*), korarima, ethiopian cardamom, false cardamom (*Aframomum corrorima*), koseret leaves (*Lippia adoensis*), lavender (*Lavandula* spp.), lemon balm (*Melissa officinalis*), lemon ironbark (*Eucalyptus staigeriana*), lemon myrtle (*Backhousia citriodora*), lemon verbena (*Lippia citriodora*), lemongrass (*Cymbopogon citratus*, c. *flexuosus*, and other *Cymbopogon* spp.), leptotes bicolor, lesser calamint (*Calamintha nepeta*), nipitella, nepitella, licorice, liquorice (*Glycyrrhiza glabra*), lime flower, linden flower (*Tilia* spp.), lovage (*Levisticum officinale*), mace (*Myristica fragrans*), mahleb, st. lucie cherry (*Prunus mahaleb*), marjoram (*Origanum majorana*), mastic (*Pistacia lentiscus*), mint (*Mentha* spp.), 25 species, hundreds of varieties, mountain horopito (*Pseudowintera colorata*), 'pepper-plant', musk mallow, abelmosk (*Abelmoschus moschatus*), mustard, black, mustard plant, mustard seed (*Brassica nigra*), mustard, brown, mustard plant, mustard seed (*Brassica juncea*), mustard, white, mustard plant, mustard seed (*Sinapis alba*), mustard, yellow (*Brassica hirta=sinapis alba*), nigella, kalonji, black caraway, black onion seed (*Nigella sativa*), njangsa, djansang (*Ricinodendron heudelotii*), nutmeg (*Myristica fragrans*), olida (*Eucalyptus olida*), oregano (*Origanum vulgare*, o. *heracleoticum*, and other species), oregano, cuban (*Plectranthus amboinicus*), orris root (*Iris germanica, i. florentina, i. pallida*), pandan flower, kewra (*Pandanus odoratissimus*), pandan leaf, screwpine (*Pandanus amaryllifolius*), paprika (*Capsicum annuum*), paracress (*Spilanthes acmella*, soleracea), parsley (*Petroselinum crispum*), pepper, black, white, and green (*Piper nigrum*), pepper, brazilian, or pink pepper (*Schinus terebinthifolius*), pepper, dorrigo (*Tasmannia stipitata*), pepper, long (*Piper longum*), pepper, mountain, cornish pepper leaf (*Tasmannia lanceolata*), peppermint (*Mentha piperata*), peppermint gum leaf (*Eucalyptus dives*), perilla, shiso (*Perilla* spp.), peruvian pepper (*Schinus molle*), quassia (*Quassia amara*), rice paddy herb (*Limnophila aromatica*), rosemary (*Rosmarinus officinalis*), rue (*Ruta graveolens*), safflower (*Carthamus tinctorius*), saffron (*Crocus sativus*), trade and use of saffron, sage (*Salvia officinalis*), saigon cinnamon (*Cinnamomum loureiroi*), salad burnet (*Sanguisorba minor*), salep (*Orchis mascula*), sassafras (*Sassafras albidum*), savory, summer (*Satureja hortensis*), savory, winter (*Satureja montana*), shiso (*Perilla frutescens*), silphium, silphion, laser, laserpicium, lasarpicium, sorrel (*Rumex acetosa*), sorrel, sheep (*Rumex acetosella*), spearmint (*Mentha spicata*), spikenard (*Nardostachys grandiflora* or n. *jatamansi*), star anise (*Illicium verum*), sumac (*Rhus coriaria*), sweet woodruff (*Galium odoratum*), szechuan pepper, sichuan pepper (*Zanthoxylum piperitum*), tarragon (*Artemisia dracunculus*), thyme (*Thymus vulgaris*), thyme, lemon (*Thymus×Citriodorus*), turmeric (*Curcuma longa*), vanilla (*Vanilla planifolia*), voatsiperifery (*Piper borbonense*), wasabi (*Wasabia japonica*), water-pepper, smartweed (*Polygonum hydropiper*), watercress (*rorippa nasturtium-aquatica*), wattleseed, wild thyme (*Thymus serpyllum*), willow herb (*Epilobium parviflorum*), wintergreen (*Gaultheria procumbens*), wood avens, herb bennet (*Geum urbanum*), woodruff (*Galium odoratum*), wormwood, absinthe (*Artemisia absinthium*), yerba buena, yarrow (*Achillea millefolium*), za'atar (Herbs from the genera *Origanum, Calamintha, Thymus,* and *Satureja*), zedoary (*Curcuma zedoaria*), herb mixes, curry, tandoor masala, garam masala, chaat masala, tikka masala, masala dosa, paan masala, biryani masala, berbere, jerk seasonings, and spice rubs.

In some embodiments, the composition comprises a sweet compound or sweet flavor enhancing compound and one or more fats, oils, or emulsions. Representative fats, oils, and emulsions include but are not limited to: corn oil, peanut oil, soybean oil, palm oil, cottonseed oil, coconut oil, canola oil, rapeseed oil, olive oil, safflower oil, sunflower oil, sesame oil, almond oil, beech nut oil, brazil nut oil, cashew oil, linseed oil, flaxseed oil, hazelnut oil, mongongo nut oil, pecan oil, pine nut oil, pistachio oil, walnut oil, grapeseed oil, grapefruit seed oil, lemon oil, orange oil, mineral oil, petrolatum, cucumber oil, bitter gourd oil, bottle gourd oil, buffalo gourd oil, butternut squash oil, squash oil, pumpkinseed oil, watermelon seed oil, hemp oil, castor oil, butter, lard, margarine, cocoa butter, butterfat, whale oil, sperm oil, fish oil, cod liver oil, shark liver oil, krill oil, shrimp oil, codfish oil, salmon oil, herring oil, anchovy oil, smelt oil, candlefish oil, sprat oil, sardine oil, mackerel oil, tilefish oil, tuna (Thunnus) oil, swordfish oil, macadamia oil, acai oil, blackcurrant seed oil, borage seed oil, evening primrose oil, amaranth oil, wheat oil, wheat germ oil, apricot oil, argan oil, artichoke oil, avocado oil, babassu oil, ben oil, tallow nut oil, borneo tallow nut oil, carob pod oil, carob oil, coriander seed oil, false flax oil, kapok seed oil, lallemantia oil, meadowfoam seed oil, mustard oil, okra seed oil, perilla seed oil, pequi oil, prune kernel oil, quinoa oil, ramtil oil, rice bran oil, rice oil, barley oil, barley seed oil, tea oil, tea tree oil, thistle oil, jatropha oil, cork tree oil, apple seed oil, balanos oil, bladderpod oil, brucea javanica oil, burdock oil, candlenut oil, carrot seed oil, chaulmoogra oil, crambe oil, cuphea oil, jojoba oil, mango oil, palm kernel oil, mowrah butter, neem oil, orange oil, rosehip seed oil, sea buckthorn oil, shea butter, snowball seed oil, tall oil, tamanu oil, tonka bean oil, chicken fat, schmaltz, beef fat, lamb fat, animal fat, tallowate, tallow, beef tallow, bacon fat, ham fat, suet, milk fat, olestra, stearic acid, lauric acid, linoleic acid, palmitic acid, palmitoleic acid, myristic acid, goose fat, duck fat, drippings from roasting, mayonnaise, and oil-in water or water-in oil emulsions.

In some embodiments, the composition comprises a sweet compound or sweet flavor enhancing compound and one or more GRAS compounds (generally recognized as safe). Representative GRAS compounds include but are not limited to: Acacia Gum (*Acacia senegal* (L.) Willd.), Acetal, Acetaldehyde, Propyl Phenethyl Acetal, Acetanisole, Acetic Acid, (Tri-)Acetin, Acetoin, Acetophenone, Aconitic Acid, Adipic Acid, Agar (*Gelidium* Spp.), Alfalfa Extract (*Medicago sativa* L.), Algin (*Laminaria* Spp. And Other Kelps), Alginates, Sodium, Calcium, And Ammonium, Allspice (*Pimenta officinalis* Lindl.), Allspice Oil (*Pimenta officinalis* Lindl.), Allspice Oleoresin (*Pimenta officinalis* Lindl.), Allyl Anthranilate, Allyl Butyrate, Allyl Cinnamate, Allyl Cyclohexaneacetate, Allyl Cyclohexanebutyrate, Allyl Cyclohexanehexanoate, Allyl Cyclohexanepropionate, Allyl Cyclohexanevalerate, Allyl Disulfide, Allyl 2-Ethylbutyrate, Allyl 2-Furoate, Allyl Heptanoate, Allyl Hexanoate, Allyl Alpha-Ionone, Allyl Isothiocyanate, Allyl Mercaptan, Allyl Nonanoate, Allyl Octanoate, Allyl Phenoxyacetate, Allyl Phenylacetate, Allyl Propionate, Allyl Sorbate, Allyl Sulfide, Allyl Tiglate, Allyl 10-Undecenoate, Allyl Isovalerate, Almond Oil, Bitter (Ffpa) (*Prunus* Spp.), Aloe Extract (*Aloe* Spp.), Althea Root (*Althea officinalis* L.), Ambergris Tincture, Ambrette Absolute Oil (*Hibiscus abelmoschus* L.), Ambrette Seed Oil (*Hibiscus abelmoschus* L.), Ambrette Tincture (*Hibiscus abelmoschus* L.), Ammonium Sulfide, Ammonium Isovalerate, Isoamyl Acetate, Amyl Alcohol, Isoamyl Alcohol, Isoamyl Benzoate, Amyl Butyrate, Isoamyl Butyrate, Alpha-Amylcinnamaldehyde, Alpha-Amylcinnamaldehyde Dimethyl Acetal, Isoamyl Cinnamate, Alpha-Amylcinnamyl Acetate, Alpha-Amylcinnamyl Alcohol, Alpha-Amylcinnamyl Formate, Alpha-Amylcinnamyl Isovalerate, Amyl Formate, Isoamyl Formate, Isoamyl 4(2-Furan)Butyrate, Isoamyl 3(2-Furan)Propionate, Amyl 2-Furoate, Amyl Heptanoate, Amyl Hexanoate, Isoamyl Hexanoate, 2-Amyl-5 Or 6-Keto-1,4-Dioxane, Isoamyl Laurate, Isoamyl Nonanoate, Amyl Octanoate, Isoamyl Octanoate, Isoamyl Phenylacetate, Isoamyl Propionate, Isoamyl Pyruvate, Isoamyl Salicylate, Isoamyl Isovalerate, Trans-Anethole, Angelica Root Extract (*Angelica archangelica* L.), Angelica Root Oil (*Angelica archangelica* L.), Angelica Seed Extract (*Angelica archangelica* L.), Angelica Seed Oil (*Angelica archangelica* L.), Angelica Stem Oil (*Angelica archangelica* L.), Angostura Extract (*Galipea offincinalis* Hancock), Anise (*Pimpinella anisum* L.), Anise Oil (*Pimpinella anisum* L.), Anise, Star (*Illicium verum* Hook, F.), Anise, Star, Oil (*Illicium verum* Hook, F.), Anisole, P-Anisyl Acetate, Anisyl Alcohol, Anisyl Butyrate, Anisyl Formate, Anisyl Propionate, Annatto Extract (*Bixa orellana* L.), Annatto Seed (*Bixa orellana* L.), Apricot Kernel Oil (*Prunus armeniaca* L.), Asafetida Fluid Extract (*Ferula assafoetida* L.), Asafetida Gum (*Ferula assafoetida* L.), Asafoetida Oil (*Ferula asafoetida* L.), Ascorbic Acid, Ash Bark, Prickly, Extract (*Xanthoxylum* Spp.), Balm (*Melissa officinalis* L.), Balm Leaves Extract (*Melissa officinalis* L.), Balm Oil (*Melissa officinalis* L.), Balsam Fir Oil (*Abies balsamea* (L.) Mill.), Balsam Fir Oleoresin (*Abies balsamea* (L.) Mill.), Balsam, Peru (*Myroxylon pereirae* Klotzsch), Balsam Oil, Peru (*Myroxylon pereirae* Klotzsch), Basil (*Ocimum basilicum* L.), Basil Oil (*Ocimum basilicum* L.), Basil Oleoresin (*Ocimum basilicum* L.), Bay Leaves, West Indian, Extract (*Pimenta acris* Kostel), Bay Leaves, West Indian, Oil (*Pimenta acris* Kostel), Bay Leaves, West Indian, Oleoresin (*Pimenta acris* Kostel), Bay, Sweet (*Laurus nobilis* L.), Bay Oil, Sweet (*Laurus nobilis* L.), Beeswax, White (*Apis mellifera* L.), Benzaldehyde, Benzaldehyde Dimethyl Acetal, Benzaldehyde Glyceryl Acetal, Benzaldehyde Propylene Glycol Acetal, Benzoic Acid, Benzoin, Benzoin Resinoid, Benzophenone, Benzyl Acetate, Benzyl Acetoacetate, Benzyl Alcohol, Benzyl Benzoate, Benzyl Butyl Ether, Benzyl Butyrate, Benzyl Isobutyrate, Benzyl Cinnamate, Benzyl 2,3-Dimethylcrotonate, Benzyl Ethyl Ether, Benzyl Formate, 3-Benzyl-4-Heptanone, Benzyl Mercaptan, Benzyl Methoxyethyl Acetal, Benzyl Phenylacetate, Benzyl Propionate, Benzyl Salicylate, Benzyl Isovalerate, Bergamot Oil, Birch, Sweet, Oil (*Betula lenta* L.), Blackberry Bark Extract (*Rubus*, Spp. Of Section Eubatus), Bois De Rose Oil, Borneol, Isoborneol, Bornyl Acetate, Isobornyl Acetate, Bornyl Formate, Isobornyl Formate, Isobornyl Propionate, Bornyl Valerate, Bornyl Isovalerate (Endo-), Isobornyl Isovalerate, Boronia Absolute (*Boronia megastigma* Nees), Buchu Leaves Oil (*Barosma* Spp.), 2-Butanone, Butter Acids, Butter Esters, Butter Starter Distillate, Butyl Acetate, Isobutyl Acetate, Butyl Acetoacetate, Isobutyl Acetoacetate, Butyl Alcohol, Isobutyl Alcohol, Isobutyl Angelate, Butyl Anthranilate, Isobutyl Anthranilate, Butylated Hydroxyanisole, Butylated Hydroxytoluene, Isobutyl Benzoate, Butyl Butyrate, Isobutyl Butyrate, Butyl Isobutyrate, Isobutyl Isobutyrate, Butyl Butyryllactate, Alpha-Butylcinnamaldehyde, Butyl Cinnamate, Isobutyl Cinnamate, Butyl 2-Decenoate, Butyl Ethyl Malonate, Butyl Formate, Isobutyl Formate, Isobutyl 3-(2-Furan)Propionate, Butyl Heptanoate, Isobutyl Heptanoate, Butyl Hexanoate, Isobutyl Hexanoate, Butyl P-Hydroxy Benzoate, 2-Butyl-5- Or 6-Keto-1,4-Dioxane, Butyl Lactate, Butyl Laurate, Butyl Levulinate, Alpha-Isobutylphenethyl Alcohol, Butyl Phenylacetate, Isobutyl Phenylacetate, Butyl Propionate, Isobutyl Propionate, Isobutyl Salicylate, Butyl Stearate, Butyl Sulfide, Butyl 10-Undecenoate, Butyl Valerate, Butyl Isovalerate, Butyraldehyde, Isobutyraldehyde, Butyric Acid, Isobutyric Acid, (Tri-)Butyrin, Caffeine, Cajeput Oil (*Melaleuca leucadendron* L.), Calcium Acetate, Camphene, D-Camphor, Camphor, Japanese, White, Oil (*Cinnamomum camphora* (L.) Nees Et Eberm.), Cananga Oil, Capsicum Extract (*Capsicum* Spp.), *Capsicum Oleoresin* (*Capsicum* Spp.), Caramel Color, Caraway (*Carum carvi* L.), Caraway, Black (*Nigella sativa* L.), Caraway Oil, Carboxymethylcellulose, Cardamom (*Elettaria cardamomum* (L.) Maton), Cardamom Seed Oil (*Elettaria cardamomum* (L.) Maton), Carmine (*Coccus cacti* L.), Carob Bean Extract (*Ceratonia siliqua* L.), Carrot Oil, Carvacrol, Carvacryl Ethyl Ether, Carveol, 4-Carvomenthenol, Carvone, Carvyl Acetate, Carvyl Propionate, Beta-Caryophyllene, Cascara Bitterless Extract (*Rhamnus purshiana* Dc.), Cascarilla Bark Extract (*Croton* Spp.), Cascarilla Bark Oil (*Croton* Spp.), Cassia (*Cinnamomum cassia* Blume), Cassia Bark Extract (*Cinnamomum cassia* Blume), Cassia Bark Oil, Cassia Buds (*Cinnamomum cassia* Blume), Cassie Absolute (*Acacia farnesiana* (L.) Willd.), Castoreum Oil, Castoreum, Liquid (*Castor* Spp.), Castor Oil (*Ricinus communis* L.), Catechu Extract (*Acacia catechu* Willd.), Catechu Powder (*Acacia catechu* Willd.), Cayenne (*Capsicum annuum* L. Var. *longum* Sendt), Cedar Leaf Oil (*Thuja occidentalis* L.), Celery Seed (*Apium graveolens* L.), Celery Seed Extract (*Apium graveolens* L.), Celery Seed Extract Solid (*Apium graveolens* L.), Celery Seed Oil, Chamomile Flower, English, Oil (*Anthemis nobilis* L.), Chamomile Flower, Hungarian, Oil (*Matricaria chamomilla* L.), Chamomile Flower, Roman, Extract (*Anthemis nobilis* L.), Chamomile Flower, Roman, Oil (*Anthemis nobilis* L.), Cherry Bark, Wild, Extract (*Prunus serotina* Ehrh.), Cherry Laurel Oil (Ffpa) (*Prunus laurocerasus* L.), Cherry Pits Extract (*Prunus* Spp.), Chervil (*Anthriscus Cerefolium* (L.) Hoffm.), Chicory Extract (*Cichorium intybus* L.), Cinchona Bark Red (*Cinchona succirubra* Pav. Or Its Hybrids), Cinchona Bark Red Extract (*Cinchona succirubra* Pav. Or Its Hybrids), Cinchona Bark Yellow (*Cinchona* Spp.), Cinchona Bark Yellow Extract (*Cinchona* Spp.), Cinchona Extract (*Cinchona* Spp.), Cinnamaldehyde, Cinnamaldehyde Ethylene Glycol Acetal, Cinnamic Acid, Cinnamon (*Cinnamomum* Spp.), Cinnamon Bark Extract (*Cinnamomum* Spp.), Cinnamon Bark Oil, Cinnamon Leaf Oil, Cinnamyl Acetate, Cinnamyl Alcohol, Cinnamyl Butyrate, Cinnamyl Isobutyrate, Cinnamyl Cinnamate, Cinnamyl Formate, Cinnamyl Phenylacetate, Cinnamyl Propionate, Cinnamyl Isovalerate, Citral, Citral Diethyl Acetal, Citral Dimethyl Acetal, Citric Acid, Citronellal, Citronella Oil, Dl-Citronellol, Citronelloxyacetaldehyde, Citronellyl Acetate, Citronellyl Butyrate, Citronellyl Isobutyrate, Citronellyl Formate, Citronellyl Phenylacetate, Citronellyl Propionate, Citronellyl Valerate, Citrus Peels Extract (*Citrus* Spp.), Civet Absolute (*Viverra civetta* Schreber And *Viverra zibetha* Schreber), Clary (*Salvia sclarea* L.), Clary Oil (*Salvia sclarea* L.), Clove Bud Extract (*Eugenia* Spp.), Clove Bud Oil (*Eugenia* Spp.), Clove Bud Oleoresin (*Eugenia* Spp.), Clove Leaf Oil, Madagascar, Clover Tops Red Extract Solid (*Trifolium pratense* L.), Cloves (*Eugenia* Spp.), Clove Stem, Oil (*Eugenia* Spp.), Coca Leaf Extract (Decocainized) (*Erythroxylon coca* Lam.), Cognac Oil, Green, Cognac Oil, White, Coriander (*Coriandrum sativum* L.), Coriander Oil (*Coriandrum sativum* L.), Corn Silk (*Zea mays* L.), Costus Root Oil (*Saussurea lappa* Clarke), P-Cresol, Cubebs (*Piper cubeba* L. F.), Cubeb Oil (*Piper cubeba* L. F.), Cumin (*Cuminum cyminum* L.), Cuminaldehyde, Cumin Black (Nigella *Sativa* L.), Cumin Oil, Curacao Peel Extract (*Citrus aurantium* L.), Curacao Peel Oil (*Citrus aurantium* L.), Currant Buds Black Absolute (*Ribes nigrum* L.), Cyclohexaneacetic Acid, Cyclohexaneethyl Acetate, Cyclohexyl Acetate, Cyclohexyl Anthranilate, Cyclohexyl Butyrate, Cyclohexyl Cinnamate, Cyclohexyl Formate, Cyclohexyl Propionate, Cyclohexyl Isovalerate, P-Cymene, Dandelion Fluid Extract (*Taraxacum* Spp.), Dandelion Root Extract Solid (*Taraxacum* Spp.), Davana Oil (*Artemisia pallens* Wall.), Gamma-Decalactone, Delta-Decalactone, Decanal, Decanal Dimethyl Acetal, Decanoic Acid, 1-Decanol, 2-Decenal, Decyl Acetate, Decyl Butyrate, Decyl Propionate, Diacetyl, Dibenzyl Ether, 4,4-Dibutyl-Gamma-Butyrolactone, Dibutyl Sebacate, Diethyl Malate, Diethyl Malonate, Diethyl Sebacate, Diethyl Succinate, Diethyl Tartrate, Dihydrocarveol (Isomer Unspecified), Dihydrocarvyl Acetate, Dihydrocoumarin, Dill (*Anethum graveolens* L.), Dill Oil (*Anethum graveolens* L.), Dill Seed Indian (*Anethum* Spp.), M-Dimethoxybenzene, P-Dimethoxybenzene, 2,4-Dimethylacetophenone, Alpha, Alpha-Dimethylbenzyl Isobutyrate, 2,6-Dimethyl-5-Heptenal, 2,6-Dimethyloctanal, 3,7-Dimethyl-1-Octanol, Alpha, Alpha-Dimethylphenethyl Acetate, Alpha,Alpha-Dimethylphenethyl Alcohol, Alpha,Alpha-Dimethylphenethyl Butyrate, Alpha,Alpha-Dimethylphenethyl Formate, Dimethyl Succinate, 1,3-Diphenyl-2-Propanone, Disodium Phosphate, Dittany Of Crete (*Origanum dictamnus* L.), Gamma-Dodecalactone, Delta-Dodecalactone, 2-Dodecenal, Doggrass Extract (*Agropyron repens* (L.) Beauv.), Dragon's Blood Extract (*Daemonorops* Spp. Or Other Botanical Sources), Dulse (*Rhodymenia palmata* (L.) Grev.), Elder Flowers (*Sambucus canadensis* L. Or *Sambucus Nigra* L.), Elemi Gum (*Canarium* Spp.), Elemi Oil (*Canarium* Spp.), Erigeron Oil (*Erigeron candensis* L.), Erythrobic Acid, Estragole, Estragon Oil (*Artemisia dracunculus* L.), P-Ethoxybenzaldehyde, Ethyl Acetate, Ethyl Acetoacetate, Ethyl 2-Acetyl-3-Phenylpropionate, Ethyl Aconitate (Mixed Esters), Ethyl Acrylate, Ethyl Alcohol, Ethyl P-Anisate, Ethyl Anthranilate, Ethyl Benzoate, Ethyl Benzoylacetate, Alpha-Ethylbenzyl Butyrate, 2-Ethylbutyl Acetate, 2-Ethylbutyraldehyde, Ethyl Butyrate, Ethyl Isobutyrate, 2-Ethylbutyric Acid, Ethyl Cinnamate, Ethyl Cyclohexanepropionate, Ethyl Decanoate, Ethyl Formate, Ethyl 3(2-Furyl)Propanoate, 4-Ethylguaiacol, Ethyl Heptanoate, 2-Ethyl-2-Heptenal, Ethyl Hexanoate, Ethyl Lactate, Ethyl Laurate, Ethyl Levulinate, Ethyl 2-Methylbutyrate, Ethyl Methylphenylglycidate, Ethyl Myristate, Ethyl Nitrite, Ethyl Nonanoate, Ethyl 2-Nonynoate, Ethyl Octanoate, Ethyl Oleate, Ethyl Palmitate, Ethyl Phenylacetate, Ethyl 4-Phenylbutyrate, Ethyl 3-Phenylglycidate, Ethyl 3-Phenylpropionate, Ethyl Propionate, Ethyl Pyruvate, Ethyl Salicylate, Ethyl Sorbate, Ethyl Tiglate, Ethyl 10-Undecenoate, Ethyl Valerate, Ethyl Isovalerate, Ethyl Vanillin, Eucalyptol, Eucalyptus Oil (*Eucalyptus globulus* Labille), Eugenol, Isoeugenol, Eugenyl Acetate, Isoeugenyl Acetate, Eugenyl Benzoate, Isoeugenyl Ethyl Ether, Eugenyl Formate, Isoeugenyl Formate, Eugenyl Methyl Ether, Isoeugenyl Methyl Ether, Isoeugenyl Phenylacetate, Farnesol, D-Fenchone, Fenchyl Alcohol, Fennel, Common (*Foeniculum vulgare* Mill.), Fennel, Sweet (*Foeniculum vulgare* Mill. Var *dulce* (D.C.), Fennel Oil, Sweet (*Foeniculum vulgare* Mill. Var. *dulce* Dc.), Fenugreek (*Trigonella foenum-graecum* L.), Fenugreek Extract (*Trigonella foenum-graecum* L.), Fenugreek Oleoresin (*Trigonella Foenumgraecum* L.), Formic Acid, Fumaric Acid, Furfural, Furfuryl Acetate, Furfuryl Alcohol, 2-Furfurylidene Butyraldehyde, Furfuryl Mercaptan, 3-(2-Furyl)Acrolein, 4-(2-Furyl)-3-Buten-2-One, (2-Furyl)-2-Propanone, Fusel Oil, Refined, Galangal Root (*Alpinia* Spp.), Galangal Root Extract (*Alpinia* Spp.), Galangal Root Oil (*Alpinia* Spp.), Galbanum Oil (*Ferula* Spp.), Galbanum Resin (*Ferula* Spp.), Garlic Oil (*Allium sativum* L.), Genet Absolute (*Spartium junceum* L.), Genet Extract (*Spartium junceum* L.), Gentian Root Extract (*Gentiana lutea* L.), Geraniol, Elemi Gum (*Canarium* Spp.), Elemi Oil (*Canarium* Spp.), Erigeron Oil (*Erigeron candensis* L.), Erythrobic Acid, Estragole, Estragon Oil (*Artemisia dracunculus* L.), P-Ethoxybenzaldehyde, Ethyl Acetate, Ethyl Acetoacetate, Ethyl 2-Acetyl-3-Phenylpropionate, Ethyl Aconitate (Mixed Esters), Ethyl Acrylate, Ethyl Alcohol, Ethyl P-Anisate, Ethyl Anthranilate, Ethyl Benzoate, Ethyl Benzoylacetate, Alpha-Ethylbenzyl Butyrate, 2-Ethylbutyl Acetate, 2-Ethylbutyraldehyde, Ethyl Butyrate, Ethyl Isobutyrate, 2-Ethylbutyric Acid, Ethyl Cinnamate, Ethyl Cyclohexanepropionate, Ethyl Decanoate, Ethyl Formate, Ethyl 3(2-Furyl) Propanoate, 4-Ethylguaiacol, Ethyl Heptanoate, 2-Ethyl-2-Heptenal, Ethyl Hexanoate, Ethyl Lactate, Ethyl Laurate, Ethyl Levulinate, Ethyl 2-Methylbutyrate, Ethyl Methylphenylglycidate, Ethyl Myristate, Ethyl Nitrite, Ethyl Nonanoate, Ethyl 2-Nonynoate, Ethyl Octanoate, Ethyl Oleate, Ethyl Palmitate, Ethyl Phenylacetate, Ethyl 4-Phenylbutyrate, Ethyl 3-Phenylglycidate, Ethyl 3-Phenylpropionate, Ethyl Propionate, Ethyl Pyruvate, Ethyl Salicylate, Ethyl Sorbate, Ethyl Tiglate, Ethyl 10-Undecenoate, Ethyl Valerate, Ethyl Isovalerate, Ethyl Vanillin, Eucalyptol, Eucalyptus Oil (*Eucalyptus globulus* Labille), Eugenol, Isoeugenol, Eugenyl Acetate, Isoeugenyl Acetate, Eugenyl Benzoate, Isoeugenyl Ethyl Ether, Eugenyl Formate, Isoeugenyl Formate, Eugenyl Methyl Ether, Isoeugenyl Methyl Ether, Isoeugenyl Phenylacetate, Farnesol, D-Fenchone, Fenchyl Alcohol, Fennel, Common (*Foeniculum vulgare* Mill.), Fennel, Sweet (*Foeniculum vulgare* Mill. Var *dulce* (D.C.), Fennel Oil, Sweet (*Foeniculum vulgare* Mill. Var. *dulce* Dc.), Fenugreek (*Trigonella foenum-graecum* L.), Fenugreek Extract (*Trigonella foenum-graecum* L.), Fenugreek Oleoresin (*Trigonella* Foenumgraecum L.), Formic Acid, Fumaric Acid, Furfural, Furfuryl Acetate, Furfuryl Alcohol, 2-Furfurylidene Butyraldehyde, Furfuryl Mercaptan, 3-(2-Furyl)Acrolein, 4-(2-Furyl)-3-Buten-2-One, (2-Furyl)-2-Propanone, Fusel Oil, Refined, Galangal Root (*Alpinia* Spp.), Galangal Root Extract (*Alpinia* Spp.), Galangal Root Oil (*Alpinia* Spp.), Galbanum Oil (*Ferula* Spp.), Galbanum Resin (*Ferula* Spp.), Garlic Oil (*Allium sativum* L.), Genet Absolute (*Spartium junceum* L.), Genet Extract (*Spartium junceum* L.), Gentian Root Extract (*Gentiana lutea* L.), Geraniol, Labdanum Absolute (*Cistus* Spp.), Labdanum Oil (*Cistus* Spp.), Labdanum Oleoresin (*Cistus* Spp.), Lactic Acid, Laurel Berries (*Laurus nobilis* L.), Laurel Leaves Extract (*Laurus nobilis* L.), Lauric Acid, Lauric Aldehyde, Lauryl Acetate, Lauryl Alcohol, Lavandin Oil (*Lavandula* hybrida), Lavender (*Lavandula officinalis* Chaix), Lavender Absolute (*Lavandula officinalis* Chaix), Lavender Concrete (*Lavandula officinalis* Chaix), Lavender Oil (*Lavandula officinalis* Chaix), Lemon Extract (*Citrus limon* (L.) Burm. F.), Lemongrass Oil, Lemon Oil, Lemon Oil Terpeneless (*Citrus limon* (L.) Burm. F.), Levulinic Acid, Licorice Extract (*Glycyrrhiza* Spp.), Licorice Extract Powder (*Glycyrrhiza glabra* L.), Licorice Root (*Glycyrrhiza glabra* L.), Lime Oil, Lime Oil, Terpeneless (*Citrus aurantifolia* (Christman) Swingle), D-Limonene, Linaloe Wood Oil (*Bursera delpechiana* Poiss. And Other *bursera* Spp.), Linalool, Linalyl Acetate, Linalyl Anthranilate, Linalyl Benzoate, Linalyl Butyrate, Linalyl Isobutyrate, Linalyl Cinnamate, Linalyl Formate, Linalyl Hexanoate, Linalyl Octanoate, Linalyl Propionate, Linalyl Isovalerate, Linden Flowers (*Tilia glabra* Vent.), Locust Gum (*Ceratonia siliqua* L.), Lovage (*Levisticum officinale* Koch), Lovage Extract (*Levisticum officinale* Koch), Lovage Oil (*Levisticum officinale* Koch), Mace (*Myristica fragrans* Houtt.), Mace Oil (*Myristica fragrans* Houtt.), Mace Oleoresin (*Myristica fragrans* Houtt.), L-Malic Acid, Maltol, Mandarin Oil, Expressed, Marigold, Pot (*Calendula officinalis* L.), Marjoram Oleoresin (*Majorana hortensis* Moench-*Origanum Majorana* L.), Marjoram, Pot (*Origanum vulgare* L.), Marjoram Seed (*Majorana hortensis* Moench-*Origanum Majorana* L.), Marjoram, Sweet (*Majorana hortensis* Moench-*Origanum Majorana* L.), Marjoram Oil, Sweet (*Origanum majorana*), P-Mentha-1,8-Dien-7-Ol, Menthol Racemic, (+)-Neoisomenthol, Menthone, Menthyl Acetate (Isomer Unspecified), Menthyl Isovalerate, P-Methoxybenzaldehyde, 2-Methoxy-4-Methylphenol, 4-(P-Methoxyphenyl)-2-Butanone, 1-(P-Methoxyphenyl)-1-Penten-3-One, 1-(P-Methoxyphenyl)-2-Propanone, 2-Methoxy-4-Vinylphenol, Methyl Acetate, 4'-Methylacetophenone, 2-Methylallyl Butyrate, Methyl Anisate, O-Methylanisole, P-Methylanisole, Methyl Anthranilate, Methyl Benzoate, Alpha-Methylbenzyl Acetate, Alpha-Methylbenzyl Alcohol, Alpha-Methylbenzyl Butyrate, Alpha-Methylbenzyl Isobutyrate, Alpha-Methylbenzyl Formate, Alpha-Methylbenzyl Propionate, Methyl P-Tert-Butylphenylacetate, 2-Methylbutyraldehyde, 3-Methylbutyraldehyde, Methyl Butyrate, Methyl Isobutyrate, 2-Methylbutyric Acid, Methyl Cellulose, Alpha-Methylcinnamaldehyde, Methyl Cinnamate, 6-Methylcoumarin, Methylcyclopentenolone, 4-(3,4-Methylenedioxyphenyl)-2-Butanone, 5-Methylfurfural, Methyl 2-Furoate, 2-Methyl-3(2-Furyl)Acrolein, Methyl Heptanoate, 2-Methylheptanoic Acid, 6-Methyl-5-Hepten-2-One, Methyl Hexanoate, Methyl 2-Hexenoate, Methyl P-Hydroxybenzoate, Methyl-Alpha-Ionone, Methyl-Beta-Ionone, Methyl-Delta-Ionone, Alpha-Iso-Methylionone, Methyl Laurate, Methyl Mercaptan, Methyl O-Methoxybenzoate, Methyl N-Methylanthranilate, Methyl 2-Methylbutyrate, Methyl 3-Methylthiopropionate, Methyl 4-Methylvalerate, Methyl Myristate, Methyl Beta-Naphthyl Ketone, Methyl Nonanoate, Methyl 2-Nonenoate, Methyl 2-Nonynoate, 2-Methyloctanal, Methyl Octanoate, Methyl 2-Octynoate, 4-Methyl-2,3-Pentanedione, 4-Methyl-2-Pentanone, Beta-Methylphenethyl Alcohol, Methyl Phenylacetate, 3-Methyl-4-Phenyl-3-Butene-2-One, 2-Methyl-4-Phenyl-2-Butyl Acetate, 2-Methyl-4-Phenyl-2-Butyl Isobutyrate, 2-Methyl-4-Phenylbutyraldehyde, 3-Methyl-2-Phenylbutyraldehyde, Methyl 4-Phenylbutyrate, 4-Methyl-1-Phenyl-2-Pentanone, Methyl 3-Phenylpropionate, Methyl Propionate, 2-Methyl-3-(P-Isopropylphenyl)Propionaldehyde, 6-Methylquinoline, Methyl Salicylate, Methyl Sulfide, 3-(Methylthio)Propionaldehyde, 2-Methyl-3-Tolylpropionaldehyde, 2-Methylundecanal, Methyl 9-Undecenoate, Methyl 2-Undecynoate, Methyl Valerate, Methyl Isovalerate, 2-Methylvaleric Acid, Mimosa Absolute (*Acacia decurrens* Willd. Var. *dealbata*), Monosodium Glutamate, Mountain Maple Extract Solid (*Acer spicatum* Lam.), Musk Tonquin (*Moschus moschiferus* L.), Mustard, Brown (*Brassica* Spp.), Mustard, Yellow (*Brassica* Spp.), Myrcene, Myristaldehyde, Myristic Acid, Myrrh Gum (*Commiphora* Spp.), Myrrh Oil (*Commiphora* Spp.), Beta-Naphthyl Anthranilate, Beta-Naphthyl Ethyl Ether, Naringen Extract (*Citrus paradisi* Macf.), Nerol, Neroli Bigarde Oil (*Citrus aurantium* L.), Nerolidol (Isomer Unspecified), Neryl Acetate, Neryl Butyrate, Neryl Isobutyrate, Neryl Formate, Neryl Propionate, Neryl Isovalerate, Nitrous Oxide, 2,6-Nonadien-1-Ol, Gamma-Nonalactone, Nonanal, 1,3-Nonanediol Acetate (Mixed Esters), Nonanoic Acid, 2-Nonanone, Nonanoyl 4-Hydroxy-3-Methoxybenzylamide, Nonyl Acetate, Nonyl Alcohol, Nonyl Octanoate, Nonyl Isovalerate, Nutmeg (*Myristica fragrans* Houtt.), Nutmeg Oil, Oak Chips Extract (*Quercus alba* L.), Oakmoss Absolute (*Evernia* Spp.), Gamma-Octalactone, Octanal, Octanal Dimethyl Acetal, Octanoic Acid, 1-Octanol, 2-Octanol, 2-Octanone, 3-Octanone, 3-(Hydroxymethyl)-2-Heptanone, 1-Octen-3-Ol, Octyl Acetate, Octyl Butyrate, Octyl Isobutyrate, Octyl Formate, Octyl Heptanoate, Octyl Octanoate, Octyl Phenylacetate, Octyl Propionate, Octyl Isovalerate, Oleic Acid, Olibanum oil (*Boswellia* Spp.), Onion Oil (*Allium cepa* L.), Orange Blossoms Absolute, Orange Flowers (*Citrus aurantium* L.), Orange Leaf Absolute (*Citrus aurantium* L.), Orange Oil Distilled (*Citrus sinensis* (L.) Osbeck), Orange Oil Terpeneless (*Citrus sinensis* (L.) Osbeck), Orange Peel Oil, Bitter (*Citrus aurantium* L.), Orange Peel, Sweet, Extract (*Citrus sinensis* L. Osbeck), Orange Peel Oil, Sweet (*Citrus sinensis* (L.) Osbeck), Orange Peel, Sweet, Oil, Terpeneless (*Citrus sinensis* L. Osbeck), Oregano (*Lippia* Spp.), *Origanum* Oil (Extractive) (*Thymus capitatus* L. Hoffmanns & Link), Orris Concrete Liquid Oil (*Iris florentina* L.), Orris Root Extract (*Iris florentina* L.), Palmarosa Oil (*Cymbopogon martini* (Roxb.) Stapf), Palmitic Acid, Paprika (*Capsicum annuum* L.), Paprika Oleoresin (*Capsicum annuum* L.), Parsley (*Petroselinum crispum* (Miller) Nyman-P. *Sativum* Hoffm.), Parsley Oil, Parsley Oleoresin (*Petroselinum* Spp.), Patchouly Oil, Pennyroyal Oil (*Mentha pulegium* L.), Omega-Pentadecalactone, 2,3-Pentanedione, 2-Pentanone, 4-Pentenoic Acid, Pepper, Black (*Piper nigrum* L.), Pepper, Black, Oil (*Piper nigrum* L.), Pepper, Black, Oleoresin (*Piper nigrum* L.), Peppermint Leaves (*Mentha piperita* L.), Peppermint Oil, Pepper, Red (*Capsicum frutescens* L. (*Capsicum annuum* L.)), Pepper, White (*Piper nigrum* L.), Pepper, White, Oil (*Piper nigrum* L.), Pepper, White, Oleoresin (*Piper nigrum* L.), Petitgrain, Lemon, Oil (*Citrus limon* L. Burm. F), Petitgrain Mandarin Oil (*Citrus reticulata* Blanco Var. Mandarin), Petitgrain Paraguay Oil, Alpha-Phellandrene, Phenethyl Acetate, Phenethyl Alcohol, Phenylethyl Anthranilate, Phenethyl Benzoate, Phenethyl Butyrate, Phenethyl Isobutyrate, Phenethyl Cinnamate, Phenethyl Formate, Phenethyl 2-Furoate, Phenethyl Phenylacetate, Phenethyl Propionate, Phenethyl Salicylate, Phenethyl Senecioate, Phenethyl Tiglate, Phenethyl Isovalerate, Phenoxyacetic Acid, 2-Phenoxyethyl Isobutyrate, Phenylacetaldehyde, Phenylacetaldehyde 2,3-Butylene Glycol Acetal, Phenylacetaldehyde Dimethyl Acetal, Phenylacetaldehyde Glyceryl Acetal, Phenylacetic Acid, 4-Phenyl-2-Butanol, 4-Phenyl-3-Buten-2-Ol, 4-Phenyl-3-Buten-2-One, 4-Phenyl-2-ButylAcetate, 1-Phenyl-3-Methyl-3-Pentanol, 1-Phenyl-1-Propanol, 3-Phenyl-1-Propanol, 2-Phenylpropionaldehyde, 3-Phenylpropionaldehyde, 2-Phenylpropionaldehyde Dimethyl Acetal, 3-Phenylpropionic Acid, 3-Phenylpropyl Acetate, 2-Phenylpropyl Butyrate, 2-Phenylpropyl Isobutyrate, 3-Phenylpropyl Isobutyrate, 3-Phenylpropyl Cinnamate, 3-Phenylpropyl Formate, 3-Phenylpropyl Hexanoate, 3-Phenylpropyl Propionate, 2-(3-Phenylpropyl) Tetrahydrofuran, 3-Phenylpropyl Isovalerate, Phosphoric Acid, Pimenta Leaf Oil, Alpha-Pinene, Beta-Pinene, Pine Needle, Dwarf, Oil (*Pinus Mugo* Turra Var. *pumilio* (Haenke) Zenari), Pine Needle Oil (*Abies* Spp.), Pine Scotch Oil (*Pinus sylvestris* L.), Pine Tar Oil (*Pinus palustris* Mill. And Other *Pinus* Spp.), Piperidine, Piperine, D-Piperitone, Piperonal, Piperonyl Acetate, Piperonyl Isobutyrate, Pipsissewa Leaves Extract (*Chimaphila umbellata* Nutt.), Polysorbate 20, Polysorbate 60, Polysorbate 80, Pomegranate Bark Extract (*Punica granatum* L.), Poppy Seed (*Papaver somniferum* L.), Potassium Acetate, Potassium Sorbate, Propenylguaethol, Propionaldehyde, Propionic Acid, Propyl Acetate, Isopropyl Acetate, P-Isopropylacetophenone, Propyl Alcohol, Isopropyl Alcohol, P-Propylanisole, Propyl Benzoate, Isopropyl Benzoate, P-Isopropylbenzyl Alcohol, Propyl Butyrate, Isopropyl Butyrate, Propyl Isobutyrate, Isopropyl Isobutyrate, Propyl Cinnamate, Isopropyl Cinnamate, Propylene Glycol, Propylene Glycol Alginate, Propylene Glycol Stearate, Propyl Formate, Isopropyl Formate, Propyl 2-Furanacrylate, Propyl 2-Furoate, Propyl Gallate, Propyl Heptanoate, Propyl Hexanoate, Isopropyl Hexanoate, Propyl P-Hydroxybenzoate, 3-Propylidenephthalide, Alpha-Propylphenethyl Alcohol, P-Isopropyl Phenylacetaldehyde, Propyl Phenylacetate, Isopropyl Phenylacetate, 3-(P-Isopropylphenyl)Propionaldehyde, Propyl Propionate, Isopropyl Propionate, Propyl Isovalerate, Isopropyl Isovalerate, Isopulegol, Pulegone, Isopulegone, Isopulegyl Acetate, Pyridine, Pyroligneous Acid, Pyroligneous Acid, Extract, Pyruvaldehyde, Pyruvic Acid, Quassia Extract (*Picrasma excelsa* (Sw.) Planch.-*Quassia amara* L.), Quebracho Bark Extract, Quillaia (*Quillaja saponaria* Molina), Quince Seed Extract (*Cydonia* Spp.), Quinine Bisulfate, Quinine Hydrochloride, Quinine Sulfate, Isoquinoline, Rhatany Extract (*Krameria* Spp.), Rhodinol, Rhodinyl Acetate, Rhodinyl Butyrate, Rhodinyl Isobutyrate, Rhodinyl Formate, Rhodinyl Phenylacetate, Rhodinyl Propionate, Rhodinyl Isovalerate, Rose Absolute (*Rosa* Spp.), Rose Oil (*Rosa damascena* Mill.), Rose Hips Extract (*Rosa* Spp.), Rosemary (*Rosemarinus officinalis* L.), Rosemary Oil (*Rosemarinus officinalis* L.), Rose Water, Stronger (*Rosa centifolia* L.), Rue (*Ruta graveolens* L.), Rue Oil (*Ruta graveolens* L.), Rum Ether, Saccharine, Sodium Salt, Saffron (*Crocus sativus* L.), Saffron Extract (*Crocus sativus* L.), Sage (*Salvia officinalis* L.), Sage Oil (*Salvia officinalis* L.), Sage Oleoresin (*Salvia officinalis* L.), Sage Oil, Spanish (*Salvia lavandulaefolia* Vahl.), Salicylaldehyde, Sandalwood Yellow Oil (*Santalum album* L.), Santalol (Alpha And Beta), Santalyl Acetate, Santalyl Phenylacetate, Sarsaparilla Extract (*Smilax* Spp.), Sassafras Bark Extract (Safrol-Free) (*Sassafras albidum* (Nutt.) Nees), Sassafras Leaves (Safrol-Free) (*Sassafras albidum* (Nutt.) Nees), Savory, Summer (*Satureja hortensis* L.), Savory Summer Oil (*Satureja hortensis* L.), Savory, Summer, Oleoresin (*Satureja hortensis* L.), Savory, Winter (*Satureja montana* L.), Savory Winter Oil (*Satureja montana* L.), Savory, Winter, Oleoresin (*Satureja montana* L.), Schinus Molle Oil (*Schinus molle* L.), Skatole, Sloe Berries (*Prunus spinosa* L.), Sloe Berries Extract (*Prunus spinosa* L.), Sloe Berries Extract Solid (*Prunus spinosa* L.), Snakeroot Oil, Canadian (*Asarum canadense* L.), Sodium Acetate, Sodium Benzoate, Sodium Citrate, Sodium Hexametaphosphate, Sorbitan Monostearate, D-Sorbitol, Spearmint (*Mentha spicata* L.), Spearmint Extract (*Mentha spicata* L.), Spearmint Oil (*Mentha spicata* L.), Spike Lavender Oil (*Lavandula* Spp.), Spruce Oil (*Tsuga* And *Picea* Spp.), Stearic Acid, Storax (*Liquidambar* Spp.), Styrax Extract (*Liquidambar* Spp.), Sucrose Octaacetate, Sulfur Dioxide, *Tagetes* Oil (*Tagetes erecta* L.; *T. patula* L.; Or *T. Glandulifera* Schrank), Tangerine Oil (*Citrus reticulata* Blanco), Tannic Acid (*Quercus* Spp.), Tarragon (*Artemisia dracunculus* L.), Tartaric Acid (D-, L-, Dl-, Meso-), Alpha-Terpineol, Terpinolene, Terpinyl Acetate (Isomer Mixture), Beta-Terpinyl Anthranilate, Terpinyl Butyrate, Terpinyl Isobutyrate, Terpinyl Cinnamate, Terpinyl Formate, Terpinyl Propionate, Terpinyl Isovalerate, Tetrahydrofurfuryl Acetate, Tetrahydrofurfuryl Alcohol, Tetrahydrofurfuryl Butyrate, Tetrahydrofurfuryl Propionate, 3,4,5,6-Tetrahydropseudoionone, Tetrahydrolinalool, Tetramethyl Ethylcyclohexenone (Mixture Of Isomers), 2-Thienyl Mercaptan, Thyme (*Thymus vulgaris* L.), Thyme Oil (*Thymus vulgaris* L.), Thyme, White, Oil (*Thymus vulgaris* L.), Thymol, Tolualdehyde Glyceryl Acetal (Mixed O-, M-, P-), Tolualdehydes (Mixed O,M,P), Tolu, Balsam, Extract (*Myroxylon* Spp.), Tolu, Balsam, Gum (*Myroxylon* Spp.), P-Tolylacetaldehyde, O-Tolyl Acetate, P-Tolyl Acetate, 4-(P-Tolyl)-2-Butanone, P-Tolyl Isobutyrate, P-Tolyl Laurate, P-Tolyl Phenylacetate, P-Tolyl Phenylacetate, 2-(P-Tolyl)Propionaldehyde, Tragacanth Gum (*Astragalus* Spp.), Tributyl Acetylcitrate, Tricalcium Phosphate, 2-Tridecenal, Triethyl Citrate, Tuberose Oil (*Polianthes Tuberosa* L.), Turmeric (*Curcuma longa* L.), Turmeric Extract (*Curcuma longa* L.), Turmeric Oleoresin (*Curcuma longa* L.), Turpentine Gum (*Pinus* Spp.), Turpentine, Steam Distilled (*Pinus* Spp.), 2,3-Undecadione, Gamma-Undecalactone, Undecanal, 2-Undecanone, 9-Undecenal, 10-Undecenal, 10-Undecen-1-Yl Acetate, Undecyl Alcohol, Valeraldehyde, Valerian Root Extract (*Valeriana officinalis* L.), Valerian Root Oil (*Valeriana officinalis* L.), Valeric Acid, Isovaleric Acid, Gamma-Valerolactone, Vanilla (*Vanilla* Spp.), Vanilla Extract (*Vanilla* Spp.), Vanilla Oleoresin (*Vanilla* Spp.), Vanillin, Vanillin Acetate, Veratraldehyde, Violet Leaves Absolute (*Viola odorata* L.), Walnut Hull Extract (*Juglans* Spp.), Wintergreen Extract (*Gaultheria procumbens* L.), Wintergreen Oil (*Gaultheria procumbens* L.), Wormwood (*Artemisia absinthium* L.), Wormwood Extract (*Artemisia absinthium* L.), Wormwood Oil (*Artemisia absinthium* L.), Yarrow Herb (*Achillea millefolium* L.), Yerba Santa Fluid Extract (Eriodictyon *Californicum* (Hook And Am) Torr, Ylang Ylang Oil (*Cananga odorata* Hook. F. And Thomas), *Yucca* Joshua Tree (*Yucca brevifolia* Engelm.), *Yucca* Mohave Extract (*Yucca* Spp.), Zedoary (*Curcuma zedoaria* (Berg.) Rosc.), Zedoary Bark Extract (*Curcuma zedoaria* (Berg.) Rosc.), Zingerone, Acetaldehyde Butyl Phenethyl Acetal, Acetylpyrazine, Allyl Methyl Disulfide, 2-Benzofurancarboxaldehyde, Biphenyl, Butylamine, Sec-Butyl Ethyl Ether, 2-Isobutyl-3-Methoxypyrazine, 2-Isobutyl-3-Methylpyrazine, 2-Isobutylthiazole, 2-Trans,4-Trans-Decadienal, 2,3-Diethylpyrazine, 2,6-Dimethoxyphenol, 3,4-Dimethoxy-1-Vinylbenzene, P-Alpha-Dimethylbenzyl Alcohol, 2,6-Dimethyl-4-Heptanol, 2,6-Dimethyl-10-Methylene-2,6,11-Dodecatrienal, 3,7-Dimethyl-6-Octenoic Acid, 2,4-Dimethyl-2-Pentenoic Acid, P,Alpha-Dimethylstyrene, 2,4-Dimethyl-5-Vinylthiazole, 2,2'-(Dithiodimethylene)-Difuran, 1-Ethyl-2-Acetylpyrrole, Ethyl Trans-2,Cis-4-Decadienoate, 2-Ethyl-3, (5 Or 6)-Dimethylpyrazine, 3-Ethyl-2,6-Dimethylpyrazine, 2-Ethyl-1-Hexanol, 3-Ethyl-2-Hydroxy-2-Cyclopenten-1-One, 5-Ethyl-3-Hydroxy-4-Methyl-2(5h)-Furanone, 2-Ethyl-5-Methylpyrazine, 2-Ethyl-3-Methylpyrazine, P-Ethylphenol, Ethyl (P-Tolyloxy)Acetate, 2-Furanmethanethiol Formate, Furfuryl Methyl Ether, Furfuryl Methyl Sulfide, Furfuryl Isopropyl Sulfide, Furfuryl Thioacetate, 2-Furyl Methyl Ketone, (2e,4e)-Heptadienal, Trans-2-Heptenal, Nootkatone, Delta-Hexalactone, 3,4-Hexanedione, Trans-2-Hexenoic Acid, 3-Hexenoic Acid, Cis-3-Hexen-1-Yl Acetate, Hexyl Isobutyrate, 1-Hydroxy-2-Butanone, 4-Hydroxy-2,5-Dimethyl-3(2h)-Furanone, Gamma-Ionone, P-Menthan-2-One, P-Mentha-8-Thiol-3-One, P-Menth-1-Ene-9-Al, P-Menth-1-En-3-Ol, 2-Mercaptopropionic Acid, O-Methoxycinnamaldehyde, P-Methoxy-Alpha-Methylcinnamaldehyde, 2,5 Or 6-Methoxy-3-Methylpyrazine (Mixture Of Isomers), 1-Methyl-2-Acetylpyrrole, Methylated Silica, 4-Methylbiphenyl, 3-Methylcrotonic Acid, 2-Methyl-3-Furanthiol, 2-Methyl-3-,5 Or 6-(Furfurylthio)Pyrazine (Mixture Of Isomers), 5-Methyl-2,3-Hexanedione, 2-Methylhexanoic Acid, 2-Methyl-5-Methoxythiazole, 1-Methylnaphthalene, 2-Methyl-2-Pentenal, 2-Methyl-2-Pentenoic Acid, 3-Methyl-2-(2-Pentenyl)-2-Cyclopenten-1-One, Alpha-Methylphenethyl Butyrate, Methyl Phenethyl Ether, 5-Methyl-2-Phenyl-2-Hexenal, 4-Methyl-2-Phenyl-2-Pentenal, Methyl Propyl Disulfide, Methyl 2-Pyrrolyl Ketone, 5-Methylquinoxaline, 4-Methyl-5-Thiazoleethanol, 4-Methyl-5-Thiazoleethanol Acetate, 2-Methylthioacetaldehyde, 1-(Methylthio)-2-Butanone, (Methylthio)Methylpyrazine (Mixture Of Isomers), 5-Methyl-2-Thiophenecarboxaldehyde, O-(Methylthio)-Phenol, 2-Methyl-5-Vinylpyrazine (Re-Gras), 2,4-Nonadienal, 2-Nonenal, Delta-Octalactone, 2-Octenal, Paraffin Wax, 2,4-Pentadienal, 2-Pentenal, Isopentylamine, Phenethylamine, Phenethyl Hexanoate, Phenethyl Octanoate, Phenol, 2-Phenyl-2-Butenal, Phenyl Disulfide, 1-Phenyl-1,2-Propanedione, Propenyl Propyl Disulfide, Propyl Disulfide, Isopropyl Tiglate, Pyrazine Ethanethiol, Pyrazinyl Methyl Sulfide, 2-Pyridinemethanethiol, 4,5,6,7-Tetrahydro-3,6-Dimethylbenzofuran, Tetrahydro-4-Methyl-2-(2-Methylpropen-1-Yl)Pyran, 2,3,5,6-Tetramethylpyrazine, 2,2'-(Thiodimethylene)-Difuran, 4-Thujanol, O-Toluenethiol, Trimethylamine, P-Alpha,Alpha-Trimethylbenzyl Alcohol, 1-(2,6,6-Trimethyl-1-Cyclohexen-1-Yl)-2-Buten-1-One, 2,3,5-Trimethylpyrazine, Undecanoic Acid, 2-Undecanol, 10-Undecenoic Acid, 2,6-Xylenol, 2-Acetyl-3-Ethylpyrazine, 2-Acetylpyridine, Beta-Alanine, Allyl Methyl Trisulfide, Arabinogalactan, L-Arabinose, Benzothiazole, Bis(2-Methyl-3-Furyl) Disulfide, Bis(2-Methyl-3-Furyl) Tetrasulfide, 2-Sec-Butylcyclohexanone, Cyclopentanethiol, L-Cysteine, 4-Decenal, Diallyl Trisulfide, 4,5-Dihydro-3(2h)Thiophenone, 2,4-Dimethyl-5-Acetylthiazole, 3,4-Dimethyl-1,2-Cyclopentadione, 3,5-Dimethyl-1,2-Cyclopentadione, Spiro(2,4-Dithia-1-Methyl-8-Oxabicyclo(3.3.0)Octane-3,3'-(1'-Oxa-2'-Methyl)-Cyclopentane), 2,3-Dimethylpyrazine, 2,5-Dimethylpyrazine, 2,6-Dimethylpyrazine, 4,5-Dimethylthiazole, Dimethyl Trisulfide, Dipropyl Trisulfide, Disodium Succinate, Ethyl 2,4-Dioxohexanoate, Ethyl 2-Mercaptopropionate, 2-Ethyl(Or Methyl)-(3,5 And 6)-Methoxypyrazine, 2-Ethylpyrazine, Ethyl Thioacetate, Furfuryl 3-Methylbutanoate, N-Furfurylpyrrole, L-Glutamic Acid, Glyceryl Tripropanoate, Glycine, 2-Heptanol, 4-Heptenal, 3-Hexanone, 4-Hydroxybutanoic Acid Lactone, 3-(Hydroxymethyl)-2-Octanone, 4-Hydroxy-3-Pentenoic Acid Lactone, 5-Hydroxyundecanoic Acid Lactone, D,L-Isoleucine, Isopropenylpyrazine, L-Leucine, 3-Mercapto-2-Butanone, 2-Mercaptomethylpyrazine, 3-Mercapto-2-Pentanone, D,L-Methionine, Methoxypyrazine, 2-Methyl-1-Butanethiol, 3-Methyl-2-Butanethiol, 1-Methyl-2,3-Cyclohexadione, 5h-5-Methyl-6,7-Dihydrocyclopenta(B) Pyrazine, 3-(5-Methyl-2-Furyl)-Butanal, Methyl Propyl Trisulfide, 2-Methylpyrazine, Methyl Thiobutyrate, Methyl 2-Thiofuroate, 3-Methylthiopropyl Isothiocyanate, 4-Methyl-5-Vinylthiazole, 2-Naphthalenthiol, 2-Nonanol, 2-Pentanol, 2-Pentylfuran, 3-Phenyl-4-Pentenal, L-Proline, Tetrahydrofurfuryl Cinnamate, 5,6,7,8-Tetrahydroquinoxaline, Thiamine Hydrochloride, 2-Thienyl Disulfide, 3,5,5-Trimethyl-1-Hexanol, 2,4,5-Trimethylthiazole, Acetone, 2-Acetyl-3,5(And 6)-Dimethylpyrazine, 2-Acetylthiazole, Allyl Thiopropionate, Benzyl Trans-2-Methyl-2-Butenoate, Bisabolene, Butan-3-One-2-Yl Butanoate, 3-Butylidenephthalide, 3-N-Butylphthalide, Di(Butan-3-One-1-Yl) Sulfide, 2,3-Diethyl-5-Methylpyrazine, Difurfuryl Ether, 5,7-Dihydro-2-Methylthieno(3,4-D)Pyrimidine, 3,7-Dimethylocta-2,6-Dienyl 2-Ethylbutanoate, 2-Ethoxythiazole, Ethyl 2-Ethyl-3-Phenylpropanoate, Ethyl 3-Hexenoate, Ethyl 3-Methylthiopropionate, Ethyl Cis-4-Octenoate, 2-Ethylthiophenol, Furfuryl Propionate, Furfuryl Thiopropionate, Heptanoic Acid, 4-Heptenal Diethyl Acetal, 3-Heptyldihydro-5-Methyl-2(3h)-Furanone, 3-Hexanol, 4-Hexene-3-One, Cis-3-Hexenyl Formate, N-Hexyl 2-Butenoate, 6-Hydroxy-3,7-Dimethyloctanoic Acid Lactone, Hydroxynonanoic Acid, Delta-Lactone, 2-Keto-4-Butanethiol, 2-Methoxy-3(5 And 6)-Isopropylpyrazine, 2-Methylbutyl 2-Methylbutyrate, 3-Methyl-2-Cyclohexen-1-One, Methyl 3,7-Dimethyl-6-Octenoate, Methyl Furfuryl Disulfide, 6-Methyl-3,5-Heptadien-2-One, Methyl 3-Hexenoate, 5-Methyl-5-Hexen-2-One, 2-Methyl-5-(Methylthio)Furan, Methyl Cis-4-Octenoate, 4-Methyl-3-Penten-2-One, 2-Methylpropyl 3-Methylbutyrate, 2-(2-Methylpropyl)Pyridine, 3-(2-Methylpropyl)Pyridine, 2-(1-Methylpropyl)Thiazole, 2-Methyltetrahydrofuran-3-One, 3-(Methylthio)Butanal, 4-(Methylthio)-2-Butanone, 4-(Methylthio)-4-Methyl-2-Pentanone, Nona-2-Trans-6-Cis-Dienal, 2,6-Nonadienal Diethyl Acetal, Trans-2-Nonen-1-Ol, 9,12-Octadecadienoic Acid (48%) And 9,12,15-Octadecatrienoic Acid (52%), 3-Oxobutanal Dimethyl Acetal, 1-Penten-3-One, 2-Pentylpyridine, Phenylacetaldehyde Diisobutyl Acetal, Propyl Thioacetate, Pyrrole, P-Tolyl 3-Methylbutyrate, 2-Tridecanone, 2,6,6-Trimethylcyclohexa-1,3-Dienyl Methanal, 1,3,3-Trimethyl-2-Norbornanyl Acetate, 3-Acetyl-2,5-Dimethylfuran, 2-Butyl-2-Butenal, N-Butyl 2-Methylbutyrate, 3-Ethylpyridine, 2-Formyl-6,6-Dimethylbicyclo(3.1.1) Hept-2-Ene, Alpha-Furfuryl Octanoate, Alpha-Furfuryl Pentanoate, Glyceryl Tribenzoate, 2-Hepten-4-One, 3-Hepten-2-One, 2-Heptylfuran, Cis-3-Hexenyl Butyrate, Cis-3-Hexenyl Hexanoate, Capsaicin, 2-Hydroxymethyl-6,6-Dimethylbicyclo(3.1.1)Hept-2-Enyl Formate, 2-Isopropyl-5-Methyl-2-Hexenal, 2-Methyl-2-Butenal, Methyl Dihydrojasmonate, 5-Methyl-3-Hexen-2-One, Methyl Jasmonate, Methyl Linoleate (48%) Methyl Linolenate (52%) Mixture, Methyl 4-(Methylthio)Butyrate, 2-Methylpentanal, 4-(Methylthio)Butanal, 3-(Methylthio)Propanol, 3-Octen-2-One, 3-Penten-2-One, Pentyl 2-Furyl Ketone, Propylene Glycol Dibenzoate, 1-(2,6,6-Trimethylcyclohexa-1,3-Dienyl)-2-Buten-1-One, 2,6,6-Trimethylcyclohex-2-Ene-1,4-Dione, 2,4-Undecadienal, 2-Undecenal, 3-Acetylpyridine, Cycloheptadeca-9-En-1-One, 1,1-Dimethoxyethane, 2,4-Dimethylbenzaldehyde, Ethyl 3-Hydroxybutyrate, Trans, Trans-2,4-Hexadienal, 4-Hexen-1-Ol, Isobutyl 2-Butenoate, 2-Methoxy-3-(1-Methylpropyl)Pyrazine, 3-Methyl-1-Cyclopentadecanone, 1-Methyl-1-Cyclopenten-3-One, 1-Methyl-3-Methoxy-4-Isopropylbenzene, 3-Methylpentanoic Acid, 3-(Methylthio)-1-Hexanol, Myrtenol, 3-Nonanone, 2,2,4-Trimethyl-1,3-Oxacyclopentane, 2,6,10-Trimethyl-2,6,10-Pentadecatrien-14-One, Valencene, D,L-Valine, Dl-(3-Amino-3-Carboxypropyl)Dimethylsulfonium Chloride, Dehydrodihydroionol, Dehydrodihydroionone, Dicyclohexyl Disulfide, 1,4-Dimethyl-4-Acetyl-1-Cyclohexene, 2,5-Dimethyl-2,5-Dihydroxy-1,4-Dithiane, 2,5-Dimethyl-3-Furanthiol, Dodecyl Isobutyrate, 3-Ethyl-2-Hydroxy-4-Methylcyclopent-2-En-1-One, 5-Ethyl-2-Hydroxy-3-Methylcyclopent-2-En-1-One, N-Ethyl-2-Isopropyl-5-Methylcyclohexane Carboxamide, Ethyl 2-Methyl-3-Pentenoate, Hexyl Phenylacetate, 2-Hydroxy-2-Cyclohexen-1-One, 2-Hydroxy-3,5,5-Trimethyl-2-Cyclohexenone, D,L-Isomenthone, 2-Isopropylphenol, Maltyl Isobutyrate, 4-Methylpentanoic Acid, 2-Methyl-3-Pentenoic Acid, Cis-6-Nonen-1-Ol, 2-Trans-6-Trans-Octadienal, Cis-3-Octen-1-Ol, 2-Phenyl-3-Carbethoxy Furan, Propiophenone, 1,5,5,9-Tetramethyl-13-Oxatricyclo(8.3.0.0 (4,9))Tridecane, Thiogeraniol, 2,2,6-Trimethylcyclohexanone, 2,6,6-Trimethyl-1-Cyclohexen-1-Acetaldehyde, Trithioacetone, Bis(2,5-Dimethyl-3-Furyl) Disulfide, 2,3-Butanedithiol, 1-Butanethiol, Candelilla Wax (Wax From Stems And Branches Of *Euphorbia Cerifera*), O-Cresol, S-(2,5-Dimethyl-3-Furyl)Thio-2-Furoate, 2,5-Dimethyl-3-Thioisovalerylfuran, 2,8-Dithianon-4-En-4-Carboxaldehyde, 1,2-Ethanedithiol, O-(Ethoxymethyl)Phenol, Ethyl Trans-2-Butenoate, Ethyl Maltol, Ethyl 2-Methylpentanoate, Ethyl 2-Methyl-4-Pentenoate, Ethyl Octadecanoate, 2-Ethyl-1,3,3-Trimethyl-2-Norbornanol, Ethyl Undecanoate, Trans-3-Heptenyl Acetate, Trans-3-Heptenyl 2-Methylpropanoate, 1,6-Hexanedithiol, Cis-4-Hexenal, 3-Hexenyl 2-Methylbutanoate, 3-Hexenyl 3-Methylbutanoate, Hexyl 2-Methylbutanoate, Hexyl Isovalerate, Linalyl Phenylacetate, 2-Mercapto-3-Butanol, 2,3 Or 10-Mercaptopinane, Methyl Benzyl Disulfide, 3-Methylbutyl 2-Methylbutanoate, 2-Methylbutyl 3-Methylbutanoate, 3-Methylbutyl 2-Methylpropanoate, Methyl 3-Hydroxyhexanoate, Alpha-Methyl-Beta-Hydroxypropyl Alpha-Methyl-Beta-Mercaptopropyl Sulfide, 4-Methyl-2-Pentenal, 2-Methyl-4-Pentenoic Acid, 2-Methyltetrahydrothiophen-3-One, 1,9-Nonanedithiol, 1,8-Octanedithiol, 1-Octen-3-One, Trans-2-Octen-1-Yl Acetate, Trans-2-Octen-1-Yl Butanoate, Octyl 2-Furoate, 2-Phenyl-4-Pentenal, 1,2-Propanedithiol, Propanethiol, O-Propylphenol, Pyrrolidine, 3,5,5-Trimethylhexanal, 2,4,5-Trimethyl-Delta-3-Oxazoline, 2-Acetoxy-3-Butanone, 1,2-Butanedithiol, 1,3-Butanedithiol, M-Cresol, Cyclohexanecarboxylic Acid, 3-Decen-2-One, Diallyl Polysulfides, 1,2-Di((1'-Ethoxy)Ethoxy)Propane, 2,3-Dimethylbenzofuran, Dimethyl Disulfide, 2,6-Dimethyl-4-Heptanone, 2,6-Dimethyl-3-((2-Methyl-3-Furyl)Thio)-4-Heptanone, 3,7-Dimethyl-1,3,6-Octatriene, 2,6-Dimethylpyridine, 3,5-Dimethyl-1,2,4-Trithiolane, 6,10-Dimethyl-5,9-Undecadien-2-One, Ethylene Brassylate, Ethyl Cyclohexanecarboxylate, Ethyl 3-Hydroxyhexanoate, 5-Ethyl-2-Methylpyridine, 3-Heptanol, 2-Hydroxyacetophenone, 6-Hydroxydihydrotheaspirane, 3-Hydroxy-2-Pentanone, Isoamyl Acetoacetate, Isojasmone, Isophorone, 5-Isopropyl-2-Methylpyrazine, 2-Isopropyl-4-Methylthiazole, Isopropyl Myristate, P-Mentha-1,8-Dien-7-Al, P-Mentha-1,3-Diene, P-Mentha-1,4-Diene, P-Mentha-1,4(8)-Dien-3-One, P-Mentha-1,8-Dien-7-Yl Acetate, P-Menthan-2-Ol, P-Menth-3-En-1-Ol, P-Menth-8-En-1-Ol, P-Menth-8-En-2-One, 1-P-Menthen-9-Yl Acetate, P-Methoxycinnamaldehyde, Methyl Cyclohexanecarboxylate, 2-Methyl-3,5 Or 6-Ethoxypyrazine, 3-((2-Methyl-3-Furyl)Thio)-4-Heptanone, 4-((2-Methyl-3-Furyl)Thio)-5-Nonanone, 5-Methylhexanoic Acid, Methyl 2-Methyl-3-Furyl Disulfide, 4-Methylnonanoic Acid, 4-Methyloctanoic Acid, Methyl 1-Propenyl Disulfide, 3-Methyl-5-Propyl-2-Cyclohexen-1-One, 2-Methyl-4-Propyl-1,3-Oxathiane, 1,4-Nonanediol Diacetate, Cis-6-Nonenal, 3-Octanol, 1-Octen-3-Yl Acetate, 3-Octyl Acetate, 1-Penten-3-Ol, L-Phenylalanine, 2-Phenyl-3-(2-Furyl)Prop-2-Enal, 2(10)-Pinen-3-Ol, 1,3-Propanedithiol, Resorcinol, Delta-Tetradecalactone, Theobromine, (2,2,3-Trimethylcyclopent-3-En-1-Yl)Acetaldehyde, 1,2,3-Tris((1'-Ethoxy)Ethoxy)Propane, Verbenol, 2,5-Xylenol, 3,4-Xylenol, Benzyl Methyl Sulfide, 2-Methoxy-4-Propylphenol, 2-Methyl-Trans-2-Butenoic Acid, 4-(Methylthio) Butanol, 2-(Methylthio)Methyl-2-Butenal, 3-Octen-2-Ol, 2-Octen-4-One, Octyl 2-Methylbutyrate, 3-Decanol, D-Xylose, Propyl 2-Methyl-3-Furyl Disulfide, 1-Hexen-3-Ol, 2-Acetyl-5-Methylfuran, Epsilon-Dodecalactone, 2-Propionylthiazole, 1-Octen-3-Yl Butyrate, Epsilon-Decalactone, 2-Propionylpyrrole, Thiazole, Benzenethiol, Benzyl Disulfide, 5-Phenylpentanol, 2-(2-Butyl)-4,5-Dimethyl-3-Thiazoline, 4,5-Dimethyl-2-Ethyl-3-Thiazoline, 4,5-Dimethyl-2-Isobutyl-3-Thiazoline, Delta-1-(2,6,6-Trimethyl-3-Cyclohexen-1-Yl)-2-Buten-1-One, 2-Ethyl-4-Hydroxy-5-Methyl-3(2h)-Furanone, Alpha-Ionol, Beta-Ionol, Dihydro-Beta-Ionone, Dihydro-Beta-Ionol, Dihydro-Alpha-Ionone, 2-Methyl-4-Phenyl-2-Butanol, 4-Methyl-2-Pentyl-1,3-Dioxolan, Cyclohexylmethyl Pyrazine, Phenylethyl 2-Methylbutyrate, 3-Hexenyl Phenylacetate, 4,5-Dimethyl-3-Hydroxy-2,5-Dihydrofuran-2-One, 4-Hydroxy-5-Methyl-3(2h)-Furanone, 2-Methyl-3-Thioacetoxy-4,5-Dihydrofuran, 2-Trans-6-Cis-Dodecadienal, 2-Trans-4-Cis-7-Cis-Tridecatrienal, 2,6,6-Trimethyl-1&2-Cyclohexen-1-Carboxaldehyde, P-Methylcinnamaldehyde, Ethyl Trans-2-Decenoate, Ethyl Trans-4-Decenoate, Ethyl Trans-2-Octenoate, 2-Methylbutyl Acetate, Cis-5-Isopropenyl-Cis-2-Methylcyclopentan-1-Carboxaldehyde, 3-Methyl-2-Butenal, 3-Methyl-2-Buten-1-ol, Propyl 2,4-Decadienoate, P-Propylphenol, Butyl Salicylate, 6-Acetoxydihydrotheaspirane, 4-(P-Acetoxyphenyl)-2-Butanone, 4-Acetyl-6-T-Butyl-1,1-Dimethylindan, 4-Acetyl-2-Methylpyrimidine, 4-Allyl-2,6-Dimethoxyphenol, L-Aspartic Acid, Campholene Acetate, 1,4-Cineole, Alpha-1-(2,6,6-Trimethyl-2-Cyclohexen-1-Yl)-2-Buten-1-One, 9-Decenoic Acid, Nerol Oxide, Dihydroxyacetophenone, 2,6-Dimethyl-6-Hepten-1-Ol, 2,5-Dimethyl-4-Methoxy-3(2h)-Furanone, 2,2-Dimethyl-5-(1-Methylpropen-1-Yl)Tetrahydrofuran, 2,6-Dimethylthiophenol, Diphenyl Ether, Disodium 5-Guanylate, Disodium 5-Inosinate, Trans,Trans-2,4-Dodecadienal, 4-Ethyl-2,6-Dimethoxyphenol, 2-Ethyl-4,5-Dimethyloxazole, 2-Ethylfuran, Ethyl 3-(Furfurylthio)Propionate, Ethyl Trans-2-Hexenoate, 1-Ethylhexyl Tiglate, Ethyl 3-Mercaptopropionate, Ethyl 2-Methyl-3,4-Pentadienoate, Ethyl 3-Methylpentanoate, 2-Ethyl-4-Methylthiazole, Ethyl 4-(Methylthio)Butyrate, Ethyl Cis-4,7-Octadienoate, Ethyl 3-Oxohexanoate, L-Glutamine, Glyceryl 5-Hydroxydecanoate, Glyceryl 5-Hydroxydodecanoate, Guaiacyl Acetate, Cis-3-Hexenyl Benzoate, Cis-3-Hexenyl Cis-3-Hexenoate, Cis-3-Hexenyl Lactate, Hexyl Benzoate, Hexyl Trans-2-Hexenoate, Hexyl 2-Methyl-3&4-Pentenoate, L-Histidine, Hydroquinone Monoethyl Ether, 5-Hydroxy-2,4-Decadienoic Acid Delta-Lactone, 2-Hydroxy-4-Methylbenzaldehyde, Isoeugenyl Benzyl Ether, Isopropyl 2-Methylbutyrate, 1-P-Menthene-8-Thiol, Methyl 1-Acetoxycyclohexyl Ketone, Methylbenzyl Acetate (Mixed O,M,P), 3-Methyl-2-Butanol, 4-Methyl-2,6-Dimethoxyphenol, 2-Methyl-1,3-Dithiolane, Methyl 2-Hydroxy-4-Methylpentanoate, Methyl 2-Methylpentanoate, Methyl 2-Methylthiobutyrate, Methyl Nicotinate, Methyl 3-Nonenoate, 2-Methyl-2-Octenal, Methyl Trans-2-Octenoate, Methyl 2-Oxo-3-Methylpentanoate, Methyl Sorbate, 7-Methyl-4,4a,5,6-Tetrahydro-2(3h)-Naphthalenone, 4-Methylthiazole, 2-(Methylthiomethyl)-3-Phenylpropenal, 3-Methyl-1,2,4-Trithiane, Beta-Naphthyl Isobutyl Ether, Cis-2-Nonen-1-Ol, Trans,Trans-2,4-Octadienal, Cis-5-Octen-1-Ol, 2-Oxobutyric Acid, 2-Pentadecanone, 2-Pentyl-1-Buten-3-One, D,L-Phenylalanine, 1-Phenyl-3 Or 5-Propylpyrazole, 4-Propenyl-2,6-Dimethoxyphenol, 4-Propyl-2, 6-Dimethoxyphenol, L-Rhamnose, 1,2,5,6-Tetrahydrocuminic Acid, Thaumatin, P-Tolyl Octanoate, O-Tolyl Salicylate, 2,2,6-Trimethyl-6-Vinyltetrahydropyran, L-Tyrosine, Vanillyl Alcohol, Vanillylidene Acetone, P-Vinylphenol, Anisyl Phenylacetate, Alpha-Campholenic Alcohol, 5- And 6-Decenoic Acid, 2,5-Diethyltetrahydrofuran, 5-Hydroxy-2-Decenoic Acid Delta-Lactone, 5-Hydroxy-7-Decenoic Acid Delta-Lactone, Linalool Oxide, Massoia Bark Oil (Cryptocarya massoio), L-Menthyl Lactate, Cis-5-Octenal, Osmanthus Absolute (Osmanthus fragrans Lour.), 2-(3-Phenylpropyl)Pyridine, Potassium 2-(1'-Ethoxy)Ethoxypropanoate, O-Tolyl Isobutyrate, Vanillin Isobutyrate, Dehydromenthofurolactone, 4-Ethylbenzaldehyde, Ethyl Methyl-P-Tolylglycidate, 5-Hydroxy-8-Undecenoic Acid Delta-Lactone, 5-Isopropenyl-2-Methyl-2-Vinyltetrahydrofuran, 1-(4-Methoxyphenyl)-4-Methyl-1-Penten-3-One, 5-Methyl-2-Hepten-4-One, 3-Methyl-1-Pentanol, 3-Methyl-2-(N-Pentanyl)-2-Cyclopenten-1-One, Mintlactone, Myrtenyl Acetate, 2-Trans-6-Trans-Nonadienal, 3-Oxodecanoic Acid Glyceride, 3-Oxododecanoic Acid Glyceride, 3-Oxohexadecanoic Acid Glyceride, 3-Oxohexanoic Acid Glyceride, 3-Oxooctanoic Acid Glyceride, 3-Oxotetradecanoic Acid Glyceride, Sodium 2-(4-Methoxyphenoxy)Propanoate, Theaspirane, Acetaldehyde Ethyl Cis-3-Hexenyl Acetal, Dihydronootkatone, 1-Ethoxy-3-Methyl-2-Butene, (Z)-3 & (E)-2-Hexenyl Propionate, Hydrogen Sulfide, 1,4-Dodec-6-Enolactone, 2 Or 4-Isobutyl-(4 Or 2),6-Dimethyldihydro-4h-1,3,5-Dithiazine, 2 Or 4-Isopropyl-(4 Or 2),6-Dimethyldihydro-4h-1,3,5-Dithiazine, Jambu Oleoresin, 3-L-Menthoxypropane-1,2-Diol, 4-Methoxy-2-Methyl-2-Butanethiol, Gamma-Methyldecalactone, 2-Methyl-3-Tetrahydrofuranthiol, Methylthio 2-(Acetyloxy)Propionate, 3-(Methylthio)Hexyl Acetate, Methylthio-2-(Propionyloxy)Propionate, Octahydrocoumarin, 2-Pentanethiol, D-Ribose, Sclareolide, 1,3,5-Undecatriene, Vanillyl Butyl Ether, 4-Acetoxy-2,5-Dimethyl-3(2h)Furanone, 2,4-Dihydroxybenzoic Acid, 1,2-Dimethoxybenzene, 4-Ethyloctanoic Acid, Ethyl Vanillin Beta-D-Glucopyranoside, 5-Hydroxy-2-Dodecenoic Acid Lactone, 4-Hydroxy-3-Methyloctanoic Acid Lactone, 2-Isopropyl-N,2,3-Trimethylbutyramide, L-Menthol Ethylene Glycol Carbonate, L-Menthol 1- And 2-Propylene Glycol Carbonate, L-Menthone 1,2-Glycerol Ketal, D,L-Menthone 1,2-Glycerol Ketal, Cis- And Trans-Menthone-8-Thioacetate, Mono Menthyl Succinate, Neohesperidin Dihydrochalcone, Sodium 3-Methoxy-4-Hydroxycinnamate, Taurine, Thaumatin B-Recombinant, Vanillyl Ethyl Ether, 3-Acetylmercaptohexyl Acetate, 2-Acetyl-2-Thiazoline, Dl-Alanine, L-Arginine, 1-Buten-1-Yl Methyl Sulfide, Delta-3-Carene, Cycloionone, Daidai Peel Oil, 1-Decen-3-Ol, Diethyl Sulfide, 2,5-Dihydroxy-1,4-Dithiane, Diisopropyl Disulfide, 2,4-Dimethylanisole, 2-(3,7-Dimethyl-2,6-Octadienyl)Cyclopentanone, (E,R)-3,7-Dimethyl-1,5,7-Octatrien-3-Ol, 1,4-Dithiane, Ethyl 2,4,7-Decatrienoate, 2-Ethylhexanethiol, Ethyl 2-(Methyldithio)Propionate, Ethyl 2-(Methylthio)Acetate, Ethyl 3-(Methylthio)Butyrate, Ethyl Vanillin Isobutyrate, Ethyl Vanillin Propylene Glycol Acetal, Alpha-Farnesene, 4-[(2-Furanmethyl)Thio]-2-Pentanone, (Z)-4-Hepten-1-Ol, 1-Hexanethiol, 3-Hydroxy-2-Oxopropionic Acid, Beta-Ionyl Acetate, Alpha-Isomethylionyl Acetate, Litsea cubeba Oil, L-Lysine, Cis- And Trans-P-1(7),8-Menthadien-2-Yl Acetate, 3-(L-Menthoxy)-2-Methylpropane-1,2-Diol, 3-Mercaptohexanol, 3-Mercaptohexyl Acetate, 3-Mercaptohexyl Butyrate, 3-Mercaptohexyl Hexanoate, 3-Mercapto-3-Methyl-1-Butanol, 3-Mercapto-3-Methylbutyl Formate, 1-Mercapto-2-Propanone, S-Methyl Benzothioate, 3-Methylbutanethiol, Methyl (E)-2-(Z)-4-Decadienoate, Methyl Ethyl Sulfide, Methyl Ethyl Trisulfide, S-Methyl Hexanethioate, 2-(4-Methyl-2-Hydroxyphenyl)Propionic Acid-Gamma-Lactone, S-Methyl 3-Methylbutanethioate, Methyl 3-Methyl-1-Butenyl Disulfide, 2-Methyl-2-(Methyldithio)Propanal, S-Methyl 4-Methylpentanethioate, (E)-7-Methyl-3-Octen-2-One, 3-Methyl-2-Oxobutanoic Acid, 3-Methyl-2-Oxopentanoic Acid, 4-Methyl-2-Oxopentanoic Acid, Methyl Phenyl Disulfide, Methyl Phenyl Sulfide, 2-Methyl-1-Propanethiol, Methylsulfinylmethane, S-Methyl Thioacetate, 3-Methylthiohexanal, Bis-(Methylthio)Methane, Methylthiomethyl Butyrate, Methylthiomethyl Hexanoate, 4-(Methylthio)-2-Oxobutanoic Acid, 1-Methylthio-2-Propanone, 3-(Methylthio)PropylAcetate, (E)-3-(Z)-6-Nonadien-1-Ol, (Z)(Z)-3,6-Nonadien-1-Ol, 8-Ocimenyl Acetate, (E)-2-Octen-1-Ol, (E)-2-Octen-4-Ol, (E)-2-(2-Octenyl)Cyclopentanone, (Z)-5-Octenyl Propionate, 2-Oxopentanedioic Acid, 2-Oxo-3-Phenylpropionic Acid, 2-Pentyl Butyrate, Phenylethyl Mercaptan, Prenyl Thioacetate, Prenylthiol, 2-Propanethiol, 1-Pyrroline, Sarcodactylis Oil, Sodium Diacetate, Sodium 3-Mercaptooxopropionate, Tea Tree Oil, 2,3,4-Trimethyl-3-Pentanol, Vanillin 3-(L-Menthoxy)Propane-1,2-Diol Acetal, Vanillin Propylene Glycol Acetal, 2-Aminoacetophenone, Bornyl Butyrate, (E)-2-Butenoic Acid, Cyclohexanone, Cyclopentanone, 2,4-Decadien-1-Ol, 9-Decenal, 2-Decenoic Acid, 4-Decenoic Acid, 2,5-Diethyl-3-Methylpyrazine, 3,5-Diethyl-2-Methylpyrazine, 6,7-Dihydro-2,3-Dimethyl-5h-Cyclopentapyrazine, P-Tert-Butylphenol, 2-Ethyl-6-Methylpyrazine, (E)-2-Heptenoic Acid, 2,4-Hexadienoic Acid, (E,E)-, 2,4-Hexadien-1-Ol, 3-Hexenal, (Z)-2-Hexen-1-Ol, Cis-3-Hexenyl Anthranilate, Trans-2-Hexenyl Butyrate, (E)-2-Hexenyl Formate, 3-Hexenyl 2-Hexenoate, Cis-3-Hexenyl Isobutyrate, Trans-2-Hexenyl Isovalerate, Cis-3-Hexenyl Tiglate, Trans-2-Hexenyl Propionate, Cis-3-Hexenyl Propionate, 3-Hexenyl 2-Oxopropionate, Trans-2-Hexenyl Pentanoate, Cis-3-Hexenyl Valerate, 5-(Cis-3-Hexenyl)Dihydro-5-Methyl-2(3h)Furanone, 4-Isopropyl-2-Cyclohexenone, 2-Isopropylpyrazine, 2-Methyl-3-(1-Oxopropoxy)-4h-Pyran-4-One, Mesquite Wood Extract, 2-Methoxybenzoic Acid, 3-Methoxybenzoic Acid, 4-Methoxybenzoic Acid, 2-Methylcyclohexanone, 3-Methylcyclohexanone, 4-Methylcyclohexanone, 2-Methyl-3-(Methylthio)Furan, Michelia Alba Oil, 2,4-Nonadien-1-Ol, (E,Z)-2,6-Nonadien-1-Ol Acetate, (E,Z)-3,6-Nonadien-1-Ol Acetate, (E)-2-Nonenoic Acid, 3-Nonen-2-One, (E,E)-2,4-Octadien-1-Ol, (E)-2-Octenoic Acid, Phenyl Acetate, 2-Phenylphenol, Phenyl Salicylate, Propylpyrazine, 3,5,5-Trimethylcyclohexanol, 2,3,6-Trimethylphenol, 2-Acetyl-3-Methylpyrazine, 1-Amino-2-Propanol, 3-Decanone, Cis-4-Decenyl Acetate, Diisopropyl Trisulfide, (E) & (Z)-4,8-Dimethyl-3,7-Nonadien-2-One, 2,5-Dimethyl-3-Oxo-(2h)-Fur-4-Yl Butyrate, Cis And Trans-2,5-Dimethyltetrahydrofuran-3-Thiol, Cis And Trans-2,5-Dimethyltetrahydro-3-Furyl Thioacetate, Ethanethioic Acid, S-(2-Methyl-3-Furanyl) Ester, Ethyl 4-(Acetylthio)Butyrate, Ethyl Cis-4-Heptenoate, Ethyl 5-Hexenoate, (+/−)-Ethyl 3-Mercaptobutyrate, Ethyl 5-(Methylthio)Valerate, Furfuryl Propyl Disulfide, (+/−)-Heptan-3-Yl Acetate, (+/−)-Heptan-2-Yl Butyrate, (Z)-3-Hexenyl (E)-2-Butenoate, (E)-2-Hexenyl Hexanoate, 4-Hydroxybenzaldehyde, 2-Hydroxybenzoic Acid, 4-Hydroxybenzoic Acid, 4-Hydroxybenzyl Alcohol, 4-Hydroxy-3-Methoxybenzoic Acid, 3(2)-Hydroxy-5-Methyl-2(3)-Hexanone, Isopentylidene Isopentylamine, Isoprenyl Acetate, D,L-Menthol(+/−)-Propylene Glycol Carbonate, Erythro And Threo-3-Mercapto-2-Methylbutan-1-Ol, 3-Mercapto-2-Methylpentanal, (+/−)-2-Mercapto-2-Methylpentan-1-Ol, 3-Mercapto-2-Methylpentan- 1-Ol (Racemic), 4-Mercapto-4-Methyl-2-Pentanone, (+/−)-2-Methyl-1-Butanol, (+/−)-3-Methyl-Gamma-Decalactone, 2-Methylheptan-3-One, (E)-6-Methyl-3-Hepten-2-One, Methyl 2-Methyl-2-Propenoate, Methyl (Methylthio)Acetate, 2-(Methylthio)Ethanol, 12-Methyltridecanal, L-Monomenthyl Glutarate, (+/−)-Nonan-3-Yl Acetate, (E,E)-3,5-Octadien-2-One, (+/−)-Octan-3-Yl Formate, Paraldehyde, 4-Pentenyl Acetate, 2-Pentyl Acetate, perilla Leaf Oil, Phenethyl Isothiocyanate, Pyrazine, Sodium 4-Methoxybenzoyloxyacetate, 2,4,6-Triisobutyl-5,6-Dihydro-4h-1,3,5-Dithiazine, 2,4,6-Trimethyldihydro-4h-1,3,5-Dithiazine, 3,7,11-Trimethyl-2,6,10-Dodecatrienal, (+/−)-(2,6,6-Trimethyl-2-Hydroxycyclohexylidene)Acetic Acid Gamma-Lactone, Trithiahexane-2,3,5, 6-Undecanone, Vanillin Erythro And Threo-Butan-2,3-Diol Acetal, Acetaldehyde Diisoamyl Acetal, Amyl Methyl Disulfide, Benzyl Hexanoate, Butyl Ethyl Disulfide, Beta-Cyclodextrin, Diethyl Trisulfide, (+/−)-3,5-Diethyl-1,2,4-Trithiolane, (+/−)-Dihydrofarnesol, Dihydromintlactone, Dihydroxyacetone, 2,5-Dimethyl-3-Furanthiol Acetate, 2,5-Dimethylthiazole, (Z)-4-Dodecenal, 4,5-Epoxy-(E)-2-Decenal, Ethyl 3-Acetoxy-2-Methyl Butyrate, S-Ethyl 2-Acetylamino Ethanethioate, Ethyl Methyl Disulfide, Ethyl Propyl Disulfide, Ethyl Propyl Trisulfide, O-Ethyl S-(2-Furylmethyl)Thiocarbonate, Geranyl Tiglate, Grape Seed Extract, Trans-4-Hexenal, (E)-2-Hexenal Diethyl Acetal, 2-Hexyl-4,5-Dimethyl-1,3-Dioxolane, 4-Hydroxy-3,5,-Dimethoxy Benzaldehyde, 4-Hydroxy-2,3-Dimethyl-2,4-Nonadienoic Acid Gamma Lactone, 4-Hydroxy-4-Methyl-5-Hexenoic Acid Gamma Lactone, 3-Hydroxy-4-Phenylbutan-2-One, P-Menthane-3,8-Diol, L-Menthyl Methylether, Methyl 5-Acetoxyhexanoate, 3-[(2-Methyl-3-Furyl)Thio]-2-Butanone, 3-Methyl-2,4-Nonanedione, (+/−)-2-(5-Methyl-5-Vinyl-Tetrahydrofuran-2-Yl)Propionaldehyde, 9-Octadecenal, 2,3-Octanedione, (+/−)-1-Phenylethylmercaptan, 4-Propenylphenol, 2-Propionylpyrroline, 2-Propionyl-2-Thiazoline, 2-Propylpyridine, (Z)-8-Tetradecenal, Tuberose Lactone, 2-Undecen-1-Ol, (+/−)-1-Acetoxy-1-Ethoxyethane, 4-Acetyl-2,5-Dimethyl-3(2h)-Furanone, 2-Acetyl-3,5-Dimethylfuran, Allyl Crotonate, Allyl Propyl Disulfide, Allyl Valerate, 4-Allylphenol, Allyl Thiohexanoate, O-Anisaldehyde, N-Benzoylanthranilic Acid, Thujyl Alcohol, L-Bornyl Acetate, 2-Butylfuran, Butyl Isothiocyanate, 2-Butyrylfuran, Carvone-5,6-Oxide, Beta-Caryophyllene Oxide, Citronellyl Anthranilate, N-Cyclopropyl-Trans-2-Cis-6-Nonadienamide, Trans-Alpha-Damascone, 2,4,7-Decatrienal, 2-Decylfuran, Dehydronootkatone, Diacetyl Tartaric Acid Esters Of Mono- And Diglycerides, Diethyl Disulfide, Mixture Of 3,6-Diethyl-1,2,4,5-Tetrathiane And 3,5-Diethyl-1,2,4-Trithiolane, 2,4-Difurfurylfuran, Diisopentyl Thiomalate, Dimercaptomethane, 1,1-Dimethoxy-Trans-2-Hexene, 2,4-Dimethyl-1,3-Dioxolane, 3,5- And 3,6-Dimethyl-2-Isobutylpyrazine, 2,5-Dimethyl-3(2h)-Furanone, (+/−)-Trans- And Cis-4,8-Dimethyl-3,7-Nonadien-2-Ol, (+/−)-Trans- And Cis-4,8-Dimethyl-3,7-Nonadien-2-Yl Acetate, 2,5-Dimethyl-4-Ethoxy-3(2h)-Furanone, (+/−)-Trans- And Cis-5-(2,2-Dimethylcyclopropyl)-3-Methyl-2-Pentenal, 2,5-Dimethylfuran, Divanillin, (+/−)-2,8-Epithio-Cis-P-Menthane, Epoxyoxophorone, Tomato Lycopene, Ethane-1,1-Dithiol, Ethyl Cis-3-Hexenoate, N-Ethyl Trans-2-Cis-6-Nonadienamide, Ethyl Furfuryl Ether, Ethyl N-Ethylanthranilate, Ethyl N-Methylanthranilate, (+/−)-4-Ethyloctanal, Eugenyl Isovalerate, Furfuryl 2-Methyl-3-Furyl Disulfide, 1-(2-Furyl)Butan-3-One, Geranic Acid, Geranyl 2-Methylbutyrate, Geranyl Valerate, Glyceryl-Lacto Esters Of Fatty Acids, Hept-Trans-2-En-1-Yl Acetate, Hept-2-En-1-Yl Isovalerate, Trans-2-Trans-4-Heptadien-1-Ol, 2-Heptanethiol, (+/−)-1-Hepten-3-Ol, Cis- And Trans-2-Heptylcyclopropanecarboxylic Acid, 2,4-Hexadienyl Propionate, 2,4-Hexadienyl Acetate, 2,4-Hexadienyl Butyrate, 2,4-Hexadienyl Isobutyrate, 2-Hexenyl Octanoate, Hexyl 3-Mercaptobutanoate, 2-Hexylthiophene, 4-Hydroxy-2-Butenoic Acid Gamma-Lactone, 3-Hydroxy-2-Octanone, 2-(2-Hydroxy-4-Methyl-3-Cyclohexenyl)Propionic Acid Gamma-Lactone, 5-Hydroxy-4-Methylhexanoic Acid Delta-Lactone, 1-(3-Hydroxy-5-Methyl-2-Thienyl)Ethanone, (+/−)-2-Hydroxypiperitone, Beta-Ionone Epoxide, Isoambrettolide, Isobornyl Isobutyrate, Isobornyl 2-Methylbutyrate, N-Isobutyldeca-Trans-2-Trans-4-Dienamide, Isobutyl N-Methylanthranilate, (+/−)-Isobutyl 3-Methylthiobutyrate, Beta-Isomethylionone, Isopropenyl Acetate, Lactylated Fatty Acid Esters Of Glycerol And Propylene Glycol, 2-(L-Menthoxy)Ethanol, Menthyl Pyrrolidone Carboxylate, Menthyl Valerate, 4-Mercapto-2-Pentanone, (+/−)-4-Mercapto-4-Methyl-2-Pentanol, 2-Mercaptoanisole, Methionyl Butyrate, Trans- And Cis-1-Methoxy-1-Decene, (S1)-Methoxy-3-Heptanethiol, 2-Methoxyacetophenone, Methyl Cis-3-Hexenoate, Methyl Cis-5-Octenoate, Methyl 3-(Methylthio)Butanoate, Methyl 3-Mercaptobutanoate, Methyl Isopentyl Disulfide, Methyl N,N-Dimethylanthranilate, Methyl N-Acetylanthranilate, Methyl N-Formylanthranilate, S-Methyl Propanethioate, 2-Methyl-1-Methylthio-2-Butene, 3-Methyl-2(3-Methylbut-2-En-1-Yl)Furan, 3-(5-Methyl-2-Furyl)Prop-2-Enal, 5-Methyl-3(2h)-Furanone, 6-Methyl-5-Hepten-2-Yl Acetate, 2-Methylbut-2-En-1-Ol, 2-Methylfuran, 4-Methylpent-2-Enoic Acid, 3-(Methylthio)-2-Butanone, 4-(Methylthio)-2-Pentanone, (+/−)-3-(Methylthio)Heptanal, 3-(Methylthio)Methylthiophene, Methylthiomethylmercaptan, Mono- And Diglycerides Of Fatty Acids, Nona-2,4,6-Trienal, 2-Nonenoic Acid Gamma-Lactone, Cis-3-Octenyl Propionate, L-Ornithine Monochlorohydrate/Ornithine, Pent-2-Enyl Hexanoate, 2-Pentanoylfuran, 2-Pentenoic Acid, (+/−)-2-Phenyl-4-Methyl-2-Hexenal, Phthalide, Phytol, Phytyl Acetate, 3-Pinanone, Piperitenone Oxide, L-Piperitone, Polyglycerol Esters Of Fatty Acids, Prenyl Acetate, Prenyl Benzoate, Prenyl Caproate, Prenyl Formate, Prenyl Isobutyrate, Propyl 2-Mercaptopropionate, Propylene Glycol Mono- And Diesters Of Fatty Acids, Tetradec-2-Enal, Thioacetic Acid, Trans- And Cis-2,4,8-Trimethyl-3,7-Nonadien-2-Ol, (+/−)-2,4,8-Trimethyl-7-Nonen-2-Ol, 3,7,11-Trimethyldodeca-2,6,10-Trienyl Acetate, 2,4,6-Trithiaheptane, Tyramine, Verbenone, Vetiverol, Vetiveryl Acetate, Cornmint Oil, *Mentha arvensis* L., *Heliopsis longipes* Extract, Scotch Spearmint Oil, *Mentha cardiaca* L., Natural Hickory Smoke Flavor, Betaine, Adenosine Monophosphate; Monosodium, Or Disodium Adenylate, Isoquercitrin, Enzymatically Modified, Glycerol Ester Of Rosin, Gum Arabic, Hydrogen Octenylbutane Dioate, (−)-Homoeriodictyol, Sodium Salt, Sugar Beet Juice Extract, (+/−)-N,N-Dimethyl Menthyl Succinamide, N1-(2-Methoxy-4-Methylbenzyl)-N2-(2-(Pyridin-2-Yl)Ethyl)Oxalamide, N-(Heptan-4-Yl)Benzo[D][1,3] Dioxole-5-Carboxamide, N1-(2,4-Dimethoxybenzyl)-N2-(2-(Pyridin-2-Yl)Ethyl)Oxalamide, N1-(2-Methoxy-4-Methylbenzyl)-N2-(2-(5-Methylpyridin-2-Yl)Ethyl) Oxalamide, 1,6-Hexalactam, Ethylamine, Propylamine, Isopropylamine, Isobutylamine, Sec-Butylamine, 2-Methylbutylamine, Pentylamine, Hexylamine, 2-Methylpiperidine, Trimethylamine Oxide, Triethylamine, Tripropylamine, N,N-Dimethylphenethylamine, 2-Acetyl-1-Pyrroline, Piperazine, Butyramide, Methyl 10-Undecenoate, N-Gluconyl Ethanolamine, N-Gluconyl Ethanolamine Phosphate, N-Lactoyl Ethanolamine, N-Lactoyl Ethanolamine Phosphate, Ethanethiol, Heptane-1-Thiol, S-Isopropyl 3-Methylbut-2-Enethioate, 3-Methylhexanal, 4-Pentenal, Propyl Propane Thiosulfonate, Alpha-Ionene, *Gardenia gummifera* Distillate, *Piper longum* Distillate, N-3,7-Dimethyl-2,6-Octadienylcyclopropylcarboxamide, (+/−)-Ethyl 2-Hydroxy-2-Methylbutyrate, (+/−)-Ethyl 2-Hydroxy-3-Methylvalerate, 2-(2-Hydroxyphenyl) Cyclopropanecarboxylic Acid Delta Lactone, 2-Decanone, (+/−)-Trans- And Cis-2-Hexenal Propylene Glycol Acetal, (+/−)-Trans- And Cis-2-Hexenal Glyceryl Acetal, Trans-2-Hexenyl 2-Methylbutyrate, 2-(4-Methyl-5-Thiazolyl)Ethyl Formate, 2-(4-Methyl-5-Thiazolyl)Ethyl Propionate, 2-(4-Methyl-5-Thiazolyl)Ethyl Butanoate, 2-(4-Methyl-5-Thiazolyl)Ethyl Isobutyrate, 2-(4-Methyl-5-Thiazolyl)Ethyl Hexanoate, 2-(4-Methyl-5-Thiazolyl)Ethyl Octanoate, 2-(4-Methyl-5-Thiazolyl)Ethyl Decanoate, (+/−)-3-(Ethylthio)Butanol, *Decalepis Hamiltonii* Extract, 2-(Trans-2-Pentenyl)Cyclopentanone, 3,9-Dimethyl-6-(1-Methylethyl)-1,4-Dioxaspiro[4.5]Decan-2-One, Cis- And Trans-2-Isobutyl-4-Methyl-1,3-Dioxolane, Cis- And Trans-2-Isopropyl-4-Methyl-1,3-Dioxolane, 4-Aminobutyric Acid, 3-Mercaptoheptyl Acetate, Ethyl Trans-2-Methyl-2-Pentenoate, Methyl Hexyl Ether, Trans-2-Trans-4-Nonadiene, 1-Octene, Cis- And Trans-Ethyl 2,4-Dimethyl-1,3-Dioxolane-2-Acetate, Citronellyl Trans-2-Methyl-2-Butenoate, 5-Acetyl-2,3-Dihydro-1,4-Thiazine, Bis(1-Mercaptopropyl)Sulfide, 2,5-Dithiahexane, Pseudoionone, Cis- And Trans-L-Mercapto-P-Menthan-3-One, Trans-2-Nonen-4-One, Trans-4-Nonenal, 1,1'-(Tetrahydro-6a-Hydroxy-2,3a,5-Trimethylfuro[2,3-D]-1,3-Dioxole-2,5-Diyl)Bis-Ethanone, Trans-2-Decenol, Cis-2-Pentenol, 2-Methylbutyl 3-Methyl-2-Butenoate, Citric And Fatty Acid Esters Of Glycerol, L-Menthyl (R,S)-3-Hydroxybutyrate, N-[(Ethoxycarbonyl)Methyl)-P-Menthane-3-Carboxamide, N-[2-(3,4-Dimethoxyphenyl)Ethyl]-3,4-Dimethoxycinnamic Acid Amide, Mixture Of Methyl Cyclohexadiene And Methylene Cyclohexene, (+/−)-Cis- And Trans-1,2-Dihydroperillaldehyde, 5,7-Dihydroxy-2-(3-Hydroxy-4-Methoxyphenyl)Chroman-4-One, Phenethyl Decanoate, 3,6-Dimethyl-2,3,3a,4,5,7a-Hexahydrobenzofuran, 2-Methylacetophenone, 1-Ethyl-2-Pyrrolecarboxaldehyde, Cis- And Trans-5-Ethyl-2,5-Dihydro-4-Methyl-2-(1-Methylpropyl)-Thiazole, Cis And Trans-5-Ethyl-4-Methyl-2-(2-Methylpropyl)-Thiazoline, 2-Methyl-3-Furyl Methylthiomethyl Disulfide, Pyrrolidino-[1,2e]-4h-2,4-Dimethyl-1,3,5-Dithiazine, S-Allyl-L-Cysteine, 5-Pentyl-3h-Furan-2-One, 3-Mercapto-3-Methyl-1-Butyl Acetate, (+/−)-3-Mercapto-1-Butyl Acetate, 5-Nonen-Trans-2-One, L-Menthyl Acetoacetate, 4-Octen-3-One, 2,4,6-Trimethylphenol, 4-Hydroxyacetophenone, (+/−)-[R-(E)]-5-Isopropyl-8-Methylnona-6,8-Dien-2-One, 1-Methyl-h-Pyrrole-2-Carboxaldehyde, 1-Pentanethiol, Pentadecanoic Acid, Tridecanal, Tridecanoic Acid, Hexyl Heptanoate, Dodecyl Propionate, Hexyl Nonanoate, Dodecyl Butyrate, Heptyl Heptanoate, Hexyl Decanoate, Ethyl 4-Methylpentanoate, Ethyl 2-Ethylbutyrate, Ethyl 2-Ethylhexanoate, 5-Methylhexyl Acetate, 4-Methylpentyl Isovalerate, 3,7-Dimethyloctanal, Cis-4-Decenol, Cis-5-Octenoic Acid, 5-Hexenol, 3-Isopropenylpentanedioic Acid, Methyl 4-Pentenoate, Cis-4-Octenol, 11-Dodecenoic Acid, Trans-3-Hexenol, Trans-4-Octenoic Acid, Isobutyl 10-Undecenoate, Cis-9-Octadecenyl Acetate, Ethyl 4-Pentenoate, Ethyl 3-Octenoate, 3-Octenoic Acid, Cis-9-Octadecenol, Decanal Propyleneglycol Acetal, Acetaldehyde Hexyl Isoamyl Acetal, Dodecanal Dimethyl Acetal, Nonanal Dimethyl Acetal, Heptanal Propyleneglycol Acetal, Hexanal Hexyl Isoamyl Acetal, Hexanal Dihexyl Acetal, Isovaleraldehyde Diethyl Acetal, Valeraldehyde Propyleneglycol Acetal, Nonanal Propyleneglycol Acetal, Undecanal Propyleneglycol Acetal, Valeraldehyde Dibutyl Acetal, Acetaldehyde 1,3-Octanediol Acetal, Hexanal Octane-1,3-Diol Acetal, Isovaleraldehyde Glyceryl Acetal, Acetaldehyde Di-Cis-3-Hexenyl Acetal, 2,6-Dimethyl-5-Heptenal Propyleneglycol Acetal, Octanal Propyleneglycol Acetal, Hexanal Butane-2,3-Diol Acetal, Pecan Shell Flour, Di-(1-Propenyl)-Sulfide (Mixture Of Isomers), 2-Pentylthiophene, 5-Ethyl-2-Methylthiazole, 2,4-Dimethylpyridine, 3-(4-Hydroxyphenyl)-1-(2,4,6-Trihydroxyphenyl)Propan-1-One, (+/−)-Ethyl 3-Hydroxy-2-Methylbutyrate, (+/−)-Ethyl 3-Mercapto-2-Methylbutanoate, (+/−)-Cis- And Trans-2-Methyl-2-(4-Methyl-3-Pentenyl)Cyclopropanecarbaldehyde, Trimethyloxazole,2,5-Dimethyl-4-Ethyloxazole, 2-Propyl-4,5-Dimethyloxazole, 2-Isobutyl-4,5-Dimethyloxazole, 2-Methyl-4,5-Benzoxazole, 2-Nonanone Propyleneglycol Acetal, 6-Methyl-5-Hepten-2-One Propyleneglycol Acetal, 2-Pentyl 2-Methylpentanoate, 3-Octyl Butyrate, Dimethylbenzyl Carbinyl Crotonate, Dimethylbenzyl Carbinyl Hexanoate, 1,5-Octadien-3-One, 10-Undecen-2-One, 2,4-Dimethyl-4-Nonanol, 8-Nonen-2-One, 8-P-Menthene-1,2-Diol, Caryophyllene Alcohol, D-2,8-P-Menthadien-1-Ol, Cis-3-Nonen-1-Ol, Trans-3-Hexenyl Acetate, 4-(Methylthio)Butyl Isothiocyanate, 6-(Methylthio)Hexyl Isothiocyanate, 5-(Methylthio)Pentyl Isothiocyanate, Amyl Isothiocyanate, 3-Butenyl Isothiocyanate, 2-Butylisothiocyanate, Ethyl Isothiocyanate, 5-Hexenyl Isothiocyanate, Hexyl Isothiocyanate, Isoamyl Isothiocyanate, Isobutyl Isothiocyanate, Isopropyl Isothiocyanate, Methyl Isothiocyanate, 4-Pentenyl Isothiocyanate, Benzyl Isothiocyanate, 2,4-Dimethyl-3-Oxazoline, 3,4-Dihydroxybenzoic Acid, 3-Hydroxybenzoic Acid, (+/−)-Acetaldehyde Ethyl Isopropyl Acetal, (+/−)-6-Methyloctanal, 5-Ethyl-2,3-Dimethylpyrazine, 2-Hydroxy-4-Methoxybenzaldehyde, 3-(Methylthio)Propyl Hexanoate, Sodium Lauryl Sulfate, Beta-Angelicalactone, 7-Decen-4-Olide, 9-Decen-5-Olide, 8-Decen-5-Olide, 6-[5(6)-Decenoyloxy]Decanoic Acid, Ethyl 5-Acetoxyoctanoate, Ethyl 5-Hydroxydecanoate, 9-Dodecen-5-Olide, Gamma-Octadecalactone, Delta-Octadecalactone, 9-Tetradecen-5-Olide, Orin Lactone, Methyl 3-Hydroxybutyrate, Methyl 3-Acetoxy-2-Methylbutyrate, Ethyl 2-Acetylhexanoate, Ethyl 3-Hydroxyoctanoate, Methyl 3-Acetoxyoctanoate, 5-Oxooctanoic Acid, 5-Oxodecanoic Acid, Ethyl 5-Oxodecanoate, 5-Oxododecanoic Acid, Ethyl 2-Acetyloctanoate, 2-Oxo-3-Ethyl-4-Butanolide, 3-Isopropenyl-6-Oxoheptanoic Acid, Hydroxyacetone, 1-Hydroxy-4-Methyl-2-Pentanone, Propyleneglycol Diacetate, Propyleneglycol Dipropionate, Propyleneglycol Dibutyrate, Propyleneglycol Mono-2-Methylbutyrate, Propyleneglycol Di-2-Methylbutyrate, Propyleneglycol Monohexanoate, Propyleneglycol Dihexanoate, Propyleneglycol Dioctanoate, Dimethyl Adipate, Dipropyl Adipate, Diisopropyl Adipate, Diisobutyl Adipate, Dioctyl Adipate, Ethyl Acetoacetate Ethyleneglycol Ketal, Methyl Levulinate, Ethyl Levulinate Propyleneglycol Ketal, Propyl Levulinate, Isoamyl Levulinate, Dodecyl Lactate, Hexadecyl Lactate, Propyl Pyruvate, Hydroxycitronellal Propyleneglycol Acetal, Citral Glyceryl Acetal, Mushroom Oil, Distilled, Propyleneglycol Monobutyrate, Cis-3-Hexenyl Acetoacetate, 2-Methoxy-6-(2-Propenyl)Phenol, Myricitrin, (R)-(−)-1-Octen-3-Ol, Cis-3-Hexenoic Acid, Ammonia (also Includes Ammonium Chloride), Naringin Dihydrochalcone, N—P-Benzeneacetonitrilementhanecarboxamide, Cubebol, 6-Methylheptanal, (+/−)-Cis- And Trans-2-Pentyl-4-Propyl-1,3-Oxathiane, Choline Chloride (also Includes Choline), 3-[(2-Methyl-3-Furyl)Thio]Butanal, (−)-Sclareol, (+)-Cedrol, D-Limonen-10-Ol, (2,4)- And (3,5)- And (3,6)-Dimethyl-3-Cyclohexenylcarbaldehyde, 1,3-P-Menthadien-7-Al, P-Menthan-7-Ol, P-Menth-1-En-9-Ol, Menthyl Formate, Menthyl Propionate, Cyclotene Propionate, 3,3,5-Trimethylcyclohexyl Acetate, Dl-Camphor, 2-Cyclopentylcyclopentanone, Carvyl Palmitate, Cyclohexanone Diethyl Ketal, 2-Cyclohexenone, 8,9-Dehydrotheaspirone, L-Fenchone, Ethylenediaminetetraacetic Acid Disodium Salt, 2,2,6,7-Tetramethylbicyclo[4.3.0]Nona-4,9 (1)-Dien-8-Ol, 2,2,6,7-Tetramethylbicyclo[4.3.0]Nona-4,9 (1)-Dien-8-One, 6-Hydroxycarvone, L-Menthyl Butyrate, Pinocarvyl Isobutyrate, 2-Pentenyl-4-Propyl-1,3-Oxathiane (Mixture Of Isomers), Acetaldehyde Di-Isobutylacetal, Acetaldehyde Ethyl Isobutyl Acetal, 4-(2,2,3-Trimethylcyclopentyl)Butanoic Acid, Perillaldehyde Propyleneglycol Acetal, 2,6,6-Trimethyl-2-Hydroxycyclohexanone, Acetoin Propyleneglycol Ketal, 4,5-Octanedione, Ethyl Maltol Isobutyrate, 2-Tetrahydrofurfuryl 2-Mercaptopropionate, Nerolidol Oxide, Furfural Propyleneglycol Acetal, Methyl 3-(Furfurylthio)Propionate, Furfuryl Decanoate, Di-2-Furylmethane, (E)-Ethyl 3-(2-Furyl)Acrylate, Furfuryl Formate, 2-Methylbenzofuran, 5-Methylfurfuryl Alcohol, 2-Methyl-3-Furyl 2-Methyl-3-Tetrahydrofuryl Disulfide, Ethyl 2,5-Dimethyl-3-Oxo-4(2h)-Furyl Carbonate, Acai Berry Extract, 4-(2-Propenyl)Phenyl-Beta-D-Glucopyranoside, N-(2-(Pyridin-2-Yl)Ethyl)-3-P-Menthanecarboxamide, (+/−)-N-Lactoyl Tyramine, Cis,Cis-3,6-Nonadienyl Acetate, Trans-2-Nonenyl Acetate, Cis-3-Nonenyl Acetate, Cis-6-Nonenyl Acetate, Dihydrogalangal Acetate, 2,3,3-Trimethylindanone, N-Ethyl-2,2-Diisopropylbutanamide, Cyclopropanecarboxylic Acid(2-Isopropyl-5-Methylcyclohexyl)Amide, Magnolol, 2-(Methylthio)Ethyl Acetate, 3-(Methylthio)Propyl Mercaptoacetate, Ethyl 2-Hydroxyethyl Sulfide, Ethyl 3-(Methylthio)-Cis-2-Propenoate, Ethyl 3-(Methylthio)-Trans-2-Propenoate, Ethyl 3-(Methylthio)-2-Propenoate, 4-Methyl-2-(Methylthiomethyl)-2-Hexenal, 5-Methyl-2-(Methylthiomethyl)-2-Hexenal, 4-Methyl-2-(Methylthiomethyl)-2-Pentenal, 1-(3-(Methylthio)-Butyryl)-2,6,6-Trimethylcyclohexene, 2-Oxothiolane, Butyl Beta-(Methylthio)Acrylate, Ethyl 3-(Ethylthio)Butyrate, Methyl Octyl Sulfide, Methyl 1-Propenyl Sulfide, Diisoamyl Disulfide, Bis(2-Methylphenyl) Disulfide, Mixture Of Butyl Propyl Disulfide And Propyl And Butyl Disulfide, Di-Sec-Butyl Disulfide, Methyl 2-Methylphenyl Disulfide, Diisoamyl Trisulfide, Dodecanethiol, 2-Hydroxyethanethiol, 4-Mercapto-4-Methyl-2-Hexanone, 3-Mercapto-3-Methylbutyl Isovalerate, 3-Mercaptohexanal, Methyl Isobutanethioate, 3-Mercaptopropionic Acid, 2-Ethylhexyl 3-Mercaptopropionate, Butanal Dibenzyl Thioacetal, Methional Diethyl Acetal, Ethyl Linalyl Ether, Myrcenyl Methyl Ether, Linalool Oxide Pyranoid, 2-Hydroxy-5-Methylacetophenone, 2-Phenylpropanal Propyleneglycol Acetal, Cinnamaldehyde Propyleneglycol Acetal, Ethyl Alpha-Acetylcinnamate, Ethyl 2-Hydroxy-3-Phenylpropionate, 3-(3,4-Methylenedioxyphenyl)-2-Methylpropanal, Trehalose, Dihydrate, Rebaudioside A, N-(2-Hydroxyethyl)-2,3-Dimethyl-2-Isopropylbutanamide, N-(1,1-Dimethyl-2-Hydroxyethyl)-2,2-Diethylbutanamide, Dimenthyl Glutarate, Trans-3-Nonen-1-Ol, 4-Formyl-2-Methoxyphenyl 2-Hydroxypropanoate, Guaiacol Butyrate, Guaiacol Isobutyrate, Guaiacol Propionate, Ethyl 5-Hydroxyoctanoate, Isopropylideneglyceryl 5-Hydroxydecanoate, 2-Ethyl-2-Hexenal, Ethyl 2-Hexenoate, Propyl Sorbate, Cis-2-Octenol, 2-Hexylidenehexanal, Trans-2-Tridecenol, 2-Phenoxyethyl Propionate, Propyl 4-Tert-Butylphenylacetate, 2-Phenoxyethanol, Phenyl Butyrate, Piperonal Propyleneglycol Acetal, Benzyl Levulinate, 4-Methylbenzyl Alcohol, Phenylacetaldehyde Diethyl Acetal, Benzyl Nonanoate, Anisaldehyde Propyleneglycol Acetal, 4-Methylbenzaldehyde Propyleneglycol Acetal, Phenylacetaldehyde Propyleneglycol Acetal, 2-Ethylhexyl Benzoate, 2-Ethyl-3-Methylthiopyrazine, 2-Ethoxy-3-Isopropylpyrazine, 2-Ethoxy-3-Ethylpyrazine, Butyl Beta-Naphthyl Ether, Isoamyl Phenethyl Ether, 2-Acetyl-4-Isopropenylpyridine, 4-Acetyl-2-Isopropenylpyridine, 2-Acetyl-4-Isopropylpyridine, 2-Methoxypyridine, 6-Methoxyquinoline, 2-Pentylthiazole, 2-Thienylmethanol, 2-Acetyl-5-Methylthiophene, 4-Methyl-3-Thiazoline, 3,4-Dimethylthiophene, 1-(2-Thienyl)Ethanethiol, 4,5-Dimethyl-2-Isobutylthiazole, Cyclotene Butyrate, 3-(Methylthio)Propylamine, 4-Methyl-Cis-2-Pentene, 1-Nonene, 1,3,5,7-Undecatetraene, Ethyl Alpha-Ethyl-Beta-Methyl-Beta-Phenylglycidate, Methyl Beta-Phenylglycidate, D-8-P-Menthene-1,2-Epoxide, L-8-P-Menthene-1,2-Epoxide, 2,3-Epoxyoctanal, 2,3-Epoxyheptanal, 2,3-Epoxydecanal, Hydroxy(4-Hydroxy-3-Methoxyphenyl)Acetic Acid, 4-Hydroxy-4-(3-Hydroxy-1-Butenyl)-3,5,5-Trimethyl-2-Cyclohexen-1-One, (+/−)-2,6,10,10-Tetramethyl-1-Oxaspiro[4,5] Deca-2,6-Dien-8-One, 4-(2-Butenylidene)-3,5,5-Trimethylcyclohex-2-En-1-One, Digeranyl Ether, 1-(4-Hydroxy-3-Methoxyphenyl)Decan-3-One, Alpha-Bisabolol, 2(4)-Ethyl-4(2),6-Dimethyldihydro-1,3,5-Dithiazine (Mixture Of Isomers), (2e,6e/Z,8e)-N-(2-Methylpropyl)-2,6,8-Decatrienamide, 4-Amino-5,6-Dimethylthieno[2,3-D]Pyrimidin-2(1h)One And 4-Amino-5,6-Dimethylthieno[2,3-D]Pyrimidin-2(1h)One Hydrochloride, 1,1-Propanedithiol, Z-5-Octenyl Acetate, (E)-4-Undecenal, Delta-Hexadecalactone, Trilobatin, L-Isoleucine, 1-(2-Furfurylthio)-Propanone, (+/−)-4-Methyl-2-Propyl-1,3-Oxathiane, N-(2-Methylcyclohexyl)-2,3,4,5,6-Pentafluorobenzamide, Arachidonic Acid Enriched Oil, 5-Isopropyl-2,6-Diethyl-2-Methyltetrahydro-2h-Pyran, (1r, 2s,5r)-N-(4-Methoxyphenyl)-5-Methyl-2-(1-Methylethyl) Cyclohexanecarboxamide, Octahydro-4,8a-Dimethyl-4a (2h)-Naphthol, 2-Methyl-4,5-Dihydrofuran-3-Thiol, (2s,5r)-N-[4-(2-Amino-2-Oxoethyl)Phenyl]-5-Methyl-2-(Propan-2-Yl)Cyclohexanecarboxamide, (+/−)-6-Octyltetrahydro-2h-Pyran-2-One, (+/−)-2-Methyltetrahydrofuran-3-Thiol Acetate, (+/−)-3-Hydroxy-3-Methyl-2,4-Nonanedione, 1,1-Dipropoxyethane, Chrysanthemum Extract, Honeysuckle Extract, Yuzunone, L-Methionylglycine, N-Cyclopropyl-5-Methyl-2-Isopropylcyclohexanecarboxamide, 3-Pentanethiol, 2-Ethyl-2,5-Dihydro-4-Methylthiazole, 1-(Methyldithio)-2-Propanone, 5-Methylfurfurylmercaptan, 4-Mercapto-3-Methyl-2-Butanol, Ferrous L-Lactate, O-Trans-Coumaric Acid, 3-[(4-Amino-2,2-Dioxido-1h-2,1, 3-Benzothiadiazin-5-Yl)Oxy]-2,2-Dimethyl-N-Propylpropanamide, 2(3),5-Dimethyl-6,7-Dihydro-5h-Cyclopentapyrazine, Cinnamyl Benzoate, Beta-Naphthyl Methyl Ether, Rosemary Oleoresin, 9-Decen-2-One, 1-(Methylthio)-3-Octanone, 3′,7-Dihydroxy-4′-Methoxyflavan, Glutamyl-Valyl-Glycine, L-Threonine, Luo Han Fruit Concentrate, L-Alanyl-L-Glutamine, Sucrose Monopalmitate, Ethyl 2-Mercapto-2-Methylpropionate, 2-(3,4-Dihydroxyphenyl)-5,7-Dihydroxy-4-Chromanon, N—[N-[3-(3-Hydroxy-4-Methoxyphenyl)Propyl]-L-Alpha-Aspartyl]-L-Phenylalanine 1-Methylester, Monohydrate, Sweet Blackberry Leaves Extract, 2-[(2-(P-Menthyloxy)Ethoxy]Ethanol, Succinic Acid, Rebaudioside C, 1-(2-Hydroxyphenyl)-3-(Pyridin-4-Yl)Propan-1-One, 1-(2-Hydroxy-4-Isobutoxyphenyl)-3-(Pyridin-2-Yl)Propan-1-One, 1-(2-Hydroxy-4-Methoxyphenyl)-3-(Pyridin-2-Yl)Propan-1-One, Trans-4-Tert-Butylcyclohexanol, 3-(1-((3,5-Dimethylisoxazol-4-Yl) Methyl)-1h-Pyrazol-4-Yl)-1-(3-Hydroxybenzyl) Imidazolidine-2,4-Dione, 3-(1-((3,5-Dimethylisoxazol-4-Yl)Methyl)-1h-Pyrazol-4-Yl)-1-(3-Hydroxybenzyl)-5,5-Dimethylimidazolidine-2,4-Dione, Clover Herb Distillate, Glucosyl Steviol Glycosides, Dl-Isomenthol, O-Ethyl S-1-

Methoxyhexan-3-Yl Carbonothioate, Cassyrane, 1,5-Octadien-3-Ol, (+/−)-2-Mercaptoheptan-4-Ol, 3-(Methylthio) Decanal, (4z,7z)-Trideca-4,7-Dienal, *Persicaria odorata* Oil, Amacha Leaves Extract, Glutamyl-2-Aminobutyric Acid, Glutamyl-Norvalyl-Glycine, Glutamyl-Norvaline, N1-(2,3-Dimethoxybenzyl)-N2-(2-(Pyridin-2-Yl)Ethyl) Oxalamide, 1-(2-Hydroxy-4-Methylcyclohexyl)Ethanone, Mexican Lime Oil, Expressed, Persian Lime Oil, Expressed, (+/−)-6-Methoxy-2,6-Dimethylheptanal, 3,5-Undecadien-2-One, (+/−)-2,5-Undecadien-1-Ol, Triethylthialdine, 4-Methylpentyl 4-Methylvalerate, Cis-3-Hexenyl Salicylate, (R)—N-(1-Methoxy-4-Methylpentan-2-Yl)-3,4-Dimethylbenzamide, N-Acetyl Glutamate, 1,3-Propanediol, Szechuan Pepper Extract, *Tasmannia lanceolata* Extract, *Mentha longifolia* Oil, Mangosteen Distillate, Ethyl 3-(2-Hydroxyphenyl)Propanoate, 1-Cyclopropanemethyl-4-Methoxybenzene, Prenyl Thioisobutyrate, Prenyl Thioisovalerate, (−)-Matairesinol, Steviosside, 1-(2,4-Dihydroxyphenyl)-3-(3-Hydroxy-4-Methoxyphenyl) Propan-1-One, Ethyl 5-Formyloxydecanoate, 3-[3-(2-Isopropyl-5-Methyl-Cyclohexyl)Ureido]Butyric Acid Ethyl Ester, 2-Isopropyl-4-Methyl-3-Thiazoline, 2,6,10-Trimethyl-9-Undecenal, 5-Mercapto-5-Methyl-3-Hexanone, Meyer Lemon Oil, Cold Pressed, *Citrus×Meyeri*, Steviol Glycoside Extract, *Stevia rebaudiana*, Rebaudioside A 60%, Steviol Glycoside Extract, *Stevia rebaudiana*, Rebaudioside A 80%, (E)-N-[2-(1,3-Benzodioxol-5-Yl)Ethyl]-3-(3,4-Dimethoxyphenyl)Prop-2-Enamide, 4-Amino-5-(3-(Isopropylamino)-2,2-Dimethyl-3-Oxopropoxy)-2-Methylquinoline-3-Carboxylic Acid, 3-Methyl-5-(2,2,3-Trimethylcyclopent-3-En-1-Yl)Pent-4-En-2-Ol, (1-Methyl-2-(1,2,2-Trimethylbicyclo[3.1.0]Hex-3-Ylmethyl)Cyclopropyl) Methanol, Erospicata Oil, *Mentha spicata*, Curly Mint Oil, *Mentha spicata* Var. *crispa*, (+/−)-2-Mercapto-5-Methylheptan-4-One, Caryophylla-3(4),8-Dien-5-Ol, L-Cysteine Methyl Ester Hydrochloride, 2(3)-Hexanethiol, Mixture Of 1-Vinyl-3-Cyclohexenecarbaldehyde And 4-Vinyl-1-Cyclohexenecarbaldehyde, (+/−)-4-Hydroxy-6-Methyl-2-Heptanone, 2-Octyl-2-Dodecenal, 2-Hexyl-2-Decenal, Trans-6-Octenal, (E)-3-Benzo[1,3]Dioxol-5-Yl-N,N-Diphenyl-2-Propenamide, 2,6-Dimethyl-5-Heptenol, (+/−)-Bicyclo [2.2.1]Hept-5-Ene-2-Carboxylic Acid, Ethyl Ester, 3-(Acetylthio)Hexanal, (+/−)-3-Mercapto-1-Pentanol, (3r,3s)-3-[[(4-Amino-2,2-Dioxido-1h-2,1,3-Benzothiadiazin-5-Yl)Oxy]Methyl]-N-Cyclopentyl-2-Oxo-3-Piperidinecarboxamide, (+/−)-1-Cyclohexylethanol, (+/−)-8-Methyldecanal, Steviol Glycoside Extract, *Stevia rebaudiana*, Rebaudioside C 30%, (+/−)-Naringenin, 2-(((3-(2,3-Dimethoxyphenyl)-1h-1,2,4-Triazol-5-Yl)Thio) Methyl)Pyridine, (2r)-3',5-Dihydroxy-4'-Methoxyflavanone, Glucosylated *Rubus suavissimus* Extract, 20-30% Glucosylated Rubusoside Glycosides, Olive Fruit Extract, (S)-1-(3-(((4-Amino-2,2-Dioxido-1h-Benzo[C][1,2,6]Thiadiazin-5-Yl)Oxy)Methyl)Piperidin-1-Yl)-3-Methylbutan-1-One, 8-Methylnonanal, Mixture Of Ricinoleic Acid, Linoleic Acid, And Oleic Acid, Steviol Glycoside Extract, *Stevia rebaudiana*, Rebaudioside A 22%, Steviol Glycoside Extract, *Stevia rebaudiana*, Rebaudioside C 22%, Pinocarvyl Acetate, N-Ethyl-5-Methyl-2-(1-Methylethenyl) Cyclohexanecarboxamide, 2-(4-Methylphenoxy)-N-(1h-Pyrazol-3-Yl)-N-(Thiophen-2-Ylmethyl)Acetamide, Ethyl-2-(4-Hydroxy-3-Methoxy-Phenyl)Acetate, Ginger Mint Oil (*Mentha×Gracilis*), Palmitoylated Green Tea Extract Catechins, 2-(5-Isopropyl-2-Methyltetrahydrothiophen-2-Yl) Ethanol, Glucosylated *Rubus suavissimus* Extract, 60% Glucosylated Rubusoside Glycosides, Sandalwood Austrocaledonicum Oil, and Sugar Cane Distillate.

In some embodiments, the ingestible composition is a beverage. In some embodiments, the beverage is selected from the group consisting of colas, lemon-lime flavored sparkling beverages, orange flavored sparkling beverages, grape flavored sparkling beverages, strawberry flavored sparkling beverages, pineapple flavored sparkling beverages, ginger-ales, root beers, fruit juices, fruit-flavored juices, juice drinks, nectars, vegetable juices, vegetable-flavored juices, sports drinks, energy drinks, enhanced water drinks, enhanced water with vitamins, near water drinks, coconut waters, tea type drinks, coffees, cocoa drinks, beverages containing milk components, beverages containing cereal extracts and smoothies. In some embodiments, the beverage is a soft drink.

In some embodiments, the ingestible composition is a food or beverage product or formulation. Examples of food and beverage products or formulations include, but are not limited to sweet coatings, frostings, or glazes for ingestible products or any entity included in the Soup category, the Dried Processed Food category, the Beverage category, the Ready Meal category, the Canned or Preserved Food category, the Frozen Processed Food category, the Chilled Processed Food category, the Snack Food category, the Baked Goods category, the Confectionery category, the Dairy Product category, the Ice Cream category, the Meal Replacement category, the Pasta and Noodle category, and the Sauces, Dressings, Condiments category, the Baby Food category, and/or the Spreads category.

In general, the Soup category refers to canned/preserved, dehydrated, instant, chilled, UHT and frozen soup. For the purpose of this definition soup(s) means a food prepared from meat, poultry, fish, vegetables, grains, fruit and other ingredients, cooked in a liquid which may include visible pieces of some or all of these ingredients. It may be clear (as a broth) or thick (as a chowder), smooth, pureed or chunky, ready-to-serve, semi-condensed or condensed and may be served hot or cold, as a first course or as the main course of a meal or as a between meal snack (sipped like a beverage). Soup may be used as an ingredient for preparing other meal components and may range from broths (consommd) to sauces (cream or cheese-based soups).

The Dehydrated and Culinary Food Category usually means: (i) Cooking aid products such as: powders, granules, pastes, concentrated liquid products, including concentrated bouillon, bouillon and bouillon like products in pressed cubes, tablets or powder or granulated form, which are sold separately as a finished product or as an ingredient within a product, sauces and recipe mixes (regardless of technology); (ii) Meal solutions products such as: dehydrated and freeze dried soups, including dehydrated soup mixes, dehydrated instant soups, dehydrated ready-to-cook soups, dehydrated or ambient preparations of ready-made dishes, meals and single serve entrees including pasta, potato and rice dishes; and (iii) Meal embellishment products such as: condiments, marinades, salad dressings, salad toppings, dips, breading, batter mixes, shelf stable spreads, barbecue sauces, liquid recipe mixes, concentrates, sauces or sauce mixes, including recipe mixes for salad, sold as a finished product or as an ingredient within a product, whether dehydrated, liquid or frozen.

The Beverage category usually means beverages, beverage mixes and concentrates, including but not limited to, carbonated and non-carbonated beverages, alcoholic and non-alcoholic beverages, ready to drink beverages, liquid concentrate formulations for preparing beverages such as sodas, and dry powdered beverage precursor mixes. The Beverage category also includes the alcoholic drinks, the soft drinks, sports drinks, isotonic beverages, and hot drinks. The alcoholic drinks include, but are not limited to beer, cider/perry, FABs, wine, and spirits. The soft drinks include, but are not limited to carbonates, such as colas and non-cola carbonates; fruit juice, such as juice, nectars, juice drinks and fruit flavored drinks; bottled water, which includes sparkling water, spring water and purified/table water; functional drinks, which can be carbonated or still and include sport, energy or elixir drinks; concentrates, such as liquid and powder concentrates in ready to drink measure. The drinks, either hot or cold, include, but are not limited to coffee or ice coffee, such as fresh, instant, and combined coffee; tea or ice tea, such as black, green, white, oolong, and flavored tea; and other drinks including flavor-, malt- or plant-based powders, granules, blocks or tablets mixed with milk or water.

The Snack Food category generally refers to any food that can be a light informal meal including, but not limited to Sweet and savory snacks and snack bars. Examples of snack food include, but are not limited to fruit snacks, chips/crisps, extruded snacks, tortilla/corn chips, popcorn, pretzels, nuts and other sweet and savory snacks. Examples of snack bars include, but are not limited to granola/muesli bars, breakfast bars, energy bars, fruit bars and other snack bars.

The Baked Goods category generally refers to any edible product the process of preparing which involves exposure to heat or excessive sunlight. Examples of baked goods include, but are not limited to bread, buns, cookies, muffins, cereal, toaster pastries, pastries, waffles, tortillas, biscuits, pies, bagels, tarts, quiches, cake, any baked foods, and any combination thereof.

The Ice Cream category generally refers to frozen dessert containing cream and sugar and flavoring. Examples of ice cream include, but are not limited to: impulse ice cream; take-home ice cream; frozen yoghurt and artisanal ice cream; soy, oat, bean (e.g., red bean and mung bean), and rice-based ice creams.

The Confectionery category generally refers to edible product that is sweet to the taste. Examples of confectionery include, but are not limited to candies, gelatins, chocolate confectionery, sugar confectionery, gum, and the likes and any combination products.

The Meal Replacement category generally refers to any food intended to replace the normal meals, particularly for people having health or fitness concerns. Examples of meal replacement include, but are not limited to slimming products and convalescence products.

The Ready Meal category generally refers to any food that can be served as meal without extensive preparation or processing. The ready meal includes products that have had recipe "skills" added to them by the manufacturer, resulting in a high degree of readiness, completion and convenience. Examples of ready meal include, but are not limited to canned/preserved, frozen, dried, chilled ready meals; dinner mixes; frozen pizza; chilled pizza; and prepared salads.

The Pasta and Noodle category includes any pastas and/or noodles including, but not limited to canned, dried and chilled/fresh pasta; and plain, instant, chilled, frozen and snack noodles.

The Canned/Preserved Food category includes, but is not limited to canned/preserved meat and meat products, fish/seafood, vegetables, tomatoes, beans, fruit, ready meals, soup, pasta, and other canned/preserved foods.

The Frozen Processed Food category includes, but is not limited to frozen processed red meat, processed poultry, processed fish/seafood, processed vegetables, meat substitutes, processed potatoes, bakery products, desserts, ready meals, pizza, soup, noodles, and other frozen food.

The Dried Processed Food category includes, but is not limited to rice, dessert mixes, dried ready meals, dehydrated soup, instant soup, dried pasta, plain noodles, and instant noodles. The Chill Processed Food category includes, but is not limited to chilled processed meats, processed fish/seafood products, lunch kits, fresh cut fruits, ready meals, pizza, prepared salads, soup, fresh pasta and noodles.

The Sauces, Dressings and Condiments category includes, but is not limited to tomato pastes and purees, bouillon/stock cubes, herbs and spices, monosodium glutamate (MSG), table sauces, soy based sauces, pasta sauces, wet/cooking sauces, dry sauces/powder mixes, ketchup, mayonnaise, mustard, salad dressings, vinaigrettes, dips, pickled products, and other sauces, dressings and condiments.

The Baby Food category includes, but is not limited to milk- or soybean-based formula; and prepared, dried and other baby food.

The Spreads category includes, but is not limited to jams and preserves, honey, chocolate spreads, nut based spreads, and yeast based spreads.

The Dairy Product category generally refers to edible product produced from mammal's milk. Examples of dairy product include, but are not limited to drinking milk products, cheese, yoghurt and sour milk drinks, and other dairy products.

Additional examples for ingestible compositions, particularly food and beverage products or formulations, are provided as follows. Exemplary ingestible compositions include one or more confectioneries, chocolate confectionery, tablets, countlines, bagged selflines/softlines, boxed assortments, standard boxed assortments, twist wrapped miniatures, seasonal chocolate, chocolate with toys, alfajores, other chocolate confectionery, mints, standard mints, power mints, boiled sweets, pastilles, gums, jellies and chews, toffees, caramels and nougat, medicated confectionery, lollipops, liquorice, other sugar confectionery, bread, packaged/industrial bread, unpackaged/artisanal bread, pastries, cakes, packaged/industrial cakes, unpackaged/artisanal cakes, cookies, chocolate coated biscuits, sandwich biscuits, filled biscuits, savory biscuits and crackers, bread substitutes, breakfast cereals, rte cereals, family breakfast cereals, flakes, muesli, other cereals, children's breakfast cereals, hot cereals, ice cream, impulse ice cream, single portion dairy ice cream, single portion water ice cream, multi-pack dairy ice cream, multi-pack water ice cream, take-home ice cream, take-home dairy ice cream, ice cream desserts, bulk ice cream, take-home water ice cream, frozen yoghurt, artisanal ice cream, dairy products, milk, fresh/pasteurized milk, full fat fresh/pasteurized milk, semi skimmed fresh/pasteurized milk, long-life/uht milk, full fat long life/uht milk, semi skimmed long life/uht milk, fat-free long life/uht milk, goat milk, condensed/evaporated milk, plain condensed/evaporated milk, flavored, functional and other condensed milk, flavored milk drinks, dairy only flavored milk drinks, flavored milk drinks with fruit juice, soy milk, sour milk drinks, fermented dairy drinks, coffee whiteners, powder milk, flavored powder milk drinks, cream, cheese, processed cheese, spreadable processed cheese, unspreadable processed cheese, unprocessed cheese, spreadable unprocessed cheese, hard cheese, packaged hard cheese, unpackaged hard cheese, yoghurt, plain/natural yoghurt, flavored yoghurt, fruited yoghurt, probiotic yoghurt, drinking yoghurt, regular drinking yoghurt, probiotic drinking yoghurt, chilled and shelf-stable desserts, dairy-based desserts, soy-based desserts, chilled snacks, fromage frais and quark, plain fromage frais and quark, flavored fromage frais and quark, savory fromage frais and quark, sweet and savory snacks, fruit snacks, chips/crisps, extruded snacks, tortilla/corn chips, popcorn, pretzels, nuts, other sweet and savory snacks, snack bars, granola bars, breakfast bars, energy bars, fruit bars, other snack bars, meal replacement products, slimming products, convalescence drinks, ready meals, canned ready meals, frozen ready meals, dried ready meals, chilled ready meals, dinner mixes, frozen pizza, chilled pizza, soup, canned soup, dehydrated soup, instant soup, chilled soup, hot soup, frozen soup, pasta, canned pasta, dried pasta, chilled/fresh pasta, noodles, plain noodles, instant noodles, cups/bowl instant noodles, pouch instant noodles, chilled noodles, snack noodles, canned food, canned meat and meat products, canned fish/seafood, canned vegetables, canned tomatoes, canned beans, canned fruit, canned ready meals, canned soup, canned pasta, other canned foods, frozen food, frozen processed red meat, frozen processed poultry, frozen processed fish/seafood, frozen processed vegetables, frozen meat substitutes, frozen potatoes, oven baked potato chips, other oven baked potato products, non-oven frozen potatoes, frozen bakery products, frozen ready meals, frozen pizza, frozen desserts, frozen soup, frozen noodles, other frozen food, dried food, dessert mixes, dried ready meals, dehydrated soup, instant soup, dried pasta, plain noodles, instant noodles, cups/bowl instant noodles, pouch instant noodles, chilled food, chilled processed meats, chilled fish/seafood products, chilled processed fish, chilled coated fish, chilled smoked fish, chilled lunch kit, chilled ready meals, chilled pizza, chilled soup, chilled/fresh pasta, chilled noodles, oils and fats, olive oil, vegetable and seed oil, cooking fats, butter, margarine, spreadable oils and fats, functional spreadable oils and fats, sauces, dressings and condiments, tomato pastes and purees, bouillon/stock cubes, stock cubes, gravy granules, liquid stocks and fonds, herbs and spices, fermented sauces, soy based sauces, pasta sauces, wet sauces, dry sauces/powder mixes, ketchup, mayonnaise, regular mayonnaise, mustard, salad dressings, regular salad dressings, low fat salad dressings, vinaigrettes, dips, pickled products, other sauces, dressings and condiments, baby food, milk formula, standard milk formula, follow-on milk formula, toddler milk formula, hypoallergenic milk formula, prepared baby food, dried baby food, other baby food, spreads, jams and preserves, honey, chocolate spreads, nut-based spreads, and yeast-based spreads. Exemplary ingestible compositions also include confectioneries, bakery products, ice creams, dairy products, sweet and savory snacks, snack bars, meal replacement products, ready meals, soups, pastas, noodles, canned foods, frozen foods, dried foods, chilled foods, oils and fats, baby foods, or spreads or a mixture thereof. Exemplary ingestible compositions also include breakfast cereals, sweet beverages or solid or liquid concentrate compositions for preparing beverages, ideally so as to enable the reduction in concentration of previously known saccharide sweeteners, or artificial sweeteners.

Some embodiments provide a food or beverage product comprising about 1% (w/w) of a compound of Formula (I). Some embodiments provide a food or beverage product comprising about 1.5% (w/w) of a compound of Formula (I). Some embodiments provide a food or beverage product comprising about 2% (w/w) of a compound of Formula (I). Some embodiments provide a food or beverage product comprising about 2.5% (w/w) of a compound of Formula (I). Some embodiments provide a food or beverage product comprising about 3% (w/w) of a compound of Formula (I). Some embodiments provide a food or beverage product comprising about 3.5% (w/w) of a compound of Formula (I). Some embodiments provide a food or beverage product comprising about 4% (w/w) of a compound of Formula (I). Some embodiments provide a food or beverage product comprising about 4.5% (w/w) of a compound of Formula (I). Some embodiments provide a food or beverage product comprising about 5% (w/w) of a compound of Formula (I). Some embodiments provide a food or beverage product comprising about 5.5% (w/w) of a compound of Formula (I). Some embodiments provide a food or beverage product comprising about 6% (w/w) of a compound of Formula (I). Some embodiments provide a food or beverage product comprising about 6.5% (w/w) of a compound of Formula (I). Some embodiments provide a food or beverage product comprising about 7% (w/w) of a compound of Formula (I). Some embodiments provide a food or beverage product comprising about 7.5% (w/w) of a compound of Formula (I). Some embodiments provide a food or beverage product comprising about 8% (w/w) of a compound of Formula (I). Some embodiments provide a food or beverage product comprising about 8.5% (w/w) of a compound of Formula (I). Some embodiments provide a food or beverage product comprising about 9% (w/w) of a compound of Formula (I). Some embodiments provide a food or beverage product comprising about 9.5% (w/w) of a compound of Formula (I). Some embodiments provide a food or beverage product comprising about 10% (w/w) of a compound of Formula (I).

Some embodiments provide a chewable composition that may or may not be intended to be swallowed. In some embodiments, the chewable composition may be gum, chewing gum, sugarized gum, sugar-free gum, functional gum, bubble gum including compounds as disclosed and described herein, individually or in combination.

Some embodiments provide supplements, nutraceuticals, functional food products (e.g., any fresh or processed food claimed to have a health-promoting and/or disease-preventing properties beyond the basic nutritional function of supplying nutrients), pharmaceutical product, over the counter (OTC) product, oral care product, cosmetic products such as sweetened lip balms, and other personal care products including compounds as disclosed and described herein, individually or in combination. The sweeteners or sweetener enhancers described herein may be used to provide a sweet flavor of any of these products. For example, in some embodiments, a compound described herein is included as an excipient in a pharmaceutical product to mask the bitterness thereof and make it more palatable to ingest. In some embodiments, a compound described herein is included in a liquid pharmaceutical or OTC product form for ingestion. In some embodiments, a compound described herein is included in a solid pharmaceutical or OTC product form for ingestion. For example, the compound may be included in a coating on a tablet, capsule, or other typical pharmaceutical form.

In general, over the counter (OTC) product and oral care product generally refer to product for household and/or personal use which may be sold without a prescription and/or without a visit to a medical professional. Examples of the OTC products include, but are not limited to analgesics; cough, cold and allergy remedies; antihistamines and/or allergy remedies; and combinations thereof. Cough, cold and allergy remedies include, but are not limited to decongestants, cough remedies, pharyngeal preparations, medicated confectionery, antihistamines and child-specific cough, cold and allergy remedies; and combination products. Antihistamines and/or allergy remedies include, but are not limited to any systemic treatments for hay fever, nasal allergies, insect bites and stings. In some embodiments, the OTC product is a nausea relief composition, an antacid, or a heartburn relief composition.

Examples of oral hygiene product include, but are not limited to mouth cleaning strips, toothpaste, toothbrushes, mouthwashes/dental rinses, denture care, mouth fresheners, breath freshening sprays, breath freshening drops, breath freshening concentrates, chewing gum, mouth moisturizers, at-home teeth whiteners and dental floss.

Some embodiments provide methods of increasing the sweetness of an ingestible composition, comprising combining at least one compound described herein with an ingestible composition that does not already comprise the compound.

Concentrates

In some embodiments, compounds as disclosed and described herein, individually or in combination, may be provided in a flavoring concentrate formulation, e.g., suitable for subsequent processing to produce a ready-to-use (i.e., ready-to-serve) product. By "a flavoring concentrate formulation", it is meant a formulation which should be reconstituted with one or more diluting medium (i.e., a "diluent") to become a ready-to-use composition. The term "ready-to-use composition" is used herein interchangeably with "ingestible composition." In one embodiment, the ready-to-use composition includes a composition that can be directly consumed by a human or animal. The flavoring concentrate formulation is typically used by mixing with or diluted by one or more diluting medium, e.g., any consumable or ingestible ingredient or product, to impart or modify one or more flavors to the diluting medium. Such a use process is often referred to as reconstitution. The reconstitution can be conducted in a household setting or an industrial setting. For example, a frozen fruit juice concentrate can be reconstituted with water or other aqueous medium by a consumer in a kitchen to obtain the ready-to-use fruit juice beverage. In another example, a soft drink syrup concentrate can be reconstituted with water or other aqueous medium by a manufacturer in large industrial scales to produce the ready-to-use soft drinks. Suitable diluants include, but are not limited to, water, carbonated water, nitrogen infused water, or solutions having the forgoing as solvents. Concentrate formulations may be used in a variety of food, beverage, and medicinal production techniques. For example, the concentrate may be dosed into a composition as part of a food or beverage manufacturing process. In some embodiments, the concentrate is dosed into an intermediate composition to which additional ingredients or added and/or additional processing is conducted upon prior to producing the final food or beverage product. Since the flavoring concentrate formulation has the flavoring agent or flavor modifying agent in a concentration higher than the ready-to-use composition, the flavoring concentrate formulation is typically not suitable for being consumed directly without reconstitution. There are many benefits of using and producing a flavoring concentrate formulation. For example, one benefit is the reduction in weight and volume for transportation as the flavoring concentrate formulation can be reconstituted at the time of usage by the addition of suitable solvent, solid or liquid.

In one embodiment, the flavoring concentrate formulation comprises i) compounds as disclosed and described herein, individually or in combination; ii) a carrier; and iii) optionally at least one adjuvant. The term "carrier" denotes a usually inactive accessory substance, such as solvents, binders, or other inert medium, which is used in combination with the present compound and one or more optional adjuvants to form the formulation. For example, water or starch can be a carrier for a flavoring concentrate formulation. In some embodiments, the carrier is the same as the diluting medium for reconstituting the flavoring concentrate formulation; and in other embodiments, the carrier is different from the diluting medium. The term "carrier" as used herein includes, but is not limited to, ingestibly acceptable carrier.

Suitable carriers for use in a concentrate formulation include but are not limited to starches (e.g., food starches), maltodextrin, gums, liquid carriers, and encapsulants. Non-limiting examples of liquid carriers include water, ethanol, propylene glycol, Triacetin, Neobee, and glycerin. Non-limiting examples of starches include modified corn starch. Non-limiting examples of gums include Gum Aragic (*Gum acadia*) and Xanthan Gum. Other suitable solid carriers for a concentrate formulation include dextrose, silicon dioxide, magnesium carbonate, and tricalcium phosphate.

The term "adjuvant" denotes an additive which supplements, stabilizes, maintains, or enhances the intended function or effectiveness of the active ingredient, such as the compound of the present invention. In one embodiment, the at least one adjuvant comprises one or more flavoring agents. The flavoring agent may be of any flavor known to one skilled in the art or consumers, such as the flavor of chocolate, coffee, tea, mocha, French vanilla, peanut butter, chai, or combinations thereof. In another embodiment, the at least one adjuvant comprises one or more sweeteners. The one or more sweeteners can be any of the sweeteners described in this application. In another embodiment, the at least one adjuvant comprises one or more ingredients selected from the group consisting of a emulsifier, a stabilizer, an antimicrobial preservative, an antioxidant, vitamins, minerals, fats, starches, protein concentrates and isolates, salts, and combinations thereof. Examples of emulsifiers, stabilizers, antimicrobial preservatives, antioxidants, vitamins, minerals, fats, starches, protein concentrates and isolates, and salts are described in U.S. Pat. No. 6,468,576, the content of which is hereby incorporated by reference in its entirety for all purposes. Non-limiting examples of stabilizers include Pectin, Xanthan Gum, CMC (Carboxyl Methyl Cellulose), Polysorbate 60, Polysorbate 80, Medium Chain Triglycerides, Cellulose Gel, Cellulose Gum, Sodium caseinate, Modified Food Starch, Gum Arabic (*Gum acacia*), and Carrageenan.

In one embodiment, the present flavoring concentrate formulation can be in a form selected from the group consisting of liquid including solution and suspension, solid, foamy material, paste, gel, cream, and a combination thereof, such as a liquid containing certain amount of solid contents. In one embodiment, the flavoring concentrate formulation is in form of a liquid including aqueous-based and nonaqueous-based. In some embodiments, the present flavoring concentrate formulation can be carbonated or non-carbonated. In some embodiments, the composition is a solid. In some embodiments, the solid is a powder.

Solid concentrate formulations can be prepared by any suitable technique, including but not limited to combining a solid production composition (such as described above) with a solid carrier and any additional ingredients. Suitable combining techniques include dry or wet mixing, spray coating, spray drying, etc.

Liquid concentrate formulations can be prepared by any suitable technique, including but not limited to dissolving or suspending a solid production composition (such as described above) and any additional ingredients in a liquid carrier. Other suitable techniques include mixing a liquid production composition (such as described above) with a liquid carrier and any additional ingredients.

The flavoring concentrate formulation may further comprise a freezing point depressant, nucleating agent, or both as the at least one adjuvant. The freezing point depressant is an ingestibly acceptable compound or agent which can depress the freezing point of a liquid or solvent to which the compound or agent is added. That is, a liquid or solution containing the freezing point depressant has a lower freezing point than the liquid or solvent without the freezing point depressant. In addition to depress the onset freezing point, the freezing point depressant may also lower the water activity of the flavoring concentrate formulation. The examples of the freezing point depressant include, but are not limited to, carbohydrates, oils, ethyl alcohol, polyol, e.g., glycerol, and combinations thereof. The nucleating agent denotes an ingestibly acceptable compound or agent which is able to facilitate nucleation. The presence of nucleating agent in the flavoring concentrate formulation can improve the mouthfeel of the frozen Blushes of a frozen slush and to help maintain the physical properties and performance of the slush at freezing temperatures by increasing the number of desirable ice crystallization centers. Examples of nucleating agents include, but are not limited to, calcium silicate, calcium carbonate, titanium dioxide, and combinations thereof.

In one embodiment, the flavoring concentrate formulation is formulated to have a low water activity for extended shelf life. Water activity is the ratio of the vapor pressure of water in a formulation to the vapor pressure of pure water at the same temperature. In one embodiment, the flavoring concentrate formulation has a water activity of less than about 0.85. In another embodiment, the flavoring concentrate formulation has a water activity of less than about 0.80. In another embodiment, the flavoring concentrate formulation has a water activity of less than about 0.75.

In one embodiment, the flavoring concentrate formulation has the present compound in a concentration that is at least 2 times of the concentration of the compound in a ready-to-use composition. In one embodiment, the flavoring concentrate formulation has the present compound in a concentration that is at least 5 times of the concentration of the compound in a ready-to-use composition. In one embodiment, the flavoring concentrate formulation has the present compound in a concentration that is at least 10 times of the concentration of the compound in a ready-to-use composition. In one embodiment, the flavoring concentrate formulation has the present compound in a concentration that is at least 15 times of the concentration of the compound in a ready-to-use composition. In one embodiment, the flavoring concentrate formulation has the present compound in a concentration that is at least 20 times of the concentration of the compound in a ready-to-use composition. In one embodiment, the flavoring concentrate formulation has the present compound in a concentration that is at least 30 times of the concentration of the compound in a ready-to-use composition. In one embodiment, the flavoring concentrate formulation has the present compound in a concentration that is at least 40 times of the concentration of the compound in a ready-to-use composition. In one embodiment, the flavoring concentrate formulation has the present compound in a concentration that is at least 50 times of the concentration of the compound in a ready-to-use composition. In one embodiment, the flavoring concentrate formulation has the present compound in a concentration that is at least 60 times of the concentration of the compound in a ready-to-use composition. In one embodiment, the flavoring concentrate formulation has the present compound in a concentration that is up to 100 times of the concentration of the compound in a ready-to-use composition.

In some embodiments, the flavoring concentrate formulation comprises a compound described herein in a concentration from about 0.1% to about 95% by weight. In some embodiments, the flavoring concentrate formulation comprises a compound described herein in a concentration from about 1% to about 95% by weight. In some embodiments, the flavoring concentrate formulation comprises a compound described herein in a concentration from about 5% to about 95% by weight. In some embodiments, the flavoring concentrate formulation comprises a compound described herein in a concentration from about 10% to about 95% by weight. In some embodiments, the flavoring concentrate formulation comprises a compound described herein in a concentration from about 50% to about 95% by weight. In some embodiments, the flavoring concentrate formulation comprises a compound described herein in a concentration from about 75% to about 95% by weight. In some embodiments, the compound is present in the flavoring concentrate formulation in an amount from about 1% to about 10% by weight. In some embodiments, the compound is present in the flavoring concentrate formulation in an amount from about 1% to about 20% by weight. In some embodiments, the compound is present in the flavoring concentrate formulation in an amount from about 5% to about 10% by weight. In some embodiments, the compound is present in the flavoring concentrate formulation in an amount from about 5% to about 20% by weight. In some embodiments, the compound is present in the flavoring concentrate formulation in an amount from about 5% to about 50% by weight.

In some embodiments, the compound is present in the flavoring concentrate formulation in an amount greater than about 0.1%, 0.5%, 1%, 2%, 5%, 10%, 20%, 30%, 50%, 75%, 90%, or 95% by weight.

In some embodiments, the flavoring concentrate formulation has a pH of less than or equal to 7. In some embodiments, the flavoring concentrate formulation has a pH of less than 7. In some embodiments, the composition has a pH greater than or equal to 7. In some embodiments, the flavoring concentrate formulation has a pH of greater than 7. In some embodiments, the flavoring concentrate formulation has a pH between 6 and 10, between 6 and 9, between 6 and 8, between 6 and 7, between 1 and 7, between 1 and 6, between 1 and 5, between 1 and 4, between 1 and 3, or between 1 and 2. In some embodiments, the flavoring concentrate formulation has a pH of about 1, of about 1.5, of about 2, of about 2.5, of about 3, of about 3.5, of about 4, of about 4.5, of about 5, of about 5.5, of about 6, of about 6.5, or of about 7.

Some embodiments provide a method of preparing an ingestible composition comprising reconstituting or otherwise diluting the flavoring concentrate formulation to form the ingestible composition. In some embodiments, the reconstitution or dilution comprises combining the flavoring concentrate formulation with one or more ingestible acceptable ingredients. Some methods of preparing a food or beverage product includes combining a first plurality of ingestibly acceptable ingredients to form an intermediate mixture followed by dispensing a dose of a concentrate as described above into the intermediate mixture. Some embodiments, include further adding one or more ingestibly acceptable ingredients. In general, the various ingredients and concentrate may be combined in any suitable order and technique.

Table Top Sweetener

Some embodiments include a table top sweetener that can be added to a food or beverage product to increase the sweetness thereof. Accordingly, some embodiments include a compound according to formula (I), and particularly one or more of Compounds 1-35 described herein, in a ready-to-use sweetener composition. In some embodiments, the composition includes a bulking agent or diluent to dilute the concentration of the compound in the composition. In some embodiments, the bulking agent is selected from one or more of maltodextrin, dextro-maltodextrin blends, corn syrup solids, sucrose, fructose, glucose, invert sugar, sorbitol, xylose, ribulose, mannose, mannitol, galactitol, lactitol, isomalt, maltose, tagatose, lactose, inulin, glycerol, propylene glycol, polydextrose, fructooligosaccharides, cellulose, cellulose derivatives, erythritol, and combinations thereof. In some embodiments, the bulking agent is a starch. In some embodiments, the bulking agent is a gum. In some embodiments, the bulking agent is selected from Gum Arabic (*Gum acacia*), Maltodextrin, Modified Corn Starch, Dextrose, Silicon dioxide, Magnesium carbonate, and Tricalcium phosphate, and combinations thereof.

In some embodiments, the compound described herein and the bulking agent are both in solid particulate form in the table top sweetener composition. In some such embodiments, the particles of the compound and the bulking agent are uniformly mixed together with any other ingredients in the composition so that the compound is present at a diluted concentration. The particles of the compound and the bulking agent may be formed by any suitable means, including by grinding, milling, spray drying, spray agglomeration, fluid bed agglomeration, and wet or dry granulation, which may be performed on each agent separately or at the same time. In other embodiments, a compound described herein is coated onto the surface of solid particles of the bulking agent. In some such embodiments, the compound is coated onto the surface of particles of the bulking agent using any suitable technique, including spray-drying a solution of the compound onto the bulking agent particles. In still other embodiments, each particle in a particulate composition includes both the compound and the bulking agent uniformly mixed. For example, particles may be formed from a solution comprising both the compound described herein and the bulking agent.

In various embodiments, the particles in the composition have an average particle size between 200 µm and 2 mm, between 200 µm and 500 µm, between 500 µm and 700 µm, or between 800 µm and 1.5 mm.

In other embodiments, the table top sweetener may be in the form of tablet, cube, or pellet, which may be formed using molds, compression of solid particles, or any other suitable means. In still other embodiments, the table top sweetener is in liquid form, such as a suspension, solution, or syrup.

In various embodiments, the weight ratio of the compound described herein to the bulking agent is from 1:1000 to 1:1, from 1:800 to 1:2, from 1:500 to 1:10, from 1:400 to 1:15, from 1:300 to 1:20, from 1:200 to 1:30, from 1:175 to 1:50, from 1:150 to 1:75, from 1:125 to 1:80, and from 1:110 to 1:90. In various embodiments, the weight percent of the compound described herein in the composition is greater than 300 ppm, greater than 500 ppm, greater than 800 ppm, greater than 0.1%, greater than 0.2%, 0.5%, greater than 1%, greater than 2%, greater than 3%, and great than 5%. In various embodiments, the weight percent of the compound described herein in the composition is from 500 ppm to 5%, from 800 ppm to 3%, from 0.1% to 3%, from 0.5% to 3%, or from 0.5% to 2%.

In various embodiments, the weight percent of the bulking agent in the composition is greater than 30%, greater than 40%, greater than 50%, greater than 60%, greater than 70%, greater than 80%, greater than 90%, greater than 95%, greater than 98%, greater than 99%, or greater than 99.5%. In various embodiments, the weight percent of the bulking agent in the composition is from 20% to 99%, from 20% to 95%, from 30% to 95%, from 40% to 95%, from 50% to 90%, from 60% to 80%, from 50% to 80%, from 5% to 50%, from 5% to 30%, from 10% to 40%, or from 10% to 30%.

In some embodiments, the table top sweetener additionally includes an anti-caking agent. Suitable anti-caking agents include, but are not limited to cream of tartar, tricalcium phosphate, powdered cellulose (including microcrystalline cellulose), magnesium stearate, sodium bicarbonate, sodium ferrocyanide, potassium ferrocyanide, calcium ferrocyanide, sodium silicate, silicon dioxide, calcium silicate, magnesium trisilicate, talcum powder, sodium aluminosilicate, potassium aluminum silicate, calcium aluminosilicate, bentonite, aluminum silicate, stearic acid, polydimethylsiloxane.

In some embodiments, the table top sweetener is included in a portion control packet or sachet. In some embodiments, the packet or sachet is designed for single-use. The packet or sachet may be in any suitable shape or dimension. Various embodiments include a packet or sachet having a width between 0.2 inches and 2 inches or a width between 0.5 inches and 1 inch and a length between 1 inch and 5 inches or a length between 1.5 inches and 3 inches. In various embodiments, the packet or sachet contains between 0.5 g and 3 g or between 0.75 g and 1.5 g of the table top sweetener composition.

One embodiment for making powder or granulated table top sweetener compositions include fluid bed agglomeration processes. Finely divided particles of a solution are sprayed onto a fluidized bed of particles under moisture and temperature conditions which promote formation of an agglomerate. The solution comprises the sweetener compound and a binding agent. The spray rate can be modified to control the average particle size. Following the spraying of the particles, the particles are allowed to dry and may optionally be screened to control the particle size distribution.

In another method for making a powder or granulated tabletop sweetener composition comprises combining at least one sweetener, bulking agent, and/or anti-caking agent with an aqueous solution to form a aqueous suspension that is thoroughly blended. The suspension is heated to approximately 50 to 90° C. under vacuum to remove the water while avoiding decomposition of the materials. Finally, the mixture is milled to the desired particle size.

Flavor Modifying Compounds and Compositions

In some embodiments, the compounds disclosed and described herein can be used as a flavor modifying compound (e.g., as a sweet flavor enhancing compound). Some such embodiments include compositions further comprising one or more sweeteners in combination with the one or more flavor modifying compound. In some embodiments, the compositions are used for ingestible or non-ingestible products, such as the compositions, products, and concentrates discussed above.

In some embodiments, the compositions can be used for modulating a chemosensory receptor and/or its ligand, including modulating the activity, structure, function, expression, and/or modification of a chemosensory receptor as well as modulating, treating, or taking prophylactic measure of a condition, e.g., physiological or pathological condition, associated with a chemosensory receptor. In general, a physiological or pathological condition associated with a chemosensory receptor includes a condition, disease, or disorder associated with the chemosensory receptor and/or its ligand, e.g., gastrointestinal disorders, metabolic disorders, functional gastrointestinal disorders, etc. In some embodiments, the composition increases or enhances sweet flavor. In some embodiments, the composition modulates a sweet receptor and/or its ligand expressed in a place of the body other than the taste buds, such as an internal organ. In some embodiments, the composition can increase or enhance the sweet taste of ingestible product by contacting the ingestible product with one or more of the present compositions to form a modified composition. In some embodiments, the composition can increase or enhance the sweet taste of ingestible product by being mixed with the ingestible product with one or more of the present compositions to form a modified composition. In some embodiments, the composition can modulate the sweet receptors and/or their ligands expressed in the body other than in the taste buds.

In some embodiments, the present compositions have sucrose modifying behavior and/or sweet agonist behavior in vitro and/or in vivo (e.g., as shown in sensory studies). In some embodiments, the present compositions demonstrate a favorable side-taste profile in vivo.

Whether or not a composition exhibits sweet modifying/agonist effects can be determined by any suitable test method. For example, the composition comprising one or more sweeteners in combination with a flavor modifying compound can be evaluated in a sensory test using a human taste panel.

In some embodiments, the composition may be diluted before being tested. In some embodiments, the composition is diluted for about 2 times, about 5, about 10, about 50, about 100, about 200, about 300, about 400, about 500, about 1000, or more times before being tested.

The tests can be conducted with and/or without additives. In some embodiments, the composition is tested to evaluate the sweet enhancement to one or more additives. In the test, the participants can provide their impression as to the similarities of the characteristics of the sweetener compositions, with and/or without additives, with those comprising sugar. A suitable procedure for determining whether a composition has a more sugar-like taste is through the use of a panel of assessors, who measure the sweetness of the compositions.

Some embodiments provide an ingestible product containing a sufficient amount of one or more sweet flavor enhancers to significant enhance the sweetness of the ingestible product. In some embodiments, the ingestible product is a food or beverage product.

Some embodiments provide methods of increasing the sweetness of an ingestible product, comprising contacting an ingestible product with a composition comprising one or more sweetness enhancers and one or more sweeteners. Some embodiments provide methods of increasing the sweetness of an ingestible product, comprising mixing an ingestible product with a composition comprising one or more sweetness enhancers and one or more sweeteners. In some embodiments, the one or more sweeteners are as described herein. In some embodiments, the one or more sweeteners are selected from one or more compounds of Formula (I). In some embodiments, the one or more sweeteners is a sweetener described above. In some embodiments, the one or more sweetener enhancer is a compound disclosed and described herein (i.e., a compound according to Formula (I)).

In some embodiments, the compound of Formula (I) is one of Compounds 1-35.

Some embodiments provide a method of enhancing sweetness of a sweetener, comprising combining one or more compounds of Formula (I), or a composition comprising one or more compounds of Formula (I), with the sweetener. In some embodiments, the compound of Formula (I) is one of Compounds 1-35.

In some embodiments, the sweetener may be common saccharide sweeteners, e.g., sucrose, fructose, glucose, and sweetener compositions comprising natural sugars, such as corn syrup (including high fructose corn syrup) or other syrups or sweetener concentrates derived from natural fruit and vegetable sources; rare natural sugars including D-allose, D-psicose, L-ribose, D-tagatose, L-glucose, L-fucose, L-arbinose, D-turanose, and D-leucrose; semi-synthetic "sugar alcohol" sweeteners such as erythritol, isomalt, lactitol, mannitol, sorbitol, xylitol, maltodextrin, and the like; and artificial sweeteners such as aspartame, saccharin, acesulfame-K, cyclamate, sucralose, and alitame. In some embodiments, the sweetener may be selected from the group consisting of cyclamic acid, mogroside, tagatose, maltose, galactose, mannose, sucrose, fructose, lactose, neotame and other aspartame derivatives, glucose, D-tryptophan, glycine, maltitol, lactitol, isomalt, hydrogenated glucose syrup (HGS), hydrogenated starch hydrolyzate (HSH), stevioside, rebaudioside A and other sweet Stevia-based glycosides, carrelame and other guanidine-based sweeteners.

In some embodiments, the compound of Formula (I) and the sweetener are present in a ratio of about 1:100,000 to 100,000:1, or any ratio in between. In some embodiments, the compound of Formula (I) and the sweetener are present in a ratio of about 1:90,000, about 1:80,000, about 1:70,000, about 1:60,000, about 1:50,000, about 1:40,000, about 1:30,000, about 1:20,000, about 1:10,000, 1:9,000, about 1:8,000, about 1:7,000, about 1:6,000, about 1:5,000, about 1:4,000, about 1:3,000, about 1:2,000, about 1:1,000, about 1:900, about 1:800, about 1:700, about 1:600, about 1:500, about 1:450, about 1:400, about 1:350, about 1:300, about 1:250, about 1:200, about 1:150, about 1:100, about 1:90, about 1:85, about 1:80, about 1:75, about 1:70, about 1:65, about 1:60, about 1:55, about 1:50, about 1:45, about 1:40, about 1:35, about 1:30, about 1:25, about 1:20, about 1:19, about 1:18, about 1:17, about 1:16, about 1:15, about 1:14, about 1:13, about 1:12, about 1:11, about 1:10, about 1:9, about 1:8, about 1:7, about 1:6, about 1:5, about 1:4, about 1:3, about 1:2, about 1:1, about 2:1, about 3:1, about 4:1, about 5:1, about 6:1, about 7:1, about 8:1, about 9:1, about 10:1, about 11:1, about 12:1, about 13:1, about 14:1, about 15:1, about 16:1, about 17:1, about 18:1, about 19:1, about 20:1, about 25:1, about 30:1, about 35:1, about 40:1, about 45:1, about 50:1, about 55:1, about 60:1, about 65:1, about 70:1, about 75:1, about 80:1, about 85:1, about 90:1, about 95:1, about 100:1, about 150:1, about 200:1, about 250:1, about 300:1, about 350:1, about 400:1, about 450:1, about 500:1, about 600:1, about 700:1, about 800:1, about 900:1, about 1,000:1, about 1,000:1, about 2,000:1, about 3,000:1, about 4,000:1, about 5,000:1, about 6,000:1, about 7,000:1, about 8000:1, about 9,000:1, about 10,000:1, about 20,000:1, about 30,000:1, about 40,000:1, about 50,000:1, about 60,000:1, about 70,000:1, about 80,000:1, about 90,000:1, about 100,000:1, or any ratio in between.

In some embodiments, the sweetener may combinations of two or more sweeteners as disclosed herein. In some embodiments, the sweetener may combinations of two, three, four or five sweeteners as disclosed herein. In some embodiments, the sweetener may be a sugar. In some embodiments, the sweetener may be a combination of one or more sugars and other natural and artificial sweeteners. In some embodiments, the sweetener is a sugar. In some embodiments, the sugar is cane sugar. In some embodiments, the sugar is beet sugar. In some embodiments, the sugar may be sucrose, fructose, glucose or combinations thereof (for example, high fructose corn syrup). In some embodiments, the sugar may be sucrose. In some embodiments, the sugar may be a combination of fructose and glucose. In some embodiments, the sugar may be a combination of about 55% fructose and about 42% glucose. In some embodiments, the sugar may be a combination of about 42% fructose and about 53% glucose. In some embodiments, the sugar may be a combination of about 90% fructose and about 10% glucose. In some embodiments, the sweetener may be a rare sugar. In some embodiments, the rare sugar is selected from the group consisting of D-allose, D-psicose, L-ribose, D-tagatose, L-glucose, L-fucose, L-arbinose, D-turanose, D-leucrose and combinations thereof. In some embodiments, the rare sugar is D-psicose. In some embodiments, the rare sugar is D-tagatose. In some embodiments, the sweetener is an artificial sweetener. In some embodiments, the artificial sweetener may be sucralose.

In some embodiments, compounds as disclosed and described herein, individually or in combination, can be used at its ligand enhancing concentrations, e.g., very low concentrations on the order of a few parts per million, in combination with one or more known sweeteners, natural or artificial, so as to reduce the concentration of the known sweetener required to prepare an ingestible composition having the desired degree of sweetness.

In some embodiments, compounds as disclosed and described herein, individually or in combination, can enhance the sweetness of a sweetener under a broad range of pH, e.g., from lower pH to neutral pH. The lower and neutral pH includes, but is not limited to, a pH from about 1.5 to about 8.5; from about 3.0 to about 8.0; from about 3.5 to about 7.5; and from about 4.0 to about 7. In certain embodiments, compounds as disclosed and described herein, individually or in combination, can enhance the perceived sweetness of a fixed concentration of a sweetener in taste tests at a compound concentration of about 5 μM, 4 μM, 3 μM, 2 μM, or 1 μM at both low to neutral pH value. In certain embodiments, the enhancement factor of the compounds as disclosed and described herein, individually or in combination, at the lower pH is substantially similar to the enhancement factor of the compounds at neutral pH. Such consistent sweet enhancing property under a broad range of pH allow a broad use in a wide variety of foods and beverages of the compounds as disclosed and described herein, individually or in combination. In some embodiments, the sweetener may be common saccharide sweeteners, e.g., sucrose, fructose, glucose, and sweetener compositions comprising natural sugars, such as corn syrup (including high fructose corn syrup) or other syrups or sweetener concentrates derived from natural fruit and vegetable sources; rare natural sugars including D-allose, D-psicose, L-ribose, D-tagatose, L-glucose, L-fucose, L-arbinose, D-turanose, and D-leucrose; semi-synthetic "sugar alcohol" sweeteners such as erythritol, isomalt, lactitol, mannitol, sorbitol, xylitol, maltodextrin, and the like; and artificial sweeteners such as aspartame, saccharin, acesulfame-K, cyclamate, sucralose, and alitame. In some embodiments, the sweetener may be selected from the group consisting of cyclamic acid, mogroside, tagatose, maltose, galactose, mannose, sucrose, fructose, lactose, neotame and other aspartame derivatives, glucose, D-tryptophan, glycine, maltitol, lactitol, isomalt, hydrogenated glucose syrup (HGS), hydrogenated starch hydrolyzate (HSH), stevioside, rebaudioside A and other sweet Stevia-based glycosides, carrelame and other guanidine-based sweeteners. In some embodiments, the sweetener may combinations of two or more sweeteners as disclosed herein.

In some embodiments, a compound according to Formula I (for example, one or more of Compounds 1-35) are used as a sweetener in combination with a flavor enhancer (e.g., a sweet flavor enhancer) and optionally one or more additional sweeteners (such as the sweeteners described above).

In some embodiments, the sweet flavor enhancers are selected from one or more compounds disclosed in PCT Application Publication Nos. WO 2016/073251; WO2008/154221; WO2005/015158; WO2005/041684; WO2006/084186; WO2006/138512; WO2007/124152; WO2009/100333; WO2009/111447; WO2010/014666; WO2010/014813; WO2011/123693; WO2012/021837; WO2012/061698; WO2013/025560; WO2014/130582; WO2014/025706; and WO2014/130513, each of which is herein incorporated by reference in their entirety, including any drawings.

In some embodiments, the sweetness enhancer is a compound defined by formula A:

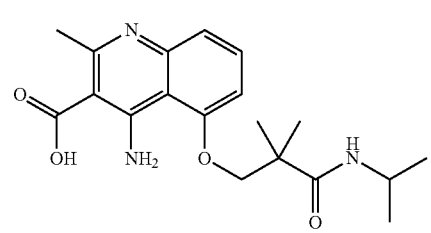

(A)

or a salt or solvate thereof.

In some embodiments, the sweetness enhancer is a compound defined by formula B:

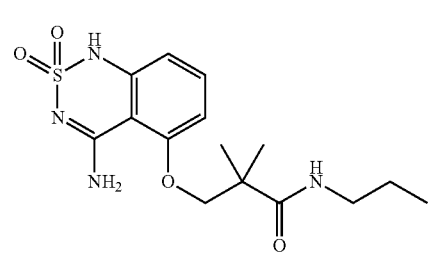

(B)

or a salt or solvate thereof.

In some embodiments, the sweetness enhancer is a compound defined by formula C:

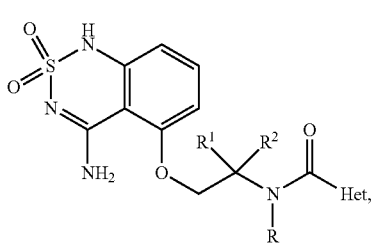

(C)

or a tautomer or salt thereof,
wherein, R¹ and R² are independently $C_1$ to $C_4$ alkyl; or alternatively, R¹ and R², together with the carbon atom to which they are attached, form a $C_3$ to $C_7$ cycloalkyl; R is hydrogen or $C_1$ to $C_6$ alkyl; and Het is heteroaryl or substituted heteroaryl.

In one embodiment of Formula (C), R is hydrogen.
In one embodiment of Formula (C), R¹ and R² are both methyl, ethyl, or propyl. That is, R¹ and R² are the same and are methyl, ethyl, or propyl.
In one embodiment of Formula (C), wherein R¹ and R², together with the carbon atom to which they are attached, form cyclopropyl, cyclobutyl, cylclopentyl, or cyclohexyl.
In one embodiment of Formula (C), wherein Het is an optionally substituted monocyclic five or six-membered heteroaryl containing one or more heteroatoms selected from the group of N, O, and S. By "optionally substituted", it is meant that the monocyclic five or six-membered heteroaryl can be unsubstituted or substituted.
In one embodiment of Formula (C), wherein Het is selected from the group consisting of pyridine, substituted pyridine, pyrimidine, substituted pyrimidine, pyrazine, substituted pyrazine, pyridazine, substituted pyridazine, triazine, and substituted triazine.
In one embodiment of Formula (C), wherein Het is an optionally substituted bicyclic eight to twelve-membered heteroaryl containing one or more heteroatoms selected from the group of N, O, and S. By "optionally substituted" in this context, it is meant that the bicyclic eight to twelve-membered heteroaryl can be unsubstituted or substituted.
In one embodiment of Formula (C), wherein Het is tetrazolopyridine, e.g., tetrazolo[1,5-a]pyridine; triazolopyridine, e.g., [1,2,4]triazolo[4,3-a]pyridine; purine, e.g., 9H-purine; pyrazolopyridine, e.g., 1H-pyrazolo[3,4-b]pyridine; quinoline, isoquinoline, isoxazolopyridine, e.g., isoxazolo[5,4-b]pyridine; or quinolinone, e.g., quinolin-2(1H)-one; each of which is optionally substituted. By "optionally substituted" in this context, it is meant that the Het can be unsubstituted or substituted.
In one embodiment of Formula (C), Het is unsubstituted or substituted with one, two, three, or four substituents independently selected from the group consisting of halo, cyano, hydroxyl, N-oxide, amine, substituted amine, alkoxy, substituted alkoxy, aryloxy, substituted aryloxy, acyl, sulfonamide, ester, alkyl, substituted alkyl, heteroalkyl, substituted heteroalkyl, aryl, substituted aryl, arylalkyl, substituted arylalkyl, heteroaryl, substituted heteroaryl, heteroarylalkyl, substituted heteroarylalkyl, carbocyclyl, substituted carbocyclyl, heterocyclyl, and substituted heterocyclyl; or alternatively, two of the substituents, taken together with the ring atoms of Het to which they are bound, form a carbocyclyl or heterocyclyl.

In some embodiments, the sweetness enhancer is a compound defined by formula D:

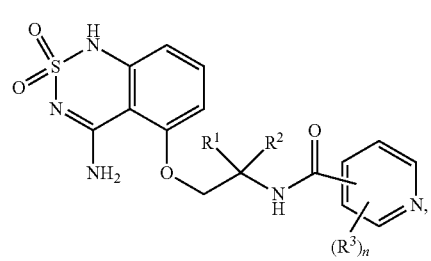

(D)

or a tautomer or salt thereof,
wherein, R¹ and R² are independently C1 to C4 alkyl; or alternatively, R¹ and R², together with the carbon atom to which they are attached, form a C3 to C7 cycloalkyl; n is 0, 1, 2, or 3; and R³ is halo, cyano, hydroxyl, amine, substituted amine, alkoxy, substituted alkoxy, aryloxy, substituted aryloxy, acyl, sulfonamide, ester, alkyl, substituted alkyl, heteroalkyl, substituted heteroalkyl, aryl, substituted aryl, arylalkyl, substituted arylalkyl, heteroaryl, substituted heteroaryl, heteroarylalkyl, substituted heteroarylalkyl, carbocyclyl, substituted carbocyclyl, heterocyclyl, or substituted heterocyclyl.

In one embodiment of Formula (D), R¹ and R² are both methyl, ethyl, or propyl. That is, R¹ and R² are the same and are methyl, ethyl, or propyl.

In one embodiment of Formula (D), R¹ and R², together with the carbon atom to which they are attached, form cyclopropyl, cyclobutyl, cylclopentyl, or cyclohexyl.

In some embodiments, the sweetness enhancer is a compound defined by formula E:

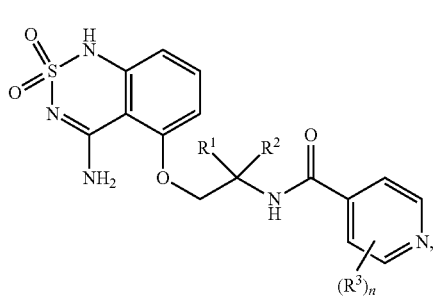

(E)

or a tautomer or salt thereof,
wherein, R¹ and R² are both methyl, ethyl, or propyl; or alternatively, R¹ and R², together with the carbon atom to which they are attached, form cyclopropyl, cyclobutyl, cylclopentyl, or cyclohexyl; n is 0, 1, 2, or 3; and R³ is halo, cyano, hydroxyl, amine, substituted amine, alkoxy, substituted alkoxy, aryloxy, substituted aryloxy, acyl, sulfonamide, ester, alkyl, substituted alkyl, heteroalkyl, substituted heteroalkyl, aryl, substituted aryl, arylalkyl, substituted arylalkyl, heteroaryl, substituted heteroaryl, heteroarylalkyl, substituted heteroarylalkyl, carbocyclyl, substituted carbocyclyl, heterocyclyl, or substituted heterocyclyl.-

In some embodiments, the sweetness enhancer is a compound defined by formula F:

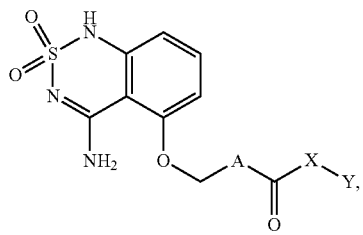

(F)

or a tautomer or salt thereof,
or a salt or solvate thereof; wherein
A is an optionally substituted four, five, six, seven, or eight-membered azacyclic ring;
X is a covalent bond or —NR$^1$—;
R$^1$ is hydrogen or C1 to C6 alkyl; and
Y is alkyl, substituted alkyl, heteroalkyl, substituted heteroalkyl, carbocyclyl, substituted carbocyclyl, heterocyclyl, substituted heterocyclyl, aryl, substituted aryl, heteroaryl, substituted heteroaryl, aralkyl, substituted aralkyl, heteroarylalkyl, or substituted heteroarylalkyl.

In one embodiment of Formula (F), X is NH.
In one embodiment of Formula (F), X is a covalent bond.
In one embodiment of Formula (F), A is an optionally substituted five, six, or seven-membered azacyclic ring. In one embodiment of Formula (F), A is an optionally substituted six-membered azacyclic ring. In one embodiment of Formula (F), A is an optionally substituted piperidine.

In some embodiments, the sweetness enhancer is a compound defined by formula G:

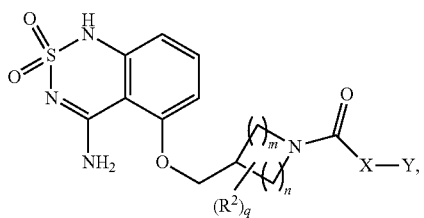

(G)

or a tautomer or salt thereof,
wherein,
m is 1, 2, 3, 4, 5, or 6;
n is 0, 1, 2, or 3; with the proviso that m+n is more than 1 and less than 7;
q is 0, 1, 2, 3, 4, 5, or 6; with the proviso that q is less than m+n;
X is a covalent bond or —NR$^1$—;
R$^1$ is hydrogen or C1 to C6 alkyl;
Y is alkyl, substituted alkyl, heteroalkyl, substituted heteroalkyl, carbocyclyl, substituted carbocyclyl, heterocyclyl, substituted heterocyclyl, aryl, substituted aryl, heteroaryl, substituted heteroaryl, aralkyl, substituted aralkyl, heteroarylalkyl, or substituted heteroarylalkyl; and each R$^2$ is independently selected from the group consisting of alkyl, heteroalkyl, halo, hydroxyl, alkoxy, amino, alkylamino, cyano, nitro, haloalkyl, carboxylic acid, amide, ester, acyl, thiol, alkylthio, and sulfonamide.

In one embodiment of Formula (G), X is NH.
In one embodiment of Formula (G), X is a covalent bond.
In one embodiment of Formula (G), m is 1, 2, 3, or 4; and n is 0, 1, or 2.

In one embodiment of Formula (G), q is 1, 2, or 3.
In one embodiment of Formula (G), q is 0.
In one embodiment of Formula (G), m is 4, and n is 0; or m is 3, and n is 1; or m and n are both 2.

In some embodiments, the sweetness enhancer is a compound defined by formula (H):

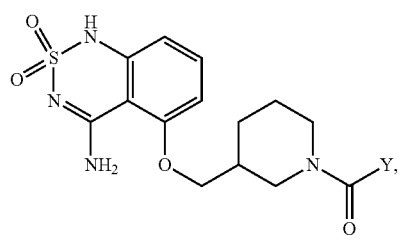

(H)

or a tautomer or salt thereof,
wherein,
Y is alkyl, substituted alkyl, heteroalkyl, substituted heteroalkyl, carbocyclyl, substituted carbocyclyl, heterocyclyl, substituted heterocyclyl, aryl, substituted aryl, heteroaryl, substituted heteroaryl, aralkyl, substituted aralkyl, heteroarylalkyl, or substituted heteroarylalkyl.

In some embodiments, the sweetness enhancer is a compound defined by formula (J):

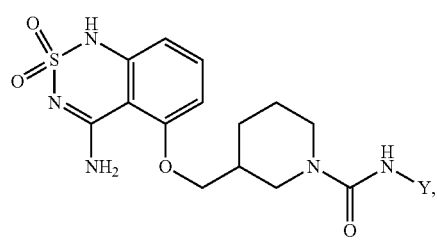

(J)

or a tautomer or salt thereof,
wherein,
Y is alkyl, substituted alkyl, heteroalkyl, substituted heteroalkyl, carbocyclyl, substituted carbocyclyl, heterocyclyl, substituted heterocyclyl, aryl, substituted aryl, heteroaryl, substituted heteroaryl, aralkyl, substituted aralkyl, heteroarylalkyl, or substituted heteroarylalkyl.

In some embodiments, the sweetness enhancer is a compound defined by formula (K):

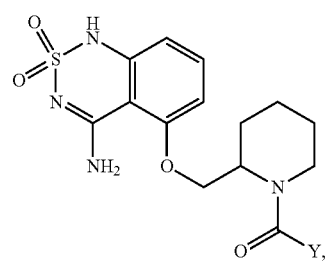

(K)

or a tautomer or salt thereof,
wherein,
Y is alkyl, substituted alkyl, heteroalkyl, substituted heteroalkyl, carbocyclyl, substituted carbocyclyl, heterocyclyl, substituted heterocyclyl, aryl, substituted aryl, heteroaryl, substituted heteroaryl, aralkyl, substituted aralkyl, heteroarylalkyl, or substituted heteroarylalkyl.

In some embodiments, the sweetness enhancer is a compound defined by formula (A1):

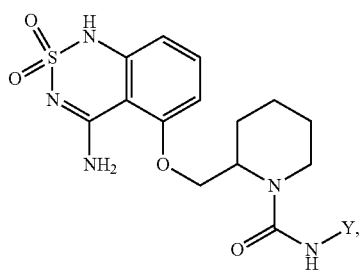

(A1)

or a tautomer or salt thereof,
wherein,
Y is alkyl, substituted alkyl, heteroalkyl, substituted heteroalkyl, carbocyclyl, substituted carbocyclyl, heterocyclyl, substituted heterocyclyl, aryl, substituted aryl, heteroaryl, substituted heteroaryl, aralkyl, substituted aralkyl, heteroarylalkyl, or substituted heteroarylalkyl.

In some embodiments, the sweetness enhancer is a compound defined by formula (B1):

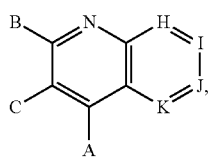

(B1)

or a tautomer or salt thereof,
wherein:
A is —$OR^1$, —$NR^1C(O)R^2$, —$NHOR^1$, —$NR^1R^2$, —$NR^1CO_2R^2$, —$NR^1C(O)NR^2R^3$, —$NR^1C(S)NR^2R^3$ or —$NR^1C(=NH)NR^2R^3$;
B is hydrogen, alkyl, substituted alkyl, aryl, substituted aryl, arylalkyl, substituted arylalkyl, acyl, substituted acyl, heteroalkyl, substituted heteroalkyl, heteroaryl, substituted heteroaryl, heteroarylalkyl, substituted heteroarylalkyl, —CN, —$OR^4$, —$S(O)_aR^4$, —$NR^4R^5$, —$C(O)NR^4R^5$, —$CO_2R^4$, —$NR^4CO_2R^5$, —$NR^4C(O)NR^5R^6$, —$NR^4C(S)NR^5R^6$, —$NR^4C(=NH)NR^5R^6$, —$SO_2NR^4R^5$, —$NR^4SO_2R^5$, —$NR^4SO_2NR^5R^6$, —$B(OR^4)(OR^5)$, —$P(O)(OR^4)(OR^5)$, or —$P(O)(R^4)(OR^5)$;
C is —$OR^7$, —$S(O)_bR^7$, $SO_3R^7$, —$C(O)NR^7R_8$, —$CO_2R^7$, —$NR^7CO_2R_8$, —$NR^7C(O)NR_8R^9$, —$NR^7C(=NH)NR_8R^9$, —$SO_2NR^7R_8$, —$NR^7SO_2R_8$, —$NR^7SO_2NR_8R^9$, —$B(OR^7)(OR_8)$, —$P(O)(OR^7)(OR_8)$, —$P(O)(R^7)(OR_8)$, or heteroaryl; a and b are independently 0, 1 or 2; and
$R^1$, $R^2$, $R^3$, $R^4$, $R^5$, $R_6$, $R^7$, $R_8$, and $R^9$ are independently hydrogen, alkyl, substituted alkyl, aryl, substituted aryl, arylalkyl, substituted arylalkyl, acyl, substituted acyl, heteroalkyl, substituted heteroalkyl, heteroaryl, substituted heteroaryl, heteroarylalkyl or substituted heteroarylalkyl; or alternatively, $R^1$ and $R^2$, $R^2$ and $R^3$, $R^4$ and $R^5$, $R^5$ and $R^6$, $R^7$ and $R_8$, or $R_8$ and $R^9$, together with the atoms to which they are bonded, form a cycloheteroalkyl or substituted cycloheteroalkyl ring;

H is —$C(R^{21})$— or —N—;
I is —$C(R^{22})$— or —N—;
J is —$C(R^{23})$— or —N—;
K is —$C(R^{24})$— or —N—;
$R^{21}$ is hydrogen, alkyl, substituted alkyl, halo, —CN, —$OR^{25}$;
$R^{22}$ is hydrogen, alkyl, substituted alkyl, halo, —CN, —$OR^{27}$;
$R^{23}$ is hydrogen, alkyl, substituted alkyl, aryl, substituted aryl, arylalkyl, substituted arylalkyl, acyl, substituted acyl, halo, heteroalkyl, substituted heteroalkyl, heteroaryl, substituted heteroaryl, heteroarylalkyl, substituted heteroarylalkyl, —CN, —$OR^{29}$, —$S(O)_fR^{29}$, —$OC(O)R^{29}$, —$NR^{29}R^{30}$, —$C(O)NR^{29}R^{30}$, —$CO_2R^{29}$, —$SO_2NR^{29}R^{30}$, —$NR^{29}SO_2R^{30}$, —$B(OR^{29})(OR^{30})$, —$P(O)(OR^{29})(OR^{30})$ or —$P(O)(R^{29})(OR^{30})$;
$R^{24}$ is hydrogen, alkyl, substituted alkyl, aryl, substituted aryl, arylalkyl, substituted arylalkyl, acyl, substituted acyl, halo, heteroalkyl, substituted heteroalkyl, heteroaryl, substituted heteroaryl, heteroarylalkyl, substituted heteroarylalkyl, —CN, —$OR^{31}$, —$S(O)_gR^{31}$, —$OC(O)R^{31}$, —$NR^{31}R^{32}$, —$C(O)NR^{31}R^{32}$, —$C(O)R^{31}$, —$CO_2R^{31}$, —$SO_2NR^{31}R^{32}$, —$NR^{31}SO_2R^{32}$, —$B(OR^{31})(OR^{32})$, —$P(O)(OR^3)(OR^{32})$ or —$P(O)(R^{31})(OR^{32})$; or alternatively $R^{23}$ and $R^{24}$, taken together with the atom to which they are attached, form a cycloalkyl, substituted cycloalkyl, cycloheteroalkyl, or substituted cycloheteroalkyl ring; f and g are independently 0, 1 or 2; and
$R^{25}$, $R^{27}$, $R^{29}$, $R^{30}$, $R^{31}$, and $R^{32}$ are independently hydrogen, alkyl, substituted alkyl, aryl, substituted aryl, arylalkyl, substituted arylalkyl, acyl, substituted acyl, heteroalkyl, substituted heteroalkyl, heteroaryl, substituted heteroaryl, heteroarylalkyl, or substituted heteroarylalkyl; or alternatively $R^{25}$ and $R^{27}$, $R^{27}$ and $R^{29}$, $R^{29}$ and $R^{30}$, $R^{29}$ and $R^{31}$, or $R^{31}$ and $R^{32}$, together with the atoms to which they are attached, form a cycloheteroalkyl or substituted cycloheteroalkyl ring; with the proviso that at most, two of H, I, J and K are —N—.

In some embodiments, the sweetness enhancer is a compound defined by formula (C1):

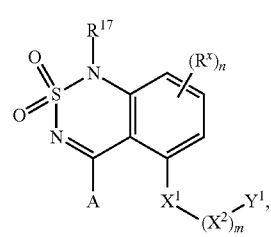

(C1)

or a tautomer or salt thereof,
wherein
A is hydrogen, alkyl, substituted alkyl, aryl, substituted aryl, arylalkyl, substituted arylalkyl, acyl, substituted acyl, heteroalkyl, substituted heteroalkyl, heteroaryl, substituted heteroaryl, heteroarylalkyl, substituted heteroarylalkyl, —CN, —$OR^9$, —$NO_2$, —$S(O)_cR^9$, —$NOR^9$, —$NHOR^9$, —$NR^9COR^{10}$, —$NR^9R^{10}$, —$CONR^9R^{10}$, —$CO_2R^9$ or —$NR^9CO_2R^{10}$;
$R^{17}$ is hydrogen, alkyl, substituted alkyl, arylalkyl, or substituted arylalkyl;
$X^1$ is —$CH_2$—, —O—, —$NR^9$—, —S—, —S(O)—, or —$S(O)_2$—;
$X^2$ is alkylene, substituted alkylene, heteroalkylene, or substituted heteroalkylene;

m is 0 or 1;

$Y^1$ is heteroaryl, substituted heteroaryl, cycloheteroalkyl, substituted cycloheteroalkyl, or

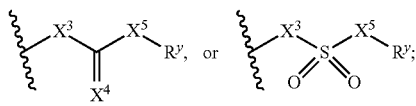

$X^3$ and $X^5$ are independently a covalent bond, —O— or —$NR^9$—;

$X^4$ is O, $NR^9$, N—$OR^9$, or S;

$R^x$ is halo, —$NO_2$, —CN, —OH, —$NH_2$, alkyl, substituted alkyl, aryl, substituted aryl, arylalkyl, substituted arylalkyl, heteroalkyl, substituted heteroalkyl, heteroaryl, substituted heteroaryl, heteroarylalkyl or substituted heteroarylalkyl;

n is 0, 1, 2, or 3;

$R^y$ is hydrogen, alkyl, substituted alkyl, aryl, substituted aryl, arylalkyl, substituted arylalkyl, heteroalkyl, substituted heteroalkyl, heteroaryl, substituted heteroaryl, heteroarylalkyl or substituted heteroarylalkyl, —$NR^9R^{10}$; and each $R^9$ and $R^{10}$ is independently hydrogen, alkyl, substituted alkyl, aryl, substituted aryl, arylalkyl, substituted arylalkyl, heteroalkyl, substituted heteroalkyl, heteroaryl, substituted heteroaryl, heteroarylalkyl or substituted heteroarylalkyl; with the proviso that when $X^1$ is —O— or —S—, and m is zero; then $X^3$ is not —O—.

In some embodiments, the sweetness enhancer is a compound defined by formulae (D1) or (E1):

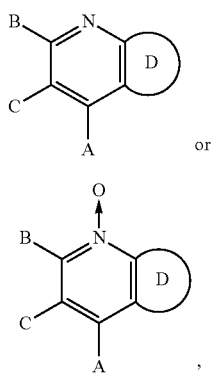

or a tautomer or salt thereof, wherein: A is —$OR^1$, —$NR^1C(O)R^2$, —$NHOR^1$, —$NR^1R^2$, —$NR^1CO_2R^2$, —NRC(O)$NR^2R^3$, —NRC(S)$NR^2R^3$ or —$NR^1C(=NH)NR^2R^3$; B is hydrogen, alkyl, substituted alkyl, aryl, substituted aryl, arylalkyl, substituted arylalkyl, acyl, substituted acyl, heteroalkyl, substituted heteroalkyl, heteroaryl, substituted heteroaryl, heteroarylalkyl, substituted heteroarylalkyl, —CN, —$OR^4$, —$S(O)_aR^4$, —$NR^4R^5$, —$C(O)NR^4R^5$, —$CO_2R^4$, —$NR^4CO_2R^5$, —$NR^4C(O)NR^5R^6$, —$NR^4C(S)NR^5R^6$, —$NR^4C(=NH)NR^5R^6$, —$SO_2NR^4R^5$, —$NR^4SO_2R^5$, —$NR^4SO_2NR^5R^6$, —$B(OR^4)(OR^5)$, —$P(O)(OR^4)(OR^5)$, or —$P(O)(R^4)(OR^5)$; is —$OR^7$, —$S(O)_bR^7$, $SO_3R^7$, —C(O)$NR^7R_8$, —$CO_2R^7$, —$NR^7CO_2R_8$, —NRC(O)$NR_8R^9$, —NRC(=NH)$NR_8R^9$, —$SO_2NR^7R_8$, —$NR^7SO_2R_8$, —$NR^7SO_2NR_8R^9$, —$B(OR^7)(OR_8)$, —$P(O)(OR^7)(OR_8)$, —$P(O)(R^7)(OR_8)$, or heteroaryl (for example, tetrazole); D is an aryl, substituted aryl, heteroaryl, substituted heteroaryl, cycloalkyl, substituted cycloalkyl, cycloheteroalkyl or substituted cycloheteroalkyl ring wherein the ring is optionally fused to another aryl, substituted aryl, heteroaryl, substituted heteroaryl, cycloalkyl, substituted cycloalkyl, cycloheteroalkyl, or substituted cycloheteroalkyl ring; a and b are independently 0, 1 or 2; and $R^1$, $R^2$, $R^3$, $R^4$, R, $R^6$, $R^7$, $R_8$, and $R^9$ are independently hydrogen, alkyl, substituted alkyl, aryl, substituted aryl, arylalkyl, substituted arylalkyl, acyl, substituted acyl, heteroalkyl, substituted heteroalkyl, heteroaryl, substituted heteroaryl, heteroarylalkyl or substituted heteroarylalkyl; or alternatively, $R^1$ and $R^2$, $R^2$ and $R^3$, $R^4$ and $R^5$, $R^5$ and $R^6$, $R^7$ and $R_8$, or $R_8$ and $R^9$, together with the atoms to which they are bonded, form a cycloheteroalkyl or substituted cycloheteroalkyl ring.

In some embodiments, the sweetness enhancer is a compound defined by formula (F1):

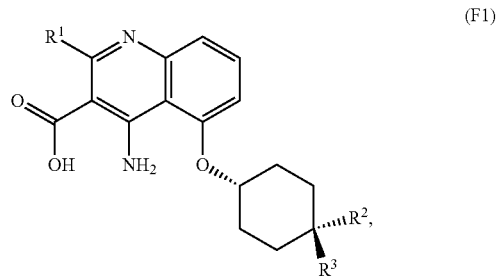

or a salt or tautomer thereof, wherein:

$R^1$ may be hydrogen or $C_{1-6}$ alkyl optionally substituted with $C_{1-6}$ alkoxy or —OH;

$R^2$ may be selected from the group consisting of hydrogen, —OH, optionally substituted $C_{1-6}$ alkoxy, $C_{1-6}$ alkyl optionally substituted with $C_{1-6}$ alkoxy;

$R^3$ may be selected from the group consisting of hydrogen, —OH, optionally substituted $C_{1-6}$ alkyl, optionally substituted $C_{3-7}$ carbocyclyl, optionally substituted $C_{1-6}$ alkoxy, —$(CH_2)_nNHC(=O)R^4$, —$(CH_2)_nNR^5R^6$, and —$(CH_2)_nC(=O)NR^5R^6$; n may be 0, 1, 2 or 3;

$R^4$ may be selected from the group consisting of optionally substituted $C_{3-7}$ carbocyclyl, optionally substituted aryl, optionally substituted 5-10 membered heteroaryl, optionally substituted 3-10 membered heterocyclyl and substituted $C_{1-6}$ alkyl;

$R^5$ may be selected from the group consisting of hydrogen, optionally substituted $C_{1-6}$ alkyl, optionally substituted $C_{3-7}$ carbocyclyl, optionally substituted aryl, and optionally substituted 5-10 membered heteroaryl; and $R^6$ may be selected from the group consisting of hydrogen, substituted $C_{1-6}$ alkyl, optionally substituted $C_{3-7}$ carbocyclyl, optionally substituted aryl and optionally substituted 5-10 membered heteroaryl, with the proviso that when both $R^2$ and $R^3$ are hydrogen then $R^1$ is not methyl or —$CH_2OH$.

In some embodiments, the flavoring agents and/or flavor enhancers are selected from a compound defined by formula (G1):

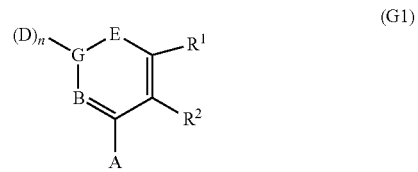

or a salt, hydrate, solvate or N-oxide thereof wherein:

G forms a single bond with either D or E and a double bond with the other of D or E;

R1 is hydrogen, alkyl, substituted alkyl, aryl, substituted aryl, arylalkyl, substituted arylalkyl, acyl, substituted acyl, heteroalkyl, substituted heteroalkyl, heteroaryl, substituted heteroaryl, heteroarylalkyl, substituted heteroarylalkyl, —CN, —NO$_2$, —OR$^3$, —S(O)$_a$R$^3$, —NR$^3$R$^4$, —CONR$^3$R$^4$, —CO$_2$R$^3$, —NR$^3$CO$_2$R$^4$, —NR$^3$CONR$^4$R$^4$, —NR$^3$CSNR$^4$R$^5$ or —NR$^3$C(=NH)NR$^4$R$^5$, —SO$_2$NR$^2$R$^3$, —NR$^2$SO$_2$R$^3$, —NR$^2$SO$_2$ NR$^3$R$^4$, —B(OR$^2$)(OR$^3$), —P(O)(OR$^2$)(OR$^3$) or —P(O)(R$^2$)(OR$^3$);

R$^2$ is hydrogen, alkyl, substituted alkyl, aryl, substituted aryl, arylalkyl, substituted arylalkyl, acyl, substituted acyl, heteroalkyl, substituted heteroalkyl, heteroaryl, substituted heteroaryl, heteroarylalkyl, substituted heteroarylalkyl, —CN, —NO$_2$, —OR$^6$, —S(O)$_b$R$^6$, —NR$^6$R$^7$, —CONR$^6$R$^7$, —CO$_2$R$^6$, —NR$^6$CO$_2$R$^7$, —NR$^6$CONR$^7$R$_8$, —NR$^6$CSNR$^7$R$^8$ or —NR$^6$C(=NH)NR$^7$R$^8$, —SO$_2$NR$^5$R$^6$, —NR$^5$SO$_2$R$^6$, —NR$^5$SO$^2$ NR$^6$R$^7$, —B(OR$^5$)(OR$^6$, —P(O)(OR$^5$)(OR$^6$), —P(O)(R$^5$)(OR$^6$) or alternatively, R$^1$ and R$^2$ together with the atoms to which they are bonded form an aryl, substituted aryl, heteroaryl, substituted heteroaryl, cycloalkyl, substituted cycloalkyl, cycloheteroalkyl or substituted cycloheteroalkyl ring where the ring is optionally fused to another aryl, substituted aryl, heteroaryl, substituted heteroaryl, cycloalkyl, substituted cycloalkyl, cycloheteroalkyl or substituted cycloheteroalkyl ring;

with the proviso that R$^1$ and R$^2$ are not both hydrogen;

A is hydrogen, alkyl, substituted alkyl, aryl, substituted aryl, arylalkyl, substituted arylalkyl, acyl, substituted acyl, heteroalkyl, substituted heteroalkyl, heteroaryl, substituted heteroaryl, heteroarylalkyl, substituted heteroarylalkyl, —CN, —N$_2$, —OR$^9$, —S(O)$_c$R$^9$, —NR$^9$R$^{10}$, NOR$^9$, —CONR$^9$R$^{10}$, —CO$_2$R$^9$, —NR$^9$CO$_2$R$^{10}$— NR$^9$CONR$^{10}$R$^{11}$—NR$^9$CSNR$^{10}$R$_{11}$ or —NR$^9$C(=NH)NR$^{10}$R$_{11}$ B is —N— or —C(R$^{12}$)—.

R$^{12}$ is hydrogen, alkyl, substituted alkyl, aryl, substituted aryl, arylalkyl, substituted arylalkyl, acyl, substituted acyl, heteroalkyl, substituted heteroalkyl, heteroaryl, substituted heteroaryl, heteroarylalkyl, substituted heteroarylalkyl, —NR$^{13}$R$^{14}$, —CN, —OR$^{13}$, —S(O)$_a$R$^{13}$, C$_2$R$^{13}$ or —CONR$^{13}$R$^{14}$;

G is —C— or —S(O)$_2$;

provided that when G is —S(O)$_2$, G forms a single bond with E;

D is hydrogen, alkyl, substituted alkyl, aryl, substituted aryl, arylalkyl, substituted arylalkyl, acyl, substituted acyl, halo, chloro, fluoro, heteroalkyl, substituted heteroalkyl, heteroaryl, substituted heteroaryl, heteroarylalkyl, substituted heteroarylalkyl, —OR$^5$, —NOR$^{15}$, —S(O)$_e$R, —NR$^{15}$R$^{16}$, —NCN, —CO$_2$R$^{15}$, —CONR$^{15}$R$^{16}$ when the bond between D and G is a single bond;

D is =O, =S, =N—OR$^{15}$, =NHNHR$^{15}$ when G form a double bond with D;

n is O when G is —S(O)r and n is 1 when G is —C—;

E is —NR$^{17}$—, —N— or —C(R$^{18}$)—.

provided that E is —NR$^{17}$— only when G forms a single bond with E;

R$^{17}$ is alkyl, substituted alkyl, aryl, substituted aryl, arylalkyl, substituted arylalkyl, acyl, substituted acyl, heteroalkyl, substituted heteroalkyl, heteroaryl, substituted heteroaryl, heteroarylalkyl, substituted heteroarylalkyl or —CO$_2$R$^{19}$;

R$^{18}$ is hydrogen, alkyl, substituted alkyl, aryl, substituted aryl, arylalkyl, substituted arylalkyl, acyl, substituted acyl, heteroalkyl, substituted heteroalkyl, heteroaryl, substituted heteroaryl, heteroarylalkyl, substituted heteroarylalkyl, —NR$^{20}$R$^{21}$, —CN, —OR$^{20}$, —S(O)$_f$R$^{20}$, —CO$_2$R$^{20}$ or —CONR$^{20}$R$^{21}$;

a, b, e, d, e and f are independently 0, 1 or 2; and

R$^3$-R$^{11}$, R$^{13}$-R$^{16}$, R$^{18}$, R$^{20}$ and R$^{21}$ are independently hydrogen, alkyl, substituted alkyl, aryl, substituted aryl, arylalkyl, substituted arylalkyl, acyl, substituted acyl, heteroalkyl, substituted heteroalkyl, heteroaryl, substituted heteroaryl, heteroarylalkyl or substituted heteroarylalkyl or alternatively, R$^3$ and R$^4$, R$^4$ and R$^5$, R$^6$ and R$^7$, R$^7$ and R$_8$, R$^9$ and R$^{10}$, R$^{10}$ and R$^{11}$, R$^{13}$ and R$^{14}$, R$^{15}$ and R$^{16}$ and R$^{20}$ and R$^{21}$ together with the atoms to which they are bonded form a cycloheteroalkyl or substituted cycloheteroalkyl ring.

In some embodiments, the flavoring agents and/or flavor enhancers are selected from a compound defined by formula (H1):

(H1)

or a salt, solvate, hydrate or N-oxide thereof wherein:

each G is independently —C(R$^{77}$)(R$^{78}$)—, —C(O)—, —NR$^{77}$— or —S(O)$_2$—;

n is 1, 2 or 3;

provided that when n is greater than one then only one G is —C(O)—, —C(S), —S(O)$_2$ or Y is —C(O)—, —C(S) or —S(O)$_2$;

R$^{70}$ is hydrogen, alkyl, substituted alkyl, aryl, substituted aryl, arylalkyl, substituted arylalkyl, acyl, substituted acyl, heteroalkyl, substituted heteroalkyl, heteroaryl, substituted heteroaryl, heteroarylalkyl, substituted heteroarylalkyl, —CN, —NO$_2$, —OR$^{72}$, —S(O)$_a$R$^{72}$, —NR$^{72}$R$^{73}$, —CONR$^{72}$R$^{73}$, —CO$_2$R$^{72}$—NR$^{72}$CO$_2$R$^{73}$— NR$^{72}$CONR$^{73}$R$^{74}$—NR$^{72}$CSNR$^{73}$R$^{74}$ or —NR$^{72}$C(=NH)NR$^{73}$R$^{74}$, —SO$_2$NR$^{72}$R$^{73}$, —NR$^{72}$SO$_2$R$^{73}$, —NR$^{72}$SO$_2$NR$^{73}$R$^{74}$, —B(OR$^{72}$)(OR$^{73}$), —P(O)(OR$^{72}$)(OR$^{73}$) or —P(O)(R$^{72}$)(OR$^{73}$);

R$^{71}$ is hydrogen, alkyl, substituted alkyl, aryl, substituted aryl, arylalkyl, substituted arylalkyl, acyl, substituted acyl, heteroalkyl, substituted heteroalkyl, heteroaryl, substituted heteroaryl, heteroarylalkyl, substituted heteroarylalkyl, —CN, —NO$_2$, —OR$^{74}$, —S(O)$_b$R$^{74}$, —NR$^{74}$R$^{75}$, —CONR$^{74}$R$^{75}$—CO$_2$R$^{74}$—NR$^{74}$CO$_2$R$^{75}$—NR, 74CONR$^{75}$R$^{76}$—NR$^{74}$CSNR$^{75}$R$^{76}$ or —NR$^{74}$C(=NH)NR$^{75}$R$^{76}$, —SO$_2$NR$^{74}$R$^{75}$, —NR$^{74}$SO$_2$R$^{75}$, —NR$^{74}$SO$_2$NR$^{75}$R$^{76}$, —B(OR$^{74}$)(OR$^{75}$), —P(O)(OR$^{74}$)(OR$^{75}$), —P(O)(R$^{74}$)(OR$^{75}$) or alternatively, R$^{71}$ and R$^{72}$ together with the atoms to which they are bonded form an aryl, substituted aryl, heteroaryl, substituted heteroaryl, cycloalkyl, substituted cycloalkyl, cycloheteroalkyl or substituted cycloheteroalkyl ring where the ring is optionally fused to another aryl, substituted aryl, heteroaryl, substituted heteroaryl, cycloalkyl, substituted cycloalkyl, cycloheteroalkyl or substituted cycloheteroalkyl ring;

a and b are independently 0, 1 or 2;

R$^{72}$-R$^{76}$ are independently hydrogen, alkyl, substituted alkyl, aryl, substituted aryl, arylalkyl, substituted arylalkyl, acyl, substituted acyl, heteroalkyl, substituted heteroalkyl, heteroaryl, substituted heteroaryl, heteroarylalkyl or substituted heteroarylalkyl or alternatively, R$^{72}$ and R$^{73}$, R$^{73}$ and R$^{74}$, R$^{74}$ and R$^{75}$ and R$^{75}$ and R$^{76}$ together with the atoms to which they are bonded form a cycloheteroalkyl or substituted cycloheteroalkyl ring; and $R^{77}$-$R^{78}$ are independently hydrogen, alkyl, substituted alkyl, aryl, substituted aryl, arylalkyl, substituted arylalkyl, acyl, substituted acyl, heteroalkyl, substituted heteroalkyl, heteroaryl, substituted heteroaryl, heteroarylalkyl or substituted heteroarylalkyl or alternatively, $R^{77}$ and $R^{78}$, together with the atoms to which they are bonded form a cycloalkyl, substituted cycloalkyl, cycloheteroalkyl or substituted cycloheteroalkyl ring.

In some embodiments, the flavoring agents and/or flavor enhancers are selected from a compound defined by formula (J1):

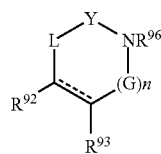

(J1)

or a salt, solvate, hydrate or N-oxide thereof wherein:
each G is independently —C($R^{94}$)($R^{95}$)—, —C(O)—, —N$R^{94}$— or —S(O)$_2$—;
n is 1, 2 or 3;
provided that when n is greater than one then only one G is —C(O)—, —S(O)$_2$— or —N$R^{94}$—; Y is —C(O)—, —C(S)— or —S(O)$_2$;
L is —C($R^{104}$)($R^{105}$)—, —O—, or —N$R^{104}$—;
$R^{92}$ is hydrogen, alkyl, substituted alkyl, aryl, substituted aryl, arylalkyl, substituted arylalkyl, acyl, substituted acyl, heteroalkyl, substituted heteroalkyl, heteroaryl, substituted heteroaryl, heteroarylalkyl, substituted heteroarylalkyl, —CN, —NO$_2$, —O$R^{98}$, —S(O)$_y$$R^{98}$, —N$R^{98}$$R^{99}$, —CON$R^{98}$$R^{99}$—CO$_2$$R^{99}$, —N$R^{98}$CO$_2$$R^{99}$— N$R^{98}$CON$R^{99}$$R^{100}$—N$R^{98}$CSN$R^{99}$$R^{100}$ or —N$R^{98}$C(=NH)N$R^{99}$$R^{100}$, —SO$_2$N$R^{98}$$R^{99}$, —N$R^{98}$SO$_2$$R^{99}$, —N$R^{98}$SO$_2$N$R^{99}$$R^{100}$, —B(O$R^{98}$)(O$R^{99}$), —P(O)(O$R^{98}$)(O$R^{99}$) or —P(O)($R^{98}$)(O$R^{99}$);
$R^{93}$ is hydrogen, alkyl, substituted alkyl, aryl, substituted aryl, arylalkyl, substituted arylalkyl, acyl, substituted acyl, heteroalkyl, substituted heteroalkyl, heteroaryl, substituted heteroaryl, heteroarylalkyl, substituted heteroarylalkyl, —CN, —NO$_2$, —O$R^{100}$, —S(O)$_y$$R^{101}$, —N$R^{101}$$R^{102}$— CON$R^{101}$$R^{102}$—CO$_2$$R^{101}$—N$R^{101}$CO$_2$$R^{102}$— N$R^{101}$CON$R^{102}$$R^{103}$—N$R^{101}$CSN$R^{102}$$R^{103}$ or —N$R^{101}$C(=NH)N$R^{102}$$R^{103}$, —SO$_2$N$R^{101}$$R^{102}$, —N$R^{101}$SO$_2$$R^{102}$, —N$R^{101}$SO$_2$N$R^{102}$$R^{103}$, —B(O$R^{101}$)(O$R^{102}$), —P(O)(O$R^{101}$)(O$R^{102}$), —P(O)($R^{101}$)(O$R^{102}$) or alternatively, $R^{92}$ and $R^{93}$ together with the atoms to which they are bonded form an aryl, substituted aryl, heteroaryl, substituted heteroaryl, cycloalkyl, substituted cycloalkyl, cycloheteroalkyl or substituted cycloheteroalkyl ring where the ring is optionally fused to another aryl, substituted aryl, heteroaryl, substituted heteroaryl, cycloalkyl, substituted cycloalkyl, cycloheteroalkyl or substituted cycloheteroalkyl ring;
x and y are independently, 0, 1 or 2;
$R^{98}$-$R^{103}$ are independently hydrogen, alkyl, substituted alkyl, aryl, substituted aryl, arylalkyl, substituted arylalkyl, acyl, substituted acyl, heteroalkyl, substituted heteroalkyl, heteroaryl, substituted heteroaryl, heteroarylalkyl or substituted heteroarylalkyl or alternatively, $R^{98}$ and $R^{99}$, $R^{99}$ and $R^{100}$, $R^{101}$ and $R^{102}$ and $R^{101}$ and $R^{102}$ together with the atoms to which they are bonded form a cycloalkyl, substituted cycloalkyl, cycloheteroalkyl or substituted cycloheteroalkyl ring;

$R^{94}$-$R^{95}$ are independently hydrogen, alkyl, substituted alkyl, aryl, substituted aryl, arylalkyl, substituted arylalkyl, acyl, substituted acyl, heteroalkyl, substituted heteroalkyl, heteroaryl, substituted heteroaryl, heteroarylalkyl or substituted heteroarylalkyl or alternatively, $R^{94}$ and $R^{95}$, together with the atoms to which they are bonded form a cycloalkyl, substituted cycloalkyl, cycloheteroalkyl or substituted cycloheteroalkyl ring;

$R^{96}$ is hydrogen, alkyl, substituted alkyl, aryl, substituted aryl, arylalkyl, substituted arylalkyl, acyl, substituted acyl, heteroalkyl, substituted heteroalkyl, heteroaryl, substituted heteroaryl, heteroarylalkyl or substituted heteroarylalkyl; and $R^{104}$-$R^{105}$ are independently hydrogen, alkyl, substituted alkyl, aryl, substituted aryl, arylalkyl, substituted arylalkyl, acyl, substituted acyl, heteroalkyl, substituted heteroalkyl, heteroaryl, substituted heteroaryl, heteroarylalkyl or substituted heteroarylalkyl or alternatively, $R^{104}$ and $R^{105}$, together with the atoms to which they are bonded form a cycloalkyl, substituted cycloalkyl, cycloheteroalkyl or substituted cycloheteroalkyl ring.

In some embodiments, the flavoring agents and/or flavor enhancers are selected from a compound defined by formula (K1):

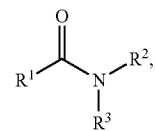

(K1)

or a salt thereof, wherein:

$R^1$ comprises an organic or hydrocarbon residue having at least three carbon atoms and optionally one or more heteroatoms independently selected from oxygen, nitrogen, sulfur, halogens, or phosphorus; and wherein optionally one of $R^2$ and $R^3$ is H, and wherein at least one of the other of $R^2$ and $R^3$ comprises an organic or hydrocarbon residue having at least three carbon atoms and optionally one or more heteroatoms independently selected from oxygen, nitrogen, sulfur, halogens, or phosphorus.

In some embodiments, the flavoring agents and/or flavor enhancers are selected from a compound defined by formula (A2):

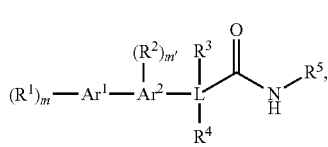

(A2)

or a salt thereof, wherein:

$Ar^1$, $Ar^2$, L, $R^1$, $R^2$, $R^3$, $R^4$, $R^5$, m and m', some of which are optional, can be and are independently further defined in various ways, as is further detailed below in the detailed description of the invention. It is however required that for all the compounds of Formula (I), L is either a carbon atom or a nitrogen atom, the $Ar^1$ and $Ar^2$ groups are independently selected from aromatic ring groups, i.e. aryl or heteroaryl ring groups, and that $R^5$ is an organic group.

In some embodiments of formula (A2):
i) $Ar^1$ and $Ar^2$ are independently selected from monocyclic aryl, fused bicyclic aryl, monocyclic heteroaryl, or fused bicyclic heteroaryl rings;
ii) m is selected from the integers 0, 1, 2, 3, 4, or 5;
iii) m' is selected from the integers 0, 1, 2, 3, or 4;
iv) each $R^1$ and $R^2$ is independently selected from the group consisting of an OH, $NH_2$, $NO_2$, SH, $SO_3H$, $PO_3H$, halogen, and a $C_1$-$C_6$ organic radical;
v) L is a carbon or nitrogen atom;
vi) $R^3$ is hydrogen, oxygen, hydroxy, halogen, or a $C_1$-$C_6$ organic radical;
vii) $R^4$ is absent, or hydrogen, oxygen, hydroxy, halogen, or a $C_1$-$C_6$ organic radical;
viii) $R^5$ is a $C_1$-$C_{14}$ organic radical comprising a normal or branched alkyl or cycloalkyl, wherein the normal or branched alkyl or cycloalkyl optionally comprises one to four substituents independently selected from OH, $NH_2$, $NO_2$, SH, $SO_3H$, $PO_3H$, halogen, and a $C_1$-$C_6$ organic radical.

In some embodiments of formula (A2), L is a carbon atom. Some embodiments of formula (A2) have the structure:

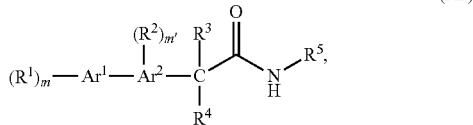

(A2)

or salt thereof, wherein:
i) $Ar^1$ and $Ar^2$ are independently selected from a phenyl, or monocyclic heteroaryl rings;
ii) m and m' are independently selected from the integers 0, 1, or 2
iii) each $R^1$ and $R^2$ is independently selected from the group consisting of OH, $NH_2$, $NO_2$, SH, $SO_3H$, $PO_3H$, halogen, and a $C_1$-$C_4$ organic radical;
iv) $R^3$ and $R^4$ are independently selected from hydrogen and a $C_1$-$C_4$ alkyl,
v) $R^5$ is a $C_3$-$C_{10}$ branched alkyl optionally comprising one, two, or three substituents independently selected from OH, $NH_2$, a halogen, and a $C_1$-$C_6$ organic radical.

In some embodiments of formula (A2):
i) $Ar^1$ and $Ar^2$ are independently selected from monocyclic aryl, fused bicyclic aryl, monocyclic heteroaryl, or fused bicyclic heteroaryl rings;
ii) m is selected from the integers 0, 1, 2, 3, 4, or 5;
iii) m' is selected from the integers 0, 1, 2, 3, or 4;
iv) each $R^1$ and $R^2$ is independently selected from the group consisting of an OH, $NH_2$, $NO_2$, SH, $SO_3H$, $PO_3H$, halogen, and a $C_1$-$C_6$ organic radical;
v) L is a carbon atom;
vi) $R^3$ is hydrogen, oxygen, hydroxy, halogen, or a $C_1$-$C_6$ organic radical;
vii) $R^4$ is hydrogen, oxygen, hydroxy, halogen, or a $C_1$-$C_6$ organic radical; and
viii) $R^5$ is a $C_1$-$C_{14}$ organic radical comprising a normal or branched alkyl or cycloalkyl, wherein the normal or branched alkyl or cycloalkyl optionally comprises one to four substituents independently selected from OH, $NH_2$, $NO_2$, SH, $SO_3H$, $PO_3H$, halogen, and a $C_1$-$C_6$ organic radical.

In some embodiments of formula (A2):
a) $Ar^1$ and $Ar^2$ are independently selected phenyl or 5 or 6 membered monocyclic heteroaryl rings,
b) each $R^1$ and $R^2$ is independently selected from the group consisting of: hydroxy, fluoro, chloro, $NH_2$, $NHCH_3$, $N(CH_3)_2$, CN, $OC(O)CH_3$, $SCH_3$, $S(O)CH_3$, $S(O)_2CH_3$, $S(O)_2NHCH_3$, $SC_2H$ methyl, ethyl, propyl, isopropyl, vinyl, allyl, CN, $CH_2OH$, $CH_2OCH_3$, $CH_2OCH_2CH_3$, $C(O)H$, $C(O)CH_3$, methoxy, ethoxy, and isopropoxy groups,
c) $R^3$ and $R^4$ are methyl, and
d) $R^5$ is a $C_3$-$C_{10}$ branched alkyl.

In some embodiments, the flavoring agents and/or flavor enhancers are selected from a compound defined by formula (B2):

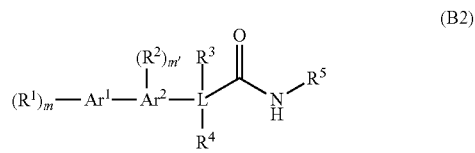

(B2)

wherein $Ar^1$, $Ar^2$, L, $R^1$, $R^2$, $R^3$, $R^4$, $R^5$, m and m', some of which are optional, can be and are independently further defined in various ways, as is further detailed below. It is however required that for all the compounds of Formula (I), L is either a carbon atom or a nitrogen atom, the $Ar^1$ and $Ar^2$ groups are independently selected from aromatic ring groups, i.e. aryl or heteroaryl ring groups, and that $R^5$ is an organic group.

In some embodiments of formula (B2):
i) $Ar^1$ and $Ar^2$ are independently selected from monocyclic aryl, fused bicyclic aryl, monocyclic heteroaryl, or fused bicyclic heteroaryl rings;
ii) m is selected from the integers 0, 1, 2, 3, 4, or 5;
iii) m' is selected from the integers 0, 1, 2, 3, or 4;
iv) each $R^1$ and $R^2$ is independently selected from the group consisting of an OH, $NH_2$, $NO_2$, SH, $SO_3H$, $PO_3H$, halogen, and a $C_1$-$C_6$ organic radical;
v) L is a carbon or nitrogen atom;
vi) $R^3$ is hydrogen, oxygen, hydroxy, halogen, or a $C_1$-$C_6$ organic radical;
vii) $R^4$ is absent, or hydrogen, oxygen, hydroxy, halogen, or a $C_1$-$C_6$ organic radical;
viii) $R^5$ is a $C_1$-$C_{14}$ organic radical comprising a normal or branched alkyl or cycloalkyl, wherein the normal or branched alkyl or cycloalkyl optionally comprises one to four substituents independently selected from OH, $NH_2$, $NO_2$, SH, $SO_3H$, $PO_3H$, halogen, and a $C_1$-$C_6$ organic radical.

In some embodiments of the compounds of Formula (B2), L is a carbon atom. In some embodiments of the compounds of Formula (B2) have the structure:

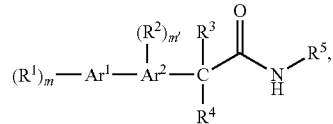

or a salt thereof, wherein:
i) $Ar^1$ and $Ar^2$ are independently selected from a phenyl, or monocyclic heteroaryl rings;

ii) m and m' are independently selected from the integers 0, 1, or 2
iii) each $R^1$ and $R^2$ is independently selected from the group consisting of OH, $NH_2$, $NO_2$, SH, $SO_3H$, $PO_3H$, halogen, and a $C_1$-$C_4$ organic radical;
iv) $R^3$ and $R^4$ are independently selected from hydrogen and a $C_1$-$C_4$ alkyl,
v) $R^5$ is a $C_3$-$C_{10}$ branched alkyl optionally comprising one, two, or three substituents independently selected from OH, $NH_2$, a halogen, and a $C_1$-$C_6$ organic radical;

In some embodiments of the compounds of Formula (B2):
i) $Ar^1$ and $Ar^2$ are independently selected from monocyclic aryl, fused bicyclic aryl, monocyclic heteroaryl, or fused bicyclic heteroaryl rings;
ii) m is selected from the integers 0, 1, 2, 3, 4, or 5;
iii) m' is selected from the integers 0, 1, 2, 3, or 4;
iv) each $R^1$ and $R^2$ is independently selected from the group consisting of an OH, $NH_2$, $NO_2$, SH, $SO_3H$, $PO_3H$, halogen, and a $C_1$-$C_6$ organic radical;
v) L is a carbon atom;
vi) $R^3$ is hydrogen, oxygen, hydroxy, halogen, or a $C_1$-$C_6$ organic radical;
vii) $R^4$ is hydrogen, oxygen, hydroxy, halogen, or a $C_1$-$C_6$ organic radical; and
viii) $R^5$ is a $C_1$-$C_{14}$ organic radical comprising a normal or branched alkyl or cycloalkyl, wherein the normal or branched alkyl or cycloalkyl optionally comprises one to four substituents independently selected from OH, $NH_2$, $NO_2$, SH, $SO_3H$, $PO_3H$, halogen, and a $C_1$-$C_6$ organic radical;

In some embodiments of the compounds of Formula (B2):
a) $Ar^1$ and $Ar^2$ are independently selected phenyl or 5 or 6 membered monocyclic heteroaryl rings,
b) each $R^1$ and $R^2$ is independently selected from the group consisting of. hydroxy, fluoro, chloro, $NH_2$, $NHCH_3$, $N(CH_3)_2$, CN, $OC(O)CH_3$, $SCH_3$, $S(O)CH_3$, $S(O)_2CH_3$, $S(O)_2NHCH_3$, $SC_2H$ methyl, ethyl, propyl, isopropyl, vinyl, allyl, CN, $CH_2OH$, $CH_2OCH_3$, $CH_2OCH_2CH_3$, C(O)H, $C(O)CH_3$, methoxy, ethoxy, and isopropoxy groups,
c) $R^3$ and $R^4$ are methyl, and
d) $R^5$ is a $C_3$-$C_{10}$ branched alkyl.

In some embodiments, the flavoring agents and/or flavor enhancers is 4-amino-5,6-dimethylthieno[2,3-d]pyrimidine-2(1H)-one or salts, solvates, and/or esters thereof.

In some embodiments, the flavoring agents and/or flavor enhancers are selected from a compound defined by formula (C2):

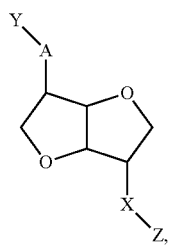

(C2)

or a salt, or the salt, solvate, N-oxide, and/or ester thereof, wherein:
A is aryl, heteroaryl, or a covalent bond;
Y is hydrogen, alkyl, substituted alkyl, alkenyl, substituted alkenyl, alkynyl, substituted alkylnyl, heteroalkyl, substituted heteroalkyl, aryl, substituted aryl, arylalkyl, substituted arylalkyl, arylalkenyl, substituted arylalkenyl, heteroaryl, substituted heteroaryl, heterocyclyl, substituted heterocyclyl, heteroarylalkyl, substituted heteroarylalkyl, heterocyclylalkyl, substituted heterocyclylalkyl, carbocyclyl, substituted carbocyclyl, acyl, halo, —CN, —$NO_2$, —$OR^1$, —$S(O)R^1$—$S(O)_2R^1$, —$OC(O)R^1$—$N(R^1)C(O)R^2$, —$NR^1R^2$, —$C(O)NR^1R^2$, —$C(O)OR^1$, —$S(O)_2NR^1R^2$, —$COR^1$—$N(R^1)S(O)_2R^2$, —$SR^1$—$C(R^1R^2R^6)$, —C(S)—$R^1$—C(=$NR^2$)—$R^1$—$N(R^1)$—C(=N—$OR^2$)$R^6$, $N(R^1)C(S)NR^2R^6$—C(=N—$OR^1$)$R^2$, —C(=$NR^1$)—: $NR^2R^6$—N($R^1$)C(=$NR^2$)$NR^6R^7$, —$N(R^1)C(S)R^2$, —$N(R^1)$—C(O)—$C(O)R^2$, —C(S)—$NR^1R^2$, —$N(R^1)C(=NR^2)OR^6$—C(=$NR^1$)O—$NR^2R^6$, —$N(R^1)N(R^2)C(O)OR^6$, —$N(R^1)C(O)OR^2$, —$N(R^1)C(O)NR^2R^6$, —$N(R^1)$—C(O)—C(O)—$NR^2R^6$, —C(O)—C(O)—$NR^1R^2$, —$P(O)(OR^1)(OR^2)$, —$P(O)(OR^1)(R^2)$, or —$P(O)R^1R^2$;

X is —O—, —S—, —S(O)—, —$S(O)_2$—, —$C(R^3R^4)$—, —C(O)—, —C(S)—, —C(=$NR^3$)—, —C(O)O—, —$N(R^3)$—, —OC(O)—, —$N(R^3)C(O)$—, —$C(O)N(R^3)$—, —$N(R^3)$—C(=N—$OR^4$)—, —C(=N—$OR^3$)—, —C(=$NR^3$)—$NR^4$—, —$N(R^3)C(S)N(R^4)$—$R^5$—$N(R^3)C(O)N(R^4)$—$R^5$—$N(R^3)C(=NR^4$—, —$N(R^3)C(S)$—, —$N(R^3)$—C(O) C(O) C(S)—$N(R^3)$—, —$N(R^3)S(O)_2$—, —$S(O)_2$—$N(R^3$—, —$N(R^3)C(=NR^4)O$—, —C(=$NR^4$)O—$N(R^3)$—, —$N(R^3)$—C(=$NR^4$)—$N(R^5)$—, —$N(R^3)N(R^4)C(O)O$—. —$N(R^3)C(O)O$—, —$N(R^3)C(O)N(R^4)$—, —$N(R^3)$—C(O)—C(O)—$NR^4$—, —C(O)—C(O)—$NR^4$—, —$P(O)(OR^3)$—, or —$P(O)R^3$—;

Z is alkyl, substituted alkyl, alkenyl, substituted alkenyl, alkynyl, substituted alkylnyl, beteroalkyl, substituted heteroalkyl, aryl, substituted aryl, arylalkyl, substituted arylalkyl, arylalkenyl, substituted arylalkenyl, heteroaryl, substituted heteroaryl, heterocyclyl, substituted beterocyclyl, heteroarylalkyl, substituted heteroarylalkyl, heterocyclylalkyl, substituted heterocyclylalkyl, carbocyclyl, or substituted carbocyclyl;

$R^1$, $R^2$, $R^3$, $R^4$, $R^5$, $R^6$, and $R^7$ are each independently hydrogen, alkyl, substituted alkyl, alkenyl, substituted alkenyl, alkynyl, substituted alkylnyl, heteroalkyl, substituted heteroalkyl, aryl, substituted aryl, arylalkyl, substituted arylalkyl, arylalkenyl, substituted arylalkenyl, heteroaryl, substituted heteroaryl, heterocyclyl, substituted heterocyclyl, carbocyclyl, substituted carbocyclyl, heteroarylalkyl, or substituted heteroarylalkyl; and with the following provisos: (a) when A is triazole or tetrazole; then —X—Z is not —O-alkyl, —O-acyl, or sulfonamido; (b) when A is tetrazole, and Z is cyclohexyl; then X is not —NH—C(O)—, —NH—C(O)—NH—; and (e) when A is a covalent bond, then Y is not hydrogen.

In some embodiments, the flavoring agents and/or flavor enhancers are selected from a compound defined by formula (D2):

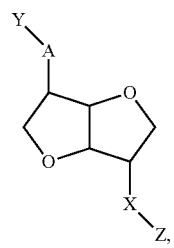

(D2)

or the salt, solvate, N-oxide, and/or ester thereof, wherein:

A is aryl, heteroaryl, or a covalent bond;

Y is hydrogen, alkyl, substituted alkyl, alkenyl, substituted alkenyl, alkynyl, substituted alkylnyl, heteroalkyl, substituted heteroalkyl, aryl, substituted aryl, arylalkyl, substituted arylalkyl, arylalkenyl, substituted arylalkenyl, heteroaryl, substituted heteroaryl, heterocyclyl, substituted heterocyclyl, heteroarylalkyl, substituted heteroarylalkyl, heterocyclylalkyl, substituted heterocyclylalkyl, carbocyclyl, substituted carbocyclyl, acyl, halo, —CN, —NO$_2$, —OR$^1$, —S(O)R$^1$—S(O)$_2$R$^1$—OC(O)R$^1$—N(R$^1$)C(O)R$^2$, —NR$^1$R$^2$, —C(O)NR$^1$R$^2$, —C(O)OR$^1$—S(O)$_2$NR$^1$R$^2$, —COR$^1$, —N(R$^1$)S(O)$_2$R$^2$, —SR$^1$, C(R$^1$R$^2$R$^6$), —C(S)—R$^1$—C(=NR$^2$)—R$^1$, —N(R$^1$)—C(=N—OR 2)R$^6$, —N(R$^1$)C(S)NR$^2$R$^6$—C(=N—OR$^1$)R$^2$, —C(=NR$^1$)—NR$^2$R$^6$, —N(R$^1$)C(=NR$^2$)NR$^6$R$^7$, —N(R$^1$)C(S)R$^2$, —N(R$^1$)—C(O)—C(O)R$^2$, —C(S)—NR$^1$R$^2$, —N(R$^1$)C(=NR$^2$)OR$^6$—C(=NR$^1$)O—NR$^2$R$^6$, —N(R$^1$)N(R$^2$)C(O)OR$^6$, —N(R$^1$)C(O)OR$^2$—N(R$^1$)C(O)NR$^2$R$^6$—N(R$^1$)—C(O)—C(O)—NR$^2$R$^6$—C(O)—C(O)—NR$^1$R$^2$—P(O)(OR$^1$)(OR$^2$), —P(O)(OR$^1$)(R$^2$), or —P(O)R$^1$R$^2$; X is —O—, —S—, —S(O)—, —S(O)$_2$—, —C(R$^3$R$^4$)—, —C(O)—, —C(S)—, —C(=NR$^3$)—, —C(O)O—, —N(R$^3$)—, —OC(O)—, —N(R$^3$)C(O)—, —C(O)N(R 3-, —N(R$^3$)—C(=N—OR 4)-, —C(=N—O R 3-, —C(=NR$^3$)—NR$^4$—, —N(R$^3$)C(S)N(R$^4$)—R$^5$, —N(R$^3$)C(O)N(R$^4$)—R$^5$, —N(R$^3$)C(=NR$^4$)—, —N(R$^3$)C(S)—, —N(R$^3$)—C(O)—C(O)—, —C(S)—N(R$^3$)—, —N(R$^3$)S(O)$_2$—, —S(O)$_2$—N(R$^3$)—, —N(R$^3$)C(=NR$^4$)O—, —C(=NR$^4$) O—N(R$^3$)—, —N(R$^3$)—C(=NR$^4$)—N(R$^5$)—, —N(R$^3$)N(R$^4$)C(O)O—, —N(R$^3$)C(O)O—, —N(R$^3$)C:(O)N(R$^4$—, —N(R$^3$)—C(O)—C(O)—NR$^4$—, —C(O)—C(O)—NR$^4$—, —P(O)(OR$^3$)—, or —P(O)R$^3$;

Z is alkyl, substituted alkyl, alkenyl, substituted alkenyl, alkynyl, substituted alkylriyl, heteroalkyl, substituted heteroalkyl, aryl, substituted aryl, arylalkyl, substituted arylalkyl, arylalkenyl, substituted arylalkenyl, heteroaryl, substituted heteroaryl, heterocyclyl, substituted heterocyclyl, heteroarylalkyl, substituted heteroarylalkyl, heterocyclylalkyl, substituted heterocyclylalkyl, carbocyclyl, or substituted carbocyclyl;

R$^1$, R$^2$, R$^3$, R$^4$, R$^5$, R$^6$, and R$^7$ are each independently hydrogen, alkyl, substituted alkyl, alkenyl, substituted alkenyl, alkynyl, substituted alkylnyl, heteroalkyl, substituted heteroalkyl, aryl, substituted aryl, arylalkyl, substituted arylalkyl, arylalkenyl, substituted arylalkenyl, heteroaryl, substituted heteroaryl, heterocyclyl, substituted heterocyclyl, carbocyclyl, substituted carbocyclyl, heteroarylalkyl, or substituted heteroarylalkyl.

In some embodiments, the sweetness enhancer is a compound selected from 5-(neopentyloxy)-1H-benzo[c][1,2,6]thiadiazin-4-amino-2,2-dioxide; 3-(4-amino-2,2-dioxide-1H-benzo[c][1,2,6]thiadiazin-5-yloxy)-2',2'-dimethyl-N-propylpropanamide; and salts and/or solvates thereof.

In some embodiments, the sweetness enhancers are selected from a compound defined by formula (E2):

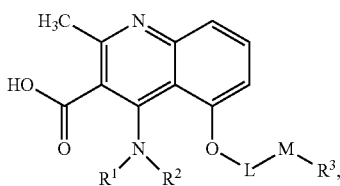

(E2)

or a salt, solvate, and/or prodrug thereof; wherein:

R$^1$ and R$^2$ are independently hydrogen or C$_1$ to C$_6$ alkyl;

L is C$_1$ to C$_{12}$ alkylene or substituted C$_1$ to C$_{12}$ alkylene;

M is —NR$^4$—C(O)— or —C(O)—NR$^4$—;

R$^4$ is hydrogen or C$_1$ to C$_6$ alkyl; or alternatively, when M is —NR$^4$—C(O)—, —R$^4$ and one or more atoms of L, together with the nitrogen to which they are attached, form a 5- to 8-membered heterocyclic ring containing one to three heteroatoms selected from nitrogen, oxygen, and sulfur; and R$^3$ is C$_1$ to C$_{12}$ alkyl, substituted C$_1$ to C$_{12}$ alkyl, 5- to 8-membered heterocyclyl, or substituted 5- to 8-membered heterocyclyl; or alternatively, when M is —C(O)—NR$^4$, —R$^4$ and one or more atoms of R$^3$, together with the nitrogen to which they are attached, form a 5- to 8-membered heterocyclic ring containing one to three heteroatoms selected from nitrogen, oxygen, and sulfur.

In some embodiments, the sweetness enhancer is present at an amount from about 0.001 ppm to 800 ppm. Thus, in some alternatives, the amount of sweetness enhancer is 0.001, 0.01, 0.1, 1, 10, 50, 100, 200, 300, 400, 500, 600, 700, or 800 ppm or a value that is within a range defined by any two of the aforementioned values.

In some embodiments, compounds as disclosed and described herein, individually or in combination, can be used in combination with one or more compounds selected from:

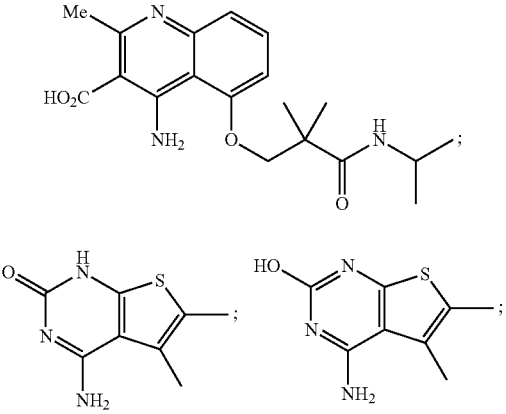

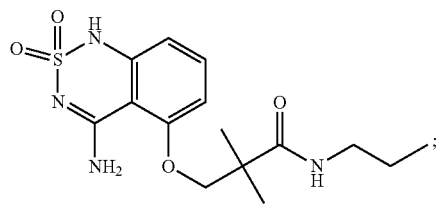

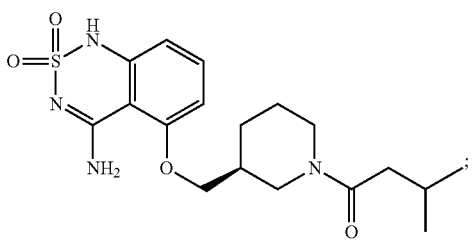

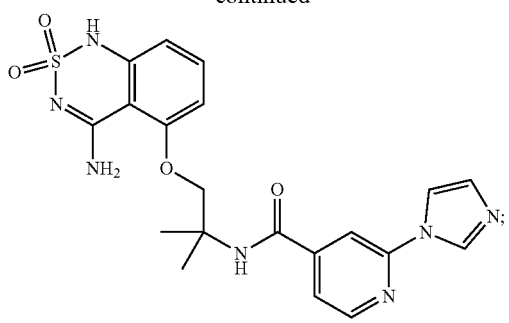

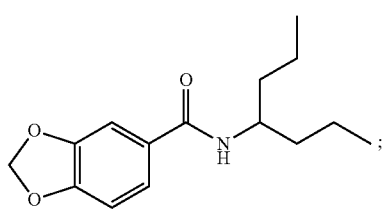

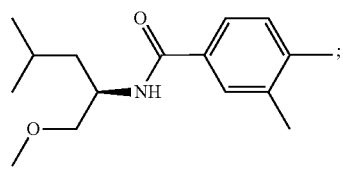

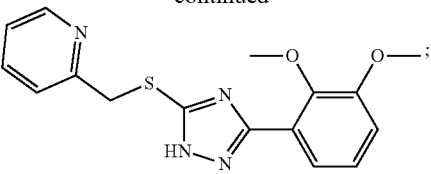

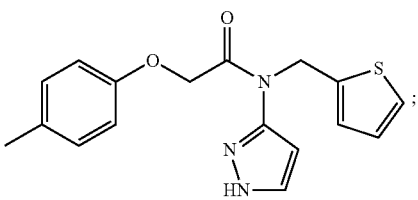

and salts thereof.

Methods of Preparation

The compounds disclosed herein may be synthesized or isolated by methods described below, or by modification of these methods. Ways of modifying the methodology include, among others, temperature, solvent, reagents etc., known to those skilled in the art. The methods shown and described herein are illustrative only and are not intended, nor are they to be construed, to limit the scope of the claims in any manner whatsoever. Those skilled in the art will be able to recognize modifications of the disclosed methods and to devise alternate routes based on the disclosures herein; all such modifications and alternate routes are within the scope of the claims.

In some embodiments, compounds disclosed herein may be obtained by isolation from *Siraitia grosvenorii*. In some such embodiments, an extract obtained from *Siraitia grosvenorii* may be fractionated using a suitable purification technique. In some embodiments, the extract is fractionated using HPLC and the appropriate fraction is collected to obtain the desired compound in isolated and purified form.

In other embodiments, compound disclosed herein may be obtained by enzymatic modification of a compound isolated from *Siraitia grosvenorii*. For example, in some embodiments, a compound isolated from *Siraitia grosvenorii* is treated with one or more enzymes (e.g., a carbohydrase) to obtain the desired compounds. The starting compound isolated from *Siraitia grosvenorii* can include, but are not limited to, Mogroside V, Mogroside III$_E$, Siamenoside I, Mogroside VI isomer, Mogroside II$_A$, Mogroside IV$_E$, or Mogroside IV$_A$. Enzymes suitable for use to generate compounds described herein can include, but are not limited to, a pectinase, a β-galactosidase (e.g., Aromase), a cellulase (e.g., Celluclast), a clyclomatlodextrin glucanotransferase (e.g., Toruzyme), an invertase, a glucostransferase (e.g., UGT76G1), a dextransucrase, a lactase, an arabanse, a xylanase, a hemicellulose, and an amylase.

Some embodiments provide a method of making Compound 1,
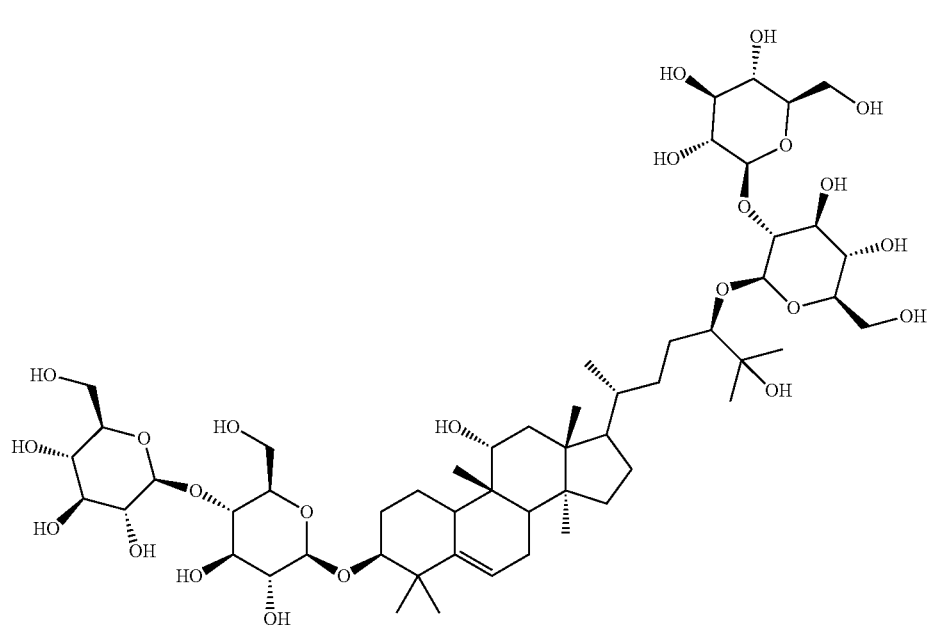
(1)
comprising fractionating an extract of *Siraitia grosvenorii* on an HPLC column and collecting an eluted fraction comprising Compound 1.
Some embodiments provide a method of making Compound 18,
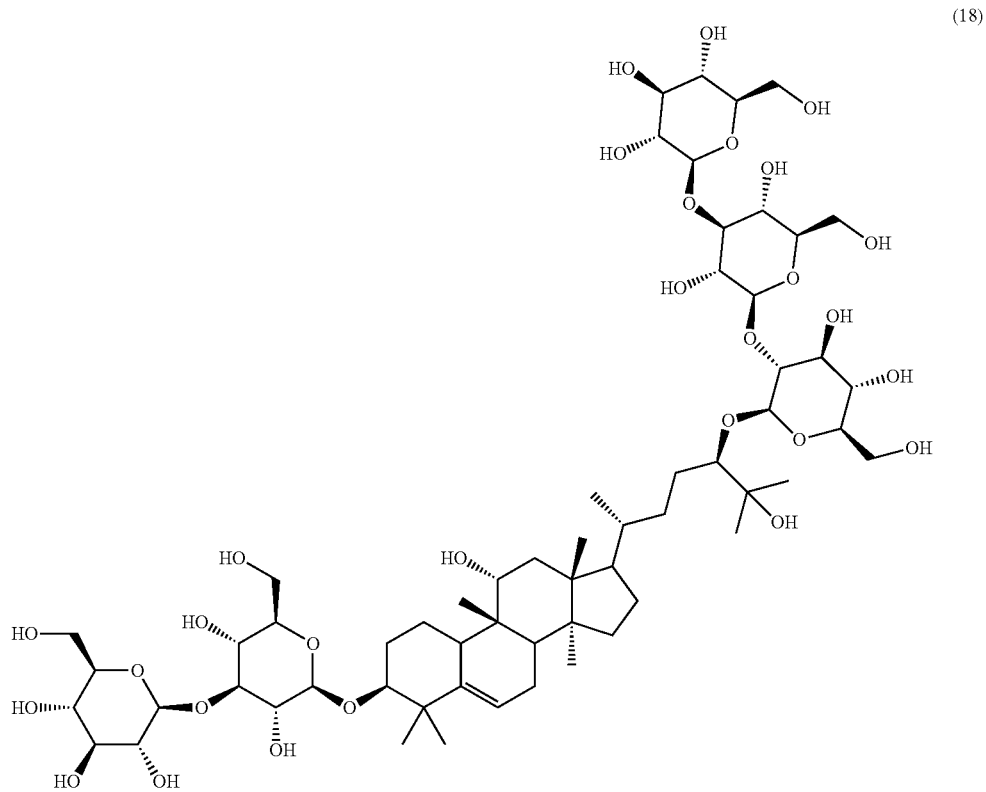 [SMILES: C[C@H](CC[C@@H](O[C@@H]1O[C@H](CO)[C@@H](O)[C@H](O)[C@H]1O[C@@H]1O[C@H](CO)[C@@H](O)[C@H](O[C@@H]2O[C@H](CO)[C@@H](O)[C@H](O)[C@H]2O)[C@H]1O)C(C)(C)O)C1CC[C@@]2(C)C3CC=C4C(CC[C@H](O[C@@H]5O[C@H](CO)[C@@H](O)[C@H](O[C@@H]6O[C@H](CO)[C@@H](O)[C@H](O)[C@H]6O)[C@H]5O)C4(C)C)[C@]3(C)[C@H](O)C[C@]12C]
(18)
comprising treating Mogroside $III_E$ with the glucose transferase enzyme UGT76G1.

Some embodiments provide methods of making a compound of Compound 3,
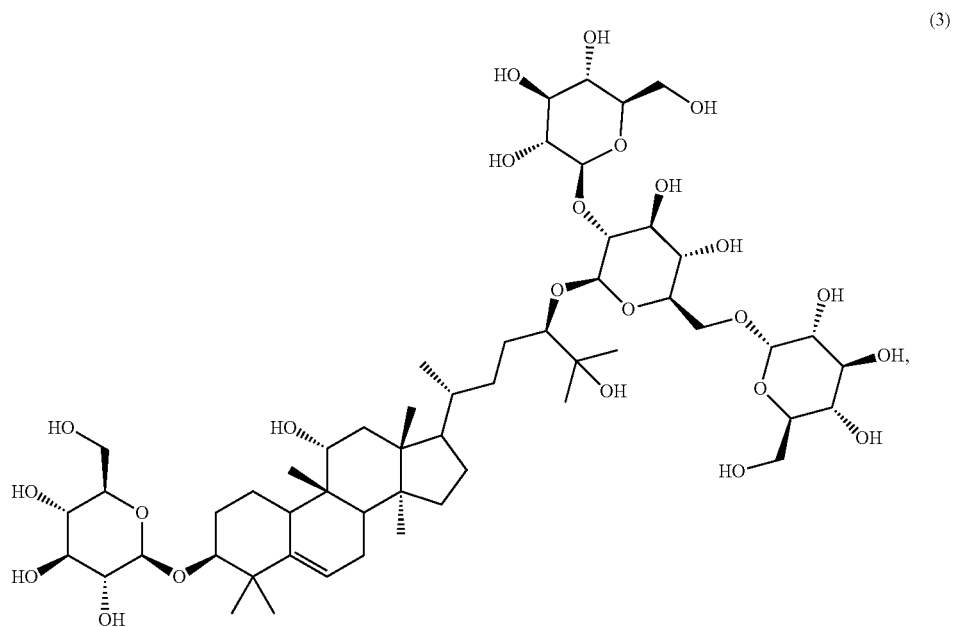 [SMILES: C[C@H](CC[C@@H](O[C@@H]1O[C@H](CO[C@H]2O[C@H](CO)[C@@H](O)[C@H](O)[C@H]2O)[C@@H](O)[C@H](O)[C@H]1O[C@@H]1O[C@H](CO)[C@@H](O)[C@H](O)[C@H]1O)C(C)(C)O)C1CC[C@@]2(C)C3CC=C4C(CC[C@H](O[C@@H]5O[C@H](CO)[C@@H](O)[C@H](O)[C@H]5O)C4(C)C)[C@]3(C)[C@H](O)C[C@]12C]
(3)
comprising treating mogroside III$_E$ with cyclomaltodextrin glucanotransferase in the presence of starch.
Some embodiments provide methods of making a compound of Compound 12,
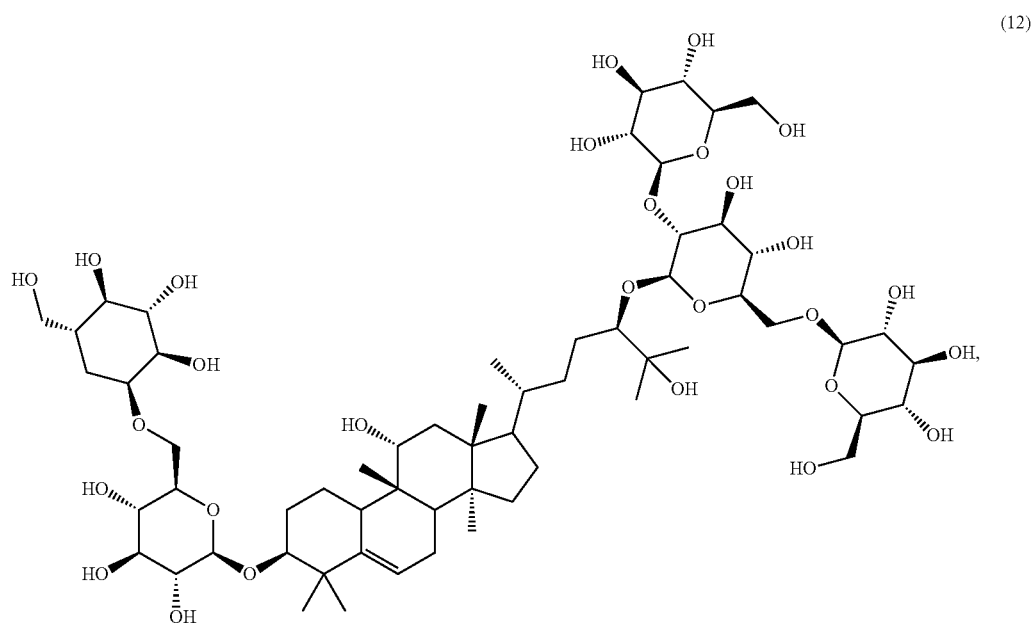 [SMILES: C[C@H](CC[C@@H](O[C@@H]1O[C@H](CO[C@@H]2O[C@H](CO)[C@@H](O)[C@H](O)[C@H]2O)[C@@H](O)[C@H](O)[C@H]1O[C@@H]1O[C@H](CO)[C@@H](O)[C@H](O)[C@H]1O)C(C)(C)O)C1CC[C@@]2(C)C3CC=C4C(CC[C@H](O[C@@H]5O[C@H](CO[C@H]6C[C@H](CO)[C@@H](O)[C@H](O)[C@H]6O)[C@@H](O)[C@H](O)[C@H]5O)C4(C)C)[C@]3(C)[C@H](O)C[C@]12C]
(12)
comprising treating mogroside VI with invertase from bakers yeast.

Some embodiments provide methods of making a compound of Compound 13,
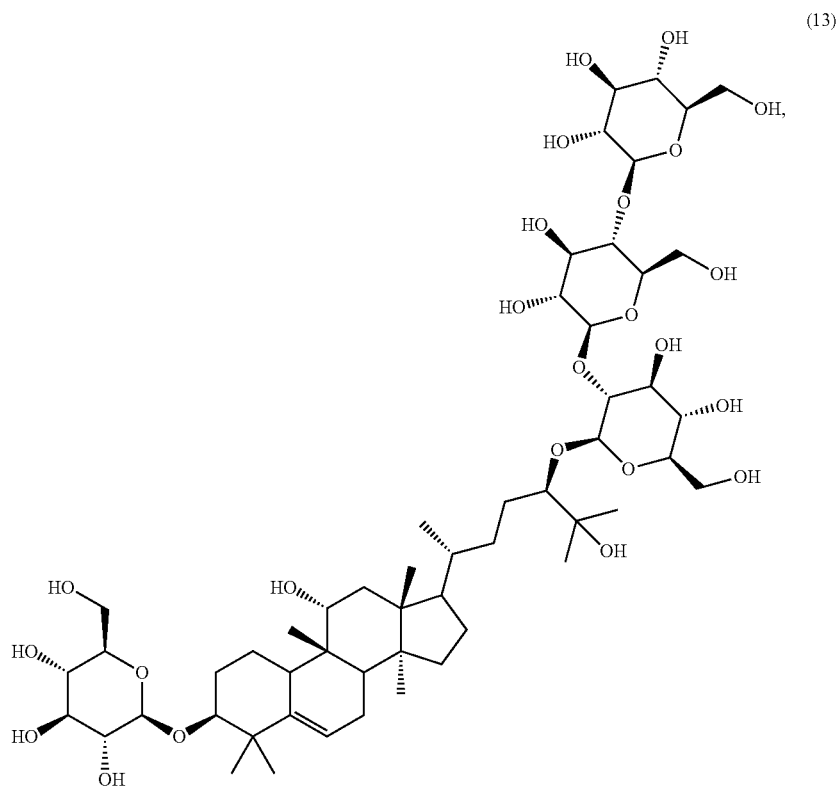 [SMILES: C[C@H](CC[C@@H](O[C@@H]1O[C@H](CO)[C@@H](O)[C@H](O)[C@H]1O[C@@H]1O[C@H](CO)[C@@H](O[C@@H]2O[C@H](CO)[C@@H](O)[C@H](O)[C@H]2O)[C@H](O)[C@H]1O)C(C)(C)O)C1CC[C@@]2(C)C3CC=C4C(CC[C@H](O[C@@H]5O[C@H](CO)[C@@H](O)[C@H](O)[C@H]5O)C4(C)C)[C@]3(C)[C@H](O)C[C@]12C]
(13)
comprising treating mogroside III$_E$ with celluclast in the presence of alpha lactose.
Some embodiments provide methods of making a compound of Compound 5,
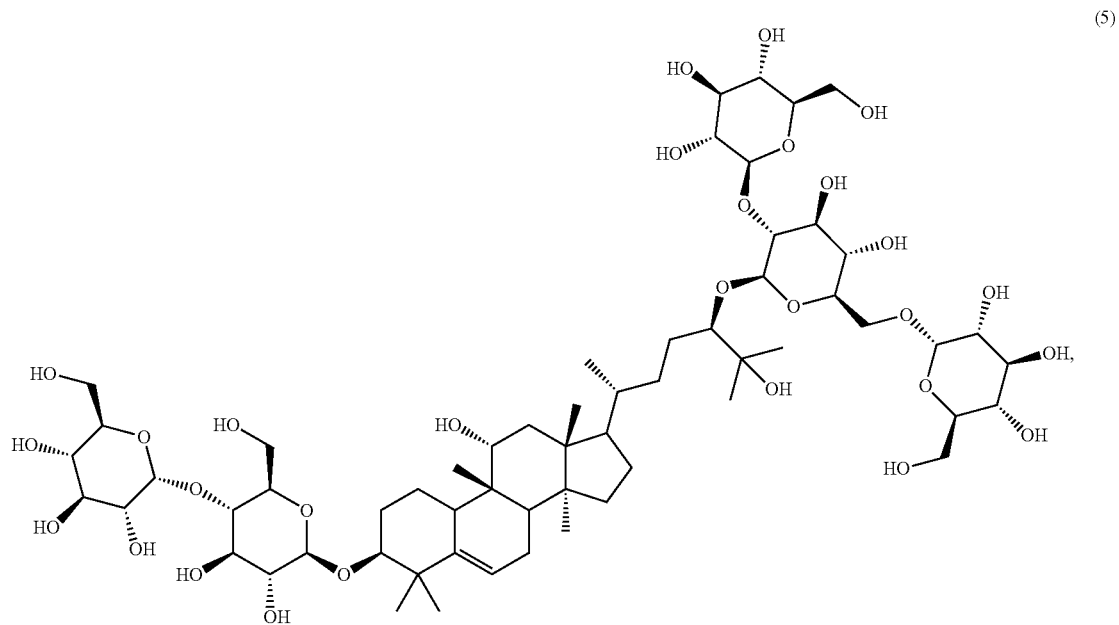 [SMILES: C[C@H](CC[C@@H](O[C@@H]1O[C@H](CO[C@H]2O[C@H](CO)[C@@H](O)[C@H](O)[C@H]2O)[C@@H](O)[C@H](O)[C@H]1O[C@@H]1O[C@H](CO)[C@@H](O)[C@H](O)[C@H]1O)C(C)(C)O)C1CC[C@@]2(C)C3CC=C4C(CC[C@H](O[C@@H]5O[C@H](CO)[C@@H](O[C@H]6O[C@H](CO)[C@@H](O)[C@H](O)[C@H]6O)[C@H](O)[C@H]5O)C4(C)C)[C@]3(C)[C@H](O)C[C@]12C]
(5)
comprising treating mogroside II$_E$ with cyclomaltodextrin glucanotransferase in the presence of starch.

Some embodiments provide methods of making a compound of Compound 4,

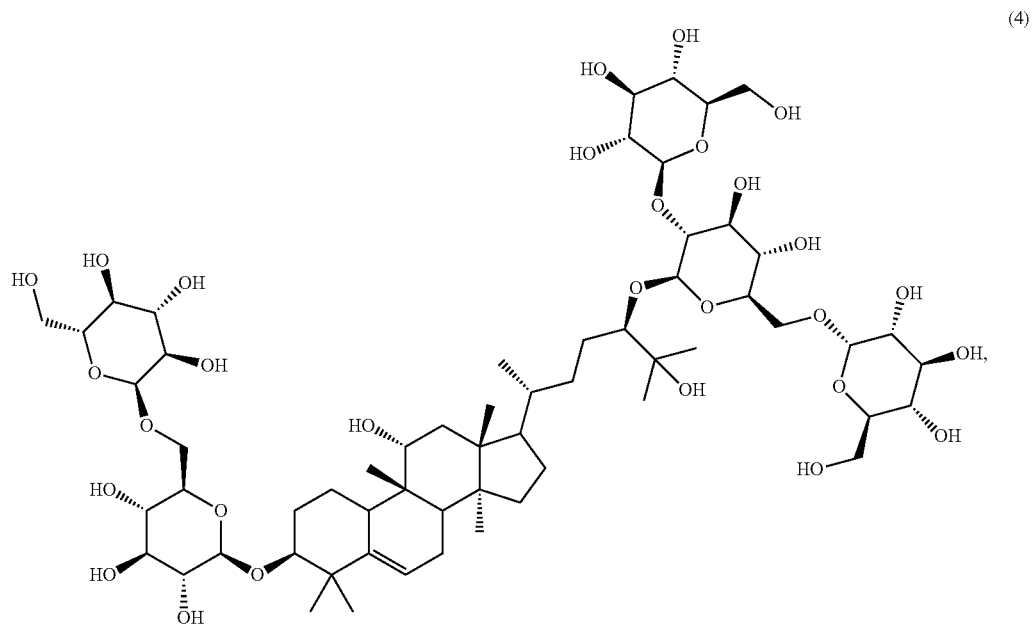 [SMILES: C[C@H](CC[C@@H](O[C@@H]1O[C@H](CO[C@H]2O[C@H](CO)[C@@H](O)[C@H](O)[C@H]2O)[C@@H](O)[C@H](O)[C@H]1O[C@@H]1O[C@H](CO)[C@@H](O)[C@H](O)[C@H]1O)C(C)(C)O)C1CC[C@@]2(C)C3CC=C4C(CC[C@H](O[C@@H]5O[C@H](CO[C@H]6O[C@H](CO)[C@@H](O)[C@H](O)[C@H]6O)[C@@H](O)[C@H](O)[C@H]5O)C4(C)C)[C@]3(C)[C@H](O)C[C@]12C]

(4)

comprising treating mogroside II$_E$ with cyclomaltodextrin glucanotransferase in the presence of starch.

EXAMPLES

Example 1: Isolation of Mogroside V

A powdered extract of *Siraitia grosvenorii* (*Fructus momordicae* extract, 50% mogroside, light yellow powder) was obtained from Xi'an Heking Bio-tech Co., Ltd. Samples of about 1.00 g were carefully weighed and dissolved in 7.0 mL of water and split into 2 equal injections. A total of 60 injections were run in this manner with a combined weight of 30.0 g of the *Fructus momordicae* extract. Purifications were done on a Waters Auto-purification system using Atlantis T3 C18 column (5×10 cm) with an ACN/water gradient. The method was t=0 min., 1%, 50 mL/min→t=0.75 min., 1%, 100 mL/min; t=2.00 min., 1%, 100 mL/min; t=2.10 min., 10%, 100 mL/min; t=30.1 min., 30%, 100 mL/min; t=30.2 min., 95%, 100 mL/min; t=35.2 min, 95%, 100 mL/min; t=35.3 min., 1%, 100 mL/min; t=42.3 min., 1%, 100 mL/min by collecting from 20.0 min. to 30.8 min. (36 fractions, 30 mL each). The desired compound was eluted in fractions 16 and 17. These FractionFractions were pooled and removed the solvent by rotary evaporation or on

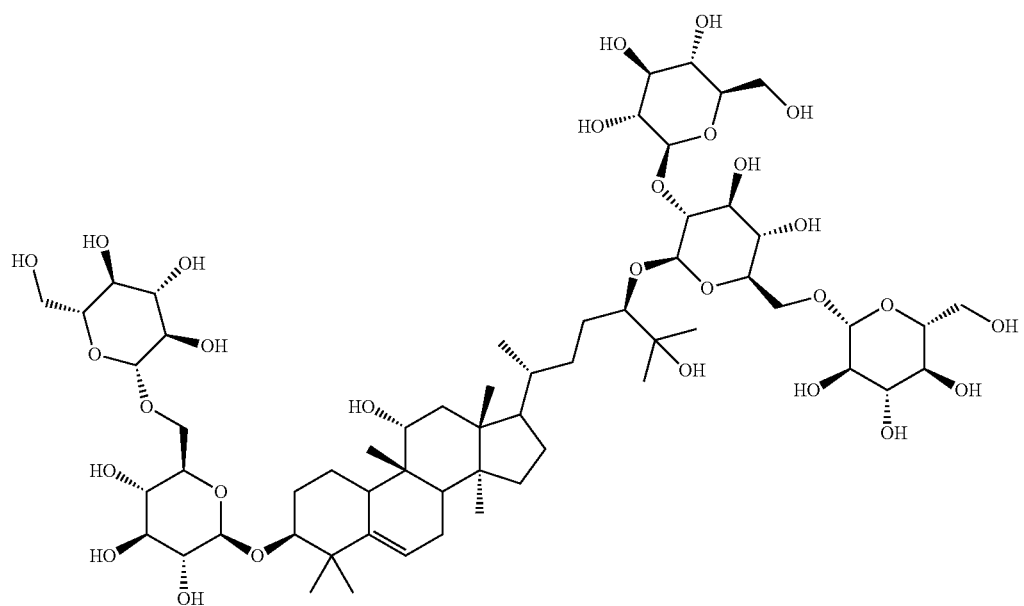

the Genevac HT12/HT24. The dried pooled sample was re-suspended in 15 mL of water and dried it again on the Genevac HT 12/HT24 followed by lyophilization for about 2 days to give 8.15g of pure Mogroside V as a white crystalline solid with ≥95% purity.

$^1$H NMR (400 MHz, Pyridine-d), selected signals: δ 5.48 (d, J=7.8 Hz, 2H, 6-H & $G_3$-1-H), 5.19 (d, J=7.7 Hz, 1H, $G_1$-1H), 4.93 (d, J=8.0 Hz, 2H, $G_2$ & $G_4$-1-H), 4.89 (d, J=7.6 Hz, 1H, $G_5$-1-H), 3.79-3.74 (m, 1H, 24-H), 3.69 (brs, 1H, 3-H), 1.53 (s, 3H, 29-Me), 1.46 (s, 3H, 27-Me), 1.34 (s, 6H, 26 and 28-Me), 1.09 (d, J=7.4 Hz, 3H, 21-Me), 1.07 (s, 3H, 19-Me), 0.92 (s, 6H, 18 & 30-Me): Exchangeable protons identified by $D_2O$ exchange in pyridine-d sample. ESIMS 1285.86 (M–H)$^-$.

Example 2: Isolation and Enzymatic Production of Siamenoside I time=45 minutes). Each run was collected in 12 tared tubes (12 fractions/plate, 1 plate per run) at 30 mL/fraction. Fractions containing the desired peak with the desired purity were pooled based on UPLC analysis and dried under reduced pressure to give a whitish powdery solid. The pure compound was re-suspended/dissolved in 10 mL of water and lyophilized to get 2.14 g of fluffy white solid with 95% purity.

Enzyme hydrolysis: To a 250 mL erlenmeyer flask, 2g of mogroside V, 100 mL of 0.1 M sodium acetate buffer pH5.0 and 1 mL pectinase from *Aspergillus aculeatus* were added and shaken the flask at 30° C. The progress of the reaction was monitored periodically by LC-MS. After 16 hours, the reaction was stopped by heating at 80° C. for 30 minutes and centrifuged at 4000 rpm for 10 minutes. The supernatant was dried under reduced pressure and fractionated on a 60g C18 column using a standard 5/35/70/100 MeOH:$H_2O$ step gradient. The desired products were eluted in 70% MeOH

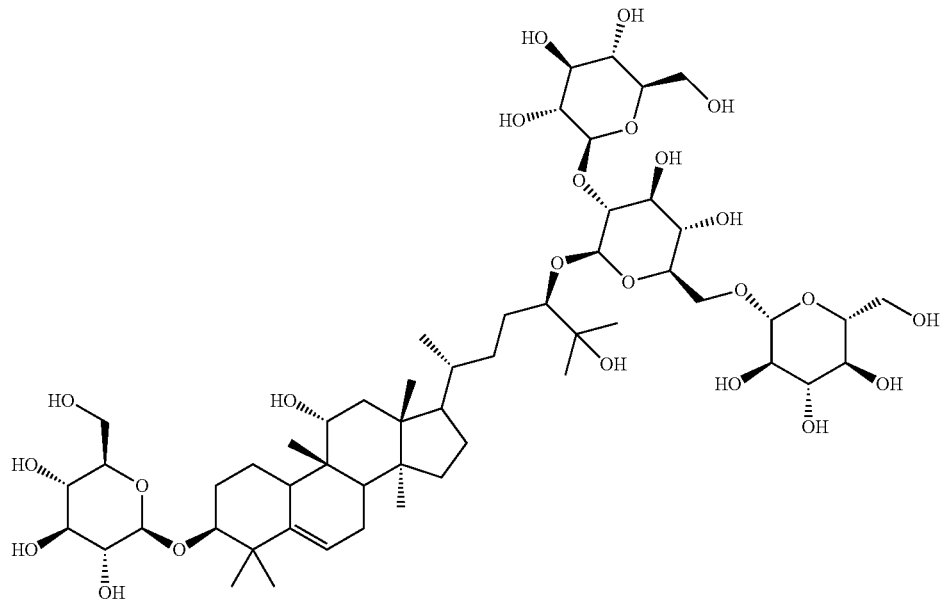 [SMILES: C[C@H](CC[C@@H](O[C@@H]1O[C@H](CO[C@@H]2O[C@H](CO)[C@@H](O)[C@H](O)[C@H]2O)[C@@H](O)[C@H](O)[C@H]1O[C@@H]1O[C@H](CO)[C@@H](O)[C@H](O)[C@H]1O)C(C)(C)O)C1CC[C@@]2(C)C3CC=C4C(CC[C@H](O[C@@H]5O[C@H](CO)[C@@H](O)[C@H](O)[C@H]5O)C4(C)C)[C@]3(C)[C@H](O)C[C@]12C]

Isolation: 100 g of *Siraitia grosvenorii* powdered extract (*Fructus momordicae* extract, 50% mogrosides, light yellow powder) was obtained from Xi'an Heking Bio-tech Co., Ltd. was fractionated on C18 HPLC (5×10 cm Atlantis prep T3 OBD column, 5 um, Waters) by 200 injections using an A/B gradient (A=water B=acetonitrile) of 1030% B over 30 minutes, with a 95% B wash, followed by re-equilibration at 1% (total run time=42 minutes). Each run was collected in 36 tared tubes (12 fractions/plate, 3 plates per run) at 30 mL/fraction. The plates were dried in the Genevac HT12/HT24. The desired compound was eluted in Fraction 21 along with other isomers. The pooled Fraction 21 (3.3g) was further fractionated in 47 runs on fluoro-phenyl HPLC column (3×10 cm, Xselect fluoro-phenyl OBD column, 5 um, Waters) using an A/B gradient (A=water, B=acetonitrile) of 15→30% B over 35 minutes, with a 95% B wash, followed by re-equilibration at 15% (total run fraction. The 70% SPE frxn (2g) was further purified on reversed phase-HPLC column (3×10 cm Atlantis T3 OBD column, 5 um, Waters) using an A/B gradient (A=water, B=acetonitrile) of 10 to 30% B over 30 minutes, with 95% B wash, followed by re-equilibration at 10% (total run time=42 minutes). Each run was collected in 12 tubes (12 fractions/plate, 1 plate per run) at 30 mL/fraction over 8 injections. Fractions containing the desired peak with the desired purity were pooled based on UPLC analysis and dried under reduced pressure to give a whitish powdery solid. The pure compound was re-suspended/dissolved in 2 mL of water and lyophilized to get 283 mg of white fluffy solid with ~90% purity.

$^1$H NMR (400 MHz, Pyridine-$d_5$), selected signals: δ 5.48 (m, 2H, 6 & $G_3$-1-H), 4.93 (d, J=7.9 Hz, 1H, $G_1$-1-H), 4.89 (m, 2H, $G_2$ & $G_4$-1-H), 3.76 (d, J=7.9 Hz, 1H, 24-H), 3.66 (d, J=2.7 Hz, 1H, 3-H), 1.56 (s, 3H, 29-Me), 1.46 (s, 3H, 27-Me), 1.34 (s, 6H, 26 & 28-Me), 1.12 (s, 3H, 19-Me), 1.07 (d, J=6.3 Hz, 3H, 21-Me), 0.92 (s, 6H, 18 & 30-Me); ESI-MS, 1123.83 (M–H)$^-$; Molecular formula, $C_4H_{92}O_{24}$.

Example 3: Isolation and Enzymatic Production of Mogroside IV$_E$

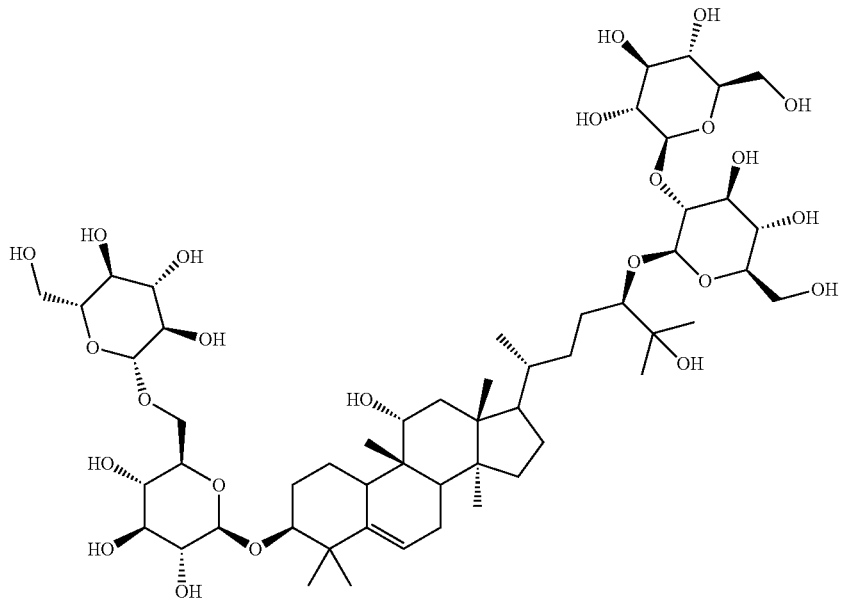 [SMILES: C[C@H](CC[C@@H](O[C@@H]1O[C@H](CO)[C@@H](O)[C@H](O)[C@H]1O[C@@H]1O[C@H](CO)[C@@H](O)[C@H](O)[C@H]1O)C(C)(C)O)C1CC[C@@]2(C)C3CC=C4C(CC[C@H](O[C@@H]5O[C@H](CO[C@@H]6O[C@H](CO)[C@@H](O)[C@H](O)[C@H]6O)[C@@H](O)[C@H](O)[C@H]5O)C4(C)C)[C@]3(C)[C@H](O)C[C@]12C]

Isolation: 11 g of *Siraitia grosvenorii* powdered extract (*Fructus momordicae* extract, 50% mogrosides, light yellow powder) was obtained from Xi'an Heking Bio-tech Co., Ltd. was fractionated on C18 HPLC (5×10 cm Atlantis prep T3 OBD column, 5 um, Waters) by 22 injections using an A/B gradient (A=water+0.1% formic acid, B=acetonitrile) of 10-30% B over 30 minutes, with a 95% B wash, followed by re-equilibration at 1% (total run time=42 minutes). Each run was collected in 36 tared tubes (12 fractions/plate, 3 plates per run) at 30 mL/fraction. The plates were dried in the Genevac HT12/HT24. The desired compound was eluted in FractionFractions 25 along with other isomers. The pooled Fraction 25 (275 mg) was further fractionated in 4 runs on fluoro-phenyl HPLC (3×10 cm, Xselect fluoro-phenyl OBD column, 5 um, Waters) using an A/B gradient (A=water, B=acetonitrile) of 15→30% B over 35 minutes, with a 95% B wash, followed by re-equilibration at 15% (total run time=45 minutes). Each run was collected in 12 tared tubes (12 fractions/plate, 1 plate per run) at 30 mL/fraction. Fractions containing the desired peak with the desired purity were pooled based on UPLC analysis and dried under reduced pressure to give a whitish powdery solid. The pure compound was re-suspended/dissolved in 5 mL of water and lyophilized to get 140 mg of fluffy white solid with ≥95% purity.

Enzyme hydrolysis: To a 250 mL erlenmeyer flask, 2g of mogroside V, 100 mL of 0.1 M sodium acetate buffer pH5.0 and 1 mL pectinase from *Aspergillus aculeatus* were added and shaken the flask at 30° C. The progress of the reaction was monitored periodically by LC-MS. After 16 hours, the reaction was stopped by heating at 80° C. for 30 minutes and centrifuged at 4000 rpm for 10 minutes. The supernatant was dried under reduced pressure and fractionated on a 60g C18 column using a standard 5/35/70/100 MeOH:H$_2$O step gradient. The desired products were eluted in 70% MeOH fraction. The 70% SPE frxn (2g) was further purified on reversed phase-HPLC column (3×10 cm Atlantis T3 OBD column, 5 um, Waters) using an A/B gradient (A=water, B=acetonitrile) of 10 to 30% B over 30 minutes, with 95% B wash, followed by re-equilibration at 10% (total run time=42 minutes). Each run was collected in 12 tubes (12 fractions/plate, 1 plate per run) at 30 mL/fraction over 8 injections. Fractions containing the desired peak with the desired purity were pooled based on UPLC analysis and dried under reduced pressure to give a whitish powdery solid. The pure compound was re-suspended/dissolved in 2 mL of water and lyophilized to get 232 mg of white fluffy solid with ~90% purity.

$^1$H NMR (400 MHz, Pyridine-d$_5$), selected signals: δ 5.42 (1H, merged with HDO peak), 5.35 (d, J=7.8 Hz, 1H), 5.11 (d, J=7.8 Hz, 1H), 5.01 (d, J=7.8 Hz, 1H), 4.77 (d, J=7.9 Hz, 1H), 3.66 (s, 1H), 1.46 (s, 6H), 1.41 (s, 3H), 1.29 (s, 3H), 1.07 (s, 3H), 1.02 (d, J=6.3 Hz, 3H), 0.83 (s, 3H), 0.82 (s, 3H); ESI-MS 1147.6 (M+Na)$^+$, 1123.80 (M−H)$^−$; Molecular formula, C$_{54}$H$_{92}$O$_{24}$.

Example 4: Isolation of Iso-Mogroside V

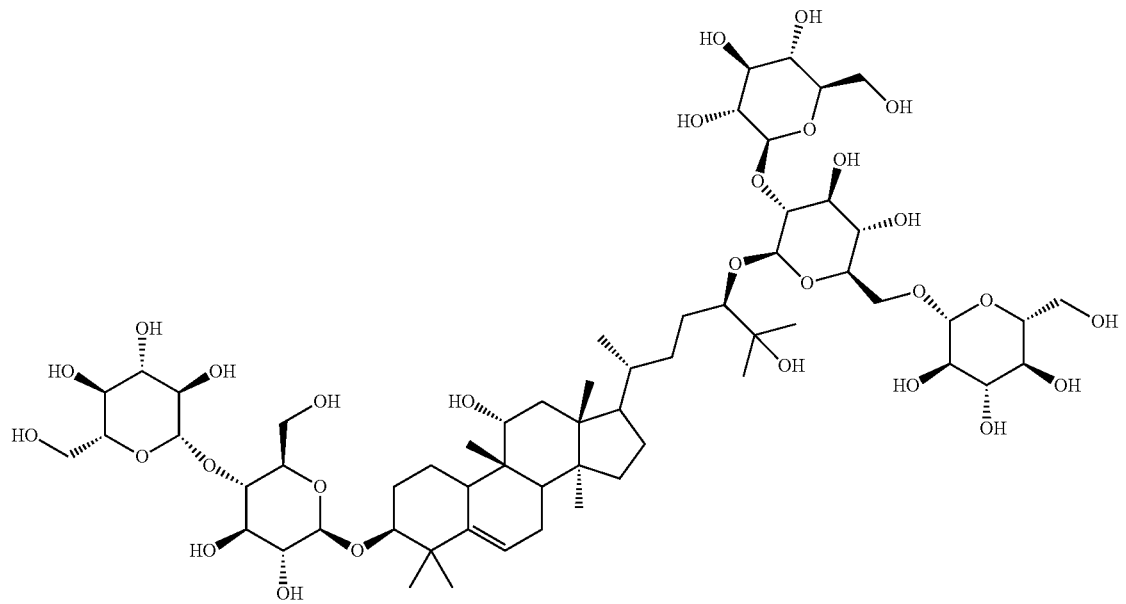 [SMILES: C[C@H](CC[C@@H](O[C@@H]1O[C@H](CO[C@@H]2O[C@H](CO)[C@@H](O)[C@H](O)[C@H]2O)[C@@H](O)[C@H](O)[C@H]1O[C@@H]1O[C@H](CO)[C@@H](O)[C@H](O)[C@H]1O)C(C)(C)O)C1CC[C@@]2(C)C3CC=C4C(CC[C@H](O[C@@H]5O[C@H](CO)[C@@H](O[C@@H]6O[C@H](CO)[C@@H](O)[C@H](O)[C@H]6O)[C@H](O)[C@H]5O)C4(C)C)[C@]3(C)[C@H](O)C[C@]12C]

180 g of *Siraitia grosvenorii* powdered extract (*Fructus momordicae* extract, 50% mogrosides, light yellow powder) was obtained from Xi'an Heking Bio-tech Co., Ltd. was fractionated on C18 HPLC (5×10 cm Atlantis prep T3 OBD column, 5 um, Waters) by 360 injections using an A/B gradient (A=water, B=acetonitrile) of 10-30% B over 30 minutes, with a 95% B wash, followed by re-equilibration at 1% (total run time=42 minutes). Each run was collected in 36 tared tubes (12 fractions/plate, 3 plates per run) at 30 mL/fraction. The plates were dried in the Genevac HT12/HT24. The desired compound was eluted in Fraction 19 along with other isomers. The pooled Fraction 19 (3.6 g) was further fractionated in 49 runs on Hilic HPLC column (3×10 cm, XBridge amide column, 5 um, Waters) using an A/B gradient (A=3:1 MeOH:H$_2$O, B=acetonitrile) of 80 to 20% B over 22 minutes, with a 95% A wash followed by re-equilibration at 80% (total run time=30.3 minutes). Each run was collected in 12 fractions (12 fractions/plate, 1 plate per run) at 30 mL/fraction. Fraction 8 and 9 contained the desired product and was pooled, concentrated under reduced pressure followed by the addition of 5 mL of H$_2$O and lyophilized the sample for 72 hours to get 1.05 g of fluffy white solid with 95% purity.

$^1$H NMR (400 MHz, Methanol-d$_4$), selected signals: δ 5.49 (d, J=6.0 Hz, 1H, 6-H), 4.78 (d, J=7.7 Hz, 1H, G1-1H), 4.44 (d, J=7.3 Hz, 1H, G2-1H), 4.41 (d, J=7.8 Hz, 1H, G3-1H), 4.31 (d, J=7.8 Hz, 1H, G4-1H), 4.28 (d, J=7.8 Hz, 1H, G5-1H), 1.19 (s, 3H, 29-Me), 1.15 (s, 3H, 27-Me), 1.11 (s, 6H, 26 & 19-Me), 1.08 (s, 3H, 28-Me), 0.98 (d, J=6.1 Hz, 3H, 21-Me), 0.92 (s, 3H, 30-Me), 0.89 (s, 3H, 18-Me); ESI-MS 1285.67 (M−H)$^−$; Molecular formula, C$_{60}$H$_{102}$O$_{29}$.

Example 5: Isolation and Enzymatic Production of Mogroside III$_E$

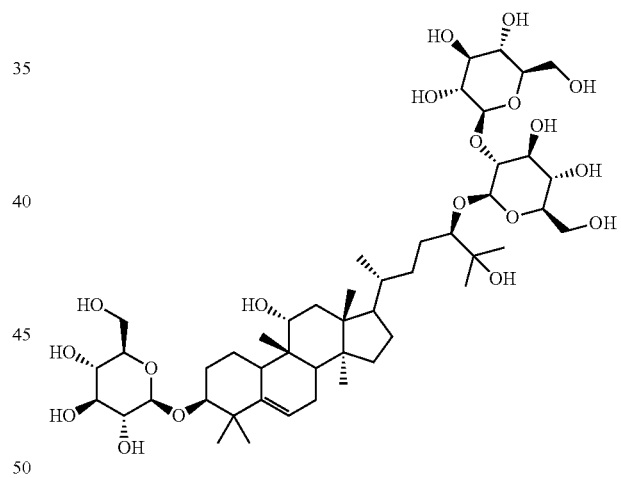

Isolation: 11 g of *Siraitia grosvenorii* powdered extract (*Fructus momordicae* extract, 50% mogrosides, light yellow powder) was obtained from Xi'an Heking Bio-tech Co., Ltd. was fractionated on C18 HPLC (5×10 cm Atlantis prep T3 OBD column, 5 um, Waters) by 22 injections using an A/B gradient (A=water+0.1% formic acid, B=acetonitrile) of 10→30% B over 30 minutes, with a 95% B wash, followed by re-equilibration at 1% (total run time=42 minutes). Each run was collected in 36 tared tubes (12 fractions/plate, 3 plates per run) at 30 mL/fraction. The plates were dried in the Genevac HT12/HT24 (lot 1). The same HPLC conditions with a slight change in the mobile phase (A=water, B=acetonitrile) were used to fractionate additional 14 g of the powder and dried the FractionFractions on Genevac HT 12/HT24 (lot 2). The desired compound was eluted in Fraction 30 along with other isomers. The pooled Fraction 30 from lot 1 and 2 (204 mg) was further fractionated in 4 runs on fluoro-phenyl HPLC column (3×10 cm, Xselect fluoro-phenyl OBD column, 5 um, Waters) using an A/B gradient (A=water, B=acetonitrile) of 15→30% B over 35 minutes, with a 95% B wash, followed by re-equilibration at 15% (total run time=45 minutes). Each run was collected in 12 tared tubes (12 fractions/plate, 1 plate per run) at 30 mL/fraction. Fractions containing the desired peak with the desired purity were pooled based on UPLC analysis and dried under reduced pressure to give a whitish powdery solid. The pure compound was re-suspended/dissolved in 5 mL of water and lyophilized to get 80 mg of fluffy white solid with ≥95% purity.

Enzyme hydrolysis: To a 2-L Erlenmeyer flask, 100g of mogrosides 50% powder (*Fructus momordicae* extract, 50% mogrosides, light yellow powder; from Xi'an Heking Bio-tech Co., Ltd.), 1 L of 0.1 M sodium acetate buffer, pH5.0 and 30 mL pectinase from *Aspergillus aculeatus* (from Sigma, catalog #E6287) was added and shook the flask at 50° C. in the shaker oven. The progress of the reaction was monitored by LC-MS analysis. After 24 hours, the reaction was stopped by heating the flask at 80° C. for 30 minutes and centrifuged at 4000 rpm for 10 minutes to remove the unreacted enzyme precipitate. The supernatant was dried under reduced pressure and fractionated on a 400g C18 column using a standard 5/35/70/100 MeOH:H$_2$O gradient in multiple runs (~10g each run). The desired mogroside III$_E$ was eluted in 70% MeOH fraction and pooled all the runs to get 60g of enriched Fraction. About 19g of the 70% MeOH fraction was further purified on RP-HPLC in 21 runs using C18 HPLC (5×10 cm Atlantis T3 OBD column, 5 um, Waters) using an A/B gradient (A=water, B=acetonitrile) of 10-30% B over 30 minutes, with a 95% B wash, followed by re-equilibration at 10% (total run time=42 minutes). Each run was collected in 36 tubes (12 fractions/plate, 3 plates per run) at 30 mL/fraction. Fractions containing the desired peak with the desired purity were pooled based on UPLC analysis and dried under reduced pressure to give a whitish powdery solid. The pure compound was re-suspended/dissolved in 20 mL of water and lyophilized to get 4.41g of fluffy white solid with ≥95% purity.

$^1$H NMR (400 MHz, Pyridine-d), selected signals: δ 5.48 (m, 1H, 6-H), 5.35 (d, J=7.7 Hz, 1H, G2-1H), 5.10 (d, J=7.7 Hz, 1H, G1-1H), 4.91 (d, J=7.8 Hz, 1H, G3-1H), 3.93 (m, 1H, 24-H), 3.68 (s, 1H, 3-H), 1.57 (s, 1H, 26-Me), 1.50 (s, 1H, 29-Me), 1.46 (s, 3H, 27-Me), 1.33 (s, 3H, 19-Me), 1.14 (s, 3H, 28-Me), 1.06 (d, J=6.3 Hz, 3H, 21-Me), 0.89 (s, 3H, 30-Me), 0.88 (s, 3H, 18-Me); ESI-MS 985.59 (M+Na)$^+$, 961.71 (M−H)$^−$; Molecular formula, C$_{48}$H$_{82}$O$_{19}$.

Example 6: Isolation of 11-Deoxy-Mogroside V

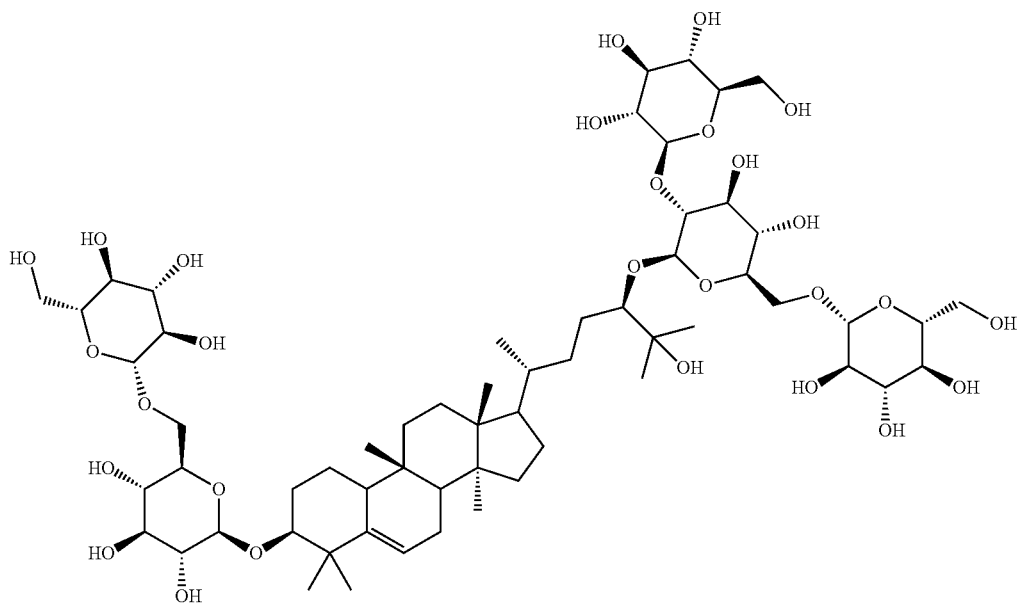 [SMILES: C[C@H](CC[C@@H](O[C@@H]1O[C@H](CO[C@@H]2O[C@H](CO)[C@@H](O)[C@H](O)[C@H]2O)[C@@H](O)[C@H](O)[C@H]1O[C@@H]1O[C@H](CO)[C@@H](O)[C@H](O)[C@H]1O)C(C)(C)O)C1CC[C@@]2(C)C3CC=C4C(CC[C@H](O[C@@H]5O[C@H](CO[C@@H]6O[C@H](CO)[C@@H](O)[C@H](O)[C@H]6O)[C@@H](O)[C@H](O)[C@H]5O)C4(C)C)[C@]3(C)CC[C@]12C]

11 g of *Siraitia grosvenorii* powdered extract (*Fructus momordicae* extract, 50% mogrosides, light yellow powder) was obtained from Xi'an Heking Bio-tech Co., Ltd. was fractionated on C18 HPLC (5×10 cm Atlantis prep T3 OBD column, 5 um, Waters) by 22 injections using an A/B gradient (A=water+0.1% formic acid, B=acetonitrile) of 10→30% B over 30 minutes, with a 95% B wash, followed by re-equilibration at 1% (total run time=42 minutes). Each run was collected in 36 tared tubes (12 fractions/plate, 3 plates per run) at 30 mL/fraction. The plates were dried in the Genevac HT12/HT24 (lot 1). The same HPLC conditions with a slight change in the mobile phase (A=water, B=acetonitrile) were used to fractionate additional 14 g of the powder and dried the FractionFractions on Genevac HT12/HT24 (lot 2). The desired compound was eluted in FractionFractions 32 and 33 in both lots along with other minor isomers. The pooled FractionFractions 32 and 33 (275 mg; dissolved in 3 mL of H$_2$O) were further fractionated in 4 HPLC runs on fluoro-phenyl column (3×10 cm, Xselect fluoro-phenyl OBD column, 5 um, Waters) using an A/B gradient (A=water, B=acetonitrile) of 15→30% B over 35 minutes, with a 95% B wash, followed by re-equilibration at 15% (total run time=45 minutes). Each run was collected in 12 tared tubes (12 fractions/plate, 1 plate per run) at 30 mL/fraction. Fractions containing the desired peak with the desired purity were pooled based on UPLC analysis and dried under reduced pressure to give a whitish powdery solid. The pure compound was re-suspended/dissolved in 5 mL of water and lyophilized to get 140 mg of fluffy white solid with ≥95% purity.

$^1$H NMR (400 MHz, Pyridine-d$_5$), selected signals: δ 5.49 (d, J=7.7 Hz, 1H, G3-1-H)), 5.45 (m, 1H, 6-H), 5.23 (d, J=7.7 Hz, 1H, G5-1-H), 4.94 (m, 1H, G1-1-H), 4.89 (m, 1H, G2-1-H), 4.84 (d, J=7.8 Hz, 1H, G4-1-H), 3.78 (m, 1H, H-24), 3.70 (brs, 1H, H-3), 1.52 (s, 3H, 27-Me), 1.47 (s, 3H, 29-Me), 1.36 (s, 3H, 26-Me), 1.09 (d, J=6.2 Hz, 3H, 21-Me), 1.04 (s, 3H, 28-Me), 0.89 (s, 3H, 19-Me), 0.84 (s, 3H, 18-Me), 0.80 (s, 3H, 30-Me). ESI-MS 1293.8 (M+Na)$^+$, 1269.8 (M−H)$^-$; Molecular formula, $C_{60}H_{102}O_{28}$.

Example 7: Isolation of 11—Oxo-Mogroside V

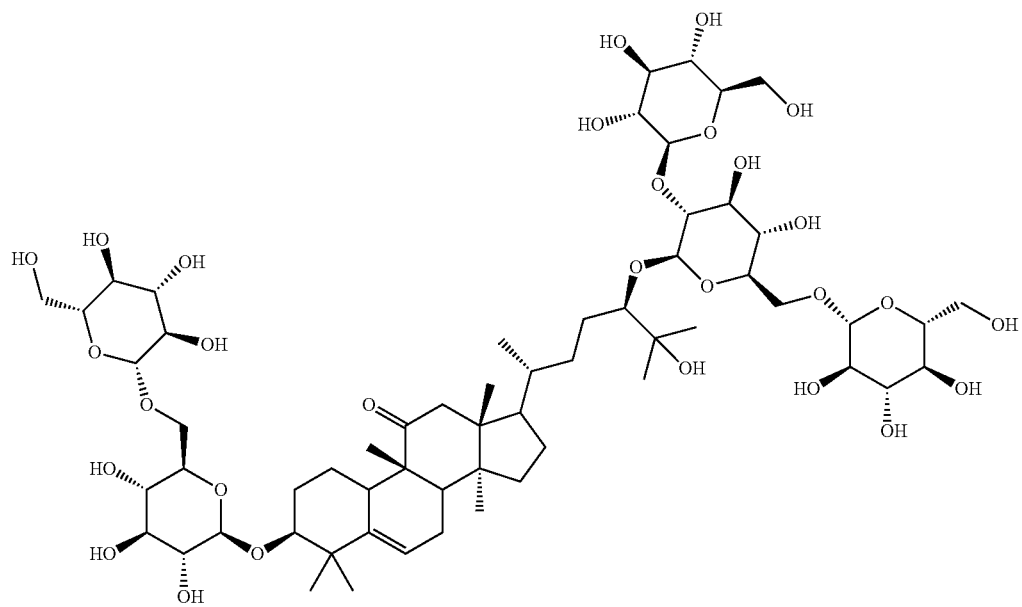 [SMILES: C[C@H](CC[C@@H](O[C@@H]1O[C@H](CO[C@@H]2O[C@H](CO)[C@@H](O)[C@H](O)[C@H]2O)[C@@H](O)[C@H](O)[C@H]1O[C@@H]1O[C@H](CO)[C@@H](O)[C@H](O)[C@H]1O)C(C)(C)O)C1CC[C@@]2(C)C3CC=C4C(CC[C@H](O[C@@H]5O[C@H](CO[C@@H]6O[C@H](CO)[C@@H](O)[C@H](O)[C@H]6O)[C@@H](O)[C@H](O)[C@H]5O)C4(C)C)[C@]3(C)C(=O)C[C@]12C]

11 g of *Siraitia grosvenorii* powdered extract (*Fructus momordicae* extract, 50% mogrosides, light yellow powder) was obtained from Xi'an Heking Bio-tech Co., Ltd. was fractionated on C18 HPLC (5×10 cm Atlantis prep T3 OBD column, 5 um, Waters) by 22 injections using an A/B gradient (A=water+0.1% formic acid, B=acetonitrile) of 10→30% B over 30 minutes, with a 95% B wash, followed by re-equilibration at 1% (total run time=42 minutes). Each run was collected in 36 tared tubes (12 fractions/plate, 3 plates per run) at 30 mL/fraction. The plates were dried in the Genevac HT12/HT24. The desired compound was eluted in Fraction 12 along with other isomers. The pooled Fraction 12 (582 mg) was further fractionated in 6 runs on fluoro-phenyl HPLC column (3×10 cm, Xselect fluoro-phenyl OBD column, 5 um, Waters) using an A/B gradient (A=water, B=acetonitrile) of 15→30% B over 35 minutes, with a 95% B wash, followed by re-equilibration at 15% (total run time=45 minutes). Each run was collected in 12 tared tubes (12 fractions/plate, 1 plate per run) at 30 mL/fraction. Fractions containing the desired peak with the desired purity were pooled based on UPLC analysis and dried under reduced pressure to give a whitish powdery solid. The pure compound was re-suspended/dissolved in 5 mL of water and lyophilized to get 209 mg of fluffy white solid with 95% purity.

$^1$H NMR (400 MHz, Pyridine-d), selected signals: δ 5.52 (d, J=7.8 Hz, 1H, H-6), 5.47 (d, J=6.0 Hz, 1H, G3-1-H), 5.17 (d, J=7.8 Hz, 1H, G1-1-H), 4.88 (d, J=7.8 Hz, 1H, G5-1-H), 4.82 (d, J=7.8 Hz, 1H, G2-1-H), 3.76 (m, 1H, 24-H), 3.67 (s, 1H, 3-H), 1.52 (s, 3H, 26-Me), 1.46 (s, 3H, 29-Me), 1.35 (s, 3H, 27-Me), 1.18 (s, 3H, 28-Me), 1.03 (s, 3H, 19-Me), 1.02 (d, J=6.7 Hz, 3H, 21-Me), 1.00 (s, 3H, 30-Me), 0.74 (s, 3H, 18-Me); ESI-MS 1307.45 (M+Na), 1283.81 (M−H)$^-$; Molecular formula, $C_6H_{100}O_{29}$.

Example 8: Isolation of Mogroside VI

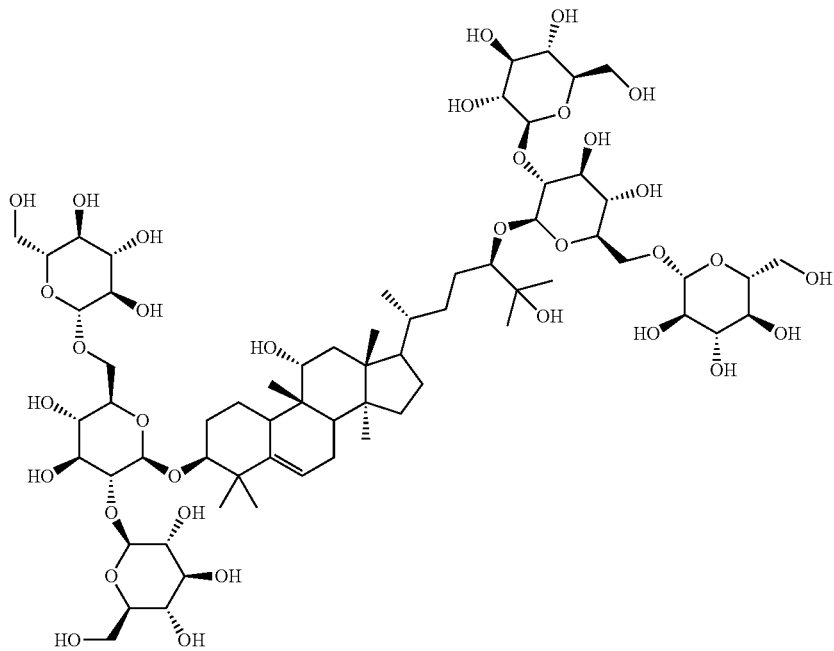 [SMILES: C[C@H](CC[C@@H](O[C@@H]1O[C@H](CO[C@@H]2O[C@H](CO)[C@@H](O)[C@H](O)[C@H]2O)[C@@H](O)[C@H](O)[C@H]1O[C@@H]1O[C@H](CO)[C@@H](O)[C@H](O)[C@H]1O)C(C)(C)O)C1CC[C@@]2(C)C3CC=C4C(CC[C@H](O[C@@H]5O[C@H](CO[C@@H]6O[C@H](CO)[C@@H](O)[C@H](O)[C@H]6O)[C@@H](O)[C@H](O)[C@H]5O[C@@H]5O[C@H](CO)[C@@H](O)[C@H](O)[C@H]5O)C4(C)C)[C@]3(C)[C@H](O)C[C@]12C]

80.2 g of *Siraitia grosvenorii* powdered extract (*Fructus momordicae* extract, 50% mogrosides, light yellow powder) was obtained from Xi'an Heking Bio-tech Co., Ltd. was fractionated on C18 HPLC (5×10 cm Atlantis prep T3 OBD column, 5 um, Waters) by 160 injections using an A/B gradient (A=water, B=acetonitrile) of 10→30% B over 30 minutes, with a 95% B wash, followed by re-equilibration at 1% (total run time=42 minutes). Each run was collected in 36 tared tubes (12 fractions/plate, 3 plates per run) at 30 mL/fraction. The plates were dried in the Genevac HT12/HT24. The desired compound was eluted in Fraction 14 along with other isomers. The pooled Fraction 14 (1.24 g) was further fractionated in 29 runs on Hilic HPLC column (3×10 cm, XBridge amide column, 5 um, Waters) using an A/B gradient (A=3:1 MeOH:H$_2$O, B=acetonitrile) of 70 to 20% B over 21 minutes, followed by re-equilibration at 70% (total run time=30.5 minutes). Each run was collected in 12 fractions (12 fractions/plate, 1 plate per run) at 30 m/fraction. Fraction 7 contained the desired product and was pooled, concentrated under reduced pressure followed by the addition and 2 mL of H$_2$O and lyophilized the sample for 48 hours to get 358 mg of fluffy white solid with 85% purity.

$^1$H NMR (400 MHz, Pyridine-d), selected signals: δ 5.5 (m, 1H, G3-1H, merged with HDO peak), 5.42 (m, 1H, 6-H), 5.19 (m, 2H, G6 & G2-1H), 4.88 (d, J=7.8 Hz, 1H, G4-1H), 4.83 (m, 2H, G1-1H), 4.77 (d, J=7.7 Hz, 1H, G5-1H), 3.69 (d, J=8.8 Hz, 1H, 24-H), 1.48 (s, 3H, 29-Me), 1.42 (s, 3H, 27-Me), 1.28 (s, 3H, 26-Me), 1.25 (s, 3H, 19-Me), 1.09 (s, 3H, 28-Me), 1.02 (d, J=6.2 Hz, 3H, 21-Me), 0.85 (s, 3H, 30-Me), 0.82 (s, 3H, 18-Me); ESI-MS 1471.51 (M+Na)$^+$, 1447.83 (M−H)$^−$; Molecular formula, C$_{66}$H$_{112}$O$_{34}$.

Example 9: Isolation and Enzymatic Production of Mogroside IV$_A$

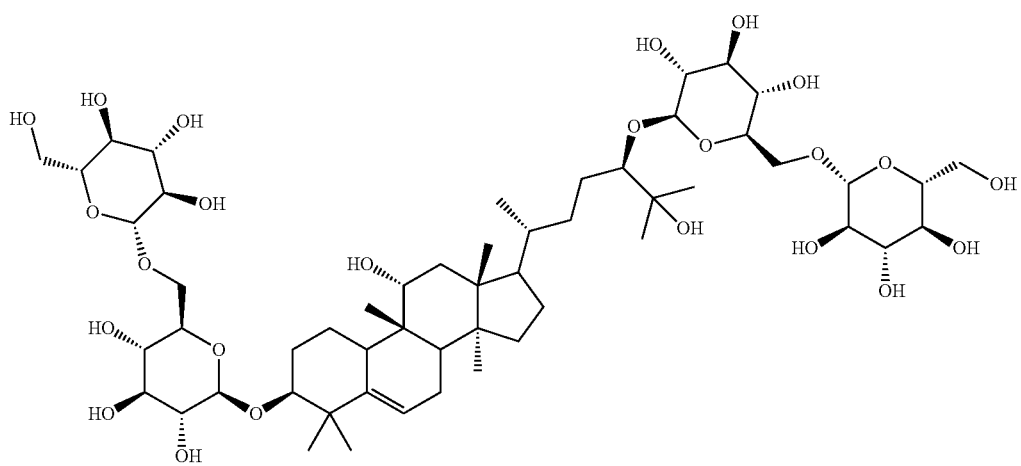 [SMILES: C[C@H](CC[C@@H](O[C@@H]1O[C@H](CO[C@@H]2O[C@H](CO)[C@@H](O)[C@H](O)[C@H]2O)[C@@H](O)[C@H](O)[C@H]1O)C(C)(C)O)C1CC[C@@]2(C)C3CC=C4C(CC[C@H](O[C@@H]5O[C@H](CO[C@@H]6O[C@H](CO)[C@@H](O)[C@H](O)[C@H]6O)[C@@H](O)[C@H](O)[C@H]5O)C4(C)C)[C@]3(C)[C@H](O)C[C@]12C]

Enzymatic: To a 250-mL round bottom flask, 500 mg of pure mogroside V, 50 mL of water, 1 mL of 1M pH 8.0 phosphate buffer, 2g of lactose and 500 mg of β-galactosidase from *Aspergillus oryzae* (from Sigma, catalog #G5160) was added and stirred the flask at 37° C. The progress of the reaction was monitored every hour by LC-MS. After 3 hours, the reaction was quenched with 40 mL ethanol followed by centrifugation at 4000 rpm for 10 minutes. The supernatant was dried under reduced pressure and fractionated on SPE using a standard 5/35/70/100 MeOH:H$_2$O gradient. The desired mogroside IV$_A$ was eluted in 70% Methanol fraction. 70% SPE Fraction was further purified on RP-HPLC using fluoro-phenyl HPLC (3×10 cm, Xselect fluoro-phenyl OBD column, 5 um, Waters) using an A/B gradient (A=water, B=acetonitrile) of 15-30% B over 35 minutes, with a 95% B wash, followed by re-equilibration at 15% (total run time=45 minutes). Each run was collected in 12 tared tubes (12 fractions/plate, 1 plate per run) at 30 mL/fraction. Fractions containing the desired peak with the desired purity were pooled based on UPLC analysis and dried under reduced pressure to give a whitish powdery solid. The pure compound was re-suspended/dissolved in 5 mL of water and lyophilized to get 135.9 mg of fluffy white solid with ≥95% purity.

Isolation: 100 g of *Siraitia grosvenorii* powdered extract (*Fructus momordicae* extract, 50% mogrosides, light yellow powder) was obtained from Xi'an Heking Bio-tech Co., Ltd. was fractionated on C18 HPLC (5×10 cm Atlantis prep T3 OBD column, 5 um, Waters) by 200 injections using an A/B gradient (A=water B=acetonitrile) of 10-30% B over 30 minutes, with a 95% B wash, followed by re-equilibration at 1% (total run time=42 minutes). Each run was collected in 36 tared tubes (12 fractions/plate, 3 plates per run) at 30 mL/fraction. The plates were dried in the Genevac HT12/HT24. The desired compound was eluted in frxn 22 along with other isomers. The pooled frxn 22 (947 mg) was further fractionated in 24 runs on Hilic HPLC column (3×10 cm, XBridge amide column, 5 um, Waters) using an A/B gradient (A=3:1 MeOH:H$_2$O, B=acetonitrile) of 80 to 40% B over 22 minutes, with a 95% A wash followed by re-equilibration at 80% (total run time=30.3 minutes). Each run was collected in 24 fractions (12 fractions/plate, 2 plates per run) at 30 mL/fraction. Fraction 7 contained the desired product and was pooled, concentrated under reduced pressure followed by the addition of 2 mL of H$_2$O and lyophilized the sample for 2 days to get 155 mg of fluffy white solid with ~85% purity.

$^1$H NMR (400 MHz, Pyridine-d), selected signals: δ 5.49 (d, J=6.0 Hz, 1H, 6-H), 5.19 (d, J=7.7 Hz, 1H, G4-1-H), 4.93 (m, 1H, G1-1-H), 4.87 (m, 2H, G2 & G3-1-H), 3.78 (brd, J=9.2 Hz, 1H, 24-H), 3.73 (s, 1H, 3-H), 1.54 (s, 3H, 29-Me), 1.46 (s, 3H, 26-Me), 1.33 (s, 6H, 19 & 27-Me), 1.12 (m, 3H, 28-Me), 0.94 (d, J=6.5 Hz, 3H, 21-Me), 0.92 (s, 3H, 18-Me), 0.84 (s, 3H, 30-Me); ESI-MS 1147.32 (M+Na)$^+$, 1123.66 (M−H)$^−$; Molecular formula, C$_{54}$H$_{92}$O$_{24}$.

Example 10: Enzymatic Production of Mogroside II$_A$ from Celluclast

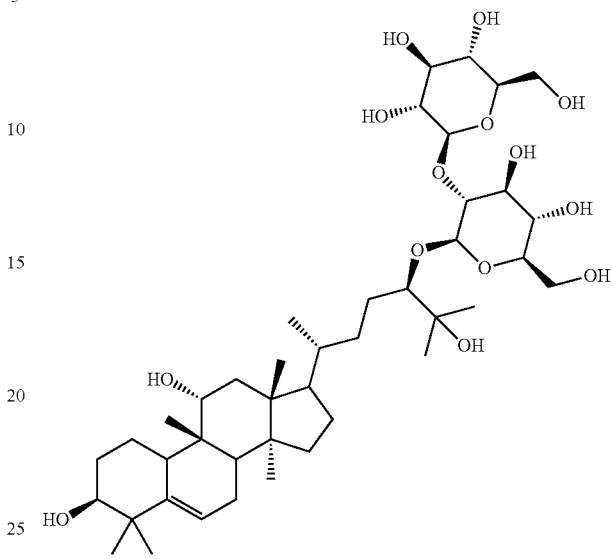

To a 250-mL baffled flask, 1 g of crude mogroside III$_E$, 53 mL of water, 15 mL of 1M sodium acetate buffer pH 5, 7 ml of Celluclast from Novozymes and 75 g of a-lactose were added and shook the flask at 220 rpm, 50° C. for 9 days. The progress of the reaction was monitored periodically by LC-MS. The same reaction was repeated 17 more times for a total of 18g of mogroside III$_E$ in two batches. After 9 days, the unreacted enzyme and excess lactose from the reaction mixtures was removed in three following steps before SPE purification. The reaction mixture was centrifuged for 10 min at 5000 rpm to remove the excess lactose followed by the incubation at 80° C. for 30 min with magnetic stirring at 500 rpm. Further approximately ~10% NH$_4$SO$_4$ solution was added to precipitate the unreacted enzymes and sugars, followed by centrifugation for 10 min at 5000 rpm and removed the precipitate. The supernatant was filtered through 0.22 m PES and loaded onto 400g SPE C18 column and fractionated using a standard 5/35/70/100 MeOH:H$_2$O gradient. The desired compound was eluted in 70% methanol fraction. The combined 70% SPE Fraction (12g) was further purified on RP-HPLC using PF column using an A/B gradient (A=water, B=acetonitrile) of 15 to 30% B over 35 minutes, with a 95% B wash, followed by re-equilibration at 15% (total run time=45 minutes). Each run was collected in 72 tubes (12 fractions/plate, 6 plates per run) at 7.5 mL/fraction in 2 collection windows of 36 fractions each. Fractions 61-66 contained the desired peak with the desired purity (≥95%) and were pooled based on UPLC analysis and dried under reduced pressure to get 530 mg of whitish powdery solid. 150 mg of a child sample was weighed out, dissolved in 2 mL of H$_2$O and lyophilized for 3 days to get a white fluffy solid.

$^1$H NMR (400 MHz, Pyridine-d), selected signals: δ 5.58 (d, J=6.0 Hz, 1H, 6-H), 5.36 (d, J=7.9 Hz, 1H, G2-1H), 5.00 (d, J=7.8 Hz, 1H, G1-1H), 3.88 (d, J=7.2 Hz, 1H, 24-H), 3.69 (d, J=3.0 Hz, 1H, 3-H), 1.46 (s, 3H, 27-Me), 1.41 (s, 3H, 26-Me), 1.38 (s, 3H, 29-Me), 1.33 (s, 3H, 19-Me), 1.14 (s, 3H, 28-Me), 1.02 (d, J=6.4 Hz, 3H, 21-Me), 0.89 (s, 3H, 30-Me), 0.84 (s, 3H, 18-Me); ESI-MS 823.56 (M+Na)$^+$, 799.6 (M−H)$^−$; Molecular formula, C$_{42}$H$_{72}$O$_{14}$.

Example 11: Enzymatic Production of Mogroside III$_{A1}$ from Aromase

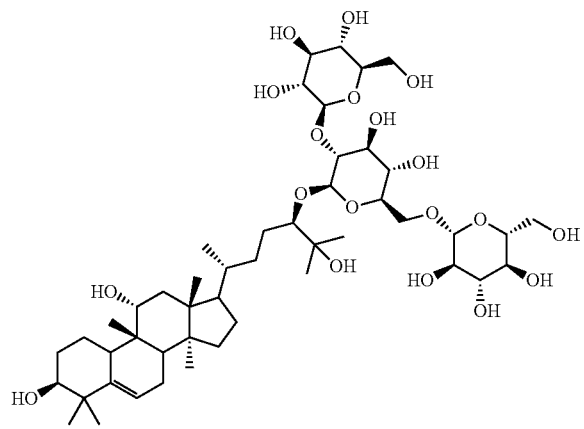 [SMILES: C[C@H](CC[C@@H](O[C@@H]1O[C@H](CO[C@@H]2O[C@H](CO)[C@@H](O)[C@H](O)[C@H]2O)[C@@H](O)[C@H](O)[C@H]1O[C@@H]1O[C@H](CO)[C@@H](O)[C@H](O)[C@H]1O)C(C)(C)O)C1CC[C@@]2(C)C3CC=C4C(CC[C@H](O)C4(C)C)[C@]3(C)[C@H](O)C[C@]12C]

10 mg of Siamenoside I was dissolved in 1 mL of 0.1M Mcilvaine's buffer (citrate/phosphate buffer system that can be volumetrically set for pH in a wide range 2.2 to 8) pH 3.4 and 5 mg of Aromase from were added to a 96-well nunc plate across 35 wells (total of 350 mg of Siamenoside I) and stirred at 50° C. Out of 35 individual reactions, couple of them was monitored periodically by LC-MS. After 6 hours, all the reactions were pooled to a flask, quenched with equal amount of ethanol and centrifuged at 4000 rpm for 10 minutes. The supernatant was dried under reduced pressure and fractionated on 60g SPE column using 5/35/70/100/5 MeOH:H$_2$O gradient. The desired product was eluted in 70% and 100% MeOH fractions and purified further on flouro-phenyl 3×10 cm column using A/B gradient (A=H$_2$O, B=acetonitrile) of 15 to 30% B over 35 minutes, followed by 95% B wash and re-equilibration (total run time=45 minutes). Each run was collected in 24 fractions (12 fractions/plate, 2 plates per run) at 30 mL/fraction. Fraction 11-12 contained the desired product and was pooled, dried down under reduced pressure and re-suspended in 5 mL of H$_2$O to get 100 mg of white fluffy powder with ≥90% purity.

$^1$H NMR (400 MHz, Pyridine-d$_5$+ D$_2$O), selected signals δ 5.59 (d, J=6.1 Hz, 1H, 6-H), 5.51 (d, J=7.8 Hz, 1H, G2-1H), 4.84 (m, 1H, G1-1H), 4.79 (d, J=7.7 Hz, 1H, G3-1H), 3.71 (d, J=9.0 Hz, 1H, 24-H), 3.68 (d, J=3.1 Hz, 1H, 3-H), 1.43 (s, 3H, 26-Me), 1.38 (s, 3H, 28-Me), 1.34 (s, 3H, 19-Me), 1.29 (s, 3H, 27-Me), 1.14 (s, 3H, 29-Me), 1.04 (d, J=6.4 Hz, 3H, 21-Me), 0.94 (s, 3H, 30-Me) and 0.87 (s, 3H, 18-Me); ESI-MS; 961.34 (M−H)$^−$; Molecular formula, C$_{48}$H$_{82}$O$_{19}$.

Example 12: Isolation of Compound 1

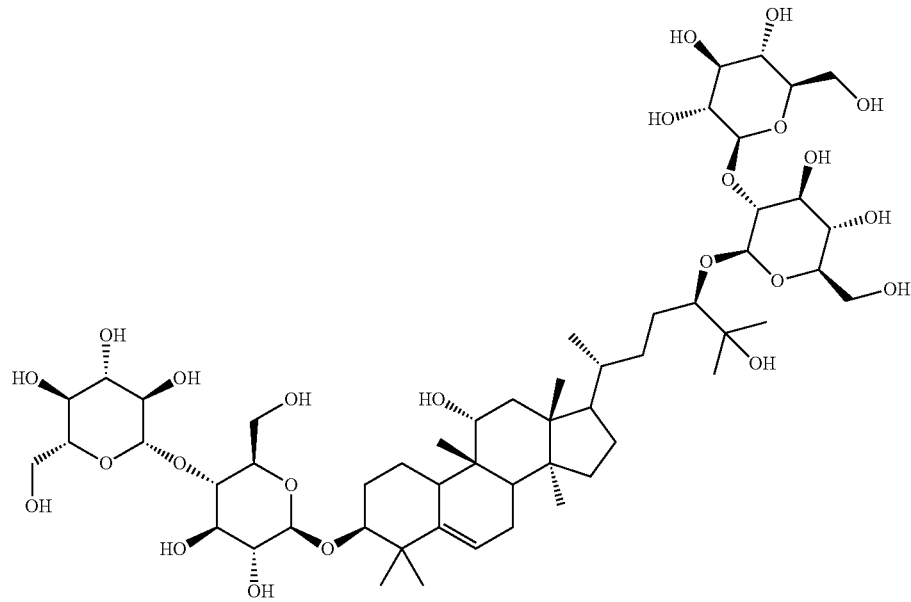 [SMILES: C[C@H](CC[C@@H](O[C@@H]1O[C@H](CO)[C@@H](O)[C@H](O)[C@H]1O[C@@H]1O[C@H](CO)[C@@H](O)[C@H](O)[C@H]1O)C(C)(C)O)C1CC[C@@]2(C)C3CC=C4C(CC[C@H](O[C@@H]5O[C@H](CO)[C@@H](O[C@@H]6O[C@H](CO)[C@@H](O)[C@H](O)[C@H]6O)[C@H](O)[C@H]5O)C4(C)C)[C@]3(C)[C@H](O)C[C@]12C]

80.2 g of *Siraitia grosvenorii* powdered extract (*Fructus momordicae* extract, 50% mogrosides, light yellow powder) was obtained from Xi'an Heking Bio-tech Co., Ltd. was fractionated on C18 HPLC (5×10 cm Atlantis prep T3 OBD column, 5 um, Waters) by 160 injections using an A/B gradient (A=water, B=acetonitrile) of 10→30% B over 30 minutes, with a 95% B wash, followed by re-equilibration at 1% (total run time=42 minutes). Each run was collected in 36 tared tubes (12 fractions/plate, 3 plates per run) at 30 mL/fraction. The plates were dried in the Genevac HT12/HT24. The desired compound was eluted in FractionFractions 27 along with other isomers. The pooled Fraction 27 (223 mg) was further fractionated in 7 runs on fluoro-phenyl HPLC (3×10 cm, Xselect fluoro-phenyl OBD column, 5 um, Waters) using an A/B gradient (A=water, B=acetonitrile) of 15→30% B over 35 minutes, with a 95% B wash, followed by re-equilibration at 15% (total run time=45 minutes). Each run was collected in 12 tared tubes (12 fractions/plate, 1 plate per run) at 30 mL/fraction. Fractions containing the desired peak with the desired purity were pooled based on UPLC analysis and dried under reduced pressure to give a whitish powdery solid. The pure compound was re-suspended/dissolved in 5 mL of water and lyophilized to get 40.9 mg of fluffy white solid.

$^1$H NMR (400 MHz, Pyridine-$d_5$+$D_2$O), selected signals: δ 5.37 (s, 1H, 6-H), 5.35 (d, J=7.8 Hz, 1H, G2-1-H), 5.14 (d, J=7.9 Hz, 1H, G4-1-H), 5.00 (d, J=7.7 Hz, 1H, G1-1-H), 4.77 (d, J=8.0 Hz, 1H, G3-1-H), 3.57 (s, 1H, 3-H), 1.49 (s, 3H, 29-Me), 1.45 (s, 3H, 27-Me), 1.41 (s, 3H, 26-Me), 1.27 (s, 3H, 19-Me), 1.10 (s, 3H, 28-Me), 1.01 (d, J=6.3 Hz, 3H, 21-Me), 0.84 (s, 3H, 30-Me), 0.83 (s, 3H, 18-Me); $^{13}$C NMR (101 MHz, pyridine) δ 144.15, 118.52, 106.79, 105.64, 104.77, 102.24, 88.77, 87.95, 82.95, 81.30, 78.43, 78.37, 78.32, 77.98, 77.91, 77.80, 76.54, 76.11, 75.88, 74.74, 72.44, 71.92, 71.29, 71.11, 63.07, 62.29, 62.20, 62.00, 50.70, 49.64, 47.35, 43.46, 42.30, 40.82, 40.07, 40.04, 36.70, 36.62, 34.49, 33.78, 28.57, 28.49, 27.63, 26.90, 26.76, 26.24, 25.48, 24.52, 19.37, 19.04, 17.00; ESI-MS 1147.74 (M+Na)$^+$, 1123.86 (M–H)$^-$; Molecular formula, $C_4H_{92}O_{24}$.

Example 13: Isolation of Compound 2

80.2 g of *Siraitia grosvenorii* powdered extract (*Fructus momordicae* extract, 50% mogrosides, light yellow powder) was obtained from Xi'an Heking Bio-tech Co., Ltd. was fractionated on C18 HPLC (5×10 cm Atlantis prep T3 OBD column, 5 um, Waters) by 160 injections using an A/B gradient (A=water B=acetonitrile) of 10-30% B over 30 minutes, with a 95% B wash, followed by re-equilibration at 1% (total run time=42 minutes). Each run was collected in 36 tared tubes (12 fractions/plate, 3 plates per run) at 30 mL/fraction. The plates were dried in the Genevac HT12/HT24. The desired compound was eluted in Fraction 8 along with other isomers. Out of 2 g of pooled Fraction 8, 220 mg was further purified in 5 runs on Hilic HPLC column (3×10 cm, XBridge amide column, 5 um, Waters) using an A/B gradient (A=3:1 MeOH:$H_2$O, B=acetonitrile) of 70 to 20% B over 21 minutes, followed by re-equilibration at 70% (total run time=30.5 minutes). Each run was collected in 12 fractions (12 fractions/plate, 1 plate per run) at 30 m/fraction. Fraction 8 contained the desired product and was pooled, concentrated under reduced pressure followed by the addition and 2 mL of $H_2$O and lyophilized the sample for 48 hours to get 109 mg of fluffy white solid with >90% purity.

$^1$H NMR (400 MHz, Pyridine-$d_5$+$D_2$O), selected signals: δ 5.51 (m, 1H, G3-1H), 5.45 (m, 1H, 6-H; merged with HDO peak), 5.38 (d, J=3.7 Hz, 1H, G5-1H), 5.10 (d, J=7.8 Hz, 1H, G2 or G6-1H), 4.79 (m, 1H, G1-1H), 4.75 (d, J=7.8 Hz, 1H, G4-1H), 4.70 (m, 1H, G2 or G6-1H), 3.69 (d, J=8.4 Hz, 1H, 24-H), 3.63 (s, 1H, 3-H), 1.46 (s, 3H, 29-Me), 1.42 (s, 3H, 26-Me), 1.28 (s, 6H, 27 & 19-Me), 1.06 (s, 3H, 28-Me), 1.03 (d, J=6.2 Hz, 3H, 21-Me), 0.88 (s, 3H, 30-Me) and 0.84 (s, 3H, 18-Me); ESI-MS 1471.96 (M+Na)$^+$, 1447.17 (M–H)$^-$; Molecular formula, $C_{66}H_{112}O_{34}$.

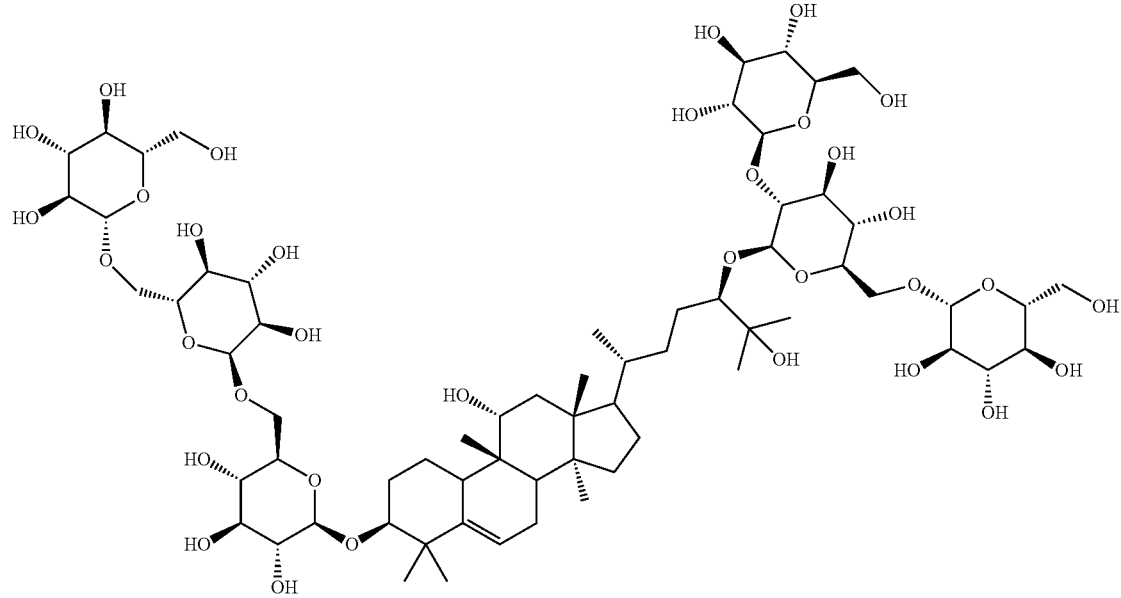 [SMILES: C[C@H](CC[C@@H](O[C@@H]1O[C@H](CO[C@@H]2O[C@H](CO)[C@@H](O)[C@H](O)[C@H]2O)[C@@H](O)[C@H](O)[C@H]1O[C@@H]1O[C@H](CO)[C@@H](O)[C@H](O)[C@H]1O)C(C)(C)O)C1CC[C@@]2(C)C3CC=C4C(CC[C@H](O[C@@H]5O[C@H](CO[C@H]6O[C@H](CO[C@H]7O[C@@H](CO)[C@H](O)[C@@H](O)[C@@H]7O)[C@@H](O)[C@H](O)[C@H]6O)[C@@H](O)[C@H](O)[C@H]5O)C4(C)C)[C@]3(C)[C@H](O)C[C@]12C]

Example 14: Isolation and Enzymatic Production of Compound 3

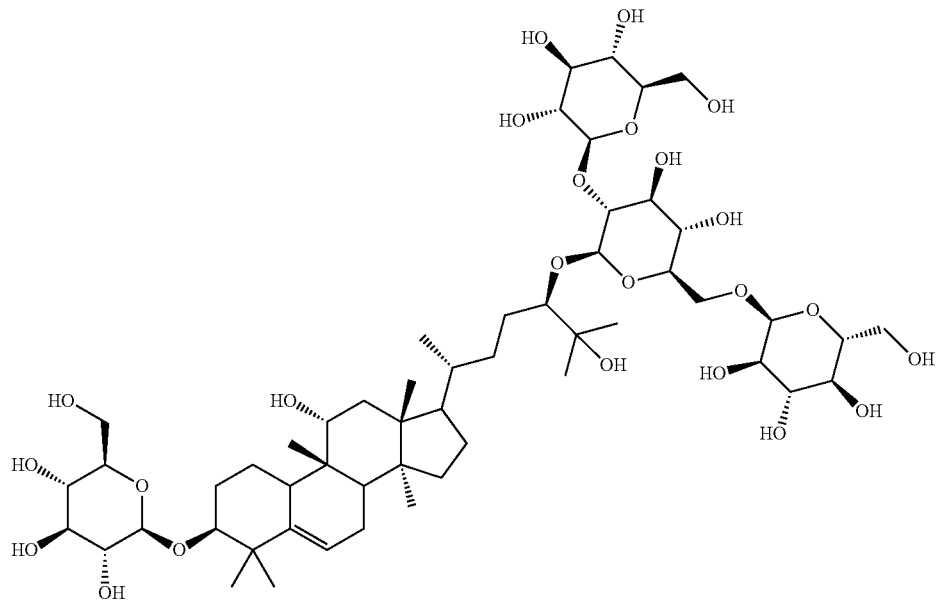 [SMILES: C[C@H](CC[C@@H](O[C@@H]1O[C@H](CO[C@H]2O[C@H](CO)[C@@H](O)[C@H](O)[C@H]2O)[C@@H](O)[C@H](O)[C@H]1O[C@@H]1O[C@H](CO)[C@@H](O)[C@H](O)[C@H]1O)C(C)(C)O)C1CC[C@@]2(C)C3CC=C4C(CC[C@H](O[C@@H]5O[C@H](CO)[C@@H](O)[C@H](O)[C@H]5O)C4(C)C)[C@]3(C)[C@H](O)C[C@]12C]

From CGTase enzyme; To a 250 mL Erlenmeyer flask, 500 mg of crude Mogroside III$_E$, 100 mL of pH 5, 0.1M sodium acetate buffer, 5g of soluble starch, and 30 mL of CGTase (Cyclomaltodextrin glucanotransferase; *Bacillus lichenformis*; Toruzyme 3.0 L; catalog #775700) from Novozyme were added and shook the flask at 50° C. The progress of the reaction was monitored periodically by LC-MS. After 24 hrs the reaction was stopped by heating at 80° C. and centrifuged at 4000 rpm for 10 minutes to remove the unreacted enzyme. The supernatant was dried down under reduced pressure. The same reaction was repeated 139 more times (total 70 g of MIII$_E$). The combined supernatant from 140 runs was fractionated on multiple SPE runs using 400 g C18 column and the standard 5/35/70/100/5 MeOH:H$_2$O gradient. The desired product was eluted in 70% MeOH SPE FractionFractions along with other minor isomers and the unreacted MIII$_E$. The combined 70% SPE Fraction (65 g) was purified on PF-HPLC using reversed phase conditions in 73 runs injecting 900 mg each time on 5×10 cm column with an A/B gradient (A=water, B=acetonitrile) of 15-30% B over 30 minutes, with a 95% B wash, followed by re-equilibration at 1% (total run time=40 minutes). Each run was collected in 36 tubes (3 plates per run) at 30 mL/fraction. The desired product was eluted in FractionFractions 13 to 16 with ~85-90% purity along with other minor MV and 11-oxo-MIV isomers. The combined lots of FractionFractions 13-14 (6.3g) and 15-16 (4.6g) were further purified on Hilic HPLC column (3×10 cm, XBridge amide column, 5 um, Waters) by 72 runs injecting about 150 mg each time with an A/B gradient (A=3:1 MeOH:H$_2$O, B=acetonitrile) of 80 to 40% B over 22 minutes, with a 95% A wash followed by re-equilibration at 80% (total run time=30 minutes). Each run was collected in 12 fractions (12 fractions/plate, 1 plate per run) at 30 mL/fraction. Fractions contained the desired product with desired purity were pooled, removed the solvents under reduced pressure, re-dissolved in H$_2$O and lyophilized the sample for about 5 days to get 4.86 g of white fluffy solid with ≥95% purity.

From Dextransucrase/dextranase enzyme; To a 3 L shake flask, 100 mL of pH 5.5 1M sodium acetate buffer, 200 g sucrose, 100 ml dextransucrase DexT (1 mg/ml crude extract, pET23a, BL21-Codon Plus-RIL, grown in 2× YT), 12.5g of Mogroside III$_E$ and 600 ml of water were added and shook the flask at 30° C., 200 rpm. The progress of the reaction was monitored periodically by LC-MS. After 72 hrs, the reaction was treated with 2.5 mL of dextranase (Amano). After 24 hrs of the addition of dextranase, the reaction was quenched by heating at 80° C. and centrifuged at 5,000 rpm for 5 minutes and the supernatant was filtered and loaded onto a 400g C18 SPE column. The sample was fractionated on a 5/25/50/75/100/5 MeOH:H$_2$O step gradient. The desired product was eluted in the 50 and 75% MeOH fractions and purified further on Hilic 3×10 cm column using an A/B gradient (A=3:1 MeOH:H$_2$O, B=acetonitrile) of 80 to 40% B over 26 minutes, followed by re-equilibration at 80% (total run time=30 minutes). Each run was collected in 24 fractions (12 fractions/plate, 1 plate per run) at 30 mL/fraction. FractionFractions contained the desired product with desired purity (F7) were pooled, removed the solvents under reduced pressure, re-dissolved in H$_2$O and lyophilized the sample for about 5 days to get 3.1 g of white fluffy solid with ≥95% purity.

Isolation; 180 g of *Siraitia grosvenorii* powdered extract (*Fructus momordicae* extract, 50% mogrosides, light yellow powder; sample ID: 50755234) was obtained from Xi'an Heking Bio-tech Co., Ltd. was fractionated on C18 HPLC (5×10 cm Atlantis prep T3 OBD column, 5 um, Waters) by 360 injections using an A/B gradient (A=water, B=acetonitrile) of 10→30% B over 30 minutes, with a 95% B wash, followed by re-equilibration at 1% (total run time=42 minutes) in two different batches of 80 and 100g. Each run was collected in 36 tared tubes (12 fractions/plate, 3 plates per run) at 30 mL/fraction. The plates were dried in the Genevac HT12/HT24. The desired compound was eluted in frxn 20 along with major siamenoside I and other minor isomers. The pooled frxn 20 from two batches (618 and 704 mg) was further fractionated in 27 runs on Hilic HPLC column (3×10 cm, XBridge amide column, 5 um, Waters)

using an A/B gradient (A=3:1 MeOH:H₂O, B=acetonitrile) of 80 to 40% B over 22 minutes, with a 95% A wash followed by re-equilibration at 80% (total run time=30.3 minutes). Each run was collected in 24 fractions (12 fractions/plate, 2 plates per run) at 15 mL/fraction. Fraction 10 contained the desired product and was pooled, concentrated under reduced pressure followed by the addition of 2 mL of H₂O and lyophilized the sample for 2 days to get 103 mg of fluffy white solid with ~85% purity.

$^1$H NMR (400 MHz, Pyridine-$d_5$+D₂O), selected signals: δ 5.44 (m, 2H, 6-H & G2-1H, merged with HDO peak), 5.37 (d, J=3.7 Hz, 1H, G3-1H), 4.86 (d, J=7.7 Hz, 1H, G1-1H), 4.81 (d, J=7.8 Hz, 1H, G4-1H), 3.72 (m, 1H, 24-H), 3.61 (s, 1H, 3-H), 1.49 (s, 3H, 29-Me), 1.42 (s, 3H, 27-Me), 1.30 (s, 3H, 26-Me), 1.27 (s, 3H, 19-Me), 1.09 (s, 3H, 28-Me), 1.01 (d, J=6.3 Hz, 3H, 21-Me), 0.87 (s, 3H, 30-Me) and 0.84 (s, 3H, 18-Me); ESI-MS 1125.94 (MH)⁺, 1123.92 (M−H)⁻; Molecular formula, $C_{54}H_{92}O_{24}$.

Example 15: Enzymatic Production of Compound 4 enzyme reaction) and dried down the supernatant. The combined supernatant was processed in 4 different batches from 46 reactions was fractionated on four SPE runs using 400 g column and the standard 5/35/70/100/5 gradient. The desired product was eluted in 70% SPE Fraction along with major siamenoside isomer, other minor isomers and the unreacted MIII$_E$. The 70% SPE Fraction from 4 batches (30 g) was fractionated on HPLC using Hilic column (3×10 cm, XBridge amide column, 5 um, Waters) by 150 runs injecting 200 mg each time with an A/B gradient (A=3:1 MeOH:H₂O, B=acetonitrile) of 80 to 20% B over 26 minutes, followed by re-equilibration at 80% (total run time=30 minutes). Each run was collected in 24 fractions (12 fractions/plate, 1 plate per run) at 15 mL/fraction. Fraction 19 contained the desired product along with other MV isomers. Fraction 19 (1g) was pooled, concentrated under reduced pressure and further purified using the same Hilic HPLC conditions with low injection amount (50 mg) and collection volume (7.5 mL per vial) to separate MV isomers. The desired compound was eluted in FractionFractions 8-10. It was pooled, removed the solvents on rotavap/genevac, added 2 mL of H₂O and

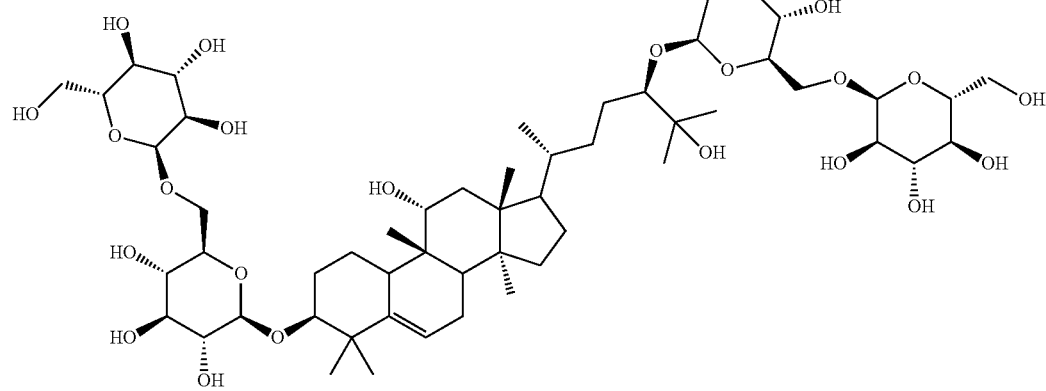

To a 250 mL round bottom flask, 500 mg of Mogroside III$_E$, 100 mL of pH 5, 0.1M sodium acetate buffer, 5g of soluble starch, and 30 mL of CGTase (Cyclomaltodextrin glucanotransferase; *Bacillus lichenformis*; Toruzyme 3.0 L) from Novozyme were added and stirred the flask at 50° C. The progress of the reaction was monitored periodically by LC-MS. After 24 hrs the reaction was quenched with 100 mL of ethanol and centrifuged at 4000 rpm for 10 minutes. The supernatant was dried down under reduced pressure. The same reaction was repeated 45 more times (23 g of MIII$_E$ produced directly from 50% powder with pectinase filtered through 0.45 um filter and dried the sample on lyophilizer to get 72 mg of 80% pure MV isomer.

$^1$H NMR (400 MHz, Pyridine-$d_5$+D₂O), selected signals: δ 5.46-5.40 (m, 3H, H-6, G2-1H & G5-1H; merged with HDO peak), 5.28 (d, J=3.7 Hz, 1H, G3-1H), 4.84 (d, J=7.8 Hz, 1H, G1-1H), 4.82 (d, J=7.8 Hz, 1H, G4-1H), 3.71 (d, J=8.0 Hz, 1H, 24-H), 3.61 (s, 1H, 3-H), 1.49 (s, 3H, 28-Me), 1.41 (s, 3H, 26-Me), 1.29 (s, 3H, 27-Me), 1.28 (s, 3H, 19-Me), 1.10 (s, 3H, 29-Me), 1.01 (d, J=5.9 Hz, 3H, 21-Me), 0.87 (s, 3H, 30-Me), 0.84 (s, 3H, 18-Me); ESI-MS 1285.84 (M−H)⁻, Molecular formula, $C_{60}H_{102}O_{29}$.

Example 16: Enzymatic Production of Compound 5

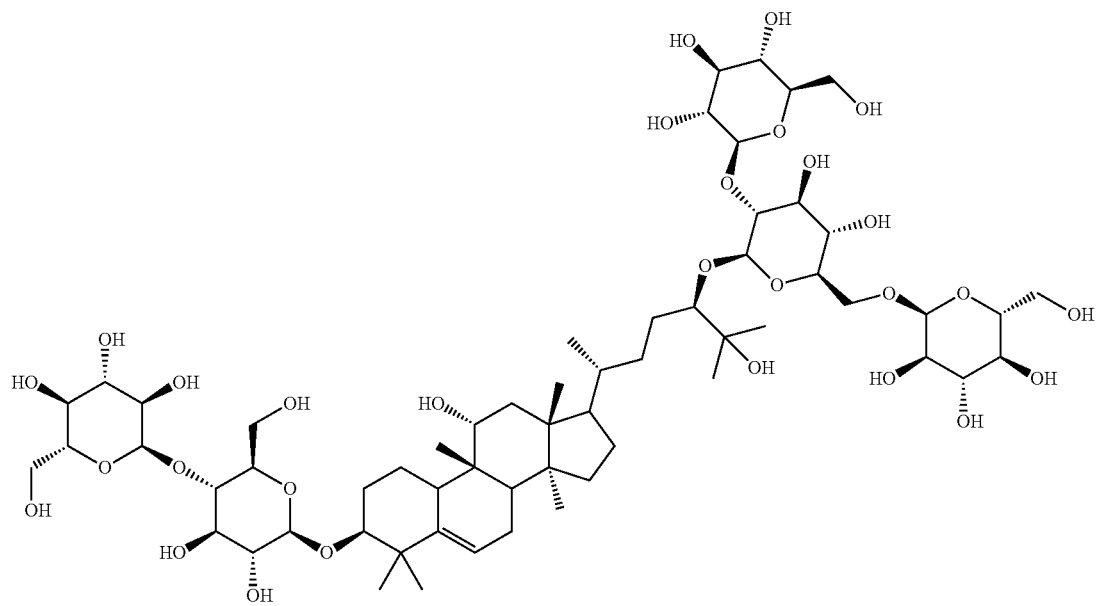 [SMILES: C[C@H](CC[C@@H](O[C@@H]1O[C@H](CO[C@H]2O[C@H](CO)[C@@H](O)[C@H](O)[C@H]2O)[C@@H](O)[C@H](O)[C@H]1O[C@@H]1O[C@H](CO)[C@@H](O)[C@H](O)[C@H]1O)C(C)(C)O)C1CC[C@@]2(C)C3CC=C4C(CC[C@H](O[C@@H]5O[C@H](CO)[C@@H](O[C@H]6O[C@H](CO)[C@@H](O)[C@H](O)[C@H]6O)[C@H](O)[C@H]5O)C4(C)C)[C@]3(C)[C@H](O)C[C@]12C]

To a 250 mL round bottom flask, 500 mg of Mogroside III$_E$, 100 mL of pH 5, 0.1M sodium acetate buffer, 5g of soluble starch, and 30 mL of CGTase (Cyclomaltodextrin glucanotransferase (CGTase); *Bacillus lichenformis*; Toruzyme 3.0 L) from Novozyme were added and stirred the flask at 50° C. The progress of the reaction was monitored periodically by LC-MS. After 24 hrs the reaction was quenched with 100 mL of ethanol and centrifuged at 4000 rpm for 10 minutes. The supernatant was dried down under reduced pressure. The same reaction was repeated 46 more times (23 g of MIII$_E$ produced directly from 50% powder with pectinase enzyme reaction) in 4 different bathes and processed further as each batch. The pooled supernatant from each batch was dried down and was fractionated separately on four SPE runs using 400 g column and the standard 5/35/70/100/5 gradient. The desired product was eluted in 70% SPE Fraction along with major siamenoside isomer (structure ID: 62071851), other minor MIV, MV & MVI isomers and the unreacted MIII$_E$. The 70% SPE Fraction from 4 batches (26 g) was fractionated on HPLC using Hilic column (3×10 cm, XBridge amide column, 5 um, Waters) by 130 runs injecting 200 mg each time with an A/B gradient (A=3:1 MeOH:H$_2$O, B=acetonitrile) of 80 to 20% B over 26 minutes, followed by re-equilibration at 80% (total run time=30 minutes). Each run was collected in 24 fractions (12 fractions/plate, 1 plate per run) at 15 mL/fraction. Fraction 19 contained the desired product along with other MV isomers. Fraction 19 (1g) was pooled, concentrated under reduced pressure and further purified using the same Hilic HPLC conditions with low injection amount (50 mg) and collection volume (7.5 mL per vial) to separate MV isomers. The desired compound was eluted in Fraction 4. It was pooled, removed the solvents on rotavap/genevac, added 2 mL of H$_2$O and filtered through 0.45 um filter and dried the sample on lyophilizer to get 70 mg of ~90% pure MV isomer.

$^1$H NMR (400 MHz, Pyridine-d$_5$+D$_2$O), selected signals: δ 5.90 (d, J=3.9 Hz, 1H, G5-1H), 5.49 (m, 1H, G2-1H), 5.46 (m, 1H, 6-H, merged with HDO peak), 5.34 (d, J=3.6 Hz, 1H, G3-1H), 4.78 (m, 2H, G1 & G4-1H), 3.65 (m, 1H, 24-H), 3.51 (brs, 1H, 3-H), 1.45 (s, 3H, 28-Me), 1.39 (s, 3H, 27-Me), 1.27 (s, 3H, 19-Me), 1.23 (s, 3H, 26-Me), 1.19 (s, 3H, 29-Me), 1.08 (d, J=6.2 Hz, 3H, 21-Me), 1.00 (s, 3H, 30-Me) & 0.87 (s, 3H, 18-Me); ESI-MS 1285.79 (M−H)$^−$; Molecular formula, C$_{60}$H$_{102}$O$_{29}$.

Example 17: Enzymatic Production of Compound 6

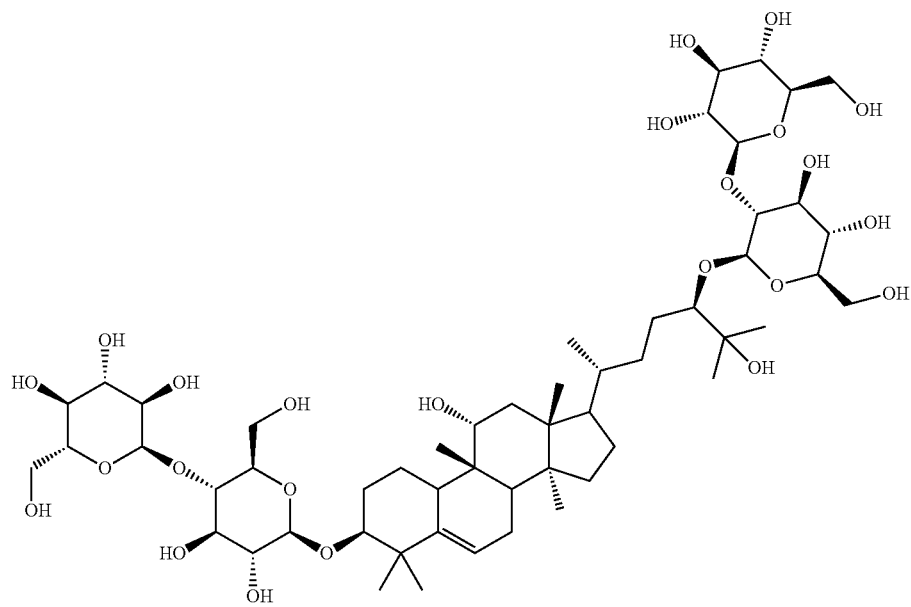 [SMILES: C[C@H](CC[C@@H](O[C@@H]1O[C@H](CO)[C@@H](O)[C@H](O)[C@H]1O[C@@H]1O[C@H](CO)[C@@H](O)[C@H](O)[C@H]1O)C(C)(C)O)C1CC[C@@]2(C)C3CC=C4C(CC[C@H](O[C@@H]5O[C@H](CO)[C@@H](O[C@H]6O[C@H](CO)[C@@H](O)[C@H](O)[C@H]6O)[C@H](O)[C@H]5O)C4(C)C)[C@]3(C)[C@H](O)C[C@]12C]

To a 250 mL round bottom flask, 550 mg of Mogroside IIIE, 100 mL of pH 5, 0.1M sodium acetate buffer, 5g of soluble starch, and 30 mL of CGTase (Cyclomaltodextrin glucanotransferase; *Bacillus lichenformis*; Toruzyme 3.0 L) from Novozyme were added and stirred at 50° C. The progress of the reaction was monitored periodically by LC-MS. After 24 hrs the reaction was quenched with 100 mL of ethanol and centrifuged at 4000 rpm for 10 minutes. The supernatant was dried down under reduced pressure. The same reaction was repeated 21 more times (~12 g of MIIIE) and dried down the supernatant. The combined supernatant from 22 reactions was fractionated on 6 SPE runs using 400 g column and the standard 5/35/70/100/5 gradient. The desired product was eluted in 70% SPE Fraction along with other minor isomers and the unreacted MIIIE. The combined 70% SPE FractionFractions (~14 g) was further purified on HPLC using Hilic column (3×10 cm, XBridge amide column, 5 um, Waters) by 95 runs injecting 150 mg each time with an A/B gradient (A=3:1 MeOH:$H_2O$, B=acetonitrile) of 80 to 20% B over 26 minutes, followed by re-equilibration at 80% (total run time=30 minutes). Each run was collected in 12 fractions (12 fractions/plate, 1 plate per run) at 30 mL/fraction. Fraction 5 contained the desired product along with other MIV isomers including siamenoside I isomer (Structure ID: 62071851). It was pooled, concentrated under reduced pressure (1.07g) and further purified using the same Hilic HPLC conditions with low injection amount (55 mg) and collection volume (15 mL per vial) to separate MIV isomers. The desired compound was eluted in Fraction 5 as a major isomer. It was pooled, removed the solvents on rotavap/genevac, added 5 mL of H2O and filtered through 0.45 um filter and dried the sample on lyophilizer to get 93 mg of 75% pure a-MIV isomer $^1$H NMR (400 MHz, Pyridine-$d_5$+D2), selected signals: δ 5.94 (d, J=3.8 Hz, 1H, G4-1H), 5.42 (m, 1H, 6-H, merged with HDO peak), 5.36 (d, J=7.8 Hz, 1H, G2-1H), 5.01 (d, J=7.8 Hz, 1H, G1-1H), 4.77 (d, J=7.8 Hz, 1H, G3-1H), 3.88 (d, J=7.9 Hz, 1H, 24-H), 3.58 (s, 1H, 3-H), 1.46 (m, 6H, 26 & 28-Me), 1.41 (s, 3H, 27-Me), 1.32 (s, 3H, 19-Me), 1.09 (s, 3H, 29-Me), 1.01 (d, J=6.3 Hz, 3H, 21-Me), 0.84 (brs, 6H, 18 & 30-Me); ESI-MS 1123.63 (M−H)$^-$; Molecular formula, $C_{54}H_{92}O_{24}$.

Example 18: Enzymatic Production of Compound 7

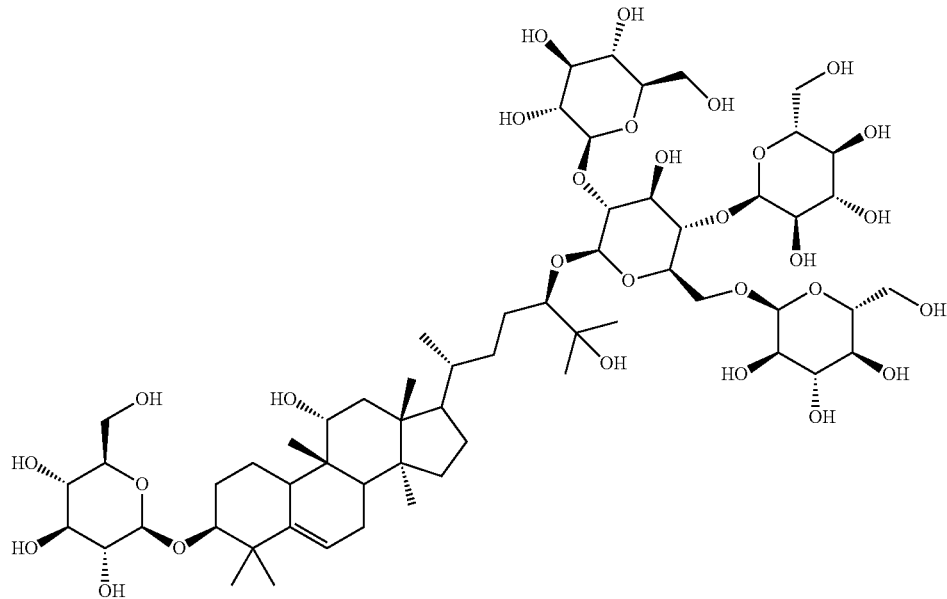 [SMILES: C[C@H](CC[C@@H](O[C@@H]1O[C@H](CO[C@H]2O[C@H](CO)[C@@H](O)[C@H](O)[C@H]2O)[C@@H](O[C@H]2O[C@H](CO)[C@@H](O)[C@H](O)[C@H]2O)[C@H](O)[C@H]1O[C@@H]1O[C@H](CO)[C@@H](O)[C@H](O)[C@H]1O)C(C)(C)O)C1CC[C@@]2(C)C3CC=C4C(CC[C@H](O[C@@H]5O[C@H](CO)[C@@H](O)[C@H](O)[C@H]5O)C4(C)C)[C@]3(C)[C@H](O)C[C@]12C]

To a 250 mL Erlenmeyer flask, 500 mg of crude Mogroside III$_E$, 100 mL of pH 5, 0.1M sodium acetate buffer, 5g of soluble starch, and 30 mL of CGTase (Cyclomaltodextrin glucanotransferase; *Bacillus lichenformis*; Toruzyme 3.0 L; catalog #775700) from Novozyme were added and shaked the flask at 50° C. The progress of the reaction was monitored periodically by LC-MS. After 24 hrs the reaction was stopped by heating at 80° C. and centrifuged at 4000 rpm for 10 minutes to remove the unreacted enzyme. The supernatant was dried down under reduced pressure. The same reaction was repeated 139 more times (total 70 g of MIII$_E$). The combined supernatant from 140 runs was fractionated on multiple SPE runs using 400 g C18 column and the standard 5/35/70/100/5 MeOH:H$_2$O gradient. The desired product was eluted in 70% MeOH SPE FractionFractions along with other minor isomers and the unreacted MIII$_E$. The combined 70% SPE Fraction (65 g) was purified on PF-HPLC using reversed phase conditions in 73 runs injecting 900 mg each time on 5×10 cm column with an A/B gradient (A=water, B=acetonitrile) of 15-30% B over 30 minutes, with a 95% B wash, followed by re-equilibration at 1% (total run time=40 minutes). Each run was collected in 36 tubes (3 plates per run) at 30 mL/fraction. The desired minor product was eluted in FractionFractions 6 with 60% purity along with other minor isomers. The combined lots of Fraction 6 (1.4g) was further purified on Hilic HPLC column (3×10 cm, XBridge amide column, 5 um, Waters) by 9 runs injecting about 150 mg each time with an A/B gradient (A=3:1 MeOH:H$_2$O, B=acetonitrile) of 80 to 40% B over 22 minutes, with a 95% A wash followed by re-equilibration at 80% (total run time=30 minutes). Each run was collected in 12 fractions (12 fractions/plate, 1 plate per run) at 30 mL/fraction. Fractions contained the desired product with desired purity were pooled, removed the solvents on rotovap, re-dissolved in H$_2$O and lyophilized the sample for about 3 days to get 240 mg of white fluffy solid with ≥95% purity.

$^1$H NMR (400 MHz, Pyridine-d$_5$+D$_2$O), selected signals: δ 5.82 (d, J=3.8 Hz, 1H, G5-1H), 5.45 (m, 1H, G2-1H, merged with HDO peak), 5.43 (m, 1H, 6-H, merged with HDO peak), 5.32 (d, J=3.8 Hz, 1H, G4-1H), 4.86 (d, J=7.4 Hz, 1H, G1-1H), 4.81 (d, J=7.8 Hz, 1H, G3-1H), 3.70 (d, J=8.4 Hz, 1H, 24-H), 3.60 (s, 1H, 3-H), 1.48 (s, 3H, 28-Me), 1.45 (s, 3H, 26-Me), 1.32 (s, 3H, 27-Me), 1.27 (s, 3H, 19-Me), 1.09 (s, 3H, 29-Me), 1.01 (d, J=6.3 Hz, 3H, 21-Me), 0.88 (s, 3H, 30-Me), 0.84 (s, 2H, 18-Me); ESI-MS 1287.76 (MH)-, 1285.96 (M–H)$^-$, Molecular formula, C$_{60}$H$_{102}$O$_{29}$.

Example 19: Enzymatic Production of Compound 8

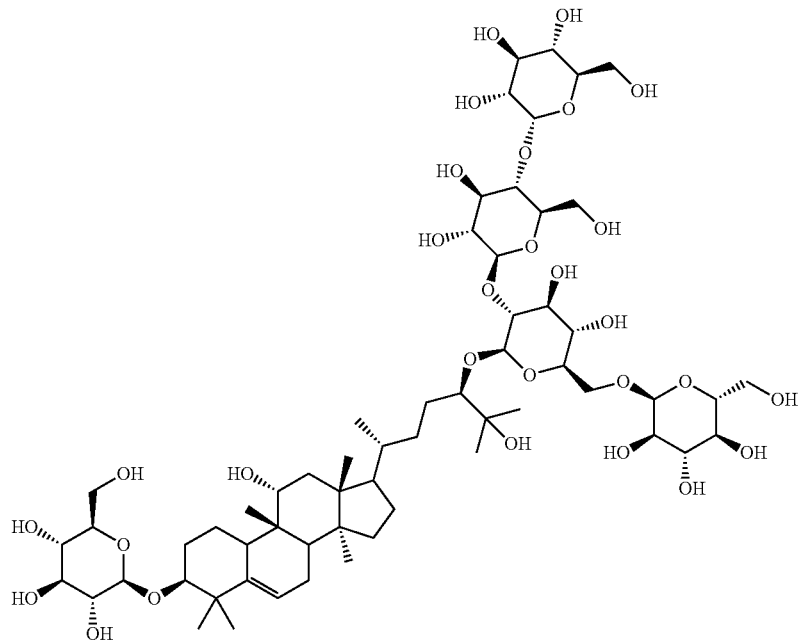 [SMILES: C[C@H](CC[C@@H](O[C@@H]1O[C@H](CO[C@H]2O[C@H](CO)[C@@H](O)[C@H](O)[C@H]2O)[C@@H](O)[C@H](O)[C@H]1O[C@@H]1O[C@H](CO)[C@@H](O[C@H]2O[C@H](CO)[C@@H](O)[C@H](O)[C@H]2O)[C@H](O)[C@H]1O)C(C)(C)O)C1CC[C@@]2(C)C3CC=C4C(CC[C@H](O[C@@H]5O[C@H](CO)[C@@H](O)[C@H](O)[C@H]5O)C4(C)C)[C@]3(C)[C@H](O)C[C@]12C]

To a 250 mL Erlenmeyer flask, 500 mg of crude Mogroside $III_E$, 100 mL of pH 5, 0.1M sodium acetate buffer, 5g of soluble starch, and 30 mL of CGTase (Cyclomaltodextrin glucanotransferase; *Bacillus lichenformis*; Toruzyme 3.0 L; catalog #775700) from Novozyme were added and shaked the flask at 50° C. The progress of the reaction was monitored periodically by LC-MS. After 24 hrs the reaction was stopped by heating at 80° C. and centrifuged at 4000 rpm for 10 minutes to remove the unreacted enzyme. The supernatant was dried down under reduced pressure. The same reaction was repeated 139 more times (total 70 g of $MIII_E$). The combined supernatant from 140 runs was fractionated on multiple SPE runs using 400 g C18 column and the standard 5/35/70/100/5 MeOH:$H_2O$ gradient. The desired product was eluted in 70% MeOH SPE FractionFractions along with other minor isomers and the unreacted $MIII_E$. The combined 70% SPE Fraction (65 g) was purified on PF-HPLC using reversed phase conditions in 73 runs injecting 900 mg each time on 5×10 cm column with an A/B gradient (A=water, B=acetonitrile) of 15-30% B over 30 minutes, with a 95% B wash, followed by re-equilibration at 1% (total run time=40 minutes). Each run was collected in 36 tubes (3 plates per run) at 30 mL/fraction. The desired minor product was eluted in FractionFractions 12 with 60% purity along with other minor isomers. The combined lots of Fraction 12 (588 mg) was further purified on Hilic HPLC column (3×10 cm, XBridge amide column, 5 um, Waters) by 6 runs injecting about 100 mg each time with an A/B gradient (A=3:1 MeOH:$H_2O$, B=acetonitrile) of 80 to 40% B over 22 minutes, with a 95% A wash followed by re-equilibration at 80% (total run time=30 minutes). Each run was collected in 12 fractions (12 fractions/plate, 1 plate per run) at 30 mL/fraction. Fractions contained the desired product with desired purity were pooled, removed the solvents on rotovap, re-dissolved in $H_2O$ and lyophilized the sample for about 3 days to get 110 mg of white fluffy solid with about 90% purity.

$^1$H NMR (400 MHz, Pyridine-$d_5$+$D_2O$), selected signals: δ 5.83 (d, J=3.9 Hz, 1H, G5-1H), 5.45 (m, 1H, 6-H, merged with HDO peak), 5.43 (m, 1H, G2-1H, merged with HDO peak), 5.37 (d, J=3.6 Hz, 1H, G4-1H), 4.86 (d, J=7.7 Hz, 1H, G1-1H), 4.73 (d, J=7.7 Hz, 1H, G3-1H), 3.72 (m, 1H, 24-H), 3.58 (s, 1H, 3-H), 1.47 (s, 3H, 28-Me), 1.41 (s, 3H, 26-Me), 1.29 (s, 3H, 27-Me), 1.26 (s, 3H, 19-Me), 1.08 (s, 3H, 29-Me), 1.01 (d, J=6.2 Hz, 3H, 21-Me), 0.86 (s, 3H, 30-Me), 0.83 (s, 3H, 18-Me). ESI-MS 1287.94 (MH)$^+$, 1285.96 (M–H)$^-$, Molecular formula, $C_{60}H_{102}O_{29}$.

Example 20: Enzymatic Production of Compound 9

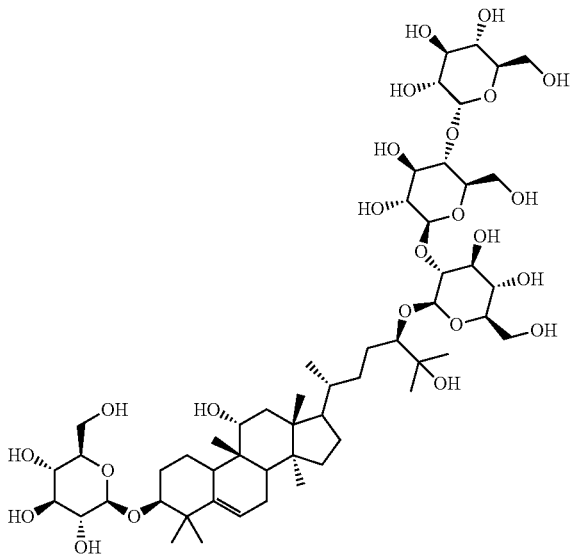 [SMILES: C[C@H](CC[C@@H](O[C@@H]1O[C@H](CO)[C@@H](O)[C@H](O)[C@H]1O[C@@H]1O[C@H](CO)[C@@H](O[C@H]2O[C@H](CO)[C@@H](O)[C@H](O)[C@H]2O)[C@H](O)[C@H]1O)C(C)(C)O)C1CC[C@@]2(C)C3CC=C4C(CC[C@H](O[C@@H]5O[C@H](CO)[C@@H](O)[C@H](O)[C@H]5O)C4(C)C)[C@]3(C)[C@H](O)C[C@]12C]

To a 250 mL round bottom flask, 500 mg of Mogroside III$_E$, 100 mL of pH 5, 0.1M sodium acetate buffer, 5g of soluble starch, and 30 mL of CGTase (Cyclomaltodextrin glucanotransferase; *Bacillus lichenformis*; Toruzyme 3.0 L) from Novozyme were added and stirred the flask at 50° C. The progress of the reaction was monitored periodically by LC-MS. After 24 hrs the reaction was quenched with 100 mL of ethanol and centrifuged at 4000 rpm for 10 minutes. The supernatant was dried down under reduced pressure. The same reaction was repeated 15 more times (7.9 g of MIII$_E$) and dried down the supernatant. The combined supernatant from 16 reactions was fractionated on four SPE runs using 400 g column and the standard 5/35/70/100 MeOH:H$_2$O step gradient. The desired product was eluted in 70% SPE Fraction along with other minor isomers and the unreacted MIII$_E$. The combined 70% SPE FractionFractions (8.8 g) was further purified on HPLC using Hilic column (3×10 cm, XBridge amide column, 5 um, Waters) by 58 runs injecting 150 mg each time with an A/B gradient (A=3:1 MeOH:H$_2$O, B=acetonitrile) of 80 to 20% B over 26 minutes, followed by re-equilibration at 80% (total run time=30 minutes). Each run was collected in 12 fractions (12 fractions/plate, 1 plate per run) at 30 mL/fraction. Fraction 5 eluted as a mixture of MIV isomers along with S1851. The combined impure Fraction 5 generated by Hilic column runs from two previous batches (total 4.8g) was further purified on PF-HPLC using reversed phase conditions in 32 runs injecting 150 mg each time with an A/B gradient (A=water, B=acetonitrile) of 19% B over 22 minutes, with a 95% B wash, followed by re-equilibration at 1% (total run time=30 minutes). Each run was collected in 12 tubes (1 plate per run) at 30 mL/fraction. Based on UPLC analysis, fractions 2-4 contained S1851 and Fraction 7 contained the desired a-MIV isomer. Fraction 7 was pooled, concentrated under reduced pressure and re-suspended/dissolved in 3 mL of water and lyophilized for 3 days to get 214.9 mg of white solid with about 90% purity.

$^1$H NMR (400 MHz, Pyridine-d$_{5+30}$ µL D$_2$O), selected signals: δ 5.87 (d, J=3.9 Hz, 1H, G4-1H), 5.44 (m, 1H, H-6, merged with HDO peak), 5.39 (d, J=7.9 Hz, 1H, G2-1H), 4.94 (d, J=7.7 Hz, 1H, G1-1H), 4.79 (d, J=7.8 Hz, 1H, G3-1H), 3.82 (d, J=8.4 Hz, 1H, 24-H), 3.55 (s, 1H, 3-H), 1.46 (s, 3H, 28-Me), 1.43 (s, 3H, 26-Me), 1.37 (s, 3H, 27-Me), 1.27 (s, 3H, 19-Me), 1.17 (s, 3H, 29-Me), 1.06 (d, J=6.3 Hz, 3H, 21-Me), 0.94 (s, 3H, 30-Me) and 0.85 (s, 3H, 18-Me); ESI-MS 1123.66 (M−H)$^−$; Molecular formula, C$_4$H$_{92}$O$_{24}$.

Example 21: Enzymatic Production of Compound 10

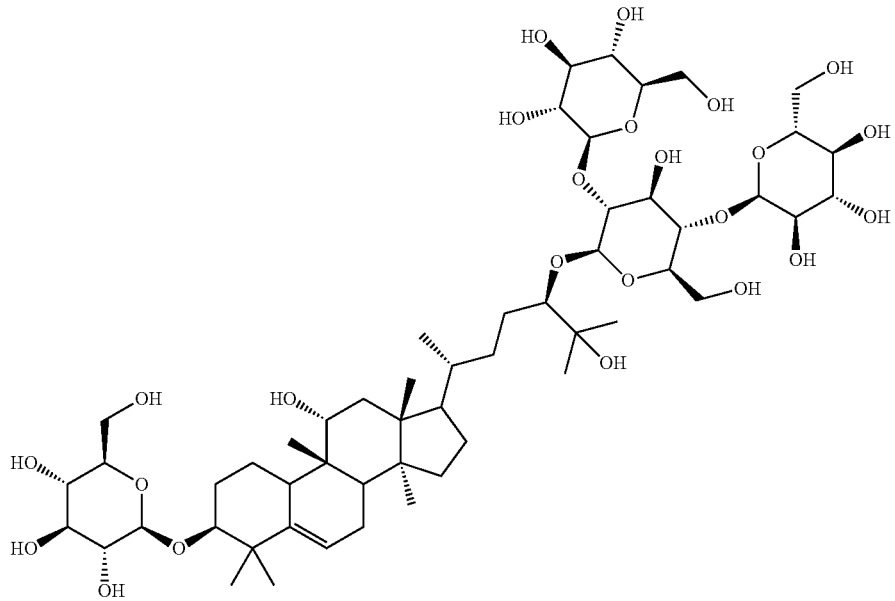 [SMILES: C[C@H](CC[C@@H](O[C@@H]1O[C@H](CO)[C@@H](O[C@H]2O[C@H](CO)[C@@H](O)[C@H](O)[C@H]2O)[C@H](O)[C@H]1O[C@@H]1O[C@H](CO)[C@@H](O)[C@H](O)[C@H]1O)C(C)(C)O)C1CC[C@@]2(C)C3CC=C4C(CC[C@H](O[C@@H]5O[C@H](CO)[C@@H](O)[C@H](O)[C@H]5O)C4(C)C)[C@]3(C)[C@H](O)C[C@]12C]

To a 250 mL round bottom flask, 500 mg of Mogroside III$_E$, 100 mL of pH 5, 0.1M sodium acetate buffer, 5g of soluble starch, and 30 mL of CGTase (Cyclomaltodextrin glucanotransferase; *Bacillus lichenformis*; Toruzyme 3.0 L) from Novozyme were added and stirred the flask at 50° C. The progress of the reaction was monitored periodically by LC-MS. After 24 hrs the reaction was quenched with 100 mL of ethanol and centrifuged at 4000 rpm for 10 minutes. The supernatant was dried down under reduced pressure. The same reaction was repeated 15 more times (7.9 g of MIII$_E$) and dried down the supernatant. The combined supernatant from 16 reactions was fractionated on four SPE runs using 400 g column and the standard 5/35/70/100 gradient. The desired product was eluted in 70% SPE Fraction along with other minor isomers and the unreacted MIII$_E$. The combined 70% SPE FractionFractions (8.8 g) was further purified on HPLC using Hilic column (3×10 cm, XBridge amide column, 5 um, Waters) by 58 runs injecting 150 mg each time with an A/B gradient (A=3:1 MeOH:H$_2$O, B=acetonitrile) of 80 to 20% B over 26 minutes, followed by re-equilibration at 80% (total run time=30 minutes). Each run was collected in 12 fractions (12 fractions/plate, 1 plate per run) at 30 mL/fraction. Fraction 5 eluted as a mixture of MIV isomers along with S1851. The combined impure Fraction 5 generated by Hilic column runs from two previous batches (total 4.8g) was further purified on PF-HPLC using reversed phase conditions in 32 runs injecting 150 mg each time with an A/B gradient (A=water, B=acetonitrile) of 19% B over 22 minutes, with a 95% B wash, followed by re-equilibration at 1% (total run time=30 minutes). Each run was collected in 12 tubes (1 plate per run) at 30 mL/fraction. Based on UPLC analysis, fractions 2-4 contained S1851 and Fraction 9 contained the desired a-MIV isomer. Fraction 9 was pooled, concentrated under reduced pressure and re-suspended/dissolved in 2 mL of water and lyophilized for 3 days to get 58 mg of white fluffy solid with about 90% purity.

$^1$H NMR (400 MHz, Pyridine-$d_5$+30 μL $D_2O$), selected signals: δ 5.83 (d, J=3.9 Hz, 1H, G4-1H), 5.44 (m, 1H, H-6, merged with HDO peak), 5.35 (d, J=7.8 Hz, 1H, G2-1H), 5.00 (d, J=7.7 Hz, 1H, G1-1H), 4.74 (d, J=7.8 Hz, 1H, G3-1H), 3.69 (d, J=8.5 Hz, 1H, 24-H), 3.59 (s, 1H, 3-H), 1.48 (s, 3H, 28-Me), 1.45 (s, 3H, 26-Me), 1.41 (s, 3H, 27-Me), 1.26 (s, 3H, 19-Me), 1.09 (s, 3H, 29-Me), 1.01 (d, J=6.3 Hz, 3H, 21-Me), 0.83 (s, 3H, 30-Me) and 0.82 (s, 3H, 18-Me); ESI-MS 1123.78 (M−H)$^−$; Molecular formula, $C_4H_{92}O_{24}$.

Example 22: Enzymatic Production of Compound 11

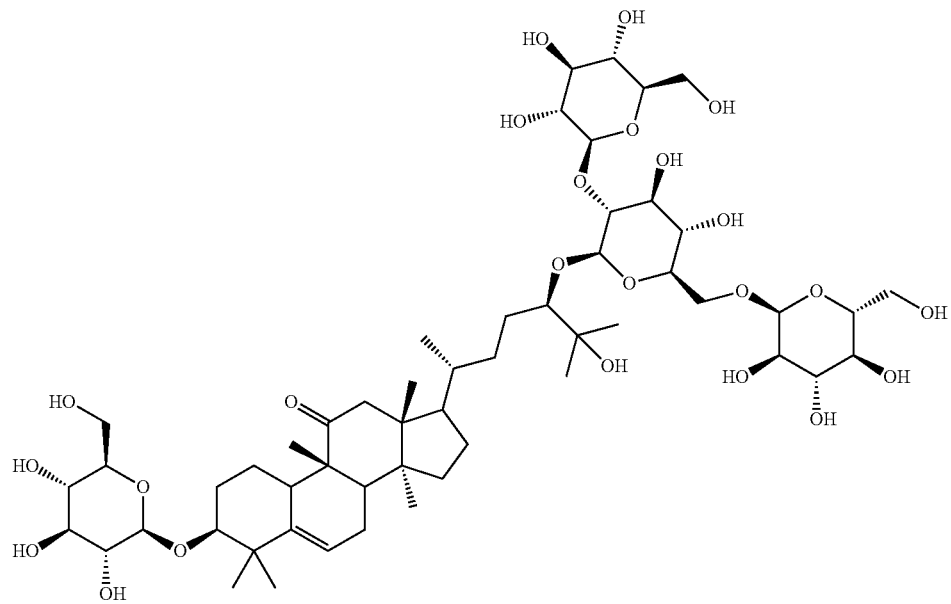 [SMILES: C[C@H](CC[C@@H](O[C@@H]1O[C@H](CO[C@H]2O[C@H](CO)[C@@H](O)[C@H](O)[C@H]2O)[C@@H](O)[C@H](O)[C@H]1O[C@@H]1O[C@H](CO)[C@@H](O)[C@H](O)[C@H]1O)C(C)(C)O)C1CC[C@@]2(C)C3CC=C4C(CC[C@H](O[C@@H]5O[C@H](CO)[C@@H](O)[C@H](O)[C@H]5O)C4(C)C)[C@]3(C)C(=O)C[C@]12C]

To a 250 mL Erlenmeyer flask, 500 mg of crude Mogroside III$_E$ with 5% of 11-oxo-MIII$_E$, 100 mL of pH 5, 0.1M sodium acetate buffer, 5g of soluble starch, and 30 mL of CGTase (Cyclomaltodextrin glucanotransferase; *Bacillus lichenformis*; *Toruzyme* 3.0 L; catalog #775700) from Novozyme were added and shaked the flask at 50° C. The progress of the reaction was monitored periodically by LC-MS. After 24 hrs the reaction was stopped by heating at 80° C. and centrifuged at 4000 rpm for 10 minutes to remove the unreacted enzyme. The supernatant was dried down under reduced pressure. The same reaction was repeated 139 more times (total 70 g of MIII$_E$). The combined supernatant from 140 runs was fractionated on multiple SPE runs using 400 g C18 column and the standard 5/35/70/100 MeOH: $H_2O$ step gradient. The desired product was eluted in 70% MeOH SPE FractionFractions along with other mogroside isomers and the unreacted MIII$_E$. The combined 70% SPE Fraction (65 g) was purified on PF-HPLC using reversed phase conditions in 73 runs injecting ~900 mg each time on 5×10 cm column with an A/B gradient (A=water, B=acetonitrile) of 15-30% B over 30 minutes, with a 95% B wash, followed by re-equilibration at 1% (total run time=40 minutes). Each run was collected in 36 tubes (3 plates per run) at 30 mL/fraction. The desired product was eluted in FractionFractions 15 to 16 along with the major compound 51851. The combined lots of FractionFractions 15-16 (4.6g) were further purified on Hilic HPLC column (3×10 cm, XBridge amide column, 5 um, Waters) by 30 runs injecting about 150 mg each time with an A/B gradient (A=3:1 MeOH:$H_2O$, B=acetonitrile) of 80 to 40% B over 22 minutes, with a 95% A wash followed by re-equilibration at 80% (total run time=30 minutes). Each run was collected in 12 fractions (12 fractions/plate, 1 plate per run) at 30 mL/fraction. Fractions containing the desired product with desired purity were pooled, removed the solvents under reduced pressure, re-dissolved in 3 mL of $H_2O$ and lyophilized the sample for about 3 days to get 118 mg of white fluffy solid with ≥95% purity.

$^1$H NMR (400 MHz, Pyridine-$d_5$+$D_2O$), selected signals: δ 5.44 (m, 2H, 6-H & G2-1H, merged with HDO), 5.37 (d, J=3.6 Hz, 1H, G3-1H), 4.87 (d, J=7.7 Hz, 1H, G1-1H), 4.80 (d, J=7.8 Hz, 1H, G4-1H), 3.72 (dd, J=8.9, 2.1 Hz, 1H, 24-H), 3.58 (s, 1H, 3-H), 1.48 (s, 3H, 29-Me), 1.43 (s, 3H, 27-Me), 1.31 (s, 3H, 26-Me), 1.10 (s, 3H, 19-Me), 1.04 (s, 3H, 28-Me), 0.94 (d, J=5.9 Hz, 6H, 30 and 21-Me), 0.67 (s, 3H, 18-Me); ESI-MS 1123.65 (MH)$^+$, 1121.70 (M−H)$^−$; Molecular formula, $C_4H_{90}O_{24}$.

Example 23: Enzymatic Production of Compound 12

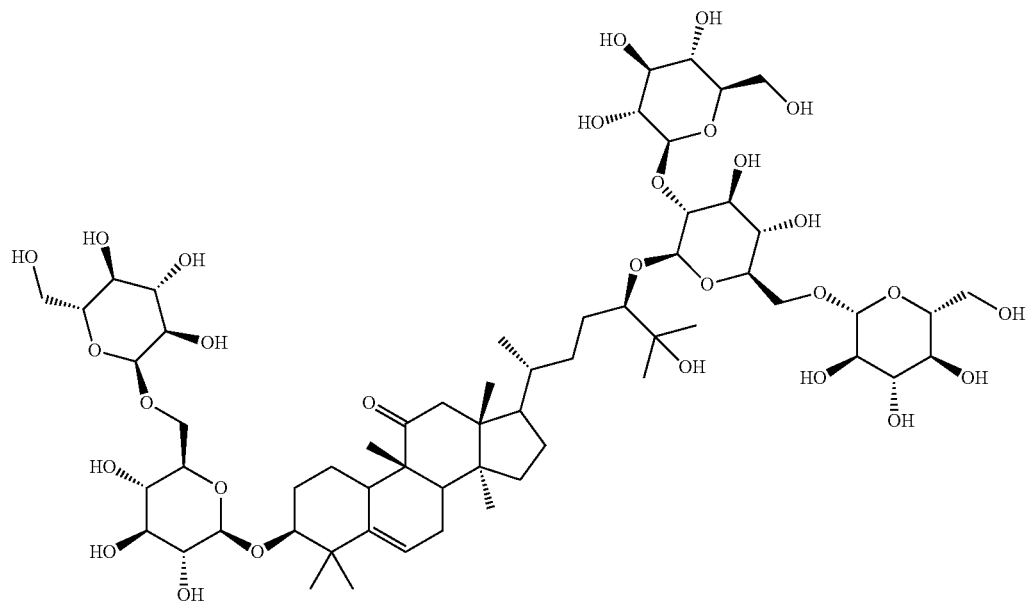 [SMILES: C[C@H](CC[C@@H](O[C@@H]1O[C@H](CO[C@@H]2O[C@H](CO)[C@@H](O)[C@H](O)[C@H]2O)[C@@H](O)[C@H](O)[C@H]1O[C@@H]1O[C@H](CO)[C@@H](O)[C@H](O)[C@H]1O)C(C)(C)O)C1CC[C@@]2(C)C3CC=C4C(CC[C@H](O[C@@H]5O[C@H](CO[C@H]6O[C@H](CO)[C@@H](O)[C@H](O)[C@H]6O)[C@@H](O)[C@H](O)[C@H]5O)C4(C)C)[C@]3(C)C(=O)C[C@]12C]

To a 100 mL round bottom flask, 150 mg of Mogroside VI isomer, 30 mL of 0.1M sodium acetate buffer, pH 5 and 60 mg of invertase enzyme from baker's yeast (*Saccharomyces cerevisiae*, lot #SLBG7298V) were added and stirred at 50° C. The progress of the reaction was monitored periodically by LC-MS. After 7 hours the reaction was quenched with 30 mL of EtOH and centrifuged at 4000 rpm for 10 minutes. The reaction was repeated twice more at 150 mg scale each for a total of 450 mg. After quenching and centrifugation, the supernatants of all three lots were pooled together and dried under reduced pressure followed by SPE fractionation using a standard 5/35/70/100 method with MeOH:H$_2$O step gradient. The desired product was eluted in 70% MeOH fraction (300 mg) and purified further on HILIC column by 6 runs using an A/B gradient (A=3:1 MeOH:H$_2$O, B=acetonitrile) of 80 to 20% B over 26 minutes, followed by re-equilibration at 80% (total run time=30 minutes). Each run was collected in 12 fractions (12 fractions/plate, 1 plate per run) at 30 mL/fraction. The desired product was eluted in fraction 7. The pooled Fraction 7 from 5 runs was concentrated under reduced pressure followed by the addition of 2 mL of H$_2$O and lyophilized for 48 hours to get 124 mg of a white fluffy powder with >90% purity.

$^1$H NMR (400 MHz, Pyridine-d$_5$+D$_2$O), selected signals: δ 5.52 (d, J=7.8 Hz, 1H, G3-1H), 5.45 (m, 1H, 6-H, merged with HDO peak), 5.38 (d, J=3.7 Hz, 1H, G5-1H), 4.81 (d, J=5.7 Hz, 1H, G4-1H), 4.79 (d, J=4.7 Hz, 1H, G1-1H), 4.70 (d, J=7.7 Hz, 1H, G2-1H), 3.69 (d, J=8.8 Hz, 1H, 24-H), 3.60 (s, 1H, 3-H), 1.49 (s, 3H, 28-Me), 1.42 (s, 3H, 26-Me), 1.28 (s, 6H, 19 & 27-Me), 1.09 (s, 3H, 29-Me), 1.02 (d, J=6.3 Hz, 3H, 21-Me), 0.88 (s, 3H, 30-Me), 0.85 (s, 3H, 18-Me); ESI-MS 1285.94 (M–H)$^-$; Molecular formula, C$_{60}$H$_{102}$O$_{29}$.

Example 24: Enzymatic Production of Compound 13

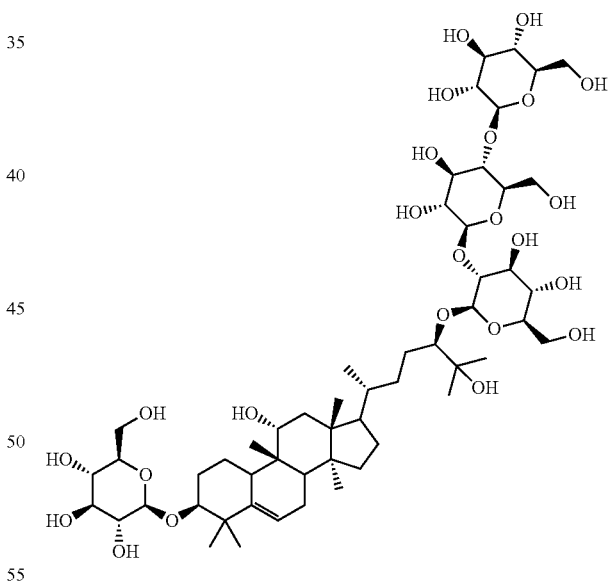

To a 250-mL baffled flask, 1 g of crude mogroside III$_E$, 53 mL of water, 15 mL of 1M sodium acetate buffer pH 5, 7 ml of celluclast from Novozymes and 75 g of a-lactose were added and shook the flask at 220 rpm, 50° C. for 9 days. The progress of the reaction was monitored periodically by LC-MS analysis. The same reaction was repeated 17 more times for a total of 18g of mogroside III$_E$ in two batches. After 9 days, the unreacted enzyme and excess lactose from the reaction mixtures were removed in three following steps before SPE purification. The reaction mixture was centrifuged for 10 min at 5000 rpm to remove the excess lactose followed by the incubation at 80° C. for 30 min with magnetic stirring at 500 rpm. Further approximately ~10% $NH_4SO_4$ solution was added to precipitate the unreacted enzymes and sugars, followed by centrifugation for 10 min at 5000 rpm and removed the precipitate. The supernatant was filtered through 0.22 m PES and loaded onto 400g SPE C18 column and fractionated using a standard 5/35/70/100 MeOH:$H_2O$ gradient. The desired compound was eluted in 70% methanol fraction. The combined 70% SPE Fraction (12g) was further purified on RP-HPLC using PF column using an A/B gradient (A=water, B=acetonitrile) of 15 to 30% B over 35 minutes, with a 95% B wash, followed by re-equilibration at 15% (total run time=45 minutes). Each run was collected in 72 tubes (12 fractions/plate, 6 plates per run) at 7.5 mL/fraction in 2 collection windows of 36 fractions each. Fractions 22-24 contained the desired peak with the desired purity and were pooled based on UPLC analysis and dried under reduced pressure to give a whitish powdery solid. The pure compound was re-suspended/dissolved in 5 mL of water and lyophilized for about 3 days to get 796 mg of white solid.

$^1$H NMR (400 MHz, Pyridine-$d_5$+$D_2O$), selected signals: δ 5.45 (m, 1H, H-6, merged with HDO peak), 5.36 (d, J=7.8 Hz, 1H, G2-1H), 5.07 (d, J=7.8 Hz, 1H, G4-1H), 5.00 (d, J=7.8 Hz, 1H, G1-1H), 4.76 (d, J=7.8 Hz, 1H, G3-1H), 3.88 (d, J=8.0 Hz, 1H, 24-H), 3.56 (s, 1H, 3-H), 1.48 (s, 3H, 29-Me), 1.45 (s, 3H, 26-Me), 1.41 (s, 3H, 27-Me), 1.27 (s, 3H, 19-Me), 1.09 (s, 3H, 28-Me), 1.01 (d, J=6.3 Hz, 3H, 21-Me), 0.83 (s, 3H, 30-Me), 0.82 (s, 3H, 18-Me); ESI-MS 1123.85 (M–H)$^-$; Molecular formula, $C_{54}H_{92}O_{24}$.

Example 25: Enzymatic Production of Compound 14 the reaction mixtures were removed in three following steps before SPE purification. The reaction mixture was centrifuged for 10 min at 5000 rpm to remove the excess lactose followed by the incubation at 80° C. for 30 min with magnetic stirring at 500 rpm. Further approximately ~10% $NH_4SO_4$ solution was added to precipitate the unreacted enzymes and sugars, followed by centrifugation for 10 min at 5000 rpm and removed the precipitate. The supernatant was filtered through 0.22 m PES and loaded onto 400g SPE C18 column and fractionated using a standard 5/35/70/100 MeOH:$H_2O$ gradient. The desired compound was eluted in 70% methanol fraction. The combined 70% SPE Fraction from both batches were further purified on RP-HPLC using PF column using an A/B gradient (A=water, B=acetonitrile) of 15 to 30% B over 35 minutes, with a 95% B wash followed by re-equilibration at 15% (total run time=45 minutes). Each run was collected in 72 tubes (12 fractions/plate, 6 plates per run) at 7.5 mL/fraction in 2 collection windows of 36 fractions each. Fractions 19-21 eluted with the desired peak along with some other isomers. These fractions were combined and re-purified on RP-HPLC using PF column with an isocratic method of 18% B (A=water, B=acetonitrile) over 30 minutes, followed by 5 minutes of 95% B wash and 5 minutes of re-equilibration at 18% (total run time=40 minutes). Each run was collected in 24 tubes (12 fractions/plate, 2 plates per run) at 15 mL/fraction. Fractions 11-12 contained the desired peak with the desired purity, pooled and dried under reduced pressure. The dried Fraction was re-suspended/dissolved in 2 mL of water and lyophilized for 3 days to get 52 mg of white fluffy solid with 95% purity.

$^1$H NMR (400 MHz, Pyridine-$d_5$+$D_2O$), selected signals: δ 5.44 (m, 1H, H-6, merged with HDO peak), 5.38 d, J=7.8

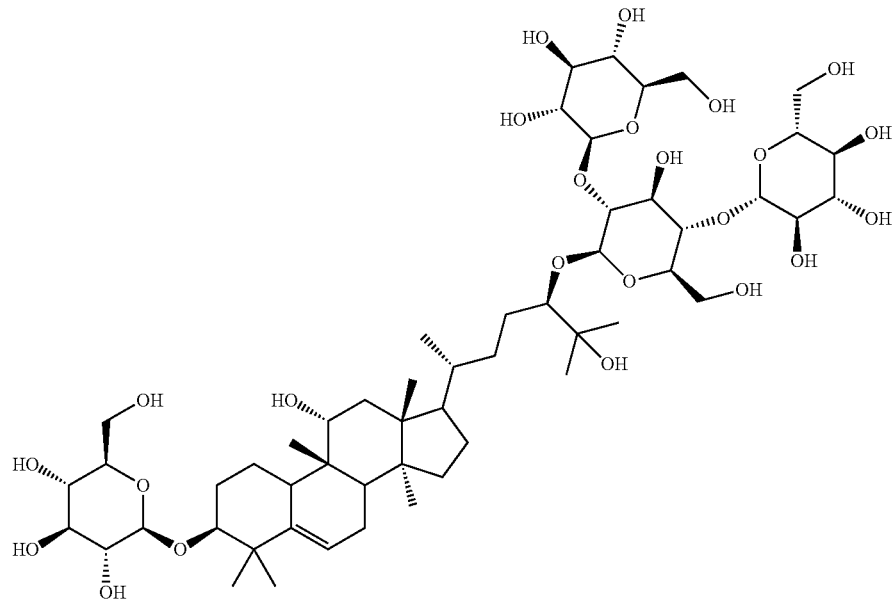 [SMILES: C[C@H](CC[C@@H](O[C@@H]1O[C@H](CO)[C@@H](O[C@@H]2O[C@H](CO)[C@@H](O)[C@H](O)[C@H]2O)[C@H](O)[C@H]1O[C@@H]1O[C@H](CO)[C@@H](O)[C@H](O)[C@H]1O)C(C)(C)O)C1CC[C@@]2(C)C3CC=C4C(CC[C@H](O[C@@H]5O[C@H](CO)[C@@H](O)[C@H](O)[C@H]5O)C4(C)C)[C@]3(C)[C@H](O)C[C@]12C]

To a 250-mL baffled flask, 1 g of crude mogroside III$_E$, 53 mL of water, 15 mL of 1M sodium acetate buffer pH 5, 7 ml of celluclast from Novozymes and 75 g of a-lactose were added and shook the flask at 220 rpm, 50° C. for 9 days. The progress of the reaction was monitored periodically by LC-MS analysis. The same reaction was repeated 17 more times for a total of 18g of mogroside III$_E$ in two batches. After 9 days, the unreacted enzyme and excess lactose from Hz, 1H, G2-1H), 4.99 (d, J=7.9 Hz, 1H, G3-1H), 4.89 (d, J=7.6 Hz, 1H, G1-1H), 4.82 (d, J=7.8 Hz, 1H, G4-1H), 3.78 (m, 1H, 24-H), 3.62 (s, 1H, 3-H), 1.49 (s, 3H, 28-Me), 1.42 (s, 3H, 26-Me), 1.38 (s, 3H, 27-Me), 1.27 (s, 3H, 19-Me), 1.10 (s, 3H, 29-Me), 0.99 (d, J=6.3 Hz, 3H, 21-Me), 0.85 (s, 3H, 30-Me), 0.82 (s, 3H, 18-Me); ESI-MS 1147.57 (M+Na)$^+$, 1123.65 (M–H)$^-$; Molecular formula, $C_{54}H_{92}O_{24}$.

Example 26: Enzymatic Production of Compound 15

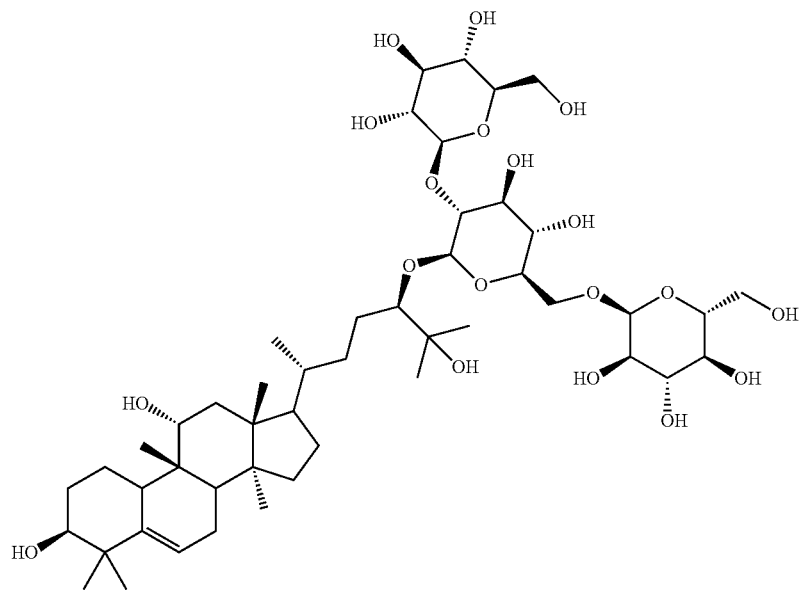 [SMILES: C[C@H](CC[C@@H](O[C@@H]1O[C@H](CO[C@H]2O[C@H](CO)[C@@H](O)[C@H](O)[C@H]2O)[C@@H](O)[C@H](O)[C@H]1O[C@@H]1O[C@H](CO)[C@@H](O)[C@H](O)[C@H]1O)C(C)(C)O)C1CC[C@@]2(C)C3CC=C4C(CC[C@H](O)C4(C)C)[C@]3(C)[C@H](O)C[C@]12C]

To a 250 mL Erlenmeyer flask, 500 mg of mogroside $II_A$, 100 mL of 0.1M sodium acetate buffer pH 5, 20 mL of Toruzyme from Novozymes and 5g of soluble starch were added and shook the flask at 200 rpm, 50° C. for 1 day. The progress of the reaction was monitored periodically by LC-MS analysis. After 24 hours, the unreacted enzyme and excess starch from the reaction mixtures was removed by the incubation at 80° C. for 30 min followed by centrifugation for 10 min at 4000 rpm and removed the precipitate. The same reaction was repeated 2 more times for a total of 1500 mg of mogroside IIA. The combined supernatant from 3 reactions was loaded onto 400g C18 SPE cartridge and fractionated using 5/35/70/100 MeOH:$H_2O$ step gradient. The desired compound was eluted in 70% methanol fraction. The 70% SPE Fraction was further purified on PF-HPLC using reversed phase conditions with an A/B gradient (A=water, B=acetonitrile) of 15 to 30% B over 35 minutes, with a 95% B wash, followed by re-equilibration at 15% (total run time=45 minutes). Each run was collected in 36 tubes (12 fractions/plate, 3 plates per run) at 15 mL/fraction. Based on UPLC analysis, fractions 21-24 contained the desired peak with the desired purity and were pooled and dried under reduced pressure to give a whitish powdery solid. The pure compound was re-suspended/dissolved in 5 mL of water and lyophilized for 3 days to get 310 mg of white fluffy solid with ≥95% purity.

$^1$H NMR (400 MHz, Pyridine-$d_5$+$D_2O$), selected signals: δ 5.58 (d, J=5.9 Hz, 1H, 6-H), 5.45 (m, 1H, G2-1H; merged with HDO peak), 5.37 (d, J=3.6 Hz, 1H, G3-1H), 4.87 (d, J=7.7 Hz, 1H, G1-1H), 3.72 (d, J=8.6 Hz, 1H, 24-H), 3.69 (s, 1H, 3-H), 1.42 (s, 3H, 26-Me), 1.37 (s, 3H, 28-Me), 1.33 (s, 3H, 19-Me), 1.30 (s, 3H, 27-Me), 1.13 (s, 3H, 29-Me), 1.02 (d, J=6.4 Hz, 3H, 21-Me), 0.92 (s, 3H, 30-Me), 0.85 (s, 3H, 18-Me); ESI-MS 963.94 (M+H)$^+$, 961.69 (M−H)$^−$; Molecular formula, $C_{48}H_{82}O_{19}$.

Example 27: Enzymatic Production of Compound 16

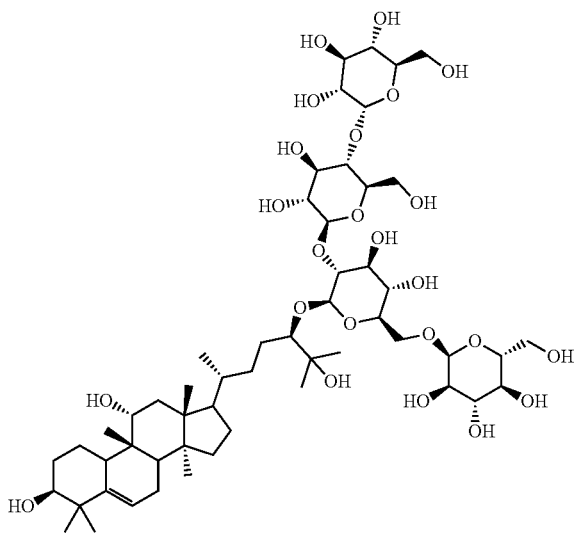 [SMILES: C[C@H](CC[C@@H](O[C@@H]1O[C@H](CO[C@H]2O[C@H](CO)[C@@H](O)[C@H](O)[C@H]2O)[C@@H](O)[C@H](O)[C@H]1O[C@@H]1O[C@H](CO)[C@@H](O[C@H]2O[C@H](CO)[C@@H](O)[C@H](O)[C@H]2O)[C@H](O)[C@H]1O)C(C)(C)O)C1CC[C@@]2(C)C3CC=C4C(CC[C@H](O)C4(C)C)[C@]3(C)[C@H](O)C[C@]12C]

To a 250 mL Erlenmeyer flask, 500 mg of mogroside $II_A$, 100 mL of 0.1M sodium acetate buffer pH 5, 20 mL of Toruzyme from Novozymes and 5g of soluble starch were added and shook the flask at 200 rpm, 50° C. for 1 day. The progress of the reaction was monitored periodically by LC-MS analysis. After 24 hours, the unreacted enzyme and excess starch from the reaction mixtures was removed by the incubation at 80° C. for 30 min followed by centrifugation for 10 min at 4000 rpm and removed the precipitate. The supernatant was loaded onto 60g C18 SPE cartridge and fractionated using 5/35/70/100 MeOH:$H_2O$ step gradient. The desired compound was eluted in 70% methanol fraction.

The 70% SPE Fraction was further purified on PF-HPLC using reversed phase conditions with an A/B gradient (A=water, B=acetonitrile) of 15 to 30% B over 35 minutes, with a 95% B wash, followed by re-equilibration at 15% (total run time=45 minutes). Each run was collected in 48 tubes (12 fractions/plate, 4 plates per run) at 15 mL/fraction. Based on UPLC analysis, Fraction 31 contained the desired peak with the desired purity and were pooled and dried under reduced pressure to give a whitish powdery solid. The pure compound was re-suspended/dissolved in 1 mL of water and lyophilized for 3 days to get 21 mg of white fluffy solid with ~85% purity.

$^1$H NMR (400 MHz, Pyridine-$d_5$+$D_2$O), selected signals: δ 5.82 (d, J=3.9 Hz, 1H), 5.58 (m, 1H), 5.40 (m, 1H, merged with HDO peak), 5.32 (d, J=3.8 Hz, 1H), 4.87 (d, J=7.5 Hz, 1H), 3.69 (m, 2H), 1.46 (s, 3H), 1.37 (s, 3H), 1.33 (s, 3H), 1.32 (s, 3H), 1.13 (s, 3H), 1.02 (d, J=6.4 Hz, 3H), 0.93 (s, 3H), 0.85 (s, 3H); $^{13}$C NMR (101 MHz, Pyridine-$d_5$+$D_2$O) δ 144.16, 119.07, 105.05, 103.55, 103.17, 99.75, 91.88, 82.06, 81.62, 78.61, 78.38, 78.07, 77.90, 76.23, 75.70, 75.53, 75.13, 75.06, 74.50, 74.28, 73.36, 72.67, 72.43, 72.17, 71.63, 71.42, 67.93, 63.25, 62.56, 61.63, 50.70, 49.70, 47.41, 43.58, 42.26, 40.90, 40.16, 36.73, 36.50, 34.54, 33.51, 30.63, 28.97, 28.56, 27.26, 26.78, 26.72, 26.22, 25.89, 25.04, 24.62, 19.49, 19.10, 17.06; ESI-MS 1123.89 (M−H)$^-$; Molecular formula, $C_4H_{92}O_{24}$.

Example 28: Enzymatic Production of Compound 17

Siamenoside I, 15 μl BSA (Bovine serum albumin, 10 mg/ml), 15 μl MgCl$_2$, 400 μl UGT76G1 (0.9 mg/ml crude extract, pQE1, XL1-gold) were added to the above flask and continued shaking for another 24 hours at 30° C. The progress of the reaction was monitored periodically by LC-MS. After 24 hrs (total 48 hrs), the unreacted enzyme was denatured by heating at 80° C. for about 30 minutes with stirring (500 rpm). The reaction mixture was then centrifuged (4000 rpm for 10 min, Eppendorf) and filtered through a 0.22 micron PES. The filtered supernatant was dried under reduced pressure and fractionated on SPE C18 60g column using standard 5/35/70/100 MeOH:H$_2$O step gradient. The desired product was eluted in 70% MeOH fraction and further purified on Fluoro-phenyl 3×10 cm column using an A/B gradient (A=H$_2$O, B=acetonitrile) of 15 to 30% B over 35 minutes, followed by 95% B wash and re-equilibration (total run time=45 minutes). Each run was collected in 36 fractions (12 fractions/plate, 3 plates per run) at 30 mL/fraction. Fractions eluted with the desired product were pooled, dried under reduced pressure and re-suspended/dissolved in 2 mL of water and lyophilized for 3 days to get 71 mg of white fluffy solid with about 95% purity.

$^1$H NMR (400 MHz, Pyridine-$d_5$+$D_2$O), selected signals: δ 5.51 (d, J=7.9 Hz, 1H, G2-1H), 5.44 (m, 1H, 6-H, merged with HDO peak), 5.31 (d, J=7.8 Hz, 1H, G5-1H), 4.85 (dd, J=7.5, 2.5 Hz, 2H, G1-1H), 4.79 (d, J=8.0 Hz, 1H, G3-1H), 4.77 (d, J=8.6 Hz, 1H, G4-1H), 3.71 (d, J=9.1 Hz, 1H,

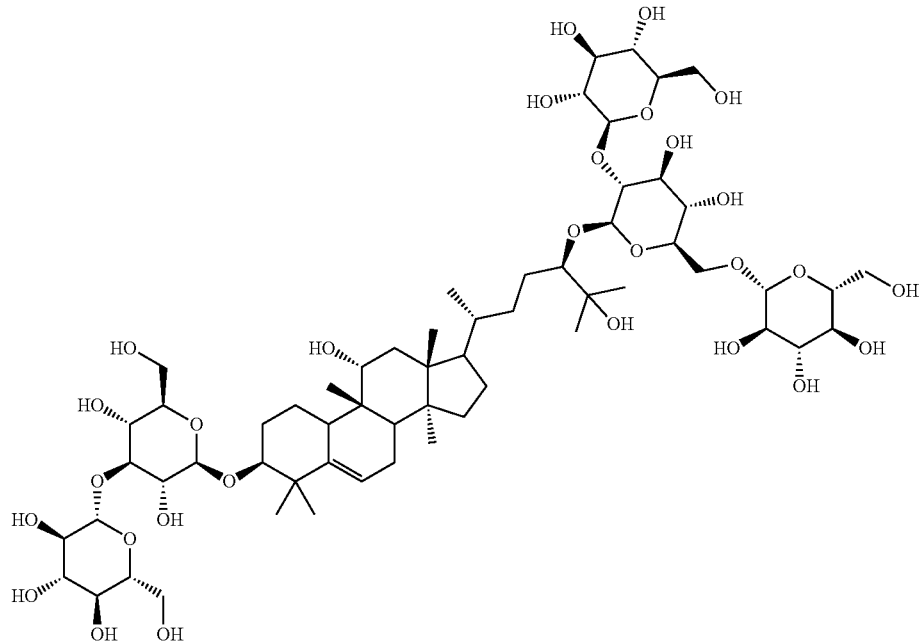 [SMILES: C[C@H](CC[C@@H](O[C@@H]1O[C@H](CO[C@@H]2O[C@H](CO)[C@@H](O)[C@H](O)[C@H]2O)[C@@H](O)[C@H](O)[C@H]1O[C@@H]1O[C@H](CO)[C@@H](O)[C@H](O)[C@H]1O)C(C)(C)O)C1CC[C@@]2(C)C3CC=C4C(CC[C@H](O[C@@H]5O[C@H](CO)[C@@H](O)[C@H](O[C@@H]6O[C@H](CO)[C@@H](O)[C@H](O)[C@H]6O)[C@H]5O)C4(C)C)[C@]3(C)[C@H](O)C[C@]12C]

24-H), 3.58 (s, 1H, 3-H), 1.48 (s, 3H, 28-Me), 1.42 (s, 3H, 26-Me), 1.29 (s, 3H, 27-Me), 1.27 (s, 3H, 19-Me), 1.10 (s, 3H, 29-Me), 1.03 (d, J=6.3 Hz, 3H, 21-Me), 0.89 (s, 3H, 30-Me), 0.86 (s, 3H, 18-Me); ESI-MS 1309.65 (M+Na)$^+$, 1285.72 (M−H)$^-$; Molecular formula, $C_{60}H_{102}O_{29}$.

To a 50 mL falcon tube, 11 ml of deionized water, 1.5 mL of pH 7.52 1M Tris-HCl, 0.03g UDP (Carbosynth), 1.6 g sucrose, and 300 μl sucrose synthase Sus1 (0.9 mg/ml crude extract, pQE1, XL1-gold) were added and shook the tube at 30° C., 200 rpm in the incubator. After 24 hours, 150 mg of

Example 29: Enzymatic Production of Compound 18

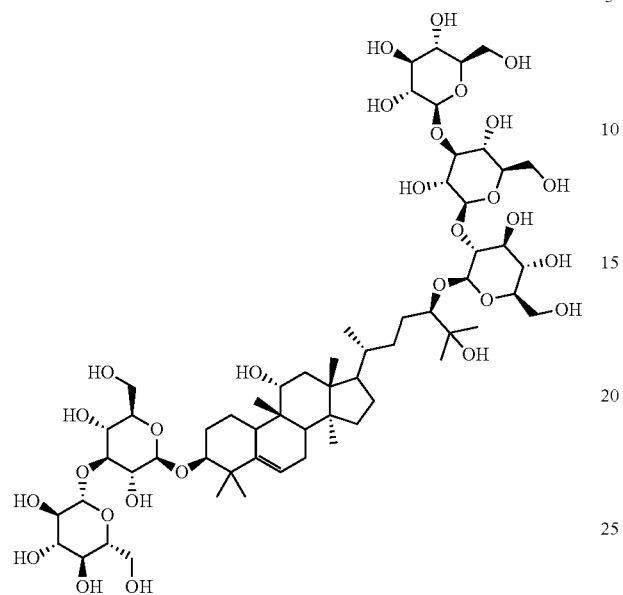

To a 250 mL shake flask, 37 mL of deionized water, 5 mL of pH 7.52 1M Tris-HCl, 0.1 g UDP (Carbosynth), 5.2 g sucrose, and 1 mL sucrose synthase Sus1 (0.9 mg/ml crude extract, pQE1, XL1-gold), 500 mg of mogroside III$_E$ (10 mM), 50 mL BSA (Bovine serum albumin, 10 mg/ml), 50 mL MgCl$_2$(1M), 1.3 mL UGT76G1 (0.9 mg/ml crude extract, pQE1, XL1-gold) were added and shook the flask at 30° C., 200 rpm in the incubator. The progress of the reaction was monitored periodically by LC-MS. After 30 hrs, the unreacted enzyme was denatured by heating at 80° C. for about 30 minutes with stirring (500 rpm). The reaction mixture was then centrifuged (4000 rpm for 10 min, Eppendorf) and filtered through a 0.22 micron PES. The supernatant was dried under reduced pressure and fractionated on SPE C18 60g column using standard MeOH:H$_2$O step-gradient 5/35/70/100. The desired product was eluted in 70% MeOH fraction (982 mg) and further purified on HPLC using Hilic column (3×10 cm, XBridge amide column, 5 um, Waters) by 5 runs injecting ~200 mg each time with an A/B gradient (A=3:1 MeOH:H$_2$O, B=acetonitrile) of 80 to 40% B over 26 minutes, followed by re-equilibration at 80% (total run time=30 minutes). Each run was collected in 12 fractions (12 fractions/plate, 1 plate per run) at 30 mL/fraction. FractionFractions 4 and 5 eluted with the mixture of MIV isomers and further purified using a different method. The desired mogroside V isomer was eluted in FractionFractions 8 &9. These two FractionFractions were pooled, concentrated under reduced pressure and re-suspended/dissolved in 5 mL of H$_2$O and lyophilized for about 3 days to get 366 mg of white fluffy solid with ≥95% purity.

$^1$H NMR (400 MHz, Pyridine-d$_5$+D$_2$O), selected signals: δ 5.55 (d, J=7.9 Hz, 1H, G2-1H), 5.44 (m, 1H, 6-H, merged with HDO peak), 5.32 (d, J=8.0 Hz, 1H, G4-1H), 5.29 (d, J=7.9 Hz, 1H, G5-1H), 4.99 (d, J=7.1 Hz, 1H, G1-1H), 4.78 (d, J=7.8 Hz, 1H, G3-1H), 3.89 (m, 1H, 24-H), 3.60 (s, 1H, 3-H), 1.48 (s, 3H, 28-Me), 1.43 (s, 3H, 26-Me), 1.39 (s, 3H, 27-Me), 1.25 (s, 3H, 19-Me), 1.08 (s, 3H, 29-Me), 1.01 (d, J=6.2 Hz, 3H, 21-Me), 0.83 (s, 3H, 30-Me), 0.82 (s, 3H, 18-Me); ESI-MS 1285.91 (M–H)$^-$; Molecular formula, C$_{60}$H$_{102}$O$_{29}$.

Example 30: Enzymatic Production of Compound 19

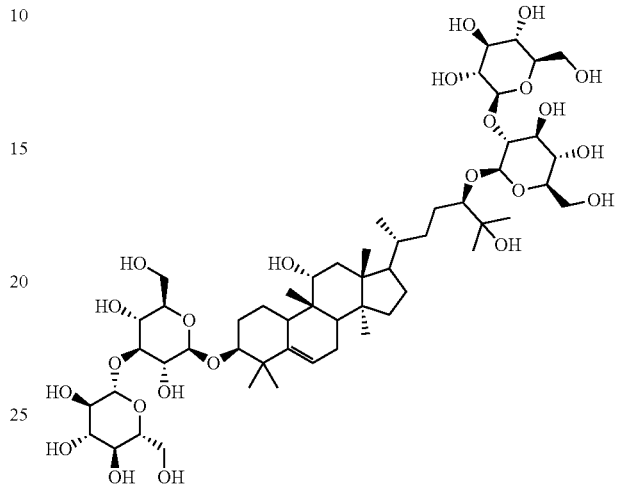

To a 250 mL shake flask, 37 mL of deionized water, 5 mL of pH 7.52 1M Tris-HCl, 0.1 g UDP (Carbosynth), 5.2 g sucrose, and 1 mL sucrose synthase Sus1 (0.9 mg/ml crude extract, pQE1, XL1-gold), 1000 mg of mogroside II$_E$ (20 mM), 50 mL BSA (Bovine serum albumin, 10 mg/ml), 50 mL MgCl$_2$(1M), 1.3 mL UGT76G1 (0.9 mg/ml crude extract, pQE1, XL1-gold) were added and shook the flask at 30° C., 200 rpm in the incubator. The progress of the reaction was monitored periodically by LC-MS. After ~30 hrs, the unreacted enzyme was denatured by heating at 80° C. for about 30 minutes with stirring (500 rpm). The reaction mixture was then centrifuged (4000 rpm for 10 min, Eppendorf) and filtered through a 0.22 micron PES. The filtrate was dried under reduced pressure and fractionated on SPE C18 60g column using standard MeOH:H$_2$O step-gradient 5/35/70/100. Mogroside IV and V isomers were eluted in 70% MeOH fraction (982 mg) and further purified on HPLC using Hilic column (3×10 cm, XBridge amide column, Sum, Waters) by 5 runs injecting ~200 mg each time with an A/B gradient (A=3:1 MeOH:H$_2$O, B=acetonitrile) of 80 to 40% B over 26 minutes, followed by re-equilibration at 80% (total run time=30 minutes). Each run was collected in 12 fractions (12 fractions/plate, 1 plate per run) at 30 mL/fraction. Mogroside V isomer was eluted in FractionFractions 8 &9. Whereas, the mixture of mogroside IV isomers were eluted in FractionFractions 4 and 5. These two FractionFractions were pooled and re-purified using Fluoro-phenyl 3×10 column, A/B gradient (A=H$_2$O, B=acetonitrile) of 15 to 30% B over 35 minutes, followed by a wash at 95% B and re-equilibration (total run time=45 minutes). Each run was collected in 24 fractions (12 fractions/plate, 3 plates per run) at 30 mL/fraction. The minor MIV isomer was eluted in Fraction 7 and the desired major MIV isomer was eluted in FractionFractions 4 and 5. These two FractionFractions were pooled, concentrated under reduced pressure and re-suspended/dissolved in 3 mL of H$_2$O and lyophilized for about 3 days to get 91.7 mg of white fluffy solid with ≥95% purity.

¹H NMR (400 MHz, Pyridine-d₅+D₂O), selected signals: 65.44 (m, 1H, 6-H, merged with HDO peak), 5.36 (d, J=7.8 Hz, 1H, G2-1H), 5.31 (d, J=7.9 Hz, 1H, G4-1H), 5.00 (d, J=7.7 Hz, 1H, G1-1H), 4.78 (d, J=7.8 Hz, 1H, G3-1H), 3.87 (d, J=7.9 Hz, 1H, 24-H), 3.59 (s, 1H, 3-H), 1.48 (s, 3H, 28-Me), 1.45 (s, 3H, 26-Me), 1.41 (s, 3H, 27-Me), 1.26 (s, 3H, 19-Me), 1.10 (s, 3H, 29-Me), 1.01 (d, J=6.3 Hz, 3H, 21-Me), 0.83 (s, 3H, 30-Me), 0.82 (s, 3H, 18-Me); ESI-MS 1125.68 (MH)⁺, 1123.74 (M−H)⁻; Molecular formula, $C_{54}H_{92}O_{24}$.

Example 31: Enzymatic Production of Compound 20

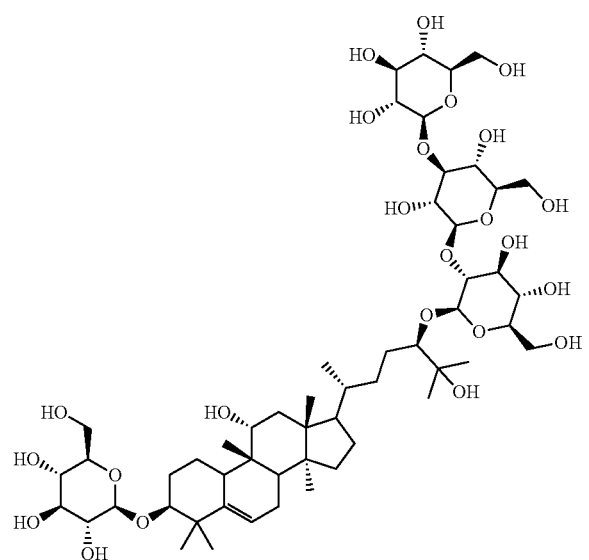 [SMILES: C[C@H](CC[C@@H](O[C@@H]1O[C@H](CO)[C@@H](O)[C@H](O)[C@H]1O[C@@H]1O[C@H](CO)[C@@H](O)[C@H](O[C@@H]2O[C@H](CO)[C@@H](O)[C@H](O)[C@H]2O)[C@H]1O)C(C)(C)O)C1CC[C@@]2(C)C3CC=C4C(CC[C@H](O[C@@H]5O[C@H](CO)[C@@H](O)[C@H](O)[C@H]5O)C4(C)C)[C@]3(C)[C@H](O)C[C@]12C]

To a 250 mL shake flask, 36 mL of deionized water, 5 mL of pH 7.52 1M Tris-HCl, 0.1 g UDP (Carbosynth), 5.2 g sucrose, and 2.7 ml sucrose synthase Sus1 (0.37 mg/ml crude extract, pQE1, XL1-gold), 500 mg of mogroside III$_E$, 50 mL BSA (Bovine serum albumin, 10 mg/ml), 50 mL MgCl₂(1M), 1.4 ml UGT76G1 (0.7 mg/ml crude extract, pQE1, XL1-gold) were added and shook the flask at 30° C., 200 rpm in the incubator. The progress of the reaction was monitored periodically by LC-MS. The reaction was repeated with another 500 mg of mogroside III$_E$ using the same reaction conditions. After ~24 hrs, the unreacted enzyme from both flasks was denatured by heating at 80° C. for about 30 minutes with stirring (500 rpm). The reaction mixture was then centrifuged (4000 rpm for 10 min, Eppendorf) and filtered through a 0.22 micron PES. The combined filtrate from two reactions was dried under reduced pressure and fractionated on SPE C18 60g column using standard MeOH:H₂O step-gradient 5/35/70/100. The desired mogroside IV and V isomers were eluted in 70% MeOH fraction and purified on Fluoro-phenyl 3×10 cm column with an A/B gradient (A=H₂O, B=acetonitrile) of 15 to 30% B over 35 minutes, followed by a wash at 95% B and re-equilibration (total run time=45 minutes). Each run was collected in 12 fractions (12 fractions/plate, 1 plate per run) at 30 mL/fraction. FractionFractions 3 to 5 were eluted as mixture of major MV and MIV isomers and FractionFractions 6 and 7 eluted with the desired product with about 80% purity. The pooled FractionFractions 6 & 7 were re-purified on HILIC 3×0 cm column with an A/B gradient (A=3:1 MeOH:H₂O, B=acetonitrile) of 80 to 40% B over 26 minutes, followed by re-equilibration at 80% (total run time=30 minutes). Each run was collected in 12 fractions (12 fractions/plate, 1 plate per run) at 30 mL/fraction. Fraction 6 contained the desired product, was pooled, concentrated under reduced pressure and re-suspended/dissolved in 3 mL of H₂O and lyophilized for about 3 days to get 70 mg of white fluffy solid with ≥95% purity.

¹H NMR (400 MHz, Pyridine-d₅+D₂O), selected signals: δ 5.56 (d, J=7.9 Hz, 1H, G2-1H), 5.43 (m, 1H, 6-H, merged with HDO peak), 5.29 (d, J=7.9 Hz, 1H, G4-1H,), 4.99 (d, J=7.0 Hz, 1H, G1-1H), 4.83 (d, J=7.8 Hz, 1H, G3-1H), 3.63 (s, 1H, 3-H), 1.50 (s, 3H, 28-Me), 1.44 (s, 3H, 26-Me), 1.39 (s, 3H, 27-Me), 1.27 (s, 3H, 19-Me), 1.09 (s, 3H, 29-Me), 1.02 (d, J=6.3 Hz, 3H, 21-Me), 0.83 (brs, 6H, 18 & 30-Me); ESI-MS 1125.96 (MH)⁺, 1123.91 (M−H)⁻; Molecular formula, $C_{54}H_{92}O_{24}$.

Example 32: Enzymatic Production of Compound 21

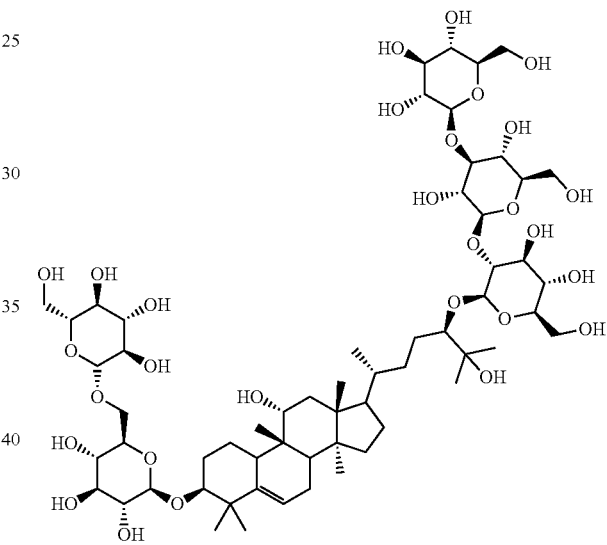

To a 50 mL falcon tube, 8 ml of deionized water, 1.5 mL of pH 7.52 1M Tris-HCl, 0.03g UDP (Carbosynth), 1.6 g sucrose, and 2.7 ml sucrose synthase Sus1 (0.37 mg/ml crude extract, pQE1, XL1-gold), 1.4 ml UGT76G1 (0.7 mg/ml crude extract, pQE1, XL1-gold), 15 μl BSA (10 mg/ml), 15 μl MgCl₂(1M), 150 mg of Mogroside IV$_E$ were added and shook the tube at 30° C., 200 rpm in the incubator. The progress of the reaction was monitored periodically by LC-MS. After 48 hrs, the reaction was quenched by heating at 80° C. for about 30 minutes with stirring (500 rpm) to denature the enzyme. The reaction mixture was then centrifuged (4000 rpm for 10 min, Eppendorf) and filtered through a 0.22 micron PES. The supernatant was dried under reduced pressure and fractionated on SPE C18 60g column using standard MeOH:H₂O step-gradient 5/35/70/100. The desired product was eluted in 70% MeOH fraction and further purified on Hilic 3×10 cm column using an A/B gradient (A=3:1 MeOH:H₂O, B=acetonitrile) of 80 to 20% B over 26 minutes, followed by re-equilibration at 80% (total run time=30 minutes). Each run was collected in 12 fractions (12 fractions/plate, 1 plate per run) at 30 mL/fraction. Fractions eluted with the desired product were pooled, dried under reduced pressure and re-suspended/dissolved in 2 mL of water and lyophilized for 3 days to get 108 mg of white fluffy solid with about 95% purity.

$^1$H NMR (400 MHz, Pyridine-d$_5$+D$_2$O), selected signals: δ 5.55 (d, J=7.9 Hz, 1H, G2-1H), 5.42 (m, 1H, 6-H, merged with HDO peak), 5.28 (d, J=7.9 Hz, 1H, G5-1H), 5.11 (d, J=7.8 Hz, 1H, G4-1H), 4.99 (d, J=7.0 Hz, 1H, G1-1H), 4.77 (d, J=7.8 Hz, 1H, G3-1H), 3.65 (d, J=2.8 Hz, 1H, 3-H), 1.46 (s, 3H, 28-Me), 1.43 (s, 3H, 26-Me), 1.39 (s, 3H, 27-Me), 1.28 (s, 3H, 19-Me), 1.05 (s, 3H, 29-Me), 1.03 (d, J=6.3 Hz, 3H, 21-Me), 0.82 (s, 6H, 18 & 30-Me); ESI-MS 1287.76 (MH)$^+$, 1285.95 (M−H)$^-$; Molecular formula, C$_{60}$H$_{102}$O$_{29}$.

Example 33: Enzymatic Production of Compound 22

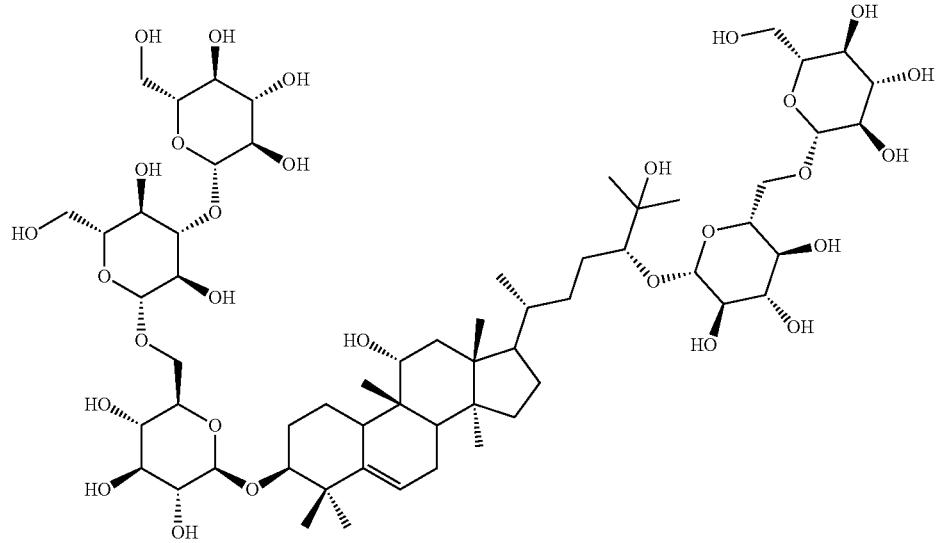

To a 50 mL falcon tube, 8 ml of deionized water, 1.5 mL of pH 7.52 1M Tris-HCl, 0.03g UDP (Carbosynth), 1.6 g sucrose, 2.7 ml sucrose synthase Sus1 (0.37 mg/ml crude extract, pQE1, XL1-gold), 1.4 ml UGT76G1 (0.7 mg/ml crude extract, pQE1, XL1-gold), 15 1 BSA (10 mg/ml), 15 μl MgCl$_2$(1M), 150 mg of Mogroside IVA were added and shook the tube at 30° C., 200 rpm in the incubator. The progress of the reaction was monitored periodically by LC-MS. 24 hrs after the addition of Mogroside IVA, the reaction was stopped by heating at 80° C. for 30 minutes with stirring (500 rpm). The reaction was then centrifuged (4000 rpm for 10 min, Eppendorf) and filtered through a 250 ml, 0.22 micron PES. The filtrate was loaded onto a 60g C18 column and fractionated using 5/35/70/100 MeOH:H$_2$O step gradient. The desired product was eluted in 70% MeOH fraction and further purified on HILIC column using an A/B gradient (A=3:1 MeOH:H$_2$O, B=acetonitrile) of 80 to 20% B over 26 minutes, followed by re-equilibration at 80% (total run time=30 minutes). Each run was collected in 12 fractions (12 fractions/plate, 1 plate per run) at 30 mL/fraction. Fraction 6 and 7 contained the desired product with 80% purity. These two FractionFractions from all the runs were pooled and re-purified on Fluoro-phenyl 3×10 cm column, A/B gradient (A=H$_2$O, B=acetonitrile) of 15 to 30% B over 35 minutes, followed by a wash at 95% B and re-equilibration (total run time=45 minutes). Each run was collected in 12 fractions (12 fractions/plate, 1 plate per run) at 30 mL/fraction. Fractions eluted with the desired product were pooled, dried under reduced pressure and re-suspended/dissolved in 1 mL of water and lyophilized for 3 days to get 18 mg of white fluffy solid with about 95% purity.

$^1$H NMR (400 MHz, Pyridine-d$_5$+D$_2$O), selected signals: δ 5.44 (m, 1H, 6-H, merged with HDO peak), 5.19 (dd, J=7.8, 1.9 Hz, 1H, G5-1H), 5.10 (d, J=7.8 Hz, 1H, G4-1H), 4.95 (d, J=7.7 Hz, 1H, G2-1H), 4.82 (d, J=7.9 Hz, 1H, G1-1H), 4.77 (d, J=7.8 Hz, 1H, G3-1H), 3.70 (m, 2H, 24 and 3-H), 1.47 (s, 3H, 28-Me), 1.35 (s, 3H, 26-Me), 1.29 (s, 6H, 27 and 19-Me), 1.07 (s, 3H, 29-Me), 0.91 (d, J=6.2 Hz, 3H, 21-Me), 0.85 (s, 3H, 30-Me), 0.77 (s, 3H, 18-Me); ESI-MS 1287.76 (MH)$^+$, 1285.95 (M−H)$^-$; Molecular formula, C$_{60}$H$_{102}$O$_{29}$.

Example 34: Isolation and Enzymatic Production of Compound 23

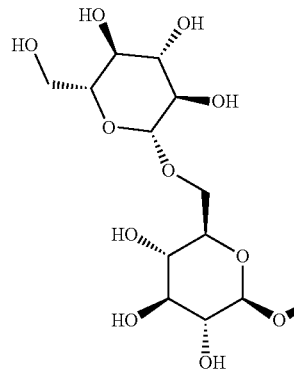
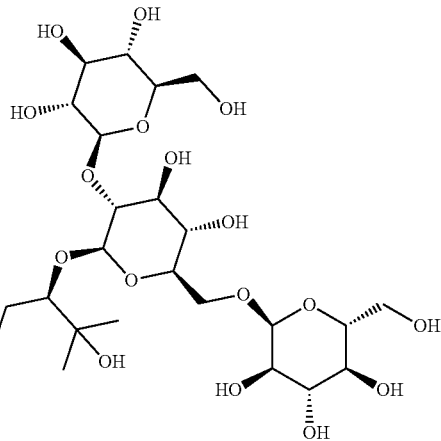

Enzymatic: To a 250 mL shake flask, 5 mL of pH 5.5 1M sodium acetate buffer, 10 g sucrose, 10 ml dextransucrase (DexT, 1 mg/ml crude extract, pET23a, BL21-Codon Plus-RIL, grown in 2× YT), 300 mg of Mogroside $IV_E$, 35 mL of water were added and shook the flask at 200 rpm, 30° C. The progress of the reaction was monitored periodically by LC-MS. After ~24 hrs, 60 uL of dextranase (Amano) was added to the reaction (hydrolyze the hyper glycosylated mogroside $IV_E$ isomers to the desired mogroside V isomer) and shook at 200 rpm, 40° C. After ~18 hrs, the reaction mixture was heated to 80° C. for ~30 minutes while shaking at 200 rpm, then it was centrifuged (4000 rpm for 10 min, Eppendorf) and the supernatant was filtered through a 250 ml, 0.22 micron PES. The supernatant was loaded onto a 60g C18 SPE column and fractionated using 5/35/70/100/5 MeOH:H$_2$O gradient. The desired product was eluted in 70% MeOH fraction along with other minor isomers and unreacted $MIV_E$. This Fraction was further purified on HILIC column (3×10 cm, XBridge amide column, Sum, Waters) using an A/B gradient (A=3:1 MeOH:H$_2$O, B=acetonitrile) of 80 to 40% B over 26 minutes, followed by re-equilibration at 80% (total run time=30 minutes). Each run was collected in 24 fractions (12 fractions/plate, 2 plates per run) at 30 mL/fraction. The desired compound was eluted in fractions 13 and 14. These two FractionFractions were pooled, concentrated under reduced pressure and re-suspended/dissolved in 3 mL of H$_2$O and lyophilized for about 2 days to get 85 mg of white fluffy solid with ≥95% purity.

Isolation: 180 g of *Siraitia grosvenorii* powdered extract (*Fructus momordicae* extract, 50% mogrosides, light yellow powder; sample ID: 50755234) was obtained from Xi'an Heking Bio-tech Co., Ltd. was fractionated on C18 HPLC (5×10 cm Atlantis prep T3 OBD column, 5 um, Waters) by 360 injections using an A/B gradient (A=water, B=acetonitrile) of 10→30% B over 30 minutes, with a 95% B wash, followed by re-equilibration at 1% (total run time=42 minutes) in two different batches of 80 and 100g. Each run was collected in 36 tared tubes (12 fractions/plate, 3 plates per run) at 30 mL/fraction. The plates were dried in the Genevac HT12/HT24. The desired compound was eluted in frxn 15 along with other isomers. The pooled frxn 15 from two batches (916 and 1913 mg) was further fractionated in 28 runs on Hilic HPLC column (3×10 cm, XBridge amide column, 5 um, Waters) using an A/B gradient (A=3:1 MeOH:H$_2$O, B=acetonitrile) of 80 to 40% B over 22 minutes, with a 95% A wash followed by re-equilibration at 80% (total run time=30.3 minutes). Each run was collected in 12 fractions (12 fractions/plate, 1 plate per run) at 30 mL/fraction. Fraction 9 contained the desired product and was pooled, concentrated under reduced pressure followed by the addition of 2 mL of H$_2$O and lyophilized the sample for 2 days to get 190 mg of fluffy white solid with ~90% purity.

$^1$H NMR (400 MHz, Pyridine-d$_5$+D$_2$O), selected signals: δ 5.43 (m, 1H, 6-H, merged with HDO peak), 5.40 (m, 1H, G2-1H, merged with HDO peak), 5.38 (d, J=3.7 Hz, 1H, G5-1H), 5.10 (d, J=7.8 Hz, 1H, G4-1H), 4.87 (d, J=7.7 Hz, 1H, G1-1H), 4.76 (d, J=7.8 Hz, 1H, G3-1H), 3.72 (d, J=8.2 Hz, 1H, 24-H), 3.64 (s, 1H, 3-H), 1.46 (s, 3H, 28-Me), 1.42 (s, 3H, 26-Me), 1.30 (s, 3H, 27-Me), 1.29 (s, 3H, 19-Me), 1.06 (s, 3H, 29-Me), 1.03 (d, J=6.3 Hz, 3H, 21-Me), 0.86 (s, 3H, 30-Me), 0.83 (s, 3H, 18-Me); ESI-MS 1287.9 (MH)$^+$, 1285.96 (M−H)$^−$, Molecular formula, C$_{60}$H$_{102}$O$_{29}$.

Examples 35 and 36: Enzymatic Production of Mogroside II$_{A1}$ and Mogroside II$_{A2}$ from Fungal Lactase

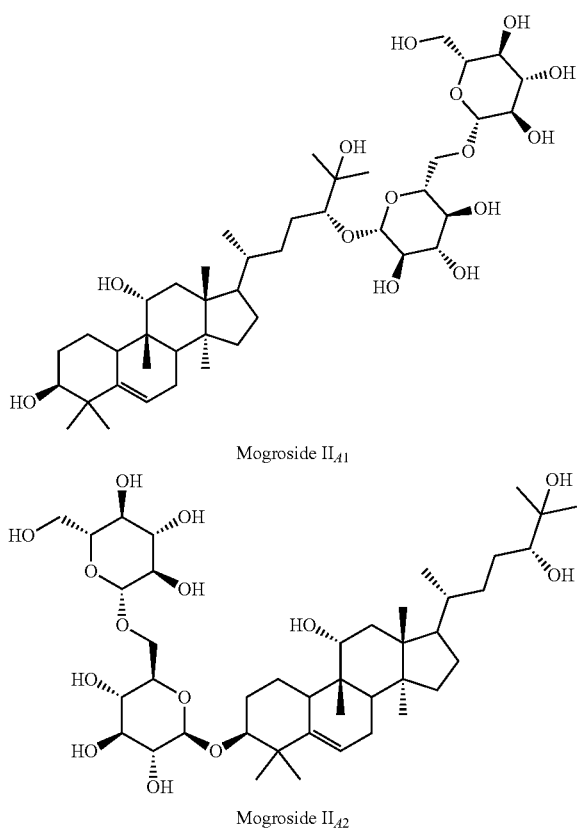

Mogroside II$_{A1}$

Mogroside II$_{A2}$

To a 250 mL round bottom flask, 1 g of mogroside V, 100 mL of 0.1M sodium acetate buffer pH 5 and 500 mg of Fungal Lactase were added and stirred the flask at 50° C. The progress of the reaction was monitored periodically by LC-MS. After 72 hours, the reaction was stopped by heating at 80° C. for ~30 minutes and centrifuged at 4000 rpm for 10 minutes. The supernatant was loaded onto a 60g C18 SPE column and fractionated using 5/35/70/100/5 MeOH:H$_2$O gradient. The desired products were eluted in 70 and 100% MeOH fractions. These two FractionFractions were further purified on HILIC column using an A/B gradient (A=3:1 MeOH:H$_2$O, B=acetonitrile) of 90 to 50% B over 26 minutes, followed by re-equilibration at 90% (total run time=30 minutes). Each run was collected in 24 fractions (12 fractions/plate, 1 plate per run) at 30 mL/fraction. The desired compounds were eluted in FractionFractions 12 and 15. These two FractionFractions from different runs were pooled separately and characterized as Mogroside II$_{A1}$ and Mogroside II$_{A2}$ by 1D and 2D NMR and LC-MS data.

Mogroside II$_{A1}$: $^1$H NMR (400 MHz, Pyridine-d$_5$+D$_2$O), selected signals: δ5.60 (d, J=6.0 Hz, 1H), 4.86 (d, J=7.9 Hz, 2H), 4.79 (d, J=7.7 Hz, 1H), 3.73 (dd, J=6.2, 3.6 Hz, 2H), 1.39 (d, J=1.6 Hz, 6H), 1.34 (s, 3H), 1.29 (s, 3H), 1.15 (s, 3H), 0.90 (d, J=6.4 Hz, 3H), 0.87 (s, 3H), 0.84 (s, 3H); ESI-MS 801.68 (MH)$^+$, 799.74 (M−H)$^−$, Molecular formula, C$_{42}$H$_{72}$O$_{14}$.

Mogroside II$_{A2}$: $^1$H NMR (400 MHz, Pyridine-d$_5$+D$_2$O), selected signals: δ5.45 (m, 1H, merged with HDO peak), 5.10 (d, J=7.8 Hz, 1H), 4.77 (d, J=7.8 Hz, 1H), 3.75 (dd, J=9.0, 2.5 Hz, 1H), 3.67 (d, J=2.9 Hz, 1H), 1.52 (s, 3H), 1.49 (s, 2H), 1.47 (s, 3H), 1.28 (s, 3H), 1.07 (s, 3H), 0.98 (d, J=6.1 Hz, 3H), 0.83 (s, 3H), 0.81 (s, 3H); ESI-MS 801.64 (MH)$^+$, 799.65 (M−H)$^−$, Molecular formula, C$_{42}$H$_{72}$O$_{14}$.

Example 37: Enzymatic Production of Mogroside$_{1A}$ from Viscozyme

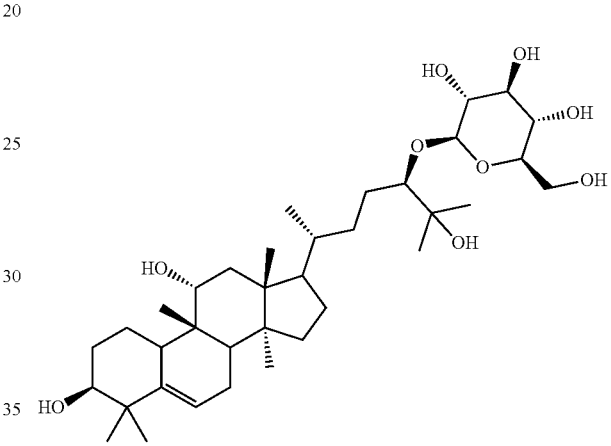

To a 100 mL round bottom flask, 300 mg of Mogroside II$_A$, 25 mL of 0.1M sodium acetate buffer pH 5 and 200 uL of Viscozyme (Novozymes) were added and stirred the flask at 50° C. The progress of the reaction was monitored periodically by LC-MS. After 24 hours the reaction was stopped by heating at 80° C. for 30 minutes and centrifuged at 4000 rpm for 10 minutes. The supernatant was dried under reduced pressure and purified on Fluoro-phenyl 3×10 cm column with an A/B gradient (A=H$_2$O, B=acetonitrile) of 20 to 60% B over 25 minutes, followed by a wash at 95% B and re-equilibration (total run time=31 minutes). Each run was collected in 24 fractions (12 fractions/plate, 2 plates per run) at 30 mL/fraction. Fractions eluted with the desired product were pooled, dried under reduced pressure and re-suspended/dissolved in 1 mL of water and lyophilized for 2 days to get 30 mg of white fluffy solid with about 90% purity.

$^1$H NMR (400 MHz, Pyridine-d$_5$+D$_2$O), selected signals: δ 5.61 (d, J=6.0 Hz, 1H), 4.97 (d, J=7.8 Hz, 1H), 3.86 (m, 1H), 3.73 (d, J=2.8 Hz, 1H), 1.42 (s, 3H), 1.40 (s, 3H), 1.38 (s, 3H), 1.34 (s, 3H), 1.16 (s, 3H), 0.94 (d, J=6.4 Hz, 3H), 0.87 (s, 3H), 0.85 (s, 3H); ESI-MS 639.39 (MH)$^+$, 637.58 (M−H)$^−$, Molecular formula, C$_{36}$H$_{62}$O$_9$.

Example 38: Enzymatic Production of Compound 24

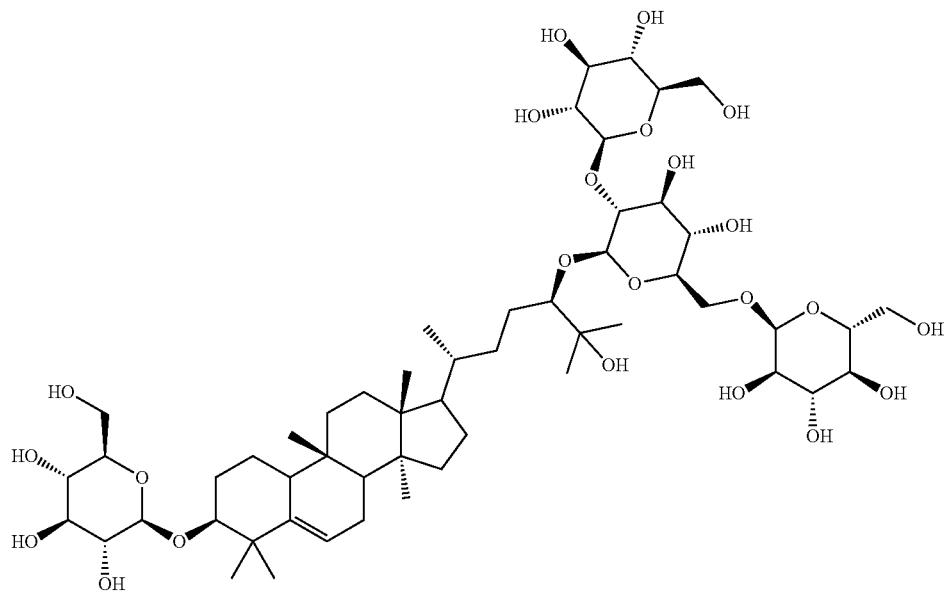 [SMILES: C[C@H](CC[C@@H](O[C@@H]1O[C@H](CO[C@H]2O[C@H](CO)[C@@H](O)[C@H](O)[C@H]2O)[C@@H](O)[C@H](O)[C@H]1O[C@@H]1O[C@H](CO)[C@@H](O)[C@H](O)[C@H]1O)C(C)(C)O)C1CC[C@@]2(C)C3CC=C4C(CC[C@H](O[C@@H]5O[C@H](CO)[C@@H](O)[C@H](O)[C@H]5O)C4(C)C)[C@]3(C)CC[C@]12C]

To a 3 L shake flask, 1 L water, 150 mL of pH 5.5 1M sodium acetate buffer, 300 g sucrose, 50 ml dextransucrase DexT (1 mg/ml crude extract, pET23a, BL21-Codon Plus-RIL, grown in 2× YT), 10 g of mogroside $III_E$ were added and shook the flask at 200 rpm, 30° C. The progress of the reaction was monitored periodically by LC-MS. After 72 hrs, the reaction mixture was treated with 1500 uL of dextranase (Amano). After 24 hrs the reaction was stopped by heating at 80° C. and centrifuged at 10,000 rpm for 5 minutes and the supernatant was filtered and stored at 4° C. The reaction was repeated 3 more times using the same conditions to raise the material. Each flask (10g) was loaded onto a 400g C18 SPE column and fractionated using 5/25/50/75/100 MeOH:H$_2$O step gradient. 1350 ml per fraction spread out over 6 flasks. The desired product was eluted in the 4$^{th}$ flask of the 75% MeOH fraction and further purified on fluoro-phenyl 3×10 cm column using an A/B gradient (A=H$_2$O, B=acetonitrile) of 15 to 30% B over 35 minutes, followed by a wash at 95% B and re-equilibration (total run time=45 minutes). Each run was collected in 24 fractions (12 fractions/plate, 2 plates per run) at 30 mL/fraction. Fractions eluted with the desired product were pooled, dried under reduced pressure and re-suspended/dissolved in 1 mL of water and lyophilized for 2 days to get 25 mg of white fluffy solid with about 90% purity.

$^1$H NMR (400 MHz, Pyridine-d$_5$+D$_2$O), selected signals: δ 5.52 (1H, m, merged with HDO), 5.48 (m, 1H), 5.44 (d, J=3.7 Hz, 1H), 4.95 (d, J=7.8 Hz, 1H), 4.89 (d, J=7.8 Hz, 1H), 3.81 (m, 1H), 3.68 (d, J=3.3 Hz, 1H), 1.54 (s, 3H), 1.50 (s, 3H), 1.39 (s, 3H), 1.09 (d, J=8.4 Hz, 6H), 0.87 (s, 3H), 0.83 (s, 3H), 0.81 (s, 3H); $^{13}$C NMR (101 MHz, Pyridine-d$_5$+D$_2$O) δ 143.23, 118.86, 107.17, 105.20, 103.35, 99.81, 91.39, 87.71, 81.89, 78.50, 78.32, 78.07, 75.68, 75.31, 75.03, 74.13, 73.82, 72.73, 72.14, 72.05, 71.62, 71.45, 67.61, 63.24, 62.82, 62.58, 50.81, 49.37, 46.46, 46.44, 43.78, 41.77, 38.51, 36.50, 35.03, 34.60, 33.58, 32.58, 30.75, 29.00, 28.38, 28.24, 26.74, 25.92, 24.96, 24.55, 22.72, 19.22, 18.11, 15.68; ESI-MS 1109.77 (MH)*, 1107.73 (M−H)$^−$, Molecular formula, C$_4$H$_{92}$O$_{23}$.

Example 39: Enzymatic Production of Compound 25

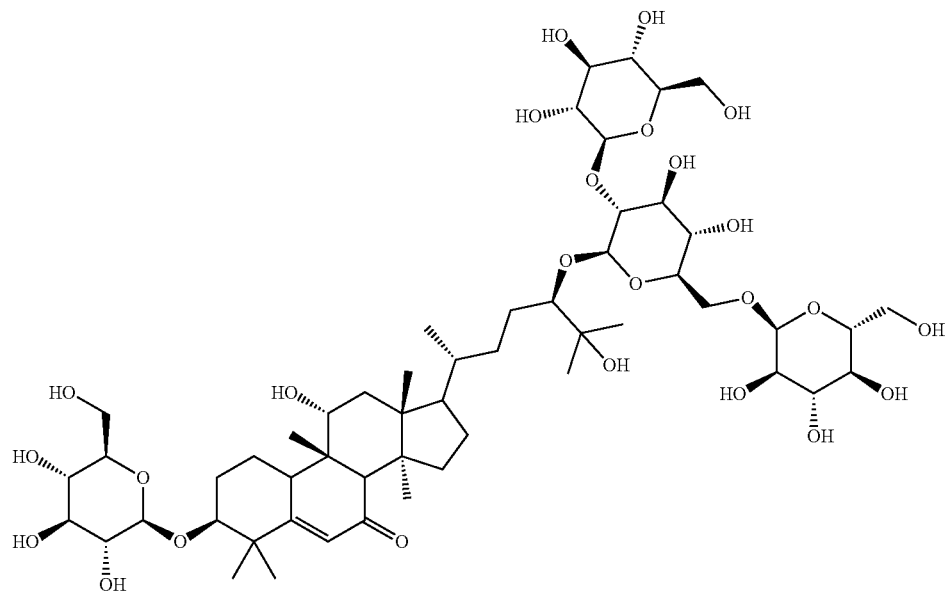 [SMILES: C[C@H](CC[C@@H](O[C@@H]1O[C@H](CO[C@H]2O[C@H](CO)[C@@H](O)[C@H](O)[C@H]2O)[C@@H](O)[C@H](O)[C@H]1O[C@@H]1O[C@H](CO)[C@@H](O)[C@H](O)[C@H]1O)C(C)(C)O)C1CC[C@@]2(C)C3C(=O)C=C4C(CC[C@H](O[C@@H]5O[C@H](CO)[C@@H](O)[C@H](O)[C@H]5O)C4(C)C)[C@]3(C)[C@H](O)C[C@]12C]

To a 1 L flask, 270 mL water, 40 mL of pH 5.5 1M sodium acetate buffer, 80 g sucrose, 8 mL dextransucrase DexT (1 mg/mL crude extract, pET23a, BL21-Codon Plus-RIL, grown in 2× YT and TB), 2g of Mogroside III$_E$ were added and shook the flask at 30° C., 200 rpm. The progress of the reaction was monitored periodically by LC-MS. After 72 hrs, the reaction was treated with 300 uL of dextranase (Amano). After 24 hrs the reaction was quenched by heating at 80° C. and centrifuged at 10,000 rpm for 5 minutes and the supernatant was filtered and fractionated on 60g C18 SPE column using 5/25/50/50/75/100 MeOH:H$_2$O step gradient. The desired product was eluted in 50% MeOH fraction and further purified on Hilic 3×10 cm column using an A/B gradient (A=3:1 MeOH:H$_2$O, B=acetonitrile) of 80 to 40% B over 26 minutes, followed by re-equilibration at 80% (total run time=30 minutes). Each run was collected in 24 fractions (12 fractions/plate, 2 plates per run) at 30 mL/fraction. Fractions eluted with the desired product were pooled, dried under reduced pressure and re-suspended/dissolved in 1 mL of water and lyophilized for ~2 days to get 11.5 mg of white fluffy solid with about 90% purity.

$^1$H NMR (400 MHz, Pyridine-d$_5$+D$_2$O), selected signals: δ 6.24 (d, J=1.5 Hz, 1H), 5.5 (m, 1H, merged with HDO peak), 5.36 (d, J=3.7 Hz, 1H), 4.86 (d, J=7.7 Hz, 1H), 4.80 (d, J=7.8 Hz, 1H), 3.70 (d, J=5.9 Hz, 2H), 1.50 (s, 3H), 1.41 (s, 3H), 1.29 (s, 3H), 1.21 (s, 3H), 1.17 (s, 3H), 1.02 (d, J=6.2 Hz, 3H), 0.93 (s, 3H), 0.84 (s, 3H); $^{13}$C NMR (101 MHz, Pyridine-d$_5$+D$_2$O) δ 200.60, 170.03, 123.51, 105.47, 103.65, 102.12, 98.40, 90.39, 86.54, 77.13, 76.93, 76.64, 75.37, 74.33, 74.24, 73.78, 73.61, 72.72, 72.52, 72.41, 71.30, 70.73, 70.63, 70.06, 66.21, 61.78, 61.29, 61.15, 58.64, 49.13, 47.22, 45.65, 42.53, 39.20, 39.01, 37.82, 35.55, 33.10, 32.12, 27.96, 27.46, 27.19, 26.15, 25.73, 25.27, 25.21, 24.16, 23.45, 18.30, 17.60, 15.36; ESI-MS 1139.47 (MH)$^+$, 1137.85 (M−H)$^−$, Molecular formula, C$_4$H$_{90}$O$_{25}$.

Example 40: Enzymatic Production of Compound

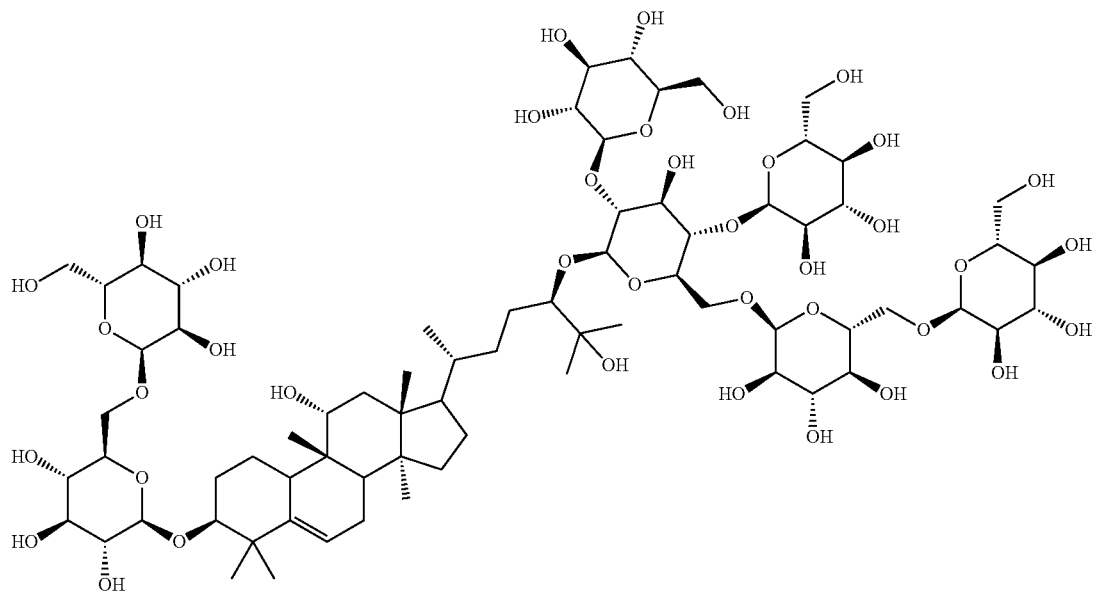 [SMILES: C[C@H](CC[C@@H](O[C@@H]1O[C@H](CO[C@H]2O[C@H](CO[C@H]3O[C@H](CO)[C@@H](O)[C@H](O)[C@H]3O)[C@@H](O)[C@H](O)[C@H]2O)[C@@H](O[C@H]2O[C@H](CO)[C@@H](O)[C@H](O)[C@H]2O)[C@H](O)[C@H]1O[C@@H]1O[C@H](CO)[C@@H](O)[C@H](O)[C@H]1O)C(C)(C)O)C1CC[C@@]2(C)C3CC=C4C(CC[C@H](O[C@@H]5O[C@H](CO[C@H]6O[C@H](CO)[C@@H](O)[C@H](O)[C@H]6O)[C@@H](O)[C@H](O)[C@H]5O)C4(C)C)[C@]3(C)[C@H](O)C[C@]12C]

To a L flask, 270 mL water, 40 mL of pH5.5 1M sodium acetate buffer, 80 g sucrose, 8 mL dextransucrase DexT (1 mg/mL crude extract, pET23a, BL21-Codon Plus-RIL, grown in 2x YT and TB), 2g of Mogroside IIE were added and shook the flask at 30° C., 200 rpm. The progress of the reaction was monitored periodically by LC-MS. After 72 hrs, the reaction was treated with 300 uL of dextranase (Amano). After 24 hrs the reaction was quenched by heating at 80° C. and centrifuged at 10,000 rpm for 5 minutes and the supernatant was filtered and fractionated on 60g C18 SPE column using 5/35/70/100 MeOH:$H_2O$ step gradient. The desired product was eluted in 70% MeOH fraction and purified on Hilic 3×10 cm column using an A/B gradient (A=3:1 MeH:$H_2O$, B acetonitrile) of 80 to 40% B over 26 minutes, followed by re-equilibration at 80% (total run time 30 minutes). Each run was collected in 24 fractions (12 fractions/plate, 2 plates per run) at 30 mL/fraction. Fraction 20 contained the desired product and was pooled with ~80% purity. It was re-purified on modified Hilic method using an A/B gradient (A=3:1 MeOH:$H_2O$, B=acetonitrile) of 80 to 20% B over 26 minutes, followed by re-equilibration at 80% (total run time=30 minutes). Each run was collected in 24 fractions (12 fractions/plate, 2 plates per run) at 30 mL/fraction. Fractions eluted with the desired product with desired purity were pooled, dried under reduced pressure and re-suspended/dissolved in 2 mL of water and lyophilized for 2 days to get 77 mg of white fluffy solid.

$^1$H NMR (400 MHz, Pyridine-$d_5$+$D_2O$), selected signals: δ 5.73 (d, J=4.0 Hz, 1H), 5.44 (m, 2H, merged with HDO peak), 5.36 (d, J=3.7 Hz, 1H), 5.32 (d, J=3.7 Hz, 1H), 5.28 (d, J=3.7 Hz, 1H), 4.83 (d, J=6.5 Hz, 1H), 4.81 (m, 1H), 3.70 (d, J=8.3 Hz, 1H), 3.61 (s, 1H), 1.49 (s, 3H), 1.40 (s, 3H), 1.28 (d, J=2.7 Hz, 5H), 1.09 (s, 3H), 1.01 (d, J=6.2 Hz, 3H), 0.87 (s, 2H), 0.84 (s, 2H); $^{13}$C NMR (101 MHz Pyridine-$d_5$+$D_2O$) δ 144.29, 118.50, 107.17, 105.18, 103.49, 101.95, 99.78, 99.73, 99.63, 91.69, 87.91, 85.40, 81.83, 78.54, 78.33, 78.09, 78.00, 77.87, 75.73, 75.43, 75.31, 74.29, 74.14, 73.57, 73.50, 72.71, 72.20, 71.95, 71.83, 71.68, 71.59, 71.45, 71.16, 67.51, 67.44, 67.37, 63.29, 62.77, 62.52, 62.03, 50.77, 49.68, 47.41, 43.52, 42.38, 40.89, 40.09, 36.74, 36.56, 34.55, 33.50, 29.50, 28.55, 27.68, 26.87, 26.73, 26.32, 24.92, 24.57, 19.47, 19.12, 17.06; ESI-MS 1612.44 (MH)$^+$, 1610.4 (M−H)$^−$, Molecular formula, $C_{72}H_{12}O_{39}$.

Example 41: Isolation of Compound 27

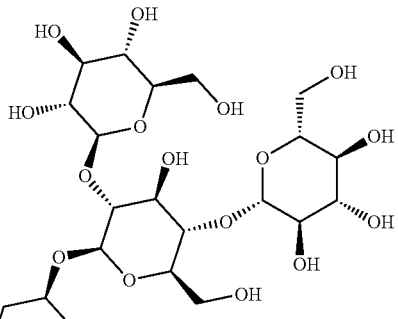
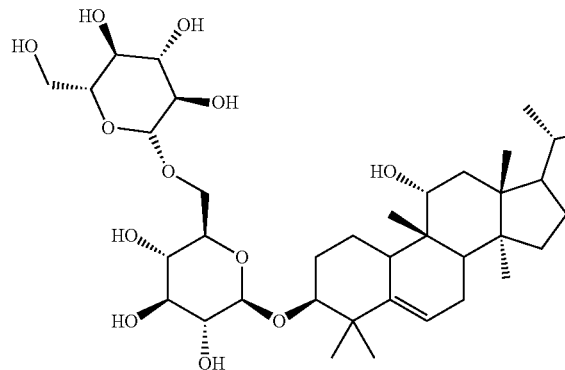

100 g of *Siraitia grosvenorii* powdered extract (*Fructus momordicae* extract, 50% mogrosides, light yellow powder) was obtained from Xi'an Heking Bio-tech Co., Ltd. was fractionated on C18 HPLC (5×10 cm Atlantis prep T3 OBD column, 5 um, Waters) by 200 injections using an A/B gradient (A=water B=acetonitrile) of 10 →30% B over 30 minutes, with a 95% B wash, followed by re-equilibration at 1% (total run time=42 minutes). Each run was collected in 36 tared tubes (12 fractions/plate, 3 plates per run) at 30 mL/fraction. The plates were dried in the Genevac HT12/HT24. The desired compound was eluted in Fraction 22 along with other isomers. The pooled Fraction 22 (947 mg) was further fractionated in 24 runs on Hilic HPLC 3×10 cm column using an A/B gradient (A=3:1 MeOH:H$_2$O, B=acetonitrile) of 80 to 40% B over 22 minutes, followed by re-equilibration at 80% (total run time=30 minutes). Each run was collected in 24 fractions (12 fractions/plate, 2 plates per run) at 30 mL/fraction. The desired compound was eluted in Fraction 12 with about 60% purity. This fraction was re-purified using the above Hilic method and the fractions containing the desired peak with the desired purity were pooled and dried under reduced pressure. The pure compound was re-suspended/dissolved in 1 mL of water and lyophilized to get 7.5 mg of fluffy white solid with 90% purity.

$^1$H NMR (400 MHz, Pyridine-d$_5$+D$_2$O), selected signals: δ 5.48 (m, 1H, merged with HDO peak), 5.35 (d, J=7.9 Hz, 1H), 5.24 (d, J=7.8 Hz, 1H), 5.04 (d, J=7.8 Hz, 1H), 4.97 (d, J=7.8 Hz, 1H), 4.82 (d, J=7.8 Hz, 1H), 3.61 (s, 1H), 1.48 (s, 3H), 1.42 (s, 3H), 1.37 (s, 3H), 1.27 (s, 3H), 1.08 (s, 3H), 1.01 (d, J=6.2 Hz, 3H), 0.82 (brs, 6H); ESI-MS 1287.94 (MH)$^+$, 1285.85 (M−H)$^−$, Molecular formula, C$_{60}$H$_{102}$O$_{29}$.

Example 42: Isolation of Compound 28

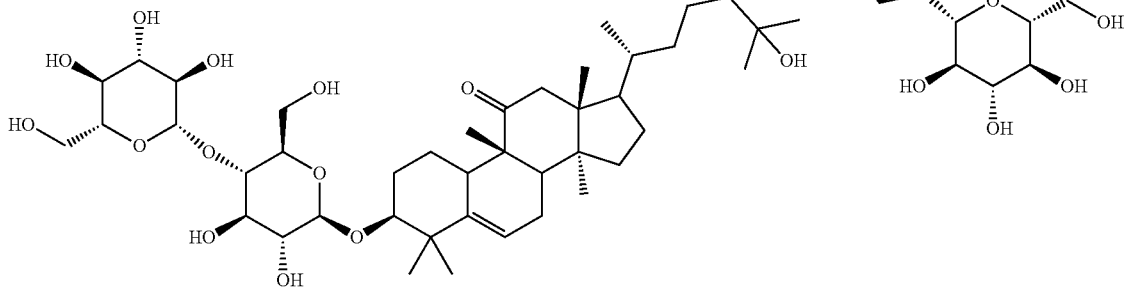

100 g of *Siraitia grosvenorii* powdered extract (*Fructus momordicae* extract, 50% mogrosides, light yellow powder) was obtained from Xi'an Heking Bio-tech Co., Ltd. was fractionated on C18 HPLC (5×10 cm Atlantis prep T3 OBD column, 5 um, Waters) by 200 injections using an A/B gradient (A=water B=acetonitrile) of 10 →30% B over 30 minutes, with a 95% B wash, followed by re-equilibration at 1% (total run time=42 minutes). Each run was collected in 36 tared tubes (12 fractions/plate, 3 plates per run) at 30 mL/fraction. The plates were dried in the Genevac HT12/HT24. The desired compound was eluted in Fraction 15 along with other isomers. The pooled Fraction 15 (3.3 g) was further fractionated in 33 runs on Hilic HPLC 3×10 cm column using an A/B gradient (A=3:1 MeOH:$H_2O$, B=acetonitrile) of 80 to 40% B over 22 minutes, followed by re-equilibration at 80% (total run time=30 minutes). Each run was collected in 12 fractions (12 fractions/plate, 1 plate per run) at 30 mL/fraction. Fractions containing the desired peak with the desired purity were pooled and dried under reduced pressure. The pure compound was re-suspended/dissolved in 1 mL of water and lyophilized to get 31 mg of fluffy white solid with 90% purity.

$^1$H NMR (400 MHz, Pyridine-$d_5$+$D_2O$), selected signals: δ 5.53 (d, J=7.8 Hz, 1H), 5.45 (m, 1H), 5.14 (d, J=7.9 Hz, 1H), 4.85 (m, 2H), 4.79 (d, J=7.7 Hz, 1H), 4.75 (d, J=7.8 Hz, 1H), 3.70 (m, 1H), 3.53 (brs, 1H), 1.47 (s, 3H), 1.43 (s, 3H), 1.30 (s, 3H), 1.10 (s, 3H), 1.04 (s, 3H), 0.96 (brd, J=6.5 Hz, 6H), 0.68 (s, 3H); $^{13}$C NMR (101 MHz, Pyridine-$d_5$+$D_2O$) δ 214.54, 141.08, 118.58, 106.69, 104.78, 104.65, 103.78, 92.48, 87.21, 81.31, 81.19, 78.57, 78.34, 78.29, 78.22, 78.07, 77.93, 77.69, 76.58, 76.35, 76.18, 75.72, 75.16, 74.76, 72.78, 72.17, 71.31, 71.21, 70.06, 63.17, 62.37, 62.23, 61.97, 49.74, 49.69, 48.99, 48.77, 43.93, 41.93, 36.15, 35.82, 34.52, 33.09, 28.97, 28.27, 26.92, 25.78, 24.54, 24.04, 22.05, 20.23, 18.73, 18.38, 17.04; ESI-MS 1285.9 (MH)$^+$, 1283.78 (M–H)$^-$, Molecular formula, $C_{60}H_{100}O_{29}$.

Example 43: Isolation of 11-oxo-Mogroside VI 11 g of *Siraitia grosvenorii* powdered extract (*Fructus momordicae* extract, 50% mogrosides, light yellow powder) was obtained from Xi'an Heking Bio-tech Co., Ltd. was fractionated on C18 HPLC (5×10 cm Atlantis prep T3 OBD column, 5 um, Waters) by 22 injections using an A/B gradient (A=water, B=acetonitrile) of 10→30% B over 30 minutes, with a 95% B wash, followed by re-equilibration at 1% (total run time=42 minutes). Each run was collected in 36 tared tubes (12 fractions/plate, 3 plates per run) at 30 mL/fraction. The plates were dried in the Genevac HT12/HT24. The desired compound was eluted in Fraction 3 with about 80% purity. The pooled Fraction 3 was dried under reduced pressure to give 80 mg of half white solid.

$^1$H NMR (400 MHz, Pyridine-$d_5$+$D_2O$) δ 5.73 (d, J=5.3 Hz, 1H), 5.54 (d, J=7.8 Hz, 1H), 5.42 (m, 1H, merged with HDO peak), 5.27 (d, J=7.7 Hz, 1H), 5.07 (d, J=7.8 Hz, 1H), 4.81 (d, J=7.8 Hz, 1H), 4.78 (d, J=8.2 Hz, 1H), 3.72 (m, 1H), 3.63 (s, 1H), 1.46 (s, 3H), 1.44 (s, 3H), 1.31 (d, J=2.7 Hz, 3H), 1.23 (s, 3H), 0.97 (m, 9H), 0.68 (s, 3H); $^{13}$C NMR (101 MHz, pyridine) δ 214.64, 140.98, 118.93, 106.43, 105.29, 104.92, 104.74, 104.54, 103.82, 92.48, 85.70, 81.63, 81.31, 78.67, 78.45, 78.38, 78.27, 78.20, 77.78, 77.63, 77.09, 76.95, 76.42, 75.79, 75.25, 75.07, 72.82, 72.22, 71.61, 71.39, 71.34, 70.14, 63.26, 62.63, 62.61, 62.42, 49.76, 49.56, 49.26, 49.07, 43.98, 41.79, 40.71, 36.04, 28.12, 27.01, 25.86, 24.61, 20.26, 18.83, 18.32, 17.12; ESI-MS, 1447.48 (MH)$^+$, 1445.96 (M–H)$^-$; Molecular formula, $C_{66}H_{110}O_{34}$.

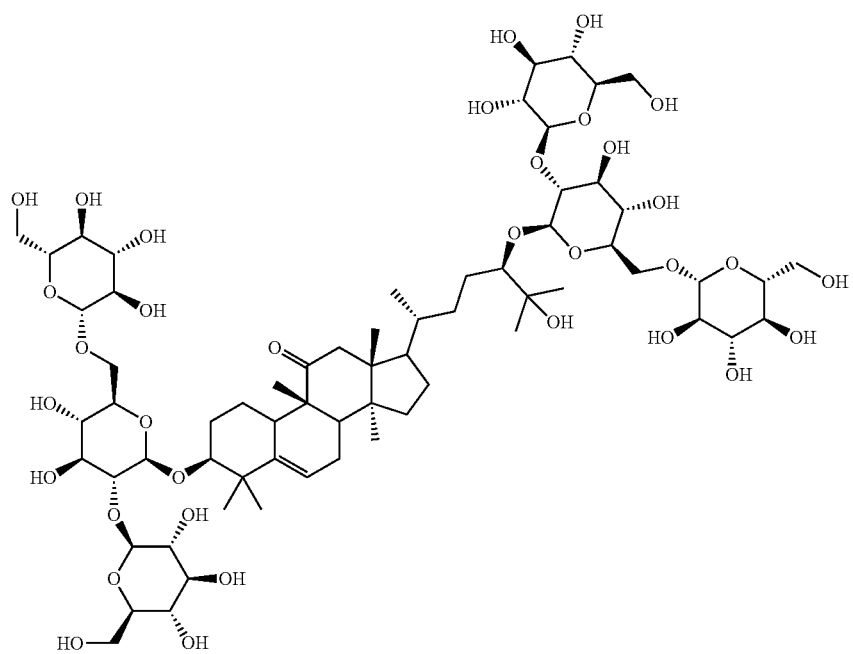 [SMILES: C[C@H](CC[C@@H](O[C@@H]1O[C@H](CO[C@@H]2O[C@H](CO)[C@@H](O)[C@H](O)[C@H]2O)[C@@H](O)[C@H](O)[C@H]1O[C@@H]1O[C@H](CO)[C@@H](O)[C@H](O)[C@H]1O)C(C)(C)O)C1CC[C@@]2(C)C3CC=C4C(CC[C@H](O[C@@H]5O[C@H](CO[C@@H]6O[C@H](CO)[C@@H](O)[C@H](O)[C@H]6O)[C@@H](O)[C@H](O)[C@H]5O[C@@H]5O[C@H](CO)[C@@H](O)[C@H](O)[C@H]5O)C4(C)C)[C@]3(C)C(=O)C[C@]12C]

Example 44: Isolation of Compound 29

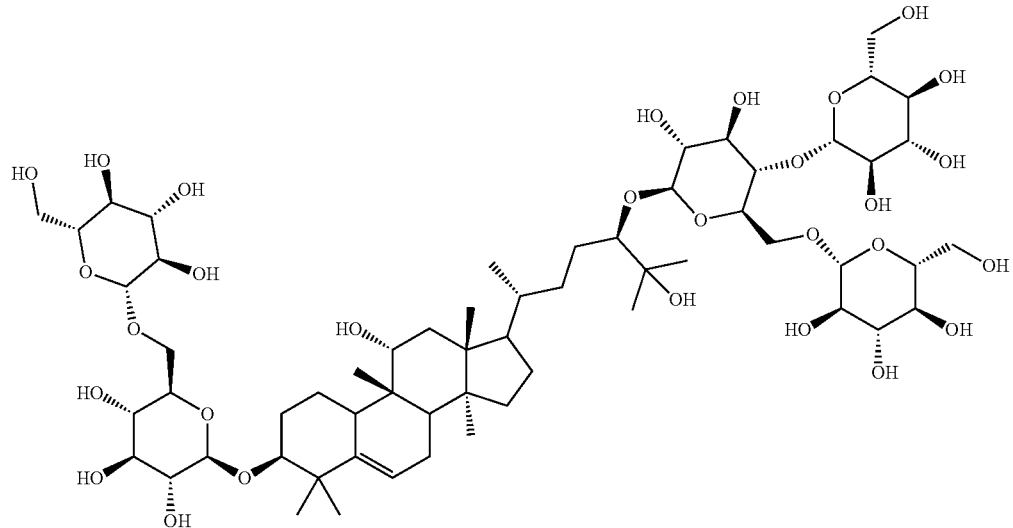 [SMILES: C[C@H](CC[C@@H](O[C@@H]1O[C@H](CO[C@@H]2O[C@H](CO)[C@@H](O)[C@H](O)[C@H]2O)[C@@H](O[C@@H]2O[C@H](CO)[C@@H](O)[C@H](O)[C@H]2O)[C@H](O)[C@H]1O)C(C)(C)O)C1CC[C@@]2(C)C3CC=C4C(CC[C@H](O[C@@H]5O[C@H](CO[C@@H]6O[C@H](CO)[C@@H](O)[C@H](O)[C@H]6O)[C@@H](O)[C@H](O)[C@H]5O)C4(C)C)[C@]3(C)[C@H](O)C[C@]12C]

80 g of *Siraitia grosvenorii* powdered extract (*Fructus momordicae* extract, 50% mogrosides, light yellow powder) was obtained from Xi'an Heking Bio-tech Co., Ltd. was fractionated on C18 HPLC (5×10 cm Atlantis prep T3 OBD column, 5 um, Waters) by 160 injections using an A/B gradient (A=water B=acetonitrile) of 10-30% B over 30 minutes, with a 95% B wash, followed by re-equilibration at 1% (total run time=42 minutes). Each run was collected in 36 tared tubes (12 fractions/plate, 3 plates per run) at 30 mL/fraction. The plates were dried in the Genevac HT12/HT24. The desired compound was eluted in Fraction 10 along with other isomers. 795 mg of Fraction 10 was further purified in 13 runs on Hilic HPLC column (3×10 cm, XBridge amide column, 5 um, Waters) using an A/B gradient (A=3:1 MeOH:$H_2O$, B=acetonitrile) of 95 to 5% B over 21 minutes, followed by re-equilibration at 95% (total run time=30.5 minutes). Each run was collected in 12 fractions (12 fractions/plate, 1 plate per run) at 30 mL/fraction. Fraction 2 contained the desired product and was pooled, concentrated under reduced pressure followed by the addition and 2 mL of $H_2O$ and lyophilized the sample for 2 days to get 167 mg of fluffy white solid with ~85% purity.

$^1$H NMR (400 MHz, Pyridine-$d_5$+$D_2O$), selected signals: δ 5.48 (d, J=7.8 Hz, 2H), 5.13 (d, J=7.8 Hz, 1H), 4.86 (d, J=7.5 Hz, 1H), 4.82 (m, 1H), 4.78 (t, J=7.4 Hz, 2H), 4.73 (m, 1H), 3.72 (d, J=9.2 Hz, 1H), 3.68 (s, 1H), 1.46 (d, J=2.0 Hz, 3H), 1.43 (s, 3H), 1.30 (s, 6H), 1.24 (s, 2H), 1.13 (d, J=6.2 Hz, 2H), 1.03 (s, 3H), 0.82 (s, 3H); $^{13}$C NMR (101 MHz, Pyridine-d+$D_2O$) δ 142.99, 119.23, 106.84, 105.10, 104.99, 104.67, 103.73, 92.45, 87.25, 81.54, 78.50, 78.34, 78.31, 78.21, 78.08, 77.73, 77.29, 76.35, 75.68, 75.18, 75.01, 72.80, 72.25, 72.04, 71.54, 71.40, 71.32, 71.19, 69.99, 63.32, 62.58, 62.39, 51.45, 49.77, 45.73, 41.85, 41.82, 40.63, 39.89, 39.16, 36.56, 35.22, 33.40, 29.30, 28.39, 28.18, 26.96, 25.86, 24.70, 24.54, 23.93, 22.97, 19.15, 18.23, 18.08; ESI-MS 1287.84 (MH)$^+$, 1285.89 (M−H)$^-$, Molecular formula, $C_{60}H_{102}O_{29}$.

Example 45: Isolation of Compound 30

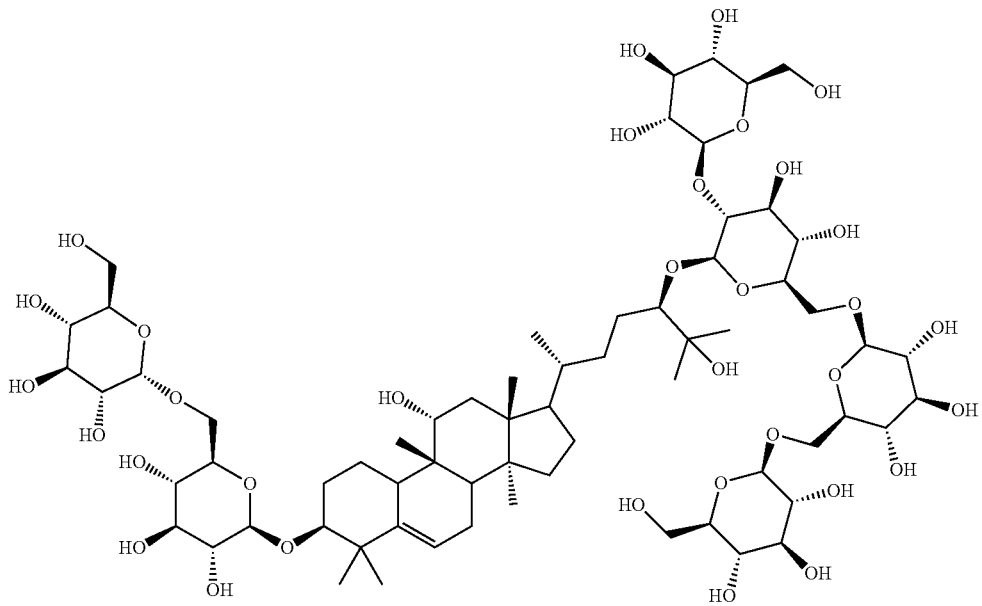 [SMILES: C[C@H](CC[C@@H](O[C@@H]1O[C@H](CO[C@@H]2O[C@H](CO[C@@H]3O[C@H](CO)[C@@H](O)[C@H](O)[C@H]3O)[C@@H](O)[C@H](O)[C@H]2O)[C@@H](O)[C@H](O)[C@H]1O[C@@H]1O[C@H](CO)[C@@H](O)[C@H](O)[C@H]1O)C(C)(C)O)C1CC[C@@]2(C)C3CC=C4C(CC[C@H](O[C@@H]5O[C@H](CO[C@H]6O[C@H](CO)[C@@H](O)[C@H](O)[C@H]6O)[C@@H](O)[C@H](O)[C@H]5O)C4(C)C)[C@]3(C)[C@H](O)C[C@]12C]

80 g of *Siraitia grosvenorii* powdered extract (*Fructus momordicae* extract, 50% mogrosides, light yellow powder) was obtained from Xi'an Heking Bio-tech Co., Ltd. was fractionated on C18 HPLC (5×10 cm Atlantis prep T3 OBD column, 5 um, Waters) by 160 injections using an A/B gradient (A=water, B=acetonitrile) of 10-30% B over 30 minutes, with a 95% B wash, followed by re-equilibration at 1% (total run time=42 minutes). Each run was collected in 36 tared tubes (12 fractions/plate, 3 plates per run) at 30 mL/fraction. The plates were dried in the Genevac HT12/HT24. The desired compound was eluted in Fraction 14 along with other isomers. The pooled Fraction 14 (1.24 g) was further purified in 29 runs on Hilic HPLC column (3×10 cm, XBridge amide column, 5 um, Waters) using an A/B gradient (A=3:1 MeOH:$H_2O$, B=acetonitrile) of 70 to 20% B over 21 minutes, followed by re-equilibration at 70% (total run time=30.5 minutes). Each run was collected in 12 fractions (12 fractions/plate, 1 plate per run) at 30 mL/fraction. Fraction 8 contained the desired product and was pooled, concentrated under reduced pressure followed by the addition and 2 mL of $H_2O$ and lyophilized the sample for 48 hours to get 240 mg of fluffy white solid with 90% purity.

$^1$H NMR (400 MHz, Pyridine-$d_5$+$D_2O$), selected signals: δ 5.50 (m, 1H), 5.45 (m, 1H, merged with HDO peak), 5.41 (d, J=3.6 Hz, 1H), 4.98 (d, J=7.8 Hz, 1H), 4.84 (m, 2H), 4.79 (d, J=7.7 Hz, 1H), 4.74 (d, J=7.8 Hz, 1H), 3.70 (d, J=9.1 Hz, 1H), 3.61 (brs, 1H), 1.45 (s, 3H), 1.42 (s, 3H), 1.28 (s, 6H), 1.03 (d, J=8.5 Hz, 6H), 0.86 (s, 3H), 0.84 (s, 3H); $^{13}$C NMR (101 MHz, Pyridine-$d_5$+$D_2O$) δ 144.38, 118.36, 106.80, 105.19, 104.87, 104.63, 103.75, 100.06, 92.49, 87.48, 81.36, 78.52, 78.25, 78.04, 77.86, 77.66, 76.97, 76.31, 76.12, 75.66, 75.14, 75.02, 74.74, 73.85, 73.71, 72.85, 72.76, 72.19, 71.75, 71.58, 71.29, 71.14, 70.03, 67.75, 63.26, 62.34, 50.80, 49.62, 47.37, 43.45, 42.26, 40.76, 40.07, 36.62, 36.31, 34.49, 33.26, 29.17, 28.52, 27.58, 26.94, 26.89, 26.24, 24.49, 19.40, 19.07, 17.02; ESI-MS, 1447.89 (M−H)$^-$; Molecular formula, $C_{66}H_{112}O_{34}$.

Example 46: Isolation of 11-oxo-MIII$_E$

A powdered extract of *Siraitia grosvenorii* (*Fructus momordicae* extract, 50% mogroside, light yellow powder) was obtained from Xi'an Heking Bio-tech Co., Ltd. Samples of about 1.00 g were carefully weighed and dissolved in 7.0 mL of water and split into 2 equal injections. A total of 60 injections were run in this manner with a combined weight of 30.0 g of the *Fructus momordicae* extract. Purifications were done on a Waters Auto-purification system using Atlantis T3 C18 column (5×10 cm) with an ACN/water gradient. The method was t=0 min., 1%, 50 mL/min→t=0.75 min., 1%, 100 mL/min; t=2.00 min., 1%, 100 mL/min; t=2.10 min., 10%, 100 mL/min; t=30.1 min., 30%, 100 mL/min; t=30.2 min., 95%, 100 mL/min; t=35.2 min, 95%, 100 mL/min; t=35.3 min., 1%, 100 mL/min; t=42.3 min., 1%, 100 mL/min by collecting from 20.0 min. to 30.8 min. (36 fractions, 30 mL each). The desired compound was eluted in fraction 28 along with other isomers. The pooled Fraction was further purified on C18 HPLC (3×10 cm Atlantis prep T3 OBD column, 5 um, Waters) by 2 injections using an A/B gradient (A=water, B=acetonitrile) of 15→30% B over 30 minutes, with a 95% B wash, followed by re-equilibration at 1% (total run time=45 minutes). Each run was collected in 36 tared tubes (12 fractions/plate, 3 plates per run) at 30 mL/fraction. Fraction 23 contained the desired product and was pooled, concentrated under reduced pressure followed by the addition and 1 mL of $H_2O$ and lyophilized the sample for 48 hours to get 19 mg of fluffy white solid with 90% purity.

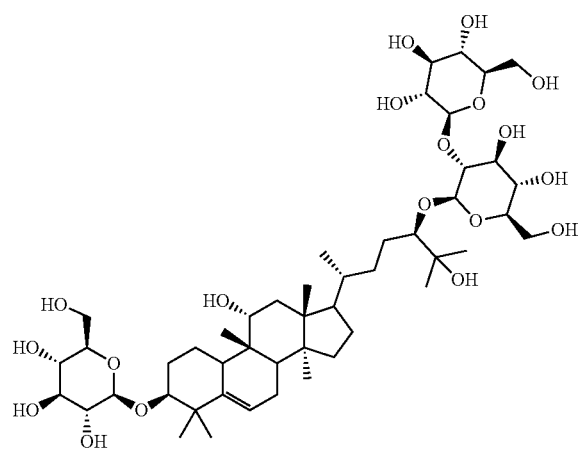 [SMILES: C[C@H](CC[C@@H](O[C@@H]1O[C@H](CO)[C@@H](O)[C@H](O)[C@H]1O[C@@H]1O[C@H](CO)[C@@H](O)[C@H](O)[C@H]1O)C(C)(C)O)C1CC[C@@]2(C)C3CC=C4C(CC[C@H](O[C@@H]5O[C@H](CO)[C@@H](O)[C@H](O)[C@H]5O)C4(C)C)[C@]3(C)[C@H](O)C[C@]12C]

$^1$H NMR (400 MHz, Pyridine-$d_5$+$D_2O$), selected signals: δ 5.42 (m, 1H, merged with HDO peak), 5.37 (d, J=8.0 Hz, 1H), 4.99 (d, J=7.8 Hz, 1H), 4.80 (d, J=7.8 Hz, 1H), 3.59 (brs, 1H), 1.49 (s, 3H), 1.46 (s, 3H), 1.42 (s, 3H), 1.10 (s, 34H), 1.05 (s, 3H), 0.94 (s, 3H), 0.92 (s, 3H), 0.66 (s, 3H); $^{13}$C NMR (101 MHz, pyridine) δ 214.54, 141.22, 118.61, 107.16, 105.64, 102.35, 88.85, 87.22, 82.90, 78.50, 78.39, 78.14, 78.03, 75.96, 75.34, 75.22, 72.51, 71.96, 71.58, 71.34, 71.19, 63.05, 62.76, 62.38, 49.70, 49.62, 49.05, 47.40, 43.97, 42.40, 42.03, 36.45, 35.92, 34.56, 28.36, 27.00, 25.89, 25.61, 20.30, 18.77, 18.36, 17.04; ESI-MS 961.85 (MH)$^+$, 959.9 (M−H)$^-$, Molecular formula, $C_{48}H_{80}O_{19}$.

Example 47: Isolation of 11-Oxo-MIV$_E$

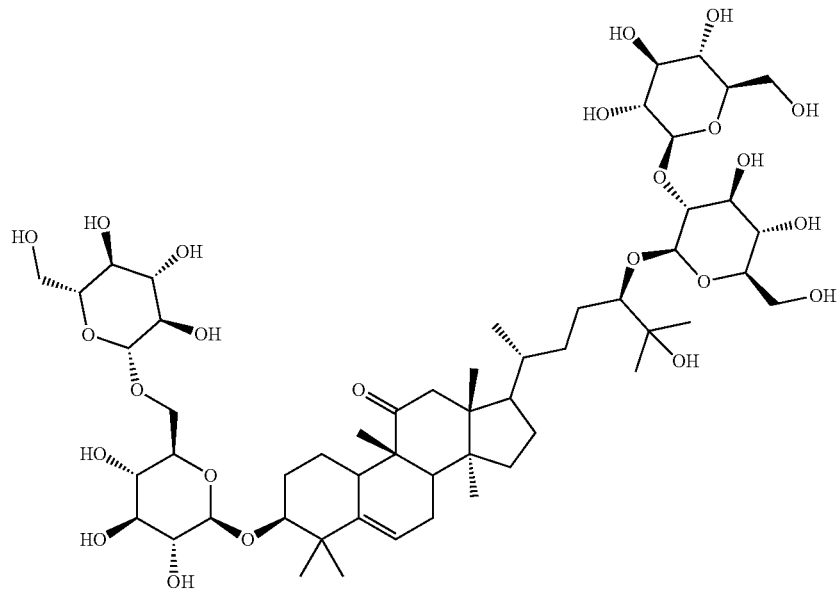 [SMILES: C[C@H](CC[C@@H](O[C@@H]1O[C@H](CO)[C@@H](O)[C@H](O)[C@H]1O[C@@H]1O[C@H](CO)[C@@H](O)[C@H](O)[C@H]1O)C(C)(C)O)C1CC[C@@]2(C)C3CC=C4C(CC[C@H](O[C@@H]5O[C@H](CO[C@@H]6O[C@H](CO)[C@@H](O)[C@H](O)[C@H]6O)[C@@H](O)[C@H](O)[C@H]5O)C4(C)C)[C@]3(C)C(=O)C[C@]12C]

11 g of *Siraitia grosvenorii* powdered extract (*Fructus momordicae* extract, 50% mogrosides, light yellow powder) was obtained from Xi'an Heking Bio-tech Co., Ltd. was fractionated on C18 HPLC (5×10 cm Atlantis prep T3 OBD column, 5 um, Waters) by 360 injections using an A/B gradient (A=water, B=acetonitrile) of 10→30% B over 30 minutes, with a 95% B wash, followed by re-equilibration at 1% (total run time=42 minutes). Each run was collected in 36 tared tubes (12 fractions/plate, 3 plates per run) at 30 mL/fraction. The plates were dried in the Genevac HT12/HT24. The desired compound was eluted in Fraction 19 along with other isomers. The pooled Fraction 19 was further fractionated on Hilic HPLC column (3×10 cm, XBridge amide column, 5 um, Waters) using an A/B gradient (A=3:1 MeOH:H$_2$O, B=acetonitrile) of 80 to 20% B over 22 minutes, with a 95% A wash followed by re-equilibration at 80% (total run time=30.3 minutes). Each run was collected in 12 fractions (12 fractions/plate, 1 plate per run) at 30 mL/fraction. Fractions 4 & 5 contained the desired product and was pooled, concentrated under reduced pressure followed by the addition of 1 mL of H$_2$O and lyophilized the sample for 72 hours to get 18 mg of fluffy white solid with ~85% purity.

$^1$H NMR (400 MHz, Pyridine-d$_5$+D$_2$O), selected signals: δ 5.44 (m, 2H, merged with HDO peak), 4.85 (m, 2H), 4.80 (d, J=7.7 Hz, 2H), 3.71 (m, 1H), 3.58 (d, J=2.6 Hz, 1H), 1.49 (s, 3H), 1.43 (s, 3H), 1.30 (s, 3H), 1.11 (s, 3H), 1.04 (s, 3H), 0.96 (m, 6H), 0.68 (s, 3H); $^{13}$C NMR (101 MHz, Pyridine-d$_5$+D$_2$O) δ 214.51, 141.18, 118.54, 107.10, 104.83, 104.67, 103.79, 92.49, 87.17, 81.21, 78.58, 78.33, 78.24, 78.08, 77.70, 76.37, 75.74, 75.30, 75.18, 72.79, 72.18, 71.54, 71.30, 71.22, 70.08, 63.19, 62.71, 62.38, 49.74, 49.70, 49.50, 49.00, 48.78, 43.95, 41.98, 36.17, 35.86, 34.54, 28.31, 26.94, 25.84, 24.56, 20.27, 18.75, 18.39, 17.04; ESI-MS 1123.88 (MH)$^+$, 1121.89 (M−H)$^−$, Molecular formula, C$_{54}$H$_{90}$O$_{24}$.

Example 48: Isolation of Mogroside V Formate Ester

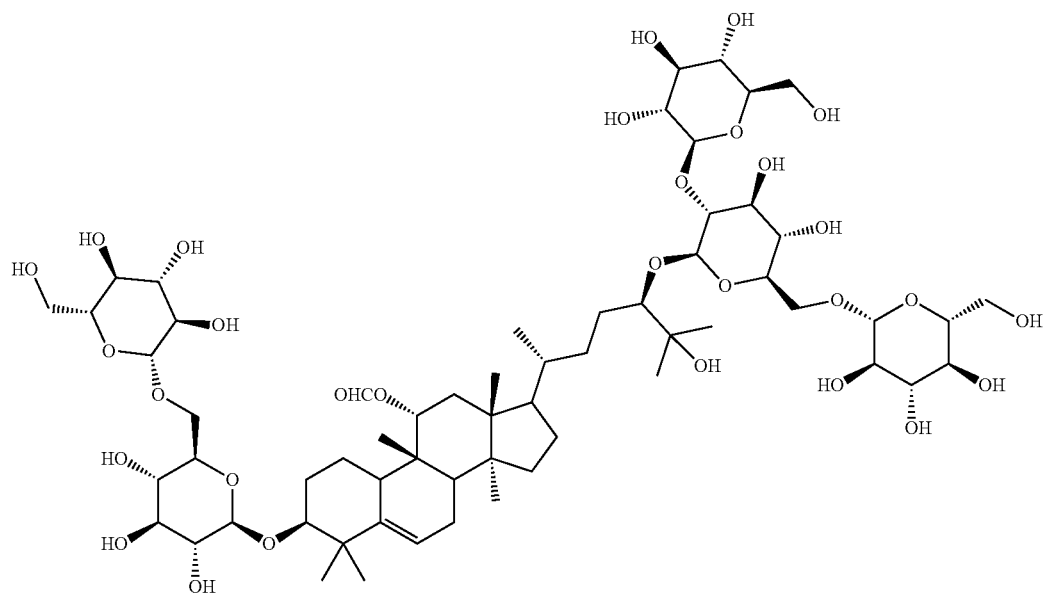

2 g of *Siraitia grosvenorii* powdered extract (*Fructus momordicae* extract, 50% mogrosides, light yellow powder) was obtained from Xi'an Heking Bio-tech Co., Ltd. was fractionated on C18 HPLC (5×10 cm Atlantis prep T3 OBD column, 5 um, Waters) by 4 injections using an A/B gradient (A=water+0.1% formic acid, B=acetonitrile) of 1→50% B over 30 minutes, with a 95% B wash, followed by re-equilibration at 1% (total run time=42 minutes). Each run was collected in 36 tared tubes (12 fractions/plate, 3 plates per run) at 30 mL/fraction. The plates were dried in the Genevac HT12/HT24. The desired compound was eluted in Fraction 8 along with mogroside V and other isomers. The pooled Fraction 8 (700 mg) was further fractionated in 4 runs on fluoro-phenyl HPLC (3×10 cm, Xselect fluoro-phenyl OBD column, 5 um, Waters) using an A/B gradient (A=water, B=acetonitrile) of 15→30% B over 35 minutes, with a 95% B wash, followed by re-equilibration at 15% (total run time=45 minutes). Each run was collected in 12 tared tubes (12 fractions/plate, 1 plate per run) at 30 mL/fraction. Fractions containing the desired peak (Fraction 8) with the desired purity were pooled based on UPLC analysis and dried under reduced pressure to give a whitish powdery solid. The pure compound was re-suspended/dissolved in 2 mL of water and lyophilized to get 65 mg of fluffy white solid with 95% purity.

$^1$H NMR (400 MHz, Pyridine-$d_5$+$D_2O$), selected signals: δ 8.50 (s, 1H), 5.48 (d, J=7.8 Hz, 1H), 5.39 (d, J=7.2 Hz, 1H), 5.13 (d, J=7.8 Hz, 1H), 4.79 (d, J=7.8 Hz, 1H), 4.76 (d, J=8.9 Hz, 1H), 3.71 (dd, J=7.1, 3.5 Hz, 1H), 3.62 (d, J=2.8 Hz, 1H), 1.45 (s, 3H), 1.42 (s, 3H), 1.30 (s, 3H), 1.06 (s, 3H), 0.99 (d, J=6.6 Hz, 3H), 0.97 (s, 3H), 0.92 (s, 3H), 0.82 (s, 3H); $^{13}$C NMR (101 MHz, Pyridine-$d_5$+$D_2O$) δ 162.28, 143.30, 118.52, 106.76, 104.95, 104.92, 104.65, 103.73, 92.38, 87.49, 81.48, 80.46, 78.51, 78.33, 78.29, 78.24, 78.19, 78.08, 78.03, 77.68, 77.35, 76.34, 75.69, 75.20, 75.15, 74.98, 72.78, 72.17, 71.44, 71.39, 71.27, 71.16, 70.05, 69.86, 63.21, 62.52, 62.35, 50.59, 49.49, 49.37, 47.46, 43.28, 42.21, 40.61, 39.33, 36.81, 36.69, 35.96, 34.13, 33.01, 29.03, 28.36, 27.47, 26.92, 26.25, 26.09, 25.27, 24.52, 24.12, 19.26, 18.98, 16.71; ESI-MS 1315.94 (MH)$^+$, 1313.81 (M−H)$^−$; Molecular formula, $C_{61}H_{102}O_{30}$.

Example 49: Isolation of Compound 31

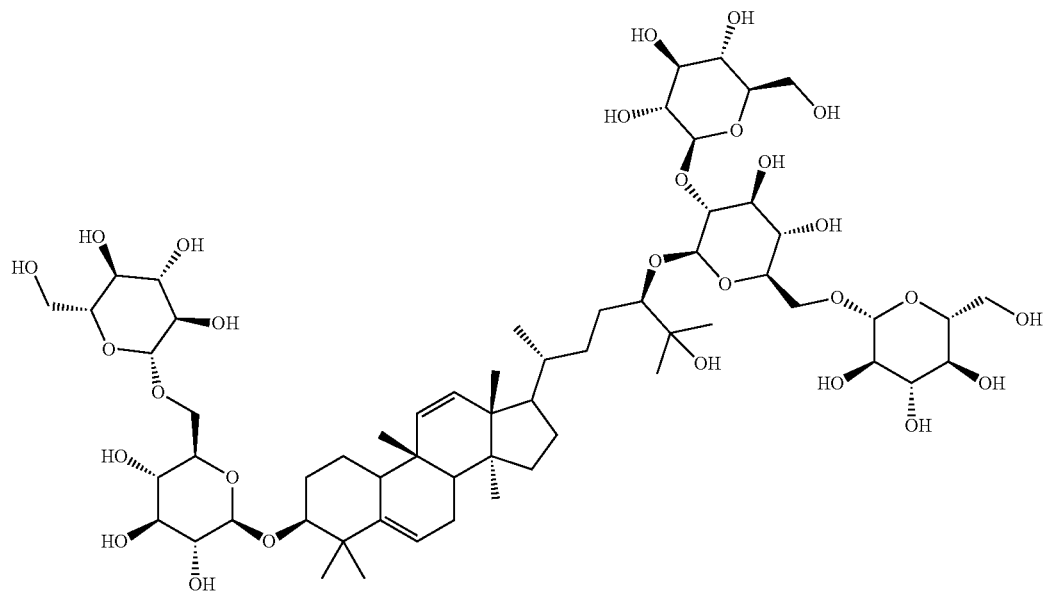 [SMILES: C[C@H](CC[C@@H](O[C@@H]1O[C@H](CO[C@@H]2O[C@H](CO)[C@@H](O)[C@H](O)[C@H]2O)[C@@H](O)[C@H](O)[C@H]1O[C@@H]1O[C@H](CO)[C@@H](O)[C@H](O)[C@H]1O)C(C)(C)O)C1CC[C@@]2(C)C3CC=C4C(CC[C@H](O[C@@H]5O[C@H](CO[C@@H]6O[C@H](CO)[C@@H](O)[C@H](O)[C@H]6O)[C@@H](O)[C@H](O)[C@H]5O)C4(C)C)[C@]3(C)C=C[C@]12C]

80.2 g of *Siraitia grosvenorii* powdered extract (*Fructus momordicae* extract, 50% mogrosides, light yellow powder) was obtained from Xi'an Heking Bio-tech Co., Ltd. was fractionated on C18 HPLC (5×10 cm Atlantis prep T3 OBD column, 5 um, Waters) by 160 injections using an A/B gradient (A=water, B=acetonitrile) of 10→30% B over 30 minutes, with a 95% B wash, followed by re-equilibration at 1% (total run time=42 minutes). Each run was collected in 36 tared tubes (12 fractions/plate, 3 plates per run) at 30 mL/fraction. The plates were dried in the Genevac HT12/HT24. The desired compound was eluted in FractionFractions 27 along with other isomers. The pooled Fraction 27 (223 mg) was further purified in 7 runs on fluoro-phenyl HPLC (3×10 cm, Xselect fluoro-phenyl OBD column, 5 um, Waters) using an A/B gradient (A=water, B=acetonitrile) of 15→30% B over 35 minutes, with a 95% B wash, followed by re-equilibration at 15% (total run time=45 minutes). Each run was collected in 12 tared tubes (12 fractions/plate, 1 plate per run) at 30 mL/fraction. Fractions containing the desired peak with the desired purity (Fraction 10) were pooled and dried under reduced pressure to give a whitish powdery solid. The pure compound was re-suspended/dissolved in 1 mL of water and lyophilized to get 11 mg of fluffy white solid.

$^1$H NMR (400 MHz, Pyridine-$d_5$+$D_2O$), selected signals: δ 5.97 (d, J=10.1 Hz, 1H), 5.4 (m, 3H, merged with HDO peak), 5.14 (d, J=7.8 Hz, 1H), 4.79 (d, J=7.5 Hz, 1H), 3.73 (m, 1H), 3.63 (m, 1H), 1.44 (s, 3H), 1.44 (s, 3H), 1.31 (s, 3H), 1.12 (d, J=6.3 Hz, 3H), 0.96 (s, 3H), 0.94 (s, 3H), 0.84 (s, 3H), 0.83 (s, 3H); $^{13}$C NMR (101 MHz, Pyridine-$d_5$+ $D_2O$) δ 141.71, 134.9 (merged with pyridine-$d_5$ peak), 132.86, 118.11, 106.70, 104.93, 104.73, 104.53, 103.65, 92.39, 87.02, 81.24, 78.39, 78.27, 78.20, 78.16, 78.04, 77.94, 77.56, 77.16, 76.25, 75.60, 75.05, 74.88, 72.75, 72.06, 71.42, 71.32, 71.20, 71.03, 69.93, 63.13, 62.48, 62.26, 49.77, 49.24, 47.16, 41.75, 41.55, 40.46, 37.60, 36.94, 33.00, 32.80, 29.03, 28.63, 28.14, 26.82, 25.79, 25.23, 24.45, 23.81, 21.55, 19.18, 18.87; ESI-MS 1269.76 (MH)$^+$, 1267.69 (M−H)$^−$; Molecular formula, $C_{65}H_{100}O_{28}$.

Examples 50 and 51: Enzymatic Production of Mogrol and Mogroside $I_E$ from Pectinase

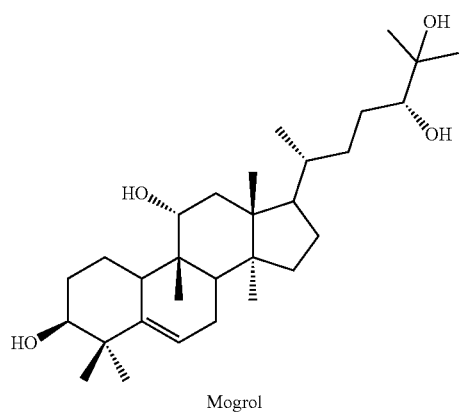

Mogrol

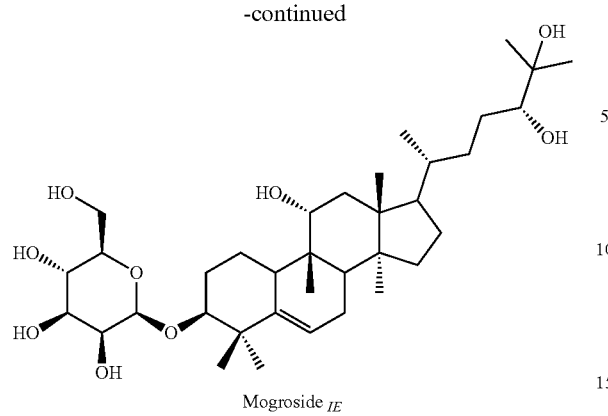

Mogroside IE

To a 250 mL round bottom flask, 1 g of mogroside V, 100 mL of 0.1M sodium acetate buffer pH 5.5, and 70 mL of pectinase enzyme from *Aspergillus aculeatus* were added and stirred the flask at 55° C. The progress of the reaction was monitored periodically by LC-MS. After 8 days, the reaction was stopped and extracted 4 times with 200 mL of ethyl acetate. The combined EtOAc extract was dried under reduced pressure and fractionated on 60g C18 SPE cartridge using the standard 5/35/70/100% MeOH:$H_2O$ step gradient. The desired products were eluted in 100% MeOH Fraction. This Fraction was further purified on HPLC using C18 column (3×10 cm Atlantis T3 OBD column, 5 um, Waters) with an A/B gradient (A=water, B=acetonitrile) of 1→95% B over 50 minutes, with a 95% B wash, followed by re-equilibration at 1% (total run time=60 minutes). Each run was collected in 72 tubes (12 fractions/plate, 6 plates per run) at 30 mL/fraction. Fractions eluted with the desired products with desired purity were pooled separately, dried under reduced pressure and re-suspended/dissolved in 2 mL of water and lyophilized for ~2 days to get 62 (F26-27) and 190 (F36-37) mg of white fluffy solid.

Mogrol: $^1$H NMR (400 MHz, Pyridine-$d_5$+$D_2O$), selected signals: δ 5.64 (d, J=5.9 Hz, 1H), 4.19 (dd, J=10.7, 5.9 Hz, 1H), 3.81-3.76 (m, 1H), 3.74 (d, J=2.8 Hz, 1H), 1.55 (s, 3H), 1.52 (s, 3H), 1.42 (s, 3H), 1.36 (s, 3H), 1.18 (s, 3H), 1.00 (d, J=6.2 Hz, 3H), 0.91 (brs, 3H), 0.88 (s, 3H); ESI-MS 477.47 (MH)$^+$; Molecular formula, $C_{30}H_{52}O_4$.

Mogroside IE: $^1$H NMR (400 MHz, Pyridine-$d_5$+$D_2O$), selected signals: δ5.48 (d, J=6.0 Hz, 0H), 4.85 (d, J=7.8 Hz, 0H), 3.77 (dd, J=9.0, 2.5 Hz, 0H), 3.65 (d, J=2.8 Hz, 0H), 1.55 (s, 1H), 1.53 (s, 1H), 1.51 (s, 1H), 1.29 (s, 1H), 1.13 (s, 1H), 0.99 (d, J=6.1 Hz, 1H), 0.86 (s, 1H), 0.85 (s, 1H); ESI-MS 639.9 (MH)$^+$, 637.63 (M–H)$^-$, Molecular formula, $C_{36}H_{62}O_9$.

Example 52: Enzymatic Production of Mogroside IIE

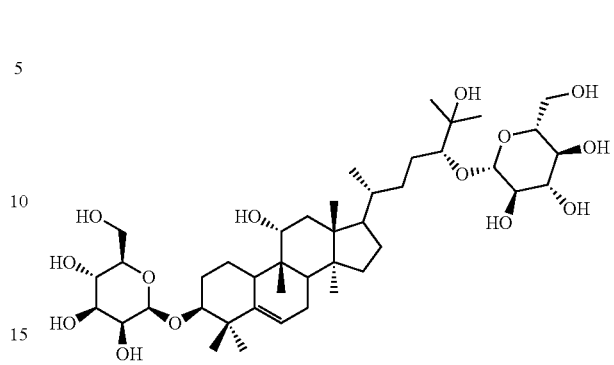

To a 250 mL round bottom flask, 200 mg of pure mogroside V, 18 mL of water, 660 uL of 1M pH 5.0 sodium acetate buffer and 350 uL of pectinase from *Aspergillus aculeatus* (from Sigma, lot #SLBM6360V) was added and stirred at 50° C. The progress of the reaction was monitored periodically by LC-MS. After 24 hours, the reaction was quenched with 50 mL ethanol and removed the solvents on Genevac. The reaction mixture was further purified on RP-HPLC using C18 column (3×10 cm Atlantis T3 OBD column, Sum, Waters) with an A/B gradient (A=water, B=acetonitrile) of 1-95% B over 50 minutes, with a 95% B wash, followed by re-equilibration at 1% (total run time=61 minutes). The run was collected in 72 tubes (12 fractions/plate, 6 plates per run) at 30 mL/fraction. The desired compound was eluted in fraction 23 and was dried under reduced pressure. The pure compound was re-suspended/dissolved in 2 mL of water and lyophilized to get 18.8 mg of fluffy white solid with 95% purity.

$^1$H NMR (400 MHz, Pyridine-$d_5$+$D_2O$), selected signals: 65.45 (m, 1H, merged with HDO peak), 4.95 (d, J=7.8 Hz, 1H), 4.83 (d, J=7.8 Hz, 1H), 3.85 (dd, J=8.5, 2.1 Hz, 1H), 3.64 (brs, 1H), 1.50 (s, 3H), 1.40 (s, 3H), 1.37 (s, 3H), 1.27 (s, 3H), 1.11 (s, 3H), 0.92 (d, J=6.3 Hz, 3H), 0.85 (s, 3H), 0.78 (s, 3H); $^{13}$C NMR (101 MHz, Pyridine-$d_5$+$D_2O$) δ 144.29, 118.53, 107.14, 105.61, 90.30, 87.82, 78.50, 78.30, 78.25, 77.98, 77.76, 75.29, 75.17, 72.22, 71.58, 71.51, 62.76, 62.47, 50.81, 49.66, 47.36, 43.48, 42.36, 40.85, 40.08, 36.77, 36.48, 34.53, 33.45, 29.51, 28.29, 27.67, 26.82, 26.77, 26.28, 26.25, 25.13, 24.54, 19.31, 18.85, 16.99; ESI-MS 801.73 (MH)$^+$, 799.74 (M–H)$^-$, Molecular formula, $C_{42}H_{72}O_{14}$.

Examples 53 and 54: Enzymatic Production of Compounds 32 and 33

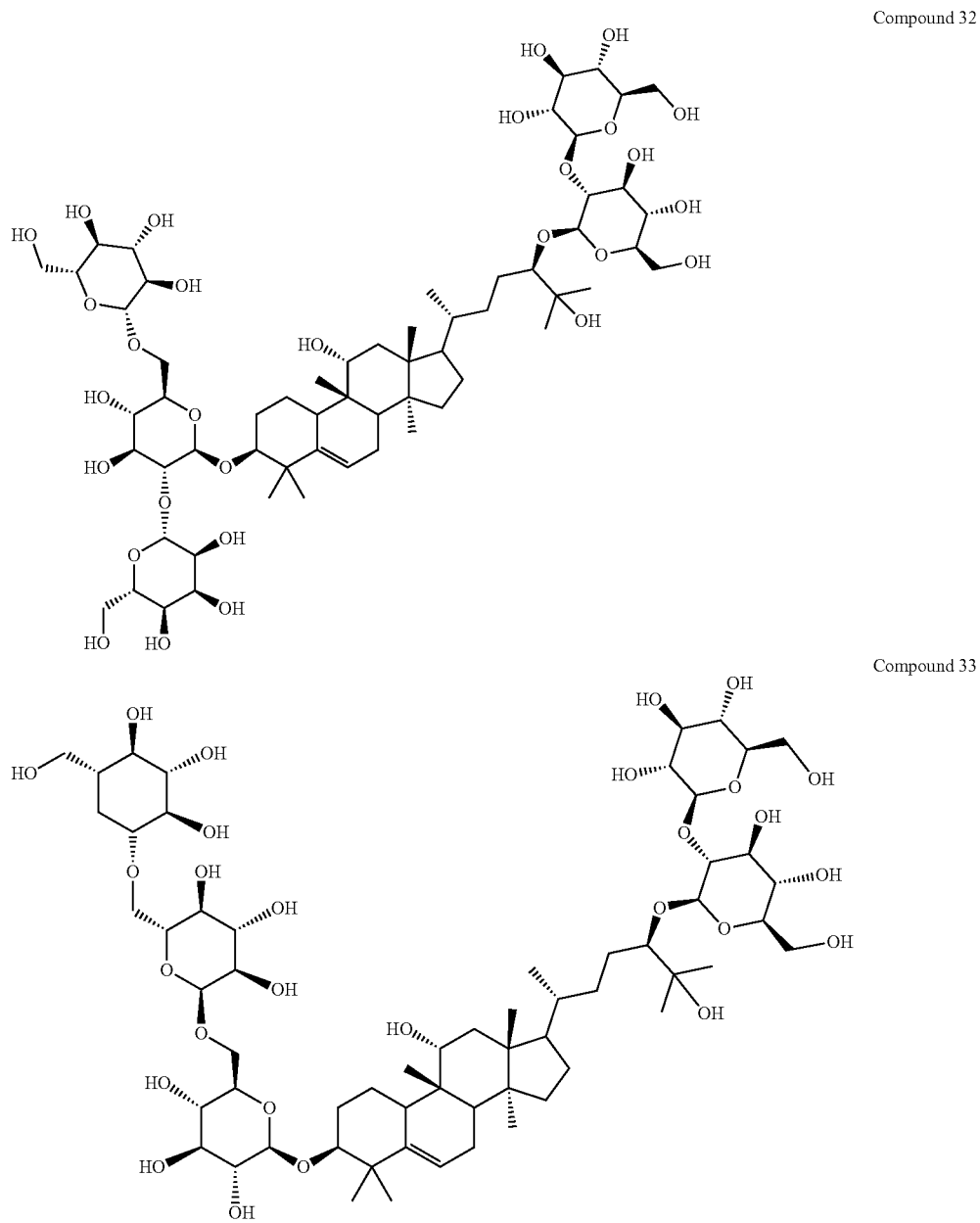

Compound 32

Compound 33

To a 1L round bottom flask, 10 g of mogroside 50% powder, 500 mL of 0.1 M sodium acetate buffer pH5.0 and 10 mL pectinase from *Aspergillus aculeatus* were added and stirred at 50° C. The progress of the reaction was monitored periodically by LC-MS. After 6 hours, the reaction was quenched with 500 mL ethanol. This process was repeated two more times using 10g of mogroside V each time and the rest of the reaction scaled up linearly. The combined 3 lots (30g total) were dried under reduced pressure and fractionated on 400g SPE cartridge using a standard 5/35/70/100 MeOH:H$_2$O gradient. The desired mogrosides were eluted in 70% MeH fraction. This Fraction was further fractionated on HPLC using C18 column (5×10 cm Atlantis T3 OBD column, 5 um, Waters) with an A/B gradient (A=water, B=acetonitrile) of 10-30% B over 30 minutes, with a 95% B wash, followed by re-equilibration at 10% (total run time=42 minutes). Each run was collected in 36 tubes (12 fractions/plate, 3 plates per run) at 30 mL/fraction. Fraction 10 was eluted with two mogroside V isomers along with other minor isomers. This Fraction was further purified on Hilic 3×10 cm HPLC column using an A/B gradient (A=3:1 MeOH:H$_2$O, B=acetonitrile) of 80 to 20% B over 22 minutes, followed by wash and re-equilibration at 80% (total run time=30 minutes). Each run was collected in 12 fractions (12 fractions/plate, 1 plate per run) at 30 mL/fraction. Fractions eluted with the desired products with desired purity were pooled separately, dried under reduced pressure and re-suspended/dissolved in 2 mL of water and lyophilized for 2 days to get 68 (F6) and 42 (F11-12) mg of white fluffy solid.

Compound 32: $^1$H NMR (400 MHz, Pyridine-d$_5$+D$_2$O), selected signals: δ 5.44 (m, 1H, merged with HDO peak), 5.35 (d, J=7.8 Hz, 1H), 5.21 (d, J=7.7 Hz, 2H), 5.00 (d, J=7.7 Hz, 1H), 4.91 (d, J=7.9 Hz, 1H), 1.51 (s, 3H), 1.46 (s, 3H), 1.41 (s, 3H), 1.26 (s, 3H), 1.10 (s, 3H), 1.03 (d, J=6.3 Hz, 3H), 0.81 (s, 6H); $^{13}$C NMR (101 MHz, Pyridine-$d_5$+$D_2O$) δ 144.43, 118.36, 106.37, 106.32, 105.70, 102.95, 102.20, 88.69, 86.70, 84.47, 83.06, 78.69, 78.44, 78.37, 78.30, 78.22, 78.16, 77.99, 77.85, 76.75, 76.35, 75.89, 75.36, 72.45, 71.93, 71.62, 71.20, 71.13, 70.96, 70.19, 63.08, 62.32, 62.25, 50.74, 49.66, 47.38, 43.48, 42.38, 40.76, 40.09, 36.72, 36.64, 34.50, 33.81, 29.62, 28.57, 27.66, 26.97, 26.92, 26.26, 26.16, 25.53, 24.54, 19.36, 19.10, 17.01; ESI-MS 1287.89 (MH)$^+$, 1285.91 (M−H)$^-$; Molecular formula, $C_{60}H_{102}O_{29}$.

Compound 33: $^1$H NMR (400 MHz, Pyridine-$d_5$+$D_2O$), selected signals: δ 5.45 (m, 2H, merged with HDO peak), 5.35 (m, 1H), 5.00 (d, J=7.8 Hz, 2H), 4.76 (d, J=7.8 Hz, 1H), 3.88 (d, J=8.1 Hz, 2H), 3.63 (s, 1H), 1.45 (s, 6H), 1.41 (s, 3H), 1.28 (s, 3H), 1.05 (s, 3H), 1.02 (d, J=6.2 Hz, 3H), 0.82 (s, 6H); $^{13}$C NMR (101 MHz, Pyridine-$d_5$+$D_2O$) δ 144.42, 118.42, 106.85, 105.70, 105.25, 102.21, 100.12, 88.70, 87.47, 83.05, 78.44, 78.37, 78.31, 78.11, 78.04, 77.99, 77.86, 77.04, 76.17, 75.90, 75.19, 75.07, 74.79, 73.90, 73.77, 72.46, 71.94, 71.82, 71.63, 71.41, 71.14, 70.18, 67.83, 63.09, 62.41, 62.32, 50.74, 49.67, 47.38, 43.48, 42.30, 40.77, 40.11, 36.68, 34.52, 33.82, 29.42, 28.62, 28.52, 27.63, 26.93, 26.25, 25.52, 24.54, 19.37, 19.08, 17.02; ESI-MS 1287.82 (MH)$^+$, 1285.94 (M−H)$^-$; Molecular formula, $C_{60}H_{102}O_{29}$.

Examples 55 and 56: Enzymatic Production of Compounds 34 and 35

Compound 34

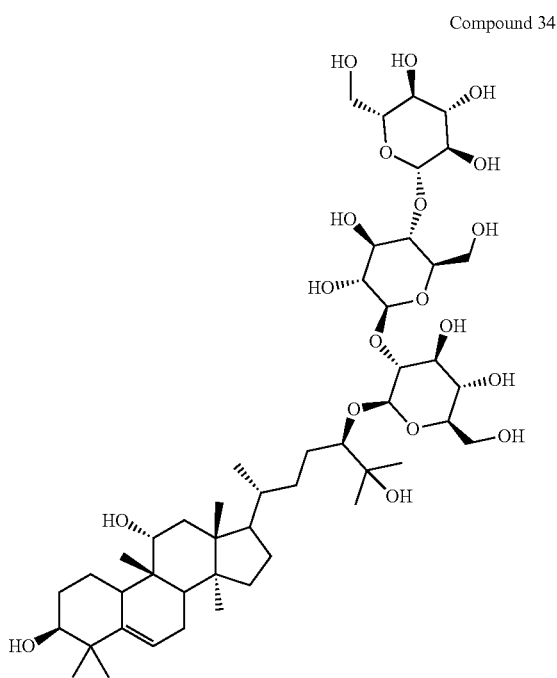

Compound 35

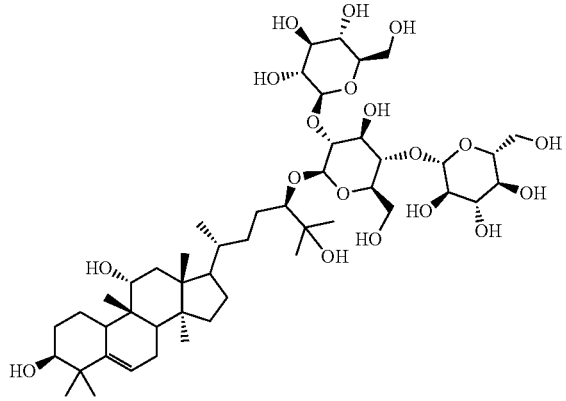

To a 250-mL baffled flask, 1 g of crude mogroside III$_E$, 53 mL of water, 15 mL of 1M sodium acetate buffer pH 5, 7 ml of celluclast from Novozymes and 75 g of a-lactose were added and shook the flask at 220 rpm, 50° C. for 9 days. The progress of the reaction was monitored periodically by LC-MS analysis. The same reaction was repeated 17 more times for a total of 18g of mogroside III$_E$ in two batches. After 9 days, the unreacted enzyme and excess lactose from the reaction mixtures were removed in three following steps before SPE purification. The reaction mixture was centrifuged for 10 min at 5000 rpm to remove the excess lactose followed by the incubation at 80° C. for 30 min with magnetic stirring at 500 rpm. Further approximately ~10% $NH_4SO_4$ solution was added to precipitate the unreacted enzyme and sugars, followed by centrifugation for 10 min at 5000 rpm and removed the precipitate. The supernatant was filtered through 0.22 m PES and loaded onto 400g SPE C18 column and fractionated using a standard 5/35/70/100 MeOH:$H_2O$ step gradient. The desired compound was eluted in 70% methanol fraction. The combined 70% SPE Fraction (12g) was further purified on RP-HPLC using PF column with an A/B gradient (A=water, B=acetonitrile) of 15 to 30% B over 35 minutes, with a 95% B wash, followed by re-equilibration at 15% (total run time=45 minutes). Each run was collected in 72 tubes (12 fractions/plate, 6 plates per run) at 7.5 mL/fraction in 2 collection windows of 36 fractions each. Fractions 45-48 and 51-54 contained the desired peaks with the desired purity and were pooled separately based on UPLC analysis and dried under reduced pressure to give whitish powdery solids. The pure compounds from these Fractions were re-suspended/dissolved in 2 mL of water and lyophilized for about 3 days to get 135 and 120 mg of white solids respectively.

Compound 34: $^1$H NMR (400 MHz, Pyridine-$d_5$+$D_2O$), selected signals: δ 5.62 (d, J=6.0 Hz, 1H), 5.24 (d, J=7.8 Hz, 1H), 5.01 (d, J=7.8, Hz, 2H), 3.85 (dt, J=6.3, 3.4 Hz, 1H), 3.70 (d, J=2.9 Hz, 1H), 1.44 (s, 3H), 1.39 (brs, 6H), 1.33 (s, 3H), 1.17 (s, 3H), 1.02 (d, J=6.4 Hz, 3H), 0.89 (s, 3H), 0.84 (s, 3H); $^{13}$C NMR (101 MHz, Pyridine-$d_5$+$D_2O$) δ 144.14, 119.11, 105.71, 105.64, 101.83, 87.86, 83.58, 82.68, 78.40, 78.06, 77.89, 77.19, 76.49, 76.22, 76.16, 75.55, 74.95, 72.41, 72.28, 71.13, 69.78, 62.45, 62.26, 61.81, 50.80, 49.71, 47.40, 43.57, 42.27, 40.85, 40.15, 36.73, 34.54, 33.96, 30.64, 28.69, 28.53, 27.31, 26.71, 26.65, 26.21, 25.89, 25.55, 24.60, 19.37, 19.03, 17.01; ESI-MS, 963.84 (MH)$^+$, 961.85 (M−H)$^-$; Molecular formula, $C_{48}H_{82}O_{19}$.

Compound 35: $^1$H NMR (400 MHz, Pyridine-$d_5$+$D_2O$), selected signals: δ 5.60 (d, J=6.3 Hz, 1H), 5.00 (d, J=7.9 Hz, 1H), 4.91 (d, J=7.7 Hz, 1H), 3.79 (dd, J=7.8, 2.3 Hz, 2H), 3.70 (t, J=2.8 Hz, 2H), 1.43 (s, 3H), 1.39 (s, 6H), 1.34 (d, J=2.8 Hz, 3H), 1.15 (s, 3H), 1.0 (m, 3H), 0.91 (s, 3H), 0.83 (s, 3H); ESI-MS, 963.81 (MH)$^+$, 961.92 (M–H)$^-$; Molecular formula, $C_{48}H_{82}O_{19}$.

Examples 57 and 58: Enzymatic Production of Mogroside III$_{A2}$ and Mogrodide III

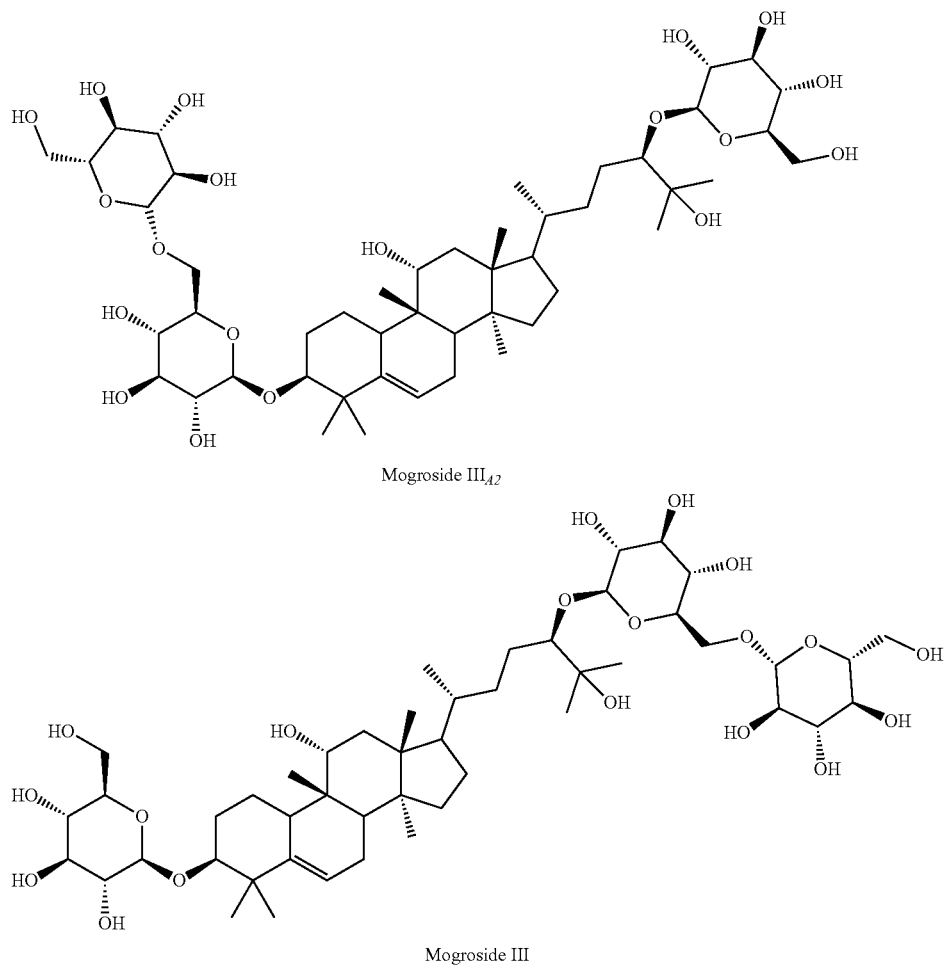

Mogroside III$_{A2}$

Mogroside III

To a 100-mL flask, 1 g of Mogroside V, 50 mL of 0.1M sodium acetate buffer pH5 and 200 mg of Fungal Lactase (Enzyme Development) were added and stirred at 50° C. The progress of the reaction was monitored by LC-MS periodically. After 24 hours, the reaction was stopped by heating at 80° C. for 30 minutes and centrifuged at 4000 rpm for 10 minutes. The filtered supernatant was further treated with 1 mL of alpha-Amylase (Sigma) and stirred at room temp for 3 days. The progress of the reaction was monitored by LC-MS periodically. The reaction was stopped by heating to 80° C. for 30 minutes and centrifuged at 4000 rpm for 10 minutes. The supernatant volume was reduced by rotary evaporation and loaded onto a 60g C18 SPE column and fractionated using 5/35/70/100 MeOH:$H_2O$ step gradient. The desired products were eluted in the 70% MeOH fraction and further purified on HILIC column using an A/B gradient (A=3:1 MeOH:$H_2O$, B=acetonitrile) of 80 to 40% B over 26 minutes, followed by re-equilibration at 80% (total run time=30 minutes). Each run was collected in 24 fractions (12 fractions/plate, 2 plates per run) at 30 mL/fraction. Fractions eluted with the desired products were pooled separately, dried under reduced pressure and re-suspended/dissolved in 1 mL of water and lyophilized for 2 days to get 24 mg of F4 and 62 mg of F6-7 as white fluffy solid with about 90% purity.

Mogroside III$_{A2}$: $^1$H NMR (400 MHz, Pyridine-$d_5$+$D_2O$), selected signals: δ5.45 (m, 1H, merged with HDO), 4.88 (m, 1H), 4.84 (t, J=7.9 Hz, 2H), 4.79 (d, J=7.7 Hz, 1H), 3.72 (d, J=8.8 Hz, 1H), 3.64 (d, J=2.9 Hz, 1H), 1.50 (s, 3H), 1.38 (s, 3H), 1.28 (s, 3H), 1.27 (s, 3H), 1.11 (s, 3H), 0.89 (d, J=6.3 Hz, 3H), 0.86 (s, 3H), 0.78 (s, 3H); ESI-MS, 963.91 (MH)$^+$, 961.85 (M–H)$^-$; Molecular formula, $C_{48}H_{82}O_{19}$.

Mogroside III: $^1$H NMR (400 MHz, Pyridine-$d_5$+$D_2O$), selected signals: δ 5.45 (m, 1H, 6-H, merged with HDO), 5.11 (d, J=7.8 Hz, 1H, G3-1H), 4.95 (d, J=7.8 Hz, 1H, G1-1H), 4.78 (d, J=7.8 Hz, 1H, G2-1H), 3.85 (1H, m, 24-H), 3.68 (d, J=2.8 Hz, 1H, 3-H), 1.47 (s, 3H, 28-Me), 1.41 (s, 3H, 26-Me), 1.37 (s, 3H, 27-Me), 1.29 (s, 3H, 19-Me), 1.08 (s, 3H, 29-Me), 0.93 (d, J=6.3 Hz, 3H, 21-Me), 0.84 (s, 2H, 30-Me), 0.77 (s, 3H, 18-Me); ESI-MS, 963.84 (MH)$^+$, 961.92 (M–H)$^-$; Molecular formula, $C_{48}H_{82}O_{19}$.

Example 59: Sweetening Packet

A packet containing a ready-to-use sweetener composition is prepared by blending a compound of Formula (I), (D)-glucose, maltodextrin, and an anti-caking agent. The mixture is then dispensed into individual paper packets such that each packet contains about 60 milligrams of a compound of Formula (I) with 890 milligrams of (D)-glucose, 40 milligrams of maltodextrin, and 10 milligrams of an anti-caking agent. Each packet containing about 1.0 grams of the sweetener composition delivers the sweetness of two teaspoons of sugar.

Example 60: Liquid Concentrate Formulation/Dilution

A concentrated liquid formulation is prepared by blending the following ingredients: a compound of Formula (I), trisodium citrate, phosphoric acid, calcium carbonate, one or more flavoring agents, one or more preservatives, one or more coloring agents, and optionally, a chelating agent. The blend is then dissolved in a solution of water and propylene glycol.

Example 61: Powder Concentrate Formulation/Dilution

A concentrated powder formulation is prepared by blending the following ingredients: a compound of Formula (I), trisodium citrate, phosphoric acid, calcium carbonate, one or more flavoring agents, one or more anti-caking agents, one or more preservatives, one or more coloring agents, and optionally, a chelating agent.

Example 62: Beverage Product

A beverage product is blending the following ingredients: a compound of Formula (I), trisodium citrate, phosphoric acid, calcium carbonate, one or more flavoring agents, one or more preservatives, one or more coloring agents, and optionally, a chelating agent. The blend is then dissolved in water to achieve the appropriate taste and consistency for consumption, and is packaged accordingly. Optionally, the water may be carbonated.

Example 63: HTS-Sweet

Compound activity ($EC_{50}$) was determined using an automated fluorometric imaging assay on a FLIPR instrument (Fluorometric Intensity Plate Reader, Molecular Devices, Sunnyvale, Calif.). Cell stably expressing the human sweet taste receptor and a promiscuous G protein were seeded into 384-well plates (at approximately 40,000 cells per well). Cells were grown for 24 hours at 37° C. Cells were then loaded with the calcium dye Fluo-4AM (Molecular Probes, Eugene, Oreg.), 4 µM in a phosphate buffered saline (D-PBS) (Invitrogen, Carlsbad, Calif.), for 1 hour at room temperature. After replacement with 25 D-PBS, stimulation was performed in the FLIPR instrument and at room temperature by the addition of 25 D-PBS supplemented with different stimuli at concentrations corresponding to twice the desired final level. Receptor activity was quantified by determining the maximal fluorescence increases (using a 480 nm excitation and 535 nm emission) after normalization to basal fluorescence intensity measured before stimulation. The activity for selected compounds ($EC_{50}$) is shown in Table 1, below. A grade of "A" indicates an $EC_{50}$ of less than 17 µM. A grade of "B" indicates an $EC_{50}$ of 17 µM to 30 µM. A grade of "C" indicates an $EC_{50}$ of greater than 30 µM.

For dose-responses analysis, stimuli were presented in duplicates at 10 different concentrations ranging from 0.4 µM to 200 µM. $EC_{50}$s were determined using a non-linear regression algorithm, where the Hill slope, bottom asymptotes and top asymptotes were allowed to vary. In order to determine the dependency of hT1R2/hT1R3 for the cell response to different stimuli, selected compounds were subjected to a similar analysis on parental cells (not expressing the human sweet receptor).

TABLE 1

Compound $EC_{50}$s for hT1R2/hT1R3

| Compound | $EC_{50}$ |
|---|---|
| Compound 1 | A |
| Compound 2 | B |
| Compound 3 | A |
| Compound 4 | A |
| Compound 5 | B |
| Compound 6 | A |
| Compound 7 | A |
| Compound 8 | A |
| Compound 9 | B |
| Compound 10 | A |
| Compound 11 | C |
| Compound 12 | B |
| Compound 13 | B |
| Compound 14 | A |
| Compound 15 | A |
| Compound 16 | B |
| Compound 17 | A |
| Compound 18 | A |
| Compound 19 | A |
| Compound 20 | A |
| Compound 21 | A |
| Compound 23 | A |
| Compound 29 | C |
| Compound 30 | C |
| Compound 31 | C |
| Compound 32 | C |
| Compound 33 | C |
| Compound 34 | C |
| Compound 35 | B |

Sensory Studies

Example 64: Paired Comparison Testing

Paired comparison tests (2-Alternative Forced Choice difference tests, i.e., 2-AFC) were used to determine sweet intensity equivalence between samples prepared with Rebaudioside A and the test sweet compound. Trained external panelists were used for the taste tests.

2-AFC tests, compound solutions were tested against 300 ppm Rebaudioside A to determine how they matched in sweet intensity. Panelists tasted both samples and indicated which sample was sweeter in each pair. Panelists rinsed their mouths with water prior to starting any test. Samples were presented to panelists in randomized, counterbalanced pairs and were labeled with 3-digit blinding codes. Panelists rinsed with water between samples as well as between pairs. There was a 90 second delay to clear the mouth of any tastes after each pair evaluation. Three replicates of each test were performed.

The 2-AFC data was analyzed to determine significant differences between 300 ppm Rebaudioside A and compound solutions using a probability table for a two-tailed test (alpha=0.05).

The paired comparison testing was performed using a 0.25 mL sample size, and all samples were made with Low Sodium Buffer (LSB) pH 7.1 and contain 0% ethanol. The panelists found that 300 ppm Compound 18 was significantly sweeter than 300 ppm Rebaudioside A ($p<0.05$) (Table 2); that 250 ppm Compound 18 was not significantly different in sweetness than 300 ppm Rebaudioside A ($p>0.05$) (Table 3); and that 300 ppm Rebaudioside A was not significantly different in sweetness than 300 ppm Compound 1 ($p>0.05$) (Table 4). Similarly, Compounds 2-17, 19-21, and 23 were found to be at least as sweet as Rebaudioside A.

TABLE 2

Sample selected as sweeter by panelists, n = 42 (14 panelists × 3 reps). Power = 84%

| Samples | Total |
|---|---|
| 300 ppm Rebaudioside A | 14 |
| 300 ppm Compound 18 | 28 |
| Total | 42 |
| p-value | 0.044 |

TABLE 3

Sample selected as sweeter by panelists, n = 36 (12 panelists × 3 reps). Power = 75%

| Samples | Total |
|---|---|
| 300 ppm Rebaudioside A | 16 |
| 250 ppm Compound 18 | 20 |
| Total | 36 |
| p-value | 0.681 |

TABLE 4

Sample selected as sweeter by panelists, n = 45 (15 panelists × 3 reps). Power = 84%

| Samples | Total |
|---|---|
| 300 ppm Rebaudioside A | 29 |
| 300 ppm Compound 1 | 16 |
| Total | 45 |
| p-value | 0.072 |

Example 65: Check-all-that-Apply Testing

Check-all-that-apply testing (i.e., CATA) is used to determine the presence of offtastes in samples, including Rebaudioside A and the test sweet compounds. Trained external panelists are used for the taste tests.

In CATA tests, compound solutions are tested along with 300 ppm Rebaudioside A to determine the presence of various attributes. Panelists tasted samples and are presented with a list of attributes and then instructed to indicate which attributes they perceived in each sample. Panelists rinsed their mouths with water prior to starting any test. Samples are presented to panelists in randomized, counterbalanced order and were labeled with 3-digit blinding codes. Panelists rinse with water between samples. There is a 60 second delay to clear the mouth of any tastes after each sample evaluation. One replicate of each test is performed.

The CATA data is tabulated and presented as the percentage of panelists that selected each attribute for each sample in the test. These studies are used to get a qualitative feel for a compound's overall taste profile. The test uncovers any significant undesired side tastes. Attributes queried include anise, astringent, bitter, cooling, delayed onset, lingering, metallic, numbing, salt, solvent, sour, sweet and umami. Compounds described herein, include Compounds 1-35 are tested. The results identifies compounds having high sweet taste with low levels of off tastes (e.g., low levels of bitter off taste).

While the invention has been described with reference to the specific embodiments thereof, it should be understood by those skilled in the art that various changes may be made and equivalents may be substituted without departing from the true spirit and scope of the invention. This includes embodiments which do not provide all of the benefits and features set forth herein. In addition, many modifications may be made to adapt a particular situation, material, composition of matter, process, process step or steps, to the objective, spirit and scope of the present invention. All such modifications are intended to be within the scope of the claims appended hereto. Accordingly, the scope of the invention is defined only by reference to the appended claims.

What is claimed is:

1. A composition, comprising a compound having the structure:

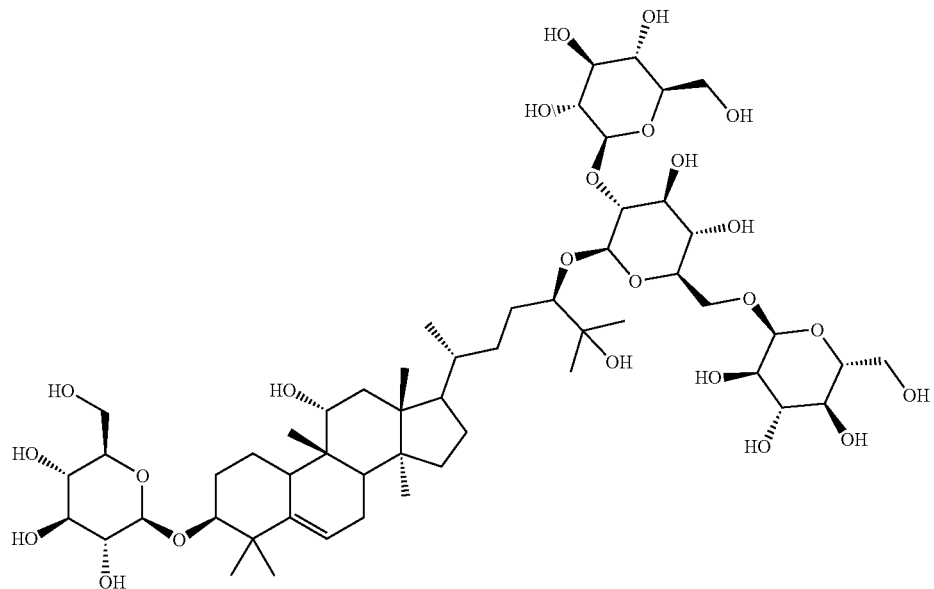

or a salt thereof, wherein the composition comprises greater than 70% by weight of the compound.

2. The composition of claim 1, comprising less than 1% by weight of Mogroside $III_E$.

3. The composition of claim 1, comprising less than 0.3% by weight of 11-oxo-Mogroside $III_E$.

4. The composition of claim 1, comprising less than 1% by weight of all isomers of Mogroside I, Mogroside II, and Mogroside III.

5. The composition of claim 1, comprising less than 1% by weight of 11-oxo-mogrol.

6. The composition of claim 1, wherein the compound is in amorphous form.

7. The composition of claim 1, wherein the compound is coating a solid carrier.

8. The composition of claim 7, wherein the solid carrier are particles selected from the group consisting of lactose, cellulose, microcrystalline cellulose, modified food starch, gum Arabic, maltodextrin, modified corn starch, dextrose, xantham gum, carboxymethylcellulose, cellulose gel, cellulose gum, sodium caseinate, carrageenan, and combinations thereof.

9. The composition of claim 6, wherein the composition is in particulate form.

10. The composition of claim 9, wherein the composition has an average particle size between 50 μm and 300 μm.

11. A composition, comprising solid particles of the composition of claim 1 and a liquid carrier.

12. The composition of claim 11, wherein the solid particles are suspended in the liquid carrier.

13. The composition of claim 11, wherein the liquid carrier is selected from water, ethanol, propylene glycol, triacetine, medium chain triglycerides, glycerin, and combinations thereof.

14. The composition of claim 11, wherein the liquid carrier is water.

15. The composition of claim 1, comprising one or more additional compounds selected from the group consisting of steviosides, rebaudiosides, glycyrrhizic acid, glycyrrhizin, GAMG (glycyrrhetinic acid monoglucuronide), thaumatin, monellin, brazzein, curculin, mabinlin, pentadin, monatin, abrusosides, albiziasaponins, Baiyunoside, bryoside, cussoracosides, cyclocarioside, mukurozioside, osladin, periandrin, phlomisoside, Polypodosides, pterocaryosides, rubusosides, telosmosides, selligueain A, hernandulcin, phlorizin, trilobatin, phylodulcin, dulcoside A, gaudichaudioside A, and combinations thereof.

16. A composition, comprising a bulking agent and a compound having the structure:

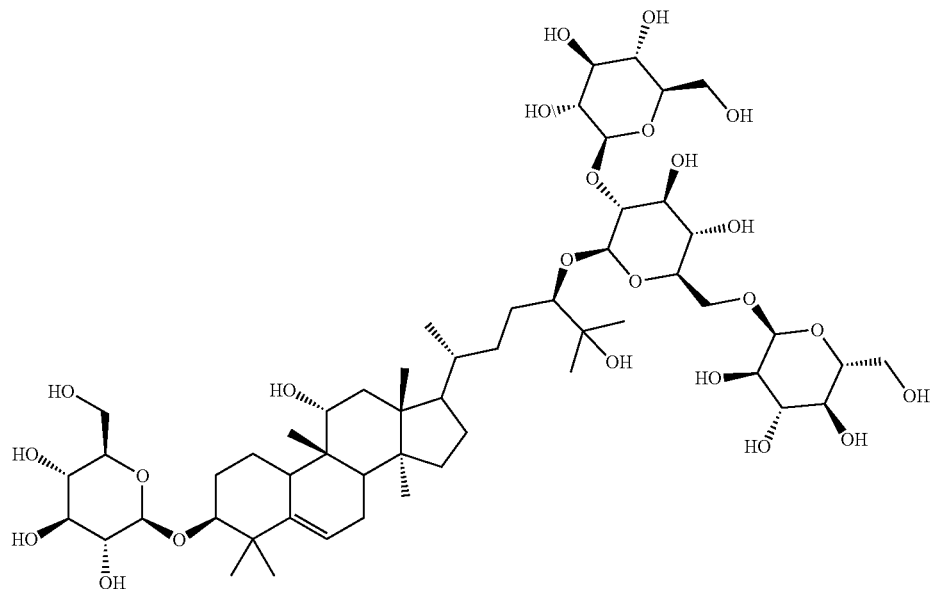

or a salt thereof, wherein the composition comprises greater than 30% by weight of the bulking agent.

17. The composition of claim 16, comprising between 0.5% and 5% by weight of the compound.

18. The composition of claim 16, comprising greater than 50% by weight of the bulking agent.

19. The composition of claim 16, comprising greater than 70% by weight of the bulking agent.

20. The composition of claim 16, comprising greater than 90% by weight of the bulking agent.

21. The composition of claim 16, wherein the bulking agent is selected from the group consisting of maltodextrin, dextro-maltodextrin blends, corn syrup solids, sucrose, fructose, glucose, invert sugar, sorbitol, xylose, ribulose, mannose, mannitol, galactitol, lactitol, isomalt, maltose, tagatose, lactose, inulin, glycerol, propylene glycol, polydextrose, fructooligosaccharides, cellulose, cellulose derivatives, erythritol, and combinations thereof.

22. The composition of claim 16, wherein the bulking agent is selected from maltodextrin, lactose, erythritol, and mannitol.

23. The composition of claim 16, wherein the bulking agent is in particulate form and the compound is present as a coating on the particles.

24. The composition of claim 16, wherein the composition is in particulate form.

25. The composition of claim 23, wherein the average particle size is between 200 μm and 2 mm.

26. The composition of claim 23, wherein the average particle size is between 200 μm and 500 μm.

27. The composition of claim 23, wherein the average particle size is between 500 μm and 700 μm.

28. The composition of claim 23, wherein the average particle size is between 800 μm and 1.5 mm.

29. The composition of claim 16, comprising one or more additional compounds selected from the group consisting of steviosides, rebaudiosides, glycyrrhizic acid, glycyrrhizin, glycyrrhetinic acid monoglucuronide, thaumatin, monellin, brazzein, curculin, mabinlin, pentadin, monatin, abrusosides, albiziasaponins, Baiyunoside, bryoside, cussoracosides, cyclocarioside, mukurozioside, osladin, periandrin, phlomisoside, Polypodosides, pterocaryosides, rubusosides, telosmosides, selligueain A, hernandulcin, phlorizin, trilobatin, phylodulcin, dulcoside A, gaudichaudioside A, and combinations thereof.

30. A tabletop sweetener product, comprising a packet containing a composition of claim 16.

31. The product of claim 30, wherein the packet is a single serving packet.

32. A flavoring concentrate, comprising a flavoring agent and a compound having the structure:

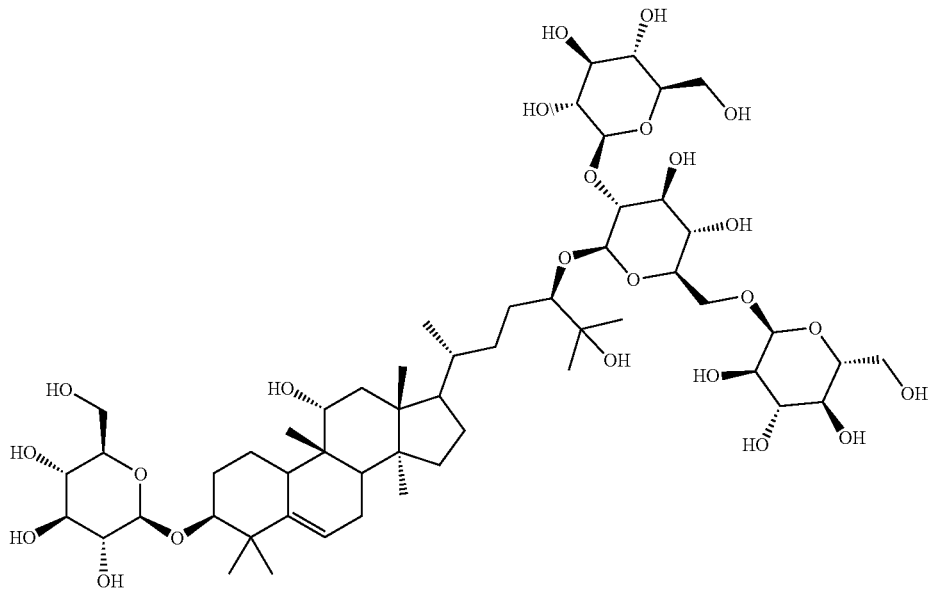

or a salt thereof, wherein the compound is at a concentration greater than 0.1% by weight.

33. The concentrate of claim 32, wherein the flavoring agent is an artificial flavoring ingredient.

34. The concentrate of claim 32, wherein the flavoring agent is a natural flavoring ingredient.

35. The concentrate of claim 32, wherein the compound is at a concentration greater than 0.5% by weight.

36. The concentrate of claim 32, wherein the compound is at a concentration greater than 1% by weight.

37. The concentrate of claim 32, wherein the concentrate is a liquid.

38. The concentrate of claim 32, wherein the concentrate is a solution.

39. The concentrate of claim 32, wherein the concentrate is a solid.

40. The concentrate of claim 32, wherein the compound is present in a concentration that is at least 2 times a concentration of the compound in a ready-to-use food or beverage product.

* * * * *

UNITED STATES PATENT AND TRADEMARK OFFICE
CERTIFICATE OF CORRECTION

PATENT NO. : 11,758,933 B2
APPLICATION NO. : 17/211144
DATED : September 19, 2023
INVENTOR(S) : Andrew P. Patron et al.

It is certified that error appears in the above-identified patent and that said Letters Patent is hereby corrected as shown below:

In the Claims

Column 475, Line 61, Claim 8, delete "xantham" and insert -- xanthan --.

Column 476, Line 65, Claim 15, delete "phylodulcin," and insert -- phyllodulcin, --.

Column 478, Line 60, Claim 29, delete "phylodulcin," and insert -- phyllodulcin, --.

Signed and Sealed this
Nineteenth Day of December, 2023

Katherine Kelly Vidal
*Director of the United States Patent and Trademark Office*